United States Patent
Zhou et al.

(10) Patent No.: US 11,780,825 B2
(45) Date of Patent: Oct. 10, 2023

(54) THYROID HORMONE RECEPTOR AGONISTS AND USE THEREOF

(71) Applicant: Eccogene (Shanghai) Co., Ltd., Shanghai (CN)

(72) Inventors: Jingye Zhou, Shanghai (CN); Jiuxiang Zhu, Shanghai (CN); Mingwei Zheng, Shanghai (CN)

(73) Assignee: Eccogene (Shanghai) Co., Ltd., Shanghai (CN)

(*) Notice: Subject to any disclaimer, the term of this patent is extended or adjusted under 35 U.S.C. 154(b) by 66 days.

(21) Appl. No.: 17/147,538

(22) Filed: Jan. 13, 2021

(65) Prior Publication Data
US 2021/0230146 A1     Jul. 29, 2021

(30) Foreign Application Priority Data

Jan. 13, 2020 (WO) .............. PCT/CN2020/071741
Aug. 7, 2020 (WO) .............. PCT/CN2020/107757

(51) Int. Cl.
| | |
|---|---|
| C07D 403/12 | (2006.01) |
| C07D 253/075 | (2006.01) |
| C07D 401/12 | (2006.01) |
| C07D 401/14 | (2006.01) |
| C07D 405/12 | (2006.01) |
| C07D 405/14 | (2006.01) |
| C07D 409/12 | (2006.01) |
| C07D 409/14 | (2006.01) |
| C07D 413/12 | (2006.01) |
| C07D 471/08 | (2006.01) |

(52) U.S. Cl.
CPC ....... *C07D 403/12* (2013.01); *C07D 253/075* (2013.01); *C07D 401/12* (2013.01); *C07D 401/14* (2013.01); *C07D 405/12* (2013.01); *C07D 405/14* (2013.01); *C07D 409/12* (2013.01); *C07D 409/14* (2013.01); *C07D 413/12* (2013.01); *C07D 471/08* (2013.01)

(58) Field of Classification Search
None
See application file for complete search history.

(56) References Cited

U.S. PATENT DOCUMENTS 8,791,266 B2 * 7/2014 Kawata .............. C07D 213/81
                                                               546/290
2020/0347035 A1   11/2020 Wang et al.

FOREIGN PATENT DOCUMENTS

| CN | 102459185 B | 6/2015 |
|---|---|---|
| CN | 109574995 A | 4/2019 |
| EP | 1088819 A2 | 4/2001 |
| EP | 1262177 A2 | 12/2002 |
| JP | 2012-106996 A | 6/2012 |
| JP | 5847533 B2 | 1/2016 |
| WO | WO 2007/009913 A1 | 1/2007 |
| WO | WO 2009/037172 A1 | 3/2009 |
| WO | WO 2010/122980 A1 | 10/2010 |
| WO | WO 2019/240938 A1 | 12/2019 |
| WO | WO 2020/169069 A1 | 8/2020 |

OTHER PUBLICATIONS

Danzi and Klein. "Cardiac specific effects of thyroid hormone analogues." Horm Metab Res. Oct. 2011;43(11):737-42. doi: 10.1055/s-0031-1291177.
Dow, et al. "Discovery of a novel series of 6-azauracil-based thyroid hormone receptor ligands: potent, TRβ subtype-selective thyromimetics," Bioorganic & Medicinal Chemistry Letters, 2003, 13, 379-382.
Joharapurkar, et al. "Selective thyromimetics using receptor and tissue selectivity approaches: prospects for dyslipidemia." J Med Chem. Jun. 28, 2012;55(12):5649-75. doi: 10.1021/jm2004706.

(Continued)

*Primary Examiner* — Samantha L Shterengarts
(74) *Attorney, Agent, or Firm* — COOLEY LLP; Chen Chen; Heng Zhang

(57) ABSTRACT

The application relates to a compound of Formula (I') or (I):

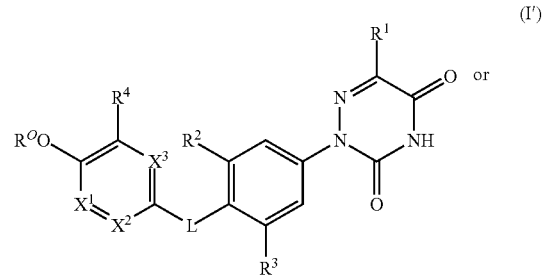

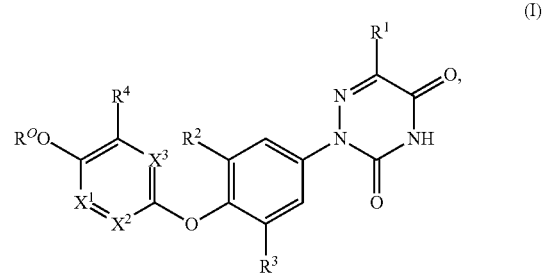

or a pharmaceutically acceptable salt, hydrate, solvate, prodrug, stereoisomer, or tautomer thereof, which modulates the activity of thyroid hormone receptors, a pharmaceutical composition comprising a compound of Formula (I') or (I), and a method of treating or preventing a disease or disorder regulated by thyroid hormone.

25 Claims, 1 Drawing Sheet
Specification includes a Sequence Listing.

(56) References Cited

OTHER PUBLICATIONS

Kelly, et al. "Discovery of 2-[3,5-Dichloro-4-(5-isopropyl-6-oxo-1,6-dihydropyridazin-3-yloxy)phenyl]-3,5-dioxo-2,3,4,5-tetrahydro[1,2,4]triazine-6-carbonitrile (MGL-3196), a highly selective thyroid hormone receptor β agonist in clinical trials for the treatment of dyslipidemia," J. Med. Chem., 2014, 57, 3912-3923.

Li, et al. "Thyroid receptor agonists for the treatment of androgenetic alopecia," Bioorganic & Medicinal Chemistry Letters, 2010, 20, 306-308.

Liu, et al. "QSAR study of selective ligands for the thyroid hormone receptor beta." Bioorg Med Chem. Aug. 1, 2007;15(15):5251-61. doi: 10.1016/j.bmc.2007.05.016.

Dow, et al. "Discovery of a novel series of 6-azauracil-based thyroid hormone receptor ligands: potent, TR beta subtype-selective thyromimetics." Bioorg Med Chem Lett. Feb. 10, 2003;13(3):379-82. doi: 10.1016/s0960-894x(02)00947-2.

Hirano, et al. "Thyromimetics: a review of recent reports and patents (2004-2009)." Expert Opin Ther Pat. Feb. 2010;20(2):213-28. doi: 10.1517/13543770903567069.

Kelly, et al. "Discovery of 2-[3,5-dichloro-4-(5-isopropyl-6-oxo-1,6-dihydropyridazin-3-yloxy)phenyl]-3,5-dioxo-2,3,4,5-tetrahydro[1,2,4]triazine-6-carbonitrile (MGL-3196), a Highly Selective Thyroid Hormone Receptor β agonist in clinical trials for the treatment of dyslipidemia." J Med Chem. May 22, 2014;57(10):3912-23. doi: 10.1021/jm4019299.

Li, et al. "Thyroid receptor agonists for the treatment of androgenetic alopecia." Bioorg Med Chem Lett. Jan. 1, 2010;20(1):306-8. doi: 10.1016/j.bmcl.2009.10.109.

\* cited by examiner

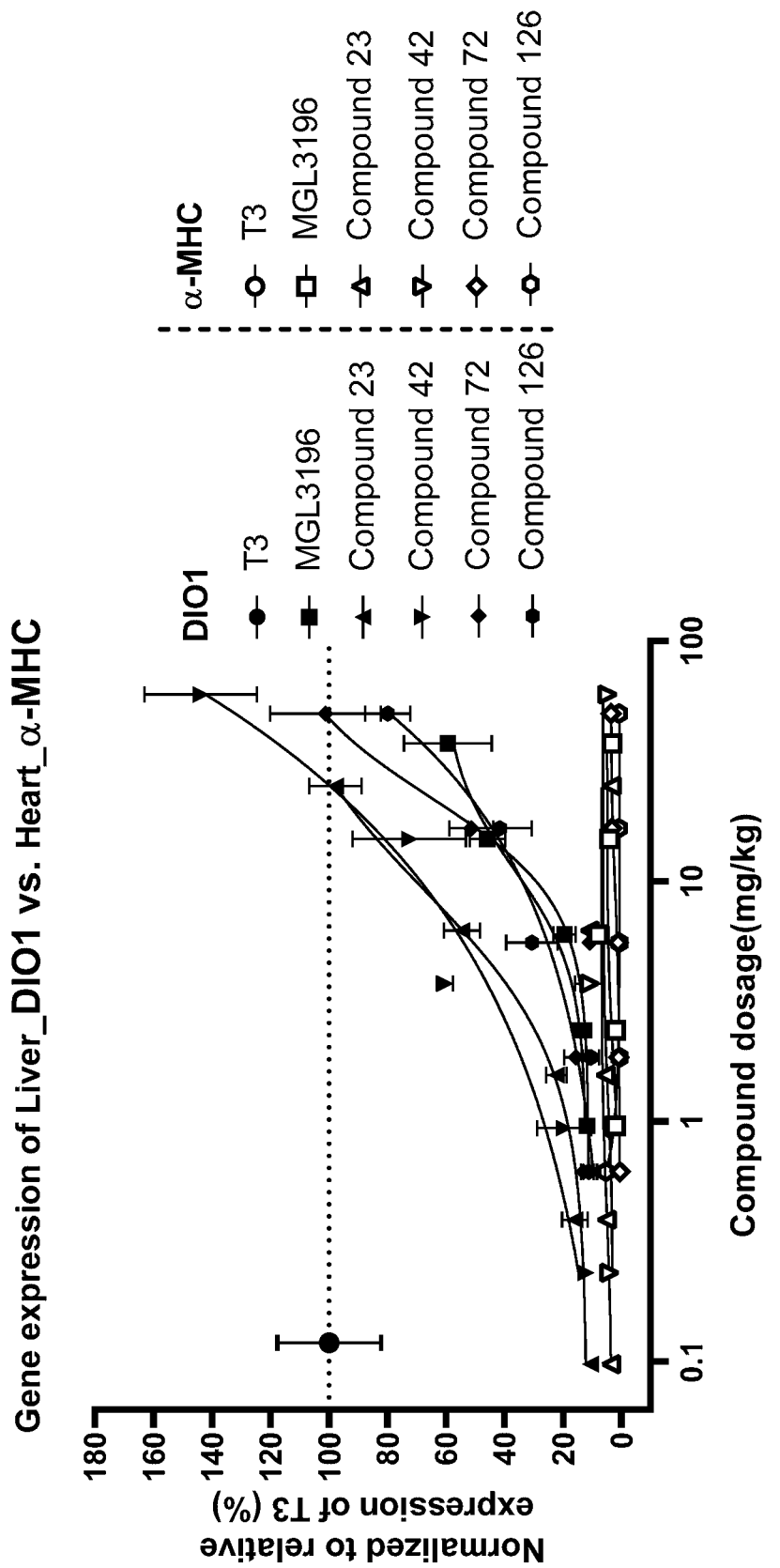

THYROID HORMONE RECEPTOR AGONISTS AND USE THEREOF

RELATED APPLICATIONS

This application claims the benefit of and priority to International Application No. PCT/CN2020/071741, filed on Jan. 13, 2020, and International Application No. PCT/CN2020/107757, filed on Aug. 7, 2020, the entire contents of each of which are incorporated herein by reference in their entireties.

SEQUENCE LISTING

The instant application contains a Sequence Listing which has been submitted in ASCII format via EFS-Web and is hereby incorporated by reference in its entirety. The ASCII copy, created on Jun. 23, 2023 is named "ECCO_003_001US_SeqList_ST25" and is 1,508 bytes in size.

BACKGROUND

Thyroid hormones are critical for normal growth and development and for maintaining metabolic homeostasis. Circulating levels of thyroid hormones are tightly regulated by feedback mechanisms in the hypothalamus/pituitary/thyroid (HPT) axis. Thyroid dysfunction leading to hypothyroidism or hyperthyroidism clearly demonstrates that thyroid hormones exert profound effects on cardiac function, body weight, metabolism, metabolic rate, body temperature, cholesterol level, maintenance of bone and muscle, and behavior. Thyroid hormones stimulate the metabolism of cholesterol to bile acids and enhance the lipolytic responses of fat cells to other hormones. Thyroid hormones also affect cardiac function. For example, tachycardia, increased stroke volume, increased cardiac index, cardiac hypertrophy, decreased peripheral vascular resistance, and increased pulse pressure are observed in patients with hyperthyroidism.

The biological activity of thyroid hormones is mediated by thyroid hormone receptors (THRs). THRs form heterodimers with the retinoid receptor that act as ligand-inducible transcription factors. THRs regulate gene expression through interactions with DNA response elements and various nuclear co-activators and co-repressors. The thyroid hormone receptors are derived from two separate genes, α and β. The major thyroid receptor isoforms are α1, α2, β1, and β2. The thyroid hormone receptor subtypes can differ in their contribution to particular biological responses. THRβ isoform are predominantly expressed in the brain and liver tissues, and are responsible for the feedback regulation of the HPT axis and the lipid lowering effect. THRα isoform selective activation is associated with the adverse effects in heart and bones. Accordingly, selective activation of the THRβ isoform in liver tissue is desirable.

Therapeutically beneficial effects of thyroid hormone include increasing metabolic rate, oxygen consumption, and heat production, and thereby reducing body weight, lowering LDL, and elevating HDL. Disorders of the thyroid are generally treated with hormone replacement, by administering either naturally occurring thyroid hormones or thyromimetic analogues which mimic the effects of thyroid hormones.

The development of thyroid hormone analogs which avoid the undesirable effects of hyperthyroidism and hypothyroidism while maintaining the beneficial effects of thyroid hormones would open new avenues of treatment for patients with metabolic diseases such as obesity, hyperlipidemia, hypercholesterolemia, diabetes, and other disorders and diseases such as liver steatosis and NASH, atherosclerosis, cardiovascular diseases, hypothyroidism, thyroid cancer, thyroid diseases, and related disorders and diseases. As such, there is a need for novel thyroid hormone analog compounds that have the beneficial effects of thyroid hormone while avoiding the undesirable effects. The present application addresses such a need.

SUMMARY

The present application provides novel thyroid hormone receptor ligands which are useful in the treatment of a disease or disorder regulated by thyroid hormone, such as those described herein, including but not limited to obesity, overweight condition, hyperlipidemia (e.g., severe high triglyceride (SHTG), familial partial lipodystrophy (FPLD), familial chylomicronemia syndrome (FCS), xanthomas, familial dysbetalipoproteinemia/hypolipoproteinemia type III, hyperlipoproteinemia, sitosterolemia), sphingolipid metabolism diseases, thyroid disease (e.g., Hashimoto's disease, thyroiditis, thyroid dysgenesis, congenital hypothyroidism, inherited thyroid hormone binding protein abnormalities), hypothyroidism, thyroid cancer, and related disorders and diseases, such as nonalcoholic fatty liver disease (NAFLD), nonalcoholic steatohepatitis (NASH), liver steatosis, liver fibrosis, hypercholesteremia, familial hypercholesterolemia (HeFH/HoFH), X-linked adrenoleukodystrophy (X-ALD), diabetes mellitus, atherosclerosis, hypertension, coronary heart disease, depression, osteoporosis, cardiac arrhythmias, glaucoma, congestive heart failure, and pancreatitis.

A first aspect of the application relates to a compound of Formula (I') or (I):

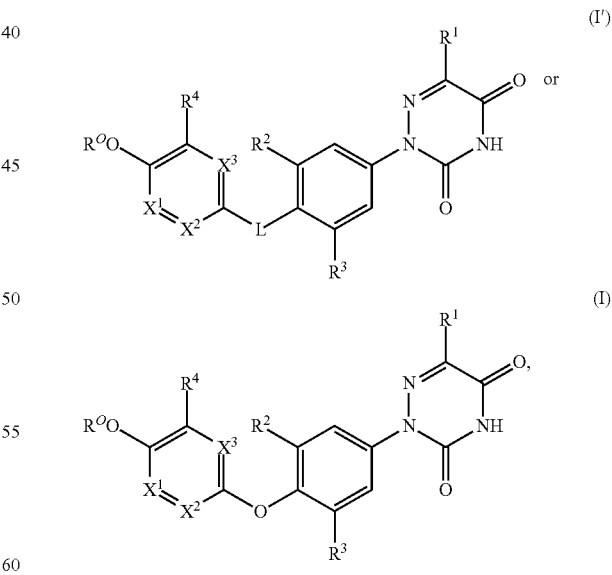

or a pharmaceutically acceptable salt, solvate, prodrug, stereoisomer, or tautomer thereof, wherein $R^O$, $R^1$, $R^2$, $R^3$, $R^4$, L, $X^1$, $X^2$, and $X^3$ are as described in detail below.

Another aspect of the application relates to a pharmaceutical composition comprising a compound of Formula (I') or (I), or a pharmaceutically acceptable salt, solvate, prodrug, stereoisomer, or tautomer thereof, and a pharmaceutically acceptable diluent, excipient, or carrier.

Another aspect of the application relates to a method of treating a disease or disorder regulated by thyroid hormones, including but not limited to a liver disease, a metabolic disease, a thyroid disease, and a cardiovascular disease, such as the disease or disorder described herein. The method comprises administering to a subject in need thereof a therapeutically effective amount of a compound of Formula (I') or (I), or a pharmaceutically acceptable salt, solvate, prodrug, stereoisomer, or tautomer thereof, or a therapeutically effective amount of a pharmaceutical composition comprising a compound of Formula (I') or (I), or a pharmaceutically acceptable salt, solvate, prodrug, stereoisomer, or tautomer thereof, and a pharmaceutically acceptable diluent, excipient, or carrier.

Another aspect of the application relates to a method of treating liver diseases. The method comprises administering to a subject in need thereof a therapeutically effective amount of a compound of Formula (I') or (I), or a pharmaceutically acceptable salt, solvate, prodrug, stereoisomer, or tautomer thereof, or a therapeutically effective amount of a pharmaceutical composition comprising a compound of Formula (I') or (I), or a pharmaceutically acceptable salt, solvate, prodrug, stereoisomer, or tautomer thereof, and a pharmaceutically acceptable diluent, excipient, or carrier.

Another aspect of the application relates to a method of treating metabolic diseases. The method comprises administering to a subject in need thereof a therapeutically effective amount of a compound of Formula (I') or (I), or a pharmaceutically acceptable salt, solvate, prodrug, stereoisomer, or tautomer thereof, or a therapeutically effective amount of a pharmaceutical composition comprising a compound of Formula (I') or (I), or a pharmaceutically acceptable salt, solvate, prodrug, stereoisomer, or tautomer thereof, and a pharmaceutically acceptable diluent, excipient, or carrier.

Another aspect of the application relates to a method of treating cardiovascular diseases. The method comprises administering to a subject in need thereof a therapeutically effective amount of a compound of Formula (I') or (I), or a pharmaceutically acceptable salt, solvate, prodrug, stereoisomer, or tautomer thereof, or a therapeutically effective amount of a pharmaceutical composition comprising a compound of Formula (I') or (I), or a pharmaceutically acceptable salt, solvate, prodrug, stereoisomer, or tautomer thereof, and a pharmaceutically acceptable diluent, excipient, or carrier.

Another aspect of the application relates to a method of reducing fibrosis (e.g., liver fibrosis). The method comprises administering to a subject in need thereof a therapeutically effective amount of a compound of Formula (I') or (I), or a pharmaceutically acceptable salt, solvate, prodrug, stereoisomer, or tautomer thereof, or a therapeutically effective amount of a pharmaceutical composition comprising a compound of Formula (I') or (I), or a pharmaceutically acceptable salt, solvate, prodrug, stereoisomer, or tautomer thereof, and a pharmaceutically acceptable diluent, excipient, or carrier.

Another aspect of the application relates to a method of treating nonalcoholic fatty liver disease (NAFLD), nonalcoholic steatohepatitis (NASH), liver steatosis, or liver fibrosis. The method comprises administering to a subject in need thereof a therapeutically effective amount of a compound of Formula (I') or (I), or a pharmaceutically acceptable salt, solvate, prodrug, stereoisomer, or tautomer thereof, or a therapeutically effective amount of a pharmaceutical composition comprising a compound of Formula (I') or (I), or a pharmaceutically acceptable salt, solvate, prodrug, stereoisomer, or tautomer thereof, and a pharmaceutically acceptable diluent, excipient, or carrier.

Another aspect of the application relates to a method of treating atherosclerosis. The method comprises administering to a subject in need thereof a therapeutically effective amount of a compound of Formula (I') or (I), or a pharmaceutically acceptable salt, solvate, prodrug, stereoisomer, or tautomer thereof, or a therapeutically effective amount of a pharmaceutical composition comprising a compound of Formula (I') or (I), or a pharmaceutically acceptable salt, solvate, prodrug, stereoisomer, or tautomer thereof, and a pharmaceutically acceptable diluent, excipient, or carrier.

Another aspect of the application relates to a method of treating stroke and complications thereof. The method comprises administering to a subject in need thereof a therapeutically effective amount of a compound of Formula (I') or (I), or a pharmaceutically acceptable salt, solvate, prodrug, stereoisomer, or tautomer thereof, or a therapeutically effective amount of a pharmaceutical composition comprising a compound of Formula (I') or (I), or a pharmaceutically acceptable salt, solvate, prodrug, stereoisomer, or tautomer thereof, and a pharmaceutically acceptable diluent, excipient, or carrier.

Another aspect of the application relates to a method of treating myocardial infarction. The method comprises administering to a subject in need thereof a therapeutically effective amount of a compound of Formula (I') or (I), or a pharmaceutically acceptable salt, solvate, prodrug, stereoisomer, or tautomer thereof, or a therapeutically effective amount of a pharmaceutical composition comprising a compound of Formula (I') or (I), or a pharmaceutically acceptable salt, solvate, prodrug, stereoisomer, or tautomer thereof, and a pharmaceutically acceptable diluent, excipient, or carrier.

Another aspect of the application relates to a method of modulating (e.g., activating) thyroid hormone receptors. The method comprises administering to a subject in need thereof a therapeutically effective amount of a compound of Formula (I') or (I), or a pharmaceutically acceptable salt, solvate, prodrug, stereoisomer, or tautomer thereof, or a therapeutically effective amount of a pharmaceutical composition comprising a compound of Formula (I') or (I), or a pharmaceutically acceptable salt, solvate, prodrug, stereoisomer, or tautomer thereof, and a pharmaceutically acceptable diluent, excipient, or carrier.

Another aspect of the application relates to a compound of Formula (I') or (I), or a pharmaceutically acceptable salt, solvate, prodrug, stereoisomer, or tautomer thereof, or a pharmaceutical composition comprising a compound of Formula (I') or (I), or a pharmaceutically acceptable salt, solvate, prodrug, stereoisomer, or tautomer thereof, and a pharmaceutically acceptable diluent, excipient, or carrier, for use in a method of treating a disease or disorder regulated by thyroid hormones, as described herein.

Another aspect of the application relates to use of a compound of Formula (I') or (I), or a pharmaceutically acceptable salt, solvate, prodrug, stereoisomer, or tautomer thereof, or a pharmaceutical composition comprising a compound of Formula (I') or (I), or a pharmaceutically acceptable salt, solvate, prodrug, stereoisomer, or tautomer thereof, and a pharmaceutically acceptable diluent, excipient, or carrier, in the manufacture of a medicament for treating a disease or disorder regulated by thyroid hormones, as described herein.

The present application further provides methods of treating a disease or disorder associated with modulation of thyroid hormone receptors including, but not limited to, liver diseases, metabolic diseases, cardiovascular diseases, fibrosis (e.g., liver fibrosis), NAFLD, NASH, liver steatosis, liver fibrosis, atherosclerosis, stroke and complications thereof, myocardial infarction, and other disease or disorder described herein, comprising administering to a subject suffering from at least one of the diseases or disorders a compound of Formula (I') or (I), or a pharmaceutically acceptable salt, solvate, prodrug, stereoisomer, or tautomer thereof.

The present application provides compounds that are therapeutic agents in the treatment of diseases such as liver diseases (e.g., NAFLD and NASH), metabolic diseases, cardiovascular diseases, and other diseases associated with the modulation of thyroid hormone receptors.

BRIEF DESCRIPTION OF DRAWINGS

FIG. 1 is a graph showing the in vivo mRNA levels for select THR-responsive genes in liver (DIO1) and heart tissue (α-MHC) for representative compounds as a function of dosage (mg/kg) measured at 24 hours.

DETAILED DESCRIPTION

Compounds of the Application

The present application relates to compounds and compositions thereof that are capable of modulating the activity of thyroid hormone receptors. The application features methods of treating, preventing, or ameliorating a disease or disorder in which thyroid hormone plays a role by administering to a subject in need thereof a therapeutically effective amount of a compound of Formula (I') or (I), or a pharmaceutically acceptable salt, solvate, prodrug, stereoisomer, or tautomer thereof. The compounds of the present application can be used in the treatment of a variety of diseases and disorders regulated by thyroid hormones, such as those described herein, by modulating the activity of thyroid hormone receptors, including, but not limited to, liver diseases (e.g., NAFLD and NASH), metabolic diseases, cardiovascular diseases, and other diseases associated with the modulation of thyroid hormone receptors.

In a first aspect of the application, a compound of Formula (I') or (I) is described:

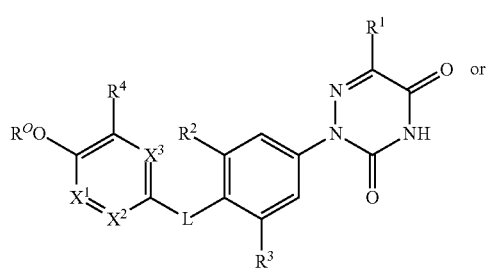

(I')

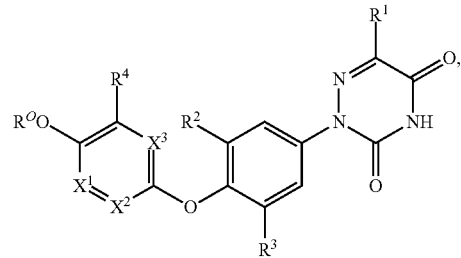

(I)

or a pharmaceutically acceptable salt, solvate, prodrug, stereoisomer, or tautomer thereof, wherein:

$R^O$ is H or $(C_1-C_4)$ alkyl;

$X^1$, $X^2$, and $X^3$ are each independently $CR^X$ or N, wherein at most one of $X^1$, $X^2$, and $X^3$ is N;

each $R^X$ is independently H, $(C_1-C_4)$ alkyl, CN, F, Cl, or $(C_3-C_5)$ cycloalkyl, wherein the alkyl or cycloalkyl is optionally substituted with one or more $R^8$, wherein when one of $X^1$, $X^2$, and $X^3$ is N and L is $CH_2$, then $R^X$ is not $(C_3-C_8)$ cycloalkyl;

L is $CH_2$, NH, N$((C_1-C_4)$ alkyl), $S(O)_2$, or O;

$R^1$ is $CH_2F$, $CHF_2$, $CF_3$, Cl, $NH_2$, or CN, or when one of $X^1$, $X^2$, and $X^3$ is N, $R^1$ is H, $(C_1-C_4)$ alkyl, $CH_2F$, $CHF_2$, $CF_3$, Cl, $NH_2$, or CN;

$R^2$ and $R^3$ are each independently H, F, Cl, or $CH_3$;

$R^4$ is $(CH_2)_{0-3}S(O)_2R^{4'}$, $S(O)_2NR^{4'}R^{4''}$, $C(O)NR^{4'}R^{4''}$, $(C_1-C_4)$ alkyl, or $(C_3-C_6)$ cycloalkyl, wherein when one of $X^1$, $X^2$, and $X^3$ is N and L is $CH_2$, then $R^4$ is not $(C_3-C_6)$ cycloalkyl, and wherein when $R^1$ is CN, then $R^4$ is not $(C_1-C_4)$ alkyl;

$R^{4'}$ and $R^{4''}$ are each independently H, $(C_1-C_4)$ alkyl, $(C_3-C_{15})$ cycloalkyl, or 3- to 10-membered heterocyclyl comprising 1 to 3 heteroatoms selected from N, O, and S, wherein the alkyl, cycloalkyl, or heterocyclyl is optionally substituted with one or more $(CH_2)_yR^5$, wherein when $R^4$ is $S(O)_2R^{4'}$, $R^{4'}$ is not H; or $R^{4'}$ and $R^{4''}$, together with the nitrogen atom to which they are attached, form a 3- to 10-membered heterocyclic ring optionally comprising 1 to 3 additional heteroatoms selected from N, O, and S and optionally substituted with one or more $(CH_2)_yR^5$;

each $R^5$ is independently F, Cl, OH, $(C_1-C_4)$ alkyl, $(C_1-C_4)$ alkoxy, oxo, CN, $(C_3-C_6)$ cycloalkyl, heterocyclyl comprising one 3- to 6-membered ring and 1 to 3 heteroatoms selected from N, O, and S, $NR^6R^{6'}$, $NR^6S(O)_2R^7$, $NR^6C(O)R^7$, $C(O)R^7$, $C(O)NR^6R^{6'}$, $S(O)_2R^7$, or $S(O)_2NR^6R^{6'}$, wherein each cycloalkyl or heterocyclyl is optionally substituted with F, Cl, OH, $(C_1-C_4)$ alkyl, $(C_1-C_4)$ alkoxy, CN, $NR^6R^{6'}$, $NR^6S(O)_2R^7$, $NR^6C(O)R^7$, $C(O)R^7$, $C(O)NR^6R^{6'}$, $S(O)_2R^7$, or $S(O)_2NR^6R^{6'}$; or when y is 0, two $R^5$, together with the atom or atoms to which they are attached, may optionally form a 3- to 6-membered ring optionally substituted with F, Cl, OH, $(C_1-C_4)$ alkyl, $(C_1-C_4)$ alkoxy, CN, $NR^6R^{6'}$, $NR^6S(O)_2R^7$, $NR^6C(O)R^7$, $C(O)R^7$, $C(O)NR^6R^{6'}$, $S(O)_2R^7$, or $S(O)_2NR^6R^{6'}$;

each $R^6$ and $R^{6'}$ is independently H, $(C_1-C_8)$ alkyl, or $(C_3-C_{10})$ cycloalkyl, wherein each alkyl or cycloalkyl is optionally substituted with one or more $R^8$; or $R^6$ and $R^{6'}$, together with the nitrogen atom to which they are attached, form a 3- to 6-membered heterocyclic ring optionally comprising one additional heteroatom selected from N, O, and S and optionally substituted with one or more $R^8$.

each $R^7$ is independently H, $(C_1-C_8)$ alkyl, or $(C_3-C_{10})$ cycloalkyl, wherein each alkyl or cycloalkyl is optionally substituted with one or more $R^8$, wherein when $R^5$ is $S(O)_2R^7$ or $NR^6S(O)_2R^7$, $R^7$ is not H;

each $R^8$ is independently halogen, $NO_2$, $NH_2$, CN, $NH((C_1-C_4)$ alkyl), $N((C_1-C_4)$ alkyl)$_2$, OH, oxo, $(C_1-C_4)$ alkyl, or $(C_1-C_4)$ alkoxy, wherein when $R^X$, $R^6$, or $R^{6'}$ is alkyl, $R^8$ is not oxo; and y is 0, 1, 2, 3, or 4.

In some embodiments, a compound of Formula (I') or (I) is of Formula (Ia') or (Ia):

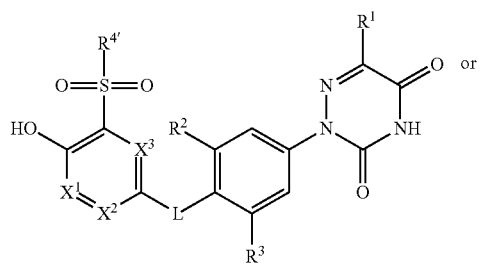

(Ia')

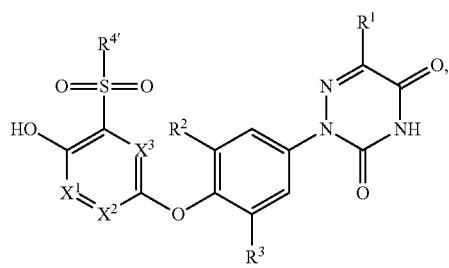

(Ia)

or a pharmaceutically acceptable salt, solvate, prodrug, stereoisomer, or tautomer thereof.

In some embodiments, a compound of Formula (I') or (I) is of Formula (Ib') or (Ib):

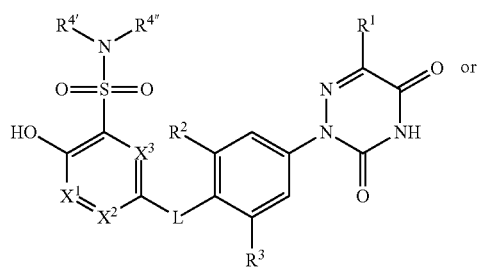

(Ib')

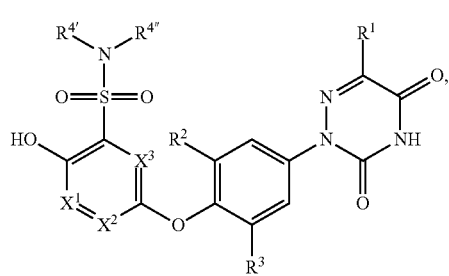

(Ib)

or a pharmaceutically acceptable salt, solvate, prodrug, stereoisomer, or tautomer thereof.

In some embodiments, a compound of Formula (I') or (I) is of Formula (Ic') or (Ic):

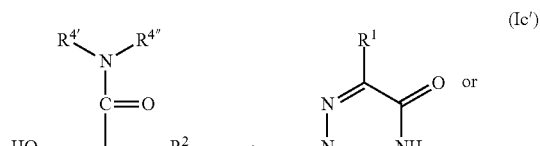

(Ic')

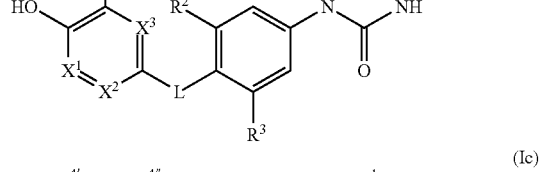

(Ic)

or a pharmaceutically acceptable salt, solvate, prodrug, stereoisomer, or tautomer thereof.

In one embodiment, for a compound of Formula (I'), (I), (Ia'), (Ia), (Ib'), (Ib), (Ic'), or (Ic), where applicable, $X^1$, $X^2$, $X^3$, L, $R^O$, $R^X$, $R^1$, $R^2$, $R^3$, $R^4$, $R^{4'}$, $R^{4''}$, $R^5$, $R^6$, $R^{6'}$, $R^7$, $R^8$, and y are each as defined below.

(1a) In one embodiment, $X^1$ is N, and $X^2$ and $X^3$ are each $CR^X$. In one embodiment, $X^2$ is N, and $X^1$ and $X^3$ are each $CR^X$. In one embodiment, $X^3$ is N, and $X^1$ and $X^2$ are each $CR^X$.

(1b) In one embodiment, $X^1$, $X^2$, and $X^3$ are each $CR^X$.

(2a-1) In one embodiment, each $R^X$ is independently H, $(C_1-C_4)$ alkyl, CN, F, or Cl.

(2a-2) In one embodiment, each $R^X$ is H.

(2b) In one embodiment, at least one $R^X$ is $(C_1-C_4)$ alkyl (e.g., methyl, ethyl, n-propyl, i-propyl, n-butyl, i-butyl, s-butyl, or t-butyl) optionally substituted with one or more $R^8$, F, Cl, CN, or $(C_3-C_8)$ cycloalkyl (e.g., cyclopropyl, cyclobutyl, cyclopentyl, cyclohexyl, cycloheptyl, or cyclooctyl) optionally substituted with one or more $R^8$. In one embodiment, one $R^X$ is $(C_1-C_4)$ alkyl (e.g., methyl, ethyl, n-propyl, i-propyl, n-butyl, i-butyl, s-butyl, or t-butyl) optionally substituted with one or more $R^8$, F, Cl, CN, or $(C_3-C_8)$ cycloalkyl (e.g., cyclopropyl, cyclobutyl, cyclopentyl, cyclohexyl, cycloheptyl, or cyclooctyl) optionally substituted with one or more $R^8$. In one embodiment, two $R^X$ are each independently $(C_1-C_4)$ alkyl (e.g., methyl, ethyl, n-propyl, i-propyl, n-butyl, i-butyl, s-butyl, or t-butyl) optionally substituted with one or more $R^8$, F, Cl, CN, or $(C_3-C_8)$ cycloalkyl (e.g., cyclopropyl, cyclobutyl, cyclopentyl, cyclohexyl, cycloheptyl, or cyclooctyl) optionally substituted with one or more $R^8$. In one embodiment, three $R^X$ are each independently $(C_1-C_4)$ alkyl (e.g., methyl, ethyl, n-propyl, i-propyl, n-butyl, i-butyl, s-butyl, or t-butyl) optionally substituted with one or more $R^8$, F, Cl, CN, or $(C_3-C_8)$ cycloalkyl (e.g., cyclopropyl, (2c) In one embodiment, at least one $R^X$ is $(C_1-C_4)$ alkyl (e.g., methyl, ethyl, n-propyl, i-propyl, n-butyl, i-butyl, s-butyl, or i-butyl) optionally substituted with one or more $R^8$. In one embodiment, one $R^X$ is $(C_1-C_4)$ alkyl (e.g., methyl, ethyl, n-propyl, i-propyl, n-butyl, i-butyl, s-butyl, or t-butyl) optionally substituted with one or more $R^8$. In one embodiment, two $R^X$ are each independently $(C_1-C_4)$ alkyl (e.g., methyl, ethyl, n-propyl, i-propyl, n-butyl, i-butyl, s-butyl, or t-butyl) optionally substituted with one or more $R^8$. In one embodiment, three $R^X$ are each independently $(C_1-C_4)$ alkyl (e.g., methyl, ethyl, n-propyl, i-propyl, n-butyl, i-butyl, s-butyl, or t-butyl) optionally substituted with one or more $R^8$.

(2d) In one embodiment, at least one $R^X$ is CN. In one embodiment, one $R^X$ is CN. In one embodiment, two $R^X$ are CN. In one embodiment, three $R^X$ are CN.

(2e) In one embodiment, at least one $R^X$ is F or Cl. In one embodiment, one $R^X$ is F or Cl. In one embodiment, two $R^X$ are each independently F or Cl. In one embodiment, three $R^X$ are each independently F or Cl.

(2f) In one embodiment, at least one $R^X$ is F. In one embodiment, one $R^X$ is F. In one embodiment, two $R^X$ are each F. In one embodiment, three $R^X$ are each F.

(2g) In one embodiment, at least one $R^X$ is Cl. In one embodiment, one $R^X$ is Cl. In one embodiment, two $R^X$ are each Cl. In one embodiment, three $R^X$ are each Cl.

(2h) In one embodiment, at least one $R^X$ is $(C_3-C_8)$ cycloalkyl (e.g., cyclopropyl, cyclobutyl, cyclopentyl, cyclohexyl, cycloheptyl, or cyclooctyl) optionally substituted with one or more $R^8$. In one embodiment, one $R^X$ is $(C_3-C_8)$ cycloalkyl (e.g., cyclopropyl, cyclobutyl, cyclopentyl, cyclohexyl, cycloheptyl, or cyclooctyl) optionally substituted with one or more $R^8$. In one embodiment, two $R^X$ are each independently $(C_3-C_5)$ cycloalkyl (e.g., cyclopropyl, cyclobutyl, cyclopentyl, cyclohexyl, cycloheptyl, or cyclooctyl) optionally substituted with one or more $R^8$. In one embodiment, three $R^X$ are each independently $(C_3-C_8)$ cycloalkyl (e.g., cyclopropyl, cyclobutyl, cyclopentyl, cyclohexyl, cycloheptyl, or cyclooctyl) optionally substituted with one or more $R^8$.

(2i) In one embodiment, none of $R^X$ is $(C_3-C_8)$ cycloalkyl.

(3a) In one embodiment, L is $S(O)_2$ or O.
(3b) In one embodiment, L is $S(O)_2$.
(3c) In one embodiment, L is O.
(3d) In one embodiment, L is NH.
(3e) In one embodiment, L is $N((C_1-C_4)$ alkyl), wherein the alkyl is selected from methyl, ethyl, n-propyl, i-propyl, n-butyl, i-butyl, s-butyl, and t-butyl).
(3f) In one embodiment, L is $(C_1-C_4)$ alkyl selected from methyl, ethyl, n-propyl, i-propyl, n-butyl, i-butyl, s-butyl, and t-butyl.
(3g) In one embodiment, L is NH, $N((C_1-C_4)$ alkyl), $S(O)_2$, or O.
(4a) In one embodiment, $R^1$ is $CH_2F$, $CHF_2$, $CF_3$, Cl, or $NH_2$.
(4b) In one embodiment, $R^1$ is $CHF_2$, $CF_3$, or Cl.
(4c) In one embodiment, $R^1$ is $CHF_2$ or $CF_3$.
(4d) In one embodiment, $R^1$ is $CHF_2$.
(4e) In one embodiment, $R^1$ is $CF_3$.
(4f) In one embodiment, $R^1$ is Cl.
(4g) In one embodiment, $R^1$ is H when one of $X^1$, $X^2$, and $X^3$ is N.
(4h) In one embodiment, $R^1$ is $(C_1-C_4)$ alkyl selected from methyl, ethyl, n-propyl, i-propyl, n-butyl, i-butyl, s-butyl, and t-butyl when one of $X^1$, $X^2$, and $X^3$ is N.

(5a) In one embodiment, $R^2$ and $R^3$ are each H.
(5b) In one embodiment, one of $R^2$ and $R^3$ is H, and the other is F, Cl, or $CH_3$.
(5c) In one embodiment, $R^2$ and $R^3$ are each independently F, Cl, or $CH_3$.
(5d) In one embodiment, $R^2$ and $R^3$ are each independently F or $CH_3$.
(5e) In one embodiment, $R^2$ and $R^3$ are each independently Cl or $CH_3$.
(5f) In one embodiment, $R^2$ and $R^3$ are each independently F or Cl.
(5g) In one embodiment, $R^2$ and $R^3$ are each F.
(5h) In one embodiment, $R^2$ and $R^3$ are each Cl.
(5i) In one embodiment, $R^2$ and $R^3$ are each $CH_3$.

(6a) In one embodiment, $R^4$ is $(CH_2)_{0-3}S(O)_2R^{4'}$, $S(O)_2NR^{4'}R^{4''}$, or $C(O)NR^{4'}R^{4''}$. In one embodiment, $R^4$ is $S(O)_2R^{4'}$, $S(O)_2NR^{4'}R^{4''}$, or $C(O)NR^{4'}R^{4''}$.
(6b) In one embodiment, $R^4$ is $(CH_2)_{0-3}S(O)_2R^{4'}$. In one embodiment, $R^4$ is $S(O)_2R^{4'}$.
(6c) In one embodiment, $R^4$ is $S(O)_2NR^{4'}R^{4''}$.
(6d) In one embodiment, $R^4$ is $C(O)NR^{4'}R^{4''}$.
(6e) In one embodiment, $R^4$ is $(C_1-C_4)$ alkyl (e.g., methyl, ethyl, n-propyl, i-propyl, n-butyl, i-butyl, s-butyl, or t-butyl).
(6f) In one embodiment, $R^4$ is $(C_3-C_6)$ cycloalkyl (e.g., cyclopropyl, cyclobutyl, cyclopentyl, or cyclohexyl).

(7a) In one embodiment, $R^{4'}$ and $R^{4''}$ are each H.
(7b) In one embodiment, $R^{4'}$ and $R^{4''}$ are each independently $(C_1-C_4)$ alkyl (e.g., methyl, ethyl, n-propyl, i-propyl, n-butyl, i-butyl, s-butyl, or t-butyl), monocyclic or multicyclic spiro-, fused-, or bridged-$(C_3-C_{15})$ cycloalkyl (e.g., cyclopropyl, cyclobutyl, cyclopentyl, cyclohexyl, cycloheptyl, cyclooctyl, cyclononyl, cyclodecyl, bicyclo[1.1.1]pentanyl, bicyclo[2.2.1]heptyl, spiro[3.3]heptanyl, bicyclo[2.2.2]octyl, or adamantyl), or 3- to 10-membered monocyclic or multicyclic spiro-, fused-, or bridged-heterocyclyl comprising 1 to 3 heteroatoms selected from N, O, and S (e.g., [1,3]dioxolanyl, pyrrolidinyl, pyrazolidinyl, pyrazolinyl, imidazolinyl, imidazolidinyl, piperidinyl, piperazinyl, 2-pyridone, oxazolidinyl, isoxazolidinyl, morpholinyl, tetrahydropyranyl, thiazolidinyl, isothiazolidinyl, tetrahydrofuryl, dioxanyl, oxetanyl, azetidinyl, thietanyl, oxiranyl, aziridinyl, thiiranyl, 2-oxa-5-azabicyclo[2.2.1]heptanyl, or 2,5-diazabicyclo[2.2.1]heptanyl), wherein the alkyl, cycloalkyl, or heterocyclyl is optionally substituted with one or more $(CH_2)_xR^5$.
(7c) In one embodiment, one of $R^{4'}$ and $R^{4''}$ is H, and the other is $(C_1-C_4)$ alkyl (e.g., methyl, ethyl, n-propyl, i-propyl, n-butyl, i-butyl, s-butyl, or t-butyl), monocyclic or multicyclic spiro-, fused-, or bridged-$(C_3-C_{15})$ cycloalkyl (e.g., cyclopropyl, cyclobutyl, cyclopentyl, cyclohexyl, cycloheptyl, cyclooctyl, cyclononyl, cyclodecyl, bicyclo[1.1.1]pentanyl, bicyclo[2.2.1]heptyl, spiro[3.3]heptanyl, bicyclo[2.2.2]octyl, or adamantyl), or 3- to 10-membered monocyclic or multicyclic spiro-, fused-, or bridged-heterocyclyl comprising 1 to 3 heteroatoms selected from N, O, and S (e.g., [1,3]dioxolanyl, pyrrolidinyl, pyrazolidinyl, pyrazolinyl, imidazolinyl, imidazolidinyl, piperidinyl, piperazinyl, 2-pyridone, oxazolidinyl, isoxazolidinyl, morpholinyl, tetrahydropyranyl, thiazolidinyl, isothiazolidinyl, tetrahydrofuryl, dioxanyl, oxetanyl, azetidinyl, thietanyl, oxiranyl, aziridinyl, thiiranyl, 2-oxa-5-azabicyclo

[2.2.1]heptanyl, or 2,5-diazabicyclo[2.2.1]heptanyl), wherein the alkyl, cycloalkyl, or heterocyclyl is optionally substituted with one or more $(CH_2)_y R^5$.

(7d) In one embodiment, one of $R^{4'}$ and $R^{4''}$ is H, and the other is $(C_1-C_4)$ alkyl (e.g., methyl, ethyl, n-propyl, i-propyl, n-butyl, i-butyl, s-butyl, or t-butyl) optionally substituted with one or more $(CH_2)_y R^5$.

(7e) In one embodiment, one of $R^{4'}$ and $R^{4''}$ is H, and the other is monocyclic or multicyclic spiro-, fused-, or bridged-$(C_3-C_{15})$ cycloalkyl (e.g., cyclopropyl, cyclobutyl, cyclopentyl, cyclohexyl, cycloheptyl, cyclooctyl, cyclononyl, cyclodecyl, bicyclo[1.1.1]pentanyl, bicyclo[2.2.1]heptyl, spiro[3.3]heptanyl, bicyclo[2.2.2]octyl, or adamantyl), or 3- to 10-membered monocyclic or multicyclic spiro-, fused-, or bridged-heterocyclyl comprising 1 to 3 heteroatoms selected from N, O, and S (e.g., [1,3]dioxolanyl, pyrrolidinyl, pyrazolidinyl, pyrazolinyl, imidazolinyl, imidazolidinyl, piperidinyl, piperazinyl, 2-pyridone, oxazolidinyl, isoxazolidinyl, morpholinyl, tetrahydropyranyl, thiazolidinyl, isothiazolidinyl, tetrahydrofuryl, dioxanyl, oxetanyl, azetidinyl, thietanyl, oxiranyl, aziridinyl, thiiranyl, 2-oxa-5-azabicyclo[2.2.1]heptanyl, or 2,5-diazabicyclo[2.2.1]heptanyl), wherein the cycloalkyl or heterocyclyl is optionally substituted with one or more $(CH_2)_y R^5$.

(7f) In one embodiment, one of $R^{4'}$ and $R^{4''}$ is H, and the other is monocyclic or multicyclic spiro-, fused-, or bridged-$(C_3—C_{15})$ cycloalkyl optionally substituted with one or more $(CH_2)_y R^5$. In one embodiment, one of $R^{4'}$ and $R^{4''}$ is H, and the other is monocyclic $(C_3-C_{15})$ cycloalkyl optionally substituted with one or more $(CH_2)_y R^5$. In one embodiment, one of $R^{4'}$ and $R^{4''}$ is H, and the other is monocyclic $(C_3-C_8)$ cycloalkyl optionally substituted with one or more $(CH_2)_y R^5$. In one embodiment, one of $R^{4'}$ and $R^{4''}$ is H, and the other is monocyclic $(C_3-C_6)$ cycloalkyl optionally substituted with one or more $(CH_2)_y R^5$. In one embodiment, one of $R^{4'}$ and $R^{4''}$ is H, and the other is multicyclic spiro-$(C_5-C_{15})$ cycloalkyl optionally substituted with one or more $(CH_2)_y R^5$. In one embodiment, one of $R^{4'}$ and $R^{4''}$ is H, and the other is multicyclic fused-$(C_5-C_{15})$ cycloalkyl optionally substituted with one or more $(CH_2)_y R^5$. In one embodiment, one of $R^{4'}$ and $R^{4''}$ is H, and the other is multicyclic bridged-$(C_5-C_{15})$ cycloalkyl optionally substituted with one or more $(CH_2)_y R^5$. In one embodiment, one of $R^{4'}$ and $R^{4''}$ is H, and the other is selected from cyclopropyl, cyclobutyl, cyclopentyl, cyclohexyl, cycloheptyl, cyclooctyl, cyclononyl, cyclodecyl, bicyclo[1.1.1]pentanyl, bicyclo[2.2.1]heptyl, spiro[3.3]heptanyl, bicyclo[2.2.2]octyl, and adamantyl, each of which is optionally substituted with one or more $(CH_2)_y R^5$.

(7g) In one embodiment, one of $R^{4'}$ and $R^{4''}$ is H, and the other is 3- to 10-membered monocyclic or multicyclic spiro-, fused-, or bridged-heterocyclyl comprising 1 to 3 heteroatoms selected from N, O, and S optionally substituted with one or more $(CH_2)_y R^5$. In one embodiment, one of $R^{4'}$ and $R^{4''}$ is H, and the other is 3- to 10-membered monocyclic heterocyclyl comprising 1 to 3 heteroatoms selected from N, O, and S optionally substituted with one or more $(CH_2)_y R^5$. In one embodiment, one of $R^{4'}$ and $R^{4''}$ is H, and the other is 3- to 6-membered monocyclic heterocyclyl comprising 1 to 3 heteroatoms selected from N, O, and S optionally substituted with one or more $(CH_2)_y R^5$. In one embodiment, one of $R^{4'}$ and $R^{4''}$ is H, and the other is 5- to 10-membered multicyclic spiro-heterocyclyl comprising 1 to 3 heteroatoms selected from N, O, and S optionally substituted with one or more $(CH_2)_y R^5$. In one embodiment, one of $R^{4'}$ and $R^{4''}$ is H, and the other is 5- to 10-membered multicyclic fused-heterocyclyl comprising 1 to 3 heteroatoms selected from N, O, and S optionally substituted with one or more $(CH_2)_y R^5$. In one embodiment, one of $R^{4'}$ and $R^{4''}$ is H, and the other is 5- to 10-membered multicyclic bridged-heterocyclyl comprising 1 to 3 heteroatoms selected from N, O, and S optionally substituted with one or more $(CH_2)_y R^5$. In one embodiment, one of $R^{4'}$ and $R^{4''}$ is H, and the other is selected from [1,3]dioxolanyl, pyrrolidinyl, pyrazolidinyl, pyrazolinyl, imidazolinyl, imidazolidinyl, piperidinyl, piperazinyl, 2-pyridone, oxazolidinyl, isoxazolidinyl, morpholinyl, tetrahydropyranyl, thiazolidinyl, isothiazolidinyl, tetrahydrofuryl, dioxanyl, oxetanyl, azetidinyl, thietanyl, oxiranyl, aziridinyl, thiiranyl, 2-oxa-5-azabicyclo[2.2.1]heptanyl, and 2,5-diazabicyclo[2.2.1]heptanyl), each of which is optionally substituted with one or more $(CH_2)_y R^5$. In one embodiment, one of $R^{4'}$ and $R^{4''}$ is H, and the other is 3- to 6-membered monocyclic heterocyclyl comprising 1 to 3 heteroatoms selected from N, O, and S (e.g., [1,3]dioxolanyl, pyrrolidinyl, pyrazolidinyl, pyrazolinyl, imidazolinyl, imidazolidinyl, piperidinyl, piperazinyl, 2-pyridone, oxazolidinyl, isoxazolidinyl, morpholinyl, tetrahydropyranyl, thiazolidinyl, isothiazolidinyl, tetrahydrofuryl, dioxanyl, oxetanyl, azetidinyl, thietanyl, oxiranyl, aziridinyl, or thiiranyl) optionally substituted with one or more $(CH_2)_y R^5$. In one embodiment, one of $R^{4'}$ and $R^{4''}$ is H, and the other is 5- to 8-membered multicyclic spiro-, fused-, or bridged-heterocyclyl comprising 1 to 3 heteroatoms selected from N, O, and S (e.g., 2-oxa-5-azabicyclo[2.2.1]heptanyl, or 2,5-diazabicyclo[2.2.1]heptanyl) optionally substituted with one or more $(CH_2)_y R^5$.

(7h) In one embodiment, $R^{4'}$ and $R^{4''}$, together with the nitrogen atom to which they are attached, form a 3- to 10-membered monocyclic or multicyclic spiro-, fused-, or bridged-heterocyclyl comprising 1 to 3 heteroatoms selected from N, O, and S optionally substituted with one or more $(CH_2)_y R^5$. In one embodiment, $R^{4'}$ and $R^{4''}$, together with the nitrogen atom to which they are attached, form a 3- to 10-membered monocyclic heterocyclyl comprising 1 to 3 heteroatoms selected from N, O, and S optionally substituted with one or more $(CH_2)_y R^5$. In one embodiment, $R^{4'}$ and $R^{4''}$, together with the nitrogen atom to which they are attached, form a 3- to 6-membered monocyclic heterocyclyl comprising 1 to 3 heteroatoms selected from N, O, and S optionally substituted with one or more $(CH_2)_y R^5$. In one embodiment, $R^{4'}$ and $R^{4''}$, together with the nitrogen atom to which they are attached, form a 5- to 10-membered multicyclic spiro-heterocyclyl comprising 1 to 3 heteroatoms selected from N, O, and S optionally substituted with one or more $(CH_2)_y R^5$. In one embodiment, $R^{4'}$ and $R^{4''}$, together with the nitrogen atom to which they are attached, form a 5- to 10-membered multicyclic fused-heterocyclyl comprising 1 to 3 heteroatoms selected from N, O, and S optionally substituted with one or more $(CH_2)_y R^5$. In one embodiment, $R^{4'}$ and $R^{4''}$, together with the nitrogen atom to which they are attached, form a 5- to 10-membered multicyclic bridged-heterocyclyl comprising 1 to 3 heteroatoms selected from N, O, and S optionally substituted with one or more $(CH_2)_y R^5$. In one embodiment, $R^{4'}$ and $R^{4''}$, together with the nitrogen atom to which they are attached, form a heterocyclyl selected from [1,3]dioxolanyl, pyrrolidinyl, pyrazolidinyl, pyrazolinyl, imidazolinyl, imidazolidinyl, piperidinyl, piperazinyl, 2-pyridone, oxazolidinyl, isoxazolidinyl, morpholinyl, tetrahydropyranyl, thiazolidinyl, isothiazolidinyl, tetrahydrofuryl, dioxanyl, oxetanyl, azetidinyl, thietanyl, oxiranyl, aziridinyl, thiiranyl, 2-oxa-5-azabicyclo[2.2.1]heptanyl, and 2,5-diazabicyclo[2.2.1]heptanyl, each of which is optionally substituted with one or more $(CH_2)_yR^5$. In one embodiment, $R^{4'}$ and $R^{4''}$, together with the nitrogen atom to which they are attached, form a 3- to 6-membered monocyclic heterocyclyl comprising 1 to 3 heteroatoms selected from N, O, and S (e.g., [1,3]dioxolanyl, pyrrolidinyl, pyrazolidinyl, pyrazolinyl, imidazolinyl, imidazolidinyl, piperidinyl, piperazinyl, 2-pyridone, oxazolidinyl, isoxazolidinyl, morpholinyl, tetrahydropyranyl, thiazolidinyl, isothiazolidinyl, tetrahydrofuryl, dioxanyl, oxetanyl, azetidinyl, thietanyl, oxiranyl, aziridinyl, or thiiranyl) optionally substituted with one or more $(CH_2)_yR^5$. In one embodiment, $R^{4'}$ and $R^{4''}$, together with the nitrogen atom to which they are attached, form a 5- to 8-membered multicyclic spiro-, fused-, or bridged-heterocyclyl comprising 1 to 3 heteroatoms selected from N, O, and S (e.g., 2-oxa-5-azabicyclo [2.2.1]heptanyl, or 2,5-diazabicyclo[2.2.1]heptanyl) optionally substituted with one or more $(CH_2)_yR^5$.

(8a) In one embodiment, at least one $R^5$ is F, Cl, OH, $(C_1-C_4)$ alkyl (e.g., methyl, ethyl, n-propyl, i-propyl, n-butyl, i-butyl, s-butyl, or t-butyl), $(C_1-C_4)$ alkoxy (e.g., methoxy, ethoxy, n-propoxy, i-propoxy, n-butoxy, i-butoxy, s-butoxy, or t-butoxy), oxo, or CN.

(8b) In one embodiment, at least one $R^5$ is $(C_3-C_6)$ cycloalkyl (e.g., cyclopropyl, cyclobutyl, cyclopentyl, or cyclohexyl) optionally substituted with F, Cl, OH, $(C_1-C_4)$ alkyl, $(C_1-C_4)$ alkoxy, CN, $NR^6R^{6'}$, $NR^6S(O)_2R^7$, $NR^6C(O)R^7$, $C(O)R^7$, $C(O)NR^6R^{6'}$, $S(O)_2R^7$, or $S(O)_2NR^6R^{6'}$. In one embodiment, at least one $R^5$ is $(C_3-C_6)$ cycloalkyl (e.g., cyclopropyl, cyclobutyl, cyclopentyl, or cyclohexyl) optionally substituted with F, Cl, OH, $(C_1-C_4)$ alkyl, $(C_1-C_4)$ alkoxy, CN, or $NR^6R^{6'}$.

(8c) In one embodiment, at least one $R^5$ is heterocyclyl comprising one 3- to 6-membered ring and 1 to 3 heteroatoms selected from N, O, and S (e.g., [1,3] dioxolanyl, pyrrolidinyl, pyrazolidinyl, pyrazolinyl, imidazolinyl, imidazolidinyl, piperidinyl, piperazinyl, 2-pyridone, oxazolidinyl, isoxazolidinyl, morpholinyl, tetrahydropyranyl, thiazolidinyl, isothiazolidinyl, tetrahydrofuryl, dioxanyl, oxetanyl, azetidinyl, thietanyl, oxiranyl, aziridinyl, or thiiranyl) optionally substituted with F, Cl, OH, $(C_1-C_4)$ alkyl, $(C_1-C_4)$ alkoxy, CN, $NR^6R^{6'}$, $NR^6S(O)_2R^7$, $NR^6C(O)R^7$, $C(O)R^7$, $C(O)NR^6R^{6'}$, $S(O)_2R^7$, or $S(O)_2NR^6R^{6'}$. In one embodiment, at least one $R^5$ is heterocyclyl comprising one 3- to 6-membered ring and 1 to 3 heteroatoms selected from N, O, and S (e.g., [1,3]dioxolanyl, pyrrolidinyl, pyrazolidinyl, pyrazolinyl, imidazolinyl, imidazolidinyl, piperidinyl, piperazinyl, 2-pyridone, oxazolidinyl, isoxazolidinyl, morpholinyl, tetrahydropyranyl, thiazolidinyl, isothiazolidinyl, tetrahydrofuryl, dioxanyl, oxetanyl, azetidinyl, thietanyl, oxiranyl, aziridinyl, or thiiranyl) optionally substituted with F, Cl, OH, $(C_1-C_4)$ alkyl, $(C_1-C_4)$ alkoxy, CN, or $NR^6R^{6'}$.

(8d) In one embodiment, at least one $R^5$ is $NR^6R^{6'}$, $NR^6S(O)_2R^7$, $NR^6C(O)R^7$, $C(O)R^7$, $C(O)NR^6R^{6'}$, $S(O)_2R^7$, or $S(O)_2NR^6R^{6'}$.

(8e) In one embodiment, two $R^5$, together with the atom or atoms to which they are attached, form a 3- to 6-membered ring optionally substituted with F, Cl, OH, $(C_1-C_4)$ alkyl, $(C_1-C_4)$ alkoxy, CN, $NR^6R^{6'}$, $NR^6 S(O)_2R^7$, $NR^6C(O)R^7$, $C(O)R^7$, $C(O)NR^6R^{6'}$, $S(O)_2R^7$, or $S(O)_2NR^6R^{6'}$. In one embodiment, two $R^5$, together with the atom or atoms to which they are attached, form $(C_3-C_6)$ cycloalkyl (e.g., cyclopropyl, cyclobutyl, cyclopentyl, or cyclohexyl) optionally substituted with F, Cl, OH, $(C_1-C_4)$ alkyl, $(C_1-C_4)$ alkoxy, CN, $NR^6R^{6'}$, $NR^6S(O)_2R^7$, $NR^6C(O)R^7$, $C(O)R^7$, $C(O)NR^6R^{6'}$, $S(O)_2R^7$, or $S(O)_2NR^6R^{6'}$. In one embodiment, two $R^5$, together with the atom or atoms to which they are attached, form heterocyclyl comprising one 3- to 6-membered ring and 1 to 3 heteroatoms selected from N, O, and S (e.g., [1,3]dioxolanyl, pyrrolidinyl, pyrazolidinyl, pyrazolinyl, imidazolinyl, imidazolidinyl, piperidinyl, piperazinyl, 2-pyridone, oxazolidinyl, isoxazolidinyl, morpholinyl, tetrahydropyranyl, thiazolidinyl, isothiazolidinyl, tetrahydrofuryl, dioxanyl, oxetanyl, azetidinyl, thietanyl, oxiranyl, aziridinyl, or thiiranyl) optionally substituted with F, Cl, OH, $(C_1-C_4)$ alkyl, $(C_1-C_4)$ alkoxy, CN, $NR^6R^{6'}$, $NR^6S(O)_2R^7$, $NR^6C(O)R^7$, $C(O)R^7$, $C(O)NR^6R^{6'}$, $S(O)_2R^7$, or $S(O)_2NR^6R^6$.

(9a) In one embodiment, $R^6$ and $R^{6'}$ are each H.

(9b) In one embodiment, one of $R^6$ and $R^{6'}$ is H, and the other is straight or branched $(C_1-C_8)$ alkyl (e.g., methyl, ethyl, n-propyl, i-propyl, n-butyl, i-butyl, s-butyl, straight or branched pentyl, straight or branched hexyl, straight or branched heptyl, or straight or branched octyl) or monocyclic or multicyclic spiro-, fused-, or bridged-$(C_3-C_{10})$ cycloalkyl, wherein the alkyl or cycloalkyl is optionally substituted with one or more $R^8$.

(9c) In one embodiment, one of $R^6$ and $R^{6'}$ is H, and the other is straight or branched $(C_1-C_8)$ alkyl (e.g., methyl, ethyl, n-propyl, i-propyl, n-butyl, i-butyl, s-butyl, straight or branched pentyl, straight or branched hexyl, straight or branched heptyl, or straight or branched octyl) optionally substituted with one or more $R^8$. In one embodiment, one of $R^6$ and $R^{6'}$ is H, and the other is $(C_1-C_4)$ alkyl (e.g., methyl, ethyl, n-propyl, i-propyl, n-butyl, i-butyl, or s-butyl) optionally substituted with one or more $R^8$.

(9d) In one embodiment, one of $R^6$ and $R^{6'}$ is H, and the other is monocyclic or multicyclic spiro-, fused-, or bridged-$(C_3-C_{10})$ cycloalkyl optionally substituted with one or more $R^8$. In one embodiment, one of $R^6$ and $R^{6'}$ is H, and the other is monocyclic $(C_3-C_{10})$ cycloalkyl optionally substituted with one or more $R^8$. In one embodiment, one of $R^6$ and $R^{6'}$ is H, and the other is monocyclic $(C_3-C_8)$ cycloalkyl optionally substituted with one or more $R^8$. In one embodiment, one of $R^6$ and $R^{6'}$ is H, and the other is monocyclic $(C_3-C_6)$ cycloalkyl optionally substituted with one or more $R^8$. In one embodiment, one of $R^6$ and $R^{6'}$ is H, and the other is multicyclic spiro-$(C_5-C_{10})$ cycloalkyl optionally substituted with one or more $R^8$. In one embodiment, one of $R^6$ and $R^{6'}$ is H, and the other is multicyclic fused-$(C_5-C_{10})$ cycloalkyl optionally substituted with one or more $R^8$. In one embodiment, one of $R^6$ and $R^{6'}$ is H, and the other is multicyclic bridged-$(C_5-C_{10})$ cycloalkyl optionally substituted with one or more $R^8$. In one embodiment, one of $R^6$ and $R^{6'}$ is H, and the other is cyclopropyl, cyclobutyl, cyclopentyl, cyclohexyl, cycloheptyl, cyclooctyl, cyclononyl, cyclodecyl, bicyclo[1.1.1]pentanyl, bicyclo[2.2.1]heptyl, spiro[3.3]heptanyl, bicyclo[2.2.2]octyl, or adamantyl, each of which is optionally substituted with one or more $R^8$.

(9e) In one embodiment, $R^6$ and $R^{6'}$ are each independently straight or branched ($C_1$-$C_8$) alkyl (e.g., methyl, ethyl, n-propyl, i-propyl, n-butyl, i-butyl, s-butyl, straight or branched pentyl, straight or branched hexyl, straight or branched heptyl, or straight or branched octyl) or ($C_3$-$C_{10}$) cycloalkyl (e.g., cyclopropyl, cyclobutyl, cyclopentyl, cyclohexyl, cycloheptyl, cyclooctyl, cyclononyl, or cyclodecyl), wherein the alkyl or cycloalkyl is optionally substituted with one or more $R^8$.

(9f) In one embodiment, $R^6$ and $R^{6'}$, together with the nitrogen atom to which they are attached, form a 3- to 6-membered heterocyclic ring (e.g., [1,3]dioxolanyl, pyrrolidinyl, pyrazolidinyl, pyrazolinyl, imidazolinyl, imidazolidinyl, piperidinyl, piperazinyl, 2-pyridone, oxazolidinyl, isoxazolidinyl, morpholinyl, tetrahydropyranyl, thiazolidinyl, isothiazolidinyl, tetrahydrofuryl, dioxanyl, oxetanyl, azetidinyl, thietanyl, oxiranyl, aziridinyl, or thiiranyl) optionally substituted with one or more $R^8$.

(10a) In one embodiment, each $R^7$ is each H.

(10b) In one embodiment, at least one $R^7$ is straight or branched ($C_1$-$C_8$) alkyl (e.g., methyl, ethyl, n-propyl, i-propyl, n-butyl, i-butyl, s-butyl, straight or branched pentyl, straight or branched hexyl, straight or branched heptyl, or straight or branched octyl), or monocyclic or multicyclic spiro-, fused-, or bridged-($C_3$-$C_{10}$) cycloalkyl, wherein the alkyl or cycloalkyl is optionally substituted with one or more $R^X$.

(10c) In one embodiment, at least one $R^7$ is straight or branched ($C_1$-$C_8$) alkyl (e.g., methyl, ethyl, n-propyl, i-propyl, n-butyl, i-butyl, s-butyl, straight or branched pentyl, straight or branched hexyl, straight or branched heptyl, or straight or branched octyl) optionally substituted with one or more $R^8$. In one embodiment, at least one $R^7$ is ($C_1$-$C_4$) alkyl (e.g., methyl, ethyl, n-propyl, i-propyl, n-butyl, i-butyl, s-butyl, or t-butyl) optionally substituted with one or more $R^8$.

(10d) In one embodiment, at least one $R^7$ is monocyclic or multicyclic spiro-, fused-, or bridged-($C_3$-$C_{10}$) cycloalkyl optionally substituted with one or more $R^8$. In one embodiment, at least one $R^7$ is monocyclic ($C_3$-$C_{10}$) cycloalkyl optionally substituted with one or more $R^8$. In one embodiment, at least one $R^7$ is monocyclic ($C_3$-$C_8$) cycloalkyl optionally substituted with one or more $R^8$. In one embodiment, at least one $R^7$ is monocyclic ($C_3$-$C_6$) cycloalkyl optionally substituted with one or more $R^8$. In one embodiment, at least one $R^7$ is multicyclic spiro-($C_5$-$C_{10}$) cycloalkyl optionally substituted with one or more $R^8$. In one embodiment, at least one $R^7$ is multicyclic fused-($C_5$-$C_{10}$) cycloalkyl optionally substituted with one or more $R^8$. In one embodiment, at least one $R^7$ is multicyclic bridged-($C_5$-$C_{10}$) cycloalkyl optionally substituted with one or more $R^8$. In one embodiment, at least one $R^7$ is cyclopropyl, cyclobutyl, cyclopentyl, cyclohexyl, cycloheptyl, cyclooctyl, cyclononyl, cyclodecyl, bicyclo[1.1.1]pentanyl, bicyclo[2.2.1]heptyl, spiro[3.3]heptanyl, bicyclo[2.2.2]octyl, or adamantyl, each of which is optionally substituted with one or more $R^8$.

(11a) In one embodiment, y is 0, 1, or 2.

(11b) In one embodiment, y is 1, 2, 3, or 4.

(11c) In one embodiment, y is 0.

(11d) In one embodiment, y is 1.

(11e) In one embodiment, y is 2.

(11f) In one embodiment, y is 3.

(11g) In one embodiment, y is 4.

(12a) In one embodiment, each $R^8$ is independently halogen (e.g., F, Cl, Br, or I), $NO_2$, $NH_2$, CN, NH(($C_1$-$C_4$) alkyl) (wherein the alkyl moiety is methyl, ethyl, n-propyl, i-propyl, n-butyl, i-butyl, s-butyl, or t-butyl), N(($C_1$-$C_4$) alkyl)$_2$ (wherein the alkyl moiety is methyl, ethyl, n-propyl, i-propyl, n-butyl, i-butyl, s-butyl, or t-butyl), OH, oxo, ($C_1$-$C_4$) alkyl (e.g., methyl, ethyl, n-propyl, i-propyl, n-butyl, i-butyl, s-butyl, or t-butyl), or ($C_1$-$C_4$) alkoxy (e.g., methoxy, ethoxy, n-propoxy, i-propoxy, n-butoxy, i-butoxy, s-butoxy, or t-butoxy).

(12b) In one embodiment, at least one $R^8$ is halogen (e.g., F, Cl, Br, or I), $NO_2$, $NH_2$, or CN.

(12c) In one embodiment, at least one $R^8$ is $NH_2$, CN, NH(($C_1$-$C_4$) alkyl) (wherein the alkyl moiety is methyl, ethyl, n-propyl, i-propyl, n-butyl, i-butyl, s-butyl, or t-butyl), or N(($C_1$-$C_4$) alkyl)$_2$ (wherein the alkyl moiety is methyl, ethyl, n-propyl, i-propyl, n-butyl, i-butyl, s-butyl, or t-butyl).

(12d) In one embodiment, at least one $R^8$ is OH, oxo, or ($C_1$-$C_4$) alkoxy (e.g., methoxy, ethoxy, n-propoxy, i-propoxy, n-butoxy, i-butoxy, s-butoxy, or t-butoxy).

(12e) In one embodiment, at least one $R^8$ is ($C_1$-$C_4$) alkyl (e.g., methyl, ethyl, n-propyl, i-propyl, n-butyl, i-butyl, s-butyl, or t-butyl), or ($C_1$-$C_4$) alkoxy (e.g., methoxy, ethoxy, n-propoxy, i-propoxy, n-butoxy, i-butoxy, s-butoxy, or t-butoxy).

(13a) In one embodiment, $R^O$ is H.

(13b) In one embodiment, $R^O$ is ($C_1$-$C_4$) alkyl (e.g., methyl, ethyl, n-propyl, i-propyl, n-butyl, i-butyl, s-butyl, or t-butyl).

In some embodiments, any group defined herein for any one of $X^1$, $X^2$, $X^3$, L, $R^O$, $R^X$, $R^1$, $R^2$, $R^3$, $R^4$, $R^{4'}$, $R^{4''}$, $R^5$, $R^6$, $R^{6'}$, $R^7$, $R^8$, and y can be combined with any group defined herein for one or more of the remainder of $X^1$, $X^2$, $X^3$, L, $R^O$, $R^X$, $R^1$, $R^2$, $R^3$, $R^4$, $R^{4'}$, $R^{4''}$, $R^5$, $R^6$, $R^{6'}$, $R^7$, $R^8$, and y.

(A1) In one embodiment, $X^1$, $X^2$, and $X^3$ are as defined in (1a), and L is as defined in (3a).

(A2) In one embodiment, $X^1$, $X^2$, and $X^3$ are as defined in (1b), and L is as defined in (3a).

(A3) In one embodiment, $X^1$, $X^2$, and $X^3$ are as defined in (1a), and L is as defined in (3b).

(A4) In one embodiment, $X^1$, $X^2$, and $X^3$ are as defined in (1b), and L is as defined in (3b).

(A5) In one embodiment, $X^1$, $X^2$, and $X^3$ are as defined in (1a), and L is as defined in (3c).

(A6) In one embodiment, $X^1$, $X^2$, and $X^3$ are as defined in (1b), and L is as defined in (3c).

(A7) In one embodiment, $X^1$, $X^2$, and $X^3$ are as defined in (1a), and L is as defined in (3d).

(A8) In one embodiment, $X^1$, $X^2$, and $X^3$ are as defined in (1b), and L is as defined in (3d).

(A9) In one embodiment, $X^1$, $X^2$, and $X^3$ are as defined in (1a), and L is as defined in (3e).

(A10) In one embodiment, $X^1$, $X^2$, and $X^3$ are as defined in (1b), and L is as defined in (3e).

(A11) In one embodiment, $X^1$, $X^2$, and $X^3$ are as defined in (1a), and L is as defined in (3f).

(A12) In one embodiment, $X^1$, $X^2$, and $X^3$ are as defined in (1b), and L is as defined in (3f).

(A13) In one embodiment, $X^1$, $X^2$, and $X^3$ are as defined in (1a), and L is as defined in (3g).
(A14) In one embodiment, $X^1$, $X^2$, and $X^3$ are as defined in (1b), and L is as defined in (3g).
(B1) In one embodiment, $X^1$, $X^2$, $X^3$, and L are as defined in any one of (A1)-(A14), and $R^1$ is as defined in (4a).
(B2) In one embodiment, $X^1$, $X^2$, $X^3$, and L are as defined in any one of (A1)-(A14), and $R^1$ is as defined in (4b).
(B3) In one embodiment, $X^1$, $X^2$, $X^3$, and L are as defined in any one of (A1)-(A14), and $R^1$ is as defined in (4c).
(B4) In one embodiment, $X^1$, $X^2$, $X^3$, and L are as defined in any one of (A1)-(A14), and $R^1$ is as defined in (4d).
(B5) In one embodiment, $X^1$, $X^2$, $X^3$, and L are as defined in any one of (A1)-(A14), and $R^1$ is as defined in (4e).
(B6) In one embodiment, $X^1$, $X^2$, $X^3$, and L are as defined in any one of (A1)-(A14), and $R^1$ is as defined in (4f).
(B7) In one embodiment, $X^1$, $X^2$, $X^3$, and L are as defined in any one of (A1)-(A14), and $R^1$ is as defined in (4g).
(B8) In one embodiment, $X^1$, $X^2$, $X^3$, and L are as defined in any one of (A1)-(A14), and $R^1$ is as defined in (4h).
(C1) In one embodiment, $R^1$ is as defined in (4a), and L is as defined in (3a).
(C2) In one embodiment, $R^1$ is as defined in (4b), and L is as defined in (3a).
(C3) In one embodiment, $R^1$ is as defined in (4c), and L is as defined in (3a).
(C4) In one embodiment, $R^1$ is as defined in (4d), and L is as defined in (3a).
(C5) In one embodiment, $R^1$ is as defined in (4e), and L is as defined in (3a).
(C6) In one embodiment, $R^1$ is as defined in (4f), and L is as defined in (3a).
(C7) In one embodiment, $R^1$ is as defined in (4g), and L is as defined in (3a).
(C8) In one embodiment, $R^1$ is as defined in (4h), and L is as defined in (3a).
(C9) In one embodiment, $R^1$ is as defined in (4a), and L is as defined in (3b).
(C10) In one embodiment, $R^1$ is as defined in (4b), and L is as defined in (3b).
(C11) In one embodiment, $R^1$ is as defined in (4c), and L is as defined in (3b).
(C12) In one embodiment, $R^1$ is as defined in (4d), and L is as defined in (3b).
(C13) In one embodiment, $R^1$ is as defined in (4e), and L is as defined in (3b).
(C14) In one embodiment, $R^1$ is as defined in (4f), and L is as defined in (3b).
(C15) In one embodiment, $R^1$ is as defined in (4g), and L is as defined in (3b).
(C16) In one embodiment, $R^1$ is as defined in (4h), and L is as defined in (3b).
(C17) In one embodiment, $R^1$ is as defined in (4a), and L is as defined in (3c).
(C18) In one embodiment, $R^1$ is as defined in (4b), and L is as defined in (3c).
(C19) In one embodiment, $R^1$ is as defined in (4c), and L is as defined in (3c).
(C20) In one embodiment, $R^1$ is as defined in (4d), and L is as defined in (3c).
(C21) In one embodiment, $R^1$ is as defined in (4e), and L is as defined in (3c).
(C22) In one embodiment, $R^1$ is as defined in (4f), and L is as defined in (3c).
(C23) In one embodiment, $R^1$ is as defined in (4g), and L is as defined in (3c).
(C24) In one embodiment, $R^1$ is as defined in (4h), and L is as defined in (3c).
(C25) In one embodiment, $R^1$ is as defined in (4a), and L is as defined in (3d).
(C26) In one embodiment, $R^1$ is as defined in (4b), and L is as defined in (3d).
(C27) In one embodiment, $R^1$ is as defined in (4c), and L is as defined in (3d).
(C28) In one embodiment, $R^1$ is as defined in (4d), and L is as defined in (3d).
(C29) In one embodiment, $R^1$ is as defined in (4e), and L is as defined in (3d).
(C30) In one embodiment, $R^1$ is as defined in (4f), and L is as defined in (3d).
(C31) In one embodiment, $R^1$ is as defined in (4g), and L is as defined in (3d).
(C32) In one embodiment, $R^1$ is as defined in (4h), and L is as defined in (3d).
(C33) In one embodiment, $R^1$ is as defined in (4a), and L is as defined in (3e).
(C34) In one embodiment, $R^1$ is as defined in (4b), and L is as defined in (3e).
(C35) In one embodiment, $R^1$ is as defined in (4c), and L is as defined in (3e).
(C36) In one embodiment, $R^1$ is as defined in (4d), and L is as defined in (3e).
(C37) In one embodiment, $R^1$ is as defined in (4e), and L is as defined in (3e).
(C38) In one embodiment, $R^1$ is as defined in (4f), and L is as defined in (3e).
(C39) In one embodiment, $R^1$ is as defined in (4g), and L is as defined in (3e).
(C40) In one embodiment, $R^1$ is as defined in (4h), and L is as defined in (3e).
(D1) In one embodiment, $R^1$ is as defined in (4a), and $R^4$ is as defined in (6a).
(D2) In one embodiment, $R^1$ is as defined in (4b), and $R^4$ is as defined in (6a).
(D3) In one embodiment, $R^1$ is as defined in (4c), and $R^4$ is as defined in (6a).
(D4) In one embodiment, $R^1$ is as defined in (4d), and $R^4$ is as defined in (6a).
(D5) In one embodiment, $R^1$ is as defined in (4e), and $R^4$ is as defined in (6a).
(D6) In one embodiment, $R^1$ is as defined in (4f), and $R^4$ is as defined in (6a).
(D7) In one embodiment, $R^1$ is as defined in (4g), and $R^4$ is as defined in (6a).
(D8) In one embodiment, $R^1$ is as defined in (4h), and $R^4$ is as defined in (6a).
(D97) In one embodiment, $R^1$ is as defined in (4a), and $R^4$ is as defined in (6b).
(D10) In one embodiment, $R^1$ is as defined in (4b), and $R^4$ is as defined in (6b).
(D11) In one embodiment, $R^1$ is as defined in (4c), and $R^4$ is as defined in (6b).
(D12) In one embodiment, $R^1$ is as defined in (4d), and $R^4$ is as defined in (6b).
(D13) In one embodiment, $R^1$ is as defined in (4e), and $R^4$ is as defined in (6b).
(D14) In one embodiment, $R^1$ is as defined in (4f), and $R^4$ is as defined in (6b).
(D15) In one embodiment, $R^1$ is as defined in (4g), and $R^4$ is as defined in (6b).
(D16) In one embodiment, $R^1$ is as defined in (4h), and $R^4$ is as defined in (6b).

(D17) In one embodiment, $R^1$ is as defined in (4a), and $R^4$ is as defined in (6c).
(D18) In one embodiment, $R^1$ is as defined in (4b), and $R^4$ is as defined in (6c).
(D19) In one embodiment, $R^1$ is as defined in (4c), and $R^4$ is as defined in (6c).
(D20) In one embodiment, $R^1$ is as defined in (4d), and $R^4$ is as defined in (6c).
(D21) In one embodiment, $R^1$ is as defined in (4e), and $R^4$ is as defined in (6c).
(D22) In one embodiment, $R^1$ is as defined in (4f), and $R^4$ is as defined in (6c).
(D23) In one embodiment, $R^1$ is as defined in (4g), and $R^4$ is as defined in (6c).
(D24) In one embodiment, $R^1$ is as defined in (4h), and $R^4$ is as defined in (6c).
(D25) In one embodiment, $R^1$ is as defined in (4a), and $R^4$ is as defined in (6d).
(D26) In one embodiment, $R^1$ is as defined in (4b), and $R^4$ is as defined in (6d).
(D27) In one embodiment, $R^1$ is as defined in (4c), and $R^4$ is as defined in (6d).
(D28) In one embodiment, $R^1$ is as defined in (4d), and $R^4$ is as defined in (6d).
(D29) In one embodiment, $R^1$ is as defined in (4e), and $R^4$ is as defined in (6d).
(D30) In one embodiment, $R^1$ is as defined in (4f), and $R^4$ is as defined in (6d).
(D31) In one embodiment, $R^1$ is as defined in (4g), and $R^4$ is as defined in (6d).
(D32) In one embodiment, $R^1$ is as defined in (4h), and $R^4$ is as defined in (6d).
(D33) In one embodiment, $R^1$ is as defined in (4a), and $R^4$ is as defined in (6e).
(D34) In one embodiment, $R^1$ is as defined in (4b), and $R^4$ is as defined in (6e).
(D35) In one embodiment, $R^1$ is as defined in (4c), and $R^4$ is as defined in (6e).
(D36) In one embodiment, $R^1$ is as defined in (4d), and $R^4$ is as defined in (6e).
(D37) In one embodiment, $R^1$ is as defined in (4e), and $R^4$ is as defined in (6e).
(D38) In one embodiment, $R^1$ is as defined in (4f), and $R^4$ is as defined in (6e).
(D39) In one embodiment, $R^1$ is as defined in (4g), and $R^4$ is as defined in (6e).
(D40) In one embodiment, $R^1$ is as defined in (4h), and $R^4$ is as defined in (6e).
(D41) In one embodiment, $R^1$ is as defined in (4a), and $R^4$ is as defined in (6f).
(D42) In one embodiment, $R^1$ is as defined in (4b), and $R^4$ is as defined in (6f).
(D43) In one embodiment, $R^1$ is as defined in (4c), and $R^4$ is as defined in (6f).
(D44) In one embodiment, $R^1$ is as defined in (4d), and $R^4$ is as defined in (6f).
(D45) In one embodiment, $R^1$ is as defined in (4e), and $R^4$ is as defined in (6f).
(D46) In one embodiment, $R^1$ is as defined in (4f), and $R^4$ is as defined in (6f).
(D47) In one embodiment, $R^1$ is as defined in (4g), and $R^4$ is as defined in (6f).
(D48) In one embodiment, $R^1$ is as defined in (4h), and $R^4$ is as defined in (6f).
(E1) In one embodiment, $R^4$ is as defined in (6a), and L is as defined in (3a).
(E2) In one embodiment, $R^4$ is as defined in (6a), and L is as defined in (3b).
(E3) In one embodiment, $R^4$ is as defined in (6a), and L is as defined in (3c).
(E4) In one embodiment, $R^4$ is as defined in (6a), and L is as defined in (3d).
(E5) In one embodiment, $R^4$ is as defined in (6a), and L is as defined in (3e).
(E6) In one embodiment, $R^4$ is as defined in (6a), and L is as defined in (3f).
(E7) In one embodiment, $R^4$ is as defined in (6a), and L is as defined in (3g).
(E8) In one embodiment, $R^4$ is as defined in (6b), and L is as defined in (3a).
(E9) In one embodiment, $R^4$ is as defined in (6b), and L is as defined in (3b).
(E10) In one embodiment, $R^4$ is as defined in (6b), and L is as defined in (3c).
(E11) In one embodiment, $R^4$ is as defined in (6b), and L is as defined in (3d).
(E12) In one embodiment, $R^4$ is as defined in (6b), and L is as defined in (3e).
(E13) In one embodiment, $R^4$ is as defined in (6b), and L is as defined in (3f).
(E14) In one embodiment, $R^4$ is as defined in (6b), and L is as defined in (3g).
(E15) In one embodiment, $R^4$ is as defined in (6c), and L is as defined in (3a).
(E16) In one embodiment, $R^4$ is as defined in (6c), and L is as defined in (3b).
(E17) In one embodiment, $R^4$ is as defined in (6c), and L is as defined in (3c).
(E18) In one embodiment, $R^4$ is as defined in (6c), and L is as defined in (3d).
(E19) In one embodiment, $R^4$ is as defined in (6c), and L is as defined in (3e).
(E20) In one embodiment, $R^4$ is as defined in (6c), and L is as defined in (3f).
(E21) In one embodiment, $R^4$ is as defined in (6c), and L is as defined in (3g).
(E22) In one embodiment, $R^4$ is as defined in (6d), and L is as defined in (3a).
(E23) In one embodiment, $R^4$ is as defined in (6d), and L is as defined in (3b).
(E24) In one embodiment, $R^4$ is as defined in (6d), and L is as defined in (3c).
(E25) In one embodiment, $R^4$ is as defined in (6d), and L is as defined in (3d).
(E26) In one embodiment, $R^4$ is as defined in (6d), and L is as defined in (3e).
(E27) In one embodiment, $R^4$ is as defined in (6d), and L is as defined in (3f).
(E28) In one embodiment, $R^4$ is as defined in (6d), and L is as defined in (3g).
(E29) In one embodiment, $R^4$ is as defined in (6e), and L is as defined in (3a).
(E30) In one embodiment, $R^4$ is as defined in (6e), and L is as defined in (3b).
(E31) In one embodiment, $R^4$ is as defined in (6e), and L is as defined in (3c).
(E32) In one embodiment, $R^4$ is as defined in (6e), and L is as defined in (3d).
(E33) In one embodiment, $R^4$ is as defined in (6e), and L is as defined in (3e).
(E34) In one embodiment, $R^4$ is as defined in (6e), and L is as defined in (3f).

(E35) In one embodiment, $R^4$ is as defined in (6e), and L is as defined in (3g).
(E36) In one embodiment, $R^4$ is as defined in (6f), and L is as defined in (3a).
(E37) In one embodiment, $R^4$ is as defined in (6f), and L is as defined in (3b).
(E38) In one embodiment, $R^4$ is as defined in (6f), and L is as defined in (3c).
(E39) In one embodiment, $R^4$ is as defined in (6f), and L is as defined in (3d).
(E40) In one embodiment, $R^4$ is as defined in (6f), and L is as defined in (3e).
(E41) In one embodiment, $R^4$ is as defined in (6f), and L is as defined in (3f).
(E42) In one embodiment, $R^4$ is as defined in (6f), and L is as defined in (3g).
(F1) In one embodiment, $R^1$ and L are as defined in any one of (C1)-(C40), and $R^4$ is as defined in (6a).
(F2) In one embodiment, $R^1$ and L are as defined in any one of (C1)-(C40), and $R^4$ is as defined in (6b).
(F3) In one embodiment, $R^1$ and L are as defined in any one of (C1)-(C40), and $R^4$ is as defined in (6c).
(F4) In one embodiment, $R^1$ and L are as defined in any one of (C1)-(C40), and $R^4$ is as defined in (6d).
(F5) In one embodiment, $R^1$ and L are as defined in any one of (C1)-(C40), and $R^4$ is as defined in (6e).
(F6) In one embodiment, $R^1$ and L are as defined in any one of (C1)-(C40), and $R^4$ is as defined in (6f).
(G1) In one embodiment, $R^4$ and L are as defined in any one of (E1)-(E42), and $X^1$, $X^2$, and $X^3$ are as defined in (1a).
(G2) In one embodiment, $R^4$ and L are as defined in any one of (E1)-(E42), and $X^1$, $X^2$, and $X^3$ are as defined in (1b).
(H1) In one embodiment, $X^1$, $X^2$, $X^3$, L, $R^1$, and $R^4$ are as defined, where applicable, in any one of (A1)-(G2), and $R^2$ and $R^3$ are as defined in (5a).
(H2) In one embodiment, $X^1$, $X^2$, $X^3$, L, $R^1$, and $R^4$ are as defined, where applicable, in any one of (A1)-(G2), and $R^2$ and $R^3$ are as defined in (5b).
(H3) In one embodiment, $X^1$, $X^2$, $X^3$, L, $R^1$, and $R^4$ are as defined, where applicable, in any one of (A1)-(G2), and $R^2$ and $R^3$ are as defined in (5c).
(H4) In one embodiment, $X^1$, $X^2$, $X^3$, L, $R^1$, and $R^4$ are as defined, where applicable, in any one of (A1)-(G2), and $R^2$ and $R^3$ are as defined in (5d).
(H5) In one embodiment, $X^1$, $X^2$, $X^3$, L, $R^1$, and $R^4$ are as defined, where applicable, in any one of (A1)-(G2), and $R^2$ and $R^3$ are as defined in (5e).
(H6) In one embodiment, $X^1$, $X^2$, $X^3$, L, $R^1$, and $R^4$ are as defined, where applicable, in any one of (A1)-(G2), and $R^2$ and $R^3$ are as defined in (5f).
(H7) In one embodiment, $X^1$, $X^2$, $X^3$, L, $R^1$, and $R^4$ are as defined, where applicable, in any one of (A1)-(G2), and $R^2$ and $R^3$ are as defined in (5g).
(H8) In one embodiment, $X^1$, $X^2$, $X^3$, L, $R^1$, and $R^4$ are as defined, where applicable, in any one of (A1)-(G2), and $R^2$ and $R^3$ are as defined in (5h).
(H9) In one embodiment, $X^1$, $X^2$, $X^3$, L, $R^1$, and $R^4$ are as defined, where applicable, in any one of (A1)-(G2), and $R^2$ and $R^3$ are as defined in (5i).
(I1) In one embodiment, $X^1$, $X^2$, $X^3$, L, $R^1$, $R^2$, $R^3$, and $R^4$ are as defined, where applicable, in any one of (A1)-(H9), and $R^{4'}$ and $R^{4''}$ are as defined in (7a).
(I2) In one embodiment, $X^1$, $X^2$, $X^3$, L, $R^1$, $R^2$, $R^3$, and $R^4$ are as defined, where applicable, in any one of (A1)-(H9), and $R^{4'}$ and $R^{4''}$ are as defined in (7b).
(I3) In one embodiment, $X^1$, $X^2$, $X^3$, L, $R^1$, $R^2$, $R^3$, and $R^4$ are as defined, where applicable, in any one of (A1)-(H9), and $R^{4'}$ and $R^{4''}$ are as defined in (7c).
(I4) In one embodiment, $X^1$, $X^2$, $X^3$, L, $R^1$, $R^2$, $R^3$, and $R^4$ are as defined, where applicable, in any one of (A1)-(H9), and $R^{4'}$ and $R^{4''}$ are as defined in (7d).
(I5) In one embodiment, $X^1$, $X^2$, $X^3$, L, $R^1$, $R^2$, $R^3$, and $R^4$ are as defined, where applicable, in any one of (A1)-(H9), and $R^{4'}$ and $R^{4''}$ are as defined in (7e).
(I6) In one embodiment, $X^1$, $X^2$, $X^3$, L, $R^1$, $R^2$, $R^3$, and $R^4$ are as defined, where applicable, in any one of (A1)-(H9), and $R^{4'}$ and $R^{4''}$ are as defined in (7f).
(I7) In one embodiment, $X^1$, $X^2$, $X^3$, L, $R^1$, $R^2$, $R^3$, and $R^4$ are as defined, where applicable, in any one of (A1)-(H9), and $R^{4'}$ and $R^{4''}$ are as defined in (7g).
(I8) In one embodiment, $X^1$, $X^2$, $X^3$, L, $R^1$, $R^2$, $R^3$, and $R^4$ are as defined, where applicable, in any one of (A1)-(H9), and $R^{4'}$ and $R^{4''}$ are as defined in (7h).
(J1) In one embodiment, $X^1$, $X^2$, $X^3$, L, $R^1$, $R^2$, $R^3$, $R^4$, $R^{4'}$, and $R^{4''}$ are as defined, where applicable, in any one of (A1)-(I8), and $R^5$ is as defined in (8a).
(J2) In one embodiment, $X^1$, $X^2$, $X^3$, L, $R^1$, $R^2$, $R^3$, $R^4$, $R^{4'}$, and $R^{4''}$ are as defined, where applicable, in any one of (A1)-(I8), and $R^5$ is as defined in (8b).
(J3) In one embodiment, $X^1$, $X^2$, $X^3$, L, $R^1$, $R^2$, $R^3$, $R^4$, $R^{4'}$, and $R^{4''}$ are as defined, where applicable, in any one of (A1)-(I8), and $R^5$ is as defined in (8c).
(J4) In one embodiment, $X^1$, $X^2$, $X^3$, L, $R^1$, $R^2$, $R^3$, $R^4$, $R^{4'}$, and $R^{4''}$ are as defined, where applicable, in any one of (A1)-(I8), and $R^5$ is as defined in (8d).
(J5) In one embodiment, $X^1$, $X^2$, $X^3$, L, $R^1$, $R^2$, $R^3$, $R^4$, $R^{4'}$, and $R^{4''}$ are as defined, where applicable, in any one of (A1)-(I8), and $R^5$ is as defined in (8e).
(K1) In one embodiment, $X^1$, $X^2$, $X^3$, L, $R^1$, $R^2$, $R^3$, $R^4$, $R^{4'}$, $R^{4''}$, and $R^5$ are as defined, where applicable, in any one of (A1)-(J5), and $R^6$ and $R^{6'}$ are as defined in (9a).
(K2) In one embodiment, $X^1$, $X^2$, $X^3$, L, $R^1$, $R^2$, $R^3$, $R^4$, $R^{4'}$, $R^{4''}$, and $R^5$ are as defined, where applicable, in any one of (A1)-(J5), and $R^6$ and $R^{6'}$ are as defined in (9b).
(K3) In one embodiment, $X^1$, $X^2$, $X^3$, L, $R^1$, $R^2$, $R^3$, $R^4$, $R^{4'}$, $R^{4''}$, and $R^5$ are as defined, where applicable, in any one of (A1)-(J5), and $R^6$ and $R^{6'}$ are as defined in (9c).
(K4) In one embodiment, $X^1$, $X^2$, $X^3$, L, $R^1$, $R^2$, $R^3$, $R^4$, $R^{4'}$, $R^{4''}$, and $R^5$ are as defined, where applicable, in any one of (A1)-(J5), and $R^6$ and $R^{6'}$ are as defined in (9d).
(K5) In one embodiment, $X^1$, $X^2$, $X^3$, L, $R^1$, $R^2$, $R^3$, $R^4$, $R^{4'}$, $R^{4''}$, and $R^5$ are as defined, where applicable, in any one of (A1)-(J5), and $R^6$ and $R^{6'}$ are as defined in (9e).
(K6) In one embodiment, $X^1$, $X^2$, $X^3$, L, $R^1$, $R^2$, $R^3$, $R^4$, $R^{4'}$, $R^{4''}$, and $R^5$ are as defined, where applicable, in any one of (A1)-(J5), and $R^6$ and $R^{6'}$ are as defined in (9f).
(L1) In one embodiment, $X^1$, $X^2$, $X^3$, L, $R^1$, $R^2$, $R^3$, $R^4$, $R^{4'}$, $R^{4''}$, $R^5$, $R^6$, and $R^{6'}$ are as defined, where applicable, in any one of (A1)-(K6), and $R^7$ is as defined in (10a).
(L2) In one embodiment, $X^1$, $X^2$, $X^3$, L, $R^1$, $R^2$, $R^3$, $R^4$, $R^{4'}$, $R^{4''}$, $R^5$, $R^6$, and $R^{6'}$ are as defined, where applicable, in any one of (A1)-(K6), and $R^7$ is as defined in (10b).
(L3) In one embodiment, $X^1$, $X^2$, $X^3$, L, $R^1$, $R^2$, $R^3$, $R^4$, $R^{4'}$, $R^{4''}$, $R^5$, $R^6$, and $R^{6'}$ are as defined, where applicable, in any one of (A1)-(K6), and $R^7$ is as defined in (10c).
(L4) In one embodiment, $X^1$, $X^2$, $X^3$, L, $R^1$, $R^2$, $R^3$, $R^4$, $R^{4'}$, $R^{4''}$, $R^5$, $R^6$, and $R^{6'}$ are as defined, where applicable, in any one of (A1)-(K6), and $R^7$ is as defined in (10d).

(M1) In one embodiment, $X^1$, $X^2$, $X^3$, L, $R^1$, $R^2$, $R^3$, $R^4$, $R^{4'}$, $R^{4''}$, $R^5$, $R^6$, $R^{6'}$, and $R^7$ are as defined, where applicable, in any one of (A1)-(L4), and $R^8$ is as defined in (12a).

(M2) In one embodiment, $X^1$, $X^2$, $X^3$, L, $R^1$, $R^2$, $R^3$, $R^4$, $R^{4'}$, $R^{4''}$, $R^5$, $R^6$, $R^{6'}$, and $R^7$ are as defined, where applicable, in any one of (A1)-(L4), and $R^8$ is as defined in (12b).

(M3) In one embodiment, $X^1$, $X^2$, $X^3$, L, $R^1$, $R^2$, $R^3$, $R^4$, $R^{4'}$, $R^{4''}$, $R^5$, $R^6$, $R^{6'}$, and $R^7$ are as defined, where applicable, in any one of (A1)-(L4), and $R^8$ is as defined in (12c).

(M4) In one embodiment, $X^1$, $X^2$, $X^3$, L, $R^1$, $R^2$, $R^3$, $R^4$, $R^{4'}$, $R^{4''}$, $R^5$, $R^6$, $R^{6'}$, and $R^7$ are as defined, where applicable, in any one of (A1)-(L4), and $R^8$ is as defined in (12d).

(M5) In one embodiment, $X^1$, $X^2$, $X^3$, L, $R^1$, $R^2$, $R^3$, $R^4$, $R^{4'}$, $R^{4''}$, $R^5$, $R^6$, $R^{6'}$, and $R^7$ are as defined, where applicable, in any one of (A1)-(L4), and $R^8$ is as defined in (12e).

(N1) In one embodiment, $X^1$, $X^2$, $X^3$, L, $R^1$, $R^2$, $R^3$, $R^4$, $R^{4'}$, $R^{4''}$, $R^5$, $R^6$, $R^{6'}$, $R^7$, and $R^8$ are as defined, where applicable, in any one of (A1)-(M5), and y is as defined in (11a).

(N2) In one embodiment, $X^1$, $X^2$, $X^3$, L, $R^1$, $R^2$, $R^3$, $R^4$, $R^{4'}$, $R^{4''}$, $R^5$, $R^6$, $R^{6'}$, $R^7$, and $R^1$ are as defined, where applicable, in any one of (A1)-(M5), and y is as defined in (11b).

(N3) In one embodiment, $X^1$, $X^2$, $X^3$, L, $R^1$, $R^2$, $R^3$, $R^4$, $R^{4'}$, $R^{4''}$, $R^5$, $R^6$, $R^{6'}$, $R^7$, and $R^8$ are as defined, where applicable, in any one of (A1)-(M5), and y is as defined in (11c).

(N4) In one embodiment, $X^1$, $X^2$, $X^3$, L, $R^1$, $R^2$, $R^3$, $R^4$, $R^{4'}$, $R^{4''}$, $R^5$, $R^6$, $R^{6'}$, $R^7$, and $R^8$ are as defined, where applicable, in any one of (A1)-(M5), and y is as defined in (11d).

(N5) In one embodiment, $X^1$, $X^2$, $X^3$, L, $R^1$, $R^2$, $R^3$, $R^4$, $R^{4'}$, $R^{4''}$, $R^5$, $R^6$, $R^{6'}$, $R^7$, and $R^8$ are as defined, where applicable, in any one of (A1)-(M5), and y is as defined in (11e).

(N6) In one embodiment, $X^1$, $X^2$, $X^3$, L, $R^1$, $R^2$, $R^3$, $R^4$, $R^{4'}$, $R^{4''}$, $R^5$, $R^6$, $R^{6'}$, $R^7$, and $R^1$ are as defined, where applicable, in any one of (A1)-(M5), and y is as defined in (11f).

(N7) In one embodiment, $X^1$, $X^2$, $X^3$, L, $R^1$, $R^2$, $R^3$, $R^4$, $R^{4'}$, $R^{4''}$, $R^5$, $R^6$, $R^{6'}$, $R^7$, and $R^8$ are as defined, where applicable, in any one of (A1)-(M5), and y is as defined in (1Ig).

In some embodiments, a compound of Formula (I') or (I) is of any one of Formula (I1'), (I1), (I2'), (I2), (I3'), (I3), (I4'), (I4), (I5'), (I5), (I6'), (I6), (I7'), (I7), (I8'), or (I8):

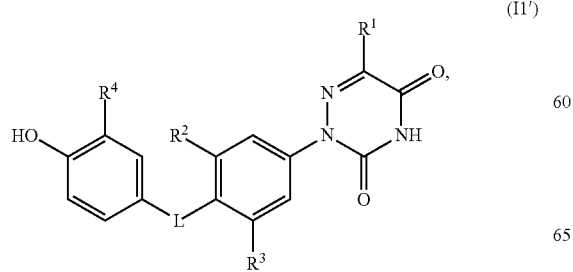
(I1')

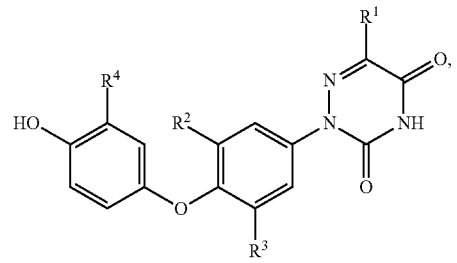
(I1)

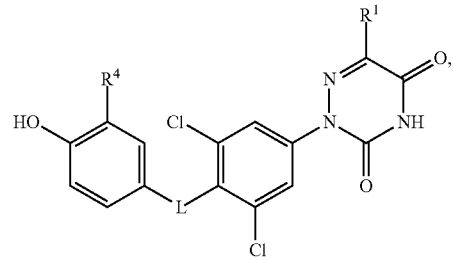
(I2')

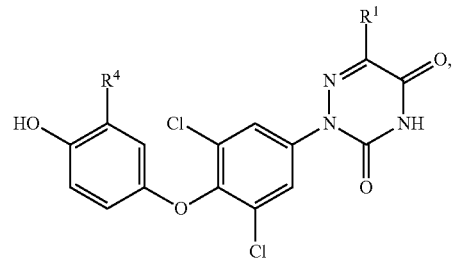
(I2)

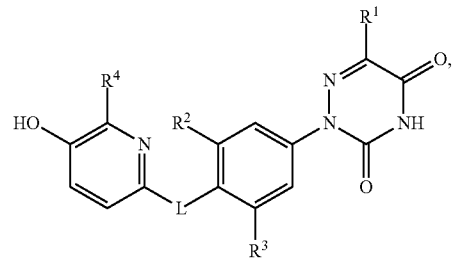
(I3')

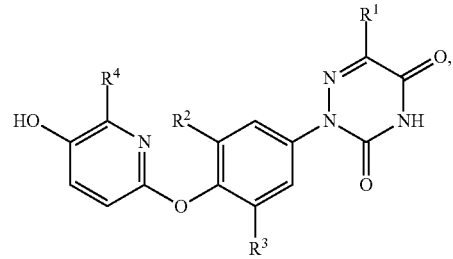
(I3)

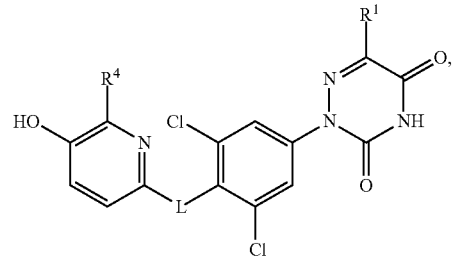
(I4')

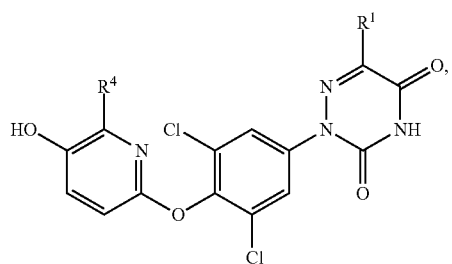
(I4)

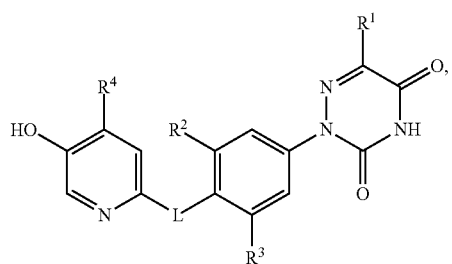
(I5')

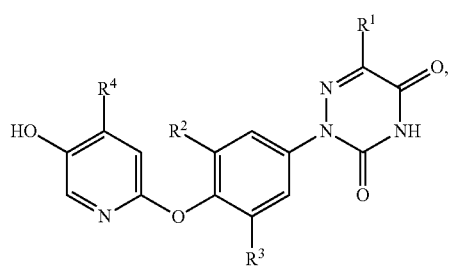
(I5)

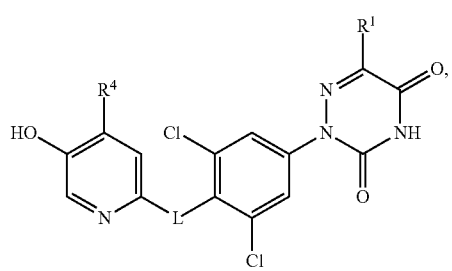
(I6')

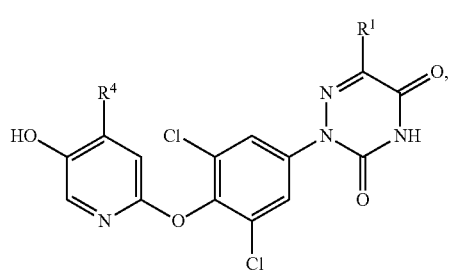
(I6)

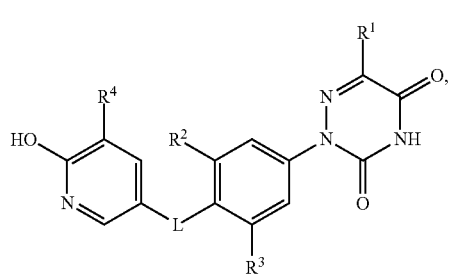
(I7')

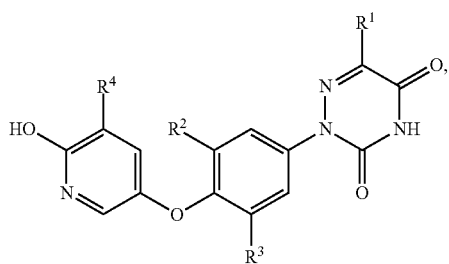
(I7)

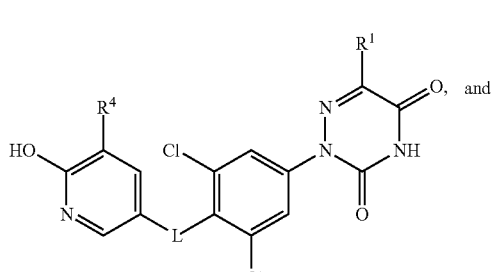
(I8')

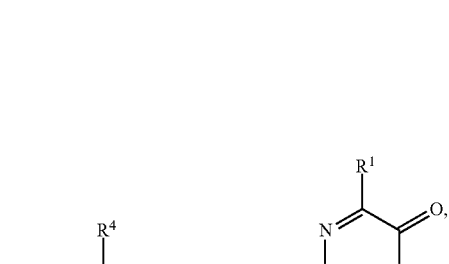
(I8)

or a pharmaceutically acceptable salt, solvate, prodrug, stereoisomer, or tautomer thereof, wherein L, $R^1$, $R^2$, $R^3$, $R^4$, $R^{4'}$, $R^{4''}$, $R^5$, $R^6$, $R^{6'}$, $R^7$, $R^8$, and y are each as defined herein, and any group defined herein for any one of L, $R^1$, $R^2$, $R^3$, $R^4$, $R^{4'}$, $R^{4''}$, $R^5$, $R^6$, $R^{6'}$, $R^7$, $R^8$, and y can be combined with any group defined herein for one or more of the remainder of L, $R^1$, $R^2$, $R^3$, $R^4$, $R^{4'}$, $R^{4''}$, $R^5$, $R^6$, $R^{6'}$, $R^7$, $R^8$, and y, for example, where applicable, as in (A1)-(N7).

In some embodiments, a compound of Formula (I') or (I) is of any one of Formula (I1a'), (I1a), (I2a'), (I2a), (I3a'), (I3a), (I4a'), (I4a), (I5a'), (I5a), (I6a'), (I6a), (I7a'), (I7a), (I8a'), or (I8a):

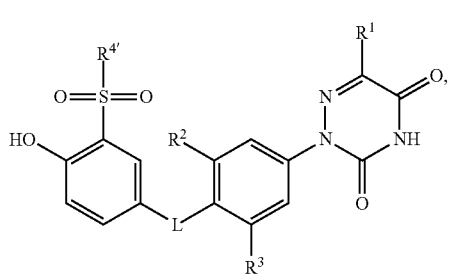
(I1a')

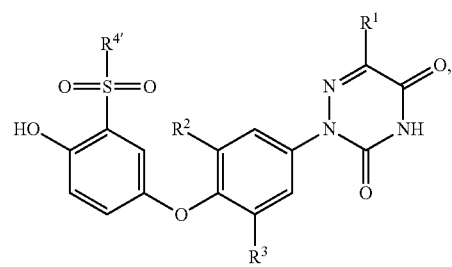
(I1a)
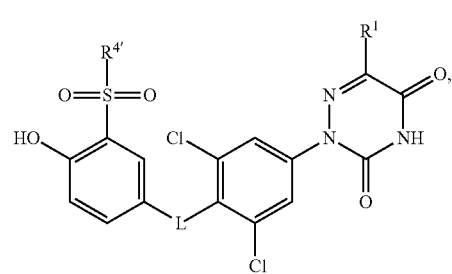
(I2a′)
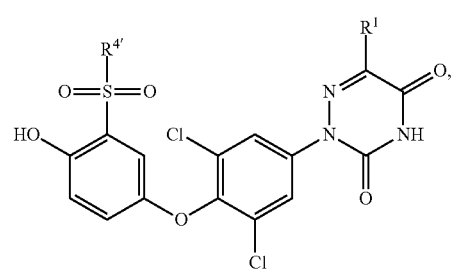
(I2a)
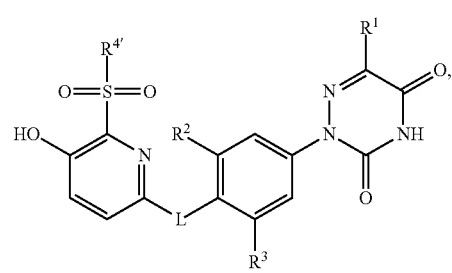
(I3a′)
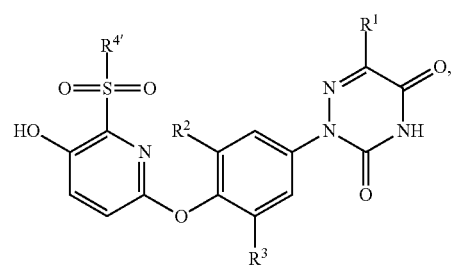
(I3a)
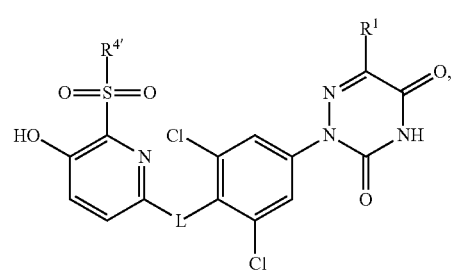
(I4a′)
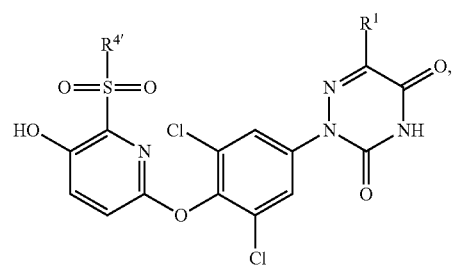
(I4a)
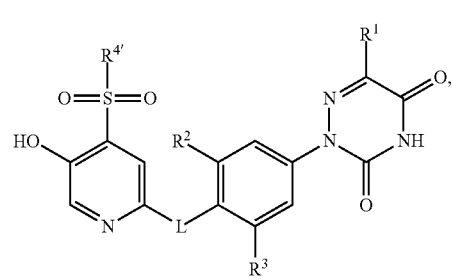
(I5a′)
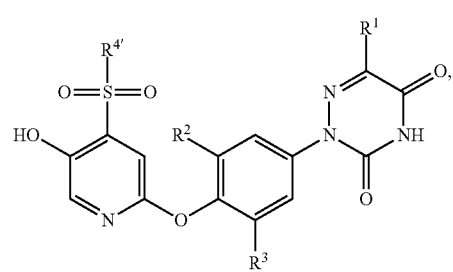
(I5a)
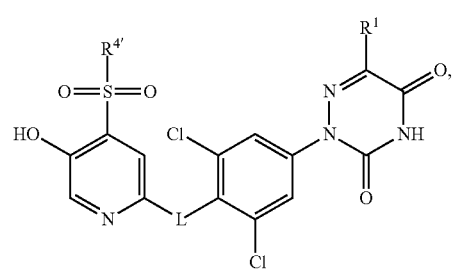
(I6a′)
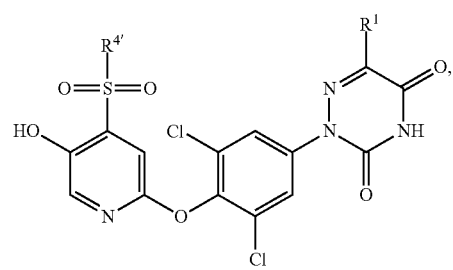
(I6a)
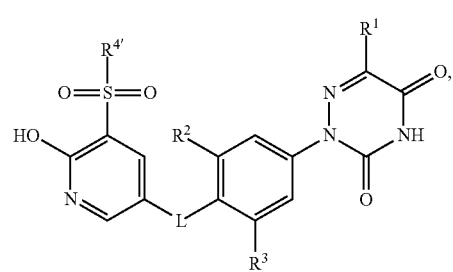
(I7a′)

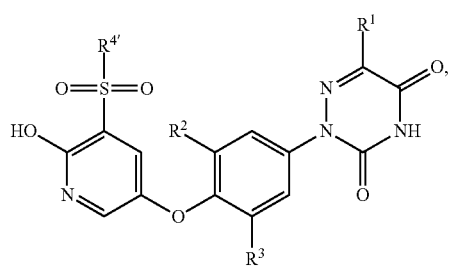
(I7a)

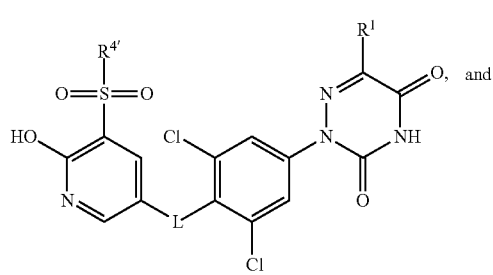
(I8a'), and

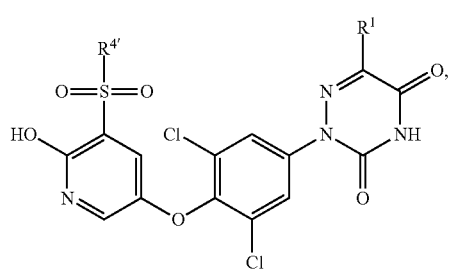
(I8a)

or a pharmaceutically acceptable salt, solvate, prodrug, stereoisomer, or tautomer thereof, wherein L, $R^1$, $R^2$, $R^3$, $R^{4'}$, $R^5$, $R^6$, $R^{6'}$, $R^7$, $R^8$, and y are each as defined herein, and any group defined herein for any one of L, $R^1$, $R^2$, $R^3$, $R^{4'}$, $R^5$, $R^6$, $R^{6'}$, $R^7$, $R^8$, and y can be combined with any group defined herein for one or more of the remainder of L, $R^1$, $R^2$, $R^3$, $R^{4'}$, $R^5$, $R^6$, $R^{6'}$, $R^7$, $R^8$, and y, for example, where applicable, as in (A1)-(N7).

In some embodiments, a compound of Formula (I') or (I) is of any one of Formula (I1b'), (I1b), (I2b'), (I2b), (I3b'), (I3b), (I4b'), (I4b), (I5b'), (I5b), (I6b'), (I6b), (I7b'), (I7b), (I8b'), or (I8b):

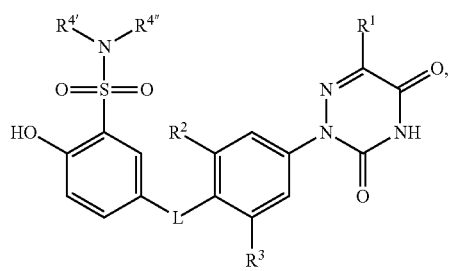
(I1b')

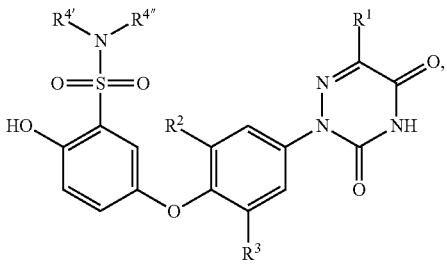
(I1b)

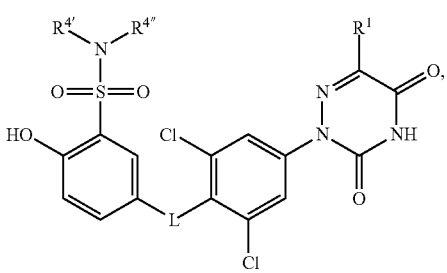
(I2b')

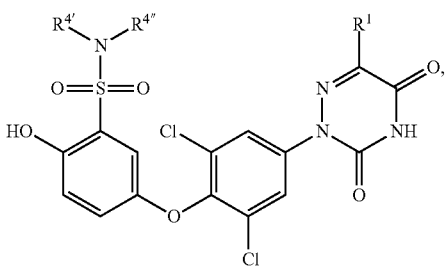
(I2b)

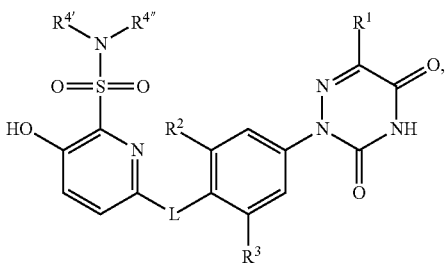
(I3b')

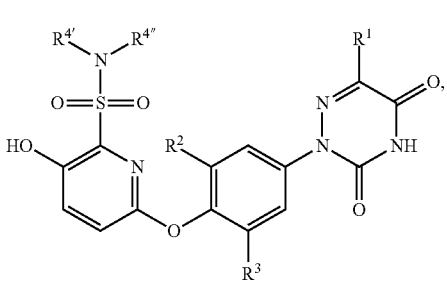
(I3b)

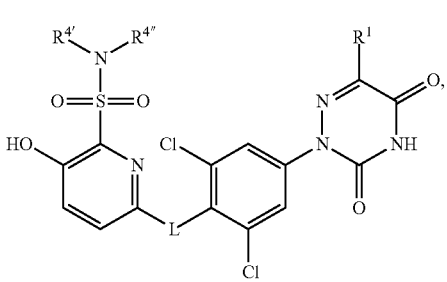
(I4b')

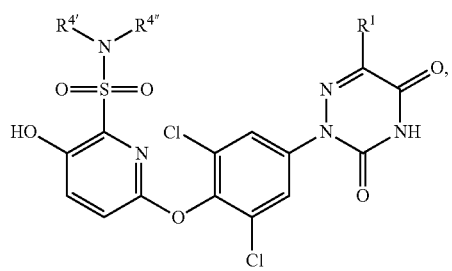
(I4b)

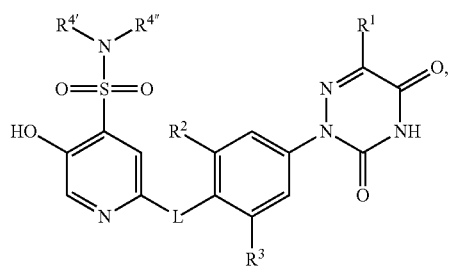
(I5b')

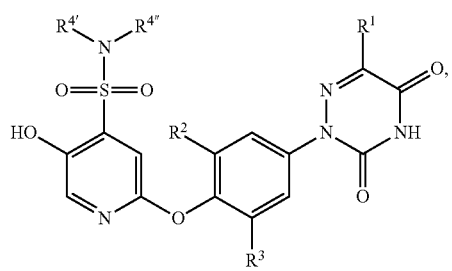
(I5b)

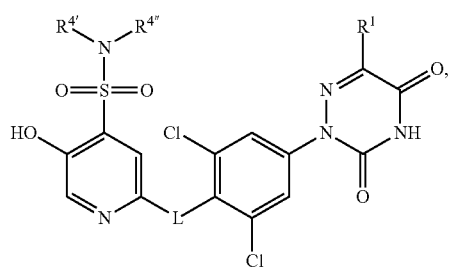
(I6b')

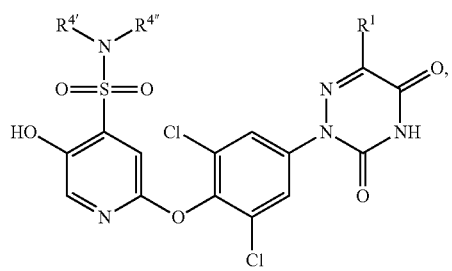
(I6b)

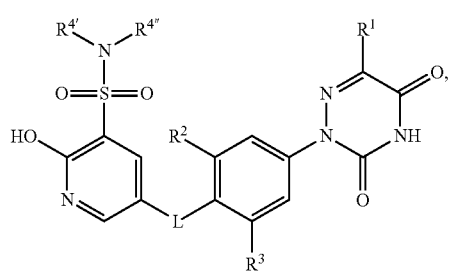
(I7b')

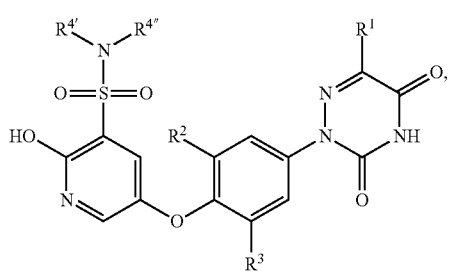
(I7b)

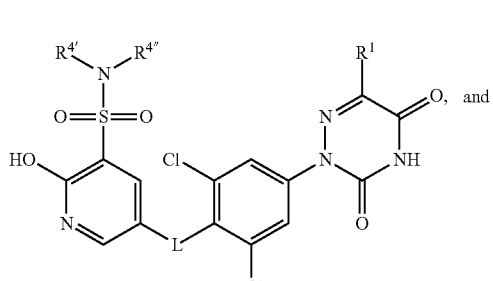
(I8b')

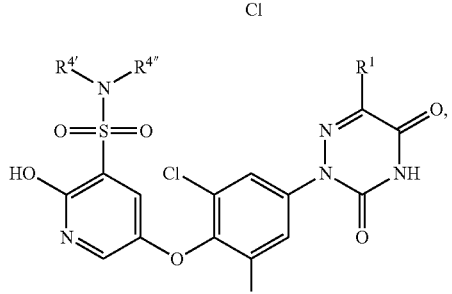
(I8b)

or a pharmaceutically acceptable salt, solvate, prodrug, stereoisomer, or tautomer thereof, wherein L, $R^1$, $R^2$, $R^3$, $R^{4'}$, $R^{4''}$, $R^5$, $R^6$, $R^{6'}$, $R^7$, $R^8$, and y are each as defined herein, and any group defined herein for any one of L, $R^1$, $R^2$, $R^3$, $R^{4'}$, $R^{4''}$, $R^5$, $R^6$, $R^{6'}$, $R^7$, $R^8$, and y can be combined with any group defined herein for one or more of the remainder of L, $R^1$, $R^2$, $R^3$, $R^{4'}$, $R^{4''}$, $R^5$, $R^6$, $R^{6'}$, $R^7$, $R^8$, and y, for example, where applicable, as in (A1)-(N7).

In some embodiments, a compound of Formula (I') or (I) is of any one of Formula (I1c'), (I1c), (I2c'), (I2c), (I3c'), (I3c), (I4c'), (I4c), (I5c'), (I5c), (I6c'), (I6c), (I7c'), (I7c), (I8c'), or (I8c):

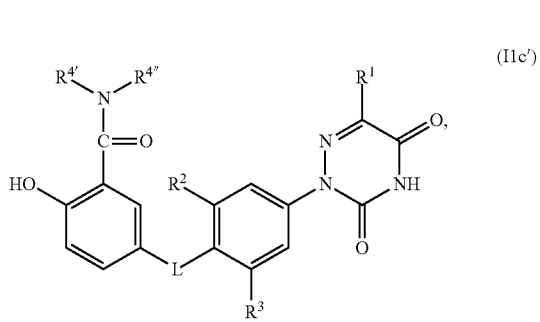
(I1c')

33
-continued
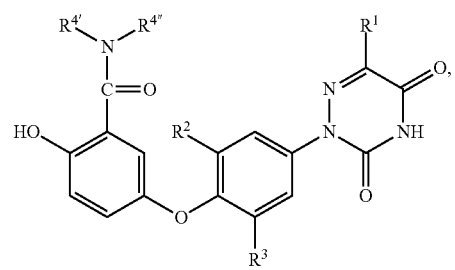
(I1c)
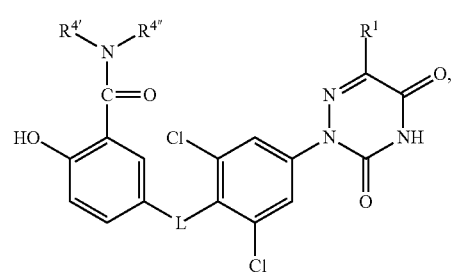
(I2c′)
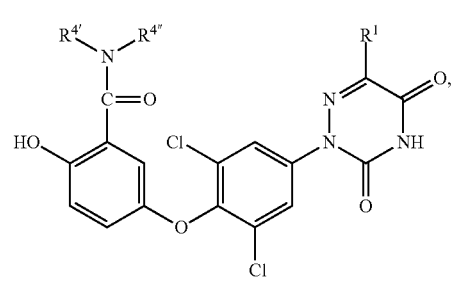
(I2c)
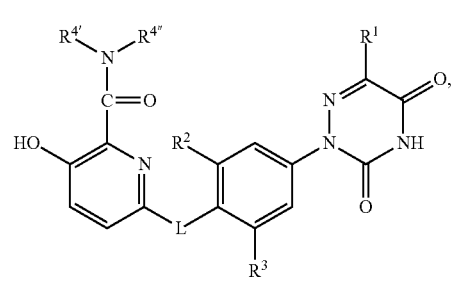
(I3c′)
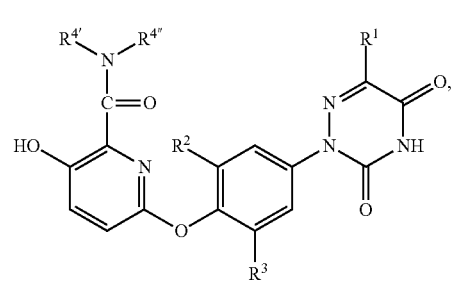
(I3c)
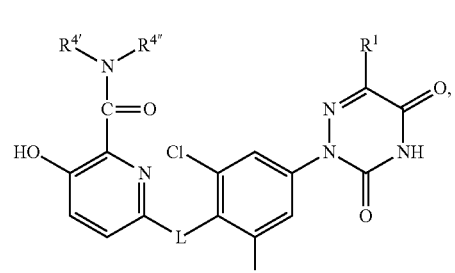
(I4c′)
34
-continued
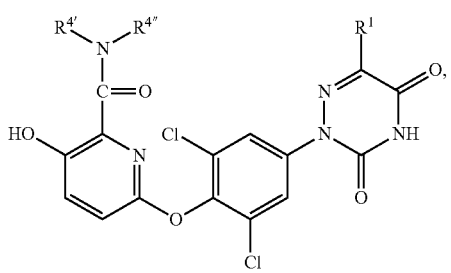
(I4c)
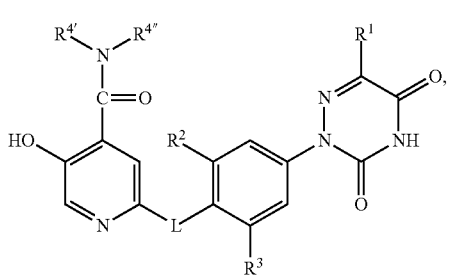
(I5c′)
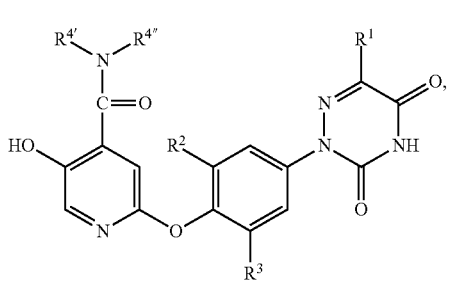
(I5c)
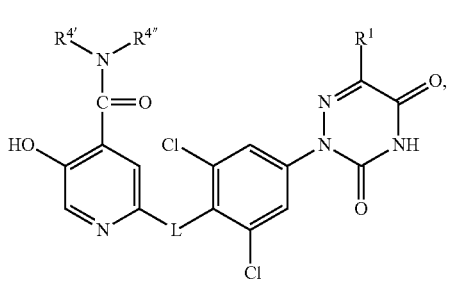
(I6c′)
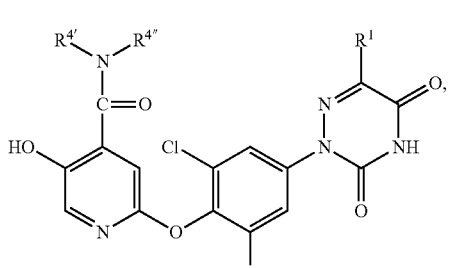
(I6c)
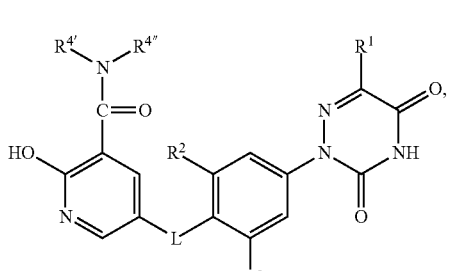
(I7c′)

-continued

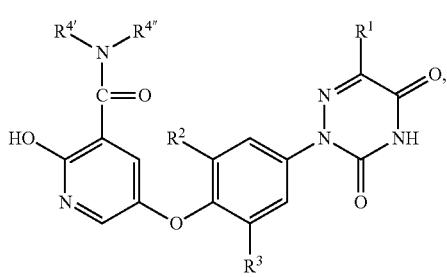

(I7c)

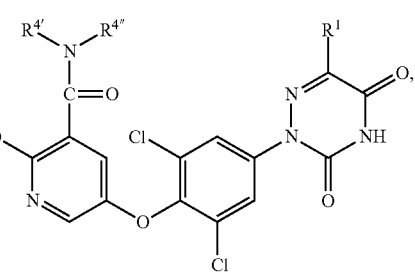

(I8c)

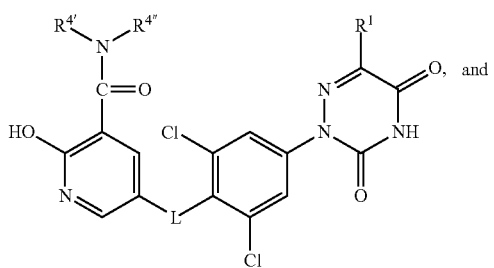

(I8c′)

or a pharmaceutically acceptable salt, solvate, prodrug, stereoisomer, or tautomer thereof, wherein L, $R^1$, $R^2$, $R^3$, $R^{4'}$, $R^{4''}$, $R^5$, $R^6$, $R^{6'}$, $R^7$, $R^8$, and y are each as defined herein, and any group defined herein for any one of L, $R^1$, $R^2$, $R^3$, $R^{4'}$, $R^{4''}$, $R^5$, $R^6$, $R^{6'}$, $R^7$, $R^8$, and y can be combined with any group defined herein for one or more of the remainder of L, $R^1$, $R^2$, $R^3$, $R^{4'}$, $R^{4''}$, $R^5$, $R^6$, $R^{6'}$, $R^7$, $R^8$, and y, for example, where applicable, as in (A1)-(N7).

Non-limiting illustrative compounds of the application include those in Table 1.

TABLE 1

| Cmpd No. | Structure | Chemical Name |
|---|---|---|
| 1 | 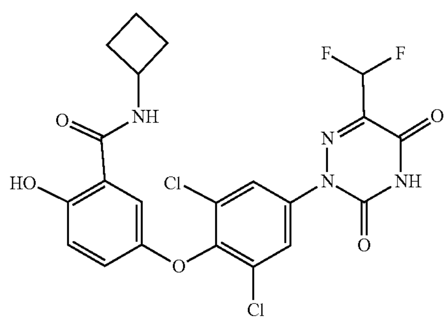 [SMILES: O=C(NC1CCC1)c1cc(Oc2c(Cl)cc(-n3nc(C(F)F)c(=O)[nH]c3=O)cc2Cl)ccc1O] | N-cyclobutyl-5-(2,6-dichloro-4-(6-(difluoromethyl)-3,5-dioxo-4,5-dihydro-1,2,4-triazin-2(3H)-yl)phenoxy)-2-hydroxybenzamide |
| 2 | 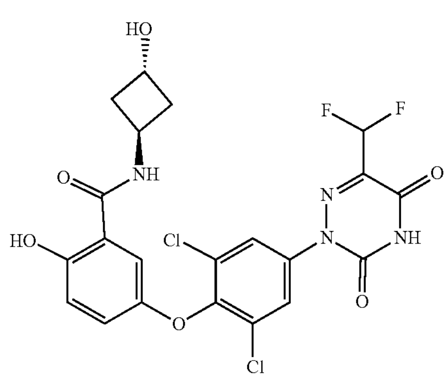 [SMILES: O=C(N[C@H]1C[C@H](O)C1)c1cc(Oc2c(Cl)cc(-n3nc(C(F)F)c(=O)[nH]c3=O)cc2Cl)ccc1O] | 5-(2,6-dichloro-4-(6-(difluoromethyl)-3,5-dioxo-4,5-dihydro-1,2,4-triazin-2(3H)-yl)phenoxy)-2-hydroxy-N-((1r,3r)-3-hydroxycyclobutyl)benzamide |

TABLE 1-continued

| Cmpd No. | Structure | Chemical Name |
|---|---|---|
| 3 | 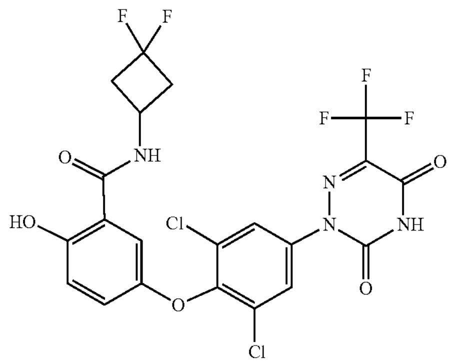 [SMILES: O=C(NC1CC(F)(F)C1)c1cc(Oc2c(Cl)cc(-n3nc(C(F)(F)F)c(=O)[nH]c3=O)cc2Cl)ccc1O] | 5-(2,6-dichloro-4-(3,5-dioxo-6-(trifluoromethyl)-4,5-dihydro-1,2,4-triazin-2(3H)-yl)phenoxy)-N-(3,3-difluorocyclobutyl)-2-hydroxybenzamide |
| 4 | 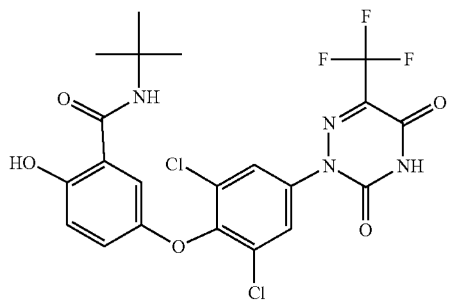 [SMILES: CC(C)(C)NC(=O)c1cc(Oc2c(Cl)cc(-n3nc(C(F)(F)F)c(=O)[nH]c3=O)cc2Cl)ccc1O] | N-(tert-butyl)-5-(2,6-dichloro-4-(3,5-dioxo-6-(trifluoromethyl)-4,5-dihydro-1,2,4-triazin-2(3H)-yl)phenoxy)-2-hydroxybenzamide |
| 5 | 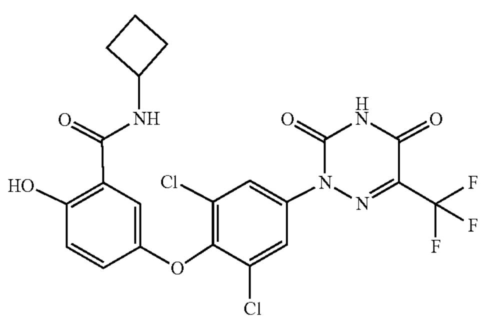 [SMILES: O=C(NC1CCC1)c1cc(Oc2c(Cl)cc(-n3nc(C(F)(F)F)c(=O)[nH]c3=O)cc2Cl)ccc1O] | N-cyclobutyl-5-(2,6-dichloro-4-(3,5-dioxo-6-(trifluoromethyl)-4,5-dihydro-1,2,4-triazin-2(3H)-yl)phenoxy)-2-hydroxybenzamide |
| 6 | 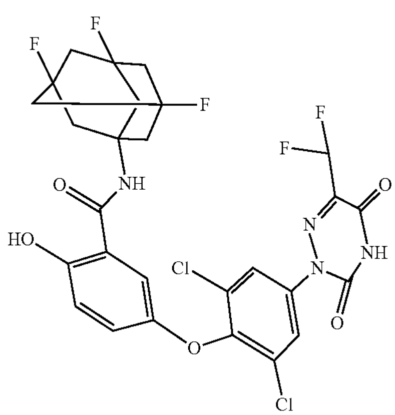 [SMILES: O=C(NC12CC3(F)CC(F)(CC(F)(C3)C1)C2)c1cc(Oc2c(Cl)cc(-n3nc(C(F)F)c(=O)[nH]c3=O)cc2Cl)ccc1O] | 5-(2,6-dichloro-4-(6-(difluoromethyl)-3,5-dioxo-4,5-dihydro-1,2,4-triazin-2(3H)-yl)phenoxy)-2-hydroxy-N-(3,5,7-trifluoroadamantan-1-yl)benzamide |

TABLE 1-continued

| Cmpd No. | Structure | Chemical Name |
|---|---|---|
| 7 | 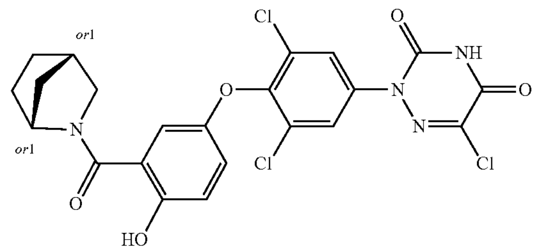 [SMILES: O=C(c1cc(Oc2c(Cl)cc(-n3nc(Cl)c(=O)[nH]c3=O)cc2Cl)ccc1O)N1C[C@H]2CC[C@@H]1C2] | 2-(4-(3-((1R,4S)-2-azabicyclo[2.2.1]heptane-2-carbonyl)-4-hydroxyphenoxy)-3,5-dichlorophenyl)-6-chloro-1,2,4-triazine-3,5(2H,4H)-dione |
| 8 | 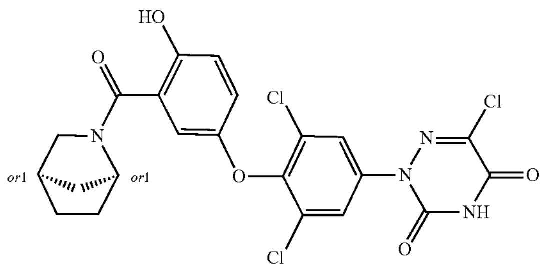 [SMILES: O=C(c1cc(Oc2c(Cl)cc(-n3nc(Cl)c(=O)[nH]c3=O)cc2Cl)ccc1O)N1C[C@@H]2CC[C@H]1C2] | 2-(4-(3-((1S,4R)-2-azabicyclo[2.2.1]heptane-2-carbonyl)-4-hydroxyphenoxy)-3,5-dichlorophenyl)-6-chloro-1,2,4-triazine-3,5(2H,4H)-dione |
| 9 | 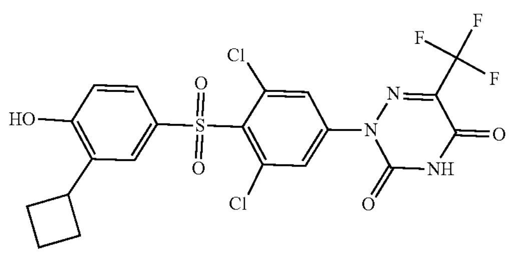 [SMILES: O=c1[nH]c(=O)n(-c2cc(Cl)c(S(=O)(=O)c3ccc(O)c(C4CCC4)c3)c(Cl)c2)nc1C(F)(F)F] | 2-(3,5-dichloro-4-((3-cyclobutyl-4-hydroxyphenyl)sulfonyl)phenyl)-6-(trifluoromethyl)-1,2,4-triazine-3,5(2H,4H)-dione |
| 10 | 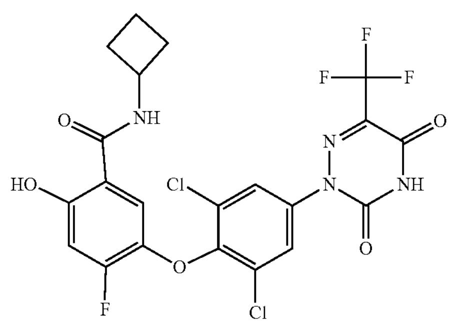 [SMILES: O=C(NC1CCC1)c1cc(Oc2c(Cl)cc(-n3nc(C(F)(F)F)c(=O)[nH]c3=O)cc2Cl)c(F)cc1O] | N-cyclobutyl-5-(2,6-dichloro-4-(3,5-dioxo-6-(trifluoromethyl)-4,5-dihydro-1,2,4-triazin-2(3H)-yl)phenoxy)-4-fluoro-2-hydroxybenzamide |
| 11 | 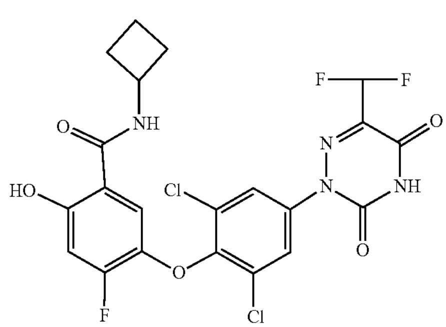 [SMILES: O=C(NC1CCC1)c1cc(Oc2c(Cl)cc(-n3nc(C(F)F)c(=O)[nH]c3=O)cc2Cl)c(F)cc1O] | N-cyclobutyl-5-(2,6-dichloro-4-(6-(difluoromethyl)-3,5-dioxo-4,5-dihydro-1,2,4-triazin-2(3H)-yl)phenoxy)-4-fluoro-2-hydroxybenzamide |

TABLE 1-continued

| Cmpd No. | Structure | Chemical Name |
|---|---|---|
| 12 | 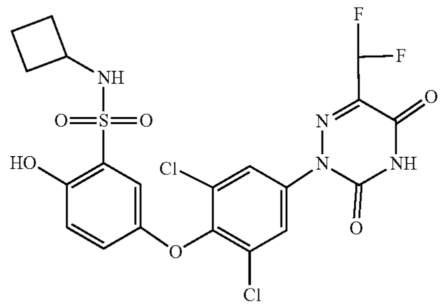 [SMILES: O=c1[nH]c(=O)n(-c2cc(Cl)c(Oc3ccc(O)c(S(=O)(=O)NC4CCC4)c3)c(Cl)c2)nc1C(F)F] | N-cyclobutyl-5-(2,6-dichloro-4-(6-(difluoromethyl)-3,5-dioxo-4,5-dihydro-1,2,4-triazin-2(3H)-yl)phenoxy)-2-hydroxybenzenesulfonamide |
| 13 | 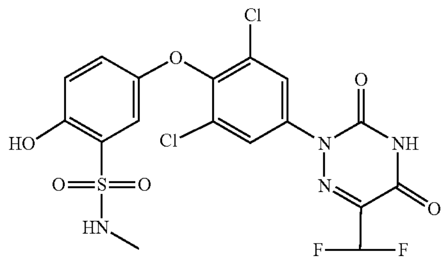 [SMILES: CNS(=O)(=O)c1cc(Oc2c(Cl)cc(-n3nc(C(F)F)c(=O)[nH]c3=O)cc2Cl)ccc1O] | 5-(2,6-dichloro-4-(6-(difluoromethyl)-3,5-dioxo-4,5-dihydro-1,2,4-triazin-2(3H)-yl)phenoxy)-2-hydroxy-N-methylbenzenesulfonamide |
| 14 | 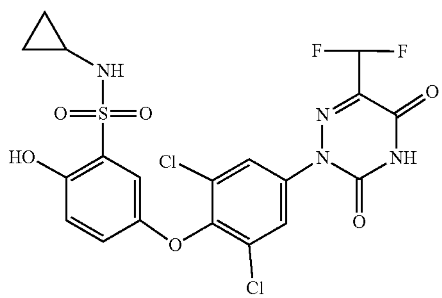 [SMILES: O=c1[nH]c(=O)n(-c2cc(Cl)c(Oc3ccc(O)c(S(=O)(=O)NC4CC4)c3)c(Cl)c2)nc1C(F)F] | N-cyclopropyl-5-(2,6-dichloro-4-(6-(difluoromethyl)-3,5-dioxo-4,5-dihydro-1,2,4-triazin-2(3H)-yl)phenoxy)-2-hydroxybenzenesulfonamide |
| 15 | 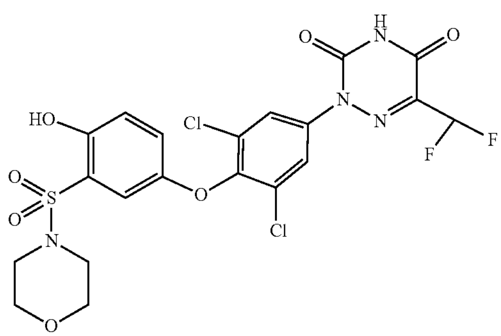 [SMILES: O=c1[nH]c(=O)n(-c2cc(Cl)c(Oc3ccc(O)c(S(=O)(=O)N4CCOCC4)c3)c(Cl)c2)nc1C(F)F] | 2-(3,5-dichloro-4-(4-hydroxy-3-(morpholinosulfonyl)phenoxy)phenyl)-6-(difluoromethyl)-1,2,4-triazine-3,5(2H,4H)-dione |
| 16 | 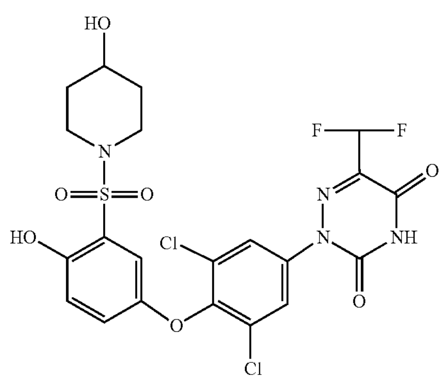 [SMILES: O=c1[nH]c(=O)n(-c2cc(Cl)c(Oc3ccc(O)c(S(=O)(=O)N4CCC(O)CC4)c3)c(Cl)c2)nc1C(F)F] | 2-(3,5-dichloro-4-(4-hydroxy-3-((4-hydroxypiperidin-1-yl)sulfonyl)phenoxy)phenyl)-6-(difluoromethyl)-1,2,4-triazine-3,5(2H,4H)-dione |

TABLE 1-continued

| Cmpd No. | Structure | Chemical Name |
| --- | --- | --- |
| 17 | 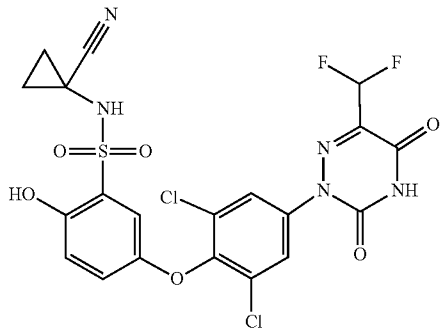 [SMILES: N#CC1(NS(=O)(=O)c2cc(Oc3c(Cl)cc(-n4nc(C(F)F)c(=O)[nH]c4=O)cc3Cl)ccc2O)CC1] | N-(1-cyanocyclopropyl)-5-(2,6-dichloro-4-(6-(difluoromethyl)-3,5-dioxo-4,5-dihydro-1,2,4-triazin-2(3H)-yl)phenoxy)-2-hydroxybenzenesulfonamide |
| 18 | 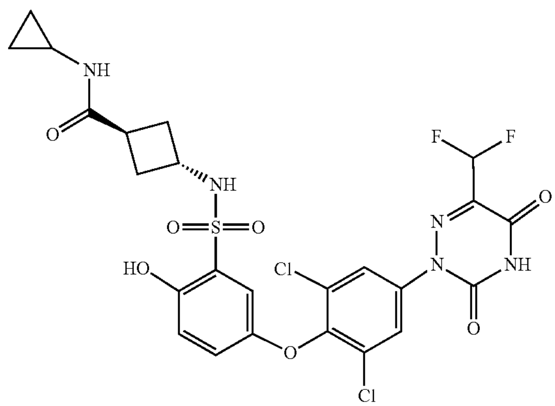 [SMILES: O=c1[nH]c(=O)n(-c2cc(Cl)c(Oc3ccc(O)c(S(=O)(=O)N[C@H]4C[C@H](C(=O)NC5CC5)C4)c3)c(Cl)c2)nc1C(F)F] | (1r,3r)-N-cyclopropyl-3-((5-(2,6-dichloro-4-(6-(difluoromethyl)-3,5-dioxo-4,5-dihydro-1,2,4-triazin-2(3H)-yl)phenoxy)-2-hydroxyphenyl)sulfonamido)cyclobutane-1-carboxamide |
| 19 | 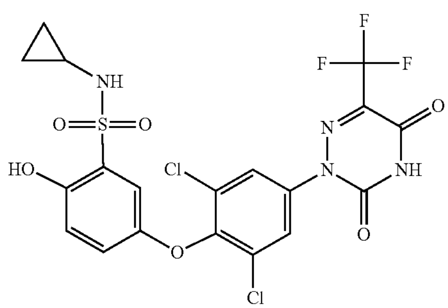 [SMILES: O=c1[nH]c(=O)n(-c2cc(Cl)c(Oc3ccc(O)c(S(=O)(=O)NC4CC4)c3)c(Cl)c2)nc1C(F)(F)F] | N-cyclopropyl-5-(2,6-dichloro-4-(3,5-dioxo-6-(trifluoromethyl)-4,5-dihydro-1,2,4-triazin-2(3H)-yl)phenoxy)-2-hydroxybenzenesulfonamide |
| 20 | 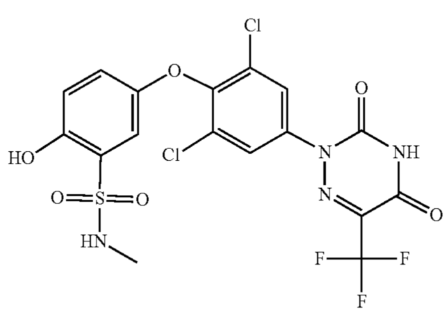 [SMILES: CNS(=O)(=O)c1cc(Oc2c(Cl)cc(-n3nc(C(F)(F)F)c(=O)[nH]c3=O)cc2Cl)ccc1O] | 5-(2,6-dichloro-4-(3,5-dioxo-6-(trifluoromethyl)-4,5-dihydro-1,2,4-triazin-2(3H)-yl)phenoxy)-2-hydroxy-N-methylbenzenesulfonamide |

TABLE 1-continued

| Cmpd No. | Structure | Chemical Name |
| --- | --- | --- |
| 21 | 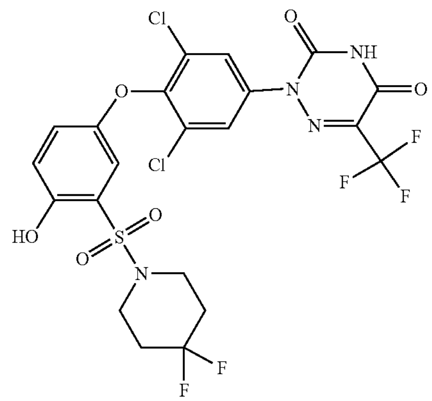 [SMILES: O=c1[nH]c(=O)n(-c2cc(Cl)c(Oc3ccc(O)c(S(=O)(=O)N4CCC(F)(F)CC4)c3)c(Cl)c2)nc1C(F)(F)F] | 2-(3,5-dichloro-4-(3-((4,4-difluoropiperidin-1-yl)sulfonyl)-4-hydroxyphenoxy)phenyl)-6-(trifluoromethyl)-1,2,4-triazine-3,5(2H,4H)-dione |
| 22 | 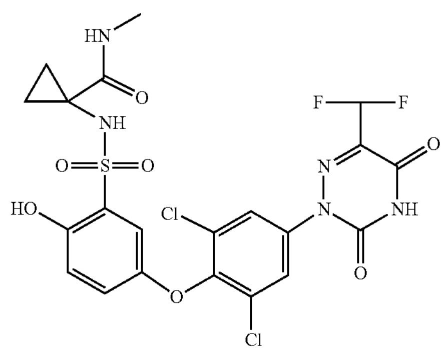 [SMILES: CNC(=O)C1(NS(=O)(=O)c2cc(Oc3c(Cl)cc(-n4nc(C(F)F)c(=O)[nH]c4=O)cc3Cl)ccc2O)CC1] | 1-((5-(2,6-dichloro-4-(6-(difluoromethyl)-3,5-dioxo-4,5-dihydro-1,2,4-triazin-2(3H)-yl)phenoxy)-2-hydroxyphenyl)sulfonamido)-N-methylcyclopropane-1-carboxamide |
| 23 | 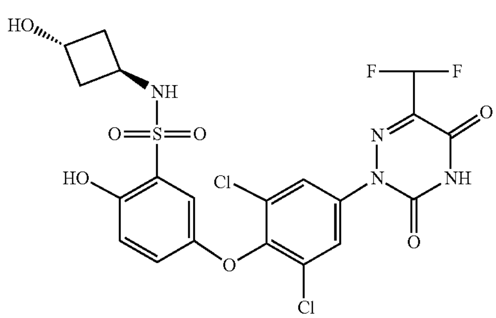 [SMILES: O=c1[nH]c(=O)n(-c2cc(Cl)c(Oc3ccc(O)c(S(=O)(=O)N[C@H]4C[C@H](O)C4)c3)c(Cl)c2)nc1C(F)F] | 5-(2,6-dichloro-4-(6-(difluoromethyl)-3,5-dioxo-4,5-dihydro-1,2,4-triazin-2(3H)-yl)phenoxy)-2-hydroxy-N-((1r,3r)-3-hydroxycyclobutyl)benzenesulfonamide |
| 24 | 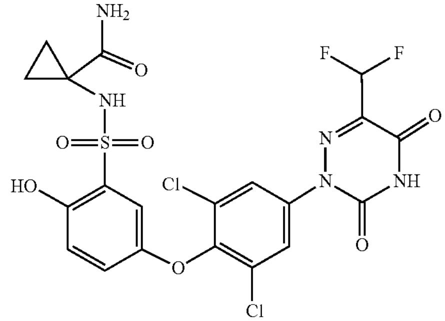 [SMILES: NC(=O)C1(NS(=O)(=O)c2cc(Oc3c(Cl)cc(-n4nc(C(F)F)c(=O)[nH]c4=O)cc3Cl)ccc2O)CC1] | 1-((5-(2,6-dichloro-4-(6-(difluoromethyl)-3,5-dioxo-4,5-dihydro-1,2,4-triazin-2(3H)-yl)phenoxy)-2-hydroxyphenyl)sulfonamido)cyclopropane-1-carboxamide |

TABLE 1-continued

| Cmpd No. | Structure | Chemical Name |
|---|---|---|
| 25 | 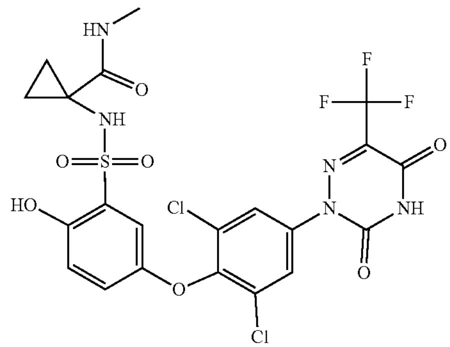 [SMILES: CNC(=O)C1(NS(=O)(=O)c2cc(Oc3c(Cl)cc(-n4nc(C(F)(F)F)c(=O)[nH]c4=O)cc3Cl)ccc2O)CC1] | 1-((5-(2,6-dichloro-4-(3,5-dioxo-6-(trifluoromethyl)-4,5-dihydro-1,2,4-triazin-2(3H)-yl)phenoxy)-2-hydroxyphenyl)sulfonamido)-N-methylcyclopropane-1-carboxamide |
| 26 | 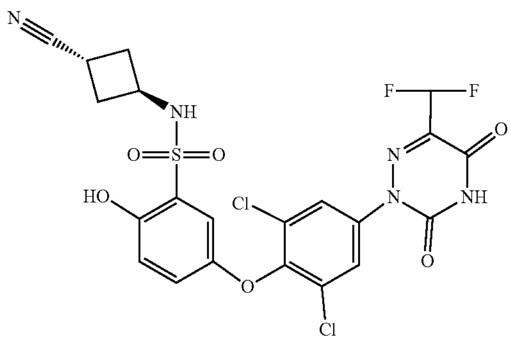 [SMILES: N#C[C@H]1C[C@H](NS(=O)(=O)c2cc(Oc3c(Cl)cc(-n4nc(C(F)F)c(=O)[nH]c4=O)cc3Cl)ccc2O)C1] | N-((1r,3r)-3-cyanocyclobutyl)-5-(2,6-dichloro-4-(6-(difluoromethyl)-3,5-dioxo-4,5-dihydro-1,2,4-triazin-2(3H)-yl)phenoxy)-2-hydroxybenzenesulfonamide |
| 27 | 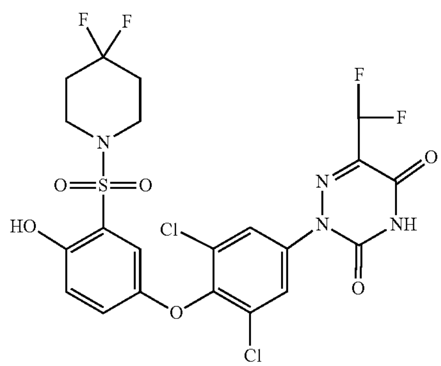 [SMILES: O=c1[nH]c(=O)n(-c2cc(Cl)c(Oc3ccc(O)c(S(=O)(=O)N4CCC(F)(F)CC4)c3)c(Cl)c2)nc1C(F)F] | 2-(3,5-dichloro-4-(3-((4,4-difluoropiperidin-1-yl)sulfonyl)-4-hydroxyphenoxy)phenyl)-6-(difluoromethyl)-1,2,4-triazine-3,5(2H,4H)-dione |
| 28 | 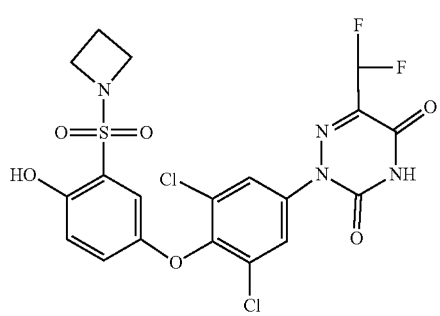 [SMILES: O=c1[nH]c(=O)n(-c2cc(Cl)c(Oc3ccc(O)c(S(=O)(=O)N4CCC4)c3)c(Cl)c2)nc1C(F)F] | 2-(4-(3-(azetidin-1-ylsulfonyl)-4-hydroxyphenoxy)-3,5-dichlorophenyl)-6-(difluoromethyl)-1,2,4-triazine-3,5(2H,4H)-dione |

TABLE 1-continued

| Cmpd No. | Structure | Chemical Name |
| --- | --- | --- |
| 29 | 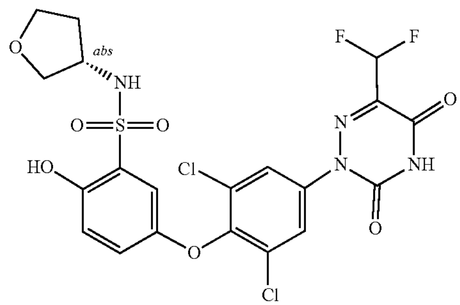 [SMILES: O=c1[nH]c(=O)n(-c2cc(Cl)c(Oc3ccc(O)c(S(=O)(=O)N[C@H]4CCOC4)c3)c(Cl)c2)nc1C(F)F] | (S)-5-(2,6-dichloro-4-(6-(difluoromethyl)-3,5-dioxo-4,5-dihydro-1,2,4-triazin-2(3H)-yl)phenoxy)-2-hydroxy-N-(tetrahydrofuran-3-yl)benzenesulfonamide |
| 30 | 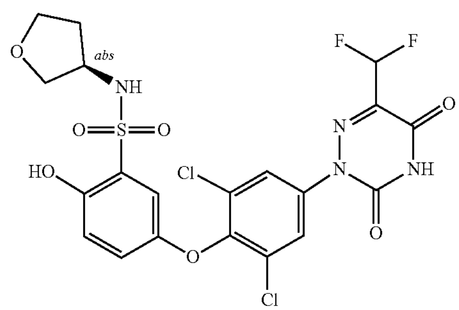 [SMILES: O=c1[nH]c(=O)n(-c2cc(Cl)c(Oc3ccc(O)c(S(=O)(=O)N[C@@H]4CCOC4)c3)c(Cl)c2)nc1C(F)F] | (R)-5-(2,6-dichloro-4-(6-(difluoromethyl)-3,5-dioxo-4,5-dihydro-1,2,4-triazin-2(3H)-yl)phenoxy)-2-hydroxy-N-(tetrahydrofuran-3-yl)benzenesulfonamide |
| 31 | 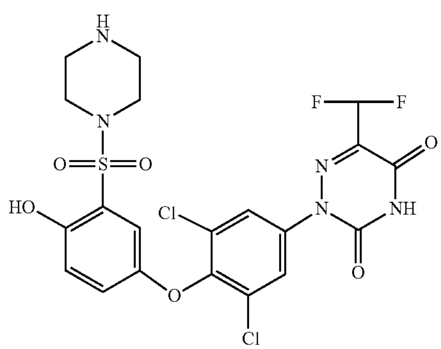 [SMILES: O=c1[nH]c(=O)n(-c2cc(Cl)c(Oc3ccc(O)c(S(=O)(=O)N4CCNCC4)c3)c(Cl)c2)nc1C(F)F] | 2-(3,5-dichloro-4-(4-hydroxy-3-(piperazin-1-ylsulfonyl)phenoxy)phenyl)-6-(difluoromethyl)-1,2,4-triazine-3,5(2H,4H)-dione |
| 32 | 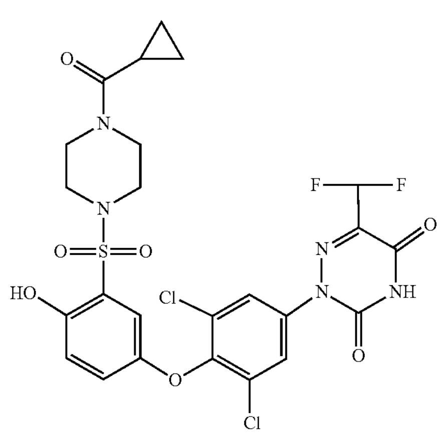 [SMILES: O=C(C1CC1)N1CCN(S(=O)(=O)c2cc(Oc3c(Cl)cc(-n4nc(C(F)F)c(=O)[nH]c4=O)cc3Cl)ccc2O)CC1] | 2-(3,5-dichloro-4-(3-((4-(cyclopropanecarbonyl)piperazin-1-yl)sulfonyl)-4-hydroxyphenoxy)phenyl)-6-(difluoromethyl)-1,2,4-triazine-3,5(2H,4H)-dione |

TABLE 1-continued

| Cmpd No. | Structure | Chemical Name |
| --- | --- | --- |
| 33 | 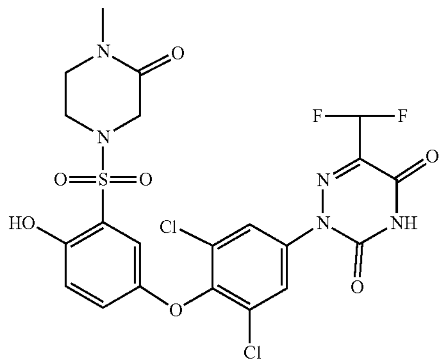 [SMILES: CN1CCN(S(=O)(=O)c2cc(Oc3c(Cl)cc(-n4nc(C(F)F)c(=O)[nH]c4=O)cc3Cl)ccc2O)CC1=O] | 2-(3,5-dichloro-4-(4-hydroxy-3-((4-methyl-3-oxopiperazin-1-yl)sulfonyl)phenoxy)phenyl)-6-(difluoromethyl)-1,2,4-triazine-3,5(2H,4H)-dione |
| 34 | 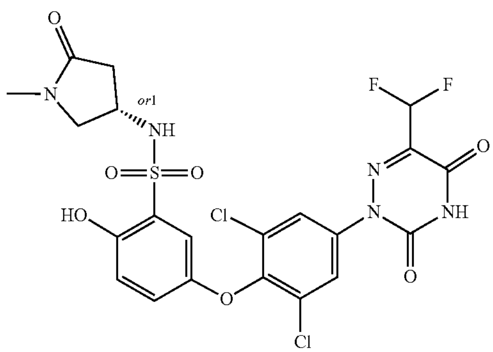 [SMILES: CN1C[C@@H](NS(=O)(=O)c2cc(Oc3c(Cl)cc(-n4nc(C(F)F)c(=O)[nH]c4=O)cc3Cl)ccc2O)CC1=O] | (S)-5-(2,6-dichloro-4-(6-(difluoromethyl)-3,5-dioxo-4,5-dihydro-1,2,4-triazin-2(3H)-yl)phenoxy)-2-hydroxy-N-(1-methyl-5-oxopyrrolidin-3-yl)benzenesulfonamide |
| 35 | 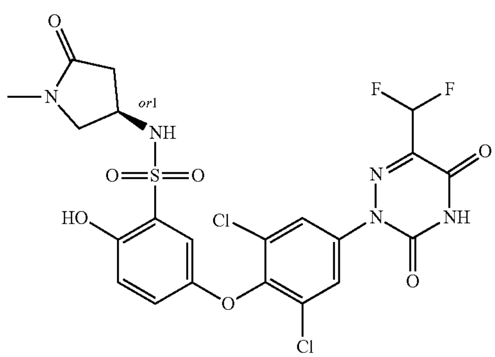 [SMILES: CN1C[C@H](NS(=O)(=O)c2cc(Oc3c(Cl)cc(-n4nc(C(F)F)c(=O)[nH]c4=O)cc3Cl)ccc2O)CC1=O] | (R)-5-(2,6-dichloro-4-(6-(difluoromethyl)-3,5-dioxo-4,5-dihydro-1,2,4-triazin-2(3H)-yl)phenoxy)-2-hydroxy-N-(1-methyl-5-oxopyrrolidin-3-yl)benzenesulfonamide |
| 36 | 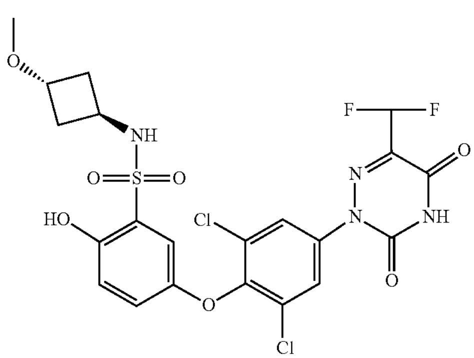 [SMILES: CO[C@H]1C[C@H](NS(=O)(=O)c2cc(Oc3c(Cl)cc(-n4nc(C(F)F)c(=O)[nH]c4=O)cc3Cl)ccc2O)C1] | 5-(2,6-dichloro-4-(6-(difluoromethyl)-3,5-dioxo-4,5-dihydro-1,2,4-triazin-2(3H)-yl)phenoxy)-2-hydroxy-N-((1r,3r)-3-methoxycyclobutyl)benzenesulfonamide |

TABLE 1-continued

| Cmpd No. | Structure | Chemical Name |
| --- | --- | --- |
| 37 | 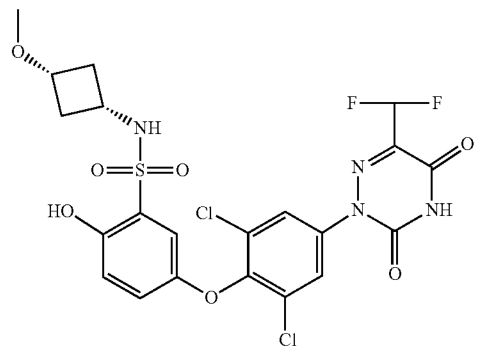 [SMILES: CO[C@H]1C[C@@H](NS(=O)(=O)c2cc(Oc3c(Cl)cc(-n4nc(C(F)F)c(=O)[nH]c4=O)cc3Cl)ccc2O)C1] | 5-(2,6-dichloro-4-(6-(difluoromethyl)-3,5-dioxo-4,5-dihydro-1,2,4-triazin-2(3H)-yl)phenoxy)-2-hydroxy-N-((1s,3s)-3-methoxycyclobutyl)benzenesulfonamide |
| 38 | 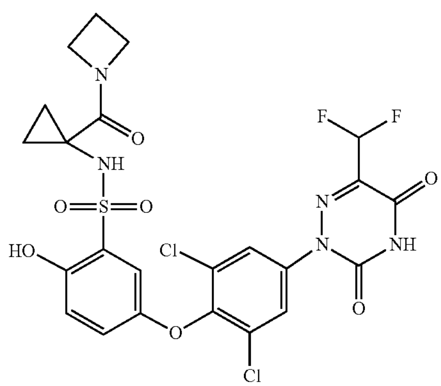 [SMILES: O=C(N1CCC1)C1(NS(=O)(=O)c2cc(Oc3c(Cl)cc(-n4nc(C(F)F)c(=O)[nH]c4=O)cc3Cl)ccc2O)CC1] | N-(1-(azetidine-1-carbonyl)cyclopropyl)-5-(2,6-dichloro-4-(6-(difluoromethyl)-3,5-dioxo-4,5-dihydro-1,2,4-triazin-2(3H)-yl)phenoxy)-2-hydroxybenzenesulfonamide |
| 39 | 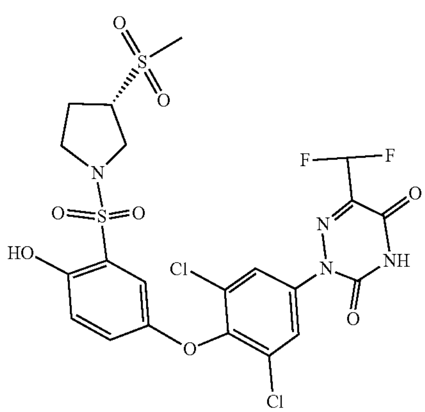 [SMILES: CS(=O)(=O)[C@H]1CCN(S(=O)(=O)c2cc(Oc3c(Cl)cc(-n4nc(C(F)F)c(=O)[nH]c4=O)cc3Cl)ccc2O)C1] | (S)-2-(3,5-dichloro-4-(4-hydroxy-3-((3-(methylsulfonyl)pyrrolidin-1-yl)sulfonyl)phenoxy)phenyl)-6-(difluoromethyl)-1,2,4-triazine-3,5(2H,4H)-dione |
| 40 | 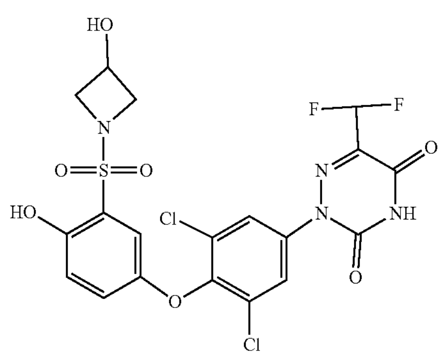 [SMILES: O=c1[nH]c(=O)n(-c2cc(Cl)c(Oc3ccc(O)c(S(=O)(=O)N4CC(O)C4)c3)c(Cl)c2)nc1C(F)F] | 2-(3,5-dichloro-4-(4-hydroxy-3-((3-hydroxyazetidin-1-yl)sulfonyl)phenoxy)phenyl)-6-(difluoromethyl)-1,2,4-triazine-3,5(2H,4H)-dione |

TABLE 1-continued

| Cmpd No. | Structure | Chemical Name |
|---|---|---|
| 41 | 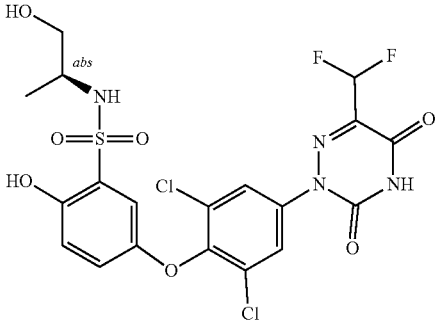 [SMILES: C[C@@H](CO)NS(=O)(=O)c1cc(Oc2c(Cl)cc(-n3nc(C(F)F)c(=O)[nH]c3=O)cc2Cl)ccc1O] | (S)-5-(2,6-dichloro-4-(6-(difluoromethyl)-3,5-dioxo-4,5-dihydro-1,2,4-triazin-2(3H)-yl)phenoxy)-2-hydroxy-N-(1-hydroxypropan-2-yl)benzenesulfonamide |
| 42 | 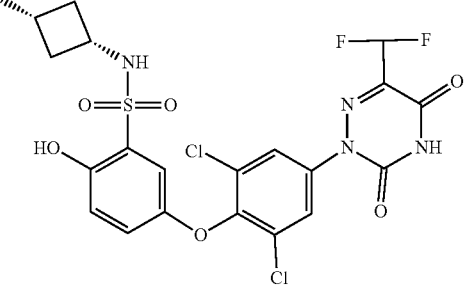 | 5-(2,6-dichloro-4-(6-(difluoromethyl)-3,5-dioxo-4,5-dihydro-1,2,4-triazin-2(3H)-yl)phenoxy)-2-hydroxy-N-((1s,3s)-3-hydroxycyclobutyl)benzenesulfonamide |
| 43 | 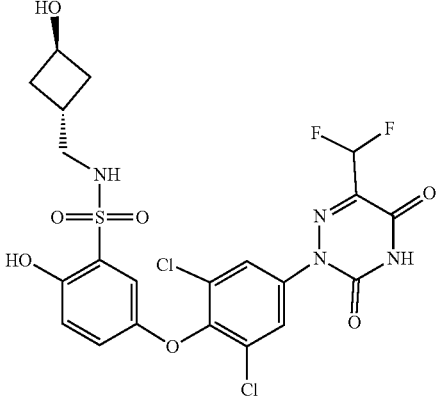 [SMILES: O=c1[nH]c(=O)n(-c2cc(Cl)c(Oc3ccc(O)c(S(=O)(=O)NC[C@H]4C[C@H](O)C4)c3)c(Cl)c2)nc1C(F)F] | 5-(2,6-dichloro-4-(6-(difluoromethyl)-3,5-dioxo-4,5-dihydro-1,2,4-triazin-2(3H)-yl)phenoxy)-2-hydroxy-N-(((1r,3r)-3-hydroxycyclobutyl)methyl)benzenesulfonamide |
| 44 | 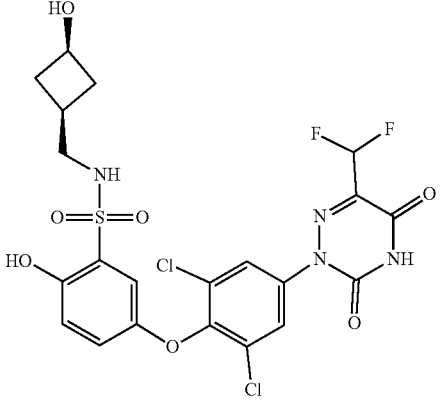 [SMILES: O=c1[nH]c(=O)n(-c2cc(Cl)c(Oc3ccc(O)c(S(=O)(=O)NC[C@H]4C[C@@H](O)C4)c3)c(Cl)c2)nc1C(F)F] | 5-(2,6-dichloro-4-(6-(difluoromethyl)-3,5-dioxo-4,5-dihydro-1,2,4-triazin-2(3H)-yl)phenoxy)-2-hydroxy-N-(((1s,3s)-3-hydroxycyclobutyl)methyl)benzenesulfonamide |

TABLE 1-continued

| Cmpd No. | Structure | Chemical Name |
|---|---|---|
| 45 | 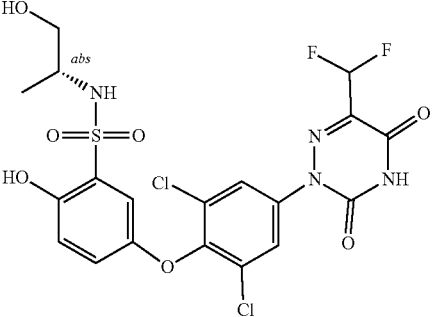 [SMILES: C[C@H](CO)NS(=O)(=O)c1cc(Oc2c(Cl)cc(-n3nc(C(F)F)c(=O)[nH]c3=O)cc2Cl)ccc1O] | (R)-5-(2,6-dichloro-4-(6-(difluoromethyl)-3,5-dioxo-4,5-dihydro-1,2,4-triazin-2(3H)-yl)phenoxy)-2-hydroxy-N-(1-hydroxypropan-2-yl)benzenesulfonamide |
| 46 | 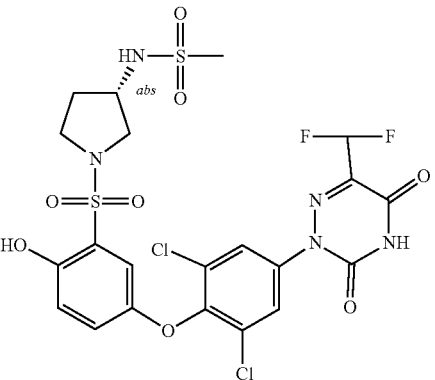 [SMILES: CS(=O)(=O)N[C@H]1CCN(S(=O)(=O)c2cc(Oc3c(Cl)cc(-n4nc(C(F)F)c(=O)[nH]c4=O)cc3Cl)ccc2O)C1] | (S)-N-(1-((5-(2,6-dichloro-4-(6-(difluoromethyl)-3,5-dioxo-4,5-dihydro-1,2,4-triazin-2(3H)-yl)phenoxy)-2-hydroxyphenyl)sulfonyl)pyrrolidin-3-yl)methanesulfonamide |
| 47 | 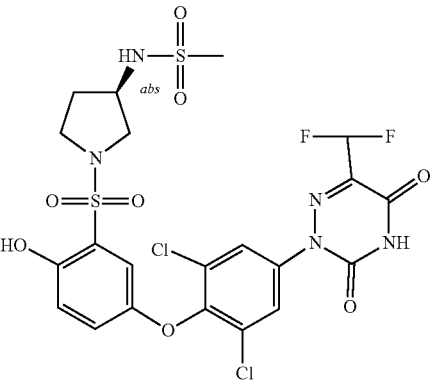 [SMILES: CS(=O)(=O)N[C@@H]1CCN(S(=O)(=O)c2cc(Oc3c(Cl)cc(-n4nc(C(F)F)c(=O)[nH]c4=O)cc3Cl)ccc2O)C1] | (R)-N-(1-((5-(2,6-dichloro-4-(6-(difluoromethyl)-3,5-dioxo-4,5-dihydro-1,2,4-triazin-2(3H)-yl)phenoxy)-2-hydroxyphenyl)sulfonyl)pyrrolidin-3-yl)methanesulfonamide |
| 48 | 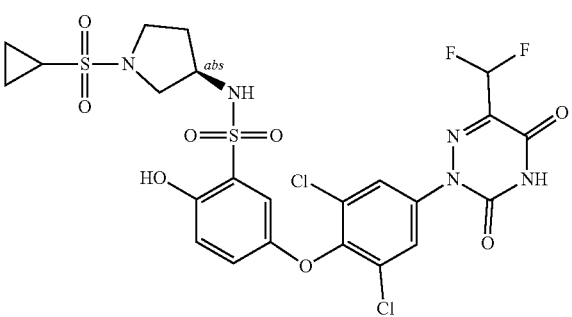 [SMILES: O=c1[nH]c(=O)n(-c2cc(Cl)c(Oc3ccc(O)c(S(=O)(=O)N[C@@H]4CCN(S(=O)(=O)C5CC5)C4)c3)c(Cl)c2)nc1C(F)F] | (R)-N-(1-(cyclopropylsulfonyl)pyrrolidin-3-yl)-5-(2,6-dichloro-4-(6-(difluoromethyl)-3,5-dioxo-4,5-dihydro-1,2,4-triazin-2(3H)-yl)phenoxy)-2-hydroxybenzenesulfonamide |

TABLE 1-continued

| Cmpd No. | Structure | Chemical Name |
|---|---|---|
| 49 | 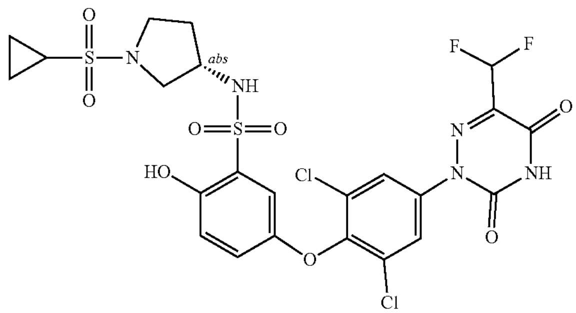 [SMILES: O=c1[nH]c(=O)n(-c2cc(Cl)c(Oc3ccc(O)c(S(=O)(=O)N[C@H]4CCN(S(=O)(=O)C5CC5)C4)c3)c(Cl)c2)nc1C(F)F] | (S)-N-(1-(cyclopropylsulfonyl)pyrrolidin-3-yl)-5-(2,6-dichloro-4-(6-(difluoromethyl)-3,5-dioxo-4,5-dihydro-1,2,4-triazin-2(3H)-yl)phenoxy)-2-hydroxybenzenesulfonamide |
| 50 | 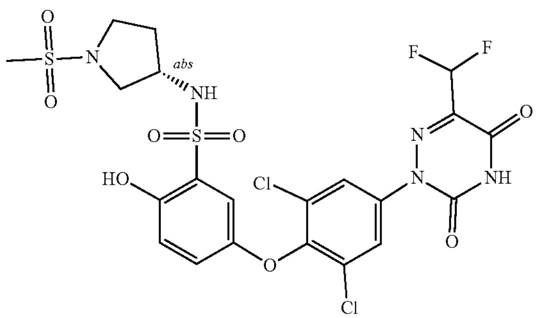 [SMILES: CS(=O)(=O)N1CC[C@H](NS(=O)(=O)c2cc(Oc3c(Cl)cc(-n4nc(C(F)F)c(=O)[nH]c4=O)cc3Cl)ccc2O)C1] | (S)-5-(2,6-dichloro-4-(6-(difluoromethyl)-3,5-dioxo-4,5-dihydro-1,2,4-triazin-2(3H)-yl)phenoxy)-2-hydroxy-N-(1-(methylsulfonyl)pyrrolidin-3-yl)benzenesulfonamide |
| 51 | 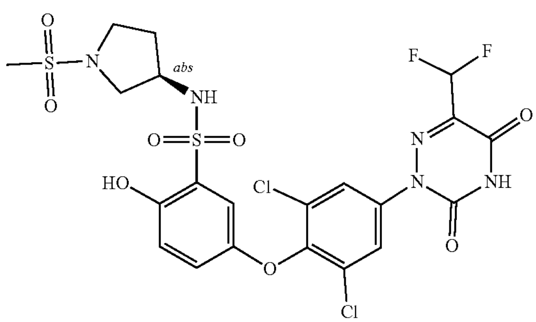 [SMILES: CS(=O)(=O)N1CC[C@@H](NS(=O)(=O)c2cc(Oc3c(Cl)cc(-n4nc(C(F)F)c(=O)[nH]c4=O)cc3Cl)ccc2O)C1] | (R)-5-(2,6-dichloro-4-(6-(difluoromethyl)-3,5-dioxo-4,5-dihydro-1,2,4-triazin-2(3H)-yl)phenoxy)-2-hydroxy-N-(1-(methylsulfonyl)pyrrolidin-3-yl)benzenesulfonamide |
| 52 | 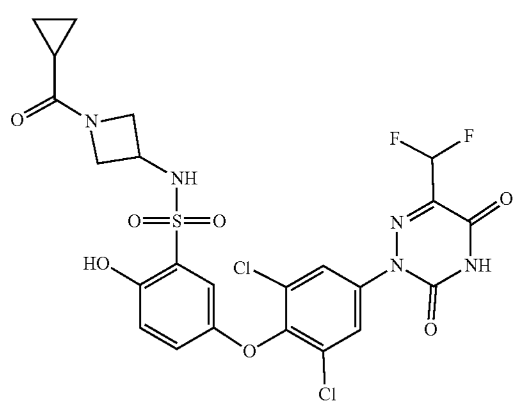 [SMILES: O=C(C1CC1)N1CC(NS(=O)(=O)c2cc(Oc3c(Cl)cc(-n4nc(C(F)F)c(=O)[nH]c4=O)cc3Cl)ccc2O)C1] | N-(1-(cyclopropanecarbonyl)azetidin-3-yl)-5-(2,6-dichloro-4-(6-(difluoromethyl)-3,5-dioxo-4,5-dihydro-1,2,4-triazin-2(3H)-yl)phenoxy)-2-hydroxybenzenesulfonamide |

TABLE 1-continued

| Cmpd No. | Structure | Chemical Name |
| --- | --- | --- |
| 53 | 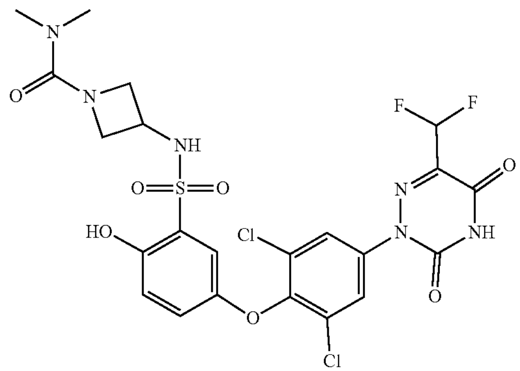 [SMILES: CN(C)C(=O)N1CC(NS(=O)(=O)c2cc(Oc3c(Cl)cc(-n4nc(C(F)F)c(=O)[nH]c4=O)cc3Cl)ccc2O)C1] | 3-((5-(2,6-dichloro-4-(6-(difluoromethyl)-3,5-dioxo-4,5-dihydro-1,2,4-triazin-2(3H)-yl)phenoxy)-2-hydroxyphenyl)sulfonamido)-N,N-dimethylazetidine-1-carboxamide |
| 54 | 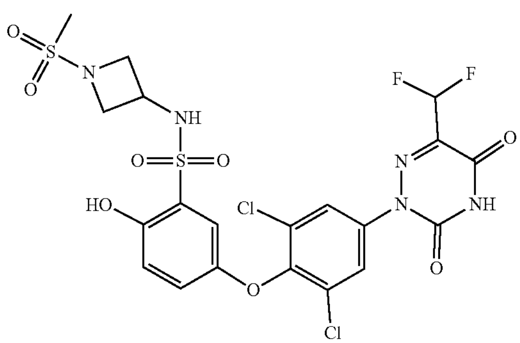 [SMILES: CS(=O)(=O)N1CC(NS(=O)(=O)c2cc(Oc3c(Cl)cc(-n4nc(C(F)F)c(=O)[nH]c4=O)cc3Cl)ccc2O)C1] | 5-(2,6-dichloro-4-(6-(difluoromethyl)-3,5-dioxo-4,5-dihydro-1,2,4-triazin-2(3H)-yl)phenoxy)-2-hydroxy-N-(1-(methylsulfonyl)azetidin-3-yl)benzenesulfonamide |
| 55 | 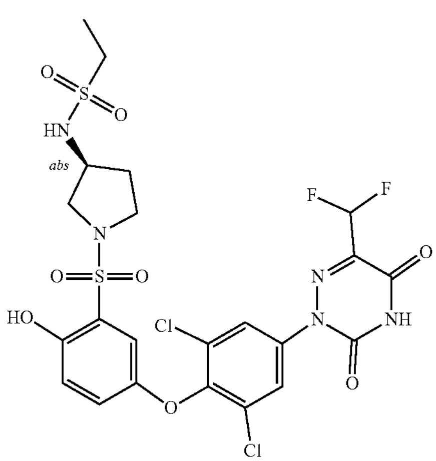 [SMILES: CCS(=O)(=O)N[C@H]1CCN(S(=O)(=O)c2cc(Oc3c(Cl)cc(-n4nc(C(F)F)c(=O)[nH]c4=O)cc3Cl)ccc2O)C1] | (S)-N-(1-((5-(2,6-dichloro-4-(6-(difluoromethyl)-3,5-dioxo-4,5-dihydro-1,2,4-triazin-2(3H)-yl)phenoxy)-2-hydroxyphenyl)sulfonyl)pyrrolidin-3-yl)ethanesulfonamide |

TABLE 1-continued

| Cmpd No. | Structure | Chemical Name |
|---|---|---|
| 56 | 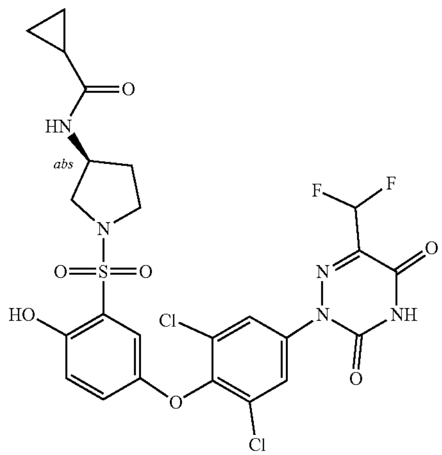 [SMILES: O=C(N[C@H]1CCN(S(=O)(=O)c2cc(Oc3c(Cl)cc(-n4nc(C(F)F)c(=O)[nH]c4=O)cc3Cl)ccc2O)C1)C1CC1] | (S)-N-(1-((5-(2,6-dichloro-4-(6-(difluoromethyl)-3,5-dioxo-4,5-dihydro-1,2,4-triazin-2(3H)-yl)phenoxy)-2-hydroxyphenyl)sulfonyl)pyrrolidin-3-yl)cyclopropanecarboxamide |
| 57 | 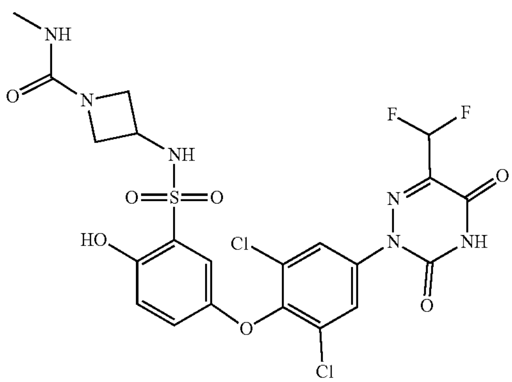 [SMILES: CNC(=O)N1CC(NS(=O)(=O)c2cc(Oc3c(Cl)cc(-n4nc(C(F)F)c(=O)[nH]c4=O)cc3Cl)ccc2O)C1] | 3-((5-(2,6-dichloro-4-(6-(difluoromethyl)-3,5-dioxo-4,5-dihydro-1,2,4-triazin-2(3H)-yl)phenoxy)-2-hydroxyphenyl)sulfonamido)-N-methylazetidine-1-carboxamide |
| 58 | 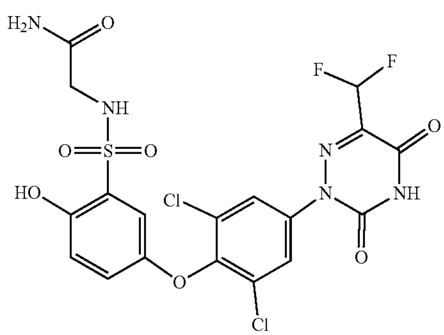 [SMILES: NC(=O)CNS(=O)(=O)c1cc(Oc2c(Cl)cc(-n3nc(C(F)F)c(=O)[nH]c3=O)cc2Cl)ccc1O] | 2-((5-(2,6-dichloro-4-(6-(difluoromethyl)-3,5-dioxo-4,5-dihydro-1,2,4-triazin-2(3H)-yl)phenoxy)-2-hydroxyphenyl)sulfonamido)acetamide |
| 59 | 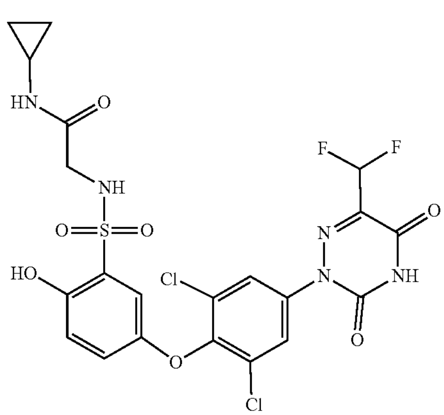 [SMILES: O=C(CNS(=O)(=O)c1cc(Oc2c(Cl)cc(-n3nc(C(F)F)c(=O)[nH]c3=O)cc2Cl)ccc1O)NC1CC1] | N-cyclopropyl-2-((5-(2,6-dichloro-4-(6-(difluoromethyl)-3,5-dioxo-4,5-dihydro-1,2,4-triazin-2(3H)-yl)phenoxy)-2-hydroxyphenyl)sulfonamido)acetamide |

TABLE 1-continued

| Cmpd No. | Structure | Chemical Name |
| --- | --- | --- |
| 60 | 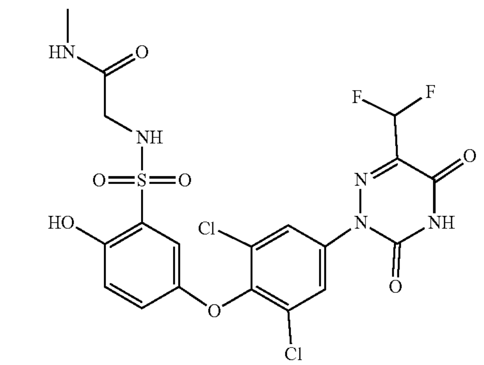 [SMILES: CNC(=O)CNS(=O)(=O)c1cc(Oc2c(Cl)cc(-n3nc(C(F)F)c(=O)[nH]c3=O)cc2Cl)ccc1O] | 2-((5-(2,6-dichloro-4-(6-(difluoromethyl)-3,5-dioxo-4,5-dihydro-1,2,4-triazin-2(3H)-yl)phenoxy)-2-hydroxyphenyl)sulfonamido)-N-methylacetamide |
| 61 | 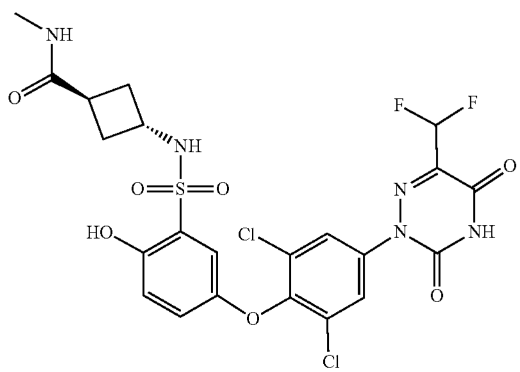 [SMILES: CNC(=O)[C@H]1C[C@H](NS(=O)(=O)c2cc(Oc3c(Cl)cc(-n4nc(C(F)F)c(=O)[nH]c4=O)cc3Cl)ccc2O)C1] | (1r,3r)-3-((5-(2,6-dichloro-4-(6-(difluoromethyl)-3,5-dioxo-4,5-dihydro-1,2,4-triazin-2(3H)-yl)phenoxy)-2-hydroxyphenyl)sulfonamido)-N-methylcyclobutane-1-carboxamide |
| 62 | 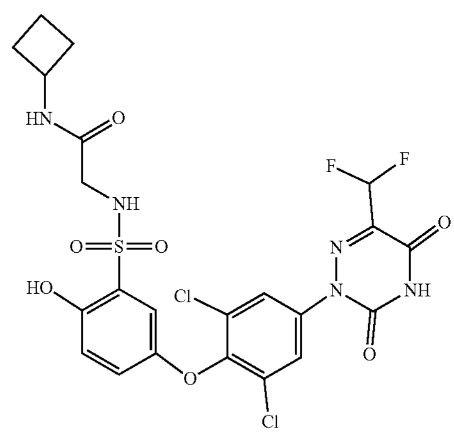 [SMILES: O=C(CNS(=O)(=O)c1cc(Oc2c(Cl)cc(-n3nc(C(F)F)c(=O)[nH]c3=O)cc2Cl)ccc1O)NC1CCC1] | N-cyclobutyl-2-((5-(2,6-dichloro-4-(6-(difluoromethyl)-3,5-dioxo-4,5-dihydro-1,2,4-triazin-2(3H)-yl)phenoxy)-2-hydroxyphenyl)sulfonamido)acetamide |
| 63 | 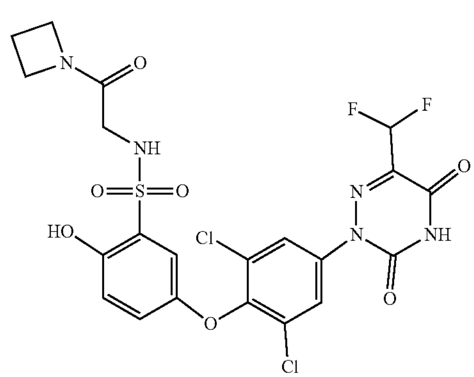 [SMILES: O=C(CNS(=O)(=O)c1cc(Oc2c(Cl)cc(-n3nc(C(F)F)c(=O)[nH]c3=O)cc2Cl)ccc1O)N1CCC1] | N-(2-(azetidin-1-yl)-2-oxoethyl)-5-(2,6-dichloro-4-(6-(difluoromethyl)-3,5-dioxo-4,5-dihydro-1,2,4-triazin-2(3H)-yl)phenoxy)-2-hydroxybenzenesulfonamide |

TABLE 1-continued

| Cmpd No. | Structure | Chemical Name |
|---|---|---|
| 64 | 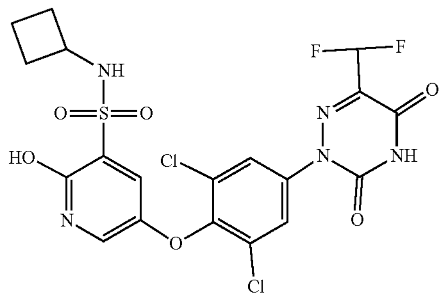 [SMILES: O=c1[nH]c(=O)n(-c2cc(Cl)c(Oc3cnc(O)c(S(=O)(=O)NC4CCC4)c3)c(Cl)c2)nc1C(F)F] | N-cyclobutyl-5-(2,6-dichloro-4-(6-(difluoromethyl)-3,5-dioxo-4,5-dihydro-1,2,4-triazin-2(3H)-yl)phenoxy)-2-hydroxypyridine-3-sulfonamide |
| 65 | 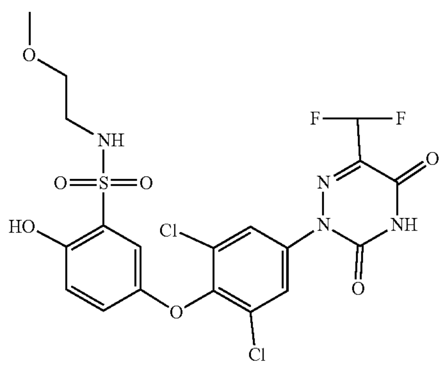 [SMILES: COCCNS(=O)(=O)c1cc(Oc2c(Cl)cc(-n3nc(C(F)F)c(=O)[nH]c3=O)cc2Cl)ccc1O] | 5-(2,6-dichloro-4-(6-(difluoromethyl)-3,5-dioxo-4,5-dihydro-1,2,4-triazin-2(3H)-yl)phenoxy)-2-hydroxy-N-(2-methoxyethyl)benzenesulfonamide |
| 66 | 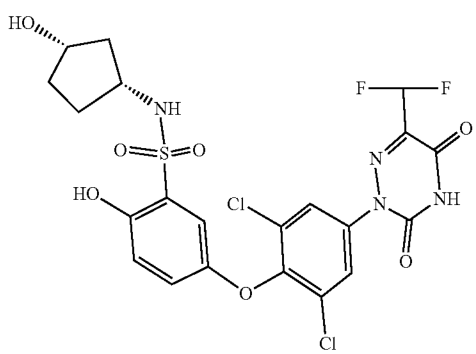 [SMILES: O=c1[nH]c(=O)n(-c2cc(Cl)c(Oc3ccc(O)c(S(=O)(=O)N[C@@H]4CC[C@H](O)C4)c3)c(Cl)c2)nc1C(F)F] | 5-(2,6-dichloro-4-(6-(difluoromethyl)-3,5-dioxo-4,5-dihydro-1,2,4-triazin-2(3H)-yl)phenoxy)-2-hydroxy-N-((1R,3S)-3-hydroxycyclopentyl)benzenesulfonamide |
| 67 | 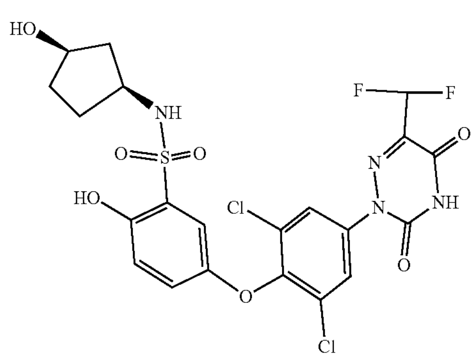 [SMILES: O=c1[nH]c(=O)n(-c2cc(Cl)c(Oc3ccc(O)c(S(=O)(=O)N[C@H]4CC[C@@H](O)C4)c3)c(Cl)c2)nc1C(F)F] | 5-(2,6-dichloro-4-(6-(difluoromethyl)-3,5-dioxo-4,5-dihydro-1,2,4-triazin-2(3H)-yl)phenoxy)-2-hydroxy-N-((1S,3R)-3-hydroxycyclopentyl)benzenesulfonamide |

TABLE 1-continued

| Cmpd No. | Structure | Chemical Name |
|---|---|---|
| 68 | 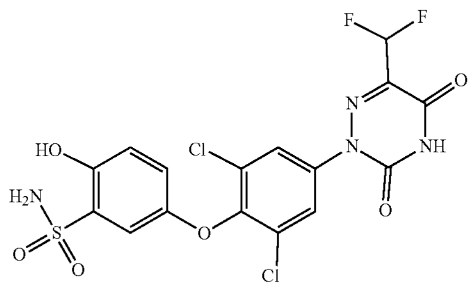 [SMILES: NS(=O)(=O)c1cc(Oc2c(Cl)cc(-n3nc(C(F)F)c(=O)[nH]c3=O)cc2Cl)ccc1O] | 5-(2,6-dichloro-4-(6-(difluoromethyl)-3,5-dioxo-4,5-dihydro-1,2,4-triazin-2(3H)-yl)phenoxy)-2-hydroxybenzenesulfonamide |
| 69 | 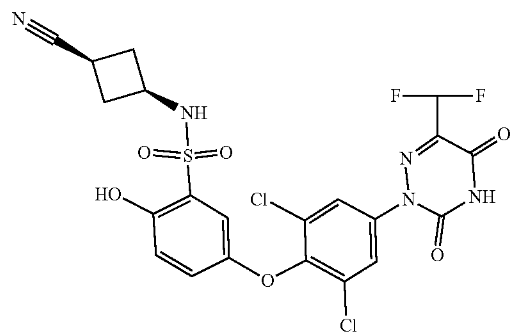 [SMILES: N#C[C@H]1C[C@@H](NS(=O)(=O)c2cc(Oc3c(Cl)cc(-n4nc(C(F)F)c(=O)[nH]c4=O)cc3Cl)ccc2O)C1] | N-((1s,3s)-3-cyanocyclobutyl)-5-(2,6-dichloro-4-(6-(difluoromethyl)-3,5-dioxo-4,5-dihydro-1,2,4-triazin-2(3H)-yl)phenoxy)-2-hydroxybenzenesulfonamide |
| 70 | 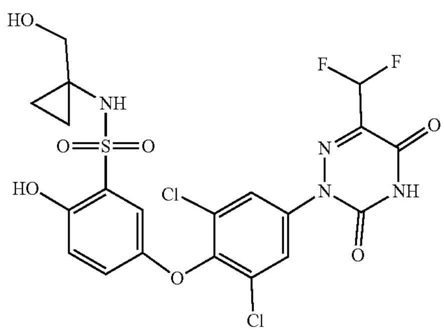 [SMILES: O=c1[nH]c(=O)n(-c2cc(Cl)c(Oc3ccc(O)c(S(=O)(=O)NC4(CO)CC4)c3)c(Cl)c2)nc1C(F)F] | 5-(2,6-dichloro-4-(6-(difluoromethyl)-3,5-dioxo-4,5-dihydro-1,2,4-triazin-2(3H)-yl)phenoxy)-2-hydroxy-N-(1-(hydroxymethyl)cyclopropyl)benzenesulfonamide |
| 71 | 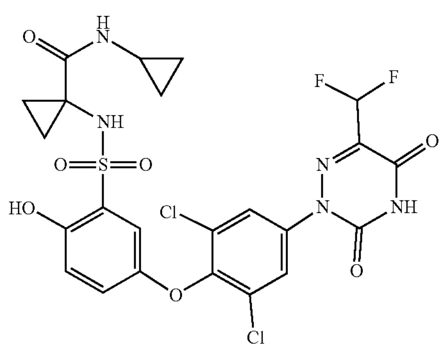 [SMILES: O=C(NC1CC1)C1(NS(=O)(=O)c2cc(Oc3c(Cl)cc(-n4nc(C(F)F)c(=O)[nH]c4=O)cc3Cl)ccc2O)CC1] | N-cyclopropyl-1-((5-(2,6-dichloro-4-(6-(difluoromethyl)-3,5-dioxo-4,5-dihydro-1,2,4-triazin-2(3H)-yl)phenoxy)-2-hydroxyphenyl)sulfonamido)cyclopropane-1-carboxamide |
| 72 | 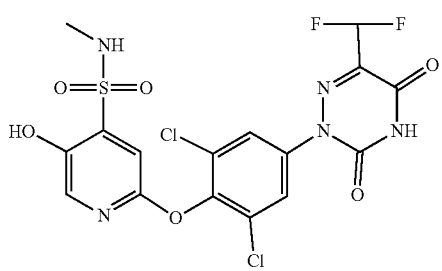 [SMILES: CNS(=O)(=O)c1cc(Oc2c(Cl)cc(-n3nc(C(F)F)c(=O)[nH]c3=O)cc2Cl)ncc1O] | 2-(2,6-dichloro-4-(6-(difluoromethyl)-3,5-dioxo-4,5-dihydro-1,2,4-triazin-2(3H)-yl)phenoxy)-5-hydroxy-N-methylpyridine-4-sulfonamide |

TABLE 1-continued

| Cmpd No. | Structure | Chemical Name |
| --- | --- | --- |
| 73 | 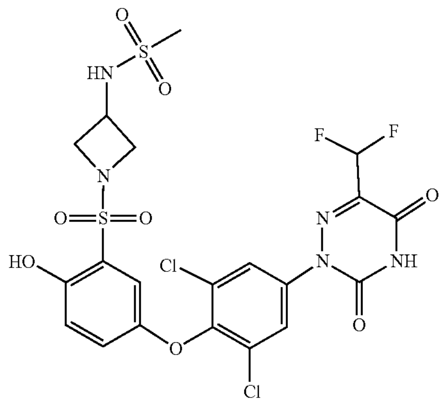 [SMILES: CS(=O)(=O)NC1CN(S(=O)(=O)c2cc(Oc3c(Cl)cc(-n4nc(C(F)F)c(=O)[nH]c4=O)cc3Cl)ccc2O)C1] | N-(1-((5-(2,6-dichloro-4-(6-(difluoromethyl)-3,5-dioxo-4,5-dihydro-1,2,4-triazin-2(3H)-yl)phenoxy)-2-hydroxyphenyl)sulfonyl)azetidin-3-yl)methanesulfonamide |
| 74 | 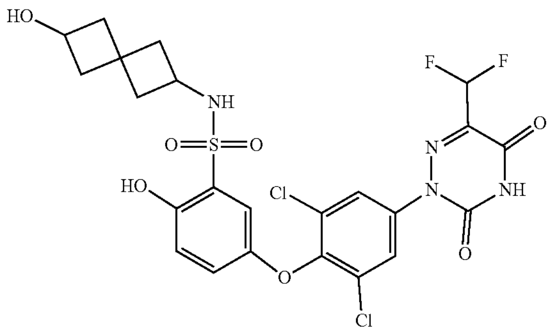 [SMILES: O=c1[nH]c(=O)n(-c2cc(Cl)c(Oc3ccc(O)c(S(=O)(=O)NC4CC5(CC(O)C5)C4)c3)c(Cl)c2)nc1C(F)F] | 5-(2,6-dichloro-4-(6-(difluoromethyl)-3,5-dioxo-4,5-dihydro-1,2,4-triazin-2(3H)-yl)phenoxy)-2-hydroxy-N-(6-hydroxyspiro[3.3]heptan-2-yl)benzenesulfonamide |
| 75 | 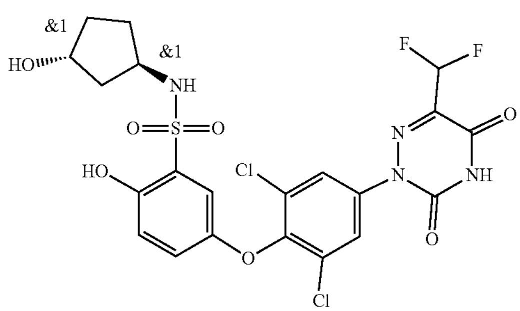 [SMILES: O=c1[nH]c(=O)n(-c2cc(Cl)c(Oc3ccc(O)c(S(=O)(=O)N[C@@H]4CC[C@@H](O)C4)c3)c(Cl)c2)nc1C(F)F] | 5-(2,6-dichloro-4-(6-(difluoromethyl)-3,5-dioxo-4,5-dihydro-1,2,4-triazin-2(3H)-yl)phenoxy)-2-hydroxy-N-((1R,3R)-3-hydroxycyclopentyl)benzenesulfonamide |
| 76 | 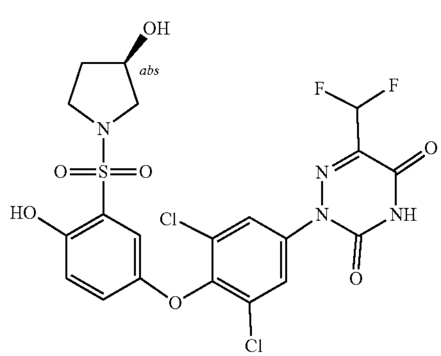 [SMILES: O=c1[nH]c(=O)n(-c2cc(Cl)c(Oc3ccc(O)c(S(=O)(=O)N4CC[C@@H](O)C4)c3)c(Cl)c2)nc1C(F)F] | (R)-2-(3,5-dichloro-4-(4-hydroxy-3-((3-hydroxypyrrolidin-1-yl)sulfonyl)phenoxy)phenyl)-6-(difluoromethyl)-1,2,4-triazine-3,5(2H,4H)-dione |

TABLE 1-continued

| Cmpd No. | Structure | Chemical Name |
|---|---|---|
| 77 | 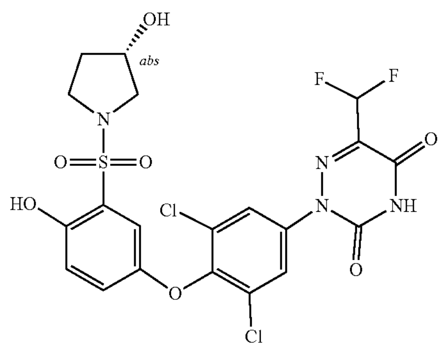 [SMILES: O=c1[nH]c(=O)n(-c2cc(Cl)c(Oc3ccc(O)c(S(=O)(=O)N4CC[C@H](O)C4)c3)c(Cl)c2)nc1C(F)F] | (S)-2-(3,5-dichloro-4-(4-hydroxy-3-((3-hydroxypyrrolidin-1-yl)sulfonyl)phenoxy)phenyl)-6-(difluoromethyl)-1,2,4-triazine-3,5(2H,4H)-dione |
| 78 | 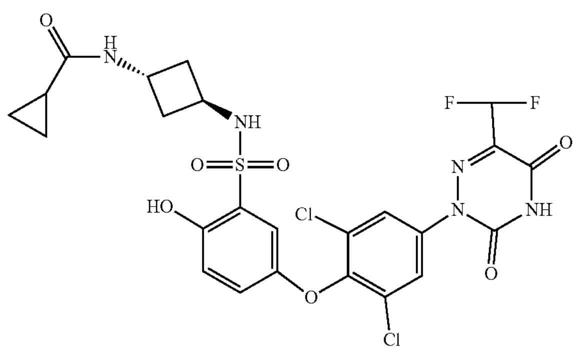 [SMILES: O=C(N[C@H]1C[C@H](NS(=O)(=O)c2cc(Oc3c(Cl)cc(-n4nc(C(F)F)c(=O)[nH]c4=O)cc3Cl)ccc2O)C1)C1CC1] | N-((1r,3r)-3-((5-(2,6-dichloro-4-(6-(difluoromethyl)-3,5-dioxo-4,5-dihydro-1,2,4-triazin-2(3H)-yl)phenoxy)-2-hydroxyphenyl)sulfonamido)cyclobutyl)cyclopropanecarboxamide |
| 79 | 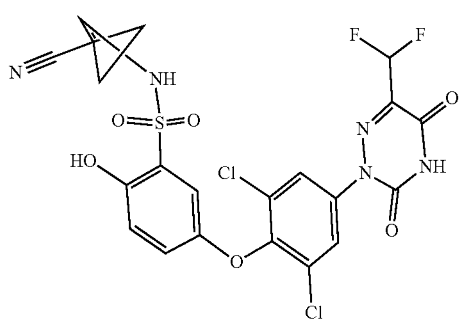 | N-(3-cyanobicyclo[1.1.1]pentan-1-yl)-5-(2,6-dichloro-4-(6-(difluoromethyl)-3,5-dioxo-4,5-dihydro-1,2,4-triazin-2(3H)-yl)phenoxy)-2-hydroxybenzenesulfonamide |
| 80 | 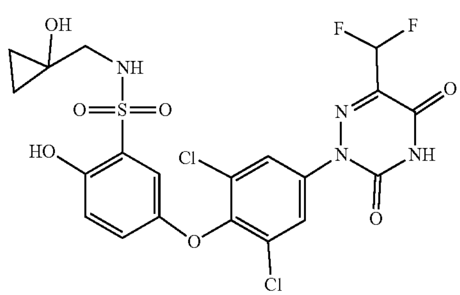 [SMILES: O=c1[nH]c(=O)n(-c2cc(Cl)c(Oc3ccc(O)c(S(=O)(=O)NCC4(O)CC4)c3)c(Cl)c2)nc1C(F)F] | 5-(2,6-dichloro-4-(6-(difluoromethyl)-3,5-dioxo-4,5-dihydro-1,2,4-triazin-2(3H)-yl)phenoxy)-2-hydroxy-N-((1-hydroxycyclopropyl)methyl)benzenesulfonamide |

TABLE 1-continued

| Cmpd No. | Structure | Chemical Name |
| --- | --- | --- |
| 81 | 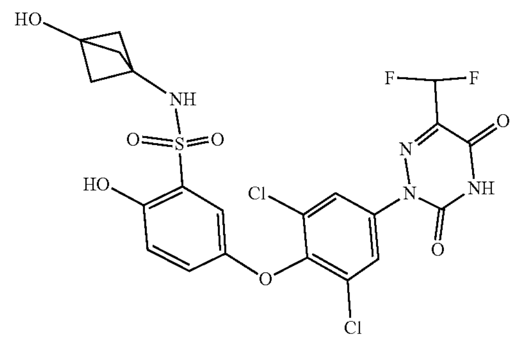 [SMILES: O=c1[nH]c(=O)n(-c2cc(Cl)c(Oc3ccc(O)c(S(=O)(=O)NC45CC(O)(C4)C5)c3)c(Cl)c2)nc1C(F)F] | 5-(2,6-dichloro-4-(6-(difluoromethyl)-3,5-dioxo-4,5-dihydro-1,2,4-triazin-2(3H)-yl)phenoxy)-2-hydroxy-N-(3-hydroxybicyclo[1.1.1]pentan-1-yl)benzenesulfonamide |
| 82 | 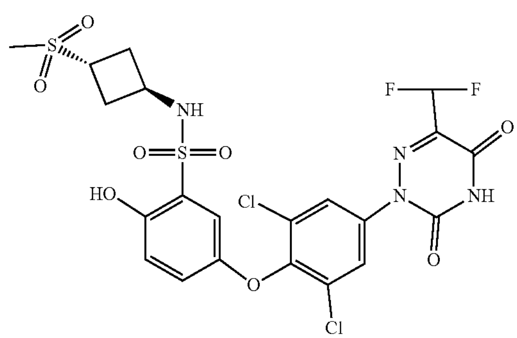 [SMILES: CS(=O)(=O)[C@H]1C[C@H](NS(=O)(=O)c2cc(Oc3c(Cl)cc(-n4nc(C(F)F)c(=O)[nH]c4=O)cc3Cl)ccc2O)C1] | 5-(2,6-dichloro-4-(6-(difluoromethyl)-3,5-dioxo-4,5-dihydro-1,2,4-triazin-2(3H)-yl)phenoxy)-2-hydroxy-N-((1r,3r)-3-(methylsulfonyl)cyclobutyl)benzenesulfonamide |
| 83 | 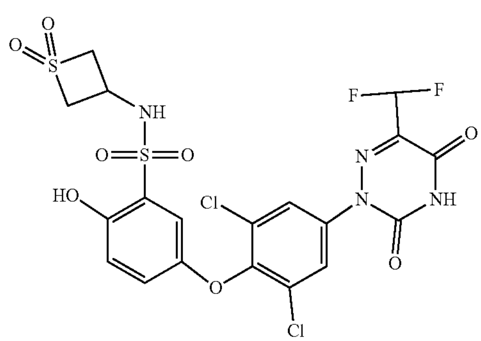 [SMILES: O=c1[nH]c(=O)n(-c2cc(Cl)c(Oc3ccc(O)c(S(=O)(=O)NC4CS(=O)(=O)C4)c3)c(Cl)c2)nc1C(F)F] | 5-(2,6-dichloro-4-(6-(difluoromethyl)-3,5-dioxo-4,5-dihydro-1,2,4-triazin-2(3H)-yl)phenoxy)-N-(1,1-dioxidothietan-3-yl)-2-hydroxybenzenesulfonamide |
| 84 | 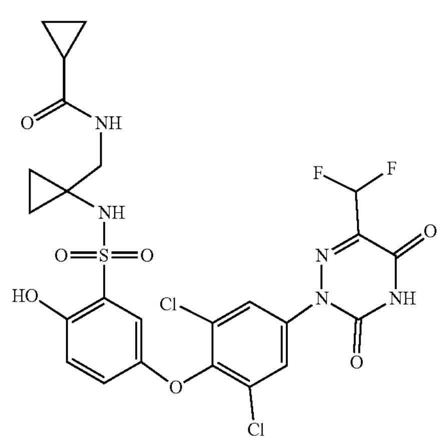 [SMILES: O=C(NCC1(NS(=O)(=O)c2cc(Oc3c(Cl)cc(-n4nc(C(F)F)c(=O)[nH]c4=O)cc3Cl)ccc2O)CC1)C1CC1] | N-((1-((5-(2,6-dichloro-4-(6-(difluoromethyl)-3,5-dioxo-4,5-dihydro-1,2,4-triazin-2(3H)-yl)phenoxy)-2-hydroxyphenyl)sulfonamido)cyclopropyl)methyl)cyclopropanecarboxamide |

TABLE 1-continued

| Cmpd No. | Structure | Chemical Name |
|---|---|---|
| 85 | 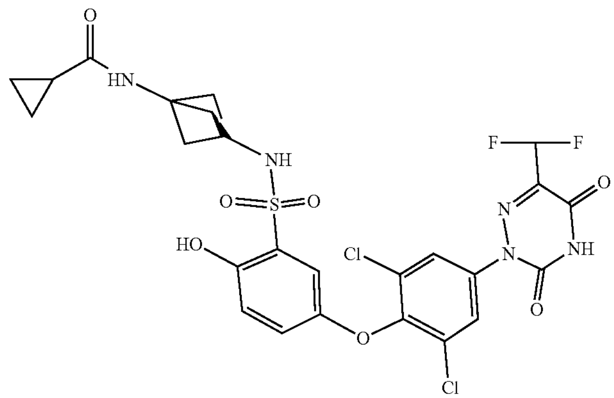 | N-(3-((5-(2,6-dichloro-4-(6-(difluoromethyl)-3,5-dioxo-4,5-dihydro-1,2,4-triazin-2(3H)-yl)phenoxy)-2-hydroxyphenyl)sulfonamido)bicyclo[1.1.1]pentan-1-yl)cyclopropanecarboxamide |
| 86 | 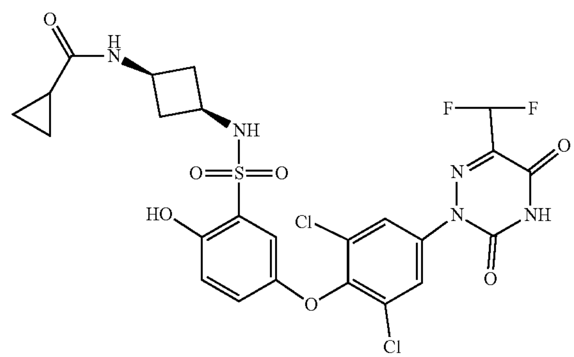 [SMILES: O=C(N[C@H]1C[C@@H](NS(=O)(=O)c2cc(Oc3c(Cl)cc(-n4nc(C(F)F)c(=O)[nH]c4=O)cc3Cl)ccc2O)C1)C1CC1] | N-((1s,3s)-3-((5-(2,6-dichloro-4-(6-(difluoromethyl)-3,5-dioxo-4,5-dihydro-1,2,4-triazin-2(3H)-yl)phenoxy)-2-hydroxyphenyl)sulfonamido)cyclobutyl)cyclopropanecarboxamide |
| 87 | 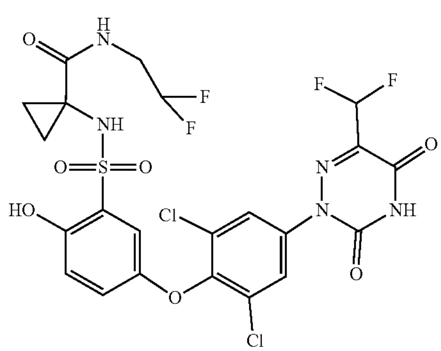 [SMILES: O=C(NCC(F)F)C1(NS(=O)(=O)c2cc(Oc3c(Cl)cc(-n4nc(C(F)F)c(=O)[nH]c4=O)cc3Cl)ccc2O)CC1] | 1-((5-(2,6-dichloro-4-(6-(difluoromethyl)-3,5-dioxo-4,5-dihydro-1,2,4-triazin-2(3H)-yl)phenoxy)-2-hydroxyphenyl)sulfonamido)-N-(2,2-difluoroethyl)cyclopropane-1-carboxamide |
| 88 | 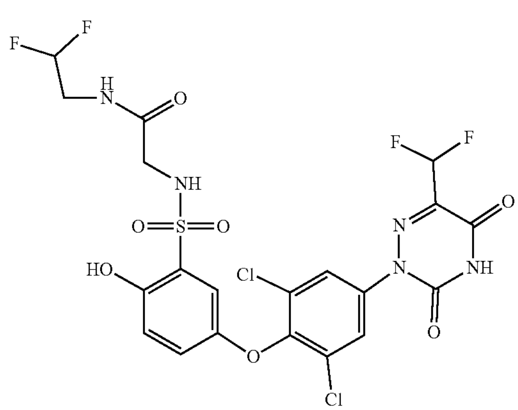 [SMILES: O=C(CNS(=O)(=O)c1cc(Oc2c(Cl)cc(-n3nc(C(F)F)c(=O)[nH]c3=O)cc2Cl)ccc1O)NCC(F)F] | 2-((5-(2,6-dichloro-4-(6-(difluoromethyl)-3,5-dioxo-4,5-dihydro-1,2,4-triazin-2(3H)-yl)phenoxy)-2-hydroxyphenyl)sulfonamido)-N-(2,2-difluoroethyl)acetamide |

TABLE 1-continued

| Cmpd No. | Structure | Chemical Name |
|---|---|---|
| 89 | 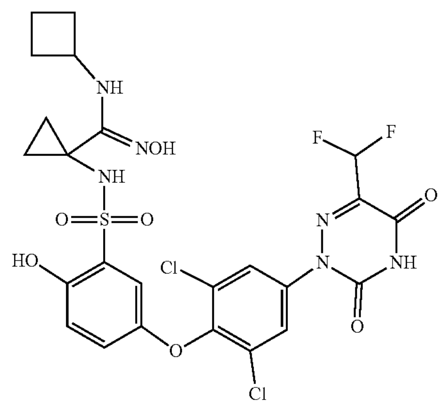 | N-cyclobutyl-1-((5-(2,6-dichloro-4-(6-(difluoromethyl)-3,5-dioxo-4,5-dihydro-1,2,4-triazin-2(3H)-yl)phenoxy)-2-hydroxyphenyl)sulfonamido)cyclopropane-1-carboxamide |
| 90 | 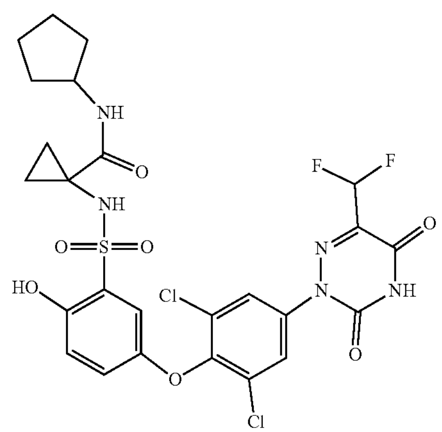 [SMILES: O=C(NC1CCCC1)C1(NS(=O)(=O)c2cc(Oc3c(Cl)cc(-n4nc(C(F)F)c(=O)[nH]c4=O)cc3Cl)ccc2O)CC1] | N-cyclopentyl-1-((5-(2,6-dichloro-4-(6-(difluoromethyl)-3,5-dioxo-4,5-dihydro-1,2,4-triazin-2(3H)-yl)phenoxy)-2-hydroxyphenyl)sulfonamido)cyclopropane-1-carboxamide |
| 91 | 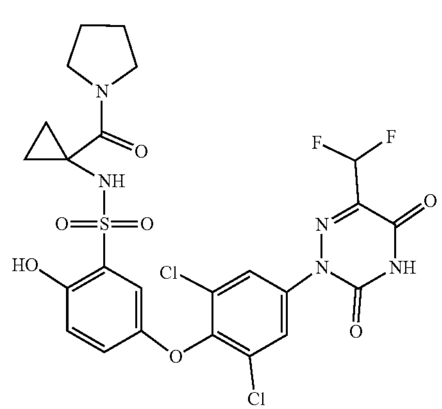 [SMILES: O=C(N1CCCC1)C1(NS(=O)(=O)c2cc(Oc3c(Cl)cc(-n4nc(C(F)F)c(=O)[nH]c4=O)cc3Cl)ccc2O)CC1] | 5-(2,6-dichloro-4-(6-(difluoromethyl)-3,5-dioxo-4,5-dihydro-1,2,4-triazin-2(3H)-yl)phenoxy)-2-hydroxy-N-(1-(pyrrolidine-1-carbonyl)cyclopropyl)benzenesulfonamide |

TABLE 1-continued

| Cmpd No. | Structure | Chemical Name |
|---|---|---|
| 92 | 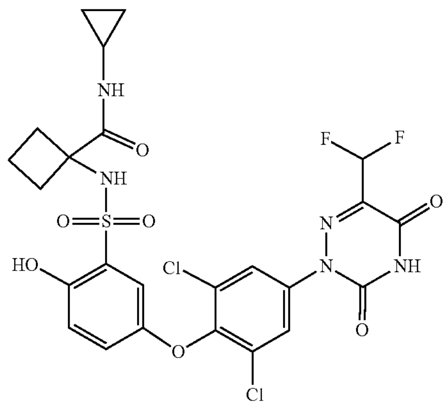 [SMILES: O=C(NC1CC1)C1(NS(=O)(=O)c2cc(Oc3c(Cl)cc(-n4nc(C(F)F)c(=O)[nH]c4=O)cc3Cl)ccc2O)CCC1] | N-cyclopropyl-1-((5-(2,6-dichloro-4-(6-(difluoromethyl)-3,5-dioxo-4,5-dihydro-1,2,4-triazin-2(3H)-yl)phenoxy)-2-hydroxyphenyl)sulfonamido)cyclobutane-1-carboxamide |
| 93 | 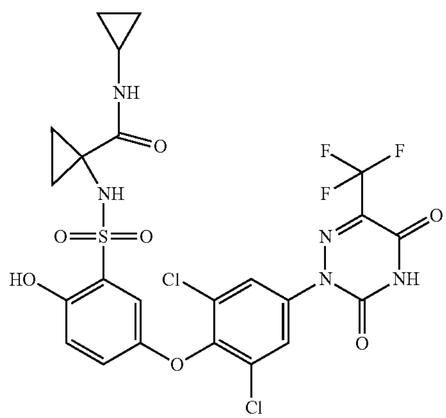 [SMILES: O=C(NC1CC1)C1(NS(=O)(=O)c2cc(Oc3c(Cl)cc(-n4nc(C(F)(F)F)c(=O)[nH]c4=O)cc3Cl)ccc2O)CC1] | N-cyclopropyl-1-((5-(2,6-dichloro-4-(3,5-dioxo-6-(trifluoromethyl)-4,5-dihydro-1,2,4-triazin-2(3H)-yl)phenoxy)-2-hydroxyphenyl)sulfonamido)cyclopropane-1-carboxamide |
| 94 | 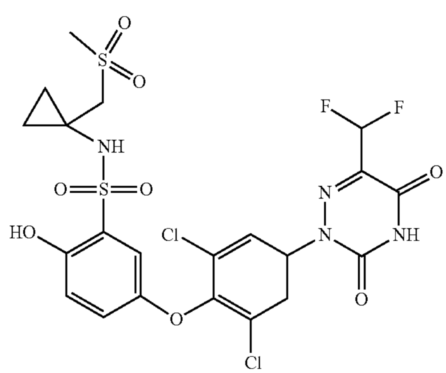 [SMILES: CS(=O)(=O)CC1(NS(=O)(=O)c2cc(OC3=C(Cl)CC(n4nc(C(F)F)c(=O)[nH]c4=O)C=C3Cl)ccc2O)CC1] | 5-(2,6-dichloro-4-(6-(difluoromethyl)-3,5-dioxo-4,5-dihydro-1,2,4-triazin-2(3H)-yl)phenoxy)-2-hydroxy-N-(1-((methylsulfonyl)methyl)cyclopropyl)benzenesulfonamide |
| 95 | 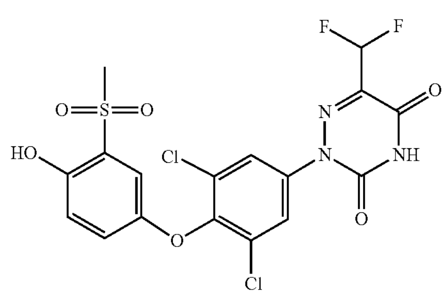 [SMILES: CS(=O)(=O)c1cc(Oc2c(Cl)cc(-n3nc(C(F)F)c(=O)[nH]c3=O)cc2Cl)ccc1O] | 2-(3,5-dichloro-4-(4-hydroxy-3-(methylsulfonyl)phenoxy)phenyl)-6-(difluoromethyl)-1,2,4-triazine-3,5(2H,4H)-dione |

TABLE 1-continued

| Cmpd No. | Structure | Chemical Name |
| --- | --- | --- |
| 96 | 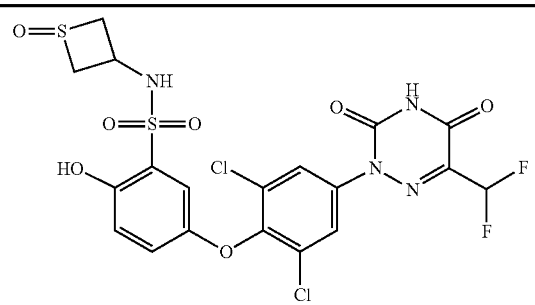 | 5-(2,6-dichloro-4-(6-(difluoromethyl)-3,5-dioxo-4,5-dihydro-1,2,4-triazin-2(3H)-yl)phenoxy)-2-hydroxy-N-(1-oxidothietan-3-yl)benzenesulfonamide |
| 97 | 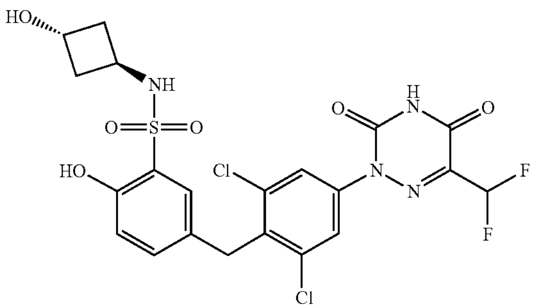 [SMILES: O=c1[nH]c(=O)n(-c2cc(Cl)c(Cc3ccc(O)c(S(=O)(=O)N[C@H]4C[C@H](O)C4)c3)c(Cl)c2)nc1C(F)F] | 5-(2,6-dichloro-4-(6-(difluoromethyl)-3,5-dioxo-4,5-dihydro-1,2,4-triazin-2(3H)-yl)benzyl)-2-hydroxy-N-((1r,3r)-3-hydroxycyclobutyl)benzenesulfonamide |
| 98 | 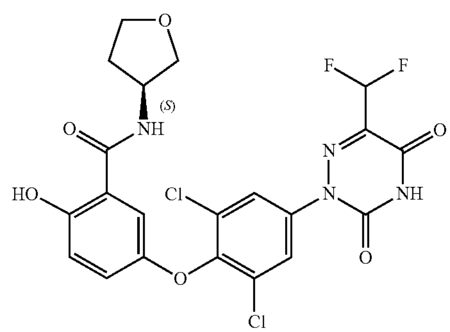 | (S)-5-(2,6-dichloro-4-(6-(difluoromethyl)-3,5-dioxo-4,5-dihydro-1,2,4-triazin-2(3H)-yl)phenoxy)-2-hydroxy-N-(tetrahydrofuran-3-yl)benzamide |
| 99 | 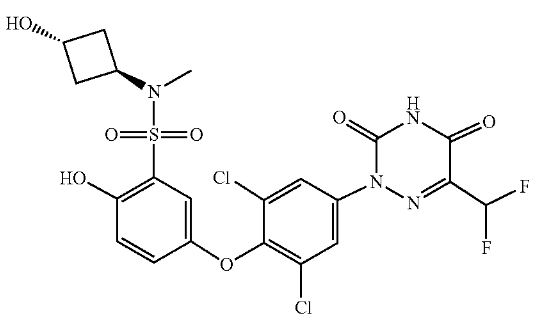 [SMILES: CN([C@H]1C[C@H](O)C1)S(=O)(=O)c1cc(Oc2c(Cl)cc(-n3nc(C(F)F)c(=O)[nH]c3=O)cc2Cl)ccc1O] | 5-(2,6-dichloro-4-(6-(difluoromethyl)-3,5-dioxo-4,5-dihydro-1,2,4-triazin-2(3H)-yl)phenoxy)-2-hydroxy-N-((1r,3r)-3-hydroxycyclobutyl)-N-methylbenzenesulfonamide |
| 100 | 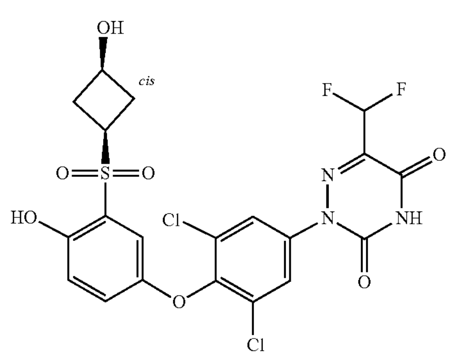 [SMILES: O=c1[nH]c(=O)n(-c2cc(Cl)c(Oc3ccc(O)c(S(=O)(=O)[C@H]4C[C@@H](O)C4)c3)c(Cl)c2)nc1C(F)F] | 2-(3,5-dichloro-4-(4-hydroxy-3-(((1s,3s)-3-hydroxycyclobutyl)sulfonyl)phenoxy)phenyl)-6-(difluoromethyl)-1,2,4-triazine-3,5(2H,4H)-dione |

TABLE 1-continued

| Cmpd No. | Structure | Chemical Name |
|---|---|---|
| 101 | 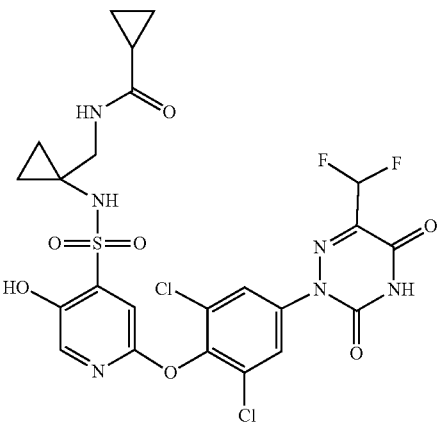 [SMILES: O=C(NCC1(NS(=O)(=O)c2cc(Oc3c(Cl)cc(-n4nc(C(F)F)c(=O)[nH]c4=O)cc3Cl)ncc2O)CC1)C1CC1] | N-((1-((2-(2,6-dichloro-4-(6-(difluoromethyl)-3,5-dioxo-4,5-dihydro-1,2,4-triazin-2(3H)-yl)phenoxy)-5-hydroxypyridine)-4-sulfonamido)cyclopropyl)methyl)cyclopropanecarboxamide |
| 102 | 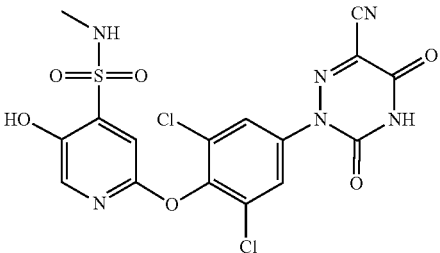 [SMILES: CNS(=O)(=O)c1cc(Oc2c(Cl)cc(-n3nc(C#N)c(=O)[nH]c3=O)cc2Cl)ncc1O] | 2-(2,6-dichloro-4-(6-cyano-3,5-dioxo-4,5-dihydro-1,2,4-triazin-2(3H)-yl)phenoxy)-5-hydroxy-N-methylpyridine-4-sulfonamide |
| 103 | 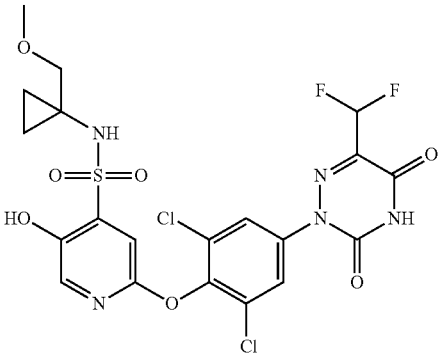 | 2-(2,6-dichloro-4-(6-(difluoromethyl)-3,5-dioxo-4,5-dihydro-1,2,4-triazin-2(3H)-yl)phenoxy)-5-hydroxy-N-(1-(methoxymethyl)cyclopropyl)pyridine-4-sulfonamide |
| 104 | 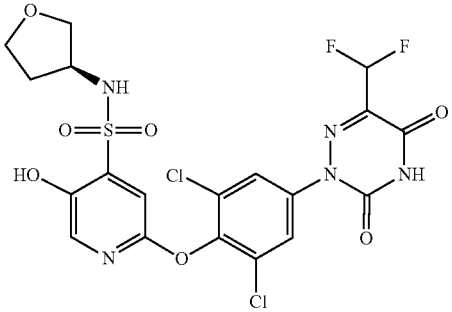 [SMILES: O=c1[nH]c(=O)n(-c2cc(Cl)c(Oc3cc(S(=O)(=O)N[C@H]4CCOC4)c(O)cn3)c(Cl)c2)nc1C(F)F] | (S)-2-(2,6-dichloro-4-(6-(difluoromethyl)-3,5-dioxo-4,5-dihydro-1,2,4-triazin-2(3H)-yl)phenoxy)-5-hydroxy-N-(tetrahydrofuran-3-yl)pyridine-4-sulfonamide |

| Cmpd No. | Structure | Chemical Name |
|---|---|---|
| 105 | 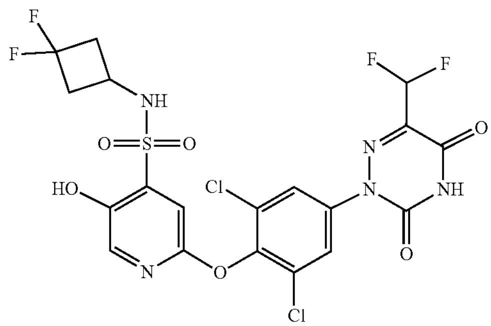 [SMILES: O=c1[nH]c(=O)n(-c2cc(Cl)c(Oc3cc(S(=O)(=O)NC4CC(F)(F)C4)c(O)cn3)c(Cl)c2)nc1C(F)F] | 2-(2,6-dichloro-4-(6-(difluoromethyl)-3,5-dioxo-4,5-dihydro-1,2,4-triazin-2(3H)-yl)phenoxy)-N-(3,3-difluorocyclobutyl)-5-hydroxypyridine-4-sulfonamide |
| 106 | 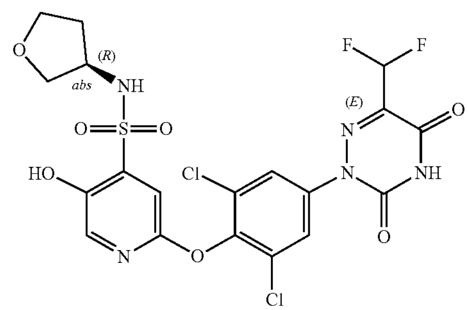 | (R)-2-(2,6-dichloro-4-(6-(difluoromethyl)-3,5-dioxo-4,5-dihydro-1,2,4-triazin-2(3H)-yl)phenoxy)-5-hydroxy-N-(tetrahydrofuran-3-yl)pyridine-4-sulfonamide |
| 107 | 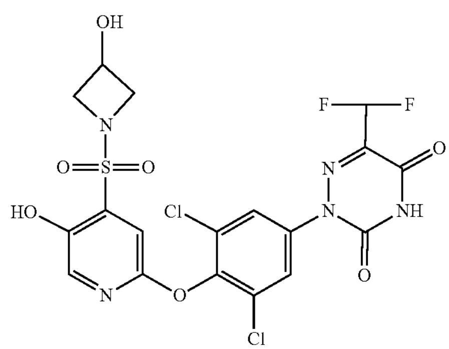 [SMILES: O=c1[nH]c(=O)n(-c2cc(Cl)c(Oc3cc(S(=O)(=O)N4CC(O)C4)c(O)cn3)c(Cl)c2)nc1C(F)F] | 2-(3,5-dichloro-4-((5-hydroxy-4-((3-hydroxyazetidin-1-yl)sulfonyl)pyridin-2-yl)oxy)phenyl)-6-(difluoromethyl)-1,2,4-triazine-3,5(2H,4H)-dione |
| 108 | 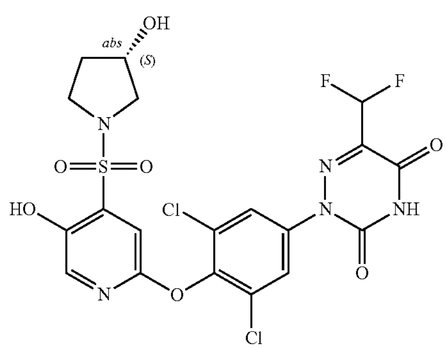 | (S)-2-(3,5-dichloro-4-((5-hydroxy-4-((3-hydroxypyrrolidin-1-yl)sulfonyl)pyridin-2-yl)oxy)phenyl)-6-(difluoromethyl)-1,2,4-triazine-3,5(2H,4H)-dione |

TABLE 1-continued

| Cmpd No. | Structure | Chemical Name |
|---|---|---|
| 109 | 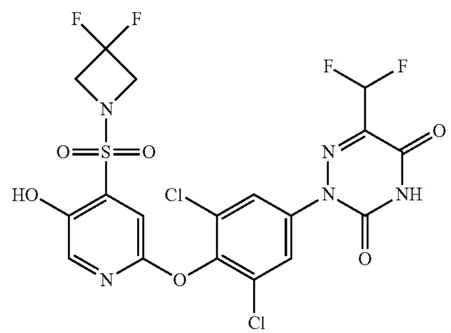 [SMILES: O=c1[nH]c(=O)n(-c2cc(Cl)c(Oc3cc(S(=O)(=O)N4CC(F)(F)C4)c(O)cn3)c(Cl)c2)nc1C(F)F] | 2-(3,5-dichloro-4-((4-((3,3-difluoroazetidin-1-yl)sulfonyl)-5-hydroxypyridin-2-yl)oxy)phenyl)-6-(difluoromethyl)-1,2,4-triazine-3,5(2H,4H)-dione |
| 110 | 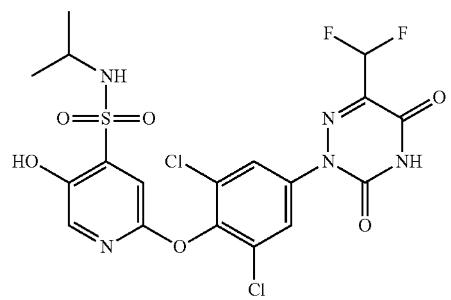 [SMILES: CC(C)NS(=O)(=O)c1cc(Oc2c(Cl)cc(-n3nc(C(F)F)c(=O)[nH]c3=O)cc2Cl)ncc1O] | 2-(2,6-dichloro-4-(6-(difluoromethyl)-3,5-dioxo-4,5-dihydro-1,2,4-triazin-2(3H)-yl)phenoxy)-5-hydroxy-N-isopropylpyridine-4-sulfonamide |
| 111 | 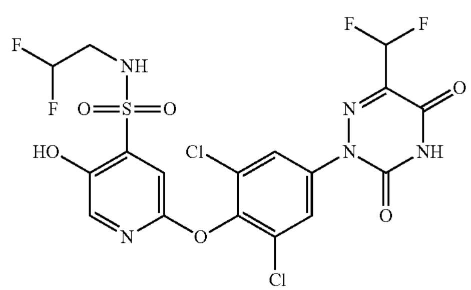 [SMILES: O=c1[nH]c(=O)n(-c2cc(Cl)c(Oc3cc(S(=O)(=O)NCC(F)F)c(O)cn3)c(Cl)c2)nc1C(F)F] | 2-(2,6-dichloro-4-(6-(difluoromethyl)-3,5-dioxo-4,5-dihydro-1,2,4-triazin-2(3H)-yl)phenoxy)-N-(2,2-difluoroethyl)-5-hydroxypyridine-4-sulfonamide |
| 112 | 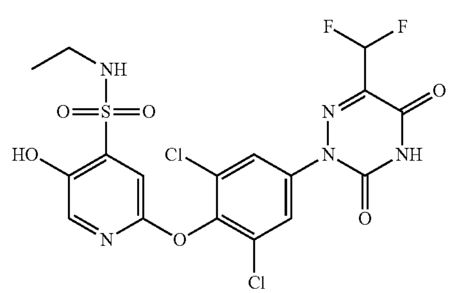 [SMILES: CCNS(=O)(=O)c1cc(Oc2c(Cl)cc(-n3nc(C(F)F)c(=O)[nH]c3=O)cc2Cl)ncc1O] | 2-(2,6-dichloro-4-(6-(difluoromethyl)-3,5-dioxo-4,5-dihydro-1,2,4-triazin-2(3H)-yl)phenoxy)-N-ethyl-5-hydroxypyridine-4-sulfonamide |
| 113 | 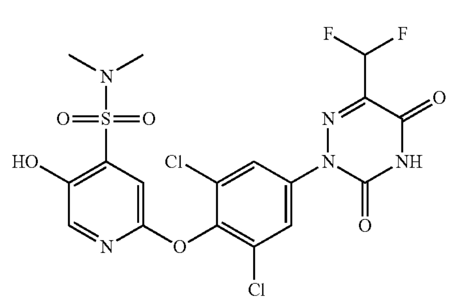 [SMILES: CN(C)S(=O)(=O)c1cc(Oc2c(Cl)cc(-n3nc(C(F)F)c(=O)[nH]c3=O)cc2Cl)ncc1O] | 2-(2,6-dichloro-4-(6-(difluoromethyl)-3,5-dioxo-4,5-dihydro-1,2,4-triazin-2(3H)-yl)phenoxy)-5-hydroxy-N,N-dimethylpyridine-4-sulfonamide |

TABLE 1-continued

| Cmpd No. | Structure | Chemical Name |
|---|---|---|
| 114 | 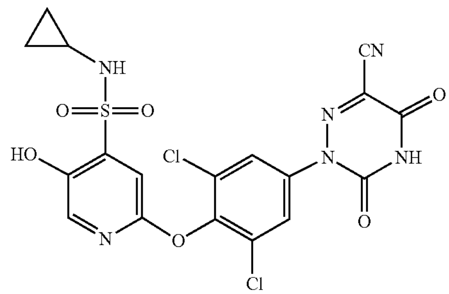 [SMILES: N#Cc1nn(-c2cc(Cl)c(Oc3cc(S(=O)(=O)NC4CC4)c(O)cn3)c(Cl)c2)c(=O)[nH]c1=O] | N-cyclopropyl-2-(2,6-dichloro-4-(6-cyano-3,5-dioxo-4,5-dihydro-1,2,4-triazin-2(3H)-yl)phenoxy)-5-hydroxypyridine-4-sulfonamide |
| 115 | 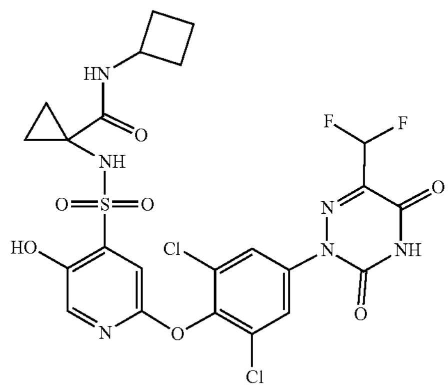 [SMILES: O=C(NC1CCC1)C1(NS(=O)(=O)c2cc(Oc3c(Cl)cc(-n4nc(C(F)F)c(=O)[nH]c4=O)cc3Cl)ncc2O)CC1] | N-cyclobutyl-1-((2-(2,6-dichloro-4-(6-(difluoromethyl)-3,5-dioxo-4,5-dihydro-1,2,4-triazin-2(3H)-yl)phenoxy)-5-hydroxypyridine)-4-sulfonamido)cyclopropane-1-carboxamide |
| 116 | 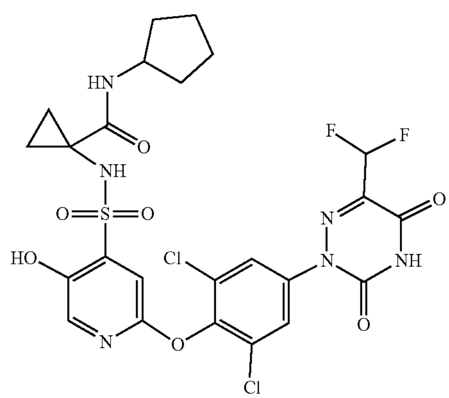 [SMILES: O=C(NC1CCCC1)C1(NS(=O)(=O)c2cc(Oc3c(Cl)cc(-n4nc(C(F)F)c(=O)[nH]c4=O)cc3Cl)ncc2O)CC1] | N-cyclopentyl-1-((2-(2,6-dichloro-4-(6-(difluoromethyl)-3,5-dioxo-4,5-dihydro-1,2,4-triazin-2(3H)-yl)phenoxy)-5-hydroxypyridine)-4-sulfonamido)cyclopropane-1-carboxamide |
| 117 | 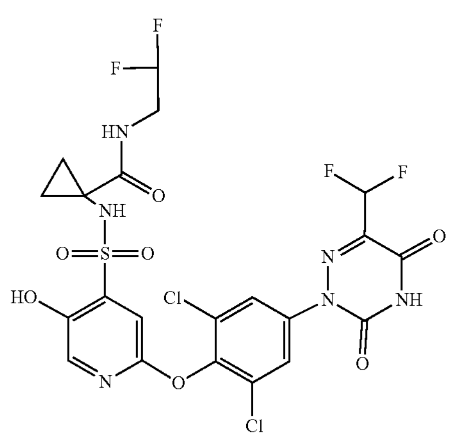 [SMILES: O=C(NCC(F)F)C1(NS(=O)(=O)c2cc(Oc3c(Cl)cc(-n4nc(C(F)F)c(=O)[nH]c4=O)cc3Cl)ncc2O)CC1] | 1-((2-(2,6-dichloro-4-(6-(difluoromethyl)-3,5-dioxo-4,5-dihydro-1,2,4-triazin-2(3H)-yl)phenoxy)-5-hydroxypyridine)-4-sulfonamido)-N-(2,2-difluoroethyl)cyclopropane-1-carboxamide |

TABLE 1-continued

| Cmpd No. | Structure | Chemical Name |
| --- | --- | --- |
| 118 | 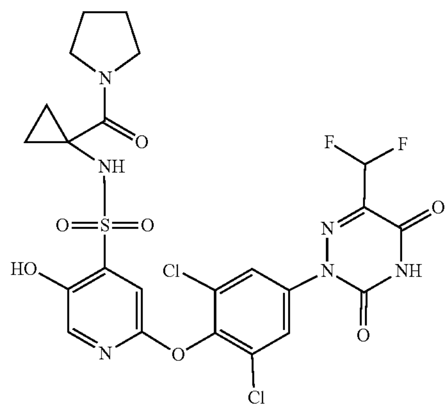 [SMILES: O=C(N1CCCC1)C1(NS(=O)(=O)c2cc(Oc3c(Cl)cc(-n4nc(C(F)F)c(=O)[nH]c4=O)cc3Cl)ncc2O)CC1] | 2-(2,6-dichloro-4-(6-(difluoromethyl)-3,5-dioxo-4,5-dihydro-1,2,4-triazin-2(3H)-yl)phenoxy)-5-hydroxy-N-(1-(pyrrolidine-1-carbonyl)cyclopropyl)pyridine-4-sulfonamide |
| 119 | 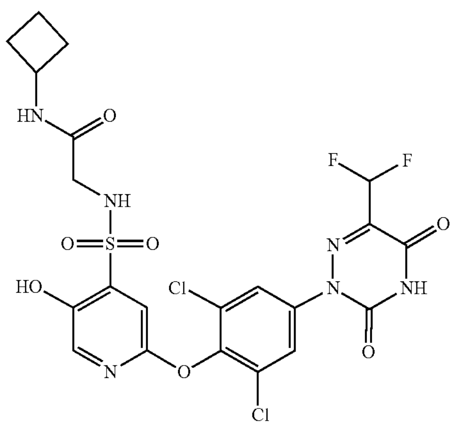 [SMILES: O=C(CNS(=O)(=O)c1cc(Oc2c(Cl)cc(-n3nc(C(F)F)c(=O)[nH]c3=O)cc2Cl)ncc1O)NC1CCC1] | N-cyclobutyl-2-((2-(2,6-dichloro-4-(6-(difluoromethyl)-3,5-dioxo-4,5-dihydro-1,2,4-triazin-2(3H)-yl)phenoxy)-5-hydroxypyridine)-4-sulfonamido)acetamide |
| 120 | 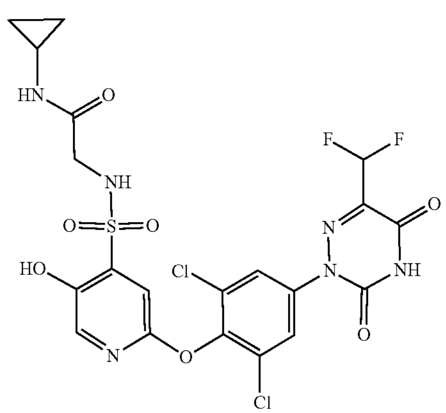 [SMILES: O=C(CNS(=O)(=O)c1cc(Oc2c(Cl)cc(-n3nc(C(F)F)c(=O)[nH]c3=O)cc2Cl)ncc1O)NC1CC1] | N-cyclopropyl-2-((2-(2,6-dichloro-4-(6-(difluoromethyl)-3,5-dioxo-4,5-dihydro-1,2,4-triazin-2(3H)-yl)phenoxy)-5-hydroxypyridine)-4-sulfonamido)acetamide |

TABLE 1-continued

| Cmpd No. | Structure | Chemical Name |
| --- | --- | --- |
| 121 | 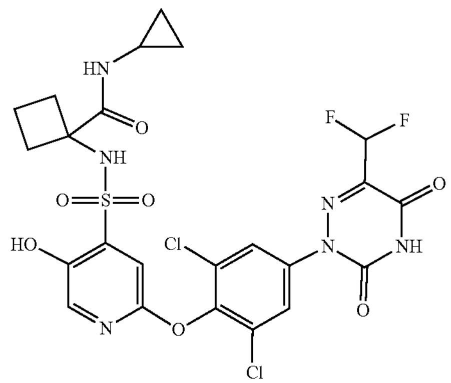 [SMILES: O=C(NC1CC1)C1(NS(=O)(=O)c2cc(Oc3c(Cl)cc(-n4nc(C(F)F)c(=O)[nH]c4=O)cc3Cl)ncc2O)CCC1] | N-cyclopropyl-1-((2-(2,6-dichloro-4-(6-(difluoromethyl)-3,5-dioxo-4,5-dihydro-1,2,4-triazin-2(3H)-yl)phenoxy)-5-hydroxypyridine)-4-sulfonamido)cyclobutane-1-carboxamide |
| 122 | 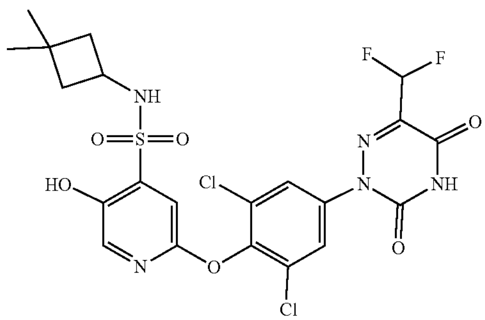 [SMILES: CC1(C)CC(NS(=O)(=O)c2cc(Oc3c(Cl)cc(-n4nc(C(F)F)c(=O)[nH]c4=O)cc3Cl)ncc2O)C1] | 2-(2,6-dichloro-4-(6-(difluoromethyl)-3,5-dioxo-4,5-dihydro-1,2,4-triazin-2(3H)-yl)phenoxy)-N-(3,3-dimethylcyclobutyl)-5-hydroxypyridine-4-sulfonamide |
| 123 | 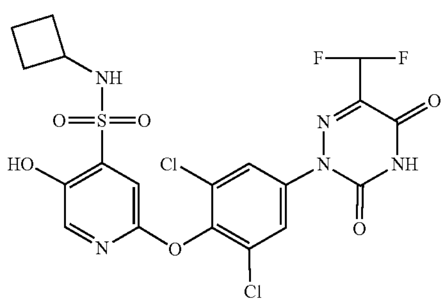 [SMILES: O=c1[nH]c(=O)n(-c2cc(Cl)c(Oc3cc(S(=O)(=O)NC4CCC4)c(O)cn3)c(Cl)c2)nc1C(F)F] | N-cyclobutyl-2-(2,6-dichloro-4-(6-(difluoromethyl)-3,5-dioxo-4,5-dihydro-1,2,4-triazin-2(3H)-yl)phenoxy)-5-hydroxypyridine-4-sulfonamide |
| 124 | 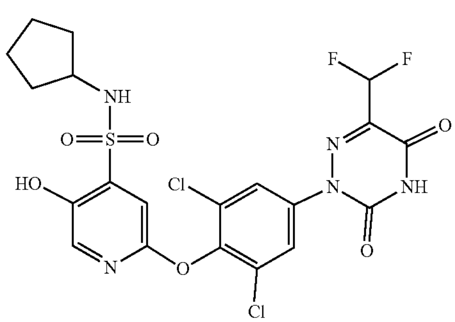 [SMILES: O=c1[nH]c(=O)n(-c2cc(Cl)c(Oc3cc(S(=O)(=O)NC4CCCC4)c(O)cn3)c(Cl)c2)nc1C(F)F] | N-cyclopentyl-2-(2,6-dichloro-4-(6-(difluoromethyl)-3,5-dioxo-4,5-dihydro-1,2,4-triazin-2(3H)-yl)phenoxy)-5-hydroxypyridine-4-sulfonamide |

TABLE 1-continued

| Cmpd No. | Structure | Chemical Name |
|---|---|---|
| 125 | 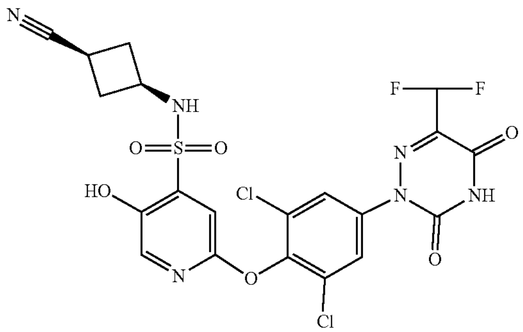 [SMILES: N#C[C@H]1C[C@@H](NS(=O)(=O)c2cc(Oc3c(Cl)cc(-n4nc(C(F)F)c(=O)[nH]c4=O)cc3Cl)ncc2O)C1] | N-((1s,3s)-3-cyanocyclobutyl)-2-(2,6-dichloro-4-(6-(difluoromethyl)-3,5-dioxo-4,5-dihydro-1,2,4-triazin-2(3H)-yl)phenoxy)-5-hydroxypyridine-4-sulfonamide |
| 126 | 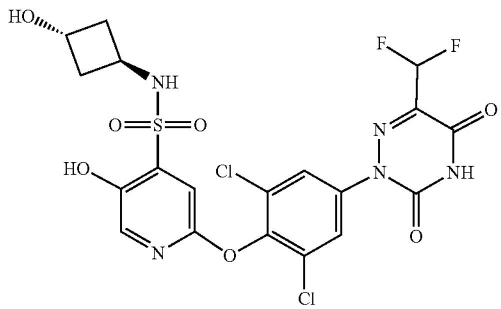 [SMILES: O=c1[nH]c(=O)n(-c2cc(Cl)c(Oc3cc(S(=O)(=O)N[C@H]4C[C@H](O)C4)c(O)cn3)c(Cl)c2)nc1C(F)F] | 2-(2,6-dichloro-4-(6-(difluoromethyl)-3,5-dioxo-4,5-dihydro-1,2,4-triazin-2(3H)-yl)phenoxy)-5-hydroxy-N-((1r,3r)-3-hydroxycyclobutyl)pyridine-4-sulfonamide |
| 127 | 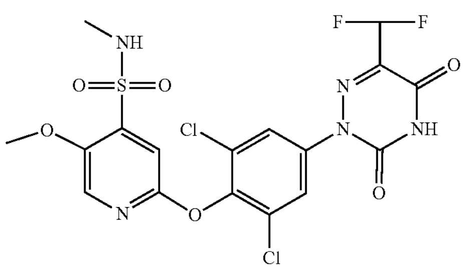 [SMILES: CNS(=O)(=O)c1cc(Oc2c(Cl)cc(-n3nc(C(F)F)c(=O)[nH]c3=O)cc2Cl)ncc1OC] | 2-(2,6-dichloro-4-(6-(difluoromethyl)-3,5-dioxo-4,5-dihydro-1,2,4-triazin-2(3H)-yl)phenoxy)-5-methoxy-N-methylpyridine-4-sulfonamide |
| 128 | 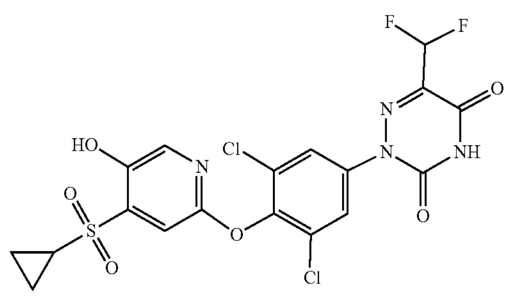 [SMILES: O=c1[nH]c(=O)n(-c2cc(Cl)c(Oc3cc(S(=O)(=O)C4CC4)c(O)cn3)c(Cl)c2)nc1C(F)F] | 2-(3,5-dichloro-4-((4-(cyclopropylsulfonyl)-5-hydroxypyridin-2-yl)oxy)phenyl)-6-(difluoromethyl)-1,2,4-triazine-3,5(2H,4H)-dione |
| 129 | 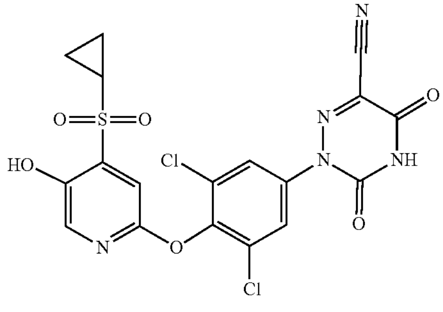 [SMILES: N#Cc1nn(-c2cc(Cl)c(Oc3cc(S(=O)(=O)C4CC4)c(O)cn3)c(Cl)c2)c(=O)[nH]c1=O] | 2-(3,5-dichloro-4-((4-(cyclopropylsulfonyl)-5-hydroxypyridin-2-yl)oxy)phenyl)-3,5-dioxo-2,3,4,5-tetrahydro-1,2,4-triazine-6-carbonitrile |

TABLE 1-continued

| Cmpd No. | Structure | Chemical Name |
|---|---|---|
| 130 | 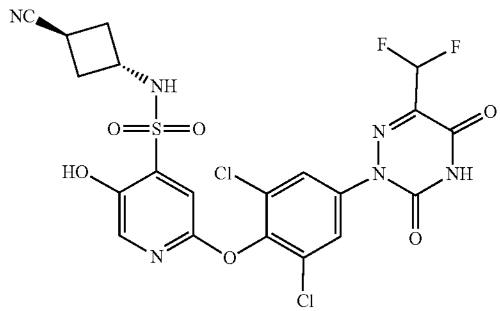 [SMILES: N#C[C@H]1C[C@H](NS(=O)(=O)c2cc(Oc3c(Cl)cc(-n4nc(C(F)F)c(=O)[nH]c4=O)cc3Cl)ncc2O)C1] | N-((1r,3r)-3-cyanocyclobutyl)-2-(2,6-dichloro-4-(6-(difluoromethyl)-3,5-dioxo-4,5-dihydro-1,2,4-triazin-2(3H)-yl)phenoxy)-5-hydroxypyridine-4-sulfonamide |
| 131 | 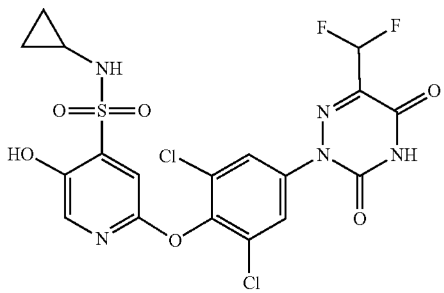 [SMILES: O=c1[nH]c(=O)n(-c2cc(Cl)c(Oc3cc(S(=O)(=O)NC4CC4)c(O)cn3)c(Cl)c2)nc1C(F)F] | N-cyclopropyl-2-(2,6-dichloro-4-(6-(difluoromethyl)-3,5-dioxo-4,5-dihydro-1,2,4-triazin-2(3H)-yl)phenoxy)-5-hydroxypyridine-4-sulfonamide |
| 132 | 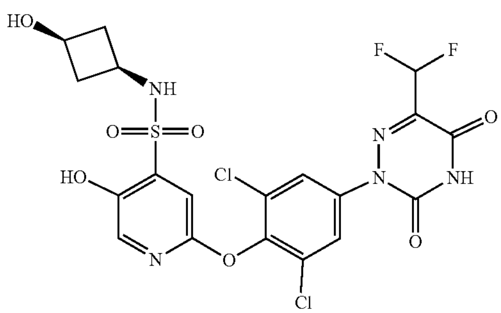 [SMILES: O=c1[nH]c(=O)n(-c2cc(Cl)c(Oc3cc(S(=O)(=O)N[C@H]4C[C@@H](O)C4)c(O)cn3)c(Cl)c2)nc1C(F)F] | 2-(2,6-dichloro-4-(6-(difluoromethyl)-3,5-dioxo-4,5-dihydro-1,2,4-triazin-2(3H)-yl)phenoxy)-5-hydroxy-N-((1s,3s)-3-hydroxycyclobutyl)pyridine-4-sulfonamide |
| 133 | 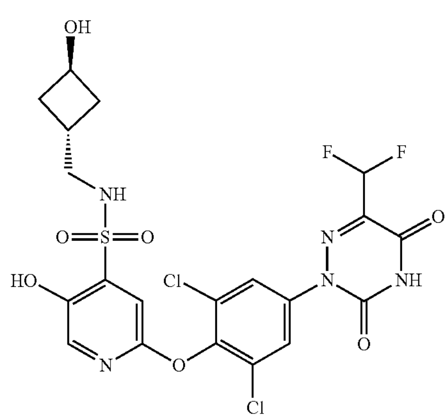 [SMILES: O=c1[nH]c(=O)n(-c2cc(Cl)c(Oc3cc(S(=O)(=O)NC[C@H]4C[C@H](O)C4)c(O)cn3)c(Cl)c2)nc1C(F)F] | 2-(2,6-dichloro-4-(6-(difluoromethyl)-3,5-dioxo-4,5-dihydro-1,2,4-triazin-2(3H)-yl)phenoxy)-5-hydroxy-N-(((1r,3r)-3-hydroxycyclobutyl)methyl)pyridine-4-sulfonamide |

TABLE 1-continued

| Cmpd No. | Structure | Chemical Name |
| --- | --- | --- |
| 134 | 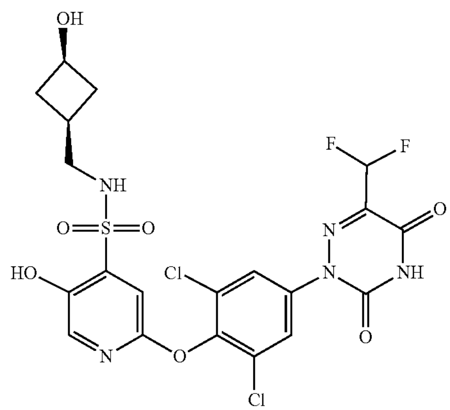 [SMILES: O=c1[nH]c(=O)n(-c2cc(Cl)c(Oc3cc(S(=O)(=O)NC[C@H]4C[C@@H](O)C4)c(O)cn3)c(Cl)c2)nc1C(F)F] | 2-(2,6-dichloro-4-(6-(difluoromethyl)-3,5-dioxo-4,5-dihydro-1,2,4-triazin-2(3H)-yl)phenoxy)-5-hydroxy-N-(((1s,3s)-3-hydroxycyclobutyl)methyl)pyridine-4-sulfonamide |
| 135 | 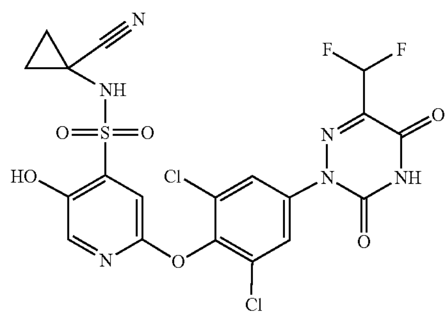 [SMILES: N#CC1(NS(=O)(=O)c2cc(Oc3c(Cl)cc(-n4nc(C(F)F)c(=O)[nH]c4=O)cc3Cl)ncc2O)CC1] | N-(1-cyanocyclopropyl)-2-(2,6-dichloro-4-(6-(difluoromethyl)-3,5-dioxo-4,5-dihydro-1,2,4-triazin-2(3H)-yl)phenoxy)-5-hydroxypyridine-4-sulfonamide |
| 136 | 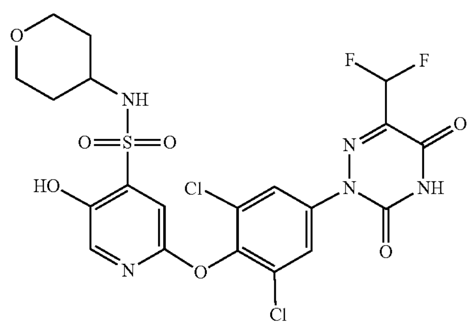 [SMILES: O=c1[nH]c(=O)n(-c2cc(Cl)c(Oc3cc(S(=O)(=O)NC4CCOCC4)c(O)cn3)c(Cl)c2)nc1C(F)F] | 2-(2,6-dichloro-4-(6-(difluoromethyl)-3,5-dioxo-4,5-dihydro-1,2,4-triazin-2(3H)-yl)phenoxy)-5-hydroxy-N-(tetrahydro-2H-pyran-4-yl)pyridine-4-sulfonamide |
| 137 | 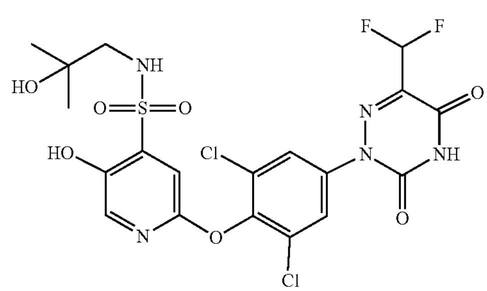 [SMILES: CC(C)(O)CNS(=O)(=O)c1cc(Oc2c(Cl)cc(-n3nc(C(F)F)c(=O)[nH]c3=O)cc2Cl)ncc1O] | 2-(2,6-dichloro-4-(6-(difluoromethyl)-3,5-dioxo-4,5-dihydro-1,2,4-triazin-2(3H)-yl)phenoxy)-5-hydroxy-N-(2-hydroxy-2-methylpropyl)pyridine-4-sulfonamide |

TABLE 1-continued

| Cmpd No. | Structure | Chemical Name |
|---|---|---|
| 138 | 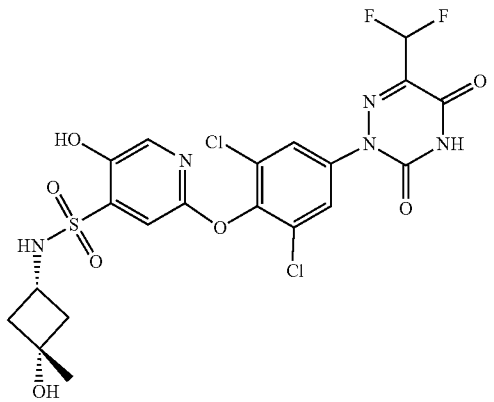 [SMILES: C[C@]1(O)C[C@@H](NS(=O)(=O)c2cc(Oc3c(Cl)cc(-n4nc(C(F)F)c(=O)[nH]c4=O)cc3Cl)ncc2O)C1] | 2-(2,6-dichloro-4-(6-(difluoromethyl)-3,5-dioxo-4,5-dihydro-1,2,4-triazin-2(3H)-yl)phenoxy)-5-hydroxy-N-((1s,3s)-3-hydroxy-3-methylcyclobutyl)pyridine-4-sulfonamide |
| 139 | 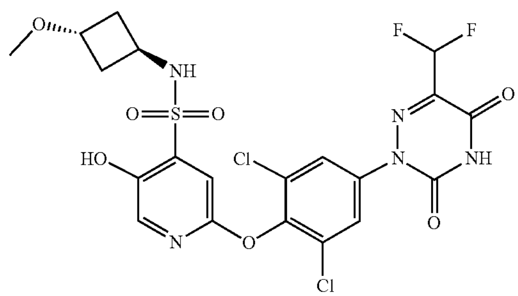 [SMILES: CO[C@H]1C[C@H](NS(=O)(=O)c2cc(Oc3c(Cl)cc(-n4nc(C(F)F)c(=O)[nH]c4=O)cc3Cl)ncc2O)C1] | 2-(2,6-dichloro-4-(6-(difluoromethyl)-3,5-dioxo-4,5-dihydro-1,2,4-triazin-2(3H)-yl)phenoxy)-5-hydroxy-N-((1r,3r)-3-methoxycyclobutyl)pyridine-4-sulfonamide |
| 140 | 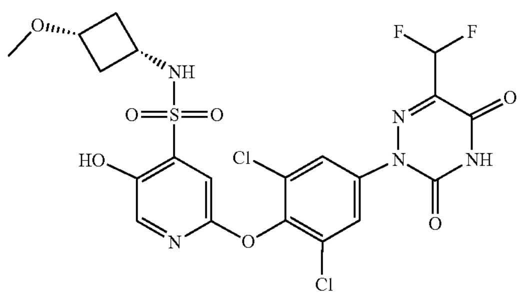 [SMILES: CO[C@H]1C[C@@H](NS(=O)(=O)c2cc(Oc3c(Cl)cc(-n4nc(C(F)F)c(=O)[nH]c4=O)cc3Cl)ncc2O)C1] | 2-(2,6-dichloro-4-(6-(difluoromethyl)-3,5-dioxo-4,5-dihydro-1,2,4-triazin-2(3H)-yl)phenoxy)-5-hydroxy-N-((1s,3s)-3-methoxycyclobutyl)pyridine-4-sulfonamide |
| 141 | 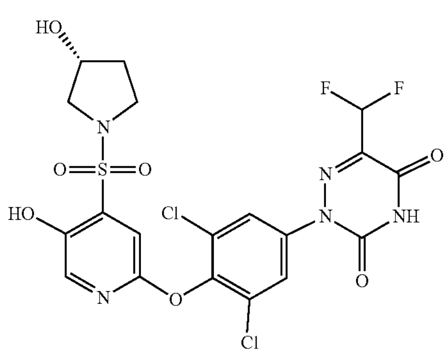 [SMILES: O=c1[nH]c(=O)n(-c2cc(Cl)c(Oc3cc(S(=O)(=O)N4CC[C@@H](O)C4)c(O)cn3)c(Cl)c2)nc1C(F)F] | (R)-2-(3,5-dichloro-4-((5-hydroxy-4-((3-hydroxypyrrolidin-1-yl)sulfonyl)pyridin-2-yl)oxy)phenyl)-6-(difluoromethyl)-1,2,4-triazine-3,5(2H,4H)-dione |

TABLE 1-continued

| Cmpd No. | Structure | Chemical Name |
|---|---|---|
| 142 | 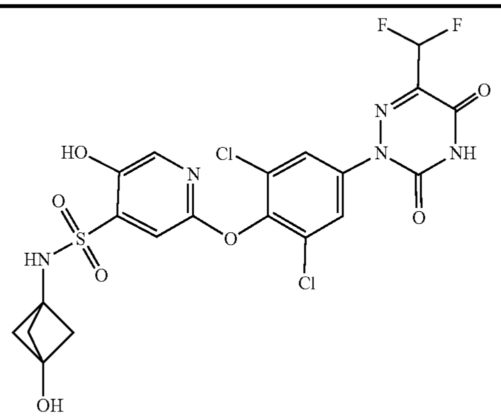 | 2-(2,6-dichloro-4-(6-(difluoromethyl)-3,5-dioxo-4,5-dihydro-1,2,4-triazin-2(3H)-yl)phenoxy)-5-hydroxy-N-(3-hydroxybicyclo[1.1.1]pentan-1-yl)pyridine-4-sulfonamide |
| 143 | 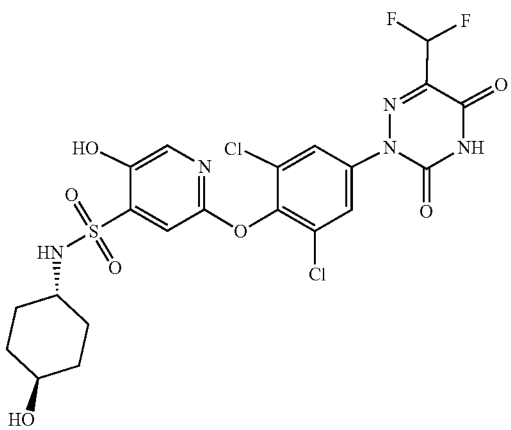 [SMILES: O=c1[nH]c(=O)n(-c2cc(Cl)c(Oc3cc(S(=O)(=O)N[C@H]4CC[C@H](O)CC4)c(O)cn3)c(Cl)c2)nc1C(F)F] | 2-(2,6-dichloro-4-(6-(difluoromethyl)-3,5-dioxo-4,5-dihydro-1,2,4-triazin-2(3H)-yl)phenoxy)-5-hydroxy-N-((1r,4r)-4-hydroxycyclohexyl)pyridine-4-sulfonamide |
| 144 | 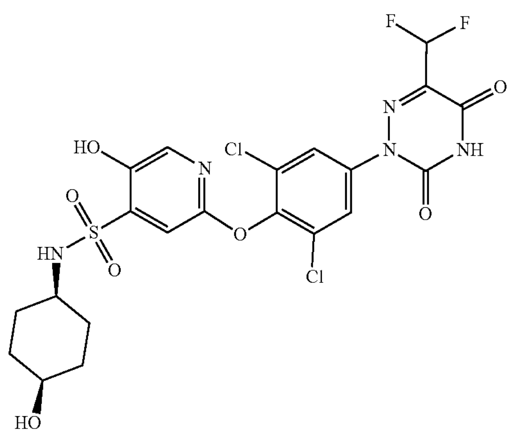 [SMILES: O=c1[nH]c(=O)n(-c2cc(Cl)c(Oc3cc(S(=O)(=O)N[C@H]4CC[C@@H](O)CC4)c(O)cn3)c(Cl)c2)nc1C(F)F] | 2-(2,6-dichloro-4-(6-(difluoromethyl)-3,5-dioxo-4,5-dihydro-1,2,4-triazin-2(3H)-yl)phenoxy)-5-hydroxy-N-((1s,4s)-4-hydroxycyclohexyl)pyridine-4-sulfonamide |
| 145 | 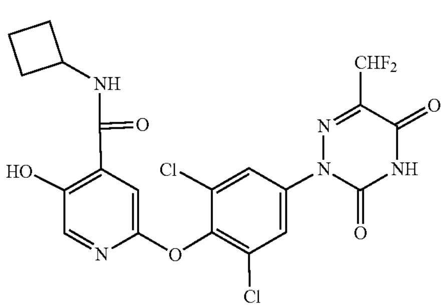 [SMILES: O=C(NC1CCC1)c1cc(Oc2c(Cl)cc(-n3nc(C(F)F)c(=O)[nH]c3=O)cc2Cl)ncc1O] | N-cyclobutyl-2-(2,6-dichloro-4-(6-(difluoromethyl)-3,5-dioxo-4,5-dihydro-1,2,4-triazin-2(3H)-yl)phenoxy)-5-hydroxyisonicotinamide |

TABLE 1-continued

| Cmpd No. | Structure | Chemical Name |
|---|---|---|
| 146 | 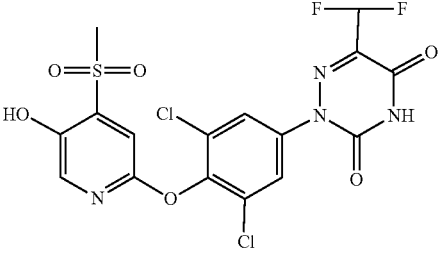 [SMILES: CS(=O)(=O)c1cc(Oc2c(Cl)cc(-n3nc(C(F)F)c(=O)[nH]c3=O)cc2Cl)ncc1O] | 2-(3,5-dichloro-4-((5-hydroxy-4-(methylsulfonyl)pyridin-2-yl)oxy)phenyl)-6-(difluoromethyl)-1,2,4-triazine-3,5(2H,4H)-dione |
| 147 | 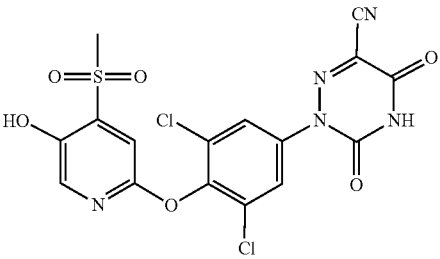 [SMILES: CS(=O)(=O)c1cc(Oc2c(Cl)cc(-n3nc(C#N)c(=O)[nH]c3=O)cc2Cl)ncc1O] | 2-(3,5-dichloro-4-((5-hydroxy-4-(methylsulfonyl)pyridin-2-yl)oxy)phenyl)-3,5-dioxo-2,3,4,5-tetrahydro-1,2,4-triazine-6-carbonitrile |
| 148 | 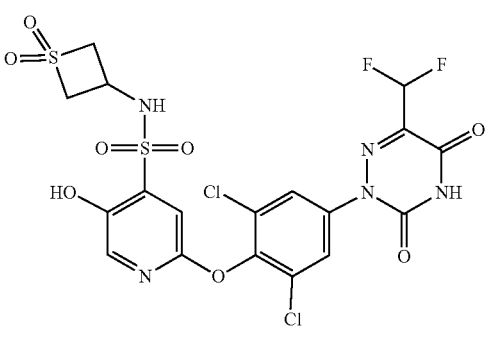 [SMILES: O=c1[nH]c(=O)n(-c2cc(Cl)c(Oc3cc(S(=O)(=O)NC4CS(=O)(=O)C4)c(O)cn3)c(Cl)c2)nc1C(F)F] | 2-(2,6-dichloro-4-(6-(difluoromethyl)-3,5-dioxo-4,5-dihydro-1,2,4-triazin-2(3H)-yl)phenoxy)-N-(1,1-dioxidothietan-3-yl)-5-hydroxypyridine-4-sulfonamide |
| 149 | 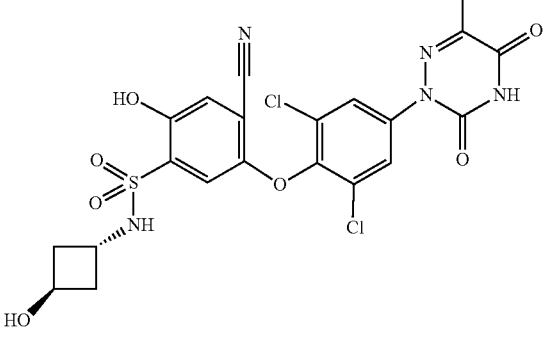 | 4-cyano-5-(2,6-dichloro-4-(6-(difluoromethyl)-3,5-dioxo-4,5-dihydro-1,2,4-triazin-2(3H)-yl)phenoxy)-2-hydroxy-N-((1r,3r)-3-hydroxycyclobutyl)benzenesulfonamide |
| 150 | 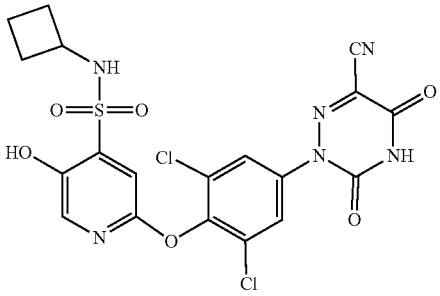 [SMILES: N#Cc1nn(-c2cc(Cl)c(Oc3cc(S(=O)(=O)NC4CCC4)c(O)cn3)c(Cl)c2)c(=O)[nH]c1=O] | N-cyclobutyl-2-(2,6-dichloro-4-(6-cyano-3,5-dioxo-4,5-dihydro-1,2,4-triazin-2(3H)-yl)phenoxy)-5-hydroxypyridine-4-sulfonamide |

TABLE 1-continued

| Cmpd No. | Structure | Chemical Name |
|---|---|---|
| 151 | 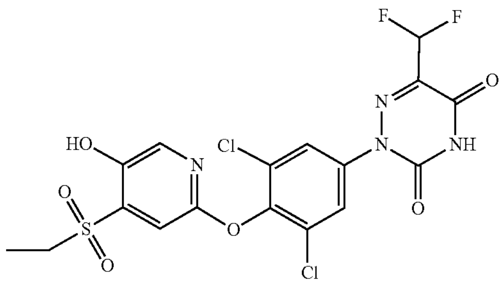 [SMILES: CCS(=O)(=O)c1cc(Oc2c(Cl)cc(-n3nc(C(F)F)c(=O)[nH]c3=O)cc2Cl)ncc1O] | 2-(3,5-dichloro-4-((4-(ethylsulfonyl)-5-hydroxypyridin-2-yl)oxy)phenyl)-6-(difluoromethyl)-1,2,4-triazine-3,5(2H,4H)-dione |
| 152 | 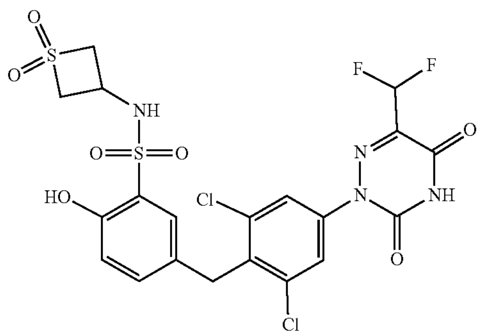 [SMILES: O=c1[nH]c(=O)n(-c2cc(Cl)c(Cc3ccc(O)c(S(=O)(=O)NC4CS(=O)(=O)C4)c3)c(Cl)c2)nc1C(F)F] | 5-(2,6-dichloro-4-(6-(difluoromethyl)-3,5-dioxo-4,5-dihydro-1,2,4-triazin-2(3H)-yl)benzyl)-N-(1,1-dioxidothietan-3-yl)-2-hydroxybenzenesulfonamide |
| 153 | 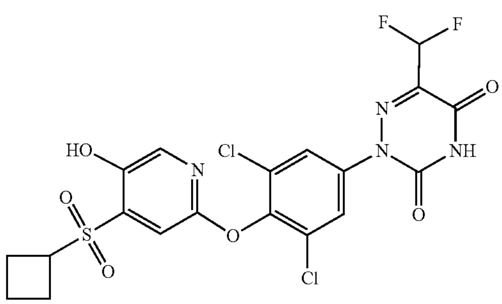 [SMILES: O=c1[nH]c(=O)n(-c2cc(Cl)c(Oc3cc(S(=O)(=O)C4CCC4)c(O)cn3)c(Cl)c2)nc1C(F)F] | 2-(3,5-dichloro-4-((4-(cyclobutylsulfonyl)-5-hydroxypyridin-2-yl)oxy)phenyl)-6-(difluoromethyl)-1,2,4-triazine-3,5(2H,4H)-dione |
| 154 | 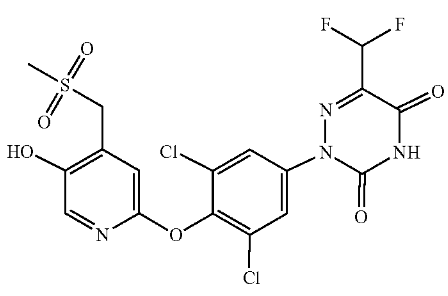 [SMILES: CS(=O)(=O)Cc1cc(Oc2c(Cl)cc(-n3nc(C(F)F)c(=O)[nH]c3=O)cc2Cl)ncc1O] | 2-(3,5-dichloro-4-((5-hydroxy-4-((methylsulfonyl)methyl)pyridin-2-yl)oxy)phenyl)-6-(difluoromethyl)-1,2,4-triazine-3,5(2H,4H)-dione |
| 156 | 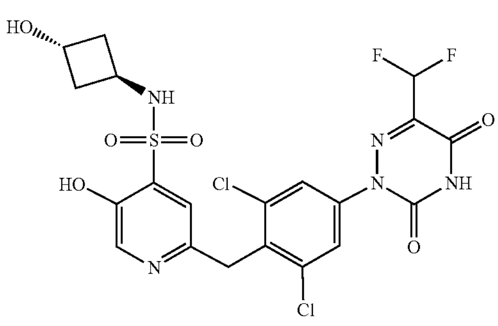 [SMILES: O=c1[nH]c(=O)n(-c2cc(Cl)c(Cc3cc(S(=O)(=O)N[C@H]4C[C@H](O)C4)c(O)cn3)c(Cl)c2)nc1C(F)F] | 2-(2,6-dichloro-4-(6-(difluoromethyl)-3,5-dioxo-4,5-dihydro-1,2,4-triazin-2(3H)-yl)benzyl)-5-hydroxy-N-((1r,3r)-3-hydroxycyclobutyl)pyridine-4-sulfonamide |

TABLE 1-continued

| Cmpd No. | Structure | Chemical Name |
| --- | --- | --- |
| 158 | 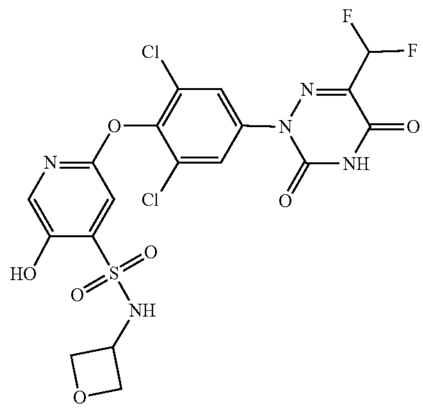 [SMILES: O=c1[nH]c(=O)n(-c2cc(Cl)c(Oc3cc(S(=O)(=O)NC4COC4)c(O)cn3)c(Cl)c2)nc1C(F)F] | 2-(2,6-dichloro-4-(6-(difluoromethyl)-3,5-dioxo-4,5-dihydro-1,2,4-triazin-2(3H)-yl)phenoxy)-5-hydroxy-N-(oxetan-3-yl)pyridine-4-sulfonamide |
| 159 | 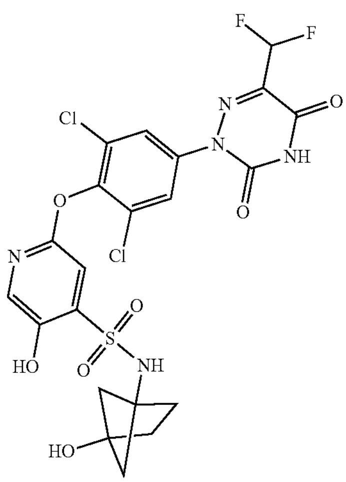 [SMILES: O=c1[nH]c(=O)n(-c2cc(Cl)c(Oc3cc(S(=O)(=O)NC45CCC(O)(C4)C5)c(O)cn3)c(Cl)c2)nc1C(F)F] | 2-(2,6-dichloro-4-(6-(difluoromethyl)-3,5-dioxo-4,5-dihydro-1,2,4-triazin-2(3H)-yl)phenoxy)-5-hydroxy-N-(4-hydroxybicyclo[2.1.1]hexan-1-yl)pyridine-4-sulfonamide |
| 160 | 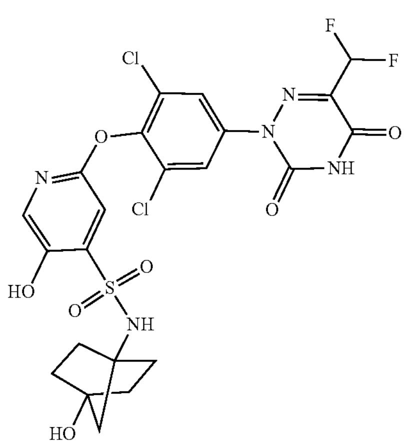 [SMILES: O=c1[nH]c(=O)n(-c2cc(Cl)c(Oc3cc(S(=O)(=O)NC45CCC(O)(CC4)C5)c(O)cn3)c(Cl)c2)nc1C(F)F] | 2-(2,6-dichloro-4-(6-(difluoromethyl)-3,5-dioxo-4,5-dihydro-1,2,4-triazin-2(3H)-yl)phenoxy)-5-hydroxy-N-(4-hydroxybicyclo[2.2.1]heptan-1-yl)pyridine-4-sulfonamide |

TABLE 1-continued

| Cmpd No. | Structure | Chemical Name |
|---|---|---|
| 161 | 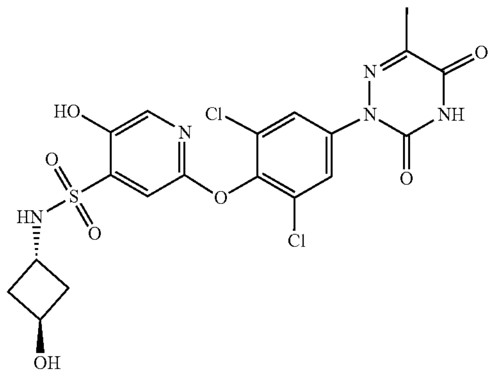 [SMILES: Cc1nn(-c2cc(Cl)c(Oc3cc(S(=O)(=O)N[C@H]4C[C@H](O)C4)c(O)cn3)c(Cl)c2)c(=O)[nH]c1=O] | 2-(2,6-dichloro-4-(6-methyl-3,5-dioxo-4,5-dihydro-1,2,4-triazin-2(3H)-yl)phenoxy)-5-hydroxy-N-((1r,3r)-3-hydroxycyclobutyl)pyridine-4-sulfonamide |
| 162 | 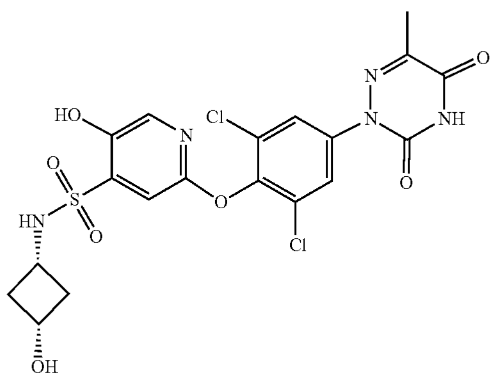 [SMILES: Cc1nn(-c2cc(Cl)c(Oc3cc(S(=O)(=O)N[C@H]4C[C@@H](O)C4)c(O)cn3)c(Cl)c2)c(=O)[nH]c1=O] | 2-(2,6-dichloro-4-(6-methyl-3,5-dioxo-4,5-dihydro-1,2,4-triazin-2(3H)-yl)phenoxy)-5-hydroxy-N-((1s,3s)-3-hydroxycyclobutyl)pyridine-4-sulfonamide |
| 163 | 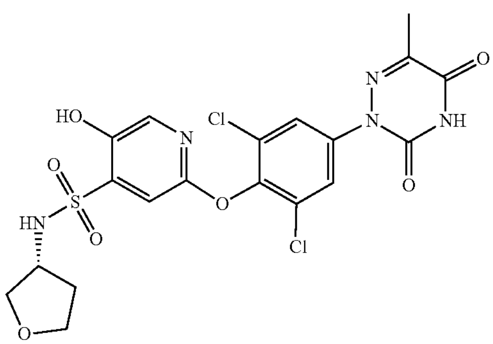 [SMILES: Cc1nn(-c2cc(Cl)c(Oc3cc(S(=O)(=O)N[C@@H]4CCOC4)c(O)cn3)c(Cl)c2)c(=O)[nH]c1=O] | (R)-2-(2,6-dichloro-4-(6-methyl-3,5-dioxo-4,5-dihydro-1,2,4-triazin-2(3H)-yl)phenoxy)-5-hydroxy-N-(tetrahydrofuran-3-yl)pyridine-4-sulfonamide |
| 164 | 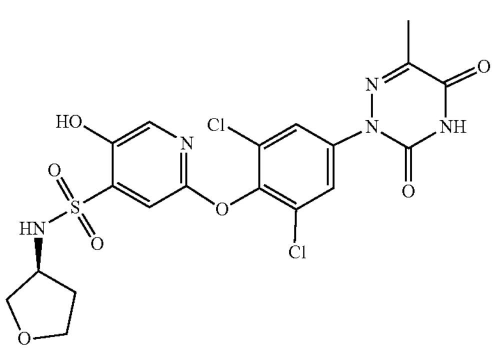 [SMILES: Cc1nn(-c2cc(Cl)c(Oc3cc(S(=O)(=O)N[C@H]4CCOC4)c(O)cn3)c(Cl)c2)c(=O)[nH]c1=O] | (S)-2-(2,6-dichloro-4-(6-methyl-3,5-dioxo-4,5-dihydro-1,2,4-triazin-2(3H)-yl)phenoxy)-5-hydroxy-N-(tetrahydrofuran-3-yl)pyridine-4-sulfonamide |

TABLE 1-continued

| Cmpd No. | Structure | Chemical Name |
|---|---|---|
| 165 | 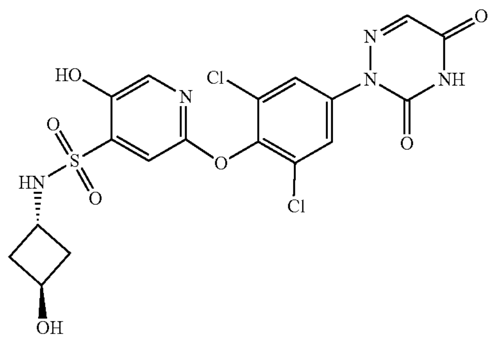 [SMILES: O=c1cnn(-c2cc(Cl)c(Oc3cc(S(=O)(=O)N[C@H]4C[C@H](O)C4)c(O)cn3)c(Cl)c2)c(=O)[nH]1] | 2-(2,6-dichloro-4-(3,5-dioxo-4,5-dihydro-1,2,4-triazin-2(3H)-yl)phenoxy)-5-hydroxy-N-((1r,3r)-3-hydroxycyclobutyl)pyridine-4-sulfonamide |
| 166 | 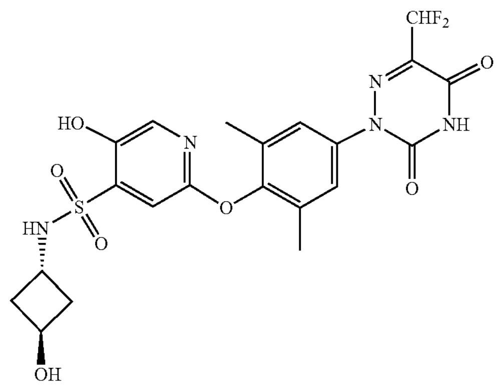 [SMILES: Cc1cc(-n2nc(C(F)F)c(=O)[nH]c2=O)cc(C)c1Oc1cc(S(=O)(=O)N[C@H]2C[C@H](O)C2)c(O)cn1] | 2-(4-(6-(difluoromethyl)-3,5-dioxo-4,5-dihydro-1,2,4-triazin-2(3H)-yl)-2,6-dimethylphenoxy)-5-hydroxy-N-((1r,3r)-3-hydroxycyclobutyl)pyridine-4-sulfonamide |
| 167 | 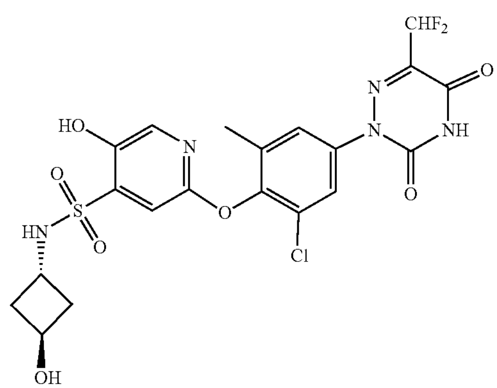 [SMILES: Cc1cc(-n2nc(C(F)F)c(=O)[nH]c2=O)cc(Cl)c1Oc1cc(S(=O)(=O)N[C@H]2C[C@H](O)C2)c(O)cn1] | 2-(2-chloro-4-(6-(difluoromethyl)-3,5-dioxo-4,5-dihydro-1,2,4-triazin-2(3H)-yl)-6-methylphenoxy)-5-hydroxy-N-((1r,3r)-3-hydroxycyclobutyl)pyridine-4-sulfonamide |
| 168 | 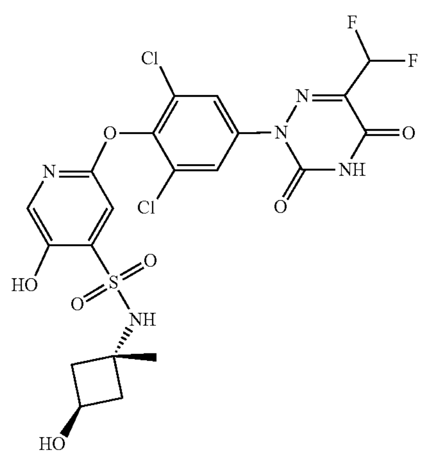 [SMILES: C[C@]1(NS(=O)(=O)c2cc(Oc3c(Cl)cc(-n4nc(C(F)F)c(=O)[nH]c4=O)cc3Cl)ncc2O)C[C@H](O)C1] | 2-[2,6-dichloro-4-[6-(difluoromethyl)-3,5-dioxo-1,2,4-triazin-2-yl]phenoxy ]-5-hydroxy-N-(3-hydroxy-1-methyl-cyclobutyl)pyridine-4-sulfonamide |

TABLE 1-continued

| Cmpd No. | Structure | Chemical Name |
|---|---|---|
| 169 | 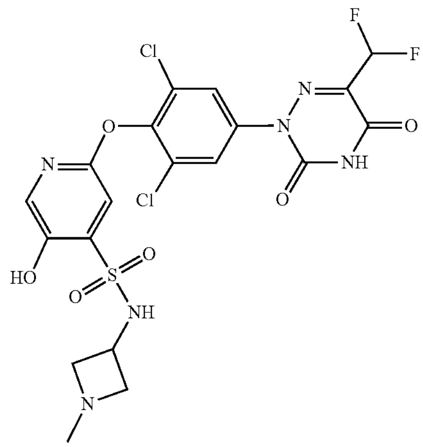 [SMILES: CN1CC(NS(=O)(=O)c2cc(Oc3c(Cl)cc(-n4nc(C(F)F)c(=O)[nH]c4=O)cc3Cl)ncc2O)C1] | 2-(2,6-dichloro-4-(6-(difluoromethyl)-3,5-dioxo-4,5-dihydro-1,2,4-triazin-2(3H)-yl)phenoxy)-5-hydroxy-N-(1-methylazetidin-3-yl)pyridine-4-sulfonamide |
| 170 | 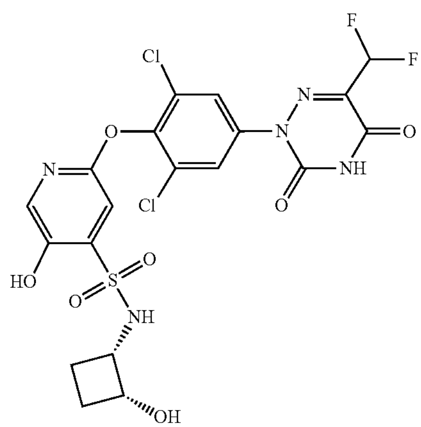 [SMILES: O=c1[nH]c(=O)n(-c2cc(Cl)c(Oc3cc(S(=O)(=O)N[C@H]4CC[C@H]4O)c(O)cn3)c(Cl)c2)nc1C(F)F] | 2-[2,6-dichloro-4-[6-(difluoromethyl)-3,5-dioxo-1,2,4-triazin-2-yl]phenoxy]-5-hydroxy-N-[(1R,2S)-2-hydroxycyclobutyl]pyridine-4-sulfonamide |
| 171 | 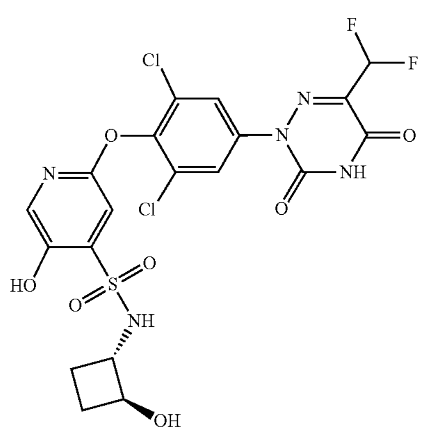 [SMILES: O=c1[nH]c(=O)n(-c2cc(Cl)c(Oc3cc(S(=O)(=O)N[C@H]4CC[C@@H]4O)c(O)cn3)c(Cl)c2)nc1C(F)F] | 2-[2,6-dichloro-4-[6-(difluoromethyl)-3,5-dioxo-1,2,4-triazin-2-yl]phenoxy]-5-hydroxy-N-[(1R,2R)-2-hydroxycyclobutyl]pyridine-4-sulfonamide |

TABLE 1-continued

| Cmpd No. | Structure | Chemical Name |
|---|---|---|
| 172 | 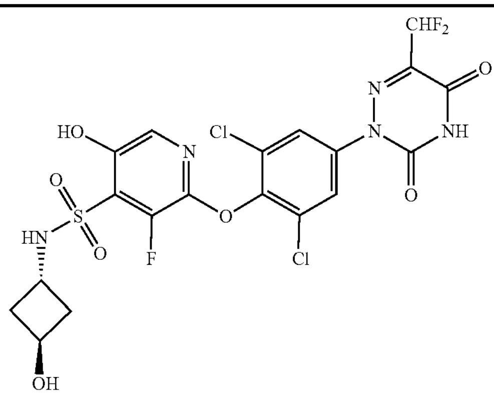 | 2-(2,6-dichloro-4-(6-(difluoromethyl)-3,5-dioxo-4,5-dihydro-1,2,4-triazin-2(3H)-yl)phenoxy)-3-fluoro-5-hydroxy-N-((1r,3r)-3-hydroxycyclobutyl)pyridine-4-sulfonamide |

In one embodiment, a compound of the application (e.g., a compound according to any of the formulae or any individual compounds disclosed herein) is deuterated, i.e., one or more of the hydrogen atoms in the compound is replaced by one or more deuterium atoms.

A compound of the application (e.g., a compound according to any of the formulae or any individual compounds disclosed herein) may be deuterated at any part of the molecule, for example, one or more hydrogen atoms in any of the groups $X^1$, $X^2$, $X^3$, L, $R^X$, $R^1$, $R^2$, $R^3$, $R^4$, $R^{4'}$, $R^{4''}$, $R^5$, $R^6$, $R^{6'}$, $R^7$, and $R^1$ are replaced with one more deuterium atoms.

In one embodiment, at least one hydrogen atom in $R^1$ and/or $R^4$ is replaced by at least one deuterium atom.

In one embodiment, at least one hydrogen atom in $R^1$ is replaced by at least one deuterium atom. In one embodiment, $R^1$ is $CH_2F$ or $CHF_2$, and one or both hydrogen atoms are replaced by deuterium atom(s). In one embodiment, $R^1$ is $CH_2F$, and one or both hydrogen atoms are replaced by deuterium atom(s). In one embodiment, $R^1$ is $CHF_2$, and the hydrogen atom is replaced by a deuterium atom.

In one embodiment, at least one hydrogen atom in $R^4$ is replaced by at least one deuterium atom.

In one embodiment, $R^4$ is $S(O)_2NR^{4'}R^{4''}$, and at least one hydrogen atom in $R^{4'}$ or $R^{4''}$ is replaced by at least one deuterium atom. In one embodiment, one of $R^{4'}$ and $R^{4''}$ is H, and the other is monocyclic or multicyclic spiro-, fused-, or bridged-($C_3$-$C_{15}$) cycloalkyl, wherein at least one of the hydrogen atoms of the monocyclic or multicyclic spiro-, fused-, or bridged-($C_3$-$C_{15}$) cycloalkyl is replaced by at least one deuterium atom.

In one embodiment, $R^4$ is $C(O)NR^{4'}R^{4''}$, and at least one hydrogen atom in $R^{4'}$ or $R^{4''}$ is replaced by at least one deuterium atom. In one embodiment, one of $R^{4'}$ and $R^{4''}$ is H, and the other is monocyclic or multicyclic spiro-, fused-, or bridged-($C_3$-$C_{15}$) cycloalkyl, wherein at least one of the hydrogen atoms of the monocyclic or multicyclic spiro-, fused-, or bridged-($C_3$-$C_{15}$) cycloalkyl is replaced by at least one deuterium atom.

In one embodiment, $R^4$ is $S(O)_2R^{4'}$, and at least one hydrogen atom in $R^{4'}$ is replaced by at least one deuterium atom. In one embodiment, $R^{4'}$ is monocyclic or multicyclic spiro-, fused-, or bridged-($C_3$-$C_{15}$) cycloalkyl, wherein at least one of the hydrogen atoms of the monocyclic or multicyclic spiro-, fused-, or bridged-($C_3$-$C_{15}$) cycloalkyl is replaced by at least one deuterium atom.

In one embodiment, one or more of the three 6-membered rings in any of the formulae or any individual compounds disclosed herein are deuterated. In one embodiment, the phenyl ring to which $R^2$ and $R^3$ are bonded is deuterated.

Non-limiting illustrative deuterated compounds of the application include those in Table 1d.

TABLE 1d

| | | |
|---|---|---|
| 173 | | 5-(2,6-dichloro-4-(6-(difluoromethyl)-3,5-dioxo-4,5-dihydro-1,2,4-triazin-2(3H)-yl)phenoxy)-2-hydroxy-N-((1r,3r)-3-hydroxycyclobutyl-3-d)benzenesulfonamide |

TABLE 1d-continued

| | | | |
|---|---|---|---|
| 174 | 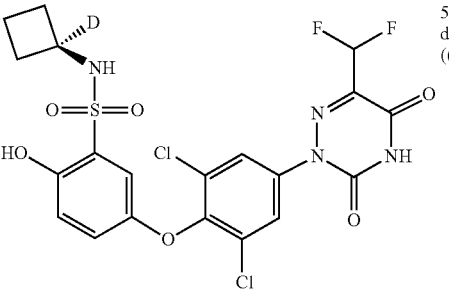 | | 5-(2,6-dichloro-4-(6-(difluoromethyl)-3,5-dioxo-4,5-dihydro-1,2,4-triazin-2(3H)-yl)phenoxy)-2-hydroxy-N-((1r,3r)-3-hydroxycyclobutyl-1-d)benzenesulfonamide |
| 175 | 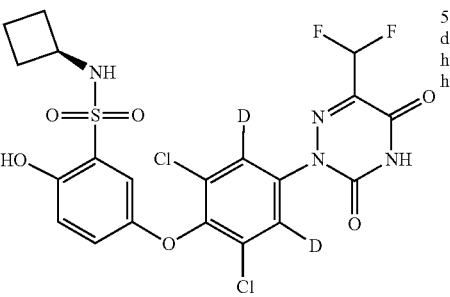 | | 5-(2,6-dichloro-4-(6-(difluoromethyl)-3,5-dioxo-4,5-dihydro-1,2,4-triazin-2(3H)-yl)phenoxy-3,5-d2)-2-hydroxy-N-((1r,3r)-3-hydroxycyclobutyl)benzenesulfonamide |
| 176 | 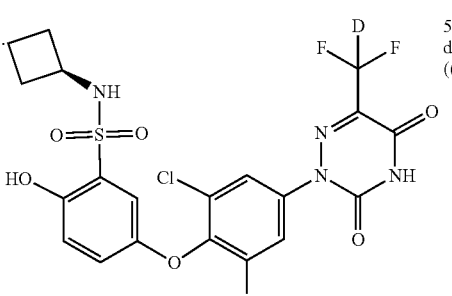 | | 5-(2,6-dichloro-4-(6-(difluoromethyl-d)-3,5-dioxo-4,5-dihydro-1,2,4-triazin-2(3H)-yl)phenoxy)-2-hydroxy-N-((1r,3r)-3-hydroxycyclobutyl)benzenesulfonamide |
| 177 | 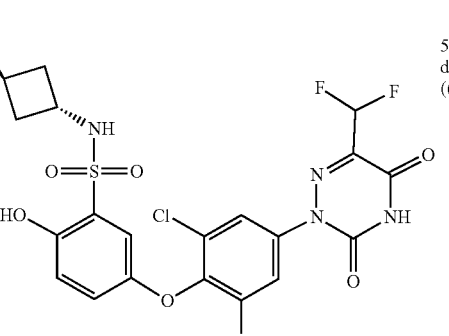 | | 5-(2,6-dichloro-4-(6-(difluoromethyl)-3,5-dioxo-4,5-dihydro-1,2,4-triazin-2(3H)-yl)phenoxy)-2-hydroxy-N-((1s,3s)-3-hydroxycyclobutyl-3-d)benzenesulfonamide |
| 178 | 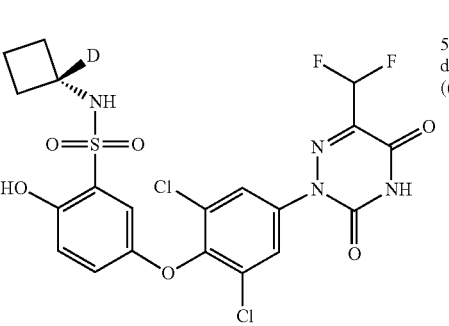 | | 5-(2,6-dichloro-4-(6-(difluoromethyl)-3,5-dioxo-4,5-dihydro-1,2,4-triazin-2(3H)-yl)phenoxy)-2-hydroxy-N-((1s,3s)-3-hydroxycyclobutyl-1-d)benzenesulfonamide |

TABLE 1d-continued

| # | Structure | Name |
|---|---|---|
| 179 | 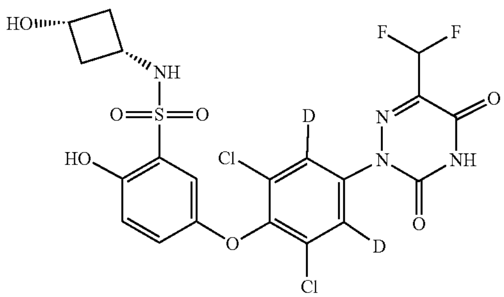 [SMILES: [2H]c1c(Cl)c(Oc2ccc(O)c(S(=O)(=O)N[C@H]3C[C@@H](O)C3)c2)c(Cl)c([2H])c1-n1nc(C(F)F)c(=O)[nH]c1=O] | 5-(2,6-dichloro-4-(6-(difluoromethyl)-3,5-dioxo-4,5-dihydro-1,2,4-triazin-2(3H)-yl)phenoxy-3,5-d2)-2-hydroxy-N-((1s,3s)-3-hydroxycyclobutyl)benzenesulfonamide |
| 180 | 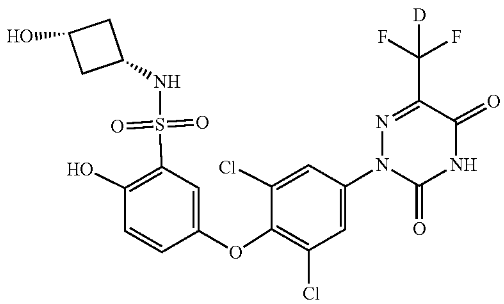 [SMILES: [2H]C(F)(F)c1nn(-c2cc(Cl)c(Oc3ccc(O)c(S(=O)(=O)N[C@H]4C[C@@H](O)C4)c3)c(Cl)c2)c(=O)[nH]c1=O] | 5-(2,6-dichloro-4-(6-(difluoromethyl-d)-3,5-dioxo-4,5-dihydro-1,2,4-triazin-2(3H)-yl)phenoxy)-2-hydroxy-N-((1s,3s)-3-hydroxycyclobutyl)benzenesulfonamide |
| 181 | 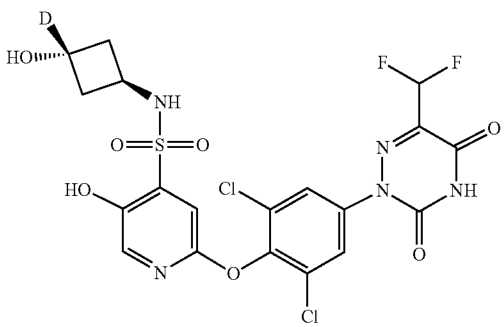 [SMILES: [2H][C@]1(O)C[C@H](NS(=O)(=O)c2cc(Oc3c(Cl)cc(-n4nc(C(F)F)c(=O)[nH]c4=O)cc3Cl)ncc2O)C1] | 2-(2,6-dichloro-4-(6-(difluoromethyl)-3,5-dioxo-4,5-dihydro-1,2,4-triazin-2(3H)-yl)phenoxy)-5-hydroxy-N-((1r,3r)-3-hydroxycyclobutyl-3-d)pyridine-4-sulfonamide |
| 182 | 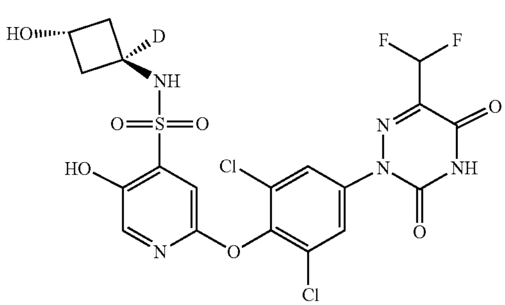 [SMILES: [2H][C@]1(NS(=O)(=O)c2cc(Oc3c(Cl)cc(-n4nc(C(F)F)c(=O)[nH]c4=O)cc3Cl)ncc2O)C[C@H](O)C1] | 2-(2,6-dichloro-4-(6-(difluoromethyl)-3,5-dioxo-4,5-dihydro-1,2,4-triazin-2(3H)-yl)phenoxy)-5-hydroxy-N-((1r,3r)-3-hydroxycyclobutyl-1-d)pyridine-4-sulfonamide |
| 183 | 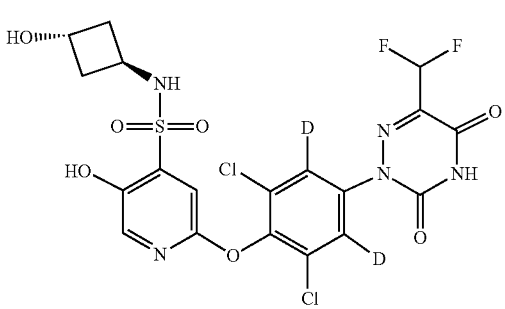 [SMILES: [2H]c1c(Cl)c(Oc2cc(S(=O)(=O)N[C@H]3C[C@H](O)C3)c(O)cn2)c(Cl)c([2H])c1-n1nc(C(F)F)c(=O)[nH]c1=O] | 2-(2,6-dichloro-4-(6-(difluoromethyl)-3,5-dioxo-4,5-dihydro-1,2,4-triazin-2(3H)-yl)phenoxy-3,5-d2)-5-hydroxy-N-((1r,3r)-3-hydroxycyclobutyl)pyridine-4-sulfonamide |

TABLE 1d-continued

| | | |
|---|---|---|
| 184 | [structure] | 2-(2,6-dichloro-4-(6-(difluoromethyl-d)-3,5-dioxo-4,5-dihydro-1,2,4-triazin-2(3H)-yl)phenoxy)-5-hydroxy-N-((1r,3r)-3-hydroxycyclobutyl)pyridine-4-sulfonamide |
| 185 | [structure] | 2-(2,6-dichloro-4-(6-(difluoromethyl)-3,5-dioxo-4,5-dihydro-1,2,4-triazin-2(3H)-yl)phenoxy)-5-hydroxy-N-((1s,3s)-3-hydroxycyclobutyl-3-d)pyridine-4-sulfonamide |
| 186 | [structure] | 2-(2,6-dichloro-4-(6-(difluoromethyl)-3,5-dioxo-4,5-dihydro-1,2,4-triazin-2(3H)-yl)phenoxy)-5-hydroxy-N-((1s,3s)-3-hydroxycyclobutyl-1-d)pyridine-4-sulfonamide |
| 187 | [structure] | 2-(2,6-dichloro-4-(6-(difluoromethyl)-3,5-dioxo-4,5-dihydro-1,2,4-triazin-2(3H)-yl)phenoxy-3,5-d2)-5-hydroxy-N-((1s,3s)-3-hydroxycyclobutyl)pyridine-4-sulfonamide |
| 188 | [structure] | 2-(2,6-dichloro-4-(6-(difluoromethyl-d)-3,5-dioxo-4,5-dihydro-1,2,4-triazin-2(3H)-yl)phenoxy)-5-hydroxy-N-((1s,3s)-3-hydroxycyclobutyl)pyridine-4-sulfonamide |

TABLE 1d-continued

| 189 | [structure] | N-(cyclobutyl-3,3-d2)-2-(2,6-dichloro-4-(6-(difluoromethyl)-3,5-dioxo-4,5-dihydro-1,2,4-triazin-2(3H)-yl)phenoxy)-5-hydroxypyridine-4-sulfonamide |
| --- | --- | --- |
| 190 | [structure] | N-cyclobutyl-2-(2,6-dichloro-4-(6-(difluoromethyl)-3,5-dioxo-4,5-dihydro-1,2,4-triazin-2(3H)-yl)phenoxy-3,5-d2)-5-hydroxypyridine-4-sulfonamide |
| 191 | [structure] | N-cyclobutyl-2-(2,6-dichloro-4-(6-(difluoromethyl-d)-3,5-dioxo-4,5-dihydro-1,2,4-triazin-2(3H)-yl)phenoxy)-5-hydroxypyridine-4-sulfonamide |

Due to the existence of double bonds, the compounds of the present application may be in cis or trans, or Z or E, configuration. It is understood that although one configuration may be depicted in the structure of the compounds or formulae of the present application, the present application also encompasses the other configuration.

In one embodiment, a compound of the present application (e.g., a compound of any of the formulae or any individual compounds disclosed herein) is a pharmaceutically acceptable salt. In another embodiment, a compound of the present application (e.g., a compound of any of the formulae or any individual compounds disclosed herein) is a solvate. In another embodiment, a compound of the present application (e.g., a compound of any of the formulae or any individual compounds disclosed herein) is a hydrate.

The details of the application are set forth in the accompanying description below. Although methods and materials similar or equivalent to those described herein can be used in the practice or testing of the present application, illustrative methods and materials are now described. Other features, objects, and advantages of the application will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this application belongs. All patents and publications cited in this specification are incorporated herein by reference in their entireties.

Definitions

The articles "a" and "an" are used in this application to refer to one or more than one (i.e., at least one) of the grammatical object of the article. By way of example, "an element" means one element or more than one element.

The term "and/or" is used in this application to mean either "and" or "or" unless indicated otherwise.

The application also includes pharmaceutical compositions comprising an effective amount of a compound of the present application (e.g., a compound of any of the formulae or any individual compounds disclosed herein) and a pharmaceutically acceptable carrier.

The term "alkyl," as used herein, refers to saturated, straight or branched-chain hydrocarbon radicals containing, in certain embodiments, between one and six carbon atoms. Examples of $C_1$-$C_8$ alkyl radicals include, but are not limited to, methyl, ethyl, propyl, isopropyl, n-butyl, tert-butyl, neopentyl, n-hexyl, n-heptyl, and n-octyl radicals. Examples of $C_1$-$C_6$ alkyl radicals include, but are not limited to, methyl, ethyl, propyl, isopropyl, n-butyl, tert-butyl, neopentyl, and n-hexyl radicals.

The term "alkenyl," as used herein, denotes a monovalent group derived from a hydrocarbon moiety containing, in certain embodiments, from two to six carbon atoms having at least one carbon-carbon double bond. The double bond may or may not be the point of attachment to another group. Alkenyl groups include, but are not limited to, for example, ethenyl, propenyl, butenyl, 1-methyl-2-buten-1-yl and the like.

The term "alkoxy" refers to an —O-alkyl radical.

The terms "hal," "halo," and "halogen," as used herein, refer to an atom selected from fluorine, chlorine, bromine and iodine.

The term "aryl," as used herein, refers to a mono- or poly-cyclic carbocyclic ring system having one or more aromatic rings, fused or non-fused, including, but not limited to, phenyl, naphthyl, tetrahydronaphthyl, indanyl, indenyl and the like.

The term "aralkyl," as used herein, refers to an alkyl residue attached to an aryl ring. Examples include, but are not limited to, benzyl, phenethyl and the like.

The term "cycloalkyl," as used herein, denotes a monovalent group derived from a monocyclic or polycyclic saturated or partially unsaturated carbocyclic ring compound (fused, bridged, or spiro rings). "Cycloalkyl", as used herein, includes monocyclic cycloalkyl groups, and multicyclic (i.e. polycyclic) cycloalkyl groups comprising two or more ring groups which may form a spiro-, fused-, or bridged-ring system. These cycloalkyls may have from 3 to 15 ring carbon atoms. Examples of $C_3$-$C_{10}$ cycloalkyl include, but not limited to, cyclopropyl, cyclobutyl, cyclopentyl, cyclohexyl, cycloheptyl, cyclooctyl, cyclononyl, cyclodecyl, bicyclo[1.1.1]pentanyl, bicyclo[2.2.1]heptyl, spiro[3.3]heptanyl, bicyclo[2.2.2]octyl, and adamantyl. Also contemplated is a monovalent group derived from a monocyclic or polycyclic carbocyclic ring compound having at least one carbon-carbon double bond by the removal of a single hydrogen atom. Examples of such groups include, but are not limited to, cyclopropenyl, cyclobutenyl, cyclopentenyl, cyclohexenyl, cycloheptenyl, cyclooctenyl, and the like.

The term "heteroaryl," as used herein, refers to a mono- or poly-cyclic (e.g., bi-, or tri-cyclic or more) fused or non-fused, radical or ring system having at least one aromatic ring, having from five to ten ring atoms of which one ring atoms is selected from S, O, and N; zero, one, or two ring atoms are additional heteroatoms independently selected from S, O, and N; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "heteroaralkyl" as used herein, refers to an alkyl residue attached to a heteroaryl ring. Examples include, but are not limited to, pyridinylmethyl, pyrimidinylethyl and the like.

The term "heterocyclyl" or "heterocycloalkyl," as used herein, refers to a saturated or unsaturated non-aromatic 3-, 4-, 5-, 6-, 7-, or 8-membered monocyclic, 7-, 8-, 9-, 10-, 11-, or 12-membered bicyclic (fused, bridged, or spiro rings), or 11-, 12, 13, or 14-membered tricyclic ring system (fused, bridged, or spiro rings), where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, and (iv) the nitrogen heteroatom may optionally be quaternized. Representative heterocycloalkyl groups include, but are not limited to, [1,3]dioxolanyl, pyrrolidinyl, pyrazolidinyl, pyrazolinyl, imidazolinyl, imidazolidinyl, piperidinyl, piperazinyl, 2-pyridone, oxazolidinyl, isoxazolidinyl, morpholinyl, tetrahydropyranyl, thiazolidinyl, isothiazolidinyl, tetrahydrofuryl, dioxanyl, oxetanyl, azetidinyl, thietanyl, oxiranyl, aziridinyl, thiiranyl, 2-oxa-5-azabicyclo[2.2.1]heptanyl, 2,5-diazabicyclo[2.2.1]heptanyl, (1S,4R)-2$\lambda^2$-azabicyclo[2.2.1]heptanyl, (1R,4S)-2$\lambda^2$-azabicyclo[2.2.1]heptanyl, 2-oxa-6-azaspiro[3.3]heptanyl, 2,6-diazaspiro[3.3]heptanyl, 1,4-dioxa-8-azaspiro[4.5]decanyl, 2-azaspiro[3.3]heptan-5-amine, 1-azaspiro[3.3]heptan-5-amine, 1-oxa-6-azaspiro[3.3]heptan-3-amine, 2-azaspiro[3.3]heptan-6-amine, 1-azaspiro[3.3]heptan-6-amine, 6-azaspiro[3.4]octan-2-amine, 5-azaspiro[3.4]octan-2-amine, 6-azaspiro[3.4]octan-1-amine, 5-azaspiro[3.4]octan-1-amine, 5-oxa-2-azaspiro[3.4]octan-7-amine, 7-amino-5-thia-2-azaspiro[3.4]octane 5,5-dioxide, 5-oxa-2-azaspiro[3.4]octan-8-amine, 8-amino-5-thia-2-azaspiro[3.4]octane 5,5-dioxide, and the like.

The term "alkylamino" refers to a group having the structure, e.g., NH($C_1$-$C_6$ alkyl), where $C_1$-$C_6$ alkyl is as previously defined.

The term "dialkylamino" refers to a group having the structure, e.g., N($C_1$-$C_6$ alkyl)$_2$, where $C_1$-$C_6$ alkyl is as previously defined.

In accordance with the application, any of the aryls, substituted aryls, heteroaryls and substituted heteroaryls described herein, can be any aromatic group. Aromatic groups can be substituted or unsubstituted.

As described herein, compounds of the application may optionally be substituted with one or more substituents, such as are illustrated generally above, or as exemplified by particular classes, subclasses, and species of the application. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. The terms "optionally substituted", "optionally substituted alkyl," "optionally substituted alkenyl," "optionally substituted cycloalkyl," "optionally substituted cycloalkenyl," "optionally substituted aryl", "optionally substituted heteroaryl," "optionally substituted aralkyl", "optionally substituted heteroaralkyl," "optionally substituted heterocyclyl," and any other optionally substituted group as used herein, refer to groups that are substituted or unsubstituted by independent replacement of one, two, or three or more of the hydrogen atoms thereon with substituents including, but not limited to: —F, —Cl, —Br, —I, —OH, protected hydroxy, —NO$_2$, —CN, —NH$_2$, protected amino, —NH—$C_1$-$C_{12}$-alkyl, —NH—$C_2$-$C_{12}$-alkenyl, —NH—$C_2$-$C_{12}$-alkenyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkenyl, —O—C3-$C_{12}$-cycloalkyl, —O-aryl, —O-heteroaryl, —O-heterocycloalkyl, —C(O)—$C_1$-$C_{12}$-alkyl, —C(O)—$C_2$-$C_{12}$-alkenyl, —C(O)—$C_2$-$C_{12}$-alkenyl, —C(O)—$C_3$-$C_{12}$-cycloalkyl, —C(O)-aryl, —C(O)-heteroaryl, —C(O)-heterocycloalkyl, —CONH$_2$, —CONH—$C_1$-$C_{12}$-alkyl, —CONH—$C_2$-$C_{12}$-alkenyl, —CONH—$C_2$-$C_{12}$-alkenyl, —CONH—$C_3$-$C_{12}$-cycloalkyl, —CONH-aryl, —CONH-heteroaryl, —CONH-heterocycloalkyl, —$OCO_2$—$C_1$-$C_{12}$-alkyl, —$OCO_2$—$C_2$-$C_{12}$-alkenyl, —$OCO_2$—$C_2$-$C_{12}$-alkenyl, —$OCO_2$—$C_3$-$C_{12}$-cycloalkyl, —$OCO_2$-aryl, —$OCO_2$-heteroaryl, —$OCO_2$-heterocycloalkyl, —$OCONH_2$, —OCONH—$C_1$-$C_{12}$-alkyl, —OCONH—$C_2$-$C_{12}$-alkenyl, —OCONH—$C_2$-$C_{12}$-alkenyl, —OCONH—$C_3$-$C_{12}$-cycloalkyl, —OCONH-aryl, —OCONH-heteroaryl, —OCONH-heterocycloalkyl, —NHC(O)—$C_1$-$C_{12}$-alkyl, —NHC(O)—$C_2$-$C_{12}$-alkenyl, —NHC(O)—$C_2$-$C_{12}$-alkenyl, —NHC(O)—$C_3$-$C_{12}$-cycloalkyl, —NHC(O)-aryl, —NHC(O)-heteroaryl, —NHC(O)-heterocycloalkyl, —$NHCO_2$—$C_1$-$C_{12}$-alkyl, —$NHCO_2$—$C_2$-$C_{12}$-alkenyl, —$NHCO_2$—$C_2$-$C_{12}$-alkenyl, —$NHCO_2$—$C_3$-$C_{12}$-cycloalkyl, —$NHCO_2$-aryl, —$NHCO_2$-heteroaryl, —$NHCO_2$-heterocycloalkyl, —NHC(O)$NH_2$, —NHC(O)NH—$C_1$-$C_{12}$-alkyl, —NHC(O)NH—$C_2$-$C_{12}$-alkenyl, —NHC(O)NH—$C_2$-$C_{12}$-alkenyl, —NHC(O)NH—$C_3$-$C_{12}$-cycloalkyl, —NHC(O)NH-aryl, —NHC(O)NH-heteroaryl, NHC(O)NH-heterocycloalkyl, —NHC(S)$NH_2$, —NHC(S)NH—$C_1$-$C_{12}$-alkyl, —NHC(S)NH—$C_2$-$C_{12}$-alkenyl, —NHC(S)NH—$C_2$-$C_{12}$-alkenyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)$NH_2$, —NHC(NH)NH—$C_1$-$C_{12}$-alkyl, —NHC(NH)NH—$C_2$-$C_{12}$-alkenyl, —NHC(NH)NH—$C_2$-$C_{12}$-alkenyl, —NHC(NH)NH—$C_3$-$C_{12}$-cycloalkyl, —NHC(NH)NH-aryl, —NHC(NH)NH-heteroaryl, —NHC(NH)NHheterocycloalkyl, —NHC(NH)—$C_1$-$C_{12}$-alkyl, —NHC(NH)—$C_2$-$C_{12}$-alkenyl, —NHC(NH)—$C_2$-$C_{12}$-alkenyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_{12}$-alkenyl, —C(NH)NH—$C_2$-$C_{12}$-alkenyl, C(NH)NH—$C_3$-$C_{12}$-cycloalkyl, —C(NH)NH-aryl, —C(NH)NH-heteroaryl, —C(NH)NHheterocycloalkyl, —S(O)—$C_1$-$C_{12}$-alkyl, —S(O)—$C_2$-$C_{12}$-alkenyl, —S(O)—$C_2$-$C_{12}$-alkenyl, —S(O)—$C_3$-$C_{12}$-cycloalkyl, —S(O)-aryl, —S(O)-heteroaryl, —S(O)-heterocycloalkyl-$SO_2NH_2$, —$SO_2$NH—$C_1$-$C_{12}$-alkyl, —$SO_2$NH—$C_2$-$C_{12}$-alkenyl, —$SO_2$NH—$C_2$-$C_{12}$-alkenyl, —$SO_2$NH—$C_3$-$C_{12}$-cycloalkyl, —$SO_2$NH-aryl, —$SO_2$NH-heteroaryl, —$SO_2$NH-heterocycloalkyl, —$NHSO_2$—$C_1$-$C_{12}$-alkyl, —$NHSO_2$—$C_2$-$C_{12}$-alkenyl, —$NHSO_2$—$C_2$-$C_{12}$-alkenyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_{12}$-alkenyl, —S—$C_2$-$C_{12}$-alkenyl, —S—$C_3$-$C_{12}$-cycloalkyl, —S-aryl, —S-heteroaryl, —S-heterocycloalkyl, or methylthiomethyl.

The term "carrier", as used in this application, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The compounds of the present application may form salts which are also within the scope of this application. Reference to a compound of the Formulae herein is understood to include reference to salts thereof, unless otherwise indicated.

Representative "pharmaceutically acceptable salts" include, e.g., water-soluble and water-insoluble salts, such as the acetate, amsonate (4,4-diaminostilbene-2,2-disulfonate), benzenesulfonate, benzoate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumerate, fumarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

The compounds of the present application, for example, including the pharmaceutically acceptable salts, solvates, prodrugs, stereoisomers, or tautomers of the compounds, can exist in a solvated form with other solvent molecules or in an unsolvated form.

"Solvate" means solvent addition forms that contain either stoichiometric or non stoichiometric amounts of solvent. Some compounds or salts have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this application, as are positional isomers (such as, for example, 4-pyridyl and 3-pyridyl). For example, if a compound of Formula (I) incorporates a double bond or a fused ring, both the cis- and trans-forms, as well as mixtures, are embraced within the scope of the application. Individual stereoisomers of the compound of the application may, for example, be substantially free of other isomers, or may be admixed, for example, as racemates or with all other, or other selected, stereoisomers. The chiral centers of the present application can have the S or R configuration as defined by the IUPAC 1974 Recommendations. The use of the terms "salt", "solvate", "ester," "prodrug" and the like, is intended to equally apply to the salt, solvate, ester and prodrug of enantiomers, stereoisomers, rotamers, tautomers, positional isomers, racemates or prodrugs of the inventive compounds.

The term "isomer" refers to compounds that have the same composition and molecular weight but differ in physical and/or chemical properties. The structural difference may be in constitution (geometric isomers) or in the ability to rotate the plane of polarized light (stereoisomers). With regard to stereoisomers, the compounds of the present application (e.g., a compound of any of the formulae or any individual compounds disclosed herein) may have one or more asymmetric carbon atom and may occur as racemates, racemic mixtures or as individual enantiomers or diastereomers.

In the present specification, the structural formula of the compound represents a certain isomer for convenience in some cases, but the present application includes all isomers, such as geometrical isomers, optical isomers based on an asymmetrical carbon, stereoisomers, tautomers, and the like.

"Isomerism" means compounds that have identical molecular formulae but differ in the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images of each other are termed "enantiomers" or sometimes optical isomers. A mixture containing equal amounts of individual enantiomeric forms of opposite chirality is termed a "racemic mixture".

The compounds of the application may contain asymmetric or chiral centers, and, therefore, exist in different stereoisomeric forms. It is intended that all stereoisomeric forms of the compounds of the application as well as mixtures thereof, including racemic mixtures, form part of the present application. In addition, the present application embraces all geometric and positional isomers. For example, if a compound of the application incorporates a double bond or a fused ring, both the cis- and trans-forms, as well as mixtures, are embraced within the scope of the application. Each compound herein disclosed includes all the enantiomers that conform to the general structure of the compound. The compound may be in a racemic or enantiomerically pure form, or any other form in terms of stereochemistry. The assay results may reflect the data collected for the racemic form, the enantiomerically pure form, or any other form in terms of stereochemistry.

A carbon atom bonded to four non-identical substituents is termed a "chiral center".

"Chiral isomer" means a compound with at least one chiral center. Compounds with more than one chiral center may exist either as an individual diastereomer or as a mixture of diastereomers, termed "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the *Sequence Rule* of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

In another embodiment of the application, the compound of the present application (e.g., a compound of any of the formulae or any individual compounds disclosed herein) is an enantiomer. In some embodiments the compound is the (S)-enantiomer. In other embodiments the compound is the (R)-enantiomer. In yet other embodiments, the compounds of the present application (e.g., a compound of any of the formulae or any individual compounds disclosed herein) may be (+) or (−) enantiomers. The compound may contain more than one stereocenter.

In another embodiment of the application, the compounds of the present application (e.g., a compound of any of the formulae or any individual compounds disclosed herein) are diastereomers. In some embodiments, the compounds are the syn diastereomer. In other embodiments, the compounds are the anti diastereomer.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Enantiomers can also be separated by use of a chiral HPLC column.

It is also possible that the compounds of the application may exist in different tautomeric forms, and all such forms are embraced within the scope of the application. Also, for example, all keto-enol and imine-enamine forms of the compounds are included in the application.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solid form, usually one tautomer predominates. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

Common tautomeric pairs are: ketone-enol, amide-nitrile, lactam-lactim, amide-imidic acid tautomerism in heterocyclic rings (e.g., in nucleobases such as guanine, thymine and cytosine), amine-enamine and enamine-imine.

The present application relates to a compound of the present application (e.g., a compound of any of the formulae or any individual compounds disclosed herein) or pharmaceutically acceptable salts, solvates, prodrugs, stereoisomers, or tautomers thereof, capable of modulating thyroid hormone receptors, which are useful for the treatment of diseases and disorders associated with modulation of thyroid hormone receptors. The application further relates to compounds of the present application (e.g., a compound of any of the formulae or any individual compounds disclosed herein), or pharmaceutically acceptable salts, solvates, prodrugs, stereoisomers, or tautomers thereof, which are useful for modulating thyroid hormone receptors.

In some embodiments, the application provides a compound of the present application (e.g., a compound of any of the formulae or any individual compounds disclosed herein), wherein the compound possesses advantageous characteristics, compared to one or more known thyroid hormone receptor ligands, including, but not limited to MGL-3196, VK-2809, eprotirome, sobetirome, and KB-141.

In some embodiments, the application provides a compound of the present application (e.g., a compound of any of the formulae or any individual compounds disclosed herein), wherein the compound is at least as potent as one or more known thyroid hormone receptor ligands, including, but not limited to MGL-3196, VK-2809, eprotirome, sobetirome, and KB-141, at modulating the activity of thyroid hormone receptors, and possesses additional advantageous characteristics, compared to one or more known thyroid hormone receptor ligands, including, but not limited to MGL-3196, VK-2809, eprotirome, sobetirome, and KB-141.

In some embodiments, the application provides a compound of the present application (e.g., a compound of any of the formulae or any individual compounds disclosed herein), wherein the compound is more potent than one or more known thyroid hormone receptor ligands, including, but not limited to MGL-3196, VK-2809, eprotirome, sobetirome, and KB-141, at modulating the activity of thyroid hormone receptors.

In some embodiments, the application provides a compound of the present application (e.g., a compound of any of the formulae or any individual compounds disclosed herein), wherein the compound is more potent than one or more known thyroid hormone receptor ligands, including, but not limited to MGL-3196, VK-2809, eprotirome, sobetirome, and KB-141, at modulating the activity of thyroid hormone receptors, and possesses additional advantageous characteristics, compared to one or more known thyroid hormone receptor ligands, including, but not limited to MGL-3196, VK-2809, eprotirome, sobetirome, and KB-141.

In some embodiments, the application provides a compound of the present application (e.g., a compound of any of the formulae or any individual compounds disclosed herein), wherein the compound has higher isoform selectivity, compared to one or more known thyroid hormone receptor ligands, including, but not limited to MGL-3196, VK-2809, eprotirome, sobetirome, and KB-141.

In some embodiments, the application provides a compound of the present application (e.g., a compound of any of the formulae or any individual compounds disclosed herein), wherein the compound has higher isoform selectivity compared to one or more known thyroid hormone receptor ligands, including, but not limited to MGL-3196, VK-2809, eprotirome, sobetirome, and KB-141, at modulating the activity of thyroid hormone receptors, and possesses additional advantageous characteristics, compared to one or more known thyroid hormone receptor ligands, including, but not limited to MGL-3196, VK-2809, eprotirome, sobetirome, and KB-141.

In some embodiments, the application provides a compound of the present application (e.g., a compound of any of the formulae or any individual compounds disclosed herein), wherein the compound has higher tissue selectivity, compared to one or more known thyroid hormone receptor ligands, including, but not limited to MGL-3196, VK-2809, eprotirome, sobetirome, and KB-141.

In some embodiments, the application provides a compound of the present application (e.g., a compound of any of the formulae or any individual compounds disclosed herein), wherein the compound has higher tissue selectivity compared to one or more known thyroid hormone receptor ligands, including, but not limited to MGL-3196, VK-2809, eprotirome, sobetirome, and KB-141, at modulating the activity of thyroid hormone receptors, and possesses additional advantageous characteristics, compared to one or more known thyroid hormone receptor ligands, including, but not limited to MGL-3196, VK-2809, eprotirome, sobetirome, and KB-141.

In some embodiments, the application provides a compound of the present application (e.g., a compound of any of the formulae or any individual compounds disclosed herein), wherein the compound has higher liver tissue selectivity, compared to one or more known thyroid hormone receptor ligands, including, but not limited to MGL-3196, VK-2809, eprotirome, sobetirome, and KB-141.

In some embodiments, the application provides a compound of the present application (e.g., a compound of any of the formulae or any individual compounds disclosed herein), wherein the compound has higher liver tissue selectivity compared to one or more known thyroid hormone receptor ligands, including, but not limited to MGL-3196, VK-2809, eprotirome, sobetirome, and KB-141, at modulating the activity of thyroid hormone receptors, and possesses additional advantageous characteristics, compared to one or more known thyroid hormone receptor ligands, including, but not limited to MGL-3196, VK-2809, eprotirome, sobetirome, and KB-141.

Potency of the agonist or activator can be determined by $EC_{50}$ value. A compound with a lower $EC_{50}$ value, as determined under substantially similar conditions, is a more potent agonist or activator relative to a compound with a higher $EC_{50}$ value.

The compounds of the present application can be converted to N-oxides by treatment with an oxidizing agent (e.g., 3-chloroperoxybenzoic acid (m-CPBA) and/or hydrogen peroxides) to afford other compounds of the present application. Thus, all shown and claimed nitrogen-containing compounds are considered, when allowed by valency and structure, to include both the compound as shown and its N-oxide derivative (which can be designated as N→O or $N^+$—$O^-$). Furthermore, in other instances, the nitrogens in the compounds of the present application can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compounds as shown and its N-hydroxy (i.e., N—OH) and N-alkoxy (i.e., N—OR, wherein R is substituted or unsubstituted $C_1$-$C_6$ alkyl, $C_1$-$C_6$ alkenyl, $C_1$-$C_6$ alkynyl, 3-14-membered carbocycle or 3-14-membered heterocycle) derivatives.

The term "prodrug," as used in this application, means a compound which is convertible in vivo by metabolic means (e.g., by hydrolysis) to a disclosed compound.

Since prodrugs are known to enhance numerous desirable qualities of pharmaceuticals (e.g., solubility, bioavailability, manufacturing, etc.) the compounds of the present application (e.g., a compound of any of the formulae or any individual compounds disclosed herein), or pharmaceutically acceptable salts, solvates, prodrugs, stereoisomers, or tautomers thereof can be delivered in prodrug form. Thus, the present application is intended to cover prodrugs of a compound of the present application (e.g., a compound of any of the formulae or any individual compounds disclosed herein), or a pharmaceutically acceptable salt, solvate, prodrug, stereoisomer, or tautomer thereof, methods of delivering the same and compositions containing the same. "Prodrugs" are intended to include any covalently bonded carriers that release an active parent drug of the present application in vivo when such prodrug is administered to a mammalian subject. Prodrugs are prepared by modifying functional groups present in the compound in such a way that the modifications are cleaved, either in routine manipulation or in vivo, to the parent compound. Prodrugs include compounds of the application wherein a hydroxyl or amino, group is bonded to any group that, when the prodrug of the present application is administered to a mammalian subject, it cleaves to form a free hydroxyl or free amino group, respectively. Examples of prodrugs include, but are not limited to, acetate, formate, and benzoate derivatives of alcohol and amine functional groups in the compounds of each of the formulae described herein or a pharmaceutically acceptable salt, solvate, prodrug, stereoisomer, or tautomer thereof.

The term "crystal polymorphs", "polymorphs" or "crystal forms" means crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate.

As used herein, the term "analog" refers to a compound that is structurally similar to another compound but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

The application also comprehends isotopically-labeled compounds, which are identical to those recited in the each of the formulae described herein, but for the fact that one or more atoms are replaced by an atom having an atomic mass or mass number different from the atomic mass or mass number most commonly found in nature. Examples of isotopes that can be incorporated into compounds of the application include isotopes of hydrogen, carbon, nitrogen, fluorine, such as $^3$H, $^{11}$C, $^{14}$C, $^2$H and $^{18}$F.

Compounds of the present application (e.g., a compound of any of the formulae or any individual compounds disclosed herein), or pharmaceutically acceptable salts, solvates, prodrugs, stereoisomers, or tautomers thereof, that contain the aforementioned isotopes and/or other isotopes of other atoms are within the scope of the present application. Isotopically-labeled compounds of the present application, for example those into which radioactive isotopes such as $^3$H, $^{14}$C are incorporated, are useful in drug and/or substrate tissue distribution assays. Tritiated, i.e., $^3$H, and carbon-14, i.e., $^{14}$C, isotopes are useful for their ease of preparation and detectability. $^{11}$C and $^{18}$F isotopes are useful in PET (positron emission tomography). PET is useful in brain imaging. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances, isotopically labeled compounds of the present application (e.g., a compound of any of the formulae or any individual compounds disclosed herein), or pharmaceutically acceptable salts, solvates, prodrugs, stereoisomers, or tautomers thereof, can generally be prepared by carrying out the procedures disclosed in the Schemes and/or in the Examples described herein, by substituting a readily available isotopically labeled reagent for a non-isotopically labeled reagent. In one embodiment, the compound of the present application (e.g., a compound of any of the formulae or any individual compounds disclosed herein) or pharmaceutically acceptable salts, solvates, prodrugs, stereoisomers, or tautomers thereof, is not isotopically labelled.

The term "administer", "administering", or "administration" as used in this application refers to either directly administering a disclosed compound or pharmaceutically acceptable salt of the disclosed compound or a composition to a subject, or administering a prodrug, derivative or analog of the compound or pharmaceutically acceptable salt of the compound or a composition to the subject, which can form an equivalent amount of active compound within the subject's body.

A "patient" or "subject" is a mammal, e.g., a human, mouse, rat, guinea pig, dog, cat, horse, cow, pig, or non-human primate, such as a monkey, chimpanzee, baboon or rhesus.

An "effective amount" or "therapeutically effective amount" when used in connection with a compound or pharmaceutical composition is an amount effective for treating or preventing a disease in a subject as described herein.

The term "treating" with regard to a subject, refers to improving at least one symptom of the subject's disorder. Treating includes curing, improving, or at least partially ameliorating the disorder.

The compounds of the present application, or a pharmaceutically acceptable salt, solvate, prodrug, stereoisomer, or tautomer thereof, can also be used to prevent a disease, condition or disorder. As used herein, "preventing" or "prevent" describes reducing or eliminating the onset of the symptoms or complications of the disease, condition or disorder.

The term "disorder" is used in this application to mean, and is used interchangeably with, the terms disease, condition, or illness, unless otherwise indicated.

As used herein, the term diseases or disorders regulated by thyroid hormone means any disease or other deleterious condition in which a thyroid hormone, is known to play a role. Accordingly, another embodiment of the present application relates to treating or lessening the severity of one or more diseases in which a thyroid hormone, is known to play a role. Specifically, the present application relates to a method of treating or lessening the severity of a disease or condition regulated by thyroid hormone selected from a liver disease (e.g., nonalcoholic fatty liver disease (NAFLD), nonalcoholic steatohepatitis (NASH), liver steatosis, liver fibrosis, hepatitis, liver cirrhosis, or hepatocellular cancer (HCC)/liver cancer), a metabolic disease (e.g., dyslipidemia, hyperlipidemia, severe high triglyceride (SHTG), familial partial lipodystrophy (FPLD), familial chylomicronemia syndrome (FCS), xanthomas, familial dysbetalipoproteinemia/hypolipoproteinemia type III), hypercholesterolemia, familial hypercholesterolemia (HeFH/HoFH), a metabolic disorder, obesity, or diabetes (e.g., Type II diabetes mellitus), a thyroid disease (e.g., hypothyroidism, resistance to thyroid hormone (RTH) syndrome, thyroid cancer, Allan-Herdon-Dudley syndrome, Graves disease, Hashimoto's disease, thyroiditis, thyroid dysgenesis, congenital hypothyroidism, or inherited thyroid hormone binding protein abnormalities), a cardiovascular disease (e.g., hypertension, atherosclerosis, heart failure, cardiac arrhythmia, coronary heart disease, or cardiac hypertrophy), a rare disease regulated by thyroid hormone (e.g., X-linked adrenoleukodystrophy (X-ALD), glycogen storage disease (GSD), androgenetic alopecia (AGA), or multiple sclerosis), pancreatitis, and other diseases regulated by thyroid hormone (e.g., fibrosis such as lung fibrosis and kidney fibrosis, or a skin disorder). In one embodiment, a disease or condition regulated by thyroid hormone is selected from a liver disease, liver inflammation, fibrosis (e.g., liver fibrosis), NAFLD, NASH, atherosclerosis, stroke and complications thereof, Alzheimer's disease, cardiovascular disease, metabolic disease, atherosclerosis, myocardial infarction. In one embodiment, a disease or condition regulated by thyroid hormone is a liver disease selected from NAFLD, NASH, liver steatosis, liver fibrosis, hepatitis, liver cirrhosis, and HCC/ liver cancer. In one embodiment, the liver disease is selected from NAFLD, NASH, liver steatosis, and liver fibrosis. In one embodiment, a disease or condition regulated by thyroid hormone is a metabolic disease selected from dyslipidemia, hyperlipidemia, hypercholesterolemia, familial hypercholesterolemia (HeFH/HoFH), a metabolic disorder, obesity, and diabetes (e.g., Type II diabetes mellitus). In one embodiment, the metabolic disease is selected from hyperlipidemia, hypercholesterolemia, and familial hypercholesterolemia (HeFH/HoFH). In one embodiment, a disease or condition regulated by thyroid hormone is a thyroid disease selected from hypothyroidism, RTH syndrome, thyroid cancer, Allan-Herdon-Dudley syndrome, and Graves disease. In one embodiment, a disease or condition regulated by thyroid hormone is a cardiovascular disease selected from hypertension, atherosclerosis, heart failure, cardiac arrhythmia, coronary heart disease, and cardiac hypertrophy. In one embodiment, a disease or condition regulated by thyroid hormone is a rare disease regulated by thyroid hormone selected from X-ALD, GSD, AGA, and multiple sclerosis. In one embodiment, a disease or condition regulated by thyroid hormone is selected from a fibrosis such as lung fibrosis and kidney fibrosis, and a skin disorder. In one embodiment, a disease or condition regulated by thyroid hormone is selected from NAFLD, NASH, liver steatosis, liver fibrosis, hyperlipidemia, hypercholesterolemia, familial hypercholesterolemia (HeFH/HoFH), and X-ALD.

Methods for Preparing the Compounds

The compounds of the present application may be made by a variety of methods, including standard chemistry. Suitable synthetic routes are depicted in the Schemes given below.

The compounds of the present application (e.g., a compound of any of the formulae or any individual compounds disclosed herein) may be prepared by methods known in the art of organic synthesis as set forth in part by the following synthetic schemes. In the scheme described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of the compounds of the present application.

Those skilled in the art will recognize if a stereocenter exists in the compounds of the present application (e.g., a compound of any of the formulae or any individual compounds disclosed herein). Accordingly, the present application includes both possible stereoisomers (unless specified in the synthesis) and includes not only racemic compound but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The compounds described herein may be made from commercially available starting materials or synthesized using known organic, inorganic, and/or enzymatic processes.

The compounds of the present application can be prepared in a number of ways well known to those skilled in the art of organic synthesis. By way of example, the compounds of the present application can be synthesized using the methods described below, together with synthetic methods known in the art of synthetic organic chemistry, or variations thereon as appreciated by those skilled in the art. Preferred methods include but are not limited to those methods described below. The compounds of the present application (i.e., a compound of the present application (e.g., a compound of any of the formulae or any individual compounds disclosed herein)) can be synthesized by following the steps outlined in General Schemes described in Examples. Starting materials are either commercially available or made by known procedures in the reported literature or as illustrated.

Analytical Methods, Materials, and Instrumentation

Unless otherwise noted, reagents and solvents were used as received from commercial suppliers. Proton and fluorine nuclear magnetic resonance (NMR) spectra were obtained on either Bruker or Varian spectrometers at 400 MHz and 376 MHz, respectively. Spectra are given in ppm ($\delta$) and coupling constants, J, are reported in Hertz. Tetramethylsilane (TMS) was used as an internal standard. Liquid chromatography-mass spectrometry (LC/MS) were collected using a SHIMADZU LCMS-2020EV or Agilent 1260-6125B LCMS. Purity and low resolution mass spectral data were measured using Agilent 1260-6125B LCMS system (with Diode Array Detector, and Agilent G6125BA Mass spectrometer) or using Waters Acquity UPLC system (with Diode Array Detector, and Waters 3100 Mass Detector). The purity was characterized by UV wavelength 214 nm, 220 nm, 254 nm and ESI. Column: Waters analytical column CORTECS C182.7 µm 4.6×30 mm; Flow rate 1.8 mL/min; Solvent A (100/0.1 water/formic acid), Solvent B (100 acetonitrile); gradient: hold 5% B to 0.3 min, 5-95% B from 0.3 to 2 min, hold 95% B to 4.8 min, 95-5% B from 4.8 to 5.4 min, then hold 5% B to 6.5 min. Or, column: Acquity UPLC BEH C18 1.7 µm 2.1×50 mm; Flow rate 0.5 mL/min; Solvent A (0.1% formic acid water), Solvent B (acetonitrile); gradient: hold 5% B for 0.2 min, 5-95% B from 0.2 to 2.0 min, hold 95% B to 3.1 min, then 5% B at 3.5 min.

Abbreviations used in the following examples and elsewhere herein are:

| | |
|---|---|
| DIPEA | N,N-diisopropylethylamine |
| DMF | N,N-dimethylformamide |
| DMSO | dimethylsulfoxide |
| IPA | iso-propyl alcohol |
| IPE | di-isopropyl ether |
| MeCN | acetonitrile |
| AMMN | Ammonia, 7.0M solution in MeOH |
| THF | tetrahydrofuran |
| m-CPBA | 3-chlorobenzenecarboperoxoic acid |
| FCC | Flash column chromatography |
| DCM | dichloromethane |
| LC-MS | liquid chromatography-mass spectrometry |

-continued

| | |
|---|---|
| MeOH | methanol |
| MS | mass spectrometry |
| n-BuOH | n-butyl alcohol |
| NMP | N-methyl pyrrolidinone |
| NMR | nuclear magnetic resonance |
| ppm | parts per million |
| TEA | triethylamine |
| EA(EtOAc) | ethyl acetate |
| PE | petroleum ether |
| BAST | [Bis(2-methoxyethyl)aminosulfur Trifluoride |
| HATU | 1-[Bis(dimethylamino)methylene]-1H-1,2,3-triazolo[4,5-b]pyridinium 3-oxide hexafluorophosphate, Hexafluorophosphate Azabenzotriazole Tetramethyl Uronium |
| TLC | Thin layer chromatography |

Biological Assays

The biological activities of the compounds of the present application can be assessed with methods and assays known in the art.

Methods of Using the Compounds

The compounds of the present application are useful for modulating (e.g., activating) thyroid hormone receptors. The relative modulating potencies of the compounds can be determined by the amount needed to modulate activity of binding of a thyroid hormone to thyroid hormone receptors in a variety of ways, e.g., in in vitro assays with recombinant human protein or with recombinant non-human enzyme, in cellular assays expressing normal enzyme, or in in vivo tests. Accordingly, the present application relates to methods of modulating (e.g., activating) thyroid hormone receptors for the treatment of a disease or disorder.

The compounds of the present application are useful for the treatment of a disease or disorder regulated by thyroid hormone. A disease or disorder regulated by thyroid hormone includes, but is not limited to, thyroid hormone disorders, fibrosis or a fibrotic disease, a liver disease, a cardiovascular disease, and a metabolic disease.

Inflammation or an inflammatory disease (e.g., inflammation or an inflammatory disease regulated by thyroid hormone) includes, but is not limited to, arthritis, synovitis, Crohn's disease, ulcerative colitis, irritable bowel disease, asthma (e.g., eosinophilic asthma, severe asthma, virally exacerbated asthma), chronic pain, chronic pain from osteoarthritis, chronic pulmonary obstructive disease, cystic fibrosis, bronchiectasis, liver autoimmune disease, autoimmune hepatitis, primary biliary cirrhosis, sclerosing cholangitis, autoimmune cholangitis, alcoholic liver disease, NAFLD, NASH, neuroinflammation, cirrhosis, atherosclerosis, chronic heart failure, congestive heart failure, ischemic disease, stroke and complications thereof, myocardial infarction and complications thereof, inflammatory cell-mediated tissue destruction following stroke, psoriasis, contact dermatitis, inflammation due to diabetes, skin inflammation, pulmonary inflammation, liver inflammation, and the like.

Fibrosis or a fibrotic disease (e.g., a fibrotic disease regulated by thyroid hormone) includes, but is not limited to, cystic fibrosis, pulmonary fibrosis (e.g., idiopathic pulmonary fibrosis), liver fibrosis, kidney fibrosis, lung fibrosis, fibrosis of other organs and tissues, radiation induced fibrosis, and other diseases where excessive fibrosis contributes to disease pathology, and the like.

A liver disease (e.g., a liver disease regulated by thyroid hormone) includes, but is not limited to, liver inflammation, liver fibrosis, liver steatosis, NASH, NAFLD, cirrhosis, liver autoimmune diseases, autoimmune hepatitis, primary biliary cirrhosis, sclerosing cholangitis, autoimmune cholangitis, alcoholic liver disease, and hepatocellular cancer.

A respiratory disease (e.g., a respiratory disease regulated by thyroid hormone) includes, but is not limited to, lung fibrosis, lung inflammation, asthma (e.g., eosinophilic asthma, severe asthma, virally exacerbated asthma), chronic pulmonary obstructive disease, cystic fibrosis, and bronchiectasis.

A metabolic disease includes, but is not limited to, dyslipidemia, hyperlipidemia, hypercholesterolemia, familial hypercholesterolemia (HeFH/HoFH), a metabolic disorder, obesity, or diabetes (e.g., Type II diabetes mellitus).

A thyroid disease includes, but is not limited to, hypothyroidism, resistance to thyroid hormone (RTH) syndrome, thyroid cancer, Allan-Herdon-Dudley syndrome, or Graves disease.

A cardiovascular disease includes, but is not limited to, hypertension, atherosclerosis, heart failure, cardiac arrhythmia, coronary heart disease, or cardiac hypertrophy.

A rare disease regulated by thyroid hormone includes, but is not limited to, X-linked adrenoleukodystrophy (X-ALD), glycogen storage disease (GSD), androgenetic alopecia (AGA), or multiple sclerosis.

Other diseases regulated by thyroid hormone includes, but is not limited to, fibrosis such as lung fibrosis and kidney fibrosis, or a skin disorder.

Another aspect of the application relates to a method of treating, preventing, inhibiting, or eliminating a disease or disorder regulated by thyroid hormone. The method comprises administering to a subject in need of a treatment for diseases or disorders associated with modulation of thyroid hormone receptors an effective amount a compound of the present application (e.g., a compound of any of the formulae or any individual compounds disclosed herein) or a pharmaceutically acceptable salt, solvate, prodrug, stereoisomer, or tautomer thereof or a pharmaceutical composition of a compound of the present application (e.g., a compound of any of the formulae or any individual compounds disclosed herein).

Another aspect of the application relates to a method of modulating thyroid hormone receptors, the method comprising administering to a subject in need thereof a therapeutically effective amount of a compound of the present application (e.g., a compound of any of the formulae or any individual compounds disclosed herein), or a pharmaceutically acceptable salt, solvate, prodrug, stereoisomer, or tautomer thereof, or a pharmaceutical composition of a compound of the present application (e.g., a compound of any of the formulae or any individual compounds disclosed herein).

Another aspect of the application relates to a compound of the present application (e.g., a compound of any of the formulae or any individual compounds disclosed herein), or a pharmaceutically acceptable salt, solvate, prodrug, stereoisomer, or tautomer thereof, for use in a method of treating a disease or disorder regulated by thyroid hormone. In one embodiment, the disease or disorder regulated by thyroid hormone is a disease or disorder described herein.

In another aspect, the present application relates to a pharmaceutical composition of a compound of the present application (e.g., a compound of any of the formulae or any individual compounds disclosed herein), or a pharmaceutically acceptable salt, solvate, prodrug, stereoisomer, or tautomer thereof, for use in a method of treating a disease or disorder regulated by thyroid hormone. In one embodiment, the disease or disorder regulated by thyroid hormone is a disease or disorder described herein.

Another aspect of the application relates to a compound of the present application (e.g., a compound of any of the formulae or any individual compounds disclosed herein), or a pharmaceutically acceptable salt, solvate, prodrug, stereoisomer, or tautomer thereof, for use in modulating thyroid hormone receptors.

In another aspect, the present application relates to a pharmaceutical composition of a compound of the present application (e.g., a compound of any of the formulae or any individual compounds disclosed herein), or a pharmaceutically acceptable salt, solvate, prodrug, stereoisomer, or tautomer thereof, for use in modulating thyroid hormone receptors.

Another aspect of the application relates to the use of a compound of the present application (e.g., a compound of any of the formulae or any individual compounds disclosed herein), or a pharmaceutically acceptable salt, solvate, prodrug, stereoisomer, or tautomer thereof, in the manufacture of a medicament for treating a disease or disorder regulated by thyroid hormone. In one embodiment, the disease or disorder regulated by thyroid hormone is a disease or disorder described herein.

In another aspect, the present application relates to the use of a pharmaceutical composition of a compound of the present application (e.g., a compound of any of the formulae or any individual compounds disclosed herein), or a pharmaceutically acceptable salt, solvate, prodrug, stereoisomer, or tautomer thereof, in the manufacture of a medicament for treating a disease or disorder regulated by thyroid hormone. In one embodiment, the disease or disorder regulated by thyroid hormone is a disease or disorder described herein.

Another aspect of the application relates to the use of a compound of the present application (e.g., a compound of any of the formulae or any individual compounds disclosed herein), or a pharmaceutically acceptable salt, solvate, prodrug, stereoisomer, or tautomer thereof, in the manufacture of a medicament for modulating thyroid hormone receptors.

In another aspect, the present application relates to the use of a pharmaceutical composition of a compound of the present application (e.g., a compound of any of the formulae or any individual compounds disclosed herein), or a pharmaceutically acceptable salt, solvate, prodrug, stereoisomer, or tautomer thereof, in the manufacture of a medicament for modulating thyroid hormone receptors.

The disclosed compound of the application can be administered in effective amounts to treat or prevent a disorder and/or prevent the development thereof in subjects.

The compound of the application can be administered in therapeutically effective amounts in a combinational therapy with one or more therapeutic agents (pharmaceutical combinations) or modalities, e.g., non-drug therapies. For example, synergistic effects can occur with other anti-proliferative, anti-cancer, immunomodulatory, or anti-inflammatory substances. In some embodiments, a compound of the present application (e.g., a compound of any of the formulae or any individual compounds disclosed herein) is administered in combination with an additional therapeutic agent selected from an anti-inflammatory agent, an immunomodulatory agent, a chemotherapeutic agent, a neurotropic factor, an agent for treating liver disease, an agent for treating metabolic disease, an agent for treating thyroid disease, an agent for treating cardiovascular disease, an agent for treating lung disease, an agent for treating kidney disease, an agent for treating ocular disease, an agent for treating skin disease, an anti-viral agent, an agent for treating blood disorders, an agent for treating diabetes, and an agent for treating immunodeficiency disorders. Where the compound of the application is administered in conjunction with other therapies, dosages of the co-administered compounds will of course vary depending on the type of co-drug employed, on the specific drug employed, on the condition being treated and so forth.

Combination therapy includes the administration of the subject compound in further combination with other biologically active ingredients (such as, but not limited to, an anti-inflammatory agent, an immunomodulatory agent, chemotherapeutic agent, a neurotropic factor, an agent for treating cardiovascular disease, an agent for treating liver disease, an anti-viral agent, an agent for treating blood disorders, an agent for treating diabetes, an agent for treating immunodeficiency disorders, and an agent for treating pain) and non-drug therapies (such as, but not limited to, surgery or radiation treatment). For instance, the compound of the application can be used in combination with other pharmaceutically active compounds, preferably compounds that are able to enhance the effect of the compound of the application. The compound of the application can be administered simultaneously (as a single preparation or separate preparation) or sequentially to the other drug therapy or treatment modality. In general, a combination therapy envisions administration of two or more drugs during a single cycle or course of therapy.

Pharmaceutical Compositions

The present application also provides pharmaceutical compositions comprising a compound of the present application (e.g., a compound of any of the formulae or any individual compounds disclosed herein), or a pharmaceutically acceptable salt, solvate, prodrug, stereoisomer, or tautomer thereof, in combination with at least one pharmaceutically acceptable excipient or carrier.

A "pharmaceutical composition" is a formulation containing the compound of the present application in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or a pharmaceutically acceptable salt, solvate, prodrug, stereoisomer, or tautomer thereof thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this application include powders, sprays, ointments, pastes, creams, lotions, gels, solutions, patches and inhalants. In one embodiment, the active compound is mixed under sterile conditions with a pharmaceutically acceptable carrier, and with any preservatives, buffers or propellants that are required.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

A pharmaceutical compositions of the application are formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A compound or pharmaceutical composition of the application can be administered to a subject in many of the well-known methods currently used for chemotherapeutic treatment. The dose chosen should be sufficient to constitute effective treatment but not as high as to cause unacceptable side effects. The state of the disease condition and the health of the patient should preferably be closely monitored during and for a reasonable period after treatment.

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In one embodiment, the disease or disorder is a disease or disorder described herein.

For any compound, the therapeutically effective amount can be estimated initially either in cell culture assays or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compound (i.e., a compound of the present application (e.g., a compound of any of the formulae or any individual compounds disclosed herein)) of the present application may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compound into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compound is delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compound is formulated into ointments, salves, gels, or creams as generally known in the art.

The active compound can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the application are dictated by and directly dependent on the unique characteristics of the active compound and the particular therapeutic effect to be achieved.

In therapeutic applications, the dosages of the pharmaceutical compositions used in accordance with the application vary depending on the agent, the age, weight, and clinical condition of the recipient patient, and the experience and judgment of the clinician or practitioner administering the therapy, among other factors affecting the selected dosage. Dosages can range from about 0.01 mg/kg per day to about 5000 mg/kg per day. An effective amount of a pharmaceutical agent is that which provides an objectively identifiable improvement as noted by the clinician or other qualified observer. As used herein, the term "dosage effective manner" refers to amount of an active compound to produce the desired biological effect in a subject or cell.

The pharmaceutical compositions can be included in a container, pack, or dispenser together with instructions for administration.

As used herein, "pharmaceutically acceptable salts" refer to derivatives of the compound of the present application wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc., Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present application also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

It should be understood that all references to pharmaceutically acceptable salts include solvent addition forms (solvates) or crystal forms (polymorphs) as defined herein, of the same salt.

The compound of the present application can also be prepared as esters, for example, pharmaceutically acceptable esters. For example, a carboxylic acid function group in a compound can be converted to its corresponding ester, e.g., a methyl, ethyl or other ester. Also, an alcohol group in a compound can be converted to its corresponding ester, e.g., an acetate, propionate or other ester.

The compound of the present application can also be prepared as prodrugs, for example, pharmaceutically acceptable prodrugs. The terms "pro-drug" and "prodrug" are used interchangeably herein and refer to any compound which releases an active parent drug in vivo. Since prodrugs are known to enhance numerous desirable qualities of pharmaceuticals (e.g., solubility, bioavailability, manufacturing, etc.), the compound of the present application can be delivered in prodrug form. Thus, the present application is intended to cover prodrugs of the presently claimed compound, methods of delivering the same and compositions containing the same. "Prodrugs" are intended to include any covalently bonded carriers that release an active parent drug of the present application in vivo when such prodrug is administered to a subject. Prodrugs in the present application are prepared by modifying functional groups present in the compound in such a way that the modifications are cleaved, either in routine manipulation or in vivo, to the parent compound. Prodrugs include the compound of the present application wherein a hydroxy, amino, sulfhydryl, carboxy or carbonyl group is bonded to any group that may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates and benzoate derivatives) and carbamates (e.g., N,N-dimethylaminocarbonyl) of hydroxy functional groups, esters (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in the compound of the application, and the like, See Bundegaard, H., *Design of Prodrugs*, p 1-92, Elsevier, New York-Oxford (1985).

The compound, or pharmaceutically acceptable salts, tautomers, prodrugs, solvates, metabolites, polymorphs, analogs or derivatives thereof, are administered orally, nasally, transdermally, pulmonary, inhalationally, buccally, sublingually, intraperintoneally, subcutaneously, intramuscularly, intravenously, rectally, intrapleurally, intrathecally and parenterally. In one embodiment, the compound or a pharmaceutically acceptable salt, solvate, prodrug, stereoisomer, or tautomer thereof is administered orally. One skilled in the art will recognize the advantages of certain routes of administration.

The dosage regimen utilizing the compound is selected in accordance with a variety of factors including type, species, age, weight, sex and medical condition of the patient; the severity of the condition to be treated; the route of administration; the renal and hepatic function of the patient; and the particular compound or pharmaceutically acceptable salt, solvate, prodrug, stereoisomer, or tautomer thereof employed. An ordinarily skilled physician or veterinarian can readily determine and prescribe the effective amount of the drug required to prevent, counter or arrest the progress of the condition.

Techniques for formulation and administration of the disclosed compound of the application can be found in *Remington: the Science and Practice of Pharmacy*, 19$^{th}$ edition, Mack Publishing Co., Easton, PA (1995). In an embodiment, the compound described herein, and the pharmaceutically acceptable salts, solvates, prodrugs, stereoisomers, or tautomers thereof, are used in pharmaceutical preparations in combination with a pharmaceutically acceptable carrier or diluent. Suitable pharmaceutically acceptable carriers include inert solid fillers or diluents and sterile aqueous or organic solutions. The compound or pharmaceutically acceptable salts, solvates, prodrugs, stereoisomers, or tautomers thereof will be present in such pharmaceutical compositions in amounts sufficient to provide the desired dosage amount in the range described herein.

All percentages and ratios used herein, unless otherwise indicated, are by weight. Other features and advantages of the present application are apparent from the different examples. The provided examples illustrate different components and methodology useful in practicing the present application. The examples do not limit the claimed application. Based on the present application the skilled artisan can identify and employ other components and methodology useful for practicing the present application.

EXAMPLES

The application is further illustrated by the following examples and synthesis schemes, which are not to be construed as limiting this application in scope or spirit to the specific procedures herein described. It is to be understood that the examples are provided to illustrate certain embodiments and that no limitation to the scope of the application is intended thereby. It is to be further understood that resort may be had to various other embodiments, modifications, and equivalents thereof which may suggest themselves to those skilled in the art without departing from the spirit of the present application and/or scope of the appended claims.

Example 1: General Scheme A—Synthesis of Intermediate A

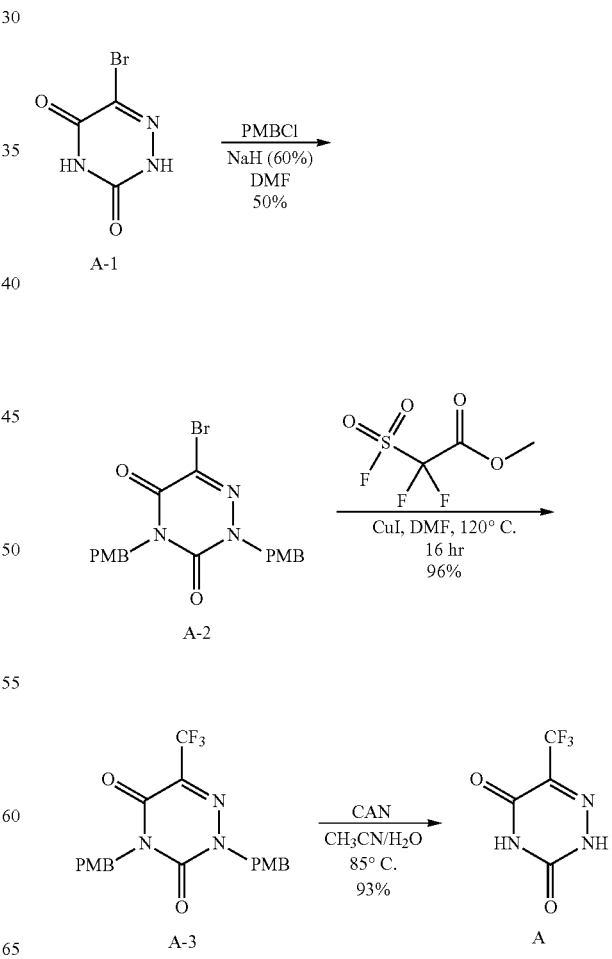

Step 1: A-2

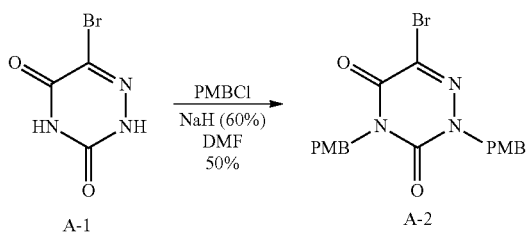

Step 3: Intermediate A

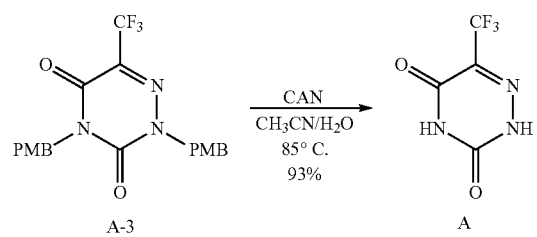

To a solution of 6-bromo-1,2,4-triazine-3,5(2H,4H)-dione A-1 (10 g, 52.09 mmol) in DMF (100 mL) at 0° C. was added Sodium hydride (8.33 g, 208.36 mmol, 60% purity) portion-wise. The reaction mixture was stirred at 0° C. for 30 min. 1-(chloromethyl)-4-methoxybenzene (20.39 g, 130.23 mmol) was added to the reaction mixture. The reaction mixture was stirred at rt for 16 hr. LCMS showed the reaction was completed. The reaction mixture was poured into water (500 mL) and extracted with EA (3×200 mL). The combined organic layer was washed with brine (200 mL), dried over anhydrous $Na_2SO_4$ and filtered. The filtrate was concentrated in vacuum to afford a residue. The residue was purified by silica gel chromatography (PE:EA=5:1) to afford 6-bromo-2,4-bis(4-methoxybenzyl)-1,2,4-triazine-3,5(2H, 4H)-dione A-2 (12 g, 26.37 mmol, 50% yield) as a light yellow solid. LCMS: $[M+Na]^+=454.0$.

Step 2: A-3

A mixture of 2,4-bis(4-methoxybenzyl)-6-(trifluoromethyl)-1,2,4-triazine-3,5(2H,4H)-dione A-3 (2.1 g, 4.98 mmol) and ceric ammonium nitrate (27.32 g, 49.84 mmol) in MeCN (57 mL) and Water (19 mL) was stirred at 85° C. under $N_2(g)$ protection for 3.5 hr. LC-MS showed the reaction was completed. The reaction mixture was poured into water (100 mL) and extracted with EA (2×30 mL). The combined organic layer was washed with brine (50 mL), dried over anhydrous $Na_2SO_4$ and filtered. The filtrate was concentrated in vacuum to afford a residue. The residue was purified by silica gel chromatography (PE:EA=3:1) to afford 6-(trifluoromethyl)-1,2,4-triazine-3,5(2H,4H)-dione Intermediate A (880 mg, 4.62 mmol, 93% yield) as a light yellow solid. LCMS: $[M+H]^+=182.0$.

Example 2: General Scheme B—Synthesis of Intermediate B

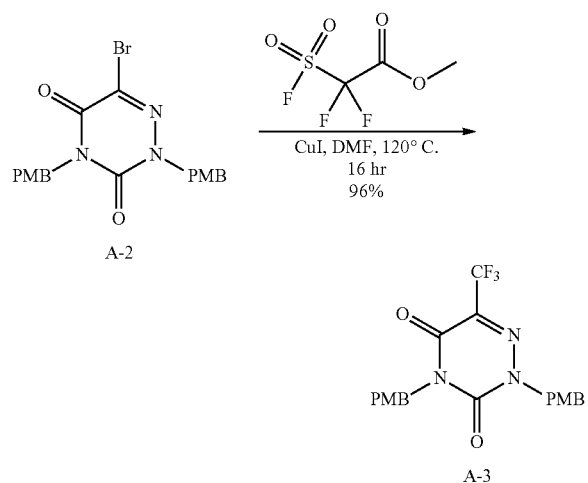

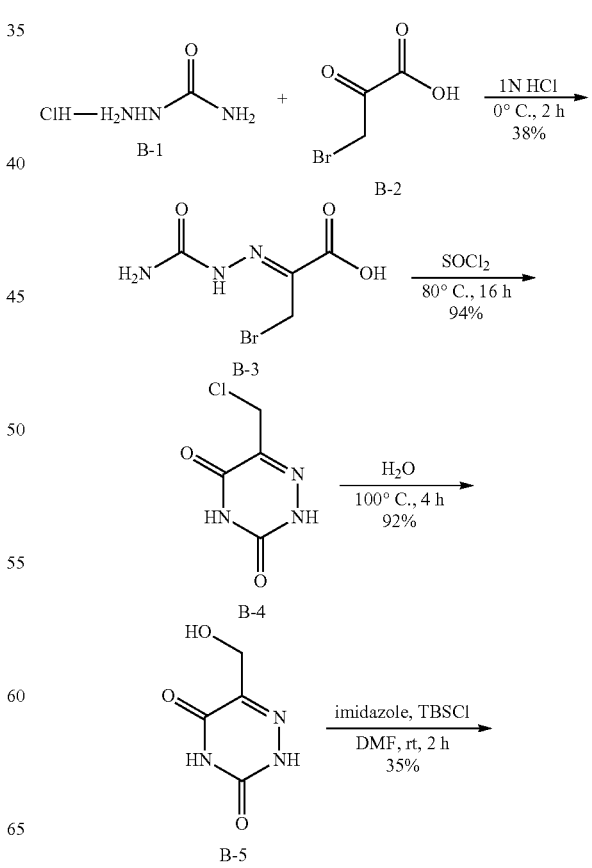

A mixture of 6-bromo-2,4-bis(4-methoxybenzyl)-1,2,4-triazine-3,5(2H,4H)-dione A-2 (3.0 g, 6.94 mmol), methyl 2,2-difluoro-2-(fluorosulfonyl) acetate (5.33 g, 27.76 mmol, 3.51 mL) and copper(I) iodide (2.64 g, 13.88 mmol) in DMF (50 mL) was stirred under $N_2(g)$ protection at 120° C. for 16 hr. LCMS showed the reaction was completed. The reaction mixture was poured into water (100 mL) and extracted with EA (2×30 mL). The combined organic layer was washed with brine (50 mL), dried over anhydrous $Na_2SO_4$ and filtered. The filtrate was concentrated in vacuum to afford a residue. The residue was purified by silica gel chromatography (PE:EA=2:1) to afford 2,4-bis(4-methoxybenzyl)-6-(trifluoromethyl)-1,2,4-triazine-3,5(2H,4H)-dione A-3 (2.8 g, 6.65 mmol, 96% yield) as a light yellow solid. LCMS: $[M+Na]^+=444.0$.

-continued

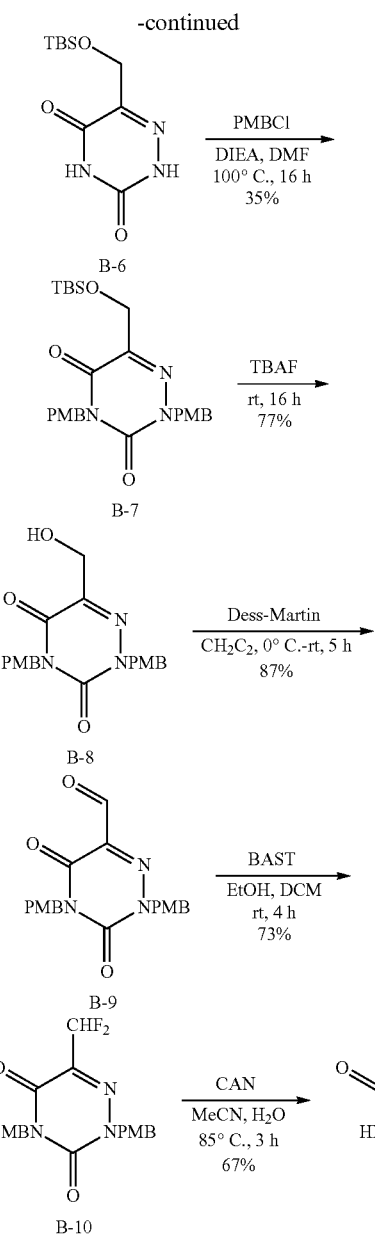

Step 1: B-3

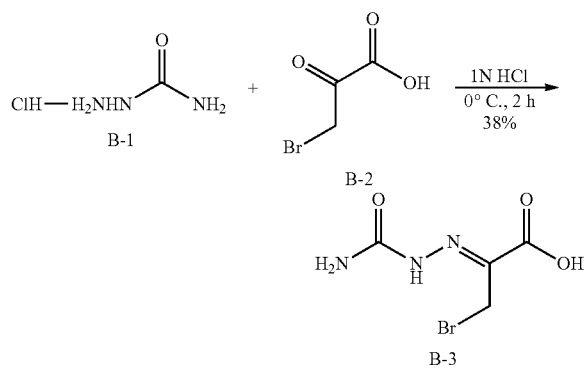

To a mixture of aminourea hydrochloride B-1 (7.5 g, 67.25 mmol) in 1N HCl (50 mL) at 0° C. was added 3-bromo-2-oxo-propanoic acid B-2 (7.50 g, 44.92 mmol). The reaction mixture was stirred at 0° C. for 2 h. The reaction mixture was filtered to afford a white solid. The white solid was dried under vacuum to afford (2Z)-3-bromo-2-(carbamoyl hydrazono) propanoic acid B-3 (6.0 g, 38% yield) as a white solid. $^1$H NMR (400 MHz, DMSO-$d_6$) δ 10.5 (s, 1H), 7.35 (brs, 1H), 6.97 (brs, 1H), 4.46 (s, 2H).

Step 2: B-4

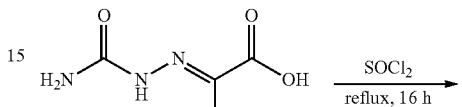

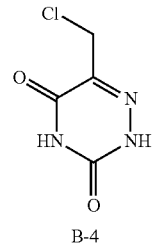

A mixture of (Z)-3-bromo-2-(2-carbamoylhydrazono) propanoic acid B-3 (6.0 g, 26.78 mmol) in SOCl$_2$ (60 mL) was stirred at 80° C. for 16 h. LCMS showed the reaction was completed. The reaction mixture was concentrated in vacuum to afford 6-(chloromethyl)-1,2,4-triazine-3,5(2H, 4H)-dione B-4 (4.3 g, 94% yield) as a yellow solid. LCMS: [M+H]$^+$=162.0.

Step 3: B-5

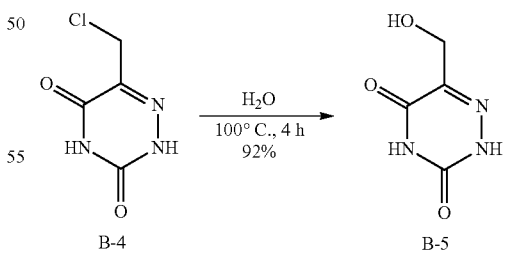

A mixture of 6-(chloromethyl)-2H-1,2,4-triazine-3,5-dione B-4 (5.5 g, 34.05 mmol) in water (80 mL) was stirred at 100° C. for 4 h. LC-MS showed the reaction was completed. The reaction mixture was concentrated in vacuum to afford a residue 6-(hydroxymethyl)-2H-1,2,4-triazine-3,5-dione B-5 (4.7 g, 92% yield) as a yellow solid. LCMS: [M+H]$^+$=144.0.

Step 4: B-6

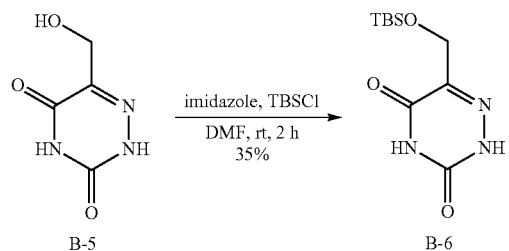

To a mixture of 6-(hydroxymethyl)-2H-1,2,4-triazine-3,5-dione B-5 (4.85 g, 33.89 mmol) and imidazole (6.92 g, 101.68 mmol) in DMF (50 mL) at rt was added tert-butyl dimethyl silyl chloride (7.66 g, 50.84 mmol). The reaction mixture was stirred at rt for 2 h. LC-MS showed the reaction was completed. The reaction mixture was poured into water (50 mL) and extracted with EA (3×20 mL). The combined organic layer was washed with brine (20 mL), dried over anhydrous $Na_2SO_4$ and filtered. The filtrate was concentrated in vacuum to afford a residue. The residue was purified by silica gel chromatography (PE:EA=5:1) to afford 6-[[tert-butyl(dimethyl)silyl] oxy methyl]-2H-1,2,4-triazine-3,5-dione B-6 (3.2 g, 35% yield) as a lightly yellow solid. LCMS: $[M+H]^+=258.1$.

Step 5: B-7

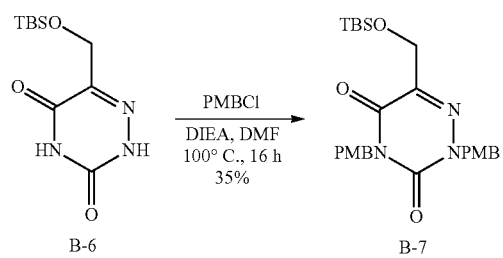

A mixture of 6-[[tert-butyl(dimethyl)silyl] oxy methyl]-2H-1,2,4-triazine-3,5-dione B-6 (1.0 g, 3.89 mmol), N,N-Diisopropylethylamine (3.01 g, 23.31 mmol, 4.06 mL) and 4-Methoxybenzylchloride (1.83 g, 11.66 mmol) in DMF (50 mL) was stirred at 100° C. for 16 h. LC-MS showed the reaction was completed. The reaction mixture was poured into water (20 mL) and extracted with EA (3×20 mL). The combined organic layer was washed with brine (40 mL), dried over anhydrous $Na_2SO_4$ and filtered. The filtrate was concentrated in vacuum to afford a residue. The residue was purified by silica gel chromatography (PE:EA=10:1-3:1) to afford 6-[[tert-butyl(dimethyl)silyl] oxy methyl]-2,4-bis[(4-methoxyphenyl) methyl]-1,2,4-triazine-3,5-dione B-7 (1.7 g, 35% yield) a lightly yellow solid. LCMS: $[M+Na]^+=520.2$.

Step 6: B-8

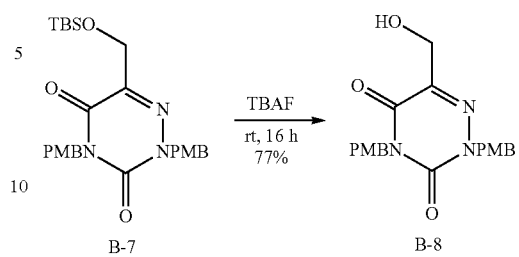

To a solution of 6-[[tert-butyl(dimethyl)silyl] oxy methyl]-2,4-bis[(4-methoxyphenyl) methyl]-1,2,4-triazine-3,5-dione B-7 (1.91 g, 3.84 mmol) in THF (20 mL) at rt was added tetrabutylammonium fluoride (1 M, 3.84 mL). The reaction mixture was stirred at rt for 16 h. LC-MS showed the reaction was completed. The reaction mixture was concentrated in vacuum to afford a residue. The residue was dissolved in EtOAc (50 mL) and washed with brine (50 mL), dried over anhydrous $Na_2SO_4$ and filtered. The filtrate was concentrated in vacuum to afford a residue. The residue was purified by silica gel chromatography (PE:EA=3:1) to afford 6-(hydroxymethyl)-2,4-bis[(4-methoxyphenyl) methyl]-1,2,4-triazine-3,5-dione B-8 (1.2 g, 77% yield) as a lightly yellow oil. LCMS: $[M+H]^+=384.1$.

Step 7: B-9

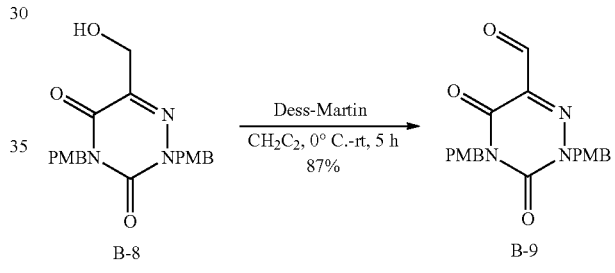

To a solution of 6-(hydroxymethyl)-2,4-bis [(4-methoxyphenyl) methyl]-1,2,4-triazine-3,5-dione B-8 (700 mg, 1.83 mmol) in $CH_2Cl_2$ (10 mL) at 0° C. was added Dess-Martin (1.55 g, 3.65 mmol). The reaction mixture was stirred at rt for 5 h. LCMS showed the reaction was completed. The reaction mixture was poured into water (50 mL) and extracted with EA (3×20 mL). The combined organic layer was washed with brine (20 mL), dried over anhydrous $Na_2SO_4$ and filtered. The filtrate was concentrated in vacuum to afford a residue. The residue was purified by silica gel chromatography (PE:EA=3:1) to afford 2,4-bis[(4-methoxyphenyl) methyl]-3,5-dioxo-1,2,4-triazine-6-carbaldehyde B-9 (634 mg, 87% yield) as a lightly yellow solid. LCMS: $[M+H]^+=382.1$.

Step 8: B-10

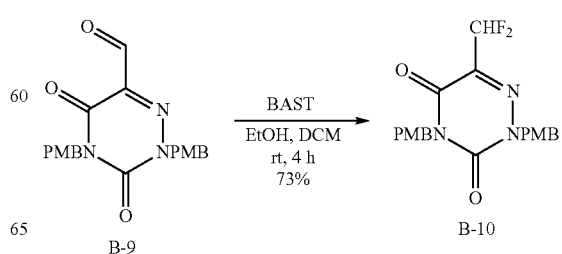

To a solution of 2,4-bis[(4-methoxyphenyl) methyl]-3,5-dioxo-1,2,4-triazine-6-carbaldehyde B-9 (814 mg, 2.13 mmol) and ethanol (19.67 mg, 426.87 umol) in CH₂Cl₂ (5 mL) at rt was added BAST (802.75 mg, 3.63 mmol) dropwise. The reaction mixture was stirred at rt for 4 h. LCMS showed the reaction was completed. The reaction mixture was poured into Sat. NaHCO₃ (50 mL) and extracted with CH₂Cl₂ (3×20 mL). The combined organic layer was washed with brine (50 mL), dried over anhydrous Na₂SO₄ and filtered. The filtrate was concentrated in vacuum to afford a residue. The residue was purified by silica gel chromatography (PE:EA=3:1) to afford 6-(difluoromethyl)-2,4-bis[(4-methoxyphenyl) methyl]-1,2,4-triazine-3,5-dione B-10 (660 mg, 73% yield) as a lightly yellow solid. LCMS: [M+Na]⁺=426.0.

Step 9: Intermediate B

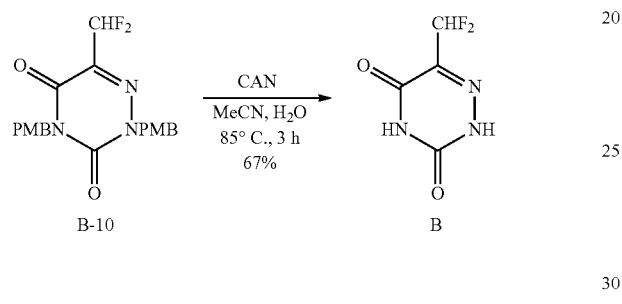

A mixture of 6-(difluoromethyl)-2,4-bis[(4-methoxyphenyl) methyl]-1,2,4-triazine-3,5-dione B-10 (660 mg, 1.64 mmol) and CAN (8.97 g, 16.36 mmol) in CH₃CN (30 mL) and water (10 mL) was stirred at 85° C. for 3 h. LCMS showed the reaction was completed. The reaction mixture was concentrated in vacuum to remove most of CH₃CN to afford a residue. The residue was extracted with EA (3×40 mL). The combined organic layer was washed with brine (50 mL), dried over anhydrous Na₂SO₄ and filtered. The filtrate was concentrated in vacuum to afford a residue. The residue was purified by silica gel chromatography (PE:EA=3:1) to afford 6-(difluoromethyl)-2H-1,2,4-triazine-3,5-dione Intermediate B (200 mg, 67% yield) a lightly yellow solid. LCMS: [M+H]⁺=164.0. ¹H NMR (400 MHz, CD₆SO) δ 12.74 (s, 1H), 12.29 (s, 1H), 6.77 (t, J=52.8 Hz, 1H). ¹⁹F NMR (376 MHz, CD₆SO) δ−122.2 (s, 2F).

Example 3: General Scheme C—Synthesis of Intermediate C

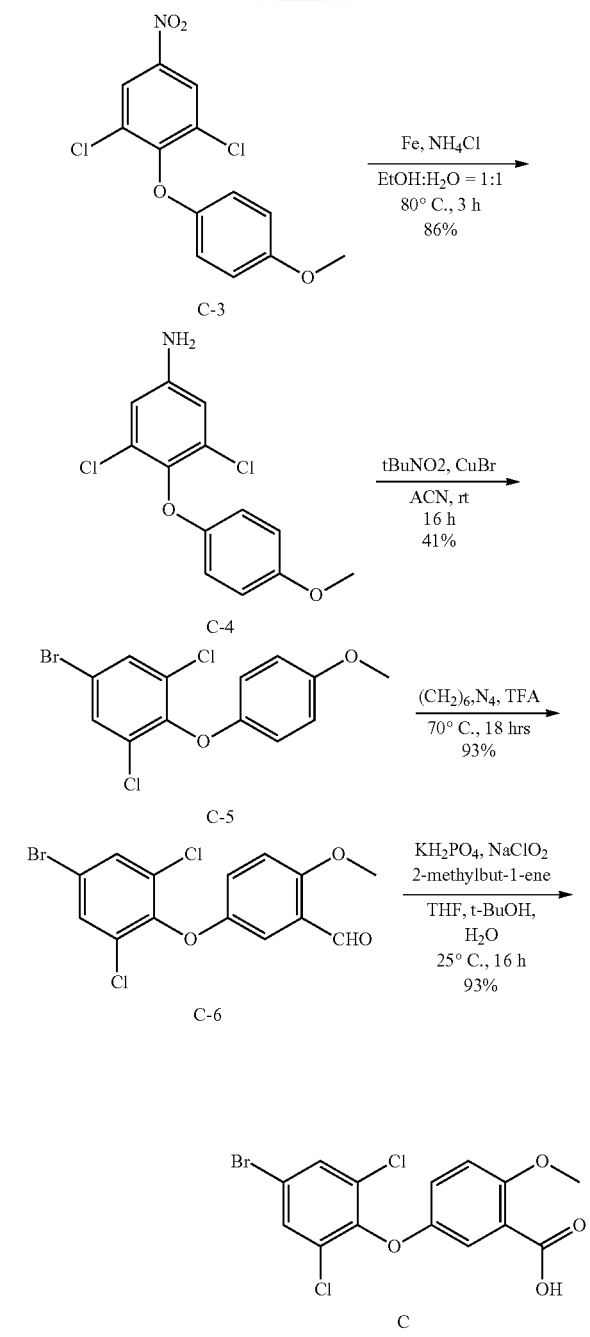

Step 1: C-3

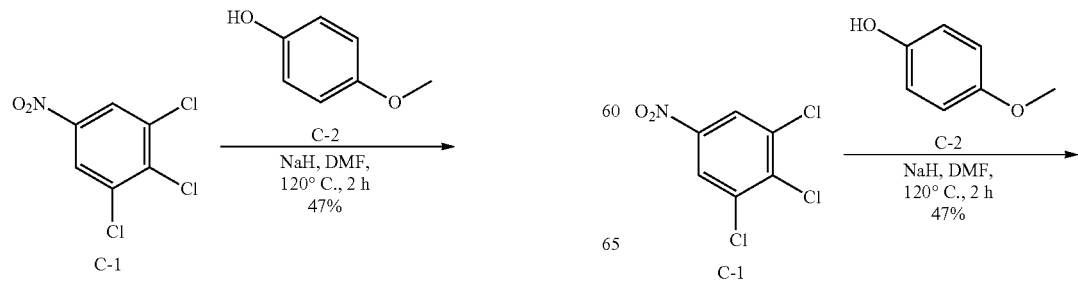

-continued

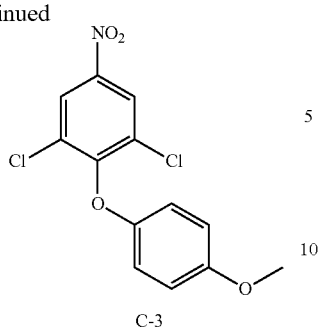

C-3

To a solution of 4-methoxyphenol C-2 (15 g, 120.83 mmol) in DMF (150 mL) was added NaH (7.25 g, 181.25 mmol, 60% purity) at 0° C. and stirred for 10 min. Then 1,2,3-trichloro-5-nitrobenzene C-1 (27.36 g, 120.83 mmol) was added and the mixture was stirred at 120° C. under $N_2$ (g) for 2 hr. TLC (PE:EtOAc=20:1) showed the reaction was completed. The reaction mixture was poured into water (500 mL) and extracted with EA (3×200 mL). The combined organic layer was washed with brine (200 mL), dried over anhydrous $Na_2SO_4$ and filtered. The filtrate was concentrated in vacuum to afford a residue. The residue was purified by silica gel chromatography (PE:EtOAc:DCM=50:1:1) to afford a crude product. The crude product was triturated with PE at rt for 16 hours and then filtered. The solid was dried in vacuo to afford 1,3-dichloro-2-(4-methoxyphenoxy)-5-nitrobenzene C-3 (18 g, 57.30 mmol, 47% yield) as a yellow solid.

Step 2: C-4

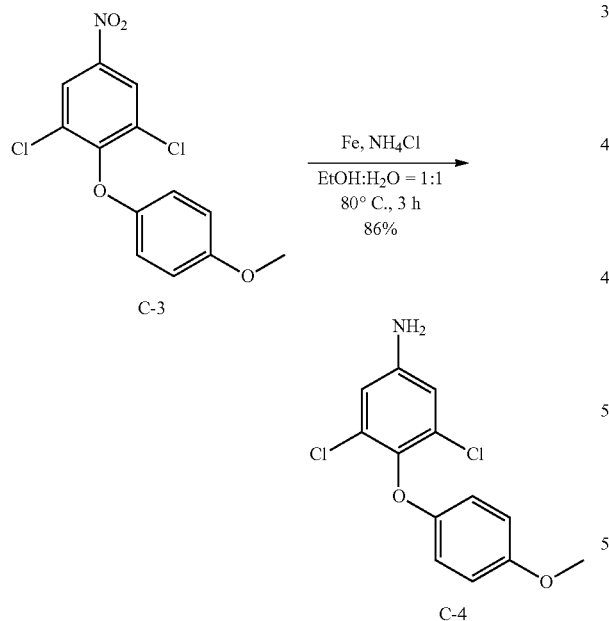

To a solution of 1,3-dichloro-2-(4-methoxyphenoxy)-5-nitrobenzene C-3 (18 g, 57.30 mmol) in Ethanol (100 mL) and Water (100 mL) were added Iron powder (32.00 g, 573.03 mmol) and $NH_4Cl$ (15.33 g, 286.51 mmol). The mixture was stirred at 80° C. under $N_2$ (g) for 3 hr. LCMS showed the reaction was completed. The reaction mixture was filtered and concentrated. The residue was diluted with water (150 mL), extracted with EA (3×100 mL). The combined organic layer was washed with brine (200 mL), dried over anhydrous $Na_2SO_4$ and filtered. The filtrate was concentrated in vacuum to afford a residue. The reside was titrated with (PE:EtOAc=20:1) at rt for 1 hour and then filtered. The solid was dried in vacuo to afford 3,5-dichloro-4-(4-methoxyphenoxy) aniline C-4 (14 g, 49.27 mmol, 86% yield) as a yellow solid. LCMS: $[M+H]^+=284.0/286.0$.

Step 3: C-5

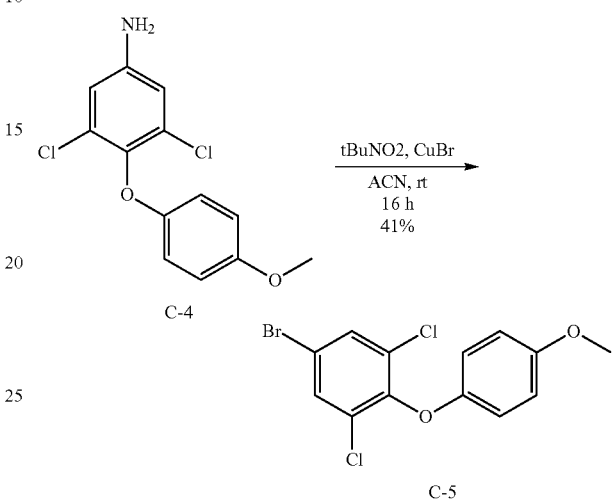

To a suspension of CuBr (6.06 g, 42.23 mmol) in MeCN (80 mL) was added tBuONO (5.81 g, 56.31 mmol) at 0° C. and stirred for 10 min. Then 3,5-dichloro-4-(4-methoxyphenoxy) aniline C-4 (8 g, 28.16 mmol) was added and the resulted mixture was stirred at 10° C. under $N_2$ (g) for 16 hr. TLC (PE:EtOAc=5:1) showed the reaction was almost completed. The reaction mixture was filtered, and the filtrate was concentrated in vacuum to afford a residue. The residue was purified by flash column chromatography (PE:EA=50:1) to afford 5-bromo-1,3-dichloro-2-(4-methoxyphenoxy) benzene C-5 (4 g, 11.49 mmol, 41% yield) as a white solid.

Step 4: C-6

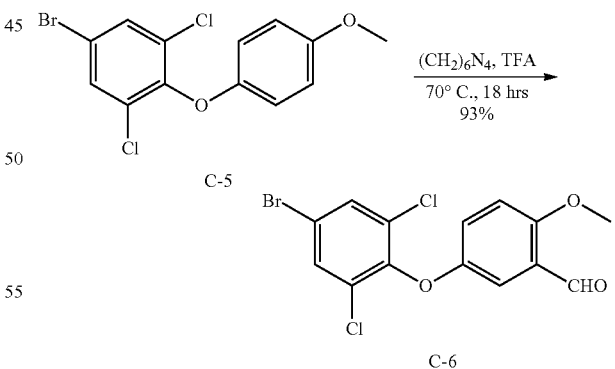

To a solution of 5-bromo-1,3-dichloro-2-(4-methoxyphenoxy) benzene C-5 (3 g, 8.62 mmol) in TFA (30 mL) was added $(CH_2)_6N_4$ (3.02 g, 21.55 mmol). The mixture was stirred at 70° C. under $N_2$ (g) for 3 hr. TLC showed the reaction was completed. The reaction mixture was concentrated. The residue was poured into aq. sat. $NaHCO_3$ (100 mL) and extracted with DCM (3×20 mL). The combined organic layer was washed with brine (20 mL), dried over anhydrous Na₂SO₄ and filtered. The filtrate was concentrated in vacuum to afford crude 5-(4-bromo-2,6-dichlorophenoxy)-2-methoxybenzaldehyde C-6 (3 g, 7.98 mmol, 93% yield) as a yellow solid, which was used to the next step directly without further purification.

Step 5: Intermediate C

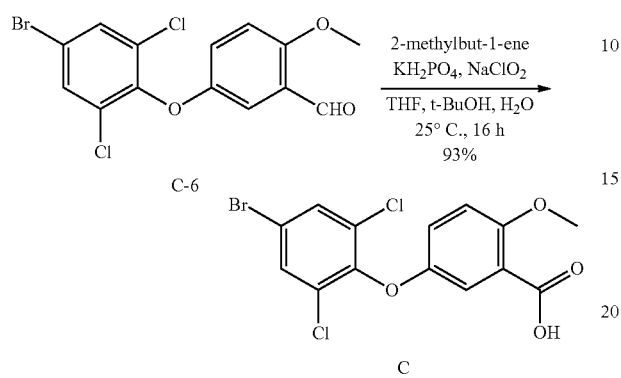

To a solution of 5-(4-bromo-2,6-dichlorophenoxy)-2-methoxybenzaldehyde C-6 (3 g, 7.98 mmol) in THF (20 mL), ᵗBuOH (60 mL) and 2-methylbut-1-ene (10 mL) was added a solution of NaClO₂ (7.22 g, 79.78 mmol) in NaH₂PO₄ (0.6 M, 106.37 mL). The mixture was stirred at 25° C. for 2 h. LCMS showed the reaction was completed. The reaction mixture was extracted with EA (3×100 mL). The combined organic layer was washed with brine (100 mL), dried over anhydrous Na₂SO₄ and filtered. The filtrate was concentrated in vacuum to afford a residue. The residue was purified by flash column chromatography (DCM) to afford 5-(4-bromo-2,6-dichlorophenoxy)-2-methoxybenzoic acid Intermediate C (2.9 g, 7.40 mmol, 93% yield) as a white solid. LCMS: [M+H]⁺=390.9/392.9/394.9.

Example 4: General Scheme D—Synthesis of Intermediate D

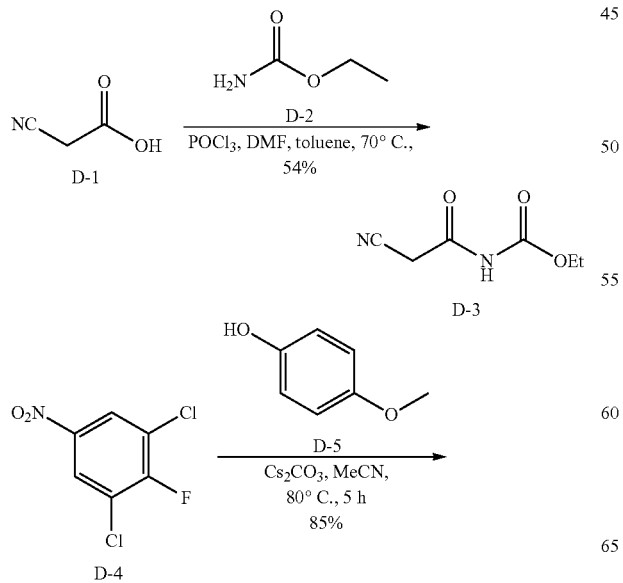

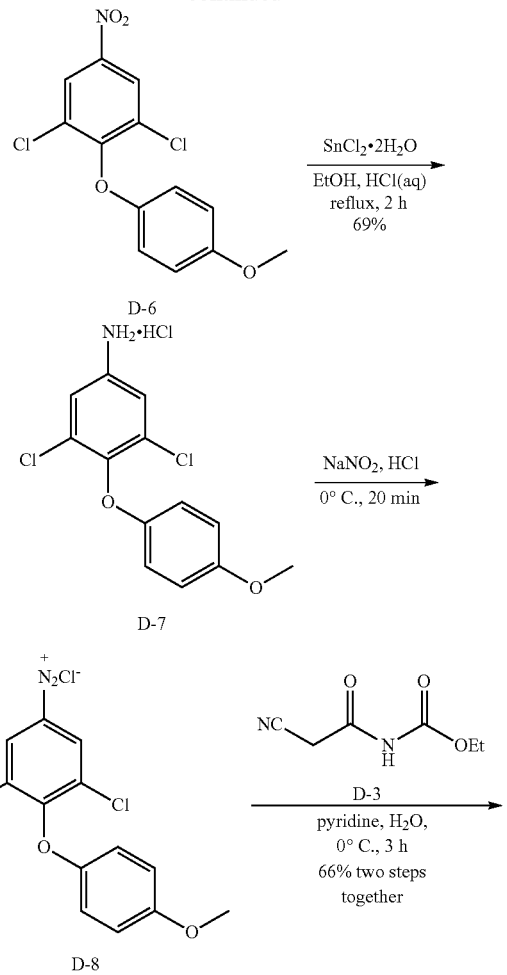

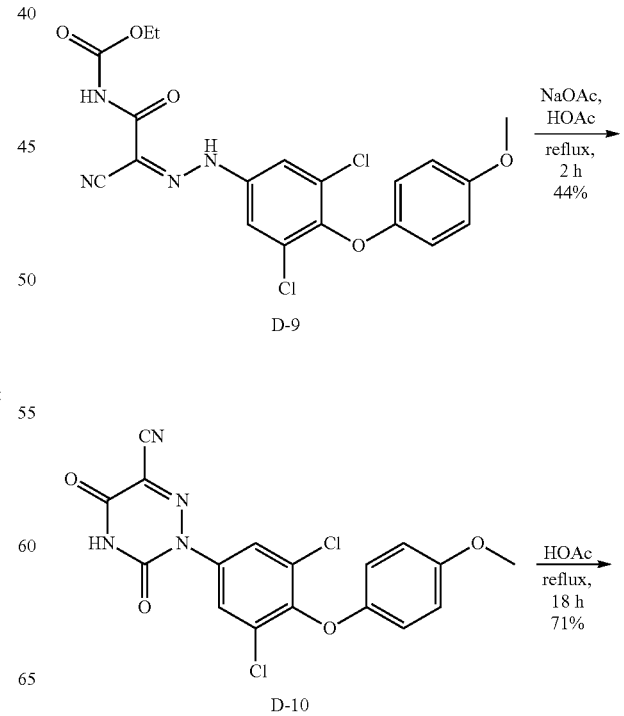

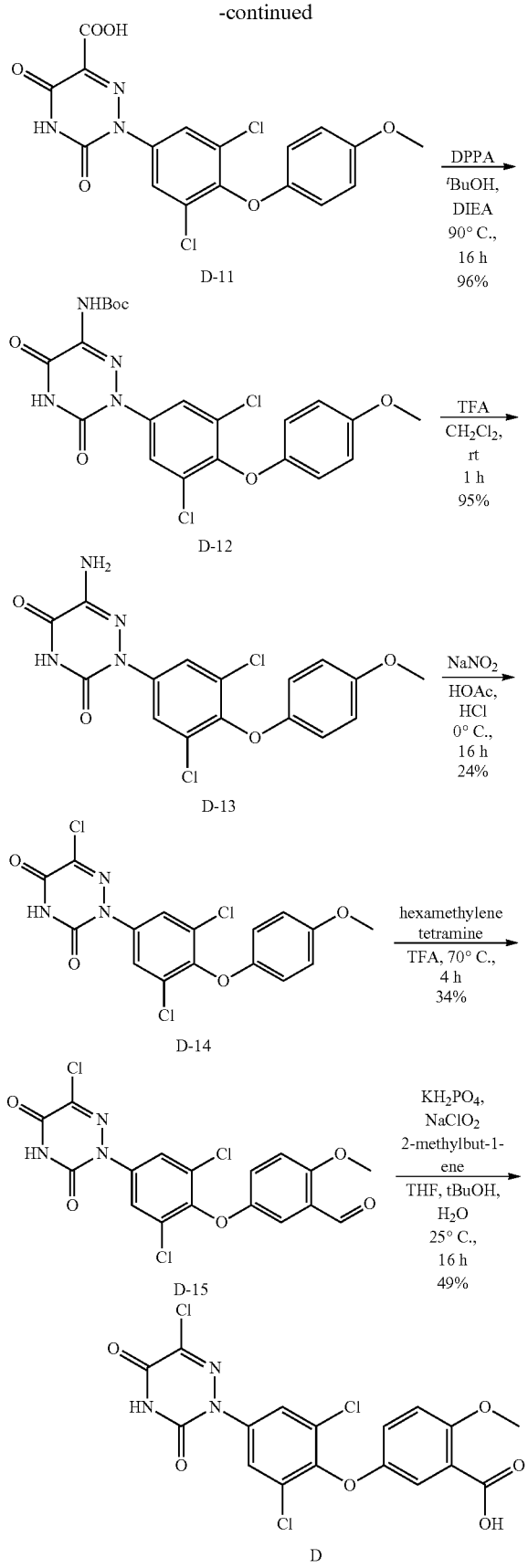

Step 1: D-3

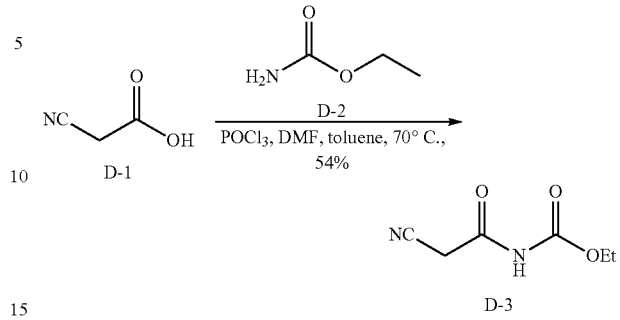

To a solution of 2-cyanoacetic acid D-1 (10 g, 11.76 mmol), ethyl carbamate D-2 (10.47g, 11.76 mmol) in dry toluene (50 mL) was slowly added DMF (0.5 ml, 0.588 mmol). Then $POCl_3$ (5.5 ml, 5.88 mmol) was added dropwise at 0° C. under nitrogen. The reaction mixture was heated up to 70° C. and stirred for 2 h. After cooled down to room temperature, the solvent and $POCl_3$ were removed under reduced pressure. The residue was poured into ice water (300 mL). Precipitate was filtered to give ethyl (2-cyanoacetyl) carbamate D-3 (10 g, 54%) as grey solid. $^1H$ NMR (400 MHz, DMSO-$d_6$) δ 10.98 (s, 1H), 4.12 (q, J=7.1 Hz, 2H), 4.09 (s, 2H), 1.21 (t, J=7.1 Hz, 3H).

Step 2: D-6

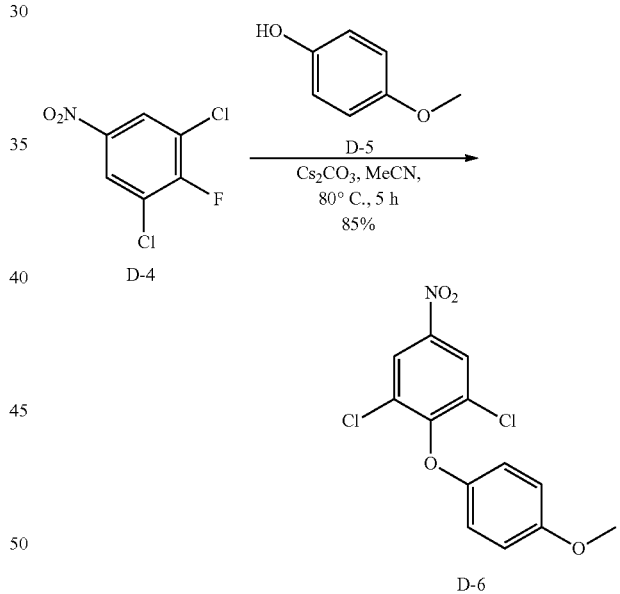

To a solution of 1,3-dichloro-2-fluoro-5-nitrobenzene D-4 (19.5 g, 0.09 mol) in DMF (800 mL) was added 4-methoxyphenol D-5 (14.0 g, 0.129 mol) and $Cs_2CO_3$ (60.0 g, 0.184 mol). The reaction mixture was heated up to 80° C. and stirred for 5 h. After cooled down to 25° C., the reaction mixture was diluted with water (500 mL) and extracted with ethyl acetate (3×500 mL). The combined organic layers were washed with $H_2O$ (3×200 mL) and brine (3×200 mL), dried over anhydrous sodium sulfate, filtered and concentrated under reduced pressure. The residue was purified by silica gel column chromatography eluted with PE to give 1,3-dichloro-2-(4-methoxyphenoxy)-5-nitrobenzene D-6 (24.8 g, 85%) as a white solid. $^1H$ NMR (400 MHz, $CDCl_3$) δ 8.30 (s, 2H), 6.86-6.82 (m, 2H), 6.79-6.75 (m, 2H), 3.78 (s, 3H).

Step 3: D-7

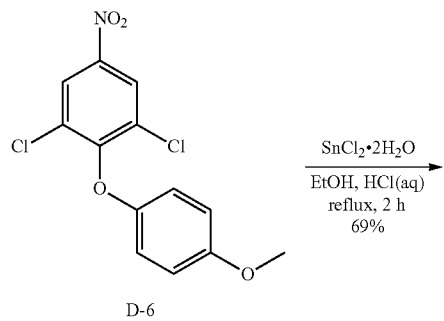

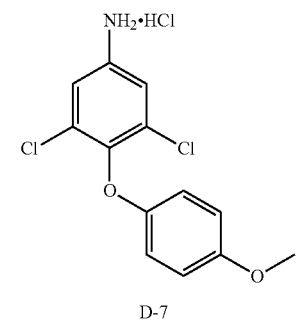

To a solution of stannous chloride dihydrate (35.6 g, 157.6 mmol) in concentrated hydrogen chloride (15 mL) was added 1,3-dichloro-2-(4-methoxyphenoxy)-5-nitrobenzene D-6 (10.998 g, 35.02 mmol) in EtOH (100 mL). The mixture was refluxed for 2 h. The resulting mixture was cooled down to 25° C. and diluted with ethyl acetate (200 mL). The mixture was made basic with 10% NaOH (aq). The organic phase was washed with water (3×20 mL), brine (3×20 mL), dried over anhydrous sodium sulfate, filtered and concentrated under reduced pressure to give 3,5-dichloro-4-(4-methoxyphenoxy) aniline (7.0 g, 70%) as a yellow oil. To a solution of 3,5-dichloro-4-(4-methoxyphenoxy) aniline (7.0 g, 27.45 mmol) in ethyl acetate was added concentrated hydrogen chloride slowly until pH=1. The suspension was set aside at 4° C. overnight and the product was collected by filtration and washed with PE to afford 3,5-dichloro-4-(4-methoxyphenoxy) aniline hydrochloride D-7 (7.8 g, 69%) as a white solid, which was used in next step without further purification. LCMS: [M+H]$^+$=284.0.

Step 4: D-8

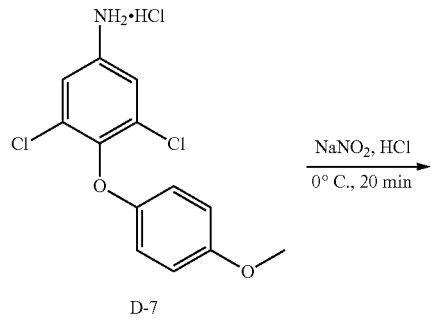

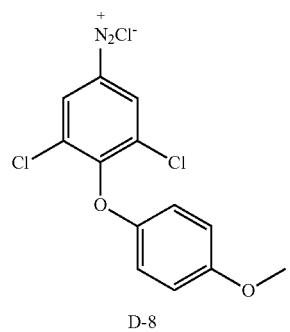

To a solution of 3,5-dichloro-4-(4-methoxyphenoxy) aniline hydrochloride D-7 (5.78 g, 16.22 mmol) in H$_2$O (200 mL) and con. HCl (724.08 mmol, 33 mL) was added a solution of NaNO$_2$ (1.25 g, 18.12 mmol) in H$_2$O (2.5 mL) at −5° C. to 0° C. dropwise. After 20 min, the yellow solution of 3,5-dichloro-4-(4-methoxyphenoxy) benzene diazonium chloride D-8 was filtered and the filtrate was used directly for next step.

Step 5: D-9

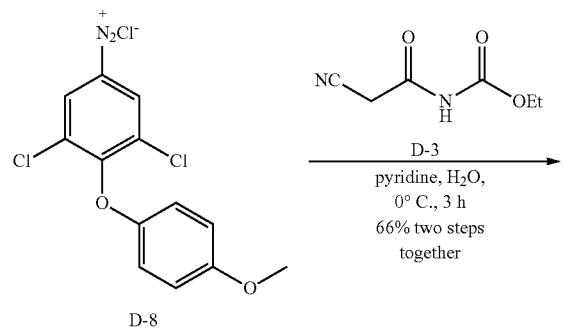

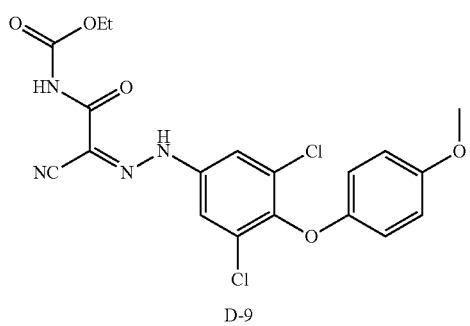

To a solution of ethyl ethyl (2-cyanoacetyl) carbamate D-3 (3.10 g, 17.84 mmol) in 100 mL of pyridine and 300 mL of H$_2$O was added 3,5-dichloro-4-(4-methoxyphenoxy) benzene diazonium chloride D-8 at 0° C. After 40 min, the red solid was collected, washed with water and air dried to afford ethyl (Z)-(2-cyano-2-(2-(3,5-dichloro-4-(4-methoxyphenoxy) phenyl) hydrazono) acetyl) carbamate D-9 (5.5 g, 66%) as a red solid. The material was used for next step without further purification. LCMS: [M+H]$^+$=451.0.

Step 6: D-10

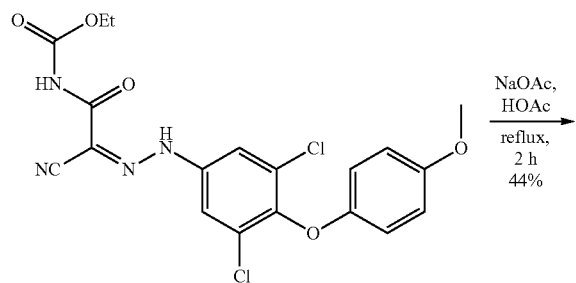

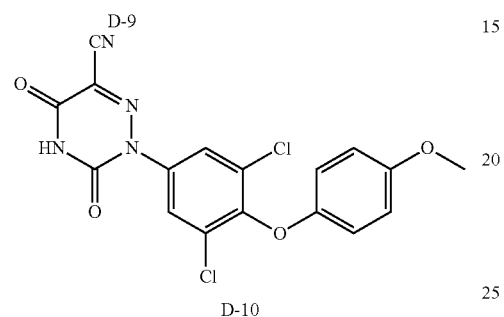

A slurry of ethyl (Z)-(2-cyano-2-(2-(3,5-dichloro-4-(4-methoxyphenoxy) phenyl) hydrazono) acetyl) carbamate D-9 (2.5 g, 5.54 mmol), anhydrous sodium acetate (2.27 g, 27.7 mmol) in HOAc (50 mL) was stirred at reflux for 2 h. After that, the resulting yellow solution was concentrated under reduced pressure. To the residue, water was added dropwise. The resulting solid was filtered and purified by silica gel column chromatography eluted with PE/EA (1:3) to give 2-(3,5-dichloro-4-(4-methoxy phenoxy) phenyl)-3,5-dioxo-2,3,4,5-tetrahydro-1,2,4-triazine-6-carbonitrile D-10 (1.0 g, 44%) as a red solid. H NMR (400 MHz, DMSO-$d_6$) δ 7.79 (s, 2H), 6.91 (d, J=9.1 Hz, 2H), 6.81 (d, J=9.1 Hz, 2H), 3.72 (s, 3H). LCMS: [M−H]$^−$=403.0.

Step 7: D-11

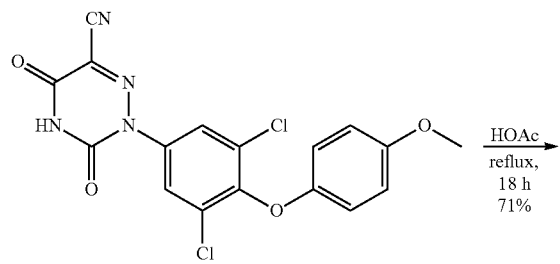

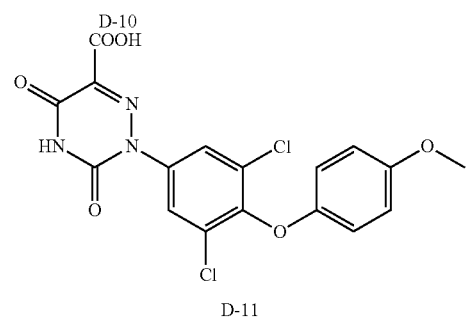

A slurry of 2-(3,5-dichloro-4-(4-methoxy phenoxy) phenyl)-3,5-dioxo-2,3,4,5-tetrahydro-1,2,4-triazine-6-carbonitrile D-10 (1.0 g, 2.47 mmol) in HOAc (20 mL) and con. HCl (5 mL) was refluxed for 18 h. The resulting clear solution was concentrated and titrated with water. The solid was filtered and dried to give crude 2-(3,5-dichloro-4-(4-methoxy phenoxy) phenyl)-3,5-dioxo-2,3,4,5-tetrahydro-1,2,4-triazine-6-carboxylic acid D-11 (0.75 g, 71%) as a yellow solid, which was used for next step directly without further purification. LCMS: [M−H]$^−$=422.1.

Step 8: D-12

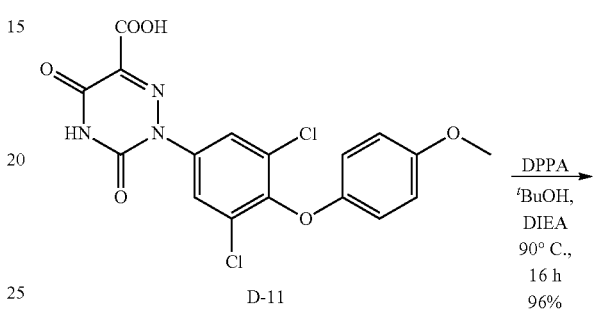

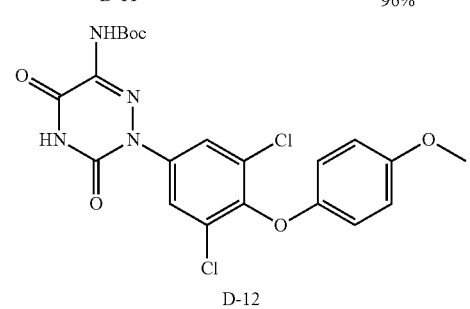

To a solution of 2-[3,5-dichloro-4-(4-methoxyphenoxy) phenyl]-3,5-dioxo-1,2,4-triazine-6-carboxylic acid D-11 (16.0 g, 37.72 mmol) in 2-methylpropan-2-ol (300 mL) was added N,N-diethyl ethanamine (5.73 g, 56.58 mmol) and [azido(phenoxy)phosphoryl]oxybenzene (15.57 g, 56.58 mmol). The resulting mixture was stirred at 90° C. for 16 h. The mixture was cooled to 25° C. and the solvent was removed under vacuum. The residue was then purified through silica gel column chromatography (PE:EA=5:1) to afford tert-butyl N-[2-[3,5-dichloro-4-(4-methoxyphenoxy) phenyl]-3,5-dioxo-1,2,4-triazin-6-yl] carbamate D-12 (18.0 g, 96%) as a red solid. LCMS: [M+H]$^+$=495.3.

Step 9: D-13

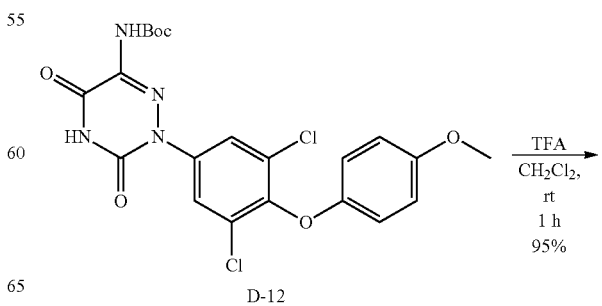

-continued

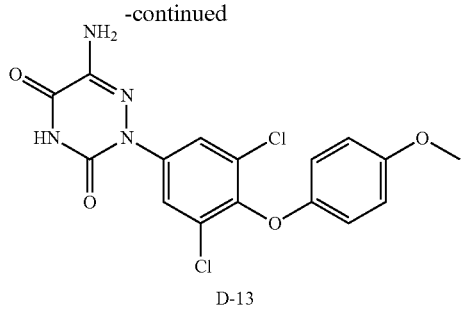

D-13

To a solution of tert-butyl N-[2-[3,5-dichloro-4-[(5-isopropyl-6-oxo-1H-pyridazin-3-yl)oxy]phenyl]-3,5-dioxo-1,2,4-triazin-6-yl]carbamate D-12 (18.0 g, 34.26 mmol) in $CH_2Cl_2$ (200 mL) was added 2,2,2-trifluoroacetic acid (60 mL). The resulting mixture was stirred at rt for 1 h. The mixture was quenched with $H_2O$ (100 mL) and extracted with EA (3×300 mL). Then the mixture was washed with $NaHCO_3$ (3×100 mL) and brine (300 mL). The organic phase was dried and concentrated. The residue was purified by silica gel column chromatography (PE:EA=3:1) to give 6-amino-2-[3,5-dichloro-4-[(5-isopropyl-6-oxo-1H-pyridazin-3-yl) oxy] phenyl]-1,2,4-triazine-3,5-dione D-13 (13.0 g, 95%). LCMS: $[M+H]^+=395.2$.

Step 10: D-14

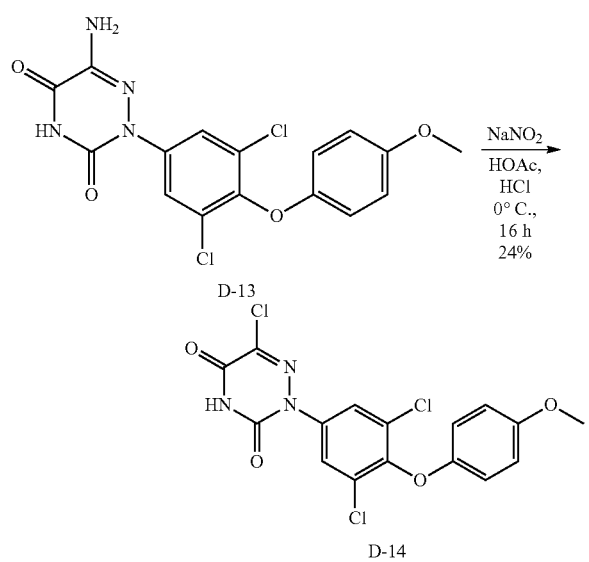

A mixture of 6-amino-2-[3,5-dichloro-4-(4-methoxyphenoxy) phenyl]-1,2,4-triazine-3,5-dione D-13 (1.5 g × 6, 2.53 mmol) in glacial acetic acid (30 mL) and hydrochloric acid (30 mL) was stirred at 0° C. for 10 min. Then sodium nitrite (261.88 mg, 3.80 mmol) was added to this solution and the mixture was stirred at 0° C. for 16 h. TLC showed a new spot formed. Then sodium nitrite (261.88 mg, 3.80 mmol) was added to the mixture which was further stirred for 4 h. The mixture was concentrated and the residue was washed with $NaHCO_3$ (3×50 mL) and brine (50 mL). The organic phase was dried and concentrated. The residue was purified through silica gel column chromatography (PE:EA=8:1) to give 6-chloro-2-[3,5-dichloro-4-(4-methoxy phenoxy) phenyl]-1,2,4-triazine-3,5-dione D-14 (2.5 g, 24%) as a yellow solid. LCMS: $[M+H]^+=414.6$.

Step 11: D-15

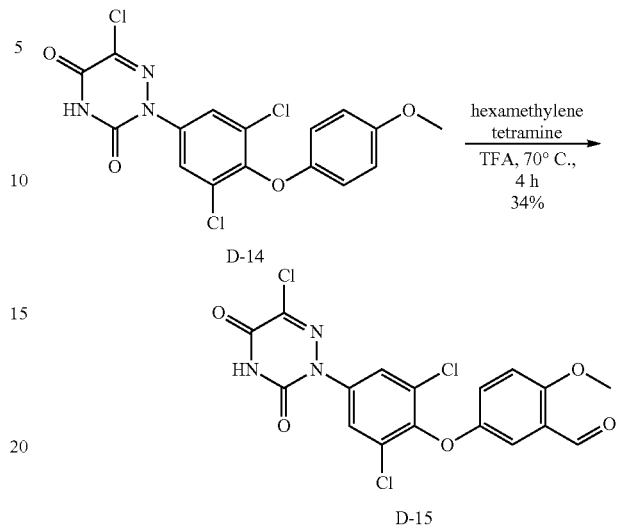

A mixture of 6-chloro-2-[3,5-dichloro-4-(4-methoxyphenoxy) phenyl]-1,2,4-triazine-3,5-dione D-14 (2.5 g, 6.03 mmol) in TFA (30 mL) was stirred at 25° C. for 10 min. Then 1,3,5,7-tetraza tricyclo [3.3.1.1] decane (1.27 g, 9.04 mmol) was added to this solution and the mixture was stirred at 70° C. for 4 h. The mixture was concentrated and the residue was washed with $NaHCO_3$ (3×50 mL) and brine (50 mL). The organic phase was dried and concentrated. The residue was purified by silica gel column chromatography (PE:EA=5:1) to give 5-[2,6-dichloro-4-(6-chloro-3,5-dioxo-1,2,4-triazin-2-yl) phenoxy]-2-methoxy-benzaldehyde D-15 (910 mg, 34%) as a yellow solid. LCMS: $[M+H]^+=442.6$.

Step 12: Intermediate D

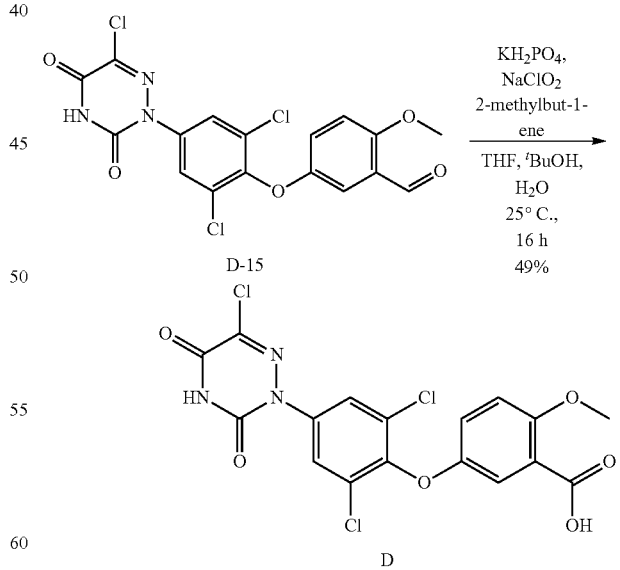

To a mixture of 5-(2,6-dichloro-4-(6-chloro-3,5-dioxo-4,5-dihydro-1,2,4-triazin-2(3H)-yl)phenoxy)-2-methoxybenzaldehyde D-15 (410 mg, 926.27 umol) and 2-methylpropan-2-ol (10 mL) in THF (3 mL) stirred at 25° C. was added potassium dihydrogen phosphate (126.05 mg, 926.27 umol).

The mixture was stirred at 25° C. for 16 h and then concentrated. The residue was washed with NaHCO$_3$ (3×50 mL) and brine (50 mL). The organic phase was dried and concentrated. The residue was purified by silica gel column chromatography (PE:EA=3:1) to give 5-(2,6-dichloro-4-(6-chloro-3,5-dioxo-4,5-dihydro-1,2,4-triazin-2(3H)-yl)phenoxy)-2-methoxybenzoic acid Intermediate D (210 mg, 49% yield) as a yellow solid. LCMS: [M+H]$^+$=458.6.

Example 5: General Scheme E—Synthesis of Intermediate E

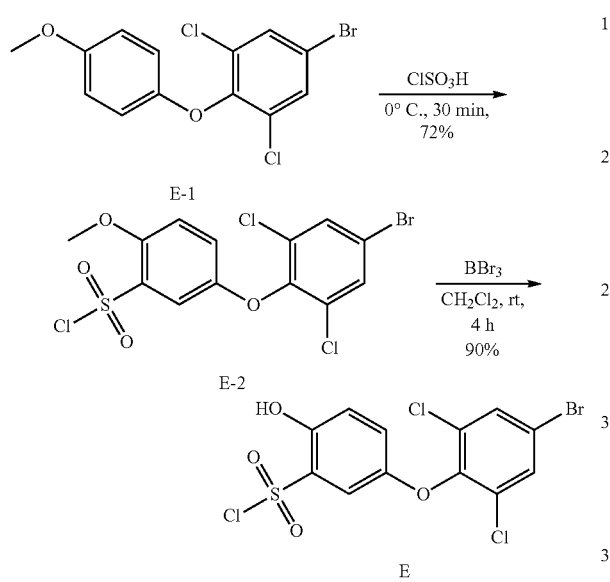

Step 1: E-2

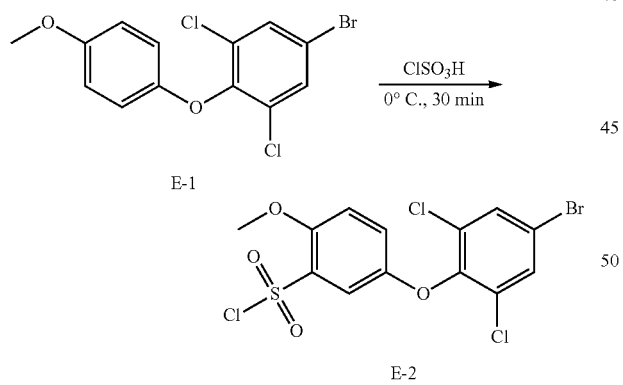

5-bromo-1,3-dichloro-2-(4-methoxyphenoxy) benzene E-1 (4.1 g, 11.78 mmol) was added into sulfurochloridic acid (17.50 g, 150.19 mmol, 10 mL) at 0° C. slowly. The mixture was stirred at 0° C. under N$_2$ (g) for 0.5 h. TLC (PE: EtOAc=10:1) showed the reaction was completed. The reaction mixture was poured into ice (100 mL) and extracted with EtOAc (3×50 mL). The combined organic layer was washed with brine (50 mL), dried over anhydrous Na$_2$SO$_4$ and filtered. The filtrate was concentrated in vacuum to afford a residue. The residue was purified by flash silica gel chromatography (PE:EtOAc=20:1) to afford 5-(4-bromo-2,6-dichloro-phenoxy)-2-methoxy-benzenesulfonyl chloride E-2 (3.8 g, 72% yield) as a white solid. $^1$H NMR (400 MHz, CDCl$_3$) δ 7.58 (s, 2H), 7.39 (d, J=2.8 Hz, 1H), 7.20 (dd, J=9.2, 3.2 Hz, 1H), 7.08 (d, J=9.2 Hz, 1H), 4.04 (s, 3H).

Step 2: Intermediate E

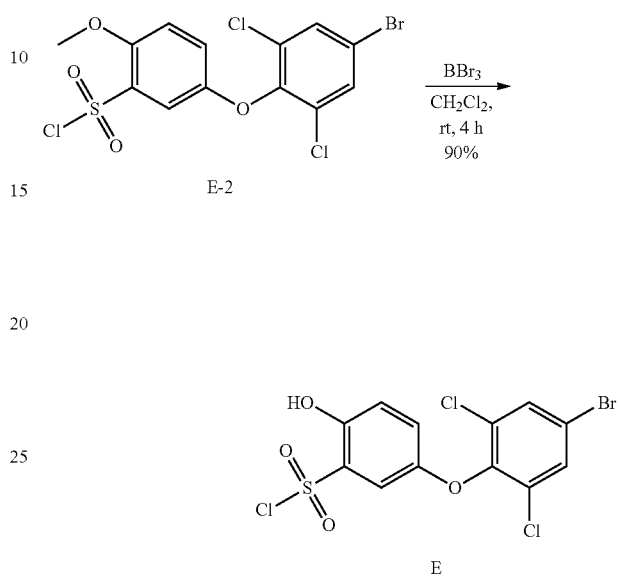

To a solution of 5-(4-bromo-2,6-dichloro-phenoxy)-2-methoxy-benzenesulfonyl chloride E-2 (400 mg, 895.80 umol) in CH$_2$Cl$_2$ (5 mL) was added BBr$_3$ (4.49 g, 17.92 mmol). The mixture was stirred at 20° C. under N$_2$ (g) for 4 h. TLC (PE:EtOAc=5:1) showed the reaction was completed. The reaction mixture was poured into ice water (50 mL) and extracted with EtOAc (3×20 mL). The combined organic layer was washed with brine (3×10 mL), dried over anhydrous Na$_2$SO$_4$ and filtered. The filtrate was concentrated in vacuum to afford 5-(4-bromo-2,6-dichloro-phenoxy)-2-hydroxy-benzenesulfonyl chloride Intermediate E (350 mg, 90% yield) as a yellow oil, which was used in next step directly without further purification.

Example 6: General Scheme F—Synthesis of Intermediate F

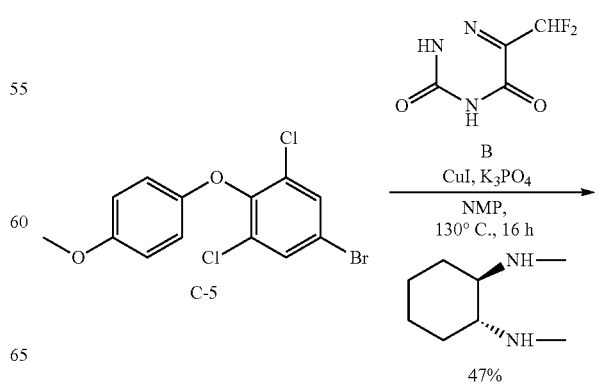

-continued

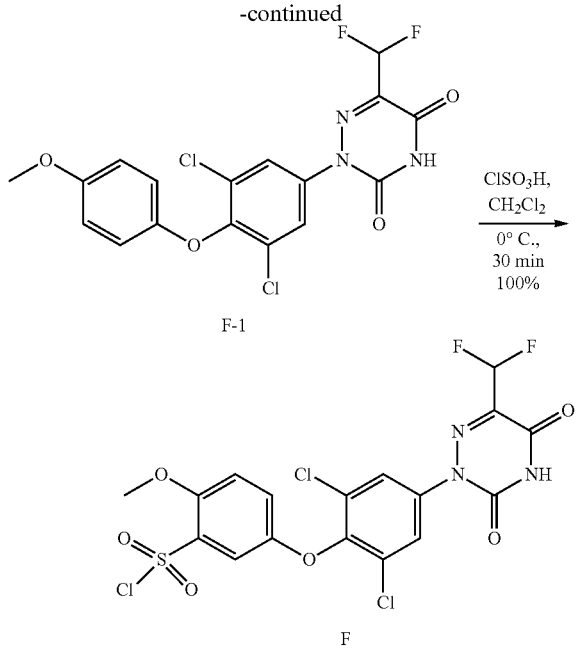

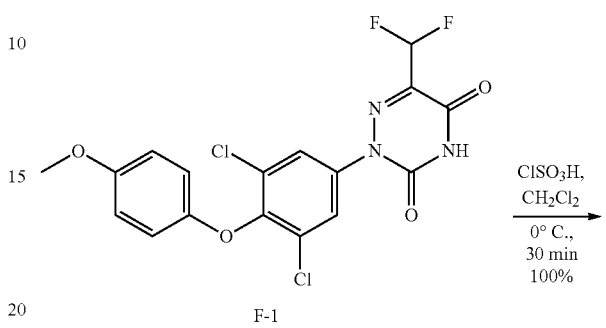

vacuum. The residue was purified by column chromatography (CH₂Cl₂:CH₃OH=20:1) to give 2-(3,5-dichloro-4-(4-methoxyphenoxy) phenyl)-6-(difluoromethyl)-1,2,4-triazine-3,5(2H,4H)-dione F-1 (1.7 g, 47% yield) as a yellow solid. LCMS: [M+H]⁺=430.0.

Step 2: Intermediate F

Step 1: F-1

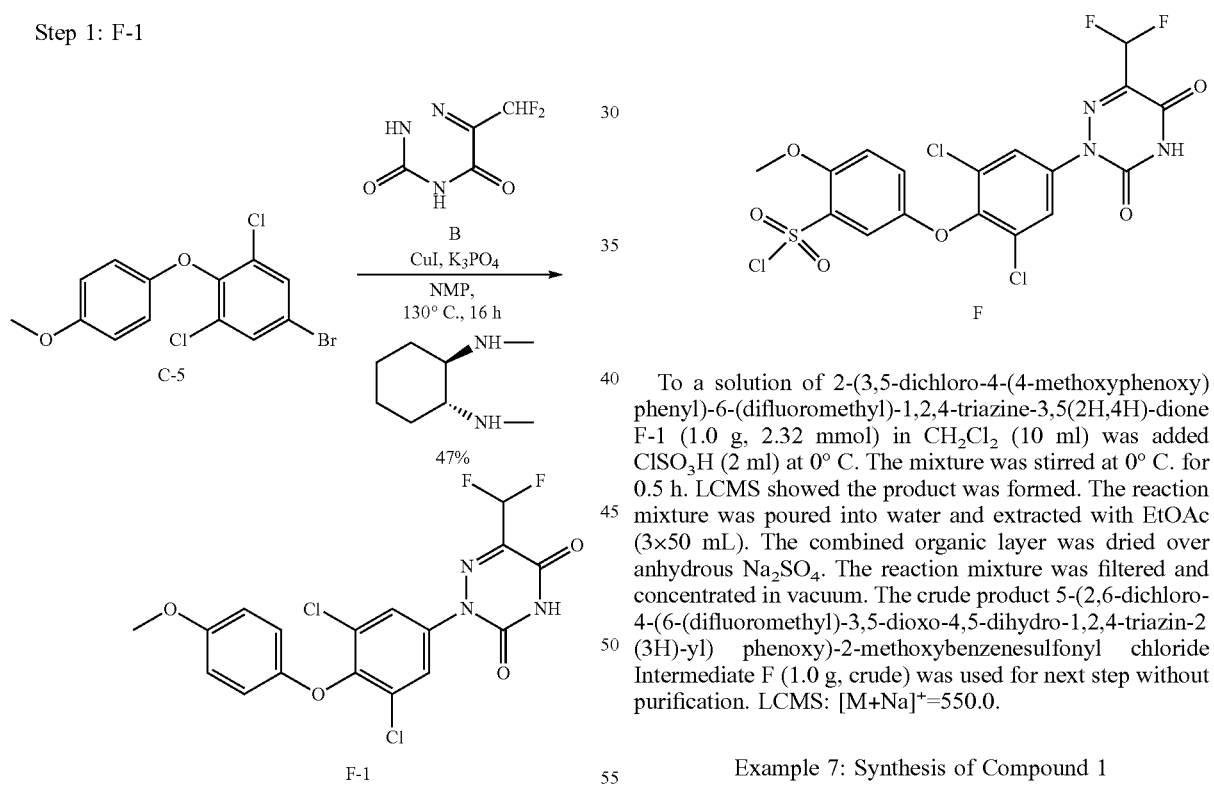

A mixture of 5-bromo-1,3-dichloro-2-(4-methoxyphenoxy)benzene C-5 (2.8 g, 8.05 mmol), (1R,2R)—N1,N2-dimethylcyclohexane-1,2-diamine (801.08 mg, 5.63 mmol), 6-(difluoromethyl)-2H-1,2,4-triazine-3,5-dione Intermediate B (Example 2) (2.62 g, 16.09 mmol), potassium phosphate (5.12 g, 24.14 mmol) and CuI (3.83 g, 20.11 mmol) in NMP (1.5 mL) was stirred at 130° C. for 16 h. LCMS showed the product was formed. The reaction mixture was poured into water and extracted with EtOAc (3×50 mL). The combined organic layer was dried over anhydrous Na₂SO₄. The reaction mixture was filtered and concentrated in To a solution of 2-(3,5-dichloro-4-(4-methoxyphenoxy) phenyl)-6-(difluoromethyl)-1,2,4-triazine-3,5(2H,4H)-dione F-1 (1.0 g, 2.32 mmol) in CH₂Cl₂ (10 ml) was added ClSO₃H (2 ml) at 0° C. The mixture was stirred at 0° C. for 0.5 h. LCMS showed the product was formed. The reaction mixture was poured into water and extracted with EtOAc (3×50 mL). The combined organic layer was dried over anhydrous Na₂SO₄. The reaction mixture was filtered and concentrated in vacuum. The crude product 5-(2,6-dichloro-4-(6-(difluoromethyl)-3,5-dioxo-4,5-dihydro-1,2,4-triazin-2 (3H)-yl) phenoxy)-2-methoxybenzenesulfonyl chloride Intermediate F (1.0 g, crude) was used for next step without purification. LCMS: [M+Na]⁺=550.0.

Example 7: Synthesis of Compound 1

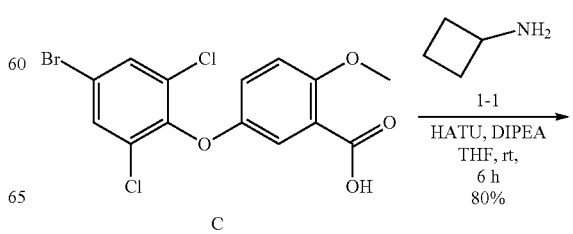

-continued

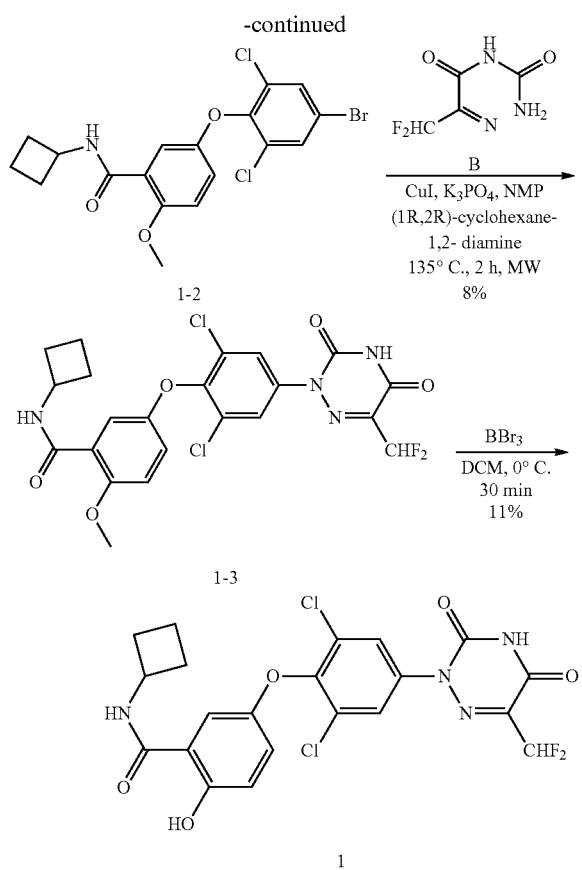

Step 1: 1-2

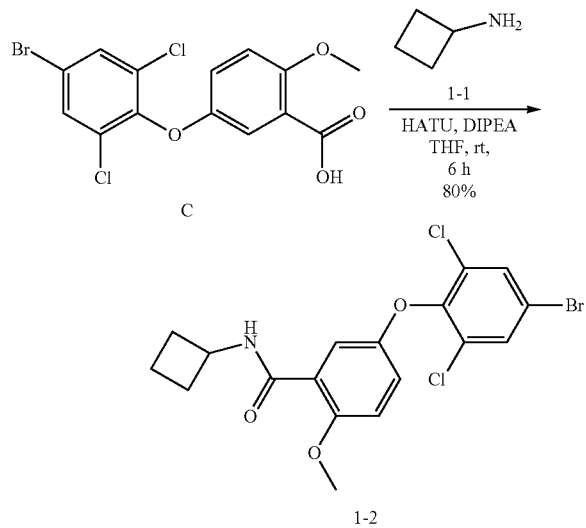

To a solution of 5-(4-bromo-2,6-dichloro-phenoxy)-2-methoxy-benzoic acid Intermediate C (Example 3) (200 mg, 510.17 umol) in THF (50 mL) was added HATU (290.97 mg, 765.25 umol). The reaction mixture was stirred at rt for 5 min and then cyclobutanamine 1-1 (72.57 mg, 1.02 mmol, 87.12 uL) was added. After reaction mixture was stirred for 5 min, N,N-Diisopropylethylamine (197.80 mg, 1.53 mmol, 266.58 uL) was added. The reaction mixture was stirred for another 6 h. LCMS showed the reaction was completed. The reaction mixture was concentrated in vacuum to afford a residue. The residue was dissolved in EtOAc (20 mL), washed with brine (20 mL), dried over anhydrous $Na_2SO_4$ and filtered. The filtrate was concentrated in vacuum to afford a residue. The residue was purified by silica gel chromatography (PE:EA=1:2) to afford 5-(4-bromo-2,6-dichloro-phenoxy)-N-cyclobutyl-2-methoxy-benzamide 1-2 (203 mg, 80% yield) as a light yellow solid. LCMS: $[M+H]^+$=443.9.

Step 2: 1-3

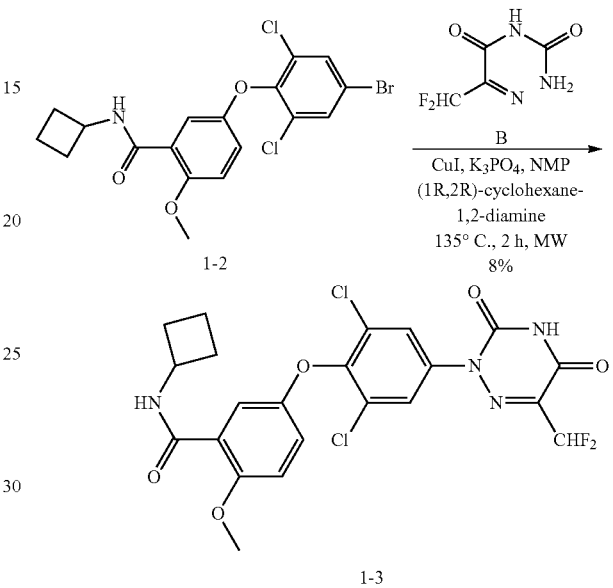

A mixture of 5-(4-bromo-2,6-dichloro-phenoxy)-N-cyclobutyl-2-methoxy-benzamide 1-2 (100 mg, 224.65 umol), 6-(difluoro methyl)-1,2,4-triazine-3,5(2H,4H)-dione Intermediate B (Example 2) (73.27 mg, 449.30 umol), copper(I) iodide (85.57 mg, 449.30 umol), potassium phosphate (143.06 mg, 673.95 umol) and (1R,2R)-cyclohexane-1,2-diamine (25.65 mg, 224.65 umol) in NMP (4 mL) was stirred at 135° C. under microwave for 2 h. LCMS showed the reaction was completed. The reaction mixture was poured into water (50 mL) and extracted with EA (3×20 mL). The combined organic layer was washed with brine (20 mL), dried over anhydrous $Na_2SO_4$ and filtered. The filtrate was concentrated in vacuum to afford a residue. The residue was purified by silica gel chromatography ($CH_2Cl_2$:MeOH=1:50) to afford N-cyclobutyl-5-[2,6-dichloro-4-[6-(difluoromethyl)-3,5-dioxo-1,2,4-triazin-2-yl] phenoxy]-2-methoxy-benzamide 1-3 (11 mg, 8% yield) as a light yellow solid. LCMS: $[M+H]^+$=527.0.

Step 3: Compound 1

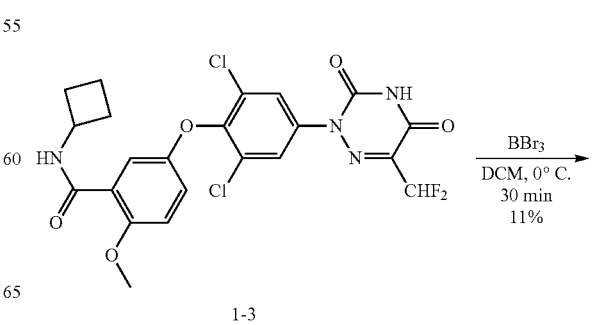

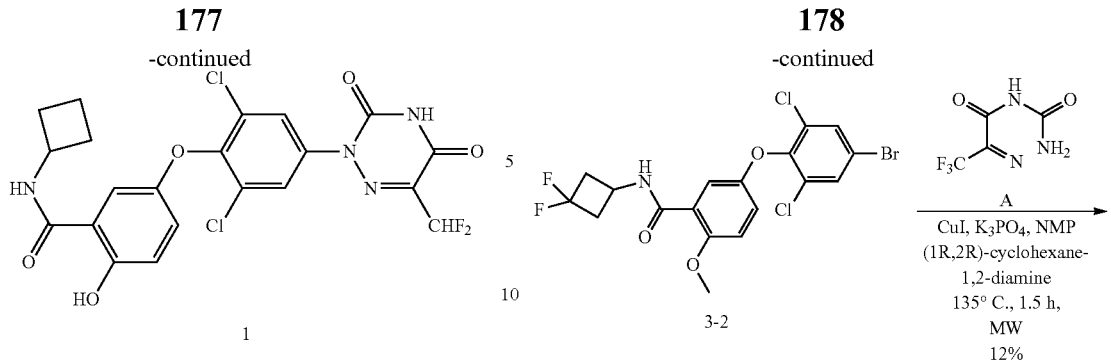

To a solution of N-cyclobutyl-5-[2,6-dichloro-4-[6-(difluoromethyl)-3,5-dioxo-1,2,4-triazin-2-yl]phenoxy]-2-methoxy-benzamide 1-3 (11 mg, 20.86 umol) in $CH_2Cl_2$ (2 mL) was added boron tribromide $CH_2Cl_2$ solution (1 M, 104.3 uL) at 0° C. The reaction mixture was stirred at 0° C. for 30 min. LCMS showed the reaction was completed. The reaction mixture was poured into sat. $NaHCO_3$ (50 mL) and extracted with $CH_2Cl_2$ (3×20 mL). The combined organic layers were washed with brine (50 mL), dried over anhydrous $Na_2SO_4$ and filtered. The filtrate was concentrated in vacuum to afford a residue. The residue was purified by Prep-HPLC (Chromatographic columns: Kromasil-C18 100×21.2 mm 5 um, ACN—$H_2O$ (0.05% $NH_3$); Gradient: 20-30.) to afford N-cyclobutyl-5-[2,6-dichloro-4-[6-(difluoromethyl)-3,5-dioxo-1,2,4-triazin-2-yl] phenoxy]-2-hydroxy-benzamide Compound 1 (1.2 mg, 11% yield) as a light yellow solid. LCMS: [M+H]$^+$=513.1. $^1$H NMR (400 MHz, $CD_3OD$) δ 7.78 (s, 2H), 7.37 (d, J=4.0 Hz, 1H), 6.94 (dd, J=8.0, 4.0 Hz, 1H), 6.88 (d, J=8.0 Hz, 1H), 6.71 (t, J=53.2 Hz, 1H), 4.52-4.41 (m, 1H), 2.39-2.30 (m, 2H), 2.12-2.01 (m, 2H), 1.81-1.72 (m, 2H). $^{19}$F NMR (376 MHz, $CD_3OD$) δ−124.2 (s).

The compounds of Formula (I') or (I) in Table 2 below were made according to Example 7 of Compound 1.

TABLE 2

| Cmpd No. | LC-MS, $^1$H and $^{19}$F-NMR data |
|---|---|
| 2 | LCMS: [M + H]$^+$ = 529.1. $^1$H NMR (400 MHz, $CD_3OD$) δ 7.79 (s, 2H), 7.39 (d, J = 3.2 Hz, 1H), 6.93 (dd, J = 9.2, 3.2 Hz, 1H), 6.88 (d, J = 9.2 Hz, 1H), 6.72 (t, J = 52.8 Hz, 1H), 4.57-4.49 (m, 1H), 4.54-4.40 (m, 1H), 2.39-2.29 (m, 4H). $^{19}$F NMR (376 MHz, $CD_3OD$) δ-124.3 (s, 2F). |

Example 8: Synthesis of Compound 3

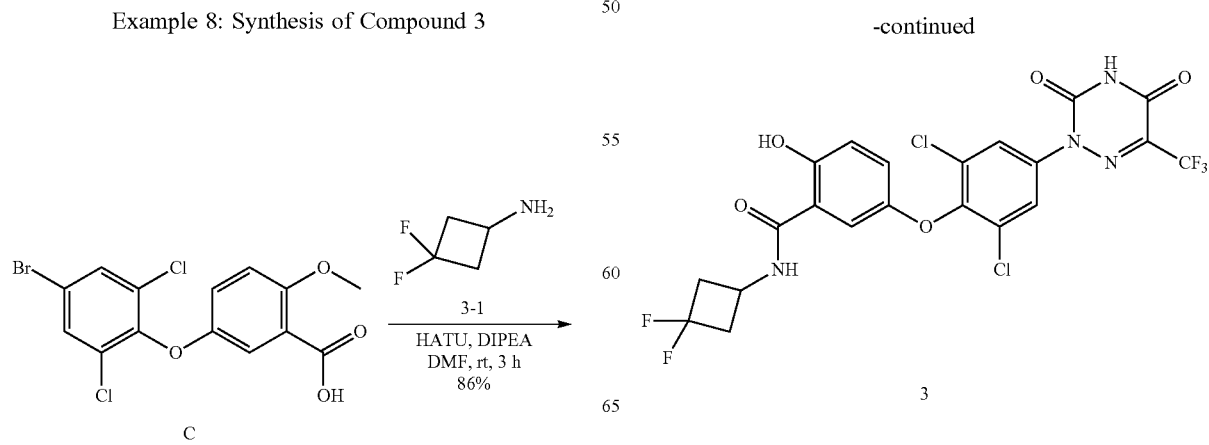

Step 1: 3-2

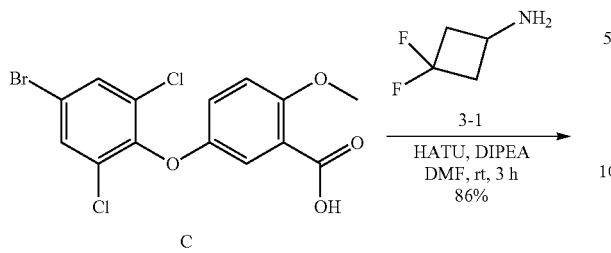

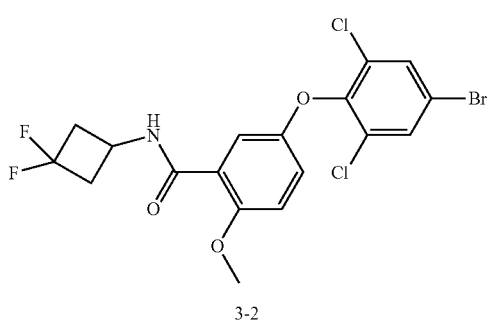

To a solution of 5-(4-bromo-2,6-dichloro-phenoxy)-2-methoxy-benzoic acid Intermediate C (Example 3) (225 mg, 573.94 umol) in DMF (3 mL) was added 3,3-difluorocyclobutanamine 3-1 (61.47 mg, 573.94 umol), HATU (436.46 mg, 1.15 mmol) and DIPEA (222.53 mg, 1.72 mmol). The mixture was stirred at room temperature for 3h. LCMS showed the reaction was completed. The reaction mixture was poured into water (100 mL) and extracted with EtOAc (2×150 mL). The combined organic layers were dried over anhydrous Na$_2$SO$_4$ and concentrated to afford a residue. The residue was purified by silica gel chromatography (PE:EtOAc=3:1) to afford 5-(4-bromo-2,6-dichloro-phenoxy)-N-(3,3-difluorocyclobutyl)-2-methoxy-benzamide 3-2 (240 mg, 86% yield) as a white solid. LCMS: [M+H]$^+$=479.9/482.0.

Step 2: 3-3

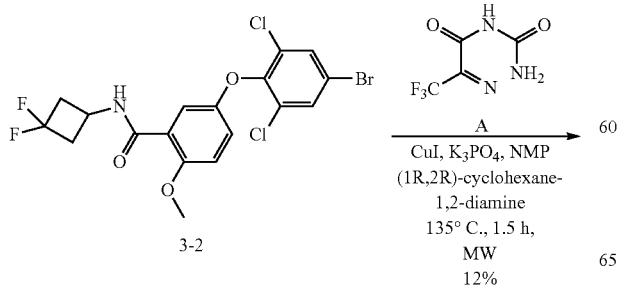

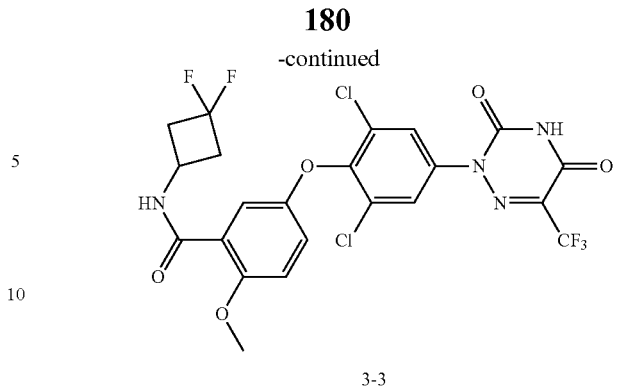

A solution of 5-(4-bromo-2,6-dichloro-phenoxy)-N-(3,3-difluorocyclobutyl)-2-methoxy-benzamide 3-2 (240 mg, 498.84 umol), 6-(trifluoromethyl)-2H-1,2,4-triazine-3,5-dione Intermediate A (Example 1) (180.65 mg, 997.68 umol), (1R,2R)-cyclohexane-1,2-diamine (56.96 mg, 498.84 umol), CuI (190.01 mg, 997.68 umol) and K$_3$PO$_4$ (317.26 mg, 1.50 mmol) in NMP (2 mL) under N$_2$ (g) was microwaved at 135° C. for 1.5 h. LCMS showed the reaction was completed. The reaction mixture was poured into water (100 mL) and extracted with EtOAc (2×150 mL). The combined organic layers were dried over anhydrous Na$_2$SO$_4$ and concentrated to afford a residue. The residue was purified by Prep-TLC (CH$_2$Cl$_2$:MeOH=20:1) to afford 5-[2,6-dichloro-4-[3,5-dioxo-6-(trifluoromethyl)-1,2,4-triazin-2-yl] phenoxy]-N-(3,3-difluorocyclobutyl)-2-methoxy-benzamide 3-3 (35 mg, 12% yield) as a yellow oil. LCMS: [M+H]$^+$=581.0/583.0.

Step 3: Compound 3

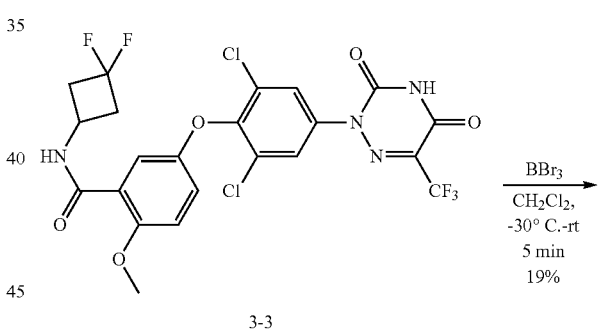

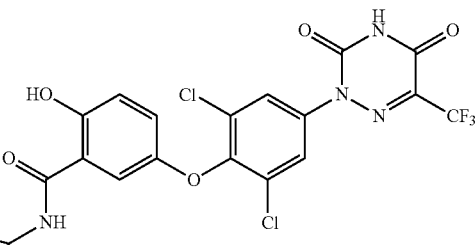

To a solution of 5-[2,6-dichloro-4-[3,5-dioxo-6-(trifluoromethyl)-1,2,4-triazin-2-yl] phenoxy]-N-(3,3-difluorocyclobutyl)-2-methoxy-benzamide 3-3 (35 mg, 60.21 umol) at −30° C. was added BBr$_3$ (75.40 mg, 300.63 umol). The mixture was stirred at −30° C. for 5 min. LCMS showed the reaction was completed. The reaction mixture was poured into water (100 mL) and extracted with EtOAc (2×150 mL). The combined organic layers were dried over anhydrous Na₂SO₄ and concentrated to afford a residue. The residue was purified by Prep-HPLC (Xbridge 5 u C18 150×19 mm, Mobile Phase: ACN—H₂O (0.05% NH₃), Gradient: 15-25) to afford 5-[2,6-dichloro-4-[3,5-dioxo-6-(trifluoromethyl)-1,2,4-triazin-2-yl] phenoxy]-N-(3,3-difluorocyclobutyl)-2-hydroxy-benzamide Compound 3 (6.8 mg, 19% yield) as a white solid. LCMS: [M+H]⁺=567.0/569.1. ¹H NMR (400 MHz, CD₃OD) δ 7.77 (s, 2H), 7.34 (d, J=2.8 Hz, 1H), 6.98 (dd, J=9.2, 3.2 Hz, 1H), 6.90 (d, J=9.2 Hz, 1H), 4.34-4.30 (m, 1H), 3.03-2.90 (m, 2H), 2.76-2.61 (m, 2H). ¹⁹F NMR (376 MHz, CD₃OD) δ−69.3 (s, 3F), 6-85.4 (d, J=198.8 Hz, 1F), −100.4 (d, J=199.2 Hz, 1F).

The compounds of Formula (I') or (I) in Table 3 below were made according to Example 8 of Compound 3.

TABLE 3

| Cmpd No. | LC-MS, ¹H and ¹⁹F-NMR data |
|---|---|
| 4 | LCMS: [M + H]⁺ = 533.1/534.9. ¹H NMR (400 MHz, CD₃OD) δ 7.77-7.77 (m, 2H), 7.39-7.38 (m, 1H), 6.93-6.86 (m, 2H), 1.44-1.43 (m, 9H). ¹⁹F NMR (376 MHz, CD₃OD) δ-69.3 (s). |
| 5 | LCMS: [M + H]⁺ = 531.0/533.0. ¹H NMR (400 MHz, CD₃OD) δ 7.79 (s, 2H), 7.36 (s, 1H), 6.94 (d, J = 8.8 Hz, 1H), 6.87 (d, J = 9.2 Hz, 1H), 4.51-4.42 (m, 1H), 2.37-2.29 (m, 2H), 2.10-2.03 (m, 2H), 1.81-1.72 (m, 2H) ¹⁹F NMR (376 MHz, MeOD) δ-69.28 (s). |

Example 9: Synthesis of Compound 6

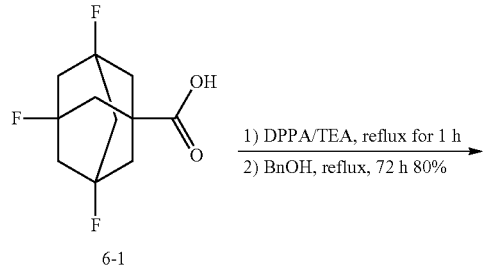

6-1

1) DPPA/TEA, reflux for 1 h
2) BnOH, reflux, 72 h 80%

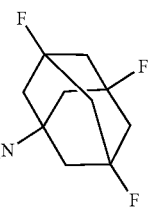

6-3

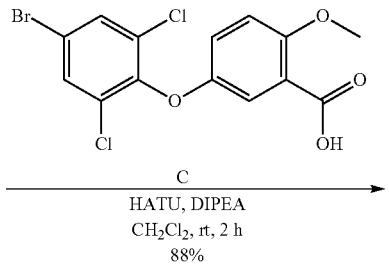

C
HATU, DIPEA
CH₂Cl₂, rt, 2 h
88%

-continued

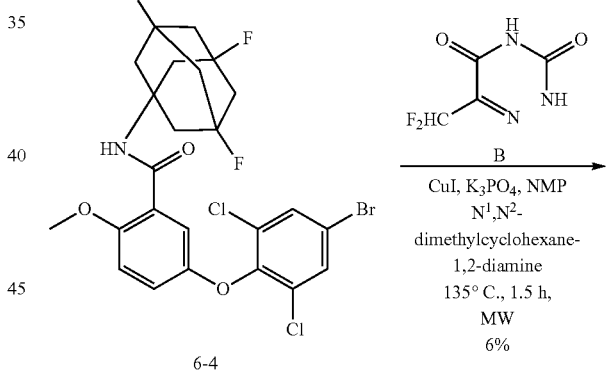

6-4

B
CuI, K₃PO₄, NMP
N¹,N²-dimethylcyclohexane-1,2-diamine
135° C., 1.5 h, MW
6%

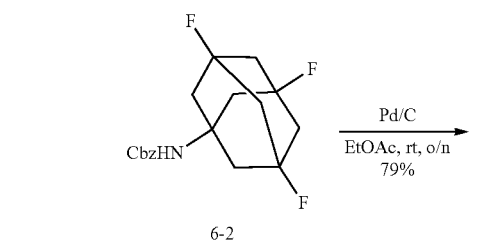

6-2

Pd/C
EtOAc, rt, o/n
79%

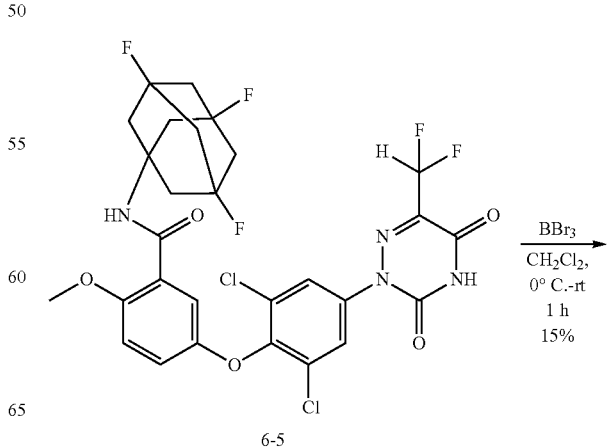

6-5

BBr₃
CH₂Cl₂,
0° C.-rt
1 h
15%

-continued

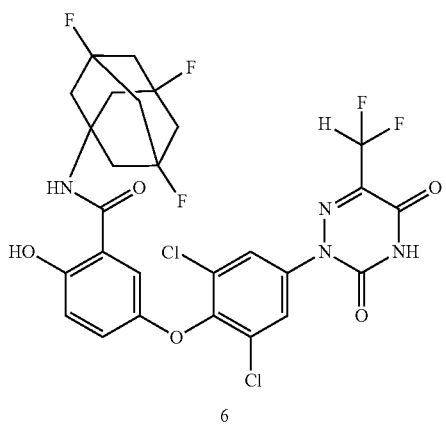

6

Step 1: 6-2

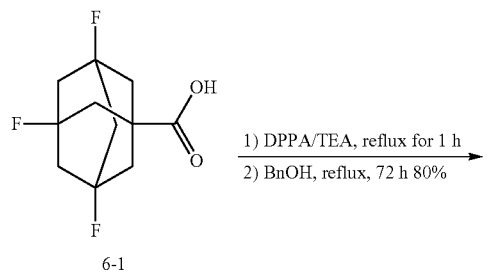

Step 2: 6-3

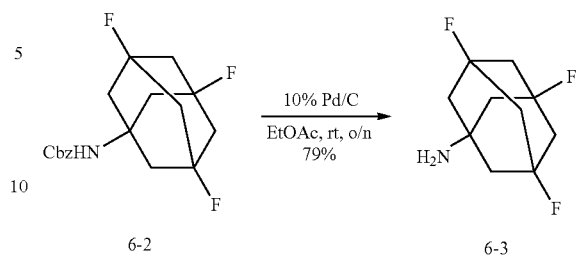

To a solution of benzyl N-(3,5,7-trifluoro-1-adamantyl) carbamate 6-2 (2.5 g, 7.37 mmol) in EtOAc (50 mL) at rt was added 10% palladium on carbon wet (500 mg). The reaction mixture was stirred at rt under H₂ (g) for 16 h. LC-MS showed the reaction was completed. The reaction mixture was filtered and the filtrate was concentrated in vacuum to afford 3,5,7-trifluoroadamantan-1-amine 6-3 (1.2 g, 79% yield) as a grey solid. LCMS: [M+H]⁺=206.2.

Step 3: 6-4

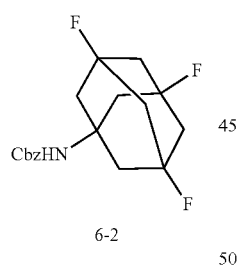

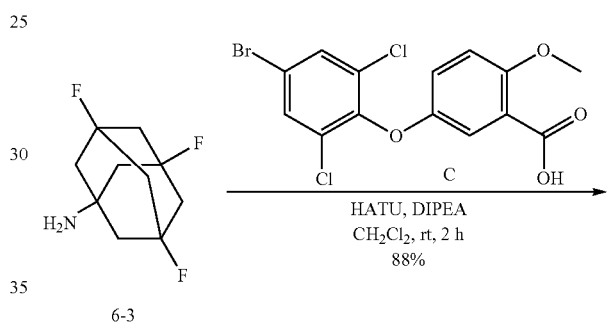

A mixture of 3,5-difluoroadamantane-1-carboxylic acid 6-1 (2.0 g, 9.25 mmol), triethylamine (940.65 mg, 9.30 mmol, 1.30 mL) and diphenyl phosphoryl azide (2.56 g, 9.30 mmol, 2.01 mL) in toluene (50 mL) was stirred at 85° C. for 1.0 h. Then the reaction mixture was cooled to rt and benzyl alcohol (1.01 g, 9.30 mmol, 957.37 uL) was added to the reaction mixture. The reaction mixture was stirred at 85° C. for 72 h. LC-MS showed the reaction was completed. The reaction mixture was concentrated in vacuum to afford a residue. The residue was purified by silica gel chromatography (PE:EtOAc=4:1) to afford benzyl N-(3,5,7-trifluoro-1-adamantyl) carbamate 6-2 (2.5 g, 80% yield) as a light yellow solid.

To a solution of 5-(4-bromo-2,6-dichlorophenoxy)-2-methoxybenzoic acid Intermediate C (Example 3) (199.94 mg, 510.02 umol) in CH₂Cl₂ (20 mL) was added HATU (290.89 mg, 765.03 umol) and 3,5,7-trifluoroadamantan-1-amine 6-3 (157 mg, 765.03 umol). The reaction mixture was stirred at rt for 10 min. Then N, N-Diisopropylethylamine (131.83 mg, 1.02 mmol, 177.67 uL) was added to the reaction mixture. The reaction mixture was stirred at rt for 2.0 h. LC-MS showed the reaction was completed. The reaction mixture was poured into water (50 mL) and extracted with CH₂Cl₂ (3×20 mL). The combined organic layer was washed with brine (20 mL), dried over anhydrous Na₂SO₄ and filtered. The filtrate was concentrated in vacuum to afford a residue. The residue was purified by silica gel chromatography (PE:EtOAc=10:1) to afford 5-(4-bromo-2,6-dichloro-phenoxy)-2-methoxy-N-(3,5,7-trifluoro-1-adamantyl) benzamide 6-4 (260 mg, 88% yield) as a light yellow solid. LCMS: [M+H]⁺=578.0/580.0.

Step 4: 6-5

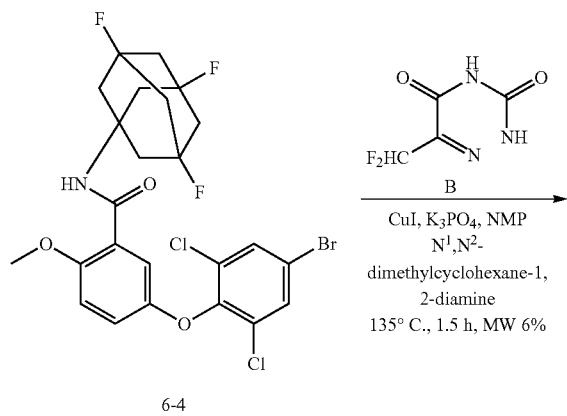

6-4

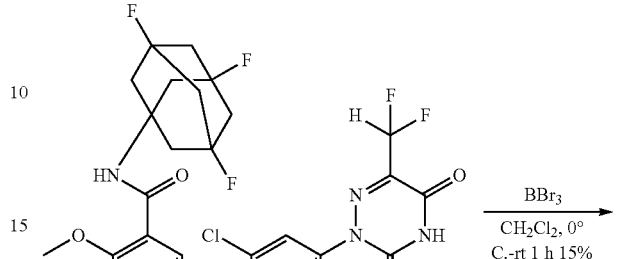

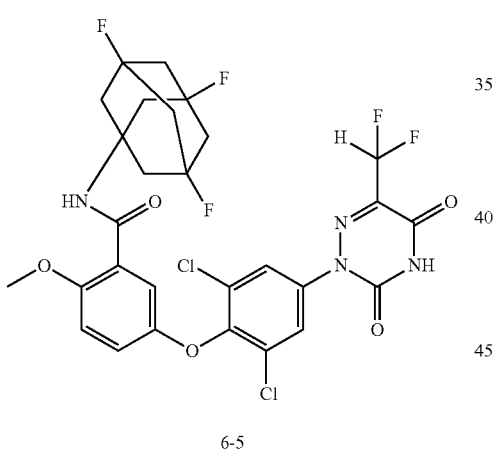

6-5

A mixture of 5-(4-bromo-2,6-dichloro-phenoxy)-2-methoxy-N-(3,5,7-trifluoro-1-adamantyl)benzamide 6-4 (200 mg, 345.28 umol), 6-(difluoromethyl)-1,2,4-triazine-3,5(2H,4H)-dione Intermediate B (Example 2) (84.46 mg, 517.93 umol), CuI (65.76 mg, 345.28 umol), N1,N2-dimethylcyclohexane-1,2-diamine (39.29 mg, 276.23 umol) and potassium phosphate (219.88 mg, 1.04 mmol) in NMP (4 mL) was stirred at 135° C. under microwave for 1.5 h. LC-MS showed the reaction worked. The reaction mixture was poured into water (100 mL) and extracted with EtOAc (3×20 mL). The combined organic layers were washed with brine (20 mL), dried over anhydrous Na₂SO₄ and filtered. The filtrate was concentrated in vacuum to afford a residue. The residue was purified by silica gel chromatography (CH₂Cl₂:MeOH=50:1) to afford 5-[2,6-dichloro-4-[6-(difluoromethyl)-3,5-dioxo-1,2,4-triazin-2-yl] phenoxy]-2-methoxy-N-(3,5,7-trifluoro-1-adamantyl) benzamide 6-5 (15 mg, 6% yield) as a light yellow solid. LCMS: [M+H]⁺=661.1/663.1.

Step 5: Compound 6

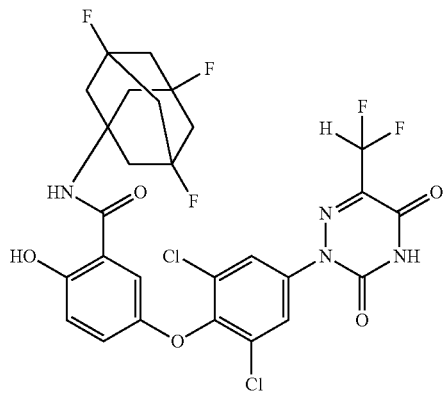

6-5

6

To a solution of 5-[2,6-dichloro-4-[6-(difluoromethyl)-3,5-dioxo-1,2,4-triazin-2-yl] phenoxy]-2-methoxy-N-(3,5,7-trifluoro-1-adamantyl) benzamide 6-5 (13 mg, 19.66 umol) in CH₂Cl₂ (4 mL) at 0° C. was added boron tribromide CH₂Cl₂ solution (1 M, 98.28 uL). The reaction mixture was stirred at 0° C. for 30 min. LC-MS showed the reaction was completed. The reaction mixture was poured into sat. NaHCO₃ (50 mL) and extracted with CH₂Cl₂ (2×10 mL). The combined organic layers were washed with brine (20 mL), dried over anhydrous Na₂SO₄ and filtered. The filtrate was concentrated in vacuum to afford a residue. The residue was purified by prep-HPLC (Chromatographic columns: Kromasil-C18 100×21.2 mm 5 um, Mobile Phase: MeCN—H₂O (0.05% NH₃), Gradient: 20-30) to afford 5-(2,6-dichloro-4-(6-(difluoromethyl)-3,5-dioxo-4,5-dihydro-1,2,4-triazin-2(3H)-yl) phenoxy)-2-hydroxy-N-(3,5,7-trifluoroadamantan-1-yl) benzamide 6 (2 mg, 15% yield) as a white solid. LCMS: [M+H]⁺=647.0/649.1. ¹H NMR (400 MHz, CD₃OD) δ 7.78 (s, 2H), 7.39 (d, J=2.8 Hz, 1H), 6.93-6.84 (m, 2H), 6.71 (t, J=52.8 Hz, 1H), 2.29 (s, 6H), 2.12 (s, 6H). ¹⁹F NMR (376 MHz, CD₃OD) δ–124.2 (s), 6-146.8 (s).

Example 10: Synthesis of Compounds 7 and 8

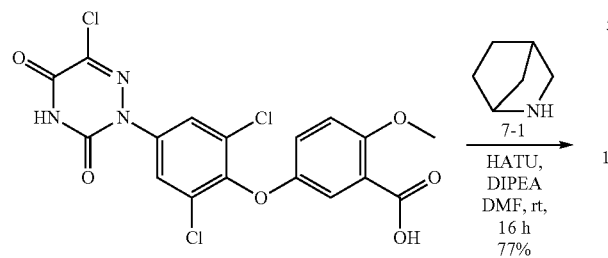

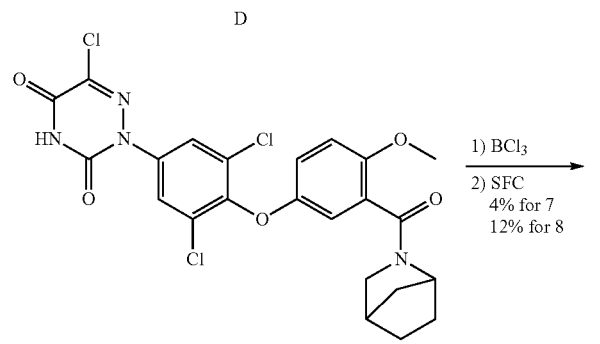

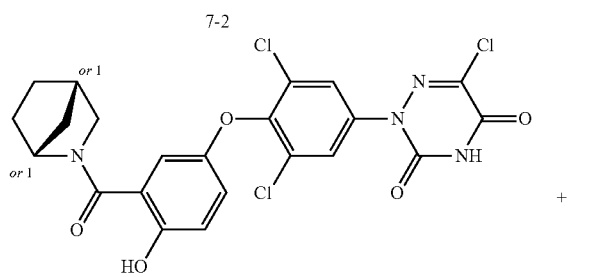

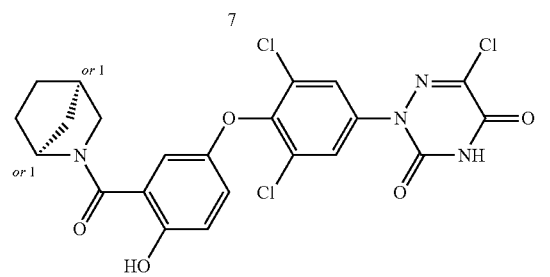

Step 1: 7-2

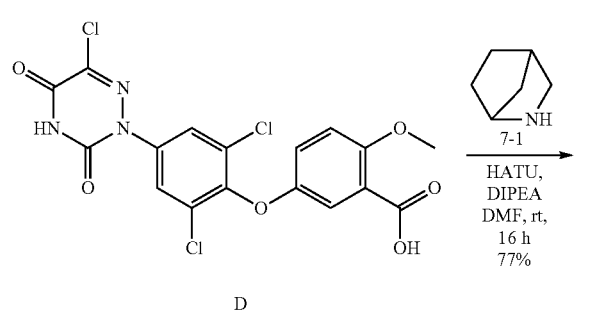

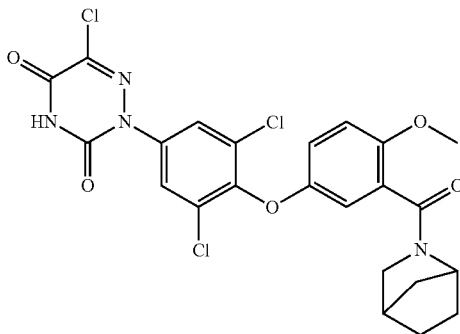

-continued

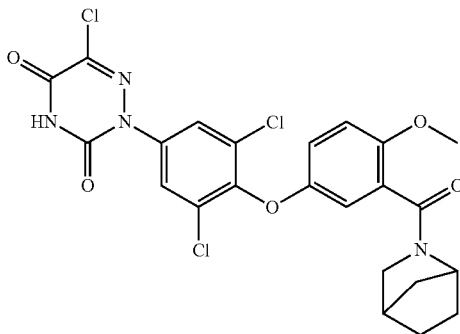

To a solution of 5-[2,6-dichloro-4-(6-chloro-3,5-dioxo-1,2,4-triazin-2-yl)phenoxy]-2-methoxy-benzoic acid Intermediate D (Example 4) (51 mg, 111.20 umol), 2-azabicyclo[2.2.1]heptane 7-1 (11.88 mg, 122.32 umol) and HATU (63.76 mg, 166.80 umol) in DMF (2.6 mL) was added DIPEA (43.12 mg, 333.60 umol, 58.11 uL) and the mixture was stirred at rt for 16 h. The mixture was diluted with water (5 mL) and extracted with EtOAc (3×5 mL). The combined organic layer was washed with brine (10 mL), dried over Na$_2$SO$_4$ and concentrated in vacuum. The residue was purified by column chromatography (0-10% MeOH in DCM) to give 2-[4-[3-(2-azabicyclo [2.2.1] heptane-2-carbonyl)-4-methoxy-phenoxy]-3,5-dichloro-phenyl]-6-chloro-1,2,4-triazine-3,5-dione 7-2 (47 mg, 77% yield) as a yellow oil. LCMS: [M+H]$^+$=537.1.

Step 2: Compounds 7 and 8

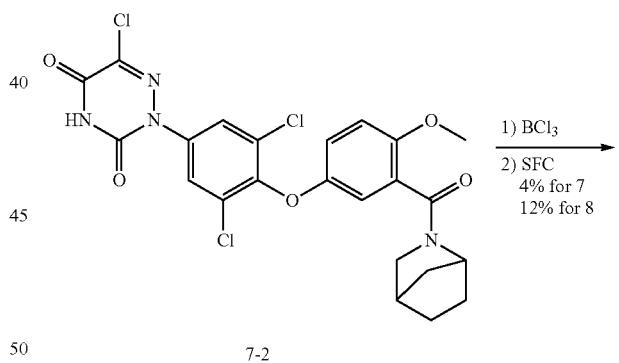

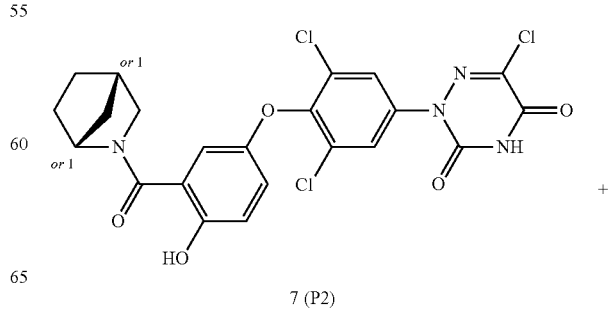

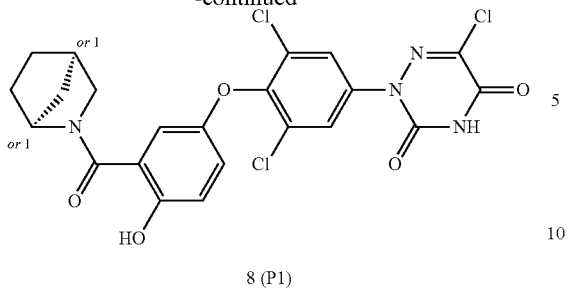

8 (P1)

To a solution of 2-[4-[3-(2-azabicyclo[2.2.1]heptane-2-carbonyl)-4-methoxy-phenoxy]-3,5-dichloro-phenyl]-6-chloro-1,2,4-triazine-3,5-dione 7-2 (47 mg, 87.40 umol) in DCM (1 mL) was added dropwise boron trichloride CH₂Cl₂ solution (1 M, 873.96 uL) at 0° C. and the mixture was stirred at 0° C. for 0.5 h. The mixture was quenched with sat. NaHCO₃ (5 mL) and extracted with EtOAc (3×3 mL). The combined organic layers were washed with brine (5 mL), dried over Na₂SO₄ and concentrated in vacuum. The residue was separated with SFC (Chromatographic columns: chiralpak-OZ; Mobile Phase: CO₂-MeOH (0.1% DEA)). The separated chiral product (P1 4.697 min and P2 5.320 min) was further purified respectively by prep-HPLC (Chromatographic columns: Kromasil-C18 100×21.2 mm 5 um; Mobile Phase: ACN—H₂O (0.05% NH₃); Gradient: 25-35) to give 2-[4-[3-[(1R,4S)-2-azabicyclo[2.2.1]heptane-2-carbonyl]-4-hydroxy-phenoxy]-3,5-dichloro-phenyl]-6-chloro-1,2,4-triazine-3,5-dione Compound 7 (5.6 mg, 12% yield) as a white solid and 2-[4-[3-[(1S,4R)-2-azabicyclo[2.2.1]heptane-2-carbonyl]-4-hydroxy-phenoxy]-3,5-dichloro-phenyl]-6-chloro-1,2,4-triazine-3,5-dione Compound 8 (1.6 mg, 4% yield) as a white solid. LCMS: [M+H]⁺=523.1.

¹H NMR for Compound 7: (400 MHz, CD₃OD) δ 7.78 (s, 2H), 6.96-6.77 (m, 2H), 6.70-6.62 (m, 1H), 3.99 (s, 1H), 3.49-3.46 (m, 1H), 3.08-3.00 (m, 1H), 2.60-2.57 (m, 1H), 1.78-1.58 (m, 4H), 1.54-1.45 (m, 2H).

¹H NMR for Compound 8 (400 MHz, CD₃OD) δ 7.78 (s, 2H), 6.95-6.77 (m, 2H), 6.70-6.62 (m, 1H), 4.00 (s, 1H), 3.50-3.47 (m, 1H), 3.11-3.00 (m, 1H), 2.61-2.57 (m, 1H), 1.86-1.57 (m, 4H), 1.55-1.46 (m, 2H).

Example 11: Synthesis of Compound 9

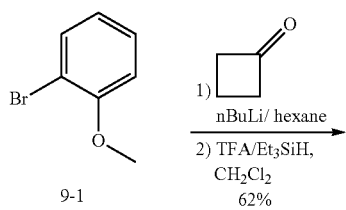

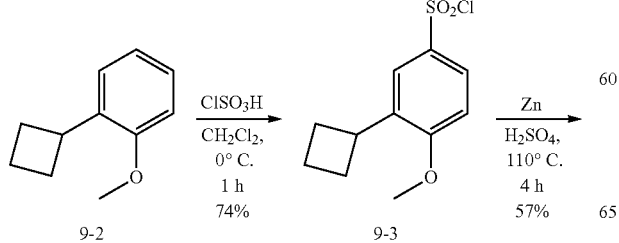

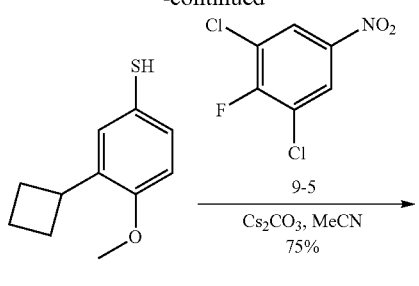

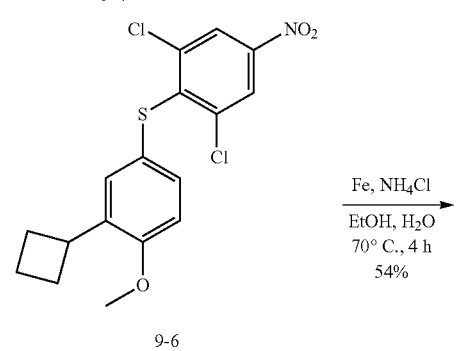

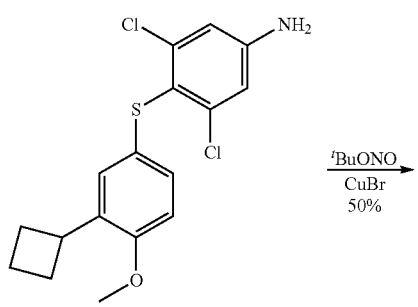

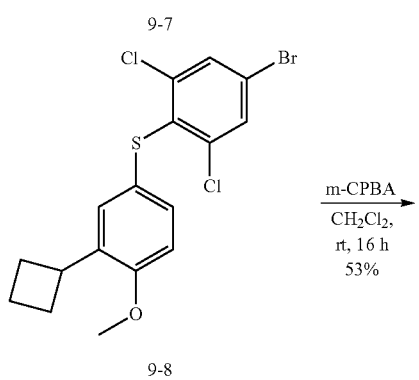

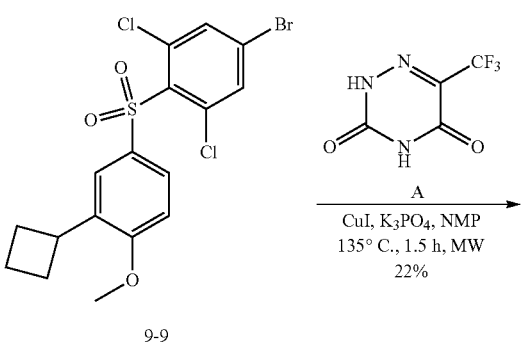

-continued

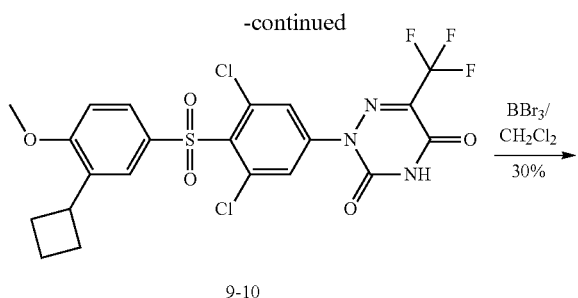

9-10

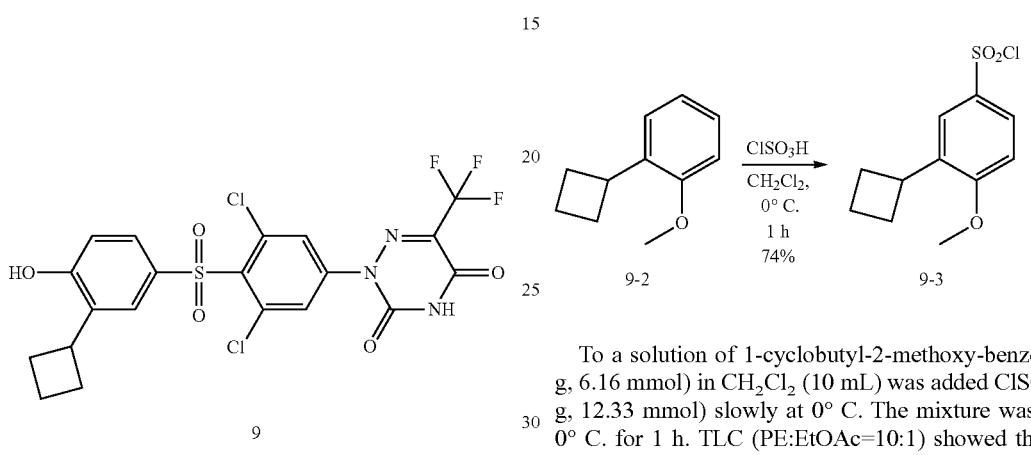

9

Step 1: 9-2

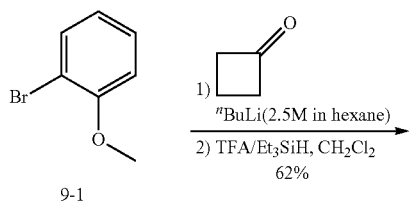

A solution of 1-bromo-2-methoxy-benzene 9-1 (3.0 g, 16.04 mmol, 2.00 mL) in THF (20 mL) was cooled with a dry ice-acetone cold bath. After the mixture was stirred for 10 min, n-BuLi (2.5 M in hexane) (12 mL) was added dropwise by syringe. The cold bath was removed and the reaction mixture was stirred at ambient temperature for 0.5 h. LCMS showed that there was no starting material left. Then cyclobutanone (1.24 g, 17.64 mmol, 1.32 mL) was added via syringe to the mixture under a dry ice-acetone cold bath. Then reaction mixture was stirred at 25° C. for 14 h. TLC (PE:EtOAc=20:1) showed the reaction was completed. The reaction was quenched by addition of 100 mL of saturated ammonium chloride. The water layer was extracted with 50 mL of EtOAc. The combined organic layers were dried over anhydrous $Na_2SO_4$. The mixture was filtered and concentrated in vacuum to afford 1-(2-methoxyphenyl) cyclobutanol (2.8 g, crude). The crude product was dissolved in $CH_2Cl_2$ (20 mL) and to the mixture was added TFA (1.79 g, 15.71 mmol, 1.21 mL) and triethyl silane (5.48 g, 47.13 mmol, 7.53 mL). The mixture was stirred at 25° C. for 16 h. TLC (PE=100%) showed the reaction was completed. The volatile material was removed in vacuum to afford a residue. The residue was purified by silica gel chromatography (PE=100%) to afford 1-cyclobutyl-2-methoxy-benzene 9-2 (1.6 g, 62% yield) as a light yellow solid.

Step 2: 9-3

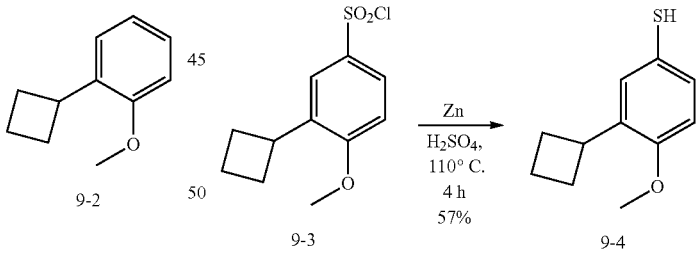

To a solution of 1-cyclobutyl-2-methoxy-benzene 9-2 (1 g, 6.16 mmol) in $CH_2Cl_2$ (10 mL) was added $ClSO_3H$ (1.44 g, 12.33 mmol) slowly at 0° C. The mixture was stirred at 0° C. for 1 h. TLC (PE:EtOAc=10:1) showed the reaction was completed. The reaction mixture was poured into ice and extracted with EtOAc (3×200 mL). The combined organic layers were dried over anhydrous $Na_2SO_4$. The reaction mixture was filtered and concentrated in vacuum to afford a residue. The residue was purified by silica gel chromatography (PE:EtOAc=10:1) to afford 3-cyclobutyl-4-methoxy-benzenesulfonyl chloride 9-3 (1.2 g, 74% yield) as a yellow solid.

Step 3: 9-4

A solution of 3-cyclobutyl-4-methoxy-benzenesulfonyl chloride 9-3 (700 mg, 2.68 mmol) and Zn (175.55 mg, 2.68 mmol) in $H_2SO_4$ (25%) (5 mL) was stirred at 110° C. for 4 h. TLC (PE=100%) showed the reaction was completed. The reaction mixture was extracted with EtOAc (3×200 mL) and washed with brine (3×100 mL). The combined organic layer was dried over anhydrous $Na_2SO_4$. The reaction mixture was filtered and concentrated in vacuum to afford a residue. The residue was purified by silica gel chromatography (PE=100%) to afford 3-cyclobutyl-4-methoxy-benzenethiol 9-4 (300 mg, 57% yield) as a yellow solid.

Step 4: 9-6

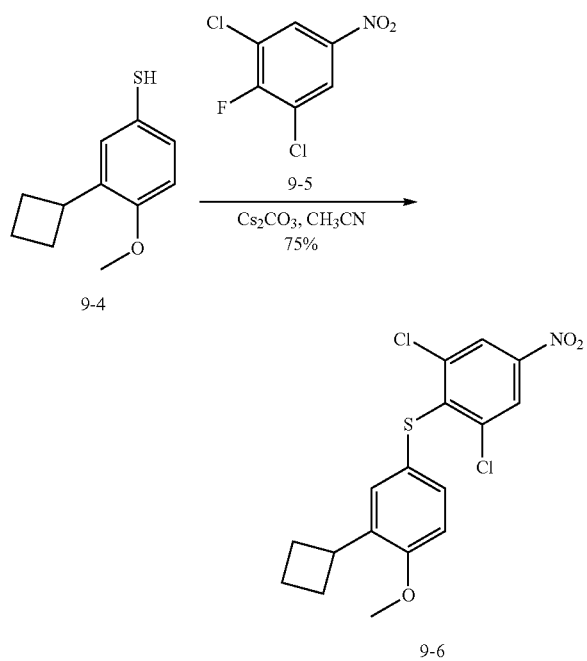

To a solution of 1,3-dichloro-2-fluoro-5-nitro-benzene 9-5 (324.24 mg, 1.54 mmol) and Cs$_2$CO$_3$ (1.00 g, 3.09 mmol) in CH$_3$CN (5 mL) was added 3-cyclobutyl-4-methoxy-benzenethiol 9-4 (300 mg, 1.54 mmol). The mixture was stirred at room temperature for 3 h. TLC (PE=100%) showed the reaction was completed. The reaction mixture was poured into water (100 mL) and extracted with EtOAc (2×150 mL). The combined organic layers were dried over anhydrous Na$_2$SO$_4$. The reaction mixture was filtered and concentrated in vacuum to afford a residue. The residue was purified by silica gel chromatography (PE=100%) to afford 1,3-dichloro-2-(3-cyclobutyl-4-methoxy-phenyl) sulfanyl-5-nitro-benzene 9-6 (450 mg, 75% yield) as a yellow oil.

Step 5: 9-7

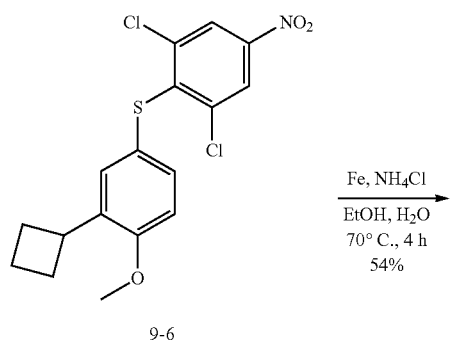

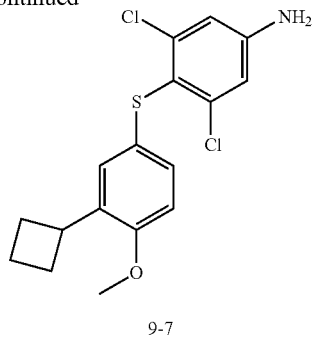

To a solution of 1,3-dichloro-2-(3-cyclobutyl-4-methoxy-phenyl) sulfanyl-5-nitro-benzene 9-6 (500 mg, 1.30 mmol), Fe (726.63 mg, 13.01 mmol), NH$_4$Cl (351.31 mg, 6.51 mmol) in EtOH (3 mL) and H$_2$O (3 mL) was stirred at 70° C. for 4 h. TLC (PE:EA=5:1) showed the reaction was completed. The reaction mixture was extracted with EtOAc (3×100 mL). The combined organic layer was washed with brine (100 ml) and dried over anhydrous Na$_2$SO$_4$. The reaction mixture was filtered and concentrated in vacuum to afford a residue. The residue was purified by silica gel chromatography (PE:EA=5:1) to afford 3,5-dichloro-4-(3-cyclobutyl-4-methoxy-phenyl) sulfanyl-aniline 9-7 (250 mg, 54% yield) as a yellow solid. LCMS: [M+H]$^+$=354.1/356.0.

Step 6: 9-8

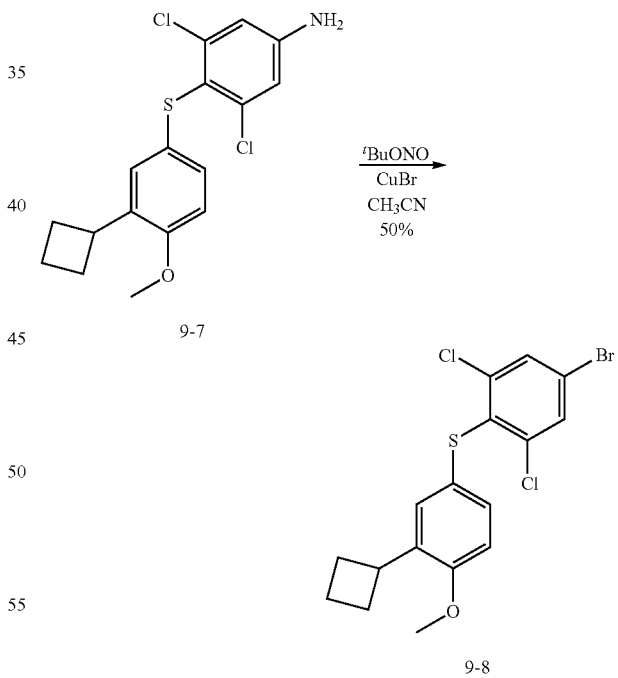

A mixture of $^t$BuONO (145.50 mg, 1.41 mmol) and CuBr (151.83 mg, 1.06 mmol) in CH$_3$CN (5 mL) was stirred for 15 minutes at 25° C. Then 3,5-dichloro-4-(3-cyclobutyl-4-methoxy-phenyl) sulfanyl-aniline 9-7 (250 mg, 705.63 umol) in CH$_3$CN (1 ml) was added to the mixture. The mixture was stirred at 25° C. for 20 h. LCMS showed the reaction was completed and TLC (PE:EtOAc=20:1) showed a new spot. The reaction mixture was poured into water (50 mL) and extracted with EtOAc (2×50 mL). The combined organic layer was dried over anhydrous Na$_2$SO$_4$. The reaction mixture was filtered and concentrated in vacuum to afford a residue. The residue was purified by silica gel chromatography (PE:EtOAc=20:1) to afford 5-bromo-1,3-dichloro-2-(3-cyclobutyl-4-methoxy-phenyl) sulfanyl-benzene 9-8 (150 mg, 50% yield) as a yellow oil.

Step 7: 9-9

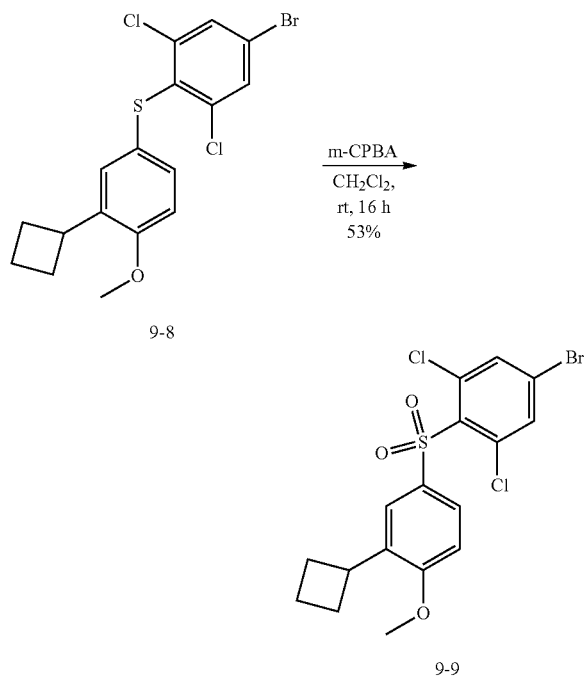

To a solution of 5-bromo-1,3-dichloro-2-(3-cyclobutyl-4-methoxy-phenyl) sulfanyl-benzene 9-8 (150 mg, 370.66 umol) in CH$_2$Cl$_2$ (3 mL) was added m-CPBA (159.38 mg, 926.65 umol) slowly at 25° C. Then the mixture was stirred at 25° C. for 16 h. TLC (PE:EtOAc=8:1) showed starting material was consumed and one new spot was detected. The mixture was quenched with NaHSO$_3$ (20 mL saturated solution) and extracted with EtOAc (2×20 mL). The combined organic layer was dried over anhydrous Na$_2$SO$_4$. The reaction mixture was filtered and concentrated in vacuum to afford a residue. The residue was purified by silica gel chromatography (PE:EtOAc=8:1) to afford 5-bromo-1,3-dichloro-2-(3-cyclobutyl-4-methoxy-phenyl) sulfonyl-benzene 9-9 (90 mg, 53% yield) as a yellow solid. LCMS: [M+H]$^+$=448.9/450.9.

Step 8: 9-10

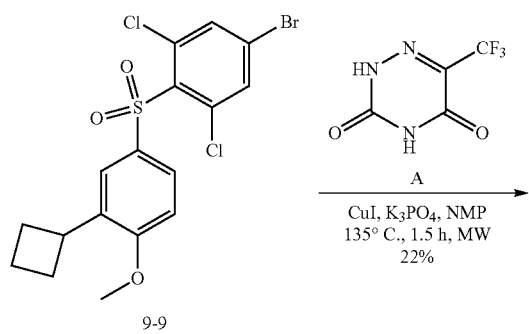

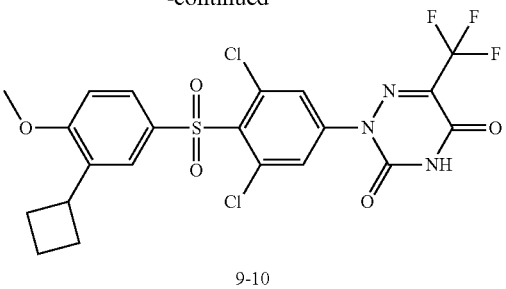

9-10

A solution of 5-bromo-1,3-dichloro-2-(3-cyclobutyl-4-methoxy-phenyl)sulfonyl-benzene 9-9 (55 mg, 122.18 umol), 6-(trifluoromethyl)-2H-1,2,4-triazine-3,5-dione Intermediate A (Example 1) (44.25 mg, 244.35 umol), (1R,2R)-cyclohexane-1,2-diamine (13.95 mg, 122.18 umol), CuI (46.54 mg, 244.35 umol) and K$_3$PO$_4$ (77.70 mg, 366.53 umol) in NMP (1.5 mL) under N$_2$ (g) was microwaved at 135° C. for 1.5 h. LCMS showed the reaction was completed. The reaction mixture was poured into water (20 mL) and extracted with EtOAc (2×20 mL). The combined organic layer was dried over anhydrous Na$_2$SO$_4$. The reaction mixture was filtered and concentrated in vacuum to afford a residue. The residue was purified by silica gel chromatography (CH$_2$Cl$_2$:MeOH=20:1) to afford 2-[3,5-dichloro-4-(3-cyclobutyl-4-methoxy-phenyl) sulfonyl-phenyl]-6-(trifluoromethyl)-1,2,4-triazine-3,5-dione 9-10 (15 mg, 22% yield) as a yellow oil. LCMS: [M+H]$^+$=550.0/551.9.

Step 9: Compound 9

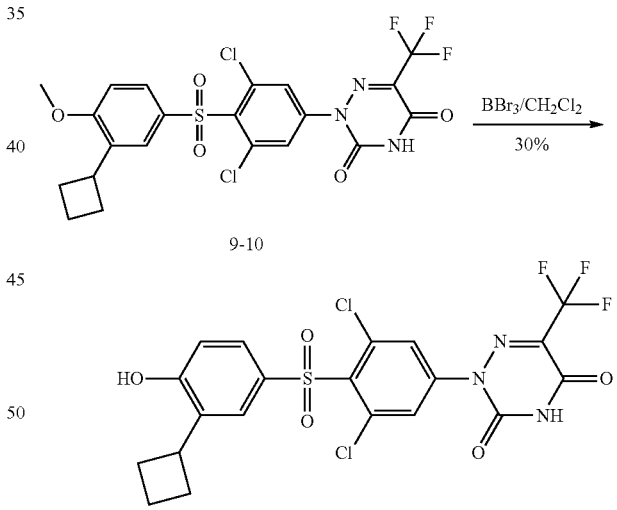

To a solution of 2-[3,5-dichloro-4-(3-cyclobutyl-4-methoxy-phenyl) sulfonyl-phenyl]-6-(trifluoromethyl)-1,2,4-triazine-3,5-dione 9-10 (15 mg, 27.26 umol) at 0° C. in CH$_2$Cl$_2$ (1 mL) was added BBr$_3$ (0.5 mL). The mixture was stirred at 0° C. for 2 h. LCMS showed the reaction was completed. The reaction mixture was poured into water (100 mL) and extracted with EtOAc (2×150 mL). The combined organic layer was dried over anhydrous Na$_2$SO$_4$. The reaction mixture was filtered and concentrated in vacuum to afford a residue. The residue was purified by Prep-HPLC (Chromatographic columns: Xbridge 5 u C18 150×19 mm, Mobile Phase: ACN—H₂O (0.05% NH₃), Gradient: 20-30) to afford 2-[3,5-dichloro-4-(3-cyclobutyl-4-hydroxy-phenyl) sulfonyl-phenyl]-6-(trifluoromethyl)-1,2,4-triazine-3,5-dione Compound 9 (4.5 mg, 30% yield) as a white solid. LCMS: [M+H]⁺=536.0/538.1. ¹H NMR (400 MHz, CD₃OD) δ 7.89 (s, 2H), 7.86 (d, J=2.0 Hz, 1H), 7.74 (dd, J=8.8, 2.4 Hz, 1H), 6.87 (d, J=8.4 Hz, 1H), 3.79-3.69 (m, 1H), 2.39-2.32 (m, 2H), 2.14-2.01 (m, 3H), 1.88-1.84 (m, 1H). ¹⁹F NMR (376 MHz, CD₃OD) δ−69.46 (s).
Example 12: Synthesis of Compound 10
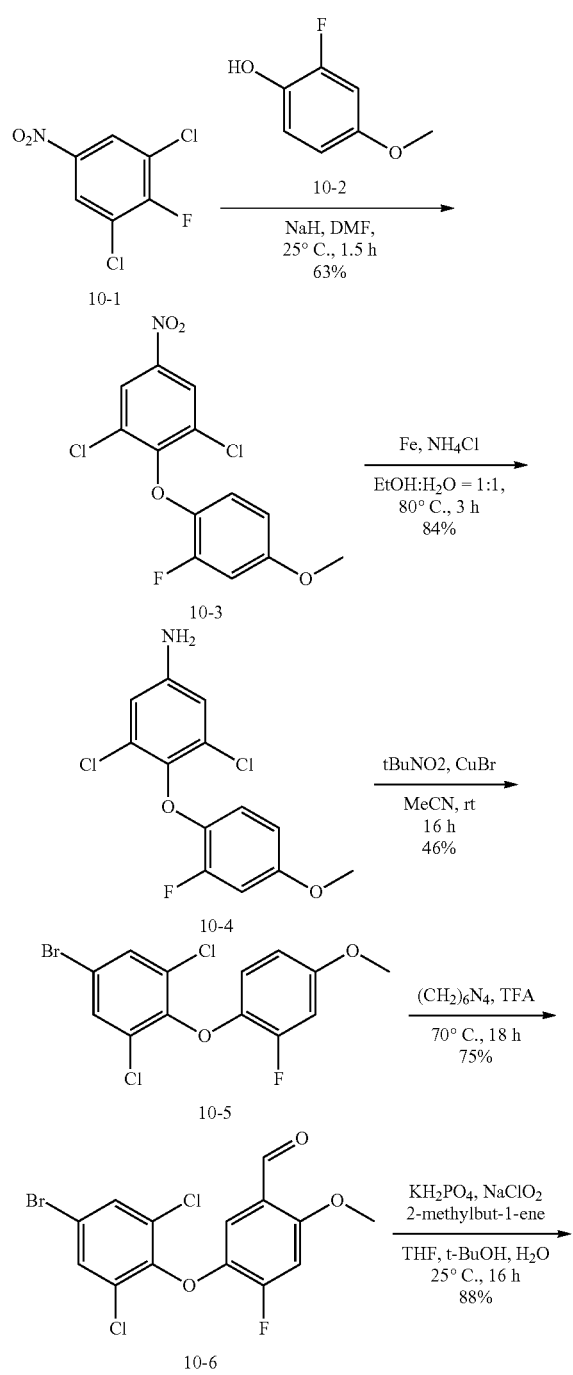
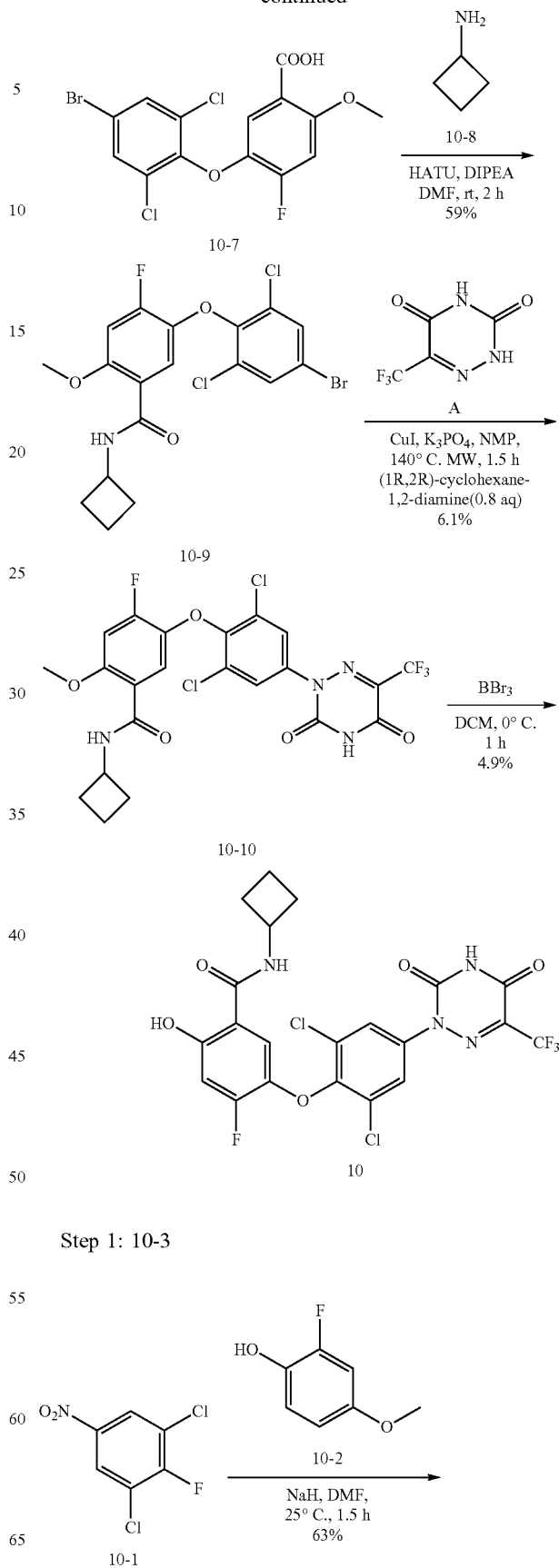
Step 1: 10-3

199

-continued

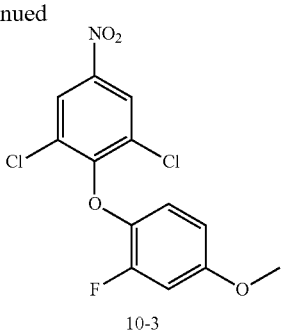

10-3

To a solution of 2-fluoro-4-methoxy-phenol 10-1 (2.0 g, 14.07 mmol) in DMF (20 mL) was added NaH (539.19 mg, 14.07 mmol, 60%) at 0° C. The mixture was stirred at 0° C. for 0.5 h and then 1,3-dichloro-2-fluoro-5-nitro-benzene 10-2 (2.95 g, 14.07 mmol) was added at 0° C. The mixture was stirred at 25° C. for 1.5 h. TLC showed starting material was consumed and a new spot was detected. The mixture was cooled to 0° C., quenched with $H_2O$ (100 mL) and extracted with EtOAc (2×100 mL). The organic layers were combined, dried over $Na_2SO_4$, filtered and the solvent was removed in vacuum to afford a residue. The residue was purified by silica gel column chromatography (eluent: PE:EtOAc=10:1) to give 1,3-dichloro-2-(2-fluoro-4-methoxy-phenoxy)-5-nitro-benzene 10-3 (3.1 g, 63% yield) as a yellow solid.

Step 2: 10-4

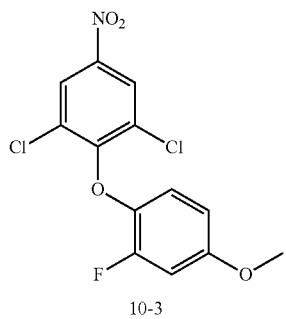

10-3

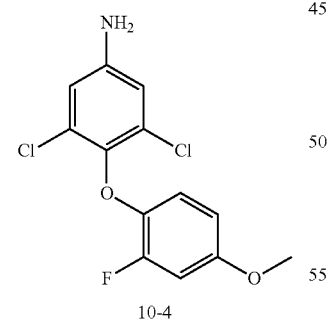

10-4

A mixture of 1,3-dichloro-2-(2-fluoro-4-methoxy-phenoxy)-5-nitro-benzene 10-3 (2.0 g, 6.02 mmol), ammonium chloride (1.61 g, 30.11 mmol, 1.05 mL) and Fe (3.36 g, 60.22 mmol, 427.87 uL) in EtOH (15 mL) and water (15 mL) was stirred at 80° C. for 3 h. TLC showed the reaction was completed. The mixture was filtered and the filtrate was extracted with EtOAc (3×13 mL). The combined organic layers were washed with brine (20 mL), dried over $Na_2SO_4$ and filtered. The filtrate was concentrated in vacuum to give

200

3,5-dichloro-4-(2-fluoro-4-methoxy-phenoxy) aniline 10-4 (1.7 g, 84% yield) as a yellow oil. LCMS [M+H]$^+$=302.0.

Step 3: 10-5

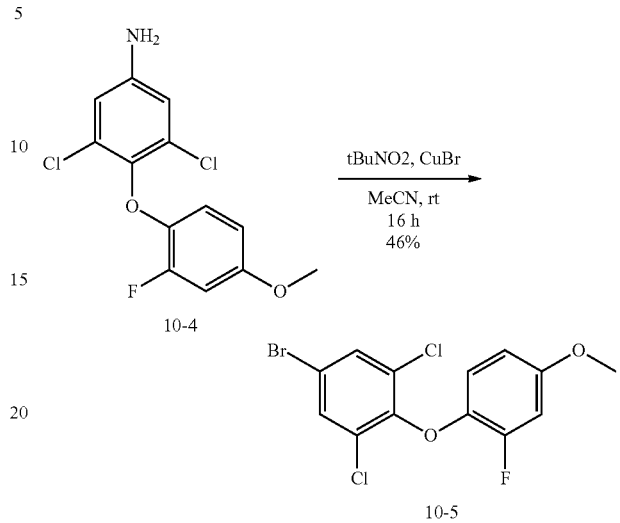

To a mixture of tert-butyl nitrite (1.16 g, 11.25 mmol, 1.34 mL) and cuprous bromide (1.21 g, 8.44 mmol) in MeCN (20 mL) was added 3,5-dichloro-4-(2-fluoro-4-methoxyphenoxy) aniline 10-4 (1.70 g, 5.62 mmol). The reaction was stirred at 25° C. for 16 h. TLC showed the reaction was completed. Water (13 mL) was added and the mixture was extracted with EtOAc (3×13 mL). The combined organic layers were washed with brine, dried over $Na_2SO_4$ and concentrated in vacuum. The residue was purified by flash chromatography (PE:EtOAc=3:1) to give 5-bromo-1,3-dichloro-2-(2-fluoro-4-methoxy-phenoxy) benzene 10-5 (1 g, 46% yield) as a white solid. LCMS [M+H]$^+$=365.0.

Step 4: 10-6

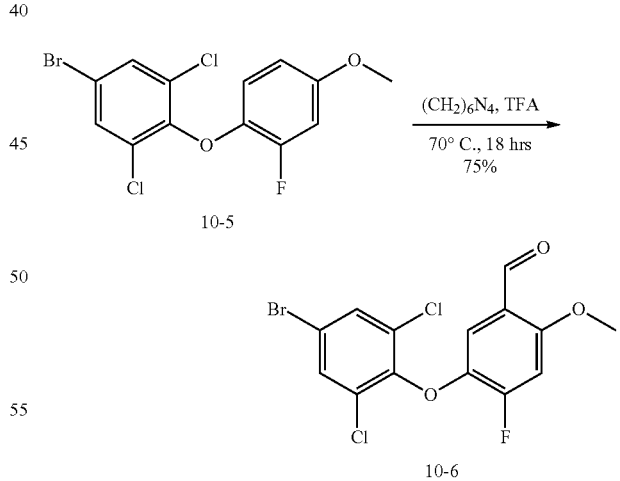

To a solution of 5-bromo-1,3-dichloro-2-(2-fluoro-4-methoxy-phenoxy) benzene 10-5 (1.0 g, 2.73 mmol) in TFA (10 mL) was added $(CH_2)_6N_4$ (574.52 mg, 4.10 mmol) at 0° C. The mixture was stirred at 70° C. for 18 h. TLC showed starting material was consumed and a new spot was detected. The mixture was cooled to 0° C. and quenched with $H_2O$ (20 mL) and extracted with EtOAc (2×20 mL). The organic solution was combined, dried with $Na_2SO_4$, filtered and the solvent was removed by vacuum to obtained a residue. The residue was purified by silica gel column chromatography (PE:EtOAc=5:1) to give 5-(4-bromo-2,6-dichloro-phenoxy)-4-fluoro-2-meth oxy-benzaldehyde 10-6 (900 mg, 75% yield) as a yellow solid.

Step 5:10-7

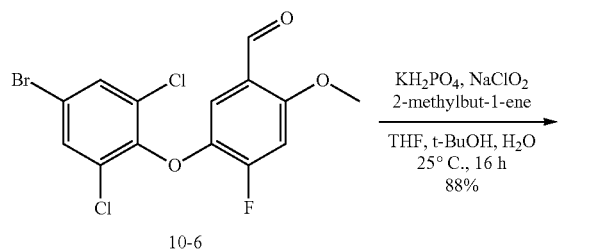

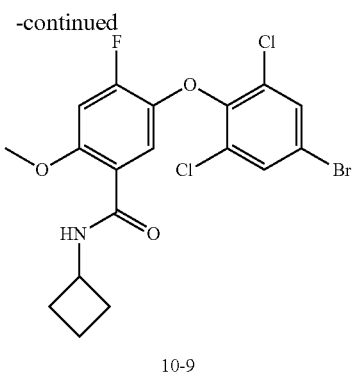

10-9

To a solution of 5-(4-bromo-2,6-dichloro-phenoxy)-4-fluoro-2-methoxy-benzoic acid 10-7 (480 mg, 1.17 mmol) in DMF (5 mL) was added DIPEA (302.60 mg, 2.34 mmol, 407.81 uL) and HATU (667.69 mg, 1.76 mmol) at 0° C. The mixture was stirred at 0° C. for 10 min and then cyclobutanamine 10-8 (124.89 mg, 1.76 mmol, 149.93 uL) was added dropwise at 0° C. The mixture was stirred at 25° C. for 2 h. LCMS showed starting material was consumed and target product was detected. The mixture was cooled to 0° C. and quenched with $H_2O$ (20 mL) and extracted with EtOAc (2×20 mL). The organic solution was combined, dried over $Na_2SO_4$, filtered and the solvent was removed in vacuum to obtain a residue. The residue was purified by silica gel column chromatography (PE:EtOAc=1:1) to give 5-(4-bromo-2,6-dichloro-phenoxy)-N-cyclobutyl-4-fluoro-2-methoxy-benzamide 10-9 (400 mg, 59% yield) as a yellow solid. LCMS $[M+H]^+$=462.0.

Step 7: 10-10

To a solution of 5-(4-bromo-2,6-dichloro-phenoxy)-4-fluoro-2-methoxy-benzaldehyde 10-6 (900 mg, 2.28 mmol) in 2-methylbut-1-ene (6 mL), t-BuOH (36 mL) and THF (12 mL) was added sodium chlorite (2.07 g, 22.84 mmol) in monopotassium phosphate (0.6 M, 30.46 mL) at 0° C. The mixture was stirred at 25° C. for 16 h. TLC showed starting material was consumed and new spots were detected. The mixture was cooled to 0° C. and quenched with $H_2O$ (20 mL) and extracted with EtOAc (2×20 mL). The organic layers were combined, dried over $Na_2SO_4$, filtered and solvent was removed in vacuum to obtained a residue. The residue was purified by silica gel column chromatography (PE:EtOAc=2:1) to give 5-(4-bromo-2,6-dichloro-phenoxy)-4-fluoro-2-methoxy-benzoic acid 10-7 (920 mg, 88% yield) as a yellow solid.

Step 6: 10-9

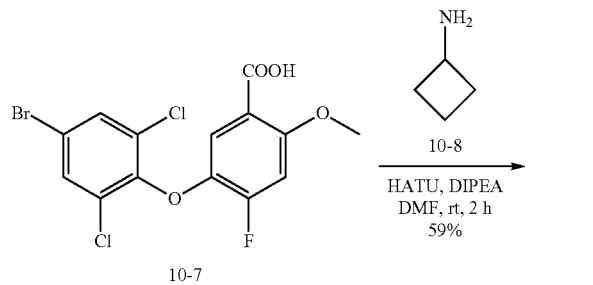

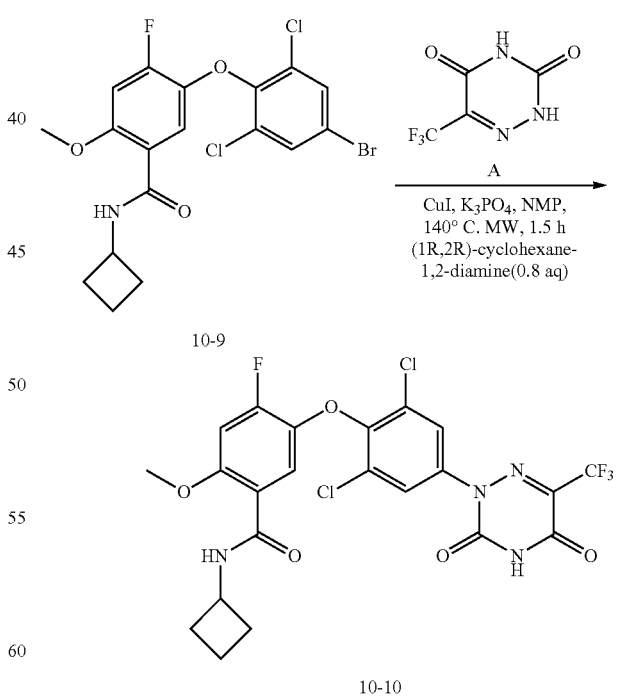

A mixture of 5-(4-bromo-2,6-dichloro-phenoxy)-N-cyclobutyl-4-fluoro-2-methoxy-benzamide 10-9 (27 mg, 58.30 umol), 6-(trifluoromethyl)-1,2,4-triazine-3,5(2H,4H)-dione A (31.67 mg, 174.90 umol), cuprous iodide (22.21 mg, 116.60 umol), potassium phosphate (37.13 mg, 174.90 umol) and (1R,2R)-cyclohexane-1,2-diamine (5.33 mg, 46.64 umol) in NMP (2 mL) was stirred at 140° C. under MW for 1.5 h. LCMS showed starting material was consumed and target product was detected. The mixture was cooled to 0° C. and quenched with H₂O (20 mL) and extracted with EtOAc (2×20 mL). The organic solution was combined, dried over Na₂SO₄ and filtered and the solvent was removed in vacuum to obtained a residue. The residue was purified by silica gel column chromatography (DCM: MeOH=10:1) to give N-cyclobutyl-5-(2,6-dichloro-4-(3,5-dioxo-6-(trifluoromethyl)-4,5-dihydro-1,2,4-triazin-2(3H)-yl) phenoxy)-4-fluoro-2-methoxybenzamide 10-10 (2 mg, 6.1% yield) as a white solid. LCMS [M+H]⁺=563.0.

Step 8: Compound 10

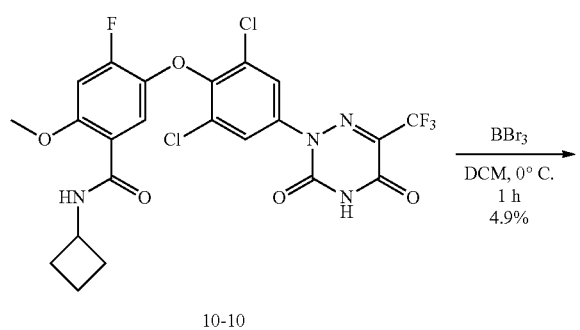

To a solution of N-cyclobutyl-5-(2,6-dichloro-4-(3,5-dioxo-6-(trifluoromethyl)-2,5-dihydro-1,2,4-triazin-4(3H)-yl) phenoxy)-4-fluoro-2-methoxybenzamide 10-10 (2.0 mg, 3.55 umol) in DCM (1 mL) was added boron tribromide (1 M, 7.1 uL) at 0° C., the mixture was stirred at 0° C. for 1 h. LCMS showed starting material was consumed and the target product was detected. The mixture was cooled to 0° C. and quenched with H₂O (0.5 mL). The mixture was filtered. The solvent was removed by vacuum to obtain a residue. The residue was purified by prep-HPLC (column: Gemini-C18; 100×21.2 mm, 5 um; mobile phase: MeCN—H₂O (0.05% NH₃); Gradient: 45-55) to give N-cyclobutyl-5-[2, 6-dichloro-4-[3,5-dioxo-6-(trifluoromethyl)-1,2,4-triazin-2-yl]phenoxy]-4-fluoro-2-hydr oxy-benzamide Compound 10 (0.5 mg, 4.9% yield) as a white solid.

LCMS [M+H]⁺=549.0. ¹H NMR (400 MHz, DMSO-d₆) δ 12.72 (s, 1H), 8.79 (d, J=2.8 Hz, 1H), 7.81 (s, 2H), 7.35 (d, J=9.6 Hz, 1H), 6.97 (d, J=12.4 Hz, 1H), 4.38-4.27 (m, 1H), 2.24-2.14 (m, 2H), 2.07-1.96 (m, 2H), 1.70-1.62 (m, 2H).

Example 13: Synthesis of Compound 11

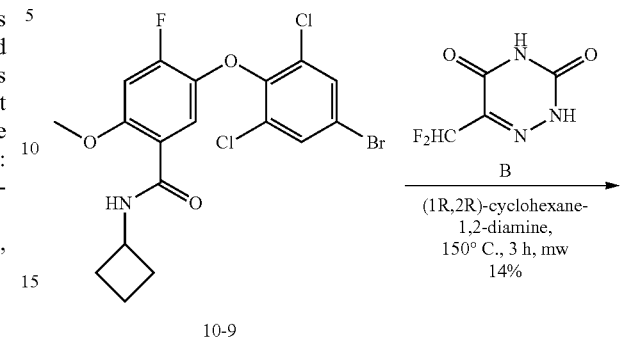

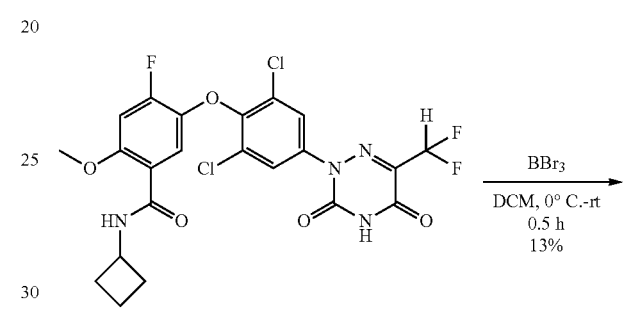

Step 1: 11-1

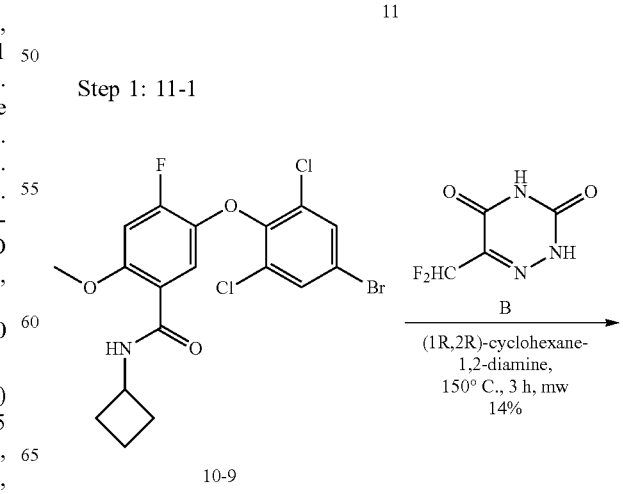

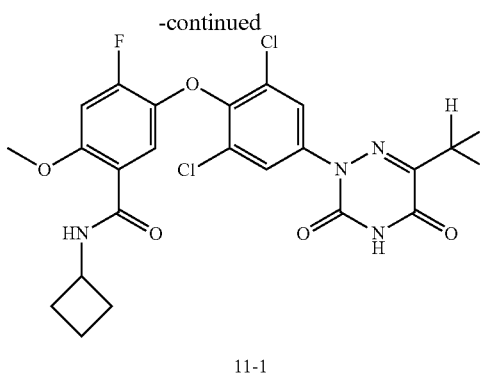

11-1

A mixture of 5-(4-bromo-2,6-dichloro-phenoxy)-N-cyclobutyl-4-fluoro-2-methoxy-benzamide 10-9 (see synthesis of Compound 10) (50 mg, 107.96 umol), 6-(difluoromethyl)-2H-1,2,4-triazine-3,5-dione Intermediate B (Example 2) (35.21 mg, 215.92 umol), (1R,2R)-cyclohexane-1,2-diamine (7.40 mg, 64.78 umol), potassium phosphate (68.75 mg, 323.89 umol) and CuI (41.12 mg, 215.92 umol) in NMP (1.5 mL) was stirred at 150° C. for 3 h under microwave. LCMS showed the reaction was completed. Water (15 mL) was added and the mixture was extracted with EtOAc (3×13 mL). The combined organic layers were washed with brine, dried over Na$_2$SO$_4$ and concentrated in vacuum. The residue was purified by flash chromatography (eluent: DCM:MeOH=10:1) to give N-cyclobutyl-5-[2,6-dichloro-4-[6-(difluoromethyl)-3,5-dioxo-1,2,4-triazin-2-yl] phenoxy]-4-fluoro-2-methoxy-benzamide 11-1 (10 mg, 14% yield) as a yellow solid. LCMS: [M+H]$^+$=545.0.

Step 2: Compound 11

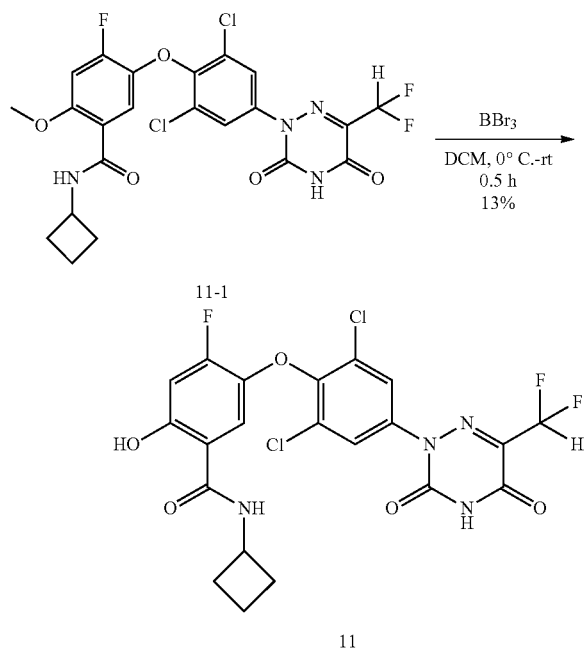

To a solution of N-cyclobutyl-5-[2,6-dichloro-4-[6-(difluoromethyl)-3,5-dioxo-1,2,4-triazin-2-yl]phenoxy]-4-fluoro-2-methoxy-benzamide 11-1 (10 mg, 18.34 umol) in DCM (1 mL) was added boron tribromide CH$_2$Cl$_2$ solution (1 M, 183.39 uL) at 0° C. The mixture was stirred at 0° C. for 0.5 h. LCMS showed the starting material was consumed and the target product was detected. The reaction was quenched by water and the residue was taken up in DCM (3×5 mL). The organic layer was washed with water (3×5 ml), dried over MgSO$_4$, filtered and the solvents were removed under reduced pressure. The residue was purified by prep-HPLC (Chromatographic columns: Kromasil-C18 100×21.2 mm 5 um Mobile Phase: MeCN—H$_2$O (0.05% NH$_3$) Gradient: 16-26) to give N-cyclobutyl-5-[2,6-dichloro-4-[6-(difluoromethyl)-3,5-dioxo-1,2,4-triazin-2-yl] phenoxy]-4-fluoro-2-hydroxy-benzamide Compound 11 (1.3 mg, 13% yield) as a white solid. LCMS [M+H]$^+$=531.0. $^1$H NMR: (400 MHz, CD$_3$OD) δ 7.80 (s, 2H), 7.24 (d, J=9.2 Hz, 1H), 6.84-6.57 (m, 2H), 4.45-4.37 (m, 1H), 2.35-2.23 (m, 2H), 2.07-1.98 (m, 2H), 1.79-1.68 (m, 2H).

Example 14: Synthesis of Compound 12

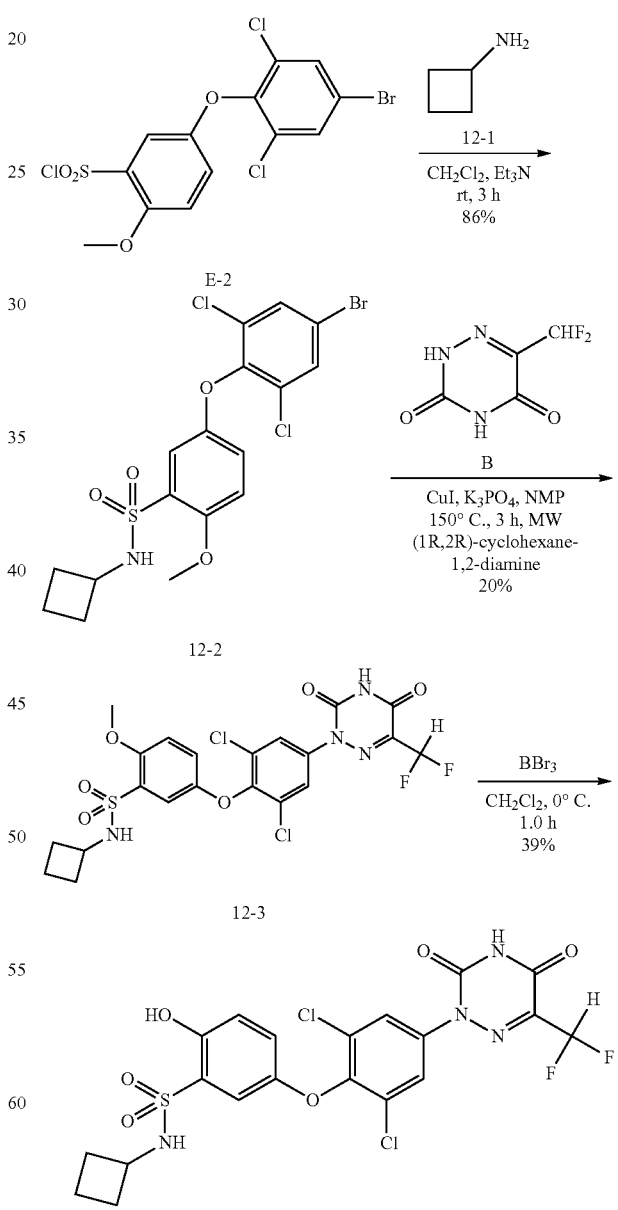

Step 1: 12-2

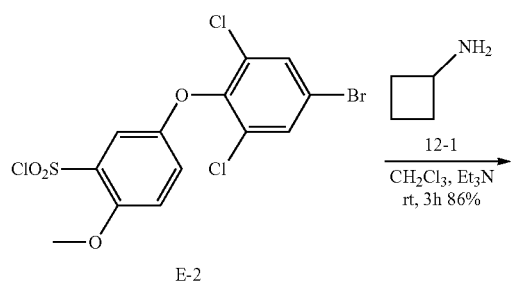

To a solution of 5-(4-bromo-2,6-dichloro-phenoxy)-2-methoxy-benzenesulfonyl chloride E-2 (Example 5) (100 mg, 223.95 umol) in dichloromethane (10 mL) was added triethylamine (45.32 mg, 447.90 umol, 62.43 uL) and cyclobutanamine 12-1 (31.85 mg, 447.90 umol, 38.24 uL) at 0° C. The reaction mixture was stirred at rt for 3 h. LC-MS showed the reaction was completed. The reaction mixture was poured into water (50 mL) and extracted with $CH_2Cl_2$ (2×20 mL). The combined organic layer was washed with brine (20 mL), dried over anhydrous $Na_2SO_4$ and filtered. The filtrate was concentrated in vacuum to afford 5-(4-bromo-2,6-dichloro-phenoxy)-N-cyclobutyl-2-methoxy-benzenesulfonamide 12-2 (93 mg, 86% yield) as a white solid. LCMS: $[M+H]^+$=482.0/483.9.

Step 2: 12-3

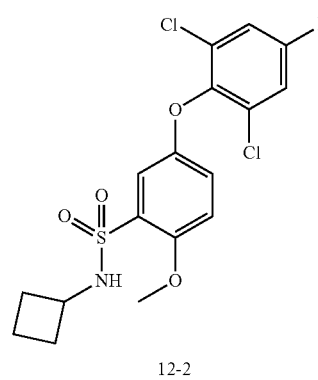

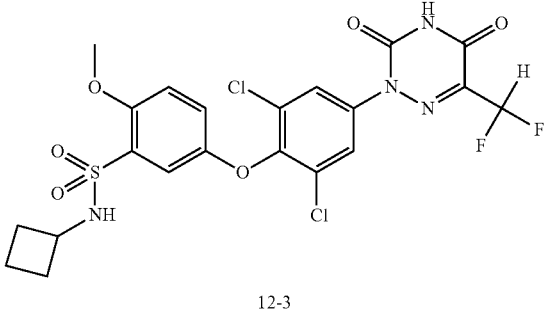

A mixture of 5-(4-bromo-2,6-dichloro-phenoxy)-N-cyclobutyl-2-methoxy-benzenesulfonamide 12-2 (30 mg, 62.35 umol), 6-(trifluoromethyl)-1,2,4-triazine-3,5(2H,4H)-dione Intermediate B (Example 2) (20.33 mg, 124.69 umol), copper(I) iodide (23.75 mg, 124.69 umol), potassium phosphate (39.70 mg, 187.04 umol) and (1R,2R)-cyclohexane-1,2-diamine (7.12 mg, 62.35 umol) in NMP (2 mL) was stirred at 150° C. for 3 h under microwave. LC-MS showed the reaction was completed. The reaction mixture was poured into water (50 mL) and extracted with EtOAc (3×20 mL). The combined organic layer was washed with brine (20 mL), dried over anhydrous $Na_2SO_4$ and filtered. The filtrate was concentrated in vacuum to afford a residue. The residue was purified by TLC ($CH_2Cl_2$:MeOH=10:1) to afford N-cyclobutyl-5-[2,6-dichloro-4-[6-(difluoromethyl)-3,5-dioxo-1,2,4-triazin-2-yl]phenoxy]-2-methoxy-benzenesulfonamide 12-3 (7 mg, 20% yield) as a light-yellow solid. LCMS: $[M+H]^+$=563.1.

Step 3: Compound 12

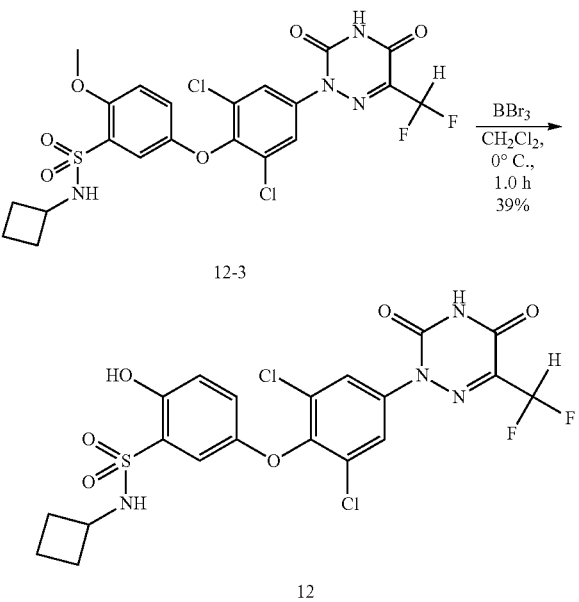

To a solution of N-cyclobutyl-5-[2,6-dichloro-4-[6-(difluoromethyl)-3,5-dioxo-1,2,4-triazin-2-yl]phenoxy]-2-methoxy-benzenesulfonamide 12-3 (7 mg, 12.43 umol) in $CH_2Cl_2$ (2 mL) was added dropwise boron tribromide (1 M, 124.25 uL) at 0° C. The reaction mixture was stirred at 0° C. for 1.0 h. LC-MS showed the reaction was completed. The reaction mixture was poured into sat. $NaHCO_3$ (50 mL) and extracted with CH$_2$Cl$_2$ (2×20 mL). The combined organic layer was washed with brine (20 mL), dried over anhydrous Na$_2$SO$_4$ and filtered. The filtrate was concentrated in vacuum to afford a residue. The residue was purified by prep-HPLC (Chromatographic columns: Kromasil-C18 100×21.2 mm 5 um Mobile Phase: MeCN—H$_2$O (0.05% NH$_3$) Gradient: 15-25) to afford N-cyclobutyl-5-[2,6-dichloro-4-[6-(difluoromethyl)-3,5-dioxo-1,2,4-triazin-2-yl]phenoxy]-2-hydroxy-benzenesulfonamide Compound 12 (2.7 mg, 39% yield) as a white solid. LCMS: [M+H]$^+$=549.0. $^1$H NMR (400 MHz, CD$_3$OD) δ 7.81 (s, 2H), 7.10-7.04 (m, 2H), 6.95 (d, J=8.8 Hz, 1H), 6.70 (t, J=53.2 Hz, 1H), 3.73-3.65 (m, 1H), 2.01-1.94 (m, 2H), 1.91-1.81 (m, 2H), 1.57-1.49 (m, 2H). $^{19}$F NMR (376 MHz, CD$_3$OD) δ−124.2 (s, 2F).

The compounds of Formula (I') or (I) in Table 4 below were made according to Example 14 of Compound 12.

TABLE 4

| Cmpd No. | LC-MS, $^1$H and $^{19}$F-NMR data |
|---|---|
| 13 | LCMS: [M + H]$^+$ = 508.9. $^1$H NMR (400 MHz, CD$_3$OD) δ 7.81 (s, 2H), 7.15 (d, J = 3.2 Hz, 1H), 7.04 (dd, J = 8.8, 3.2 Hz, 1H), 6.97 (d, J = 8.8 Hz, 1H), 6.70 (t, J = 53.2 Hz, 1H), 2.52 (s, 3H). $^{19}$F NMR (376 MHz, CD$_3$OD) δ-124.2 (s, 2F). |
| 14 | LCMS: [M + H]$^+$ = 535.0. $^1$H NMR (400 MHz, CD$_3$OD) δ 7.81 (s, 2H), 7.15 (d, J = 3.2 Hz, 1H), 7.09 (dd, J = 9.2, 3.2 Hz, 1H), 6.98 (d, J = 9.2 Hz, 1H), 6.70 (t, J = 52.8 Hz, 1H), 2.20-2.15 (m, 1H), 0.51-0.49 (m, 4H). $^{19}$F NMR (376 MHz, CD$_3$OD) δ-124.2 (s, 2F). |
| 15 | LCMS: [M + H] $^+$ = 565.0. $^1$H NMR (400 MHz, CD$_3$OD) δ 7.82 (s, 2H), 7.07-7.10 (m, 2H), 7.01 (d, J = 9.6 Hz, 1H), 6.71 (t, J = 53.1 Hz, 1H), 3.70-3.65 (m, 4H), 3.16-3.13 (m, 4H). $^{19}$F NMR (376 MHz, CD$_3$OD) δ-124.2 (s, 2F). |
| 16 | LCMS: [M + H]$^+$ = 579 $^1$H NMR (400 MHz, CD$_3$OD) δ 7.82 (s, 2H), 7.05-7.07 (m, 2H), 6.98 (dd, J = 8, 1.6 Hz, 1H), 6.69 (t, J = 53.3 Hz, 1H), 3.72-3.67 (m, 1H), 3.48-3.51 (m, 2H), 2.93-2.99 (m, 2H), 1.82-1.90 (m, 2H), 1.58-1.48 (m, 2H). $^{19}$F NMR (376 MHz, CD$_3$OD) δ-123.9 (s, 2F). |
| 17 | LCMS: [M + H] $^+$ = 560.0. $^1$H NMR (400 MHz, CD$_3$OD) δ 7.82 (s, 2H), 7.19 (d, J = 2.8 Hz, 1H), 7.10 (dd, J = 8.8, 2.8 Hz, 1H), 7.00 (d, J = 8.8 Hz, 1H), 6.71 (t, J = 52.8 Hz, 1H), 1.40-1.31 (m, 4H). $^{19}$F NMR (376 MHz, CD$_3$OD) δ-124.2 (s, 2F). |

Example 15: Synthesis of Compound 18

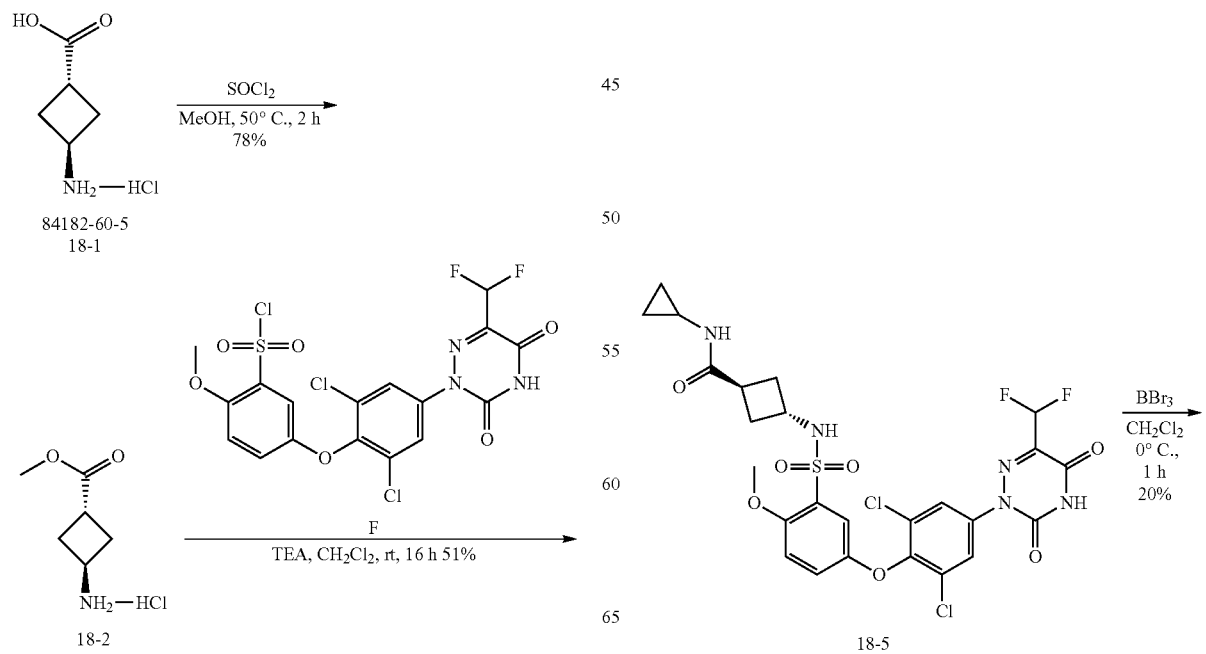

-continued

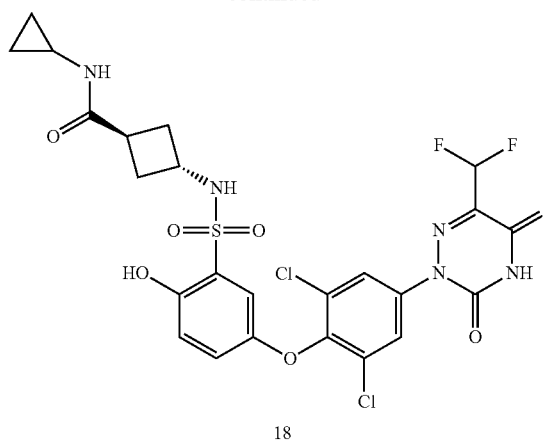

18

Step 1: 18-2

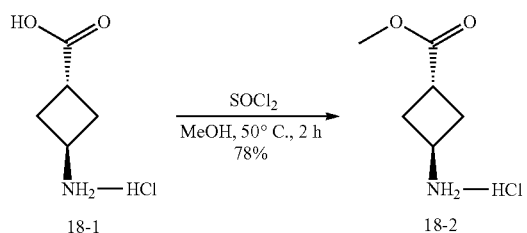

To a solution of 3-aminocyclobutanecarboxylic acid; hydrochloride 18-1 (0.3 g, 1.98 mmol) in MeOH (5 mL) was added thionyl chloride (1.18 g, 9.90 mmol) slowly at 0° C. The mixture was stirred at 50° C. for 2 h. LCMS showed the product was formed. The mixture was concentrated to give methyl 3-aminocyclobutanecarboxylate 18-2 (200 mg, 78% yield) as a white solid. LCMS: [M+H]$^+$=130.2

Step 2: 18-3

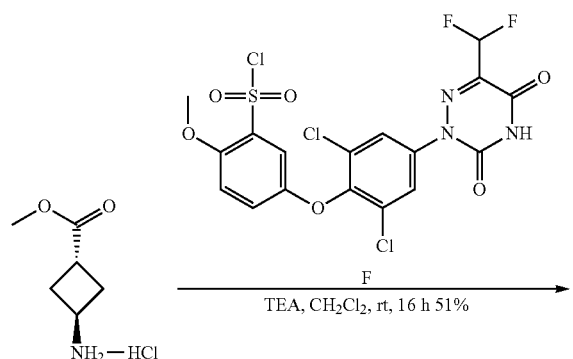

-continued

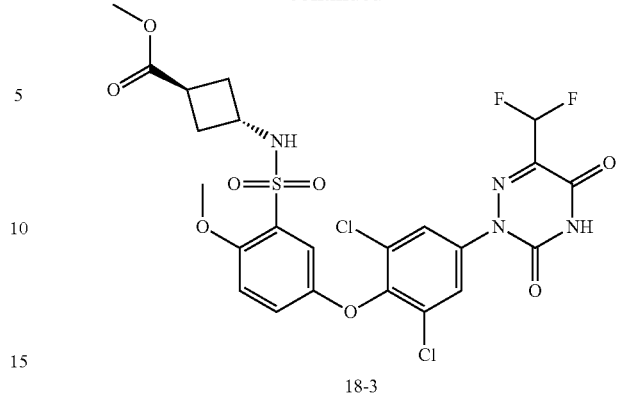

18-3

A solution of methyl 3-aminocyclobutanecarboxylate 18-2 (36.64 mg, 283.72 umol), 5-[2,6-dichloro-4-[6-(difluoromethyl)-3,5-dioxo-1,2,4-triazin-2-yl]phenoxy]-2-methoxy-benzenesulfonyl chloride F (50 mg, 94.57 umol) and TEA (28.71 mg, 283.72 umol) in CH$_2$Cl$_2$ (2 mL) was stirred at 25° C. for 16 h. LCMS showed the product was formed. The mixture was added water (20 mL). The aqueous solution was extracted with EtOAc (3×50 mL). The combined organic layer was washed with brine (50 mL), dried over Na$_2$SO$_4$ and concentrated in vacuum. The residue was purified by Prep-TLC (CH$_2$Cl$_2$:CH$_3$OH=15:1) to give methyl 3-[[5-[2,6-dichloro-4-[6-(difluoromethyl)-3,5-dioxo-1,2,4-triazin-2-yl] phenoxy]-2-methoxy-phenyl]sulfonyl amino] cyclobutene carboxylate 18-3 (30 mg, 51% yield) as a yellow solid. LCMS: [M+H]$^+$=621.1.

Step 3: 18-5

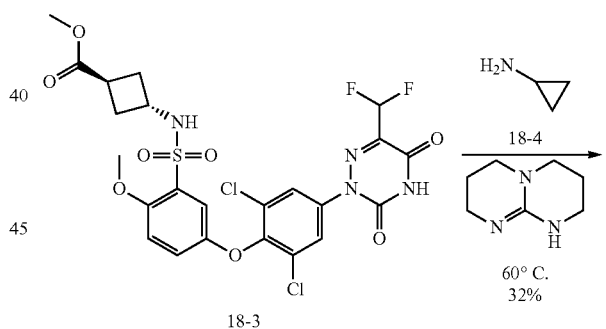

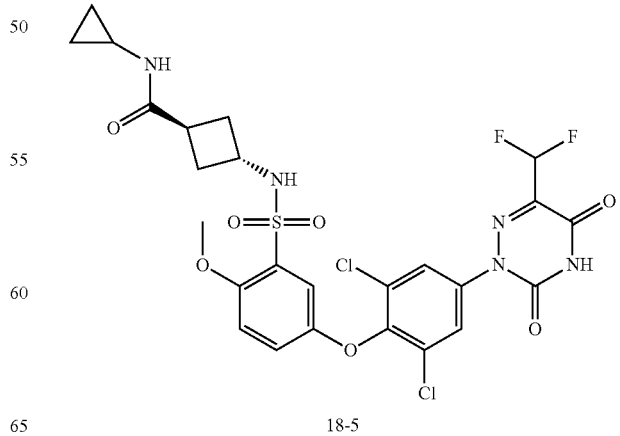

18-5

A mixture of methyl 3-[[5-[2,6-dichloro-4-[6-(difluoromethyl)-3,5-dioxo-1,2,4-triazin-2-yl]phenoxy]-2-[(4-methoxyphenyl)methoxy]phenyl]sulfonylamino]cyclobutanecarboxylate 18-3 (30 mg, 41.24 umol), 3,4,6,7,8,9-hexahydro-2H-pyrimido[1,2-a]pyrimidine (5.74 mg, 41.24 umol) and cyclopropane amine 18-4 (1 mL) in a sealed tube was stirred at 60° C. for 16 h. LCMS showed the reaction was completed. The solution was concentrated by vacuum. The residue was purified by prep-TLC (eluent: EtOAc: PE=1:1) to give N-cyclopropyl-3-[[5-[2,6-dichloro-4-[6-(difluoromethyl)-3,5-dioxo-1,2,4-triazin-2-yl]phenoxy]-2-[(4-methoxyphenyl)methoxy]phenyl]sulfonylamino]cyclobutanecarboxamide 18-5 (10 mg, 32% yield) as a yellow oil. LCMS: [M+H]$^+$=646.1.

Step 4: Compound 18

To a solution of N-[3-(cyclopropane carbonyl) cyclobutyl]-5-[2,6-dichloro-4-[6-(difluoromethyl)-3,5-dioxo-1,2,4-triazin-2-yl] phenoxy]-2-methoxy-benzenesulfonamide 18-5 (10.29 mg, 16.30 umol) in $CH_2Cl_2$ (2 mL) was added $BBr_3$ (886.29 mg, 3.55 mmol) slowly at 0° C. The mixture was stirred at 0° C. for 1 h. LCMS showed the product was formed. The reaction mixture was poured into water and extracted with EtOAc (3×50 mL). The combined organic layer was dried over anhydrous $Na_2SO_4$, filtered and concentrated in vacuum. The residue was purified by Prep-HPLC (Kromasil 100-5 C18 5 um 100×21.5 mm, Mobile Phase: MeCN—$H_2O$ (0.1% F A), Gradient: 50-60) to afford N-[3-(cyclopropane carbonyl) cyclobutyl]-5-[2,6-dichloro-4-[6-(difluoromethyl)-3,5-dioxo-1,2,4-triazin-2-yl] phenoxy]-2-hydroxy-benzenesulfonamide Compound 18 (2.1 mg, 20% yield) as a white solid. LCMS: [M+H]632.0. $^1$H NMR (400 MHz, $CD_3OD$) δ 7.72 (s, 2H), 7.01 (d, J=3.2 Hz, 1H), 6.95 (dd, J=8.8, 3.2 Hz, 1H), 6.85 (d, J=8.8 Hz, 1H), 6.61 (t, J=52.8 Hz, 1H), 3.91-3.87 (m, 1H), 2.66-2.60 (m, 1H), 2.53-2.47 (m, 1H), 2.17-2.08 (m, 2H), 2.08-1.97 (m, 2H), 0.60-0.55 (m, 2H), 0.36-0.27 (m, 2H). $^{19}$F NMR (376 MHz, $CD_3OD$) δ−124.2 (s, 2F).

Example 16: Synthesis of Compound 19

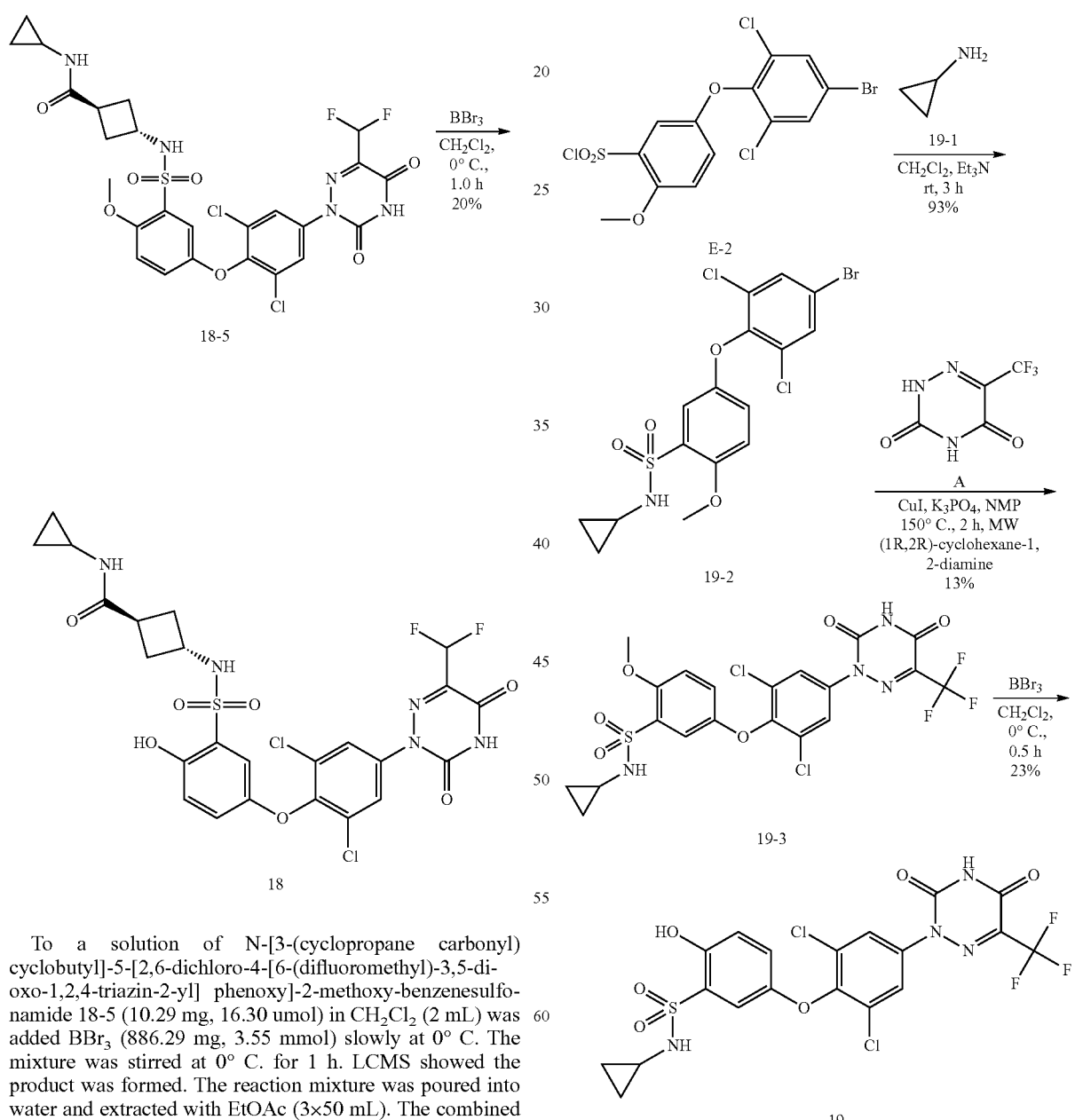

Step 1: 19-2

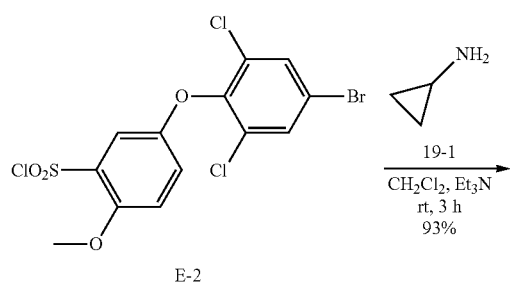

To a solution of 5-(4-bromo-2,6-dichloro-phenoxy)-2-methoxy-benzenesulfonyl chloride E-2 (Example 5) (250 mg, 559.88 umol) in CH$_2$Cl$_2$ (10 mL) was added triethylamine (113.31 mg, 1.12 mmol, 156.07 uL) and cyclopropanamine 19-1 (63.93 mg, 1.12 mmol, 77.59 uL) at 0° C. The reaction mixture was stirred at rt for 3 h. LC-MS showed the reaction was completed. The reaction mixture was poured into water (50 mL) and extracted with CH$_2$Cl$_2$ (2×20 mL). The combined organic layer was washed with brine (20 mL), dried over anhydrous Na$_2$SO$_4$ and filtered. The filtrate was concentrated in vacuum to afford 5-(4-bromo-2,6-dichloro-phenoxy)-N-cyclopropyl-2-methoxy-benzenesulfonamide 19-2 (244 mg, 93% yield) as a white solid. LCMS: [M+H]$^+$=467.9/469.9.

Step 2: 19-3

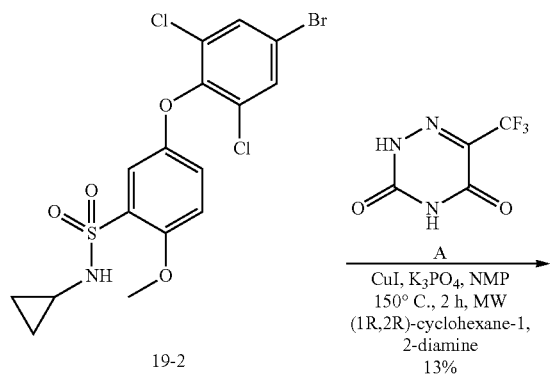

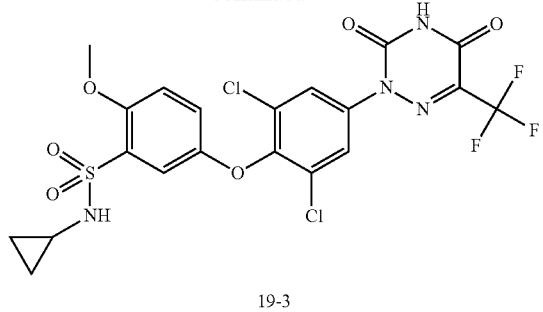

A mixture of 5-(4-bromo-2,6-dichloro-phenoxy)-N-cyclopropyl-2-methoxy-benzenesulfonamide 19-2 (50 mg, 107.03 umol), 6-(trifluoromethyl)-2H-1,2,4-triazine-3,5-dione Intermediate A (Example 1) (38.76 mg, 214.06 umol), (1R,2R)-cyclohexane-1,2-diamine (12.22 mg, 107.03 umol), tripotassium; phosphate (68.16 mg, 321.09 umol) and copper iodide (40.77 mg, 214.06 umol) in NMP (1 mL) was stirred at 150° C. for 2 h under microwave. LC-MS showed the reaction was completed. The reaction mixture was poured into water (50 mL) and extracted with EtOAc (3×20 mL). The combined organic layer was washed with brine (20 mL), dried over anhydrous Na$_2$SO$_4$ and filtered. The filtrate was concentrated in vacuum to afford a residue. The residue was purified by Prep-TLC (CH$_2$Cl$_2$:MeOH=10:1) to afford N-cyclopropyl-5-[2,6-dichloro-4-[3,5-dioxo-6-(trifluoromethyl)-1,2,4-triazin-2-yl]phenoxy]-2-methoxy-benzenesulfonamide 19-3 (8 mg, 13% yield) as a light-yellow solid. LCMS: [M+H]$^+$=567.0.

Step 3: Compound 19

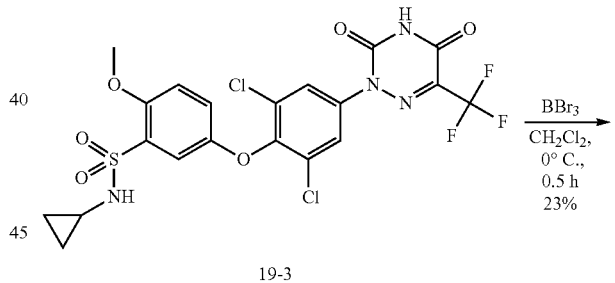

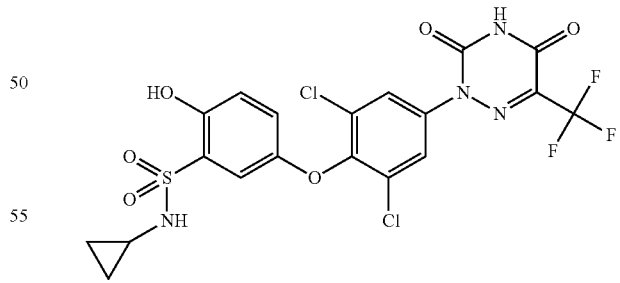

To a solution of N-cyclopropyl-5-[2,6-dichloro-4-[3,5-dioxo-6-(trifluoromethyl)-1,2,4-triazin-2-yl]phenoxy]-2-methoxy-benzenesulfonamide 19-3 (8 mg, 14.10 umol) in CH$_2$Cl$_2$ (1 mL) was added boron tribromide (1 M, 141.01 uL) at 0° C. The reaction mixture was stirred at 0° C. for 0.5 h. LC-MS showed the reaction was completed. The reaction mixture was poured into sat. NaHCO$_3$ (50 mL) and extracted with CH$_2$Cl$_2$ (2×20 mL). The combined organic layer was washed with brine (20 mL), dried over anhydrous Na$_2$SO$_4$ and filtered. The filtrate was concentrated in vacuum to afford a residue. The residue was purified by prep-HPLC (Chromatographic columns: Viridis Silica OBD, Mobile Phase: MeCN—H$_2$O (0.05% NH$_3$)) to afford N-cyclopropyl-5-[2,6-dichloro-4-[3,5-dioxo-6-(trifluoromethyl)-1,2,4-triazin-2-yl]phenoxy]-2-hydroxy-benzenesulfonamide Compound 19 (1.8 mg, 23% yield) as a white solid. LCMS: [M+H]$^+$=553.2. $^1$H NMR (400 MHz, CD$_3$OD) δ 7.79 (s, 2H), 7.15 (d, J=3.2 Hz, 1H), 7.08 (dd, J=9.2, 3.2 Hz, 1H), 6.98 (d, J=9.2 Hz, 1H), 2.20-2.15 (m, 1H), 0.52-0.50 (m, 4H). $^{19}$F NMR (376 MHz, CD$_3$OD) δ−69.3 (s, 3F).

The compounds of Formula (I') or (I) in Table 5 below were made according to Example 16 of Compound 19.

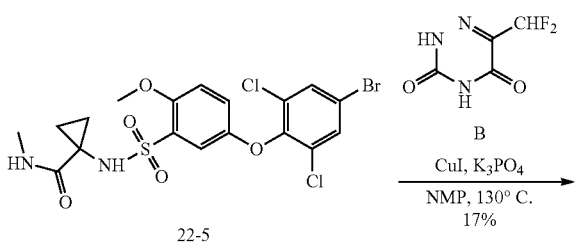

TABLE 5

| Cmpd No. | LC-MS, $^1$H and $^{19}$F-NMR data |
|---|---|
| 20 | LCMS: [M + H]$^+$ = 526.9. $^1$H NMR (400 MHz, CD$_3$OD) δ 7.78 (s, 2H), 7.19 (d, J = 3.2 Hz, 1H), 7.01 (dd, J = 8.8, 3.2 Hz, 1H), 6.95 (d, J = 8.8 Hz, 1H), 2.52 (s, 3H).$^{19}$F NMR (376 MHz, CD$_3$OD) δ-69.4 (s, 3F). |
| 21 | LCMS: [M + H]$^+$ = 617.0. $^1$H NMR (400 MHz, CD$_3$OD) δ 7.78 (s, 2H), 7.21 (d, J = 2.8 Hz, 1H), 7.04 (dd, J = 8.8, 3.2 Hz, 1H), 6.97 (d, J = 9.2 Hz, 1H), 3.40-3.29 (m, 2H), 3.07-2.99 (m, 1H), 2.68-2.65 (m, 1H), 2.05-1.97 (m, 2H), 1.31-1.27 (m, 2H). $^{19}$F NMR (376 MHz, CD$_3$OD) δ-69.3 (s, 3F), −100.3 (s, 1F), −103.4 (s, 1F). |

Example 17: Synthesis of Compound 22

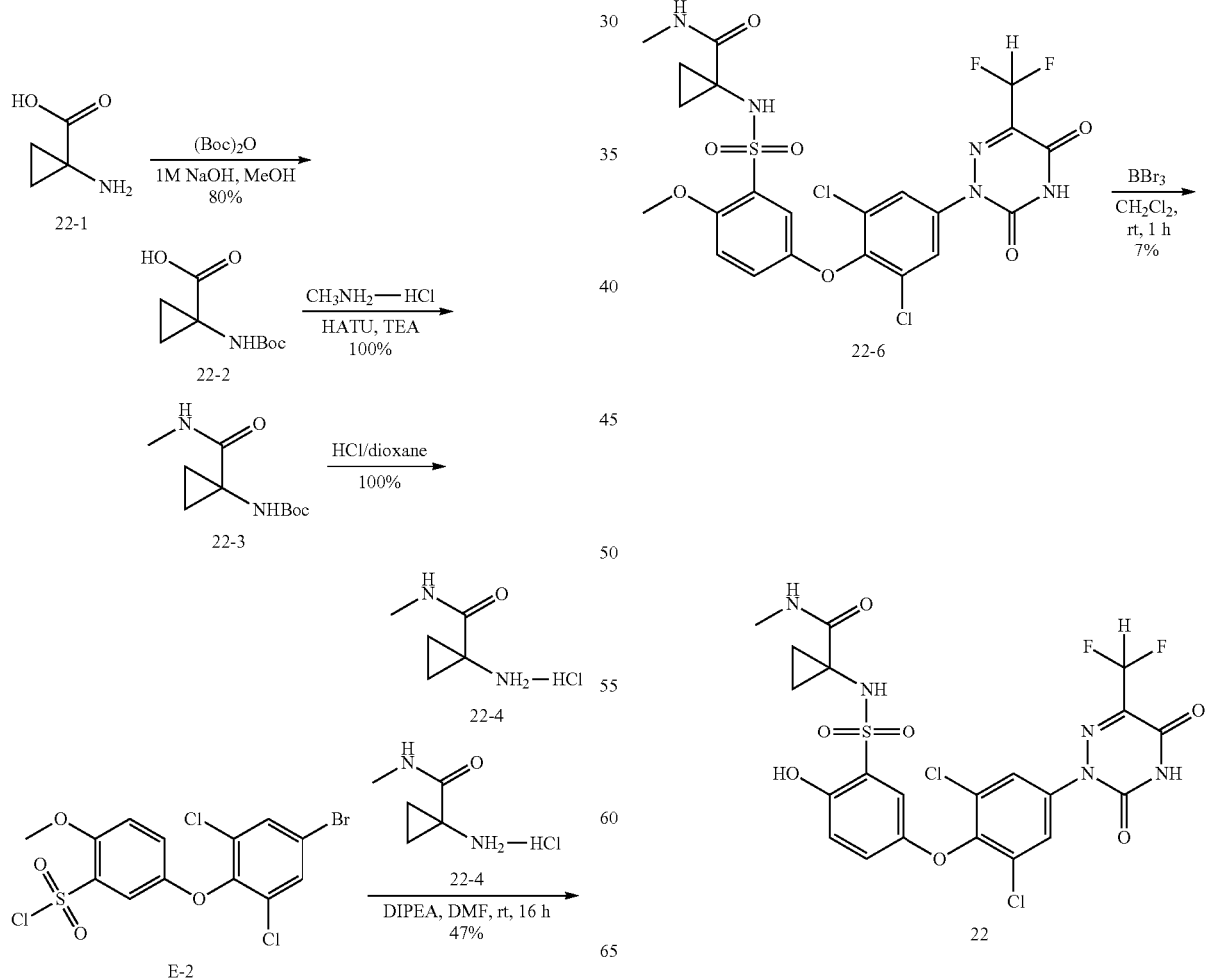

Step 1: 22-2

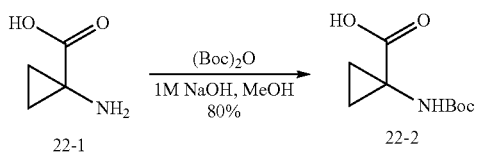 [SMILES: "(Boc)2O" ; NC1(C(=O)O)CC1 ; "1M NaOH, MeOH80%" ; CC(C)(C)OC(=O)NC1(C(=O)O)CC1]

To a solution of 1-aminocyclopropanecarboxylic acid 22-1 (1.0 g, 9.89 mmol) in MeOH was added 1 M NaOH (9.89 mmol, 8 mL) followed by di-tert-butyl dicarbonate (2.7 g, 12.36 mmol). The reaction was stirred at 25° C. for 15 h. LCMS showed the reaction was completed. The reaction mixture was acidified with dilute aqueous hydrogen chloride and extracted with EtOAc (3×50 mL). The organic phase was washed with brine, dried over anhydrous $Na_2SO_4$ and filtered. The filtrate was concentrated in vacuum to afford 1-((tert-butoxycarbonyl) amino) cyclopropane-1-carboxylic acid 22-2 (1.6 g, 80%) as a residue. The residue was used for next step without further purification. LCMS: $[M+Na]^+=224.0$.

Step 2: 22-3

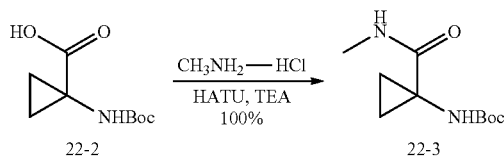

To a solution of 1-(tert-butoxycarbonylamino) cyclopropanecarboxylic acid 22-2 (1.1 g, 5.47 mmol), methylamine hydrochloride (1.85 g, 27.33 mmol) and TEA (4.43 g, 43.73 mmol, 6.10 mL) in DMF (5 ml) was added HATU (3.12 g, 8.20 mmol) at 0° C. The reaction was stirred at 25° C. for 15 h. LCMS showed the reaction was completed. The reaction mixture was diluted with EtOAc (20 mL), washed with sat. $NaHCO_3$ (10 mL), 5% aqueous solution of lithium chloride (10 mL) and water (10 mL). The combined organic layer was dried over anhydrous $Na_2SO_4$ and filtered. The filtrate was concentrated in vacuum to afford tert-butyl (1-(methyl carbamoyl) cyclopropyl) carbamate 22-3 (2.0 g, 100%). The residue was used for next step without further purification. LCMS: $[M+Na]^+=237.1$.

Step 3: 22-4

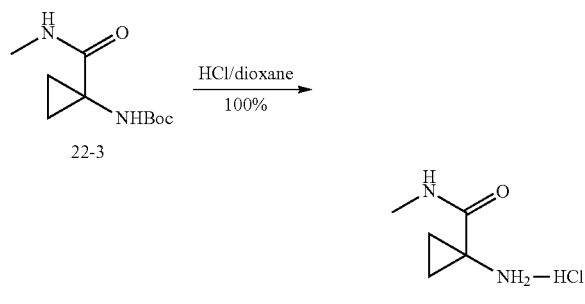

A solution of tert-butyl N-[1-(methyl carbamoyl) cyclopropyl] carbamate 22-3 (2.0 g, 9.33 mmol) in 4M HCl in dioxane (5 mL) was stirred at 90° C. for 1.5 h. LCMS showed reaction was completed. Solvent was removed under reduced pressure. The residue was azeotropized with toluene twice to remove HCl and the residue was dried under high vacuum to afford 1-amino-N-methylcyclopropane-1-carboxamide hydrochloride 22-4 (2.0 g, 100%). The residue was used for next step without further purification. LCMS: $[M+H]^+=115.1$.

Step 4: 22-5

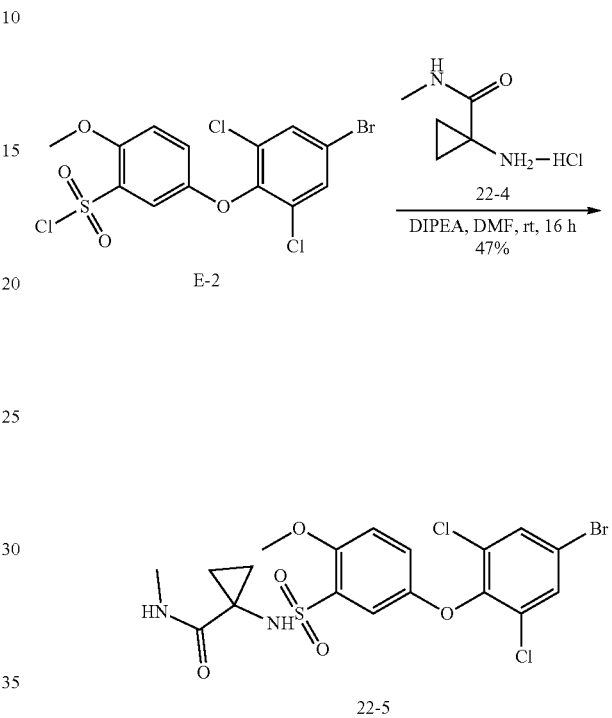

A solution of 5-(4-bromo-2,6-dichloro-phenoxy)-2-methoxy-benzenesulfonyl chloride E-2 (Example 5) (500 mg, 1.12 mmol), 1-amino-N-methyl-cyclopropanecarboxamide; hydrochloride 22-4 (337.28 mg, 2.24 mmol) and DIPEA (3.36 mmol, 0.5 ml) in DMF (5 mL) was stirred at 25° C. for 16 h. LCMS showed the reaction was completed. The reaction mixture was poured into water and extracted with EtOAc (3×50 mL). The combined organic layer was dried over anhydrous $Na_2SO_4$ and filtered. The filtrate was concentrated in vacuum. The residue was purified by silica gel chromatography ($CH_2Cl_2$:MeOH=20:1) to afford 1-[[5-(4-bromo-2,6-dichloro-phenoxy)-2-methoxy-phenyl] sulfonylamino]-N-methyl-cyclopropanecarboxamide 22-5 (280 mg, 47% yield) as a yellow solid. LCMS: $[M+H]^+=522.9/525.0$.

Step 5: 22-6

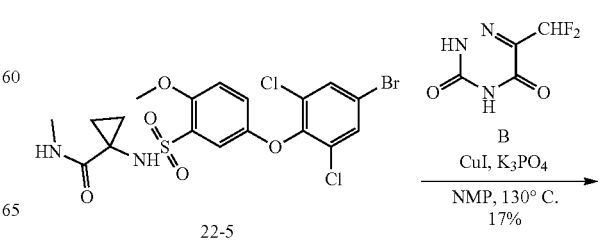

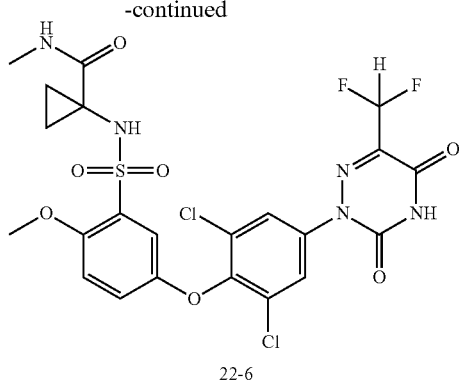

22-6

A mixture of 1-[[5-(4-bromo-2,6-dichloro-phenoxy)-2-methoxy-phenyl] sulfonyl amino]-N-methyl-cyclopropane carboxamide 22-5 (100 mg, 190.76 umol), 6-(difluoromethyl)-2H-1,2,4-triazine-3,5-dione Intermediate B (Example 2) (62.22 mg, 381.52 umol), CuI (90.83 mg, 476.91 umol) and $K_3PO_4$ (121.32 mg, 572.29 umol) in NMP (2 mL) was stirred in a sealed tube at 130° C. for 15 h. LCMS showed the reaction was completed. The reaction mixture was poured into water and extracted with EtOAc (3×50 mL). The combined organic layer was dried over anhydrous $Na_2SO_4$ and filtered. The filtrate was concentrated in vacuum. The residue was purified by Prep-TLC ($CH_2Cl_2$:MeOH=20:1) to afford 1-[[5-[2,6-dichloro-4-[6-(difluoromethyl)-3,5-dioxo-1,2,4-triazin-2-yl] phenoxy]-2-methoxy-phenyl] sulfonyl amino]-N-methyl-cyclopropane carboxamide 22-6 (20 mg, 17% yield) as a yellow solid. LCMS: [M+H]$^+$=606.1/608.1.

Step 6: Compound 22

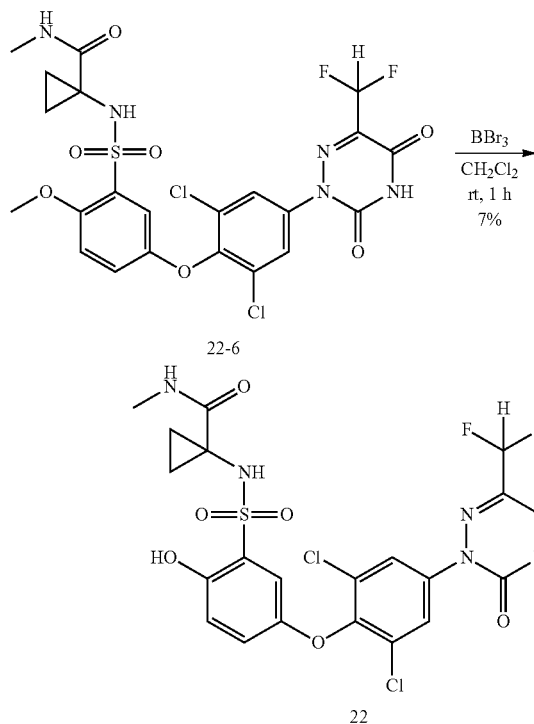

To a solution of 1-[[5-[2,6-dichloro-4-[6-(difluoromethyl)-3,5-dioxo-1,2,4-triazin-2-yl]phenoxy]-2-methoxy-phenyl] sulfonylamino]-N-methyl-cyclopropanecarboxamide 22-6 (60 mg, 99 mmol) in $CH_2Cl_2$ (2 mL) was added $BBr_3$ (247.37 mg) slowly at 0° C. The mixture was stirred at 0° C. for 1 h. LCMS showed the reaction was completed. The reaction mixture was poured into water and extracted with EtOAc (3×50 mL). The combined organic layer was dried over anhydrous $Na_2SO_4$ and filtered. The filtrate was concentrated in vacuum. The residue was purified by Prep-HPLC (Chromatographic columns: Xbridge 5 u C18 150×19 mm, Mobile Phase: MeCN—$H_2O$ (0.10% FA), Gradient: 30-40) to afford 1-[[5-[2,6-dichloro-4-[6-(difluoromethyl)-3,5-dioxo-1,2,4-triazin-2-yl] phenoxy]-2-hydroxy-phenyl] sulfonyl amino]-N-methyl-cyclopropane carboxamide Compound 22 (4.1 mg, 7% yield) as a white solid. LCMS: [M+H]$^+$=592.0/594.0. $^1$H NMR (400 MHz, $CD_3OD$) δ 7.82 (s, 2H), 7.12-7.09 (m, 2H), 6.99-6.97 (m, 1H), 6.71 (t, J=52.8 Hz, 1H), 2.75-1.74 (m, 3H), 1.25-1.22 (m, 2H), 0.95-0.92 (m, 2H). $^{19}$F NMR (376 MHz, $CD_3OD$) δ−124.2 (s, 2F).

Example 18: Synthesis of Compound 23

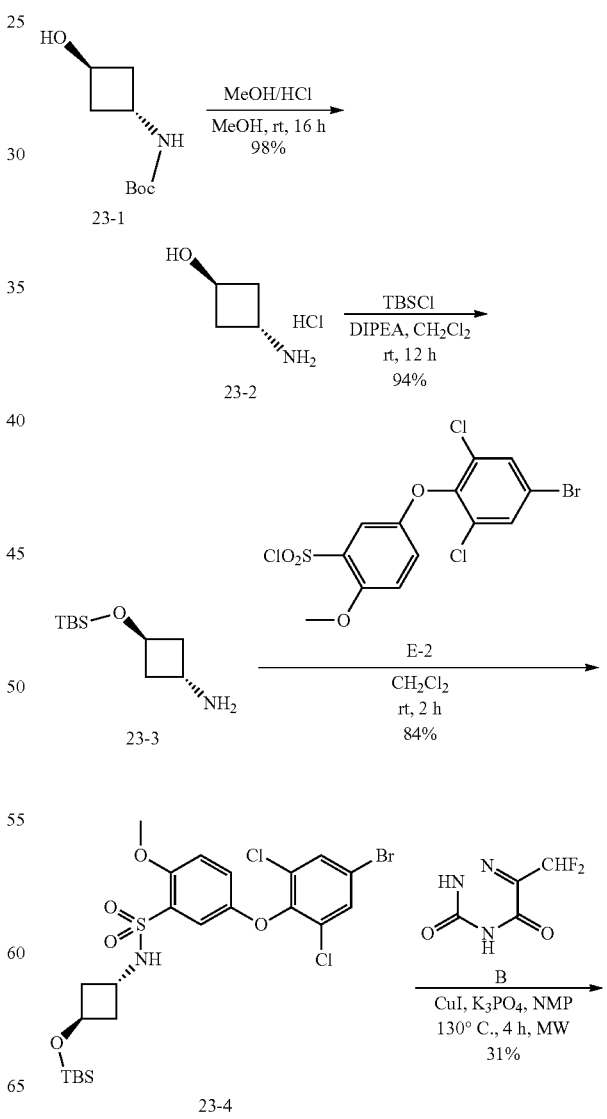

-continued

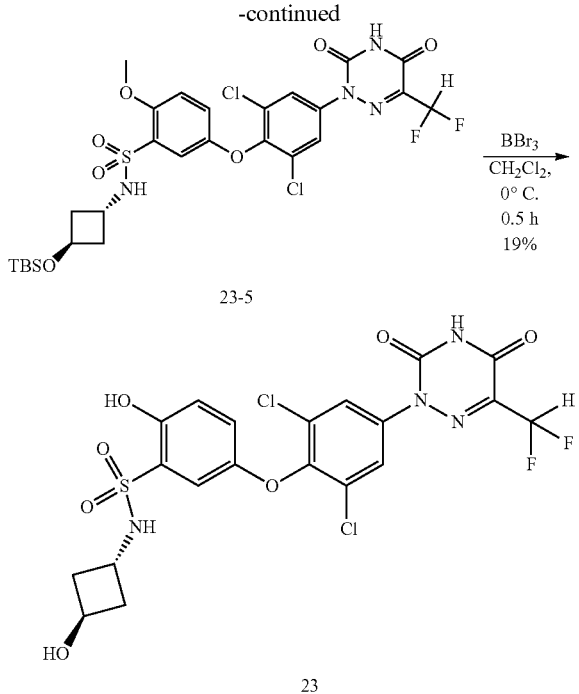

Step 1: 23-2

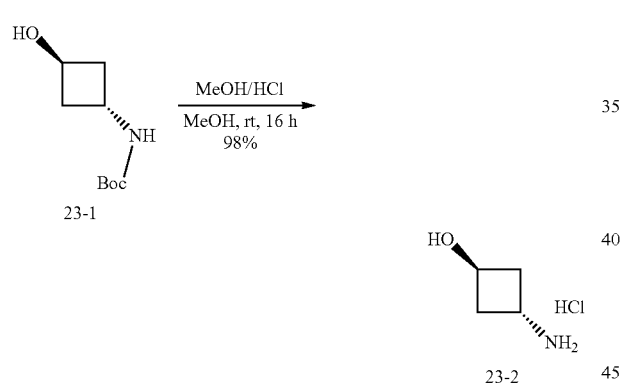

To a solution of tert-butyl N-(3-hydroxycyclobutyl) carbamate 23-1 (500 mg, 2.67 mmol) in methanol (5 mL) was added HCl (4 M in MeOH, 2.00 mL) The mixture was stirred at 20° C. under $N_2$ (g) for 16 h. LC-MS showed the reaction was completed. The reaction mixture was concentrated in vacuum to afford a residue. The residue was crude 3-aminocyclobutanol 23-2 (230 mg, 98% yield). It's a yellow oil and used for next step directly without further purification. LCMS: $[M+H]^+$=88.2.

Step 2: 23-3

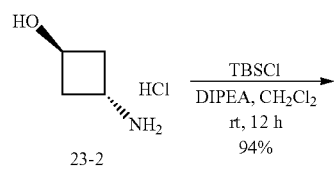

-continued

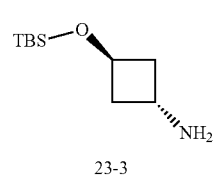

To a solution of 3-aminocyclobutanol 23-2 (230 mg, 2.64 mmol) and DIPEA (1.02 g, 7.92 mmol, 1.38 mL) in $CH_2Cl_2$ (10 mL) was added tert-butyl-chloro-dimethyl-silane (795.82 mg, 5.28 mmol). The mixture was stirred at 20° C. under $N_2$ (g) for 12 h. LC-MS showed the reaction was completed. The reaction mixture was poured into water (40 mL) and extracted with EtOAc (3×20 mL). The combined organic layer was washed with brine (20 mL), dried over anhydrous $Na_2SO_4$ and filtered. The filtrate was concentrated in vacuum to afford a residue. The residue was crude 3-[tert-butyl(dimethyl)silyl] oxycyclobutanamine 23-3 (500 mg, 94% yield). It's a yellow oil and used for next step directly without further purification. LCMS: $[M+H]^+$=202.1.

Step 3: 23-4

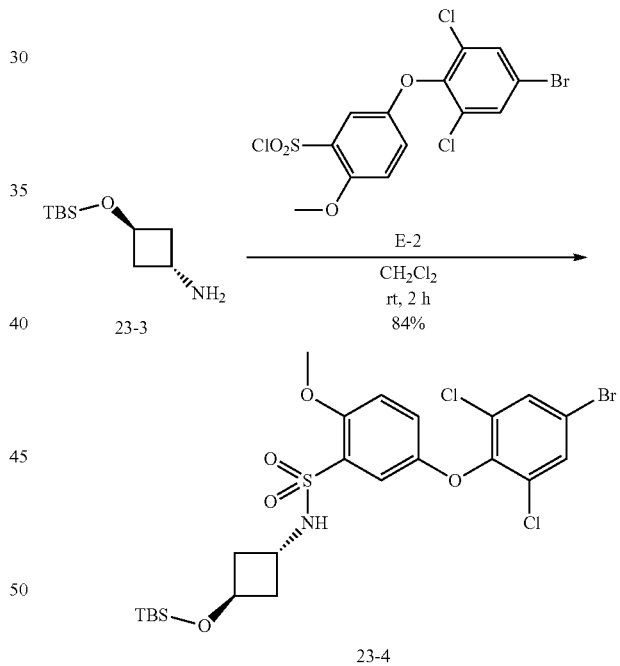

To a solution of 3-[tert-butyl(dimethyl)silyl] oxycyclobutanamine 23-3 (405.89 mg, 2.02 mmol) in $CH_2Cl_2$ (10 mL) was added 5-(4-bromo-2,6-dichloro-phenoxy)-2-methoxy-benzenesulfonyl chloride E-2 (Example 5) (300 mg, 671.85 umol). The mixture was stirred at 20° C. under $N_2$ (g) for 1 h. TLC (PE:EtOAc=5:1) showed the reaction was completed. The reaction mixture was concentrated in vacuum to afford a residue. The residue was purified by silica gel chromatography (PE:EtOAc=5:1) to afford 5-(4-bromo-2,6-dichloro-phenoxy)-N-[3-[tert-butyl(dimethyl)silyl] oxycyclobutyl]-2-methoxy-benzenesulfonamide 23-4 (348 mg, 84% yield) as a white solid.

Step 4: 23-5

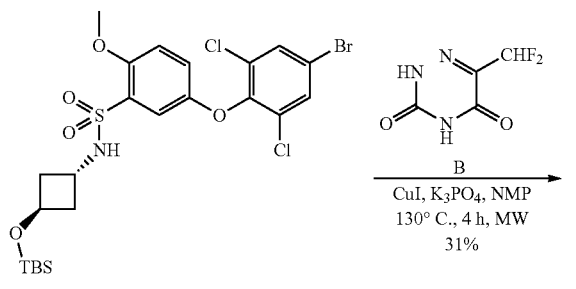

23-4

To a solution of 5-(4-bromo-2,6-dichloro-phenoxy)-N-[3-[tert-butyl(dimethyl)silyl]oxycyclobutyl]-2-methoxy-benzenesulfonamide 23-4 (50 mg, 81.77 umol) and 6-(difluoromethyl)-2H-1,2,4-triazine-3,5-dione Intermediate B (Example 2) (26.67 mg, 163.55 umol) in NMP (1 mL) was added (1R,2R)-cyclohexane-1,2-diamine (6.54 mg, 57.24 umol), CuI (38.93 mg, 204.43 umol) and K₃PO₄ (52.07 mg, 245.32 umol). The mixture was irradiated under microwave at 130° C. for 4 h. LC-MS showed product was formed. The reaction mixture was poured into water (20 mL) and extracted with EA (3×20 mL). The combined organic layer was washed with brine (3×20 mL), dried over anhydrous Na₂SO₄ and filtered. The filtrate was concentrated in vacuum to afford a residue. The residue was purified by Prep-TLC (CH₂Cl₂:MeOH=20:1) to afford 5-[2,6-dichloro-4-[6-(difluoromethyl)-3,5-dioxo-1,2,4-triazin-2-yl] phenoxy]-N-(3-hydroxycyclobutyl)-2-methoxy-benzenesulfonamide 23-5 (15 mg, 31% yield) as a yellow solid. LCMS: [M+Na]⁺=693.1.

Step 5: Compound 23

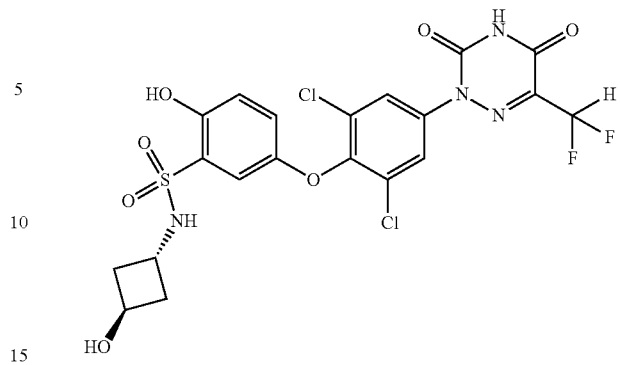

23-5

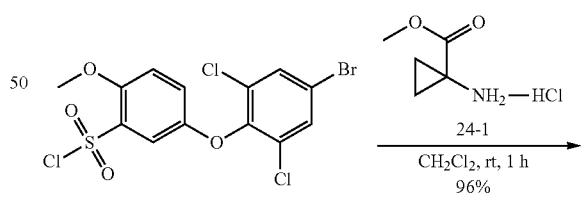

23

To a solution of 5-(2,6-dichloro-4-(6-(difluoromethyl)-3,5-dioxo-4,5-dihydro-1,2,4-triazin-2(3H)-yl)phenoxy)-N-((1r,3r)-3-hydroxycyclobutyl)-2-methoxybenzenesulfonamide 23-5 (15 mg, 25.89 umol) in CH₂Cl₂ (1 mL) was added BBr₃ (64.86 mg, 258.91 umol). The mixture was stirred at 25° C. for 0.5 h. LC-MS showed the reaction was completed. The reaction mixture was poured into water (10 mL) and extracted with EtOAc (3×10 mL). The combined organic layer was washed with brine (10 mL), dried over anhydrous Na₂SO₄ and filtered. The filtrate was concentrated in vacuum to afford a residue. The residue was purified by Prep-HPLC(Chromatographic columns: Kromasil 100-5 C18 5 um 100×21.5 mm, Mobile Phase: MeCN—H₂O (0.1% FA), Gradient: 40-50) to afford 5-(2,6-dichloro-4-(6-(difluoromethyl)-3,5-dioxo-4,5-dihydro-1,2,4-triazin-2 (3H)-yl) phenoxy)-2-hydroxy-N-((1r,3r)-3-hydroxycyclobutyl) benzene sulfonamide Compound 23 (2.9 mg, 19% yield) as a white solid. LCMS: [M+H]⁺=565.0. ¹H NMR (400 MHz, CD₃OD) 7.82 (s, 2H), 7.09-7.05 (m, 2H), 6.97 (d, J=8.8 Hz, 1H), 6.71 (t, J=52.8 Hz, 1H), 4.27-4.22 (m, 1H), 3.92-3.85 (m, 1H), 2.18-2.11 (m, 2H), 2.04-1.98 (m, 2H). ¹⁹F NMR (376 MHz, CD₃OD) δ−123.2 (s, 2F).

Example 19: Synthesis of Compound 24

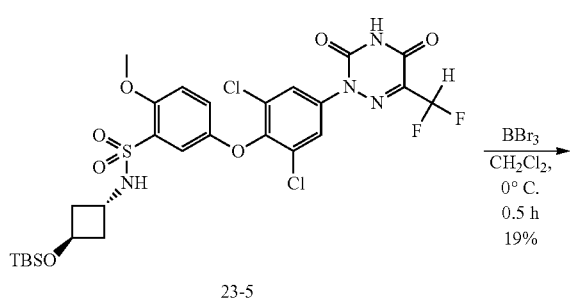

E-2

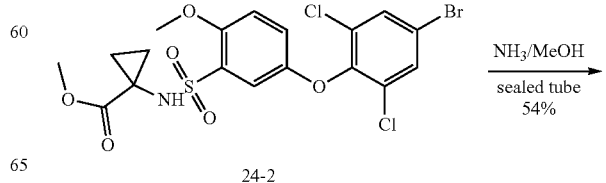

24-2

-continued

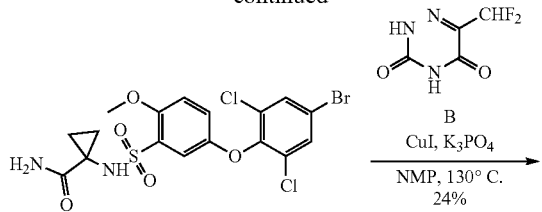

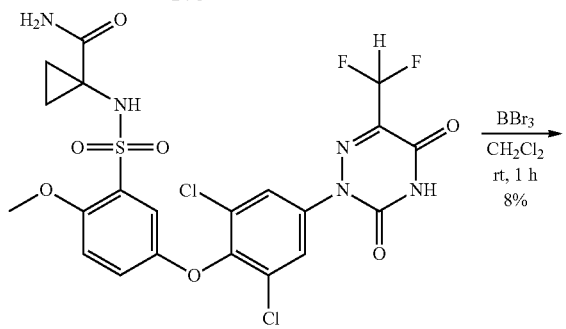

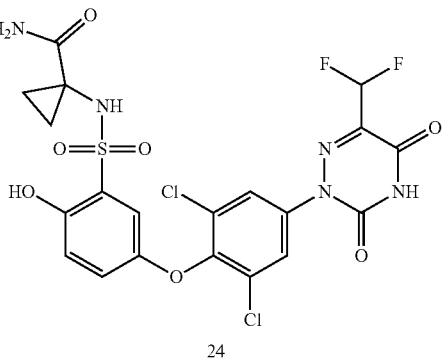

Step 1: 24-2

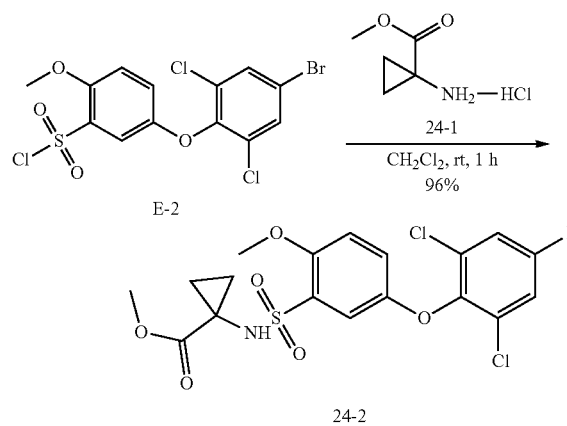

A solution of 5-(4-bromo-2,6-dichloro-phenoxy)-2-methoxy-benzenesulfonyl chloride E-2 (Example 5) (600 mg, 1.34 mmol), methyl 1-aminocyclopropanecarboxylate 24-1 (309.40 mg, 2.69 mmol) and DIPEA (347.32 mg, 2.69 mmol) in CH$_2$Cl$_2$ (10 mL) was stirred at 25° C. for 15 h. LCMS showed the product was formed. The mixture was filtered and concentrated in vacuum. The aqueous solution was extracted with EtOAc (3×50 mL). The combined organic layer was washed with brine (50 mL), dried over Na$_2$SO$_4$ and concentrated in vacuum. The residue was purified by column chromatography (PE:EtOAc=2:1) to give methyl 1-[[5-(4-bromo-2,6-dichloro-phenoxy)-2-methoxy-phenyl] sulfonylamino] cyclopropanecarboxylate 24-2 (680 mg, 96% yield) as a yellow solid. LCMS: [M+H]$^+$=524.0/525.9

Step 2: 24-3

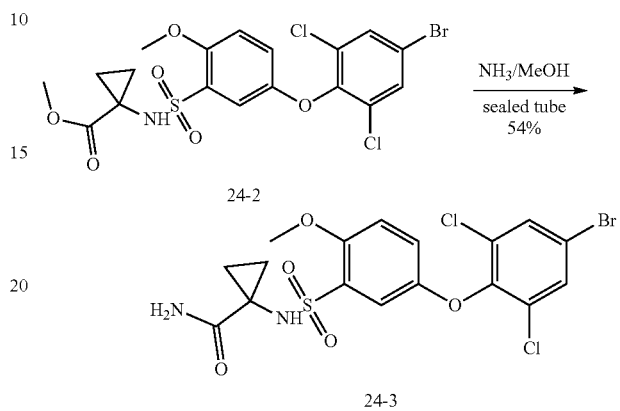

A mixture of methyl 1-[[5-(4-bromo-2,6-dichloro-phenoxy)-2-methoxy-phenyl] sulfonylamino]cyclopropanecarboxylate 24-2 (680 mg, 1.29 mmol) in 7 M ammonia methanol solution (2 ml, 14 mmol) was stirred at 50° C. in a sealed tube for 15 h under N$_2$. LCMS showed the desired product was formed. The mixture was concentrated in vacuum. The aqueous solution was extracted with EtOAc (3×50 mL). The combined organic layer was washed with brine (50 mL), dried over Na$_2$SO$_4$ and concentrated in vacuum. The residue was purified by column chromatography (CH$_2$Cl$_2$:MeOH=10:1) to give 1-[[5-(4-bromo-2,6-dichloro-phenoxy)-2-methoxy-phenyl] sulfonylamino] cyclopropanecarboxamide 24-3 (360 mg, 54% yield) as a white solid. LCMS: [M+H]$^+$=509.0/510.9

Step 3: 24-4

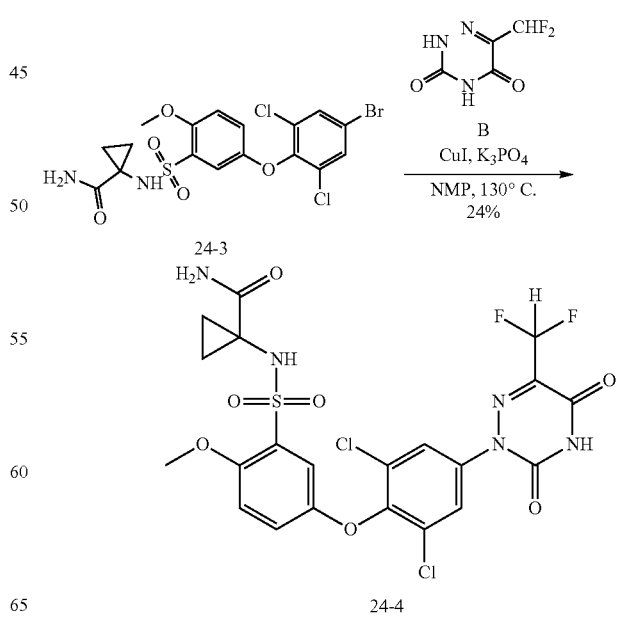

A solution of 1-[[5-(4-bromo-2,6-dichloro-phenoxy)-2-methoxy-phenyl]sulfonylamino]cyclopropanecarboxamide 24-3 (250 mg, 490.02 umol), 6-(difluoromethyl)-2H-1,2,4-triazine-3,5-dione Intermediate B (Example 2) (159.83 mg, 980.04 umol), N1,N2-dimethylcyclohexane-1,2-diamine (55.76 mg, 392.01 umol), CuI (233.31 mg, 1.23 mmol) and $K_3PO_4$ (311.65 mg, 1.47 mmol) in NMP (2 mL) was stirred in a sealed tube at 130° C. for 15 h. LCMS showed the product was formed. The reaction mixture was poured into water and extracted with EtOAc (3×50 mL). The combined organic layer was dried over anhydrous $Na_2SO_4$. The reaction mixture was filtered and concentrated in vacuum to afford a residue. The residue was purified by Prep-TLC ($CH_2Cl_2$:MeOH=10:1) to afford 1-[[5-[2,6-dichloro-4-[6-(difluoromethyl)-3,5-dioxo-1,2,4-triazin-2-yl] phenoxy]-2-methoxy-phenyl] sulfonylamino]cyclopropanecarboxamide 24-4 (70 mg, 24% yield) as a yellow solid. LCMS: $[M+H]^+$=592.0/594.0

Step 4: Compound 24

To a solution of 1-[[5-[2,6-dichloro-4-[6-(difluoromethyl)-3,5-dioxo-1,2,4-triazin-2-yl]phenoxy]-2-methoxy-phenyl] sulfonylamino] cyclopropanecarboxamide 24-4 (70 mg, 118.17 umol) in $CH_2Cl_2$ (2 mL) was added $BBr_3$ (886.29 mg, 3.55 mmol) slowly at 0° C. The mixture was stirred at 0° C. for 1 h. LCMS showed the product was formed. The reaction mixture was poured into water and extracted with EtOAc (3×50 mL). The combined organic layer was dried over anhydrous $Na_2SO_4$ and filtered. The filtrate was concentrated in vacuum. The residue was purified by Prep-HPLC (Kromasil 100-5 C18 5 um 100×21.5 mm, Mobile Phase: MeCN—$H_2O$ (0.1% TFA), Gradient: 32-42) to afford 1-[[5-[2,6-dichloro-4-[6-(difluoromethyl)-3,5-dioxo-1,2,4-triazin-2-yl] phenoxy]-2-hydroxy-phenyl]sulfonylamino]cyclopropanecarboxamide Compound 24 (5.8 mg, 8% yield) as a white solid. LCMS: $[M+H]^+$=578.0/580.0. $^1H$ NMR (400 MHz, $CD_3OD$) δ 7.82 (s, 2H), 7.13-7.08 (m, 2H), 7.98-6.96 (m, 1H), 6.70 (t, J=53.2, 1H), 1.27-1.24 (m, 2H), 0.96-0.92 (m, 2H). $^{19}F$ NMR (376 MHz, $CD_3OD$) δ−124.1 (s, 2F).

The compounds of Formula (I') or (I) in Table 6 below were made according to Example 19 of Compound 24.

TABLE 6

| Cmpd No. | LC-MS, $^1H$ and $^{19}F$-NMR data |
| --- | --- |
| 25 | LCMS: $[M + H]^+$ = 610.0. $^1H$ NMR (400 MHz, $CD_3OD$) δ 7.80 (s, 2H), 7.11-7.08 (m, 2H), 6.99-6.97 (m, 1H), 2.75-2.74 (m, 3H), 1.24-1.22 (m, 2H), 0.95-0.92 (m, 2H). $^{19}F$ NMR (376 MHz, $CD_3OD$) δ-69.3 (s, 3F). |

Example 20: Synthesis of Compound 26

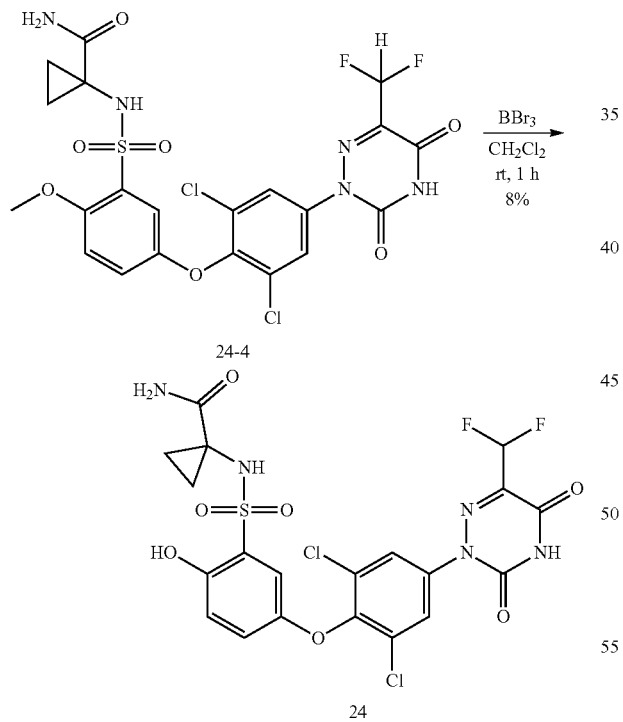

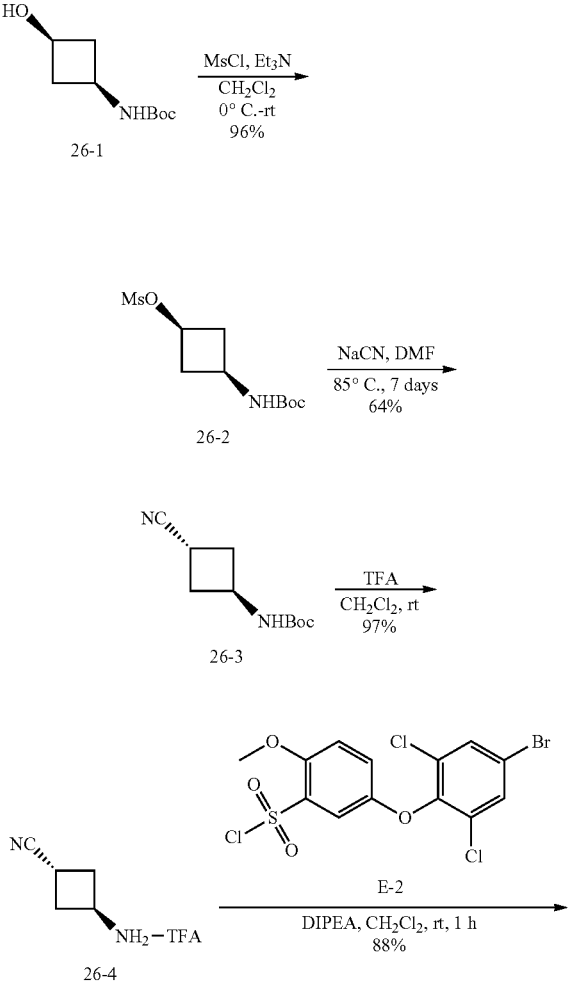

-continued

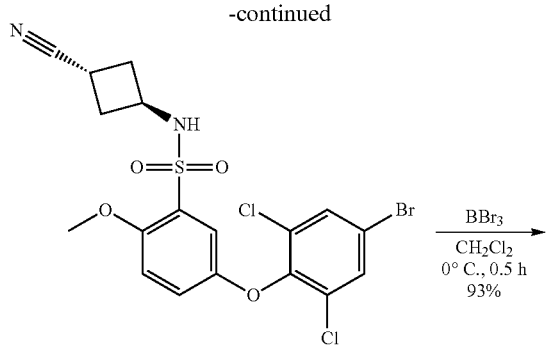

26-5

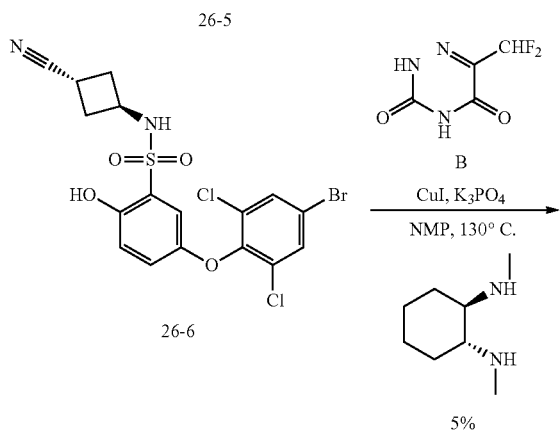

26-6

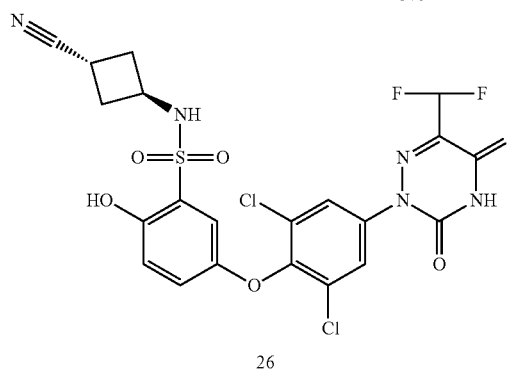

26

Step 1: 26-2

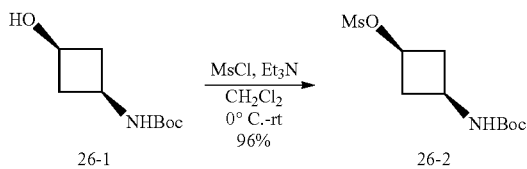

To a solution of tert-butyl ((1s,3s)-3-hydroxycyclobutyl) carbamate 26-1 (3.0 g, 16.02 mmol) and triethylamine (4.86 g, 48.07 mmol, 6.70 mL) in CH$_2$Cl$_2$ (30 mL) at 0° C. was added methane sulfonyl chloride (2.20 g, 19.23 mmol, 1.49 mL) dropwise. The reaction mixture was stirred at rt for 16 h. LC-MS showed the reaction was completed. The reaction mixture was poured into water (50 mL) and extracted with EtOAc (3×20 mL). The combined organic layer was washed with brine (20 mL), dried over anhydrous Na$_2$SO$_4$ and filtered. The filtrate was concentrated in vacuum to afford (1s,3s)-3-((tert-butoxy carbonyl) amino) cyclobutyl meth- ane sulfonate 26-2 (4.1 g, 96% yield) as a yellow oil. The yellow oil was used directly for next step without purification. LCMS: [M+Na]$^+$=288.2.

Step 2: 26-3

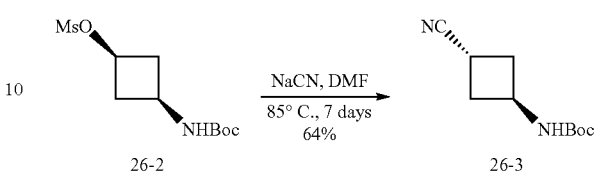

To a solution of (1s,3s)-3-((tert-butoxy carbonyl) amino) cyclobutyl methane sulfonate 26-2 (2.0 g, 7.54 mmol) in DMF (10 mL) was added sodium cyanide (567 mg, 11.57 mmol). The reaction mixture was stirred at 85° C. for 16 h. Then another batch of sodium cyanide (779 mg, 15.90 mmol) was added into the reaction mixture. The reaction mixture was stirred at 85° C. for 7 days. LC-MS showed the reaction was completed. The reaction mixture was poured into water (50 mL) and extracted with EtOAc (3×20 mL). The combined organic layer was washed with brine (20 mL), dried over anhydrous Na$_2$SO$_4$ and filtered. The filtrate was concentrated under vacuum. The residue was purified by silica gel chromatography (PE:EtOAc=2:1) to afford tert-butyl ((1r,3r)-3-cyano cyclobutyl) carbamate 26-3 (0.96 g, 64% yield) as a light-yellow solid. LCMS: [M+H]$^+$=197.2.

Step 3: 26-4

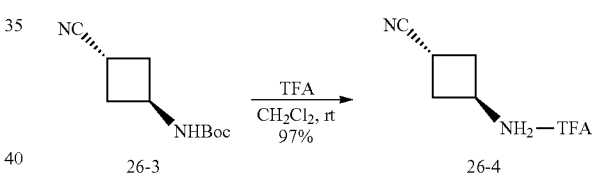

To a solution of tert-butyl ((1r,3r)-3-cyano cyclobutyl) carbamate 26-3 (100 mg, 509.57 umol) in CH$_2$Cl$_2$ (4 mL) was added TFA (2 mL). The reaction mixture was stirred at rt for 16 h. LC-MS showed the reaction was completed. The reaction mixture was concentrated in vacuum to afford a residue as (1r,3r)-3-((2,2,2-trifluoroacetyl)-14-azanyl) cyclobutane-1-carbonitrile 26-4 (48 mg, 97% yield) as a yellow oil. The residue was used directly for next step without purification. LCMS: [M+H]$^+$=97.2.

Step 4: 26-5

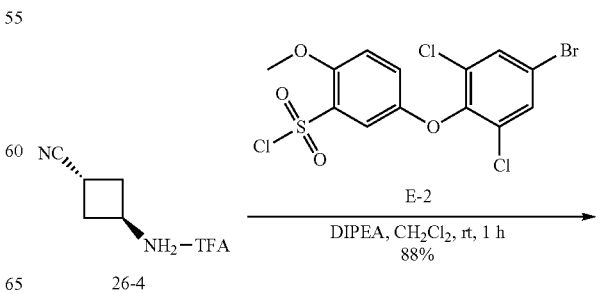

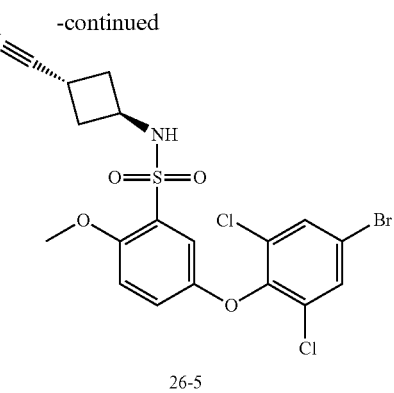

26-5

To a solution of (1r,3r)-3-((2,2,2-trifluoroacetyl)-14-azanyl) cyclobutane-1-carbonitrile 26-4 (102.9 mg, 535.55 umol) and N,N-Diisopropylethylamine (346.37 mg, 2.68 mmol, 466.81 uL) in CH$_2$Cl$_2$ (10 mL) at 0° C. was added 5-(4-bromo-2,6-dichloro-phenoxy)-2-methoxy-benzenesulfonyl chloride E-2 (Example 5) (239.34 mg, 536.00 umol). The reaction mixture was stirred at rt for 4 h. LC-MS showed the reaction was completed. The reaction mixture was poured into water (50 mL) and extracted with EtOAc (3×20 mL). The combined organic layer was washed with brine (20 mL), dried over anhydrous Na$_2$SO$_4$ and filtered. The filtrate was concentrated in vacuum. The residue was purified by silica gel chromatography (PE:EtOAc=2:1) to afford 5-(4-bromo-2,6-dichlorophenoxy)-N-((1r,3r)-3-cyanocyclobutyl)-2-methoxy benzene sulfonamide 26-5 (240 mg, 88% yield) as a light-yellow solid. LCMS: [M+H]$^+$=505.0/507.0.

Step 5: 26-6

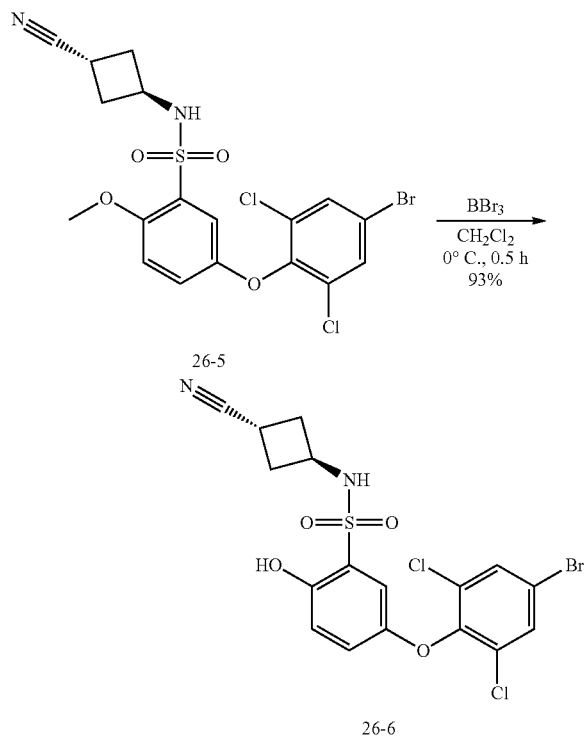

To a solution of 5-(4-bromo-2,6-dichlorophenoxy)-N-((1r,3r)-3-cyanocyclobutyl)-2-methoxy benzene sulfonamide 26-5 (506.2 mg, 1.00 mmol) in CH$_2$Cl$_2$ (10 mL) at 0° C. was added boron tribromide (2.51 g, 10.00 mmol). The reaction mixture was stirred at 0° C. for 30 mins. LC-MS showed the reaction was completed. The reaction mixture was poured into sat. NaHCO$_3$ (50 mL) and extracted with CH$_2$Cl$_2$ (3×20 mL). The combined organic layer was washed with brine (20 mL), dried over anhydrous Na$_2$SO$_4$ and filtered. The filtrate was concentrated in vacuum to afford 5-(4-bromo-2,6-dichlorophenoxy)-N-((1r,3r)-3-cyanocyclobutyl)-2-hydroxybenzene sulfonamide 26-6 (460 mg, 93% yield) as a light-yellow solid. The residue was used directly for next step without purification. LCMS: [M+H]$^+$=491.0/493.0.

Step 6: Compound 26

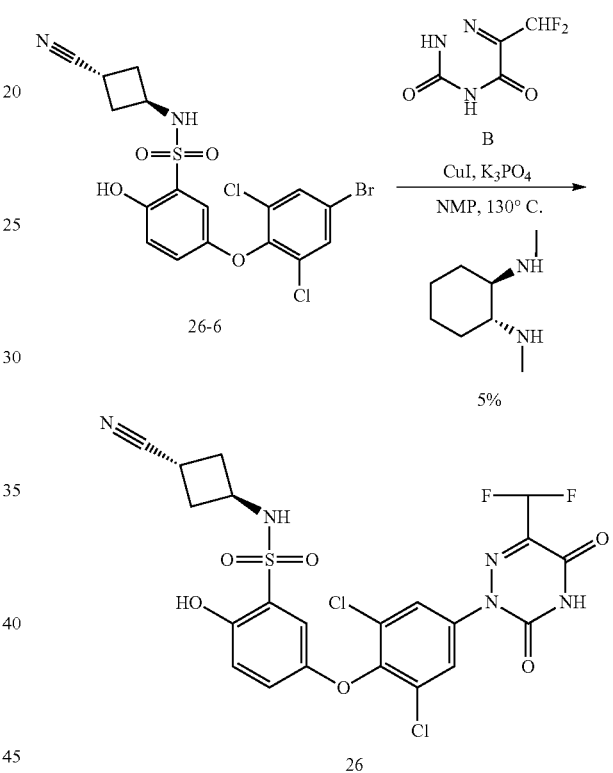

A mixture of 5-(4-bromo-2,6-dichlorophenoxy)-N-((1r,3r)-3-cyanocyclobutyl)-2-hydroxybenzene sulfonamide 26-6 (340 mg, 690.82 umol), 6-(difluoromethyl)-2H-1,2,4-triazine-3,5-dione Intermediate B (Example 2) (225.32 mg, 1.38 mmol), cuprous iodide (328.92 mg, 1.73 mmol), potassium phosphate (439.91 mg, 2.07 mmol) and (1R,2R)—N1,N2-dimethylcyclohexane-1,2-diamine (78.61 mg, 552.65 umol) in NMP (4 mL) was stirred at 130° C. for 16 h. LC-MS showed the reaction was completed. The reaction mixture was poured into water (50 mL) and extracted with EtOAc (3×20 mL). The combined organic layer was washed with brine (20 mL), dried over anhydrous Na$_2$SO$_4$ and filtered. The filtrate was concentrated in vacuum. The residue was purified by Prep-TLC (CH$_2$Cl$_2$:MeOH=10:1) to afford a crude product. The crude product was further purified by Prep-HPLC (Chromatographic columns: Kromasil-C18 100×21.2 mm 5 um Mobile Phase: MeCN—H$_2$O (0.1% FA), Gradient: 45-55) to afford N-(3-cyanocyclobutyl)-5-[2,6-dichloro-4-[6-(difluoromethyl)-3,5-dioxo-1,2,4-triazin-2-yl]phenoxy]-2-hydroxy-benzenesulfonamide Compound 26 (19.8 mg, 5% yield) as a white solid. LCMS: [M+H]⁺=573.8. ¹H NMR (400 MHz, CD₃OD) δ 7.82 (s, 2H), 7.12 (d, J=2.8 Hz, 1H), 7.10 (dd, J=8.8, 2.8 Hz, 1H), 6.98 (d, J=8.8 Hz, 1H), 6.71 (t, J=53.2 Hz, 1H), 4.10-4.02 (m, 1H), 3.07-2.99 (m, 1H), 2.36-2.29 (m, 4H), ¹⁹F NMR (376 MHz, CD₃OD) δ−124.1 (s, 2F).

Example 21: Synthesis of Compound 27

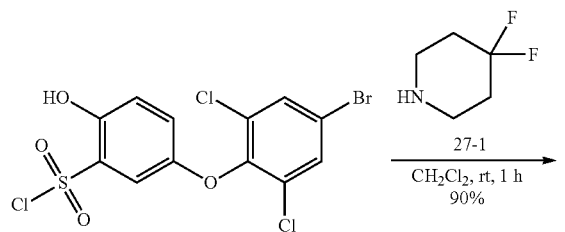

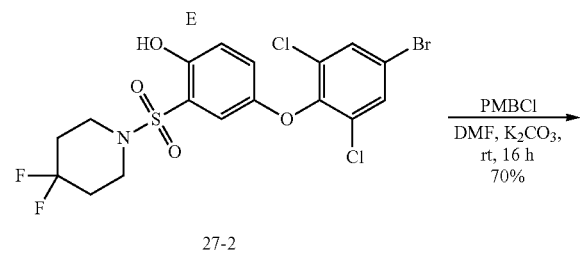

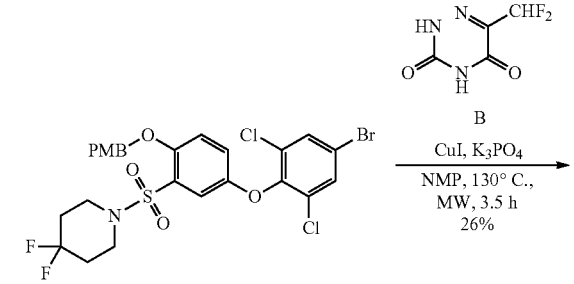

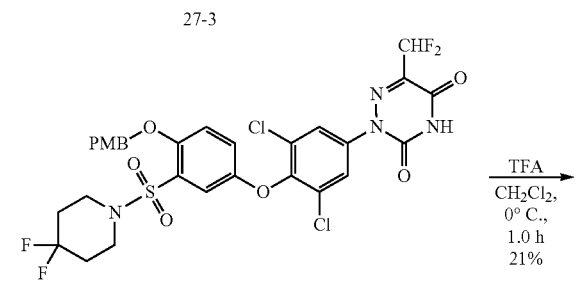

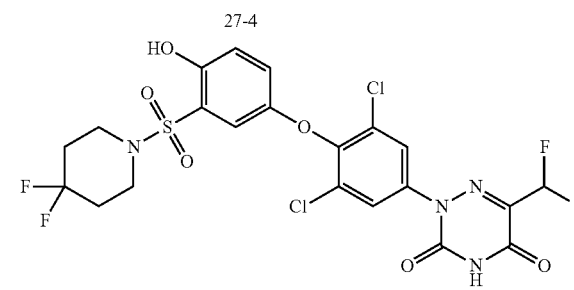

Step 1: 27-2

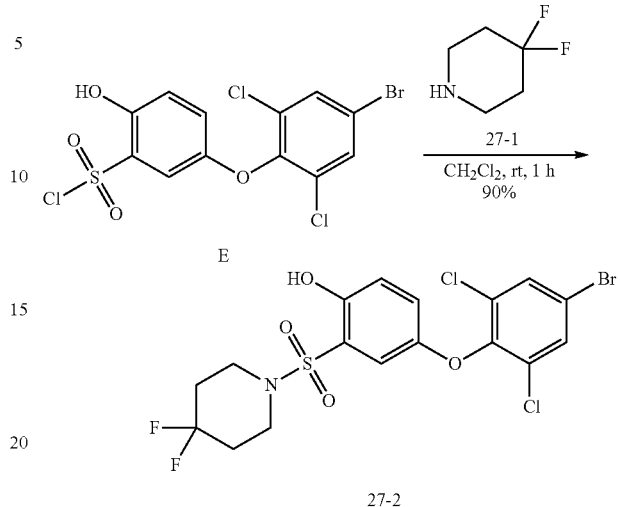

To a solution of 4,4-difluoropiperidine 27-1 (98.02 mg, 809.25 umol) and pyridine (192.03 mg, 2.43 mmol) in CH₂Cl₂ (10 mL) was added 5-(4-bromo-2,6-dichloro-phenoxy)-2-hydroxy-benzenesulfonyl chloride Intermediate E (Example 5) (350 mg, 809.25 umol). The mixture was stirred at 20° C. under N₂ for 16 h. TLC (PE:EtOAc=5:1) showed the reaction was completed. The reaction mixture was poured into water (20 mL) and extracted with CH₂Cl₂ (3×20 mL). The combined organic layer was washed with brine (20 mL), dried over anhydrous Na₂SO₄ and filtered. The filtrate was concentrated in vacuum to afford a residue. The residue was purified by silica gel chromatography (PE:EtOAc=5:1) to afford 4-(4-bromo-2,6-dichloro-phenoxy)-2-[(4,4-difluoro-1-piperidyl) sulfonyl] phenol 27-2 (380 mg, 90% yield) as a white solid.

Step 2: 27-3

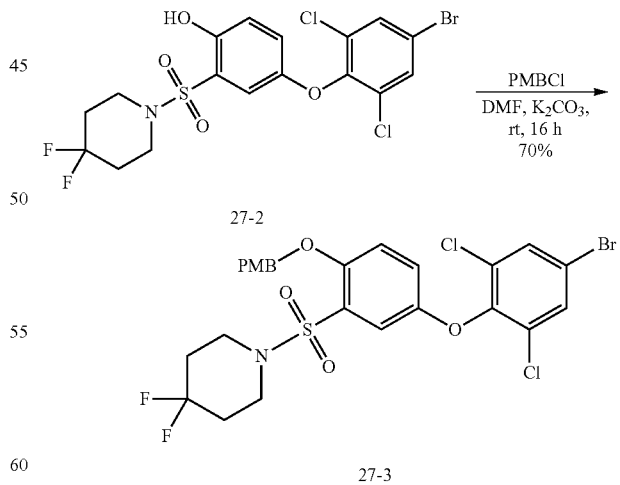

To a solution of 4-(4-bromo-2,6-dichloro-phenoxy)-2-[(4,4-difluoro-1-piperidyl) sulfonyl]phenol 27-2 (150 mg, 290.04 umol) in DMF (2 mL) was added K₂CO₃ (120.26 mg, 870.12 umol) and 1-(chloromethyl)-4-methoxy-benzene (90.85 mg, 580.08 umol). The mixture was stirred at 20° C. under N₂ for 16 h. TLC (PE:EtOAc=5:1) showed the reaction was completed. The reaction mixture was poured into water (20 mL) and extracted with EtOAc (3×20 mL). The combined organic layer was washed with brine (3×20 mL), dried over anhydrous Na₂SO₄ and filtered. The filtrate was concentrated in vacuum to afford a residue. The residue was purified by Prep-TLC (PE:EtOAc=5:1) to afford 1-[5-(4-bromo-2,6-dichloro-phenoxy)-2-[(4-methoxyphenyl)methoxy] phenyl] sulfonyl-4,4-difluoro-piperidine 27-3 (130 mg, 70% yield) as a white solid.

Step 3: 27-4

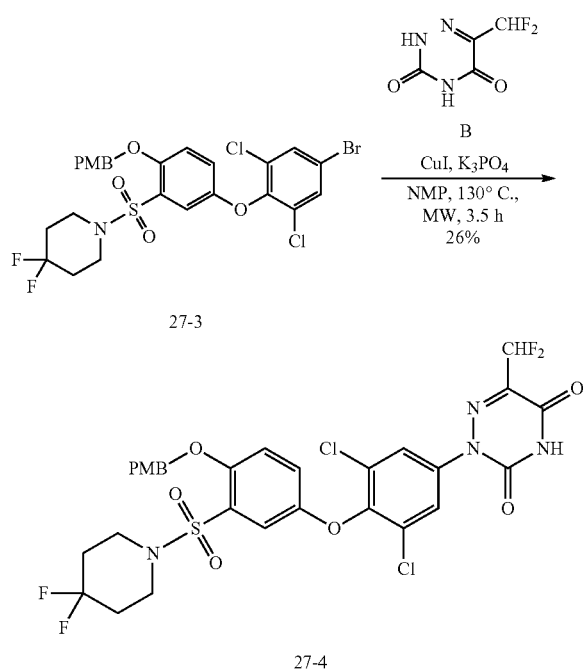

To a solution of 1-[5-(4-bromo-2,6-dichloro-phenoxy)-2-[(4-methoxyphenyl)methoxy]phenyl]sulfonyl-4,4-difluoro-piperidine 27-3 (50 mg, 78.45 umol) and 6-(difluoromethyl)-2H-1,2,4-triazine-3,5-dione Intermediate B (Example 2) (25.59 mg, 156.91 umol) in NMP (1 mL) was added (1R,2R)-cyclohexane-1,2-diamine (6.27 mg, 54.92 umol), CuI (37.35 mg, 196.13 umol) and K₃PO₄ (49.96 mg, 235.36 umol). The mixture was irradiated under microwave at 130° C. for 3.5 h. LC-MS showed the product was formed. The reaction mixture was diluted with EtOAc (50 mL). The organic layer was washed with brine (3×20 mL), dried over anhydrous Na₂SO₄ and filtered. The filtrate was concentrated in vacuum to afford a residue. The residue was purified by Prep-TLC (CH₂Cl₂:MeOH=20:1) to afford 2-[3,5-dichloro-4-[3-[(4,4-difluoro-1-piperidyl)sulfonyl]-4-[(4-methoxyphenyl)methoxy]phenoxy]phenyl]-6-(difluoromethyl)-1,2,4-triazine-3,5-dione 27-4 (15 mg, 26% yield) as a yellow solid. LCMS: [M+Na]⁺=740.9.

Step 4: Compound 27

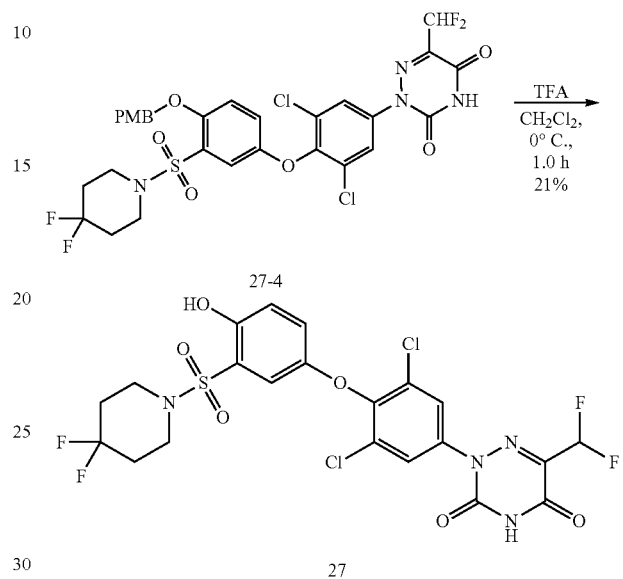

To a solution of 2-[3,5-dichloro-4-[3-[(4,4-difluoro-1-piperidyl) sulfonyl]-4-[(4-methoxyphenyl) methoxy] phenoxy] phenyl]-6-(difluoromethyl)-1,2,4-tri azine-3,5-di one 27-4 (15 mg, 20.85 umol) in CH₂Cl₂ (1 mL) was added TFA (0.1 mL). The mixture was stirred at 25° C. for 1 h. LC-MS showed the reaction was completed. The reaction mixture was concentrated in vacuum to afford a residue. The residue was purified by Prep-HPLC (Chromatographic columns: Xtimate 10 u C18 250×30 mm, Mobile Phase: MeCN—H₂O (0.10% FA), Gradient: 52-62). The prepared solution was cooled to 0° C. and was added 1 M HCl (0.5 mL). The mixture was freeze-dried to give 2-[3,5-dichloro-4-[3-[(4,4-difluoro-1-piperidyl) sulfonyl]-4-hydroxy-phenoxy] phenyl]-6-(difluoromethyl)-1,2,4-tri azine-3,5-dione Compound 27. LCMS: [M+H]⁺=599.0. ¹H NMR (400 MHz, CD₃OD) 7.82 (s, 2H), 7.14 (d, J=3.2 Hz, 1H), 7.08 (dd, J=8.8, 3.2 Hz, 1H), 6.99 (d, J=8.8 Hz, 1H), 6.69 (t, J=53.2 Hz, 1H), 3.39-3.36 (8, 4H), 2.05-1.94 (t, 4H). ¹⁹F NMR (376 MHz, CD₃OD) δ–100.3 (s, 2F), 6-124.3 (s, 2F).

The compounds of Formula (I') or (I) in Table 7 below were made according to Example 21 of Compound 27.

TABLE 7

| Cmpd No. | LC-MS, ¹H and ¹⁹F-NMR data |
|---|---|
| 28 | LCMS: [M + H]⁺ = 535.0. ¹H NMR (400 MHz, CD₃OD) δ 7.83 (s, 2H), 7.16 (dd, J = 9.2, 3.2 Hz, 1H), 7.07-7.05 (m, 2H), 6.72 (t, J = 52.8 Hz, 1H), 3.89 (t, J = 7.6 Hz, 4H), 2.18-2.07 (m, 2H). ¹⁹F NMR (376 MHz, CD₃OD) δ-124.3 (s, 2F). |
| 29 | LCMS: [M + H]⁺ = 565.0. ¹H NMR (400 MHz, CD₃OD) δ 7.81 (s, 2H), 7.15 (d, J = 3.2 Hz, 1H), 7.07 (dd, J = 9.2, 3.2 Hz, 1H), 6.97 (d, J = 9.2 Hz, 1H), 6.68 (t, J = 53.2 Hz, 1H), 3.87-3.77 (m, 2H), 3.68 (m, 2H), 3.53-3.49 (m, 1H), 2.03-1.97 (m, 1H), 1.79-1.73 (m, 1H). ¹⁹F NMR (376 MHz, CD₃OD) δ-123.9 (s, 2F). ee % = 100%. |
| 30 | LCMS: [M + H]⁺ = 564.9/567.0. ¹H NMR (400 MHz, CD₃OD) δ 7.82 (s, 2H), 7.14 (d, J = 3.2 Hz, 1H), 7.08 (dd, J = 9.2, 3.2 Hz, 1H), 6.98 (d, J = 8.8 Hz, 1H), 6.71 (t, J = 53.2 Hz, 1H), 3.89-3.78 (m, 2H), 3.71-3.65 (m, 2H), 3.51-3.49 (m, 1H), 2.05-1.96 (m, 1H), 1.80-1.73 (m, 1H). ¹⁹F NMR (376 MHz, CD₃OD) δ-124.2 (s, 2F). |

TABLE 7-continued

| Cmpd No. | LC-MS, $^1$H and $^{19}$F-NMR data |
|---|---|
| 31 | LCMS: [M + H]$^+$ = 564.1/566.1. $^1$H NMR (400 MHz, CD$_3$OD) δ 7.80 (s, 2H), 7.13 (d, J = 3.2 Hz, 1H), 7.07-6.97 (m, 2H), 6.67 (t, J = 53.2 Hz, 1H), 3.19-3.17 (m, 4H), 2.88-2.85 (m, 4H). $^{19}$F NMR (376 MHz, CD$_3$OD) δ-123.9 (s, 2F). |
| 32 | LCMS [M + H] $^+$ = 632.0. $^1$H NMR (400 MHz, CD$_3$OD) δ 7.82 (s, 2H), 7.09 (m, 2H), 7.00 (d, J = 8.4 Hz, 1H), 6.70 (t, J = 52.8 Hz, 1H), 3.80 (s, 2H), 3.62 (s, 2H), 3.12-3.25 (m, 4H), 1.90-1.95 (m, 1H), 0.92-0.71 (m, 4H). $^{19}$F NMR (376 MHz, CD$_3$OD) δ-124.1 (s, 2F). |
| 33 | LCMS: [M + H]$^+$ = 592.0. $^1$H NMR (400 MHz, CD$_3$OD) δ 7.83 (s, 2H), 7.20 (d, J = 3.2 Hz, 1H), 7.07 (dd, J = 8.8, 3.2 Hz, 1H), 6.98 (d, J = 9.2 Hz, 1H), 6.70 (t, J = 53.2 Hz, 1H), 3.96 (s, 2H), 3.55 (t, J = 5.2 Hz, 2H), 3.28 (t, J = 5.2 Hz, 2H), 2.90 (s, 3H).$^{19}$F NMR (376 MHz, CD$_3$OD) δ-124.1 (s, 2F) |
| 34 | LCMS: [M + H] $^+$ = 592.0. $^1$H NMR (400 MHz, CD$_3$OD) δ 7.81 (s, 2H), 7.18 (d, J = 3.2 Hz, 1H), 7.07 (dd, J = 8.8, 3.2 Hz, 1H), 6.98 (d, J = 9.2 Hz, 1H), 6.69 (t, J = 53.2 Hz, 1H), 4.10-3.98 (m, 1H), 3.61-3.54 (m, 1H), 3.30-3.24 (m, 1H), 2.77 (s, 3H), 2.50 (dd, J = 17.2, 8.8 Hz, 1H), 2.25 (dd, J = 17.2, 5.6 Hz, 1H). $^{19}$F NMR (376 MHz, CD$_3$OD) δ-124.21 (s, 2F). |
| 35 | LCMS: [M + H] $^+$ = 592.1. $^1$H NMR (400 MHz, CD$_3$OD) δ 7.82 (s, 2H), 7.16 (d, J = 2.8 Hz, 1H), 7.09 (dd, J = 9.2, 3.2 Hz, 1H), 6.99 (d, J = 8.8 Hz, 1H), 6.71 (t, J = 53.2 Hz, 1H), 4.06-3.97 (m, 1H), 3.60-3.53 (m, 1H), 3.29-3.23 (m, 1H), 2.77 (s, 3H), 2.50 (dd, J = 16.8, 8.4 Hz, 1H), 2.25 (dd, J = 17.2, 5.6 Hz, 1H). $^{19}$F NMR (376 MHz, CD$_3$OD) δ-124.1 (s, 2F). |
| 36 | LCMS: [M + H] $^+$ = 579.0. $^1$H NMR (400 MHz, CD$_3$OD) δ 7.82 (s, 2H), 7.12-7.03 (m, 2H), 6.95 (d, J = 9.6 Hz, 1H), 6.69 (t, J = 53.6 Hz, 1H), 3.90-3.80 (m, 2H), 3.14 (s, 3H), 2.05-2.08 (m, 4H). $^{19}$F NMR (376 MHz, CD$_3$OD) δ-123.9 (s, 2F). |
| 37 | LCMS: [M + H]$^+$ = 579.1. $^1$H NMR (400 MHz, CD$_3$OD) δ 7.82 (s, 2H), 7.09-7.03 (m, 2H), 6.96 (d, J = 8.8 Hz, 1H), 6.70 (t, J = 53.6 Hz, 1H), 3.55-3.42 (m, 1H), 3.30-3.32 (m, 1H), 3.14 (s, 3H), 2.42-2.29 (m, 2H), 1.78-1.67 (m, 2H). $^{19}$F NMR (376 MHz, CD$_3$OD) δ-124.1 (s, 2F). |
| 38 | LCMS: [M + H]$^+$ = 618.1/620.1. $^1$H NMR (400 MHz, CD$_3$OD) δ 7.82 (s, 2H), 7.09-7.06 (m, 2H), 6.97-6.94 (m, 1H), 6.71 (t, J = 52.8 Hz, 1H), 4.68-4.66 (m, 2H), 4.00-3.94 (m, 2H), 2.28-2.24 (m, 2H), 1.17-1.16 (m, 2H), 0.76-0.74 (m, 2H). $^{19}$F NMR (376 MHz, CD$_3$OD) δ-124.2 (s, 2F). |
| 39 | LCMS: [M + H]$^+$ = 626.9. $^1$H NMR (400 MHz, CD$_3$OD) δ 7.81 (s, 2H), 7.18 (d, J = 2.8 Hz, 1H), 7.07 (dd, J = 8.8, 3.2 Hz, 1H), 6.99 (d, J = 8.8 Hz, 1H), 6.70 (t, J = 53.2 Hz, 1H), 3.89-3.81 (m, 2H), 3.74-3.7 (m, 1H), 3.57-3.51 (m, 1H), 3.45-3.39 (m, 1H), 2.93 (s, 3H), 2.32-2.26 (m, 2H). $^{19}$F NMR (376 MHz, CD$_3$OD) δ-124.1 (s, 2F). |

Example 22: Synthesis of Compound 40

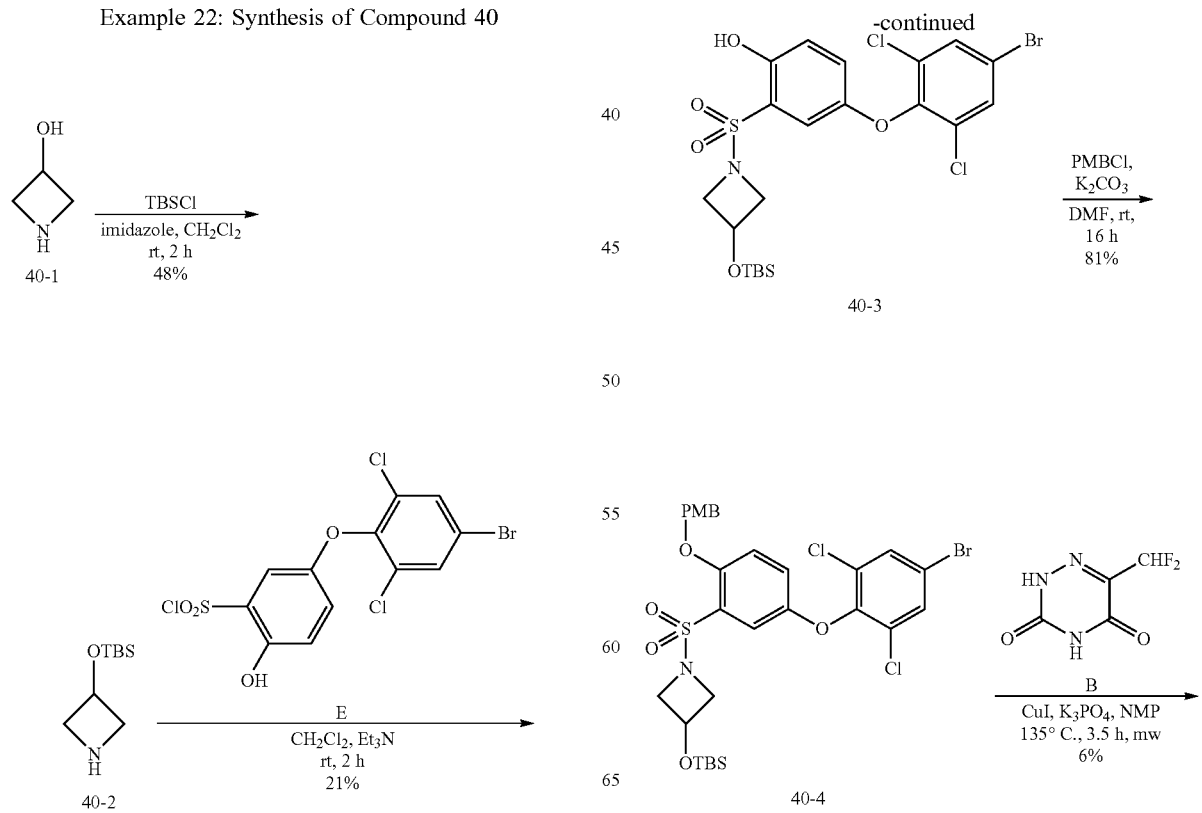

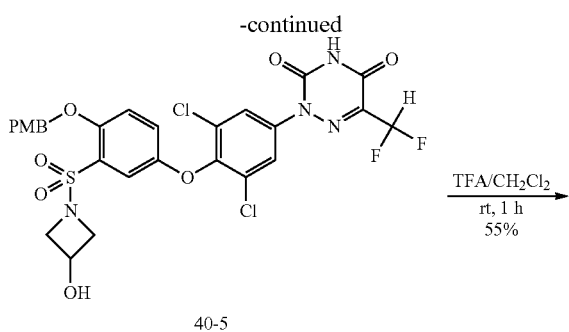

40-5

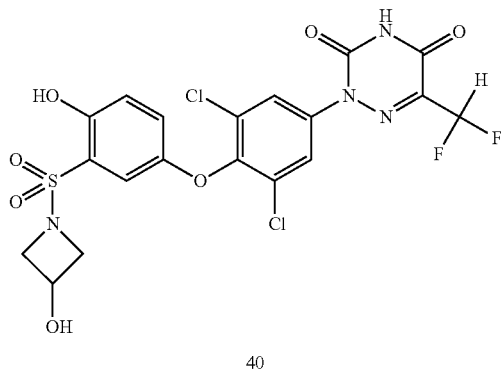

40

Step 1: 40-2

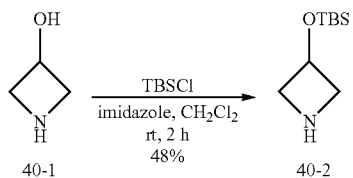 [SMILES: OC1CNC1 ; "TBSCl" ; CC(C)(C)[Si](C)(C)OC1CNC1]

To a solution of azetidin-3-ol 40-1 (500 mg, 6.84 mmol) and imidazole (931.41 mg, 13.68 mmol) in CH₂Cl₂ (20 mL) was added tert-butyl-chloro-dimethyl-silane (1.34 g, 8.89 mmol, 1.65 mL) at 0° C. The reaction mixture was stirred at rt for 2 h. LCMS showed the reaction was completed. The mixture was added water (50 mL) and extracted with EtOAc (2×50 mL). The organic solution was combined, dried over Na₂SO₄, filtered and the solvent was removed under vacuum to obtained azetidin-3-yloxy-tert-butyl-dimethyl-silane 40-2 (616 mg, 48% yield) as a yellow oil. LCMS: [M+H]⁺=188.2.

Step 2: 40-3

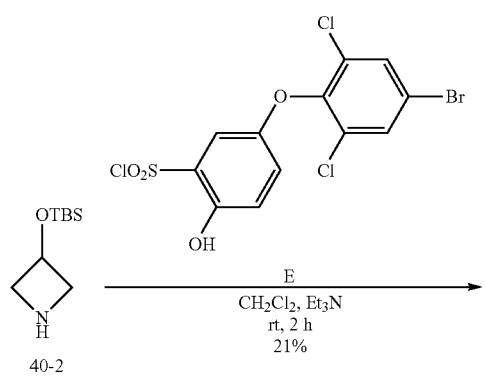

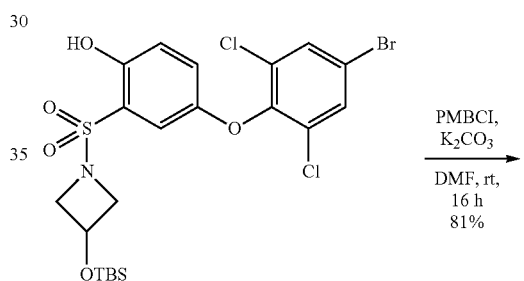

40-3

To a solution of azetidin-3-yloxy-tert-butyl-dimethyl-silane 40-2 (616 mg, 3.29 mmol) in CH₂Cl₂ (10 mL) was added 5-(4-bromo-2,6-dichloro-phenoxy)-2-hydroxy-benzenesulfonyl chloride Intermediate E (Example 5) (355.51 mg, 821.97 umol) at 0° C. The reaction mixture was stirred at rt for 2 h. LCMS showed the reaction was completed. The reaction mixture was diluted with 30 mL of water and extracted with EtOAc (3×20 ml). The organic layer was dried over Na₂SO₄ and concentrated. The residue was purified by flash chromatography (PE:EtOAc=5:1) to give 4-(4-bromo-2,6-dichloro-phenoxy)-2-[3-[tert-butyl(dimethyl)silyl]oxyazetidin-1-yl]sulfonyl-phenol 40-3 (395 mg, 21% yield) as a yellow solid. LCMS: [M+Na]⁺=582.0.

Step 3: 40-4

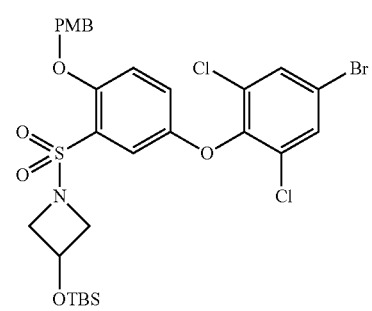

40-4

A mixture of 4-(4-bromo-2,6-dichloro-phenoxy)-2-[3-[tert-butyl(dimethyl)silyl]oxyazetidin-1-yl]sulfonyl-phenol 40-3 (395 mg, 677.07 umol), K₂CO₃ (280.73 mg, 2.03 mmol) and 1-(chloromethyl)-4-methoxy-benzene (212.07 mg, 1.35 mmol) in DMF (12 mL) was stirred at rt for 16 h. LCMS showed the product was formed. The reaction mixture was poured into water and extracted with EtOAc (3×50 mL). The combined organic layer was dried over anhydrous Na₂SO₄, filtered and concentrated in vacuum to afford a residue. The residue was purified by Prep-TLC (eluent: PE:EtOAc=5:1) to afford [1-[5-(4-bromo-2,6-dichloro-phenoxy)-2-[(4-methoxyphenyl)methoxy]phenyl]sulfonylazetidin-3-yl]oxy-tert-butyl-dimethyl-silane 40-4 (386 mg, 81% yield) as a yellow oil. LCMS: [M+Na]$^+$=724.2/726.2.

Step 4: 40-5

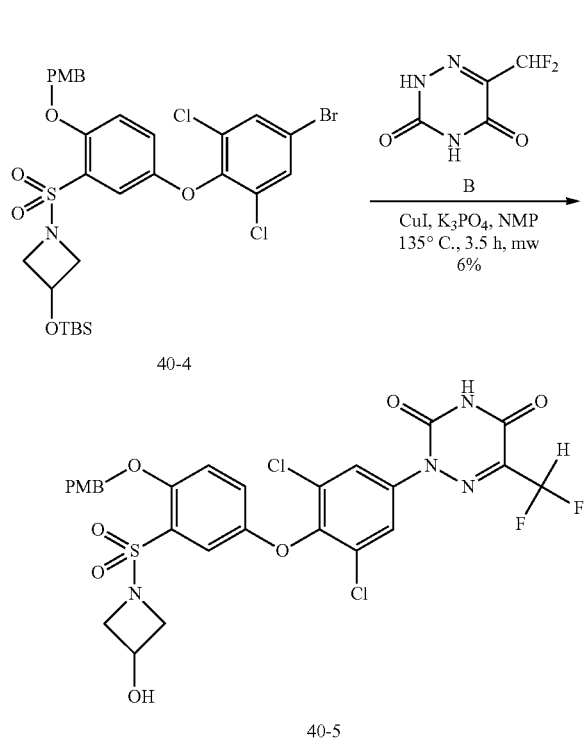

40-4

40-5

A mixture of [1-[5-(4-bromo-2,6-dichloro-phenoxy)-2-[(4-methoxyphenyl)methoxy]phenyl]sulfonylazetidin-3-yl]oxy-tert-butyl-dimethyl-silane 40-4 (100 mg, 142.14 umol), 6-(difluoromethyl)-2H-1,2,4-triazine-3,5-dione Intermediate B (Example 2) (46.36 mg, 284.28 umol), tripotassium; phosphate (90.51 mg, 426.41 umol), (1R,2R)-cyclohexane-1,2-diamine (12.98 mg, 113.71 umol) and copper iodide (67.68 mg, 355.34 umol) in NMP (2 mL) under $N_2$ was stirred at 130° C. under microwave for 3.5 h. LCMS showed the product was formed. The reaction mixture was poured into water and extracted with EtOAc (3×50 mL). The combined organic layer was dried over anhydrous $Na_2SO_4$, filtered and concentrated in vacuum to afford a residue. The residue was purified by prep-TLC (CH$_2$Cl$_2$:MeOH=10:1) to afford 2-[3,5-dichloro-4-[3-(3-hydroxyazetidin-1-yl)sulfonyl-4-[(4-methoxyphenyl)methoxy]phenoxy]phenyl]-6-(difluoromethyl)-1,2,4-triazine-3,5-dione 40-5 (6 mg, 6% yield) as a yellow solid. LCMS: [M+Na]$^+$=693.0/695.1.

Step 5: Compound 40

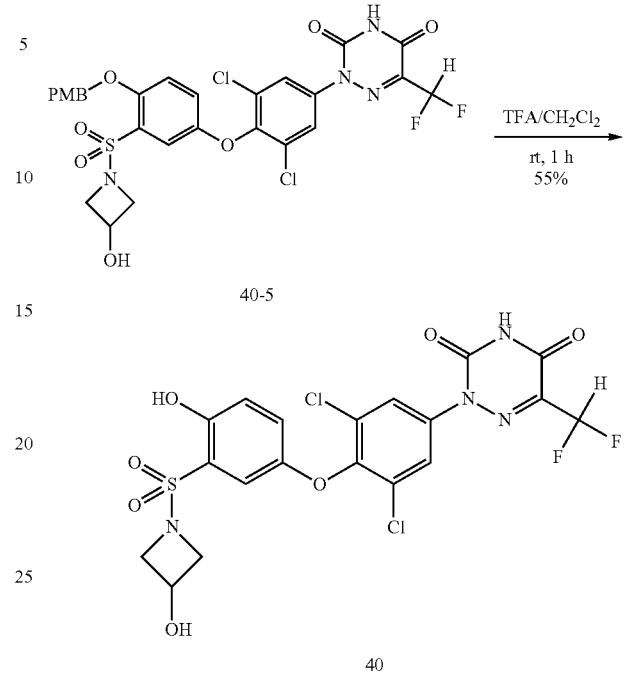

40-5

40

To a solution of 2-[3,5-dichloro-4-[3-(3-hydroxyazetidin-1-yl)sulfonyl-4-[(4-methoxyphenyl)methoxy]phenoxy]phenyl]-6-(difluoromethyl)-1,2,4-triazine-3,5-dione 40-5 (25 mg, 37.23 umol) in CH$_2$Cl$_2$ (1 mL) was added TFA (148.00 mg, 1.30 mmol, 0.1 mL). The resulting mixture was stirred at rt for 1 h. LCMS showed the product was formed. The reaction mixture was poured into water and extracted with EtOAc (3×100 mL). The combined organic layer was dried over anhydrous Na$_2$SO$_4$, filtered and concentrated in vacuum to afford a residue. The residue was purified by Prep-HPLC (Chromatographic columns: Kromasil 100-5 C18 5 um 100×21.5 mm, Mobile Phase: MeCN—H$_2$O (0.1% FA), Gradient: 37-47) to afford 2-[3,5-dichloro-4-[4-hydroxy-3-(3-hydroxyazetidin-1-yl)sulfonyl-phenoxy]phenyl]-6-(difluoromethyl)-1,2,4-triazine-3,5-dione Compound 40 (11.3 mg, 55% yield) as a white solid. LCMS: [M+H]$^+$=551.0/553.0. $^1$H NMR (400 MHz, CD$_3$OD) δ 7.83 (s, 2H), 7.15-7.04 (m, 3H), 6.71 (t, J=52.8 Hz, 1H), 4.46-4.39 (m, 1H), 4.05-4.01 (m, 2H), 3.71-3.67 (m, 2H). $^{19}$F NMR (376 MHz, CD$_3$OD) δ−124.2 (s, 2F).

The compounds of Formula (I') or (I) in Table 8 below were made according to Example 22 of Compound 40.

TABLE 8

| Cmpd No. | LC-MS, $^1$H and $^{19}$F-NMR data |
|---|---|
| 41 | LCMS: [M + H]$^+$ = 553.1. $^1$H NMR (400 MHz, CD$_3$OD) δ 7.81 (s, 2H), 7.16 (d, J = 2.8 Hz, 1H), 7.07 (dd, J = 8.8, 3.2 Hz, 1H), 6.97 (d, J = 9.2 Hz, 1H), 6.68 (t, J = 52.8 Hz, 1H), 3.45-3.43 (m, 1H), 3.33-3.23 (m, 2H), 1.01 (d, J = 6.4 Hz, 3H). $^{19}$F NMR (376 MHz, CD$_3$OD) δ-124.0 (s, 2F). |
| 42 | LCMS: [M + H]$^+$ = 564.8/567.0. $^1$H NMR (400 MHz, CD$_3$OD) δ 7.79 (s, 2H), 7.13 (d, J = 3.2 Hz, 1H), 7.02 (dd, J = 8.8, 3.2 Hz, 1H), 6.92 (d, J = 9.2 Hz, 1H), 6.66 (t, J = 54.0 Hz, 1H), 3.82-3.75 (m, 1H), 3.25-3.21 (m, 1H), 2.40-2.33 (m, 2H), 1.77-1.70 (m, 2H). $^{19}$F NMR (376 MHz, CD$_3$OD) δ-123.8 (s, 2F). |
| 43 | LCMS: [M + Na]$^+$ = 601.0/603.1. $^1$H NMR (400 MHz, CD$_3$OD) δ 7.82 (s, 2H), 7.11 (d, J = 2.8 Hz, 1H), 7.06 (dd, J = 8.8, 3.2 Hz, 1H), 6.97 (d, J = 9.2 Hz, 1H), 6.70 (t, J = 53.2 Hz, 1H), 4.23-4.19 (m, 1H), 2.91 (d, J = 7.6 Hz, 2H), 2.26-2.18 (m, 1H), 2.05-1.97 (m, 2H), 1.96-1.89 (m, 2H). |

TABLE 8-continued
| Cmpd No. | LC-MS, $^1$H and $^{19}$F-NMR data |
|---|---|
| 44 | LCMS: [M + H]$^+$ = 579.0. $^1$H NMR (400 MHz, CD$_3$OD) δ 7.82 (m, 2H), 7.12 (d, J = 3.2 Hz, 1H), 7.07 (dd, J = 8.8, 3.2 Hz, 1H), 6.98 (d, J = 8.8 Hz, 1H), 6.71 (t, J = 52.8 Hz, 1H), 4.00-3.92 (m, 1H), 2.92-2.85 (m, 2H), 2.31-2.21 (m, 2H), 1.87-1.78 (m, 1H), 1.54-1.43 (m, 2H). $^{19}$F NMR (376 MHz, CD$_3$OD) δ-124.1 (s, 2F). |
| 45 | LCMS: [M + H]$^+$ = 553.1. $^1$H NMR (400 MHz, CD$_3$OD) δ 7.81 (s, 2H), 7.16 (d, J = 2.8 Hz, 1H), 7.07 (dd, J = 8.8, 3.2 Hz, 1H), 6.97 (d, J = 9.2 Hz, 1H), 6.68 (t, J = 52.8 Hz, 1H), 3.45-3.43 (m, 1H), 3.33-3.23 (m, 2H), 1.01 (d, J = 6.4 Hz, 3H). $^{19}$F NMR (376 MHz, CD$_3$OD) δ-124.0 (s, 2F). |
Example 23: Synthesis of Compound 46
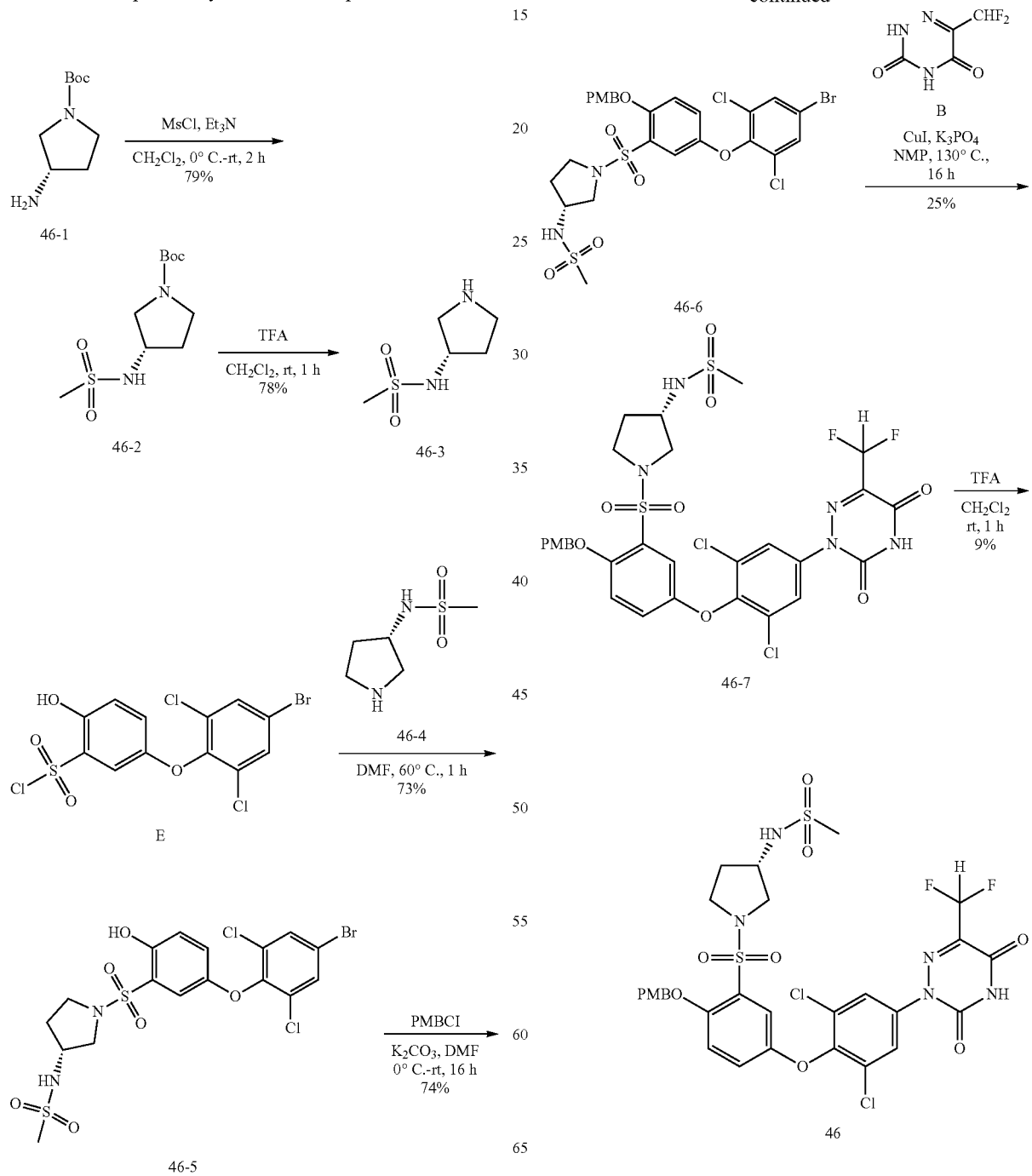

Step 1: 46-2

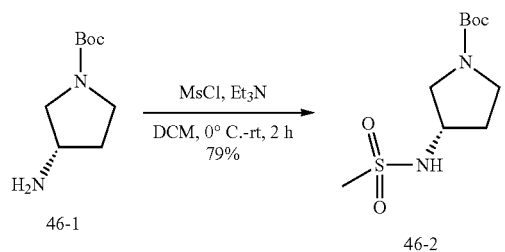 [SMILES: CC(C)(C)OC(=O)N1CC[C@H](N)C1 ; CC(C)(C)OC(=O)N1CC[C@H](NS(C)(=O)=O)C1]

A solution of tert-butyl (S)-3-aminopyrrolidine-1-carboxylate 46-1 (2.0 g, 10.74 mmol, 1.87 mL) and Et₃N (3.26 g, 32.21 mmol, 4.49 mL) in CH₂Cl₂ (20 mL) was added methanesulfonyl chloride (1.85 g, 16.11 mmol, 1.25 mL) was stirred at 25° C. for 2 h. LCMS showed the reaction was completed. The reaction mixture was poured into water and extracted with EtOAc (3×50 mL). The combined organic layer was dried over anhydrous Na₂SO₄ to give tert-butyl (S)-3-(methylsulfonamido) pyrrolidine-1-carboxylat 46-2 (2.5 g, 79% yield) as a pink solid. LCMS: [M+Na]⁺=287.1.

Step 2: 46-3

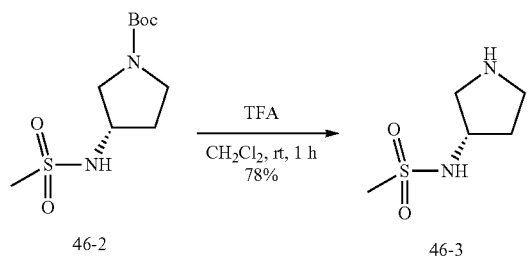

A solution of tert-butyl (S)-3-(methylsulfonamido) pyrrolidine-1-carboxylat 46-2 (2.8 g, 10.59 mmol) and TFA (2 mL) in CH₂Cl₂ (10 mL) was stirred at 25° C. for 1 h. LCMS showed the reaction was completed. The reaction mixture was concentrated to give N-[(3S)-pyrrolidin-3-yl] methanesulfonamide 46-3 (1.5 g, 78% yield) as a pink solid. LCMS: [M+H]⁺=165.1.

Step 3: 46-5

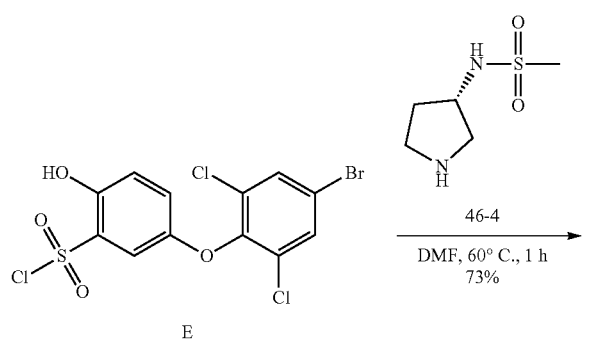

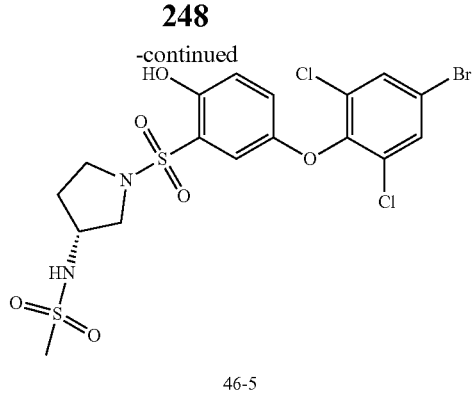

A mixture of 5-(4-bromo-2,6-dichloro-phenoxy)-2-hydroxy-benzenesulfonyl chloride Intermediate E (Example 5) (101 mg, 233.53 umol), N-[(3S)-pyrrolidin-3-yl]methanesulfonamide 46-4 (76.70 mg, 467.05 umol) and DIPEA (0.4 mL) in DMF (2 mL) was stirred at 60° C. for 1 h. LCMS showed the reaction was completed. Water (15 mL) was added and the mixture was extracted with EtOAc (3×15 mL). The combined organic layers were washed with brine, dried over Na₂SO₄ and concentrated in vacuum. The residue was purified by flash chromatography (PE:EtOAc=1:1) to give N-[(3S)-1-[5-(4-bromo-2,6-dichloro-phenoxy)-2-hydroxy-phenyl] sulfonylpyrrolidin-3-yl] methanesulfonamide 46-5 (100 mg, 73% yield) as a yellow solid. LCMS: [M+H]⁺=560.9.

Step 4: 46-6

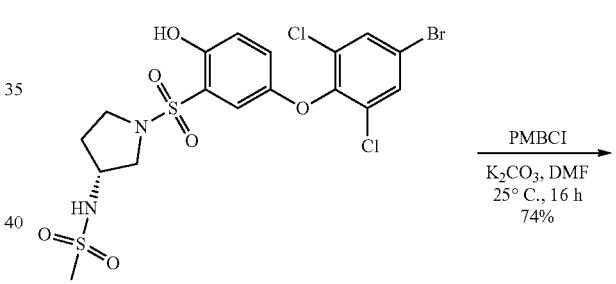

A mixture of 1-(chloromethyl)-4-methoxy-benzene (69.88 mg, 446.22 umol), N-[(3S)-1-[5-(4-bromo-2,6-dichloro-phenoxy)-2-hydroxy-phenyl]sulfonylpyrrolidin-3-yl]methanesulfonamide 46-5 (100 mg, 178.49 umol) and potassium carbonate (74.00 mg, 535.46 umol) in DMF (2 mL) was stirred at 25° C. for 16 h. LCMS showed the reaction was completed. Water (15 mL) was added and the mixture was extracted with EtOAc (3×13 mL). The combined organic layers were washed with brine, dried over Na₂SO₄ and concentrated in vacuum. The residue was purified by flash chromatography (PE:EtOAc=1:1) to give N-[(3S)-1-[5-(4-bromo-2,6-dichloro-phenoxy)-2-[(4-methoxyphenyl) methoxy] phenyl] sulfonylpyrrolidin-3-yl] methanesulfonamide 46-6 (100 mg, 74% yield) as a yellow solid. LCMS: [M+Na]⁺=702.0.

Step 5: 46-7

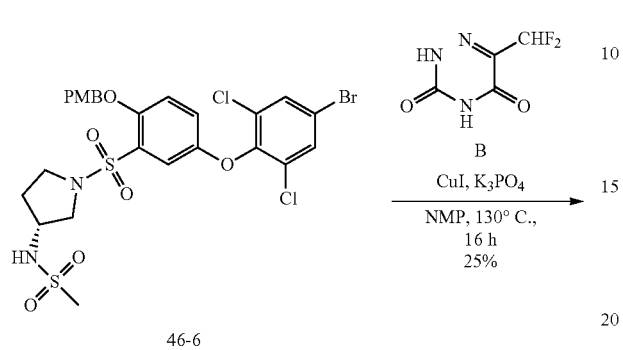

46-6

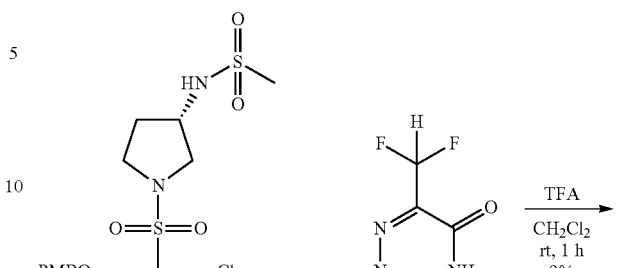

Step 6: Compound 46

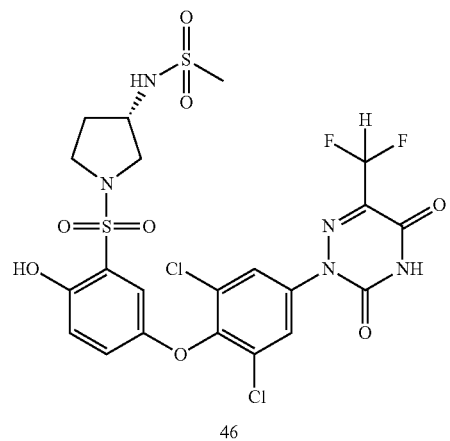

46-7

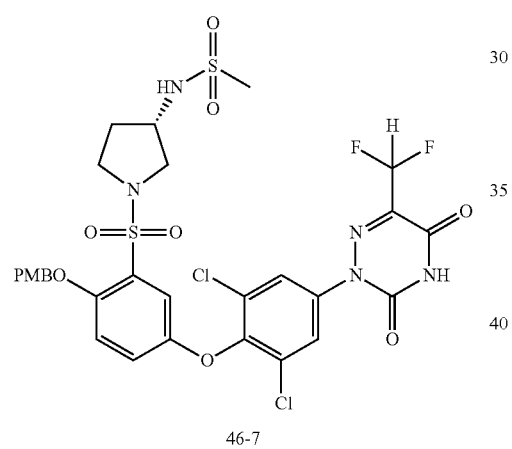

46-7

A mixture of (1R,2R)—N1,N2-dimethylcyclohexane-1,2-diamine (14.63 mg, 102.88 umol), 6-(difluoromethyl)-2H-1,2,4-triazine-3,5-dione Intermediate B (Example 2) (47.94 mg, 293.94 umol), N-[(3S)-1-[5-(4-bromo-2,6-dichloro-phenoxy)-2-[(4-methoxyphenyl)methoxy]phenyl]sulfonylpyrrolidin-3-yl]methanesulfonamide 46-6 (100 mg, 146.97 umol), CuI (69.98 mg, 367.42 umol) and potassium phosphate (93.59 mg, 440.91 umol) in NMP (3 mL) was stirred at 130° C. for 16 h. LCMS showed the reaction was completed. Water (15 mL) was added and the mixture was extracted with EtOAc (3×15 mL). The combined organic layers were washed with brine, dried over Na₂SO₄ and concentrated in vacuum. The residue was purified by flash chromatography (CH₂Cl₂:MeOH=10:1) to give N-[(3S)-1-[5-[2,6-dichloro-4-[6-(difluoromethyl)-3,5-dioxo-1,2,4-triazin-2-yl]phenoxy]-2-[(4-methoxyphenyl)methoxy]phenyl]sulfonylpyrrolidin-3-yl]methanesulfonamide 46-7 (32 mg, 25% yield) as a yellow solid. LCMS: [M+Na]⁺=784.1.

To a solution of N-[(3S)-1-[5-[2,6-dichloro-4-[6-(difluoromethyl)-3,5-dioxo-1,2,4-triazin-2-yl]phenoxy]-2-[(4-methoxyphenyl)methoxy]phenyl]sulfonylpyrrolidin-3-yl] methanesulfonamide 46-7 (32 mg, 41.96 umol) in CH₂Cl₂ (3 mL) was added TFA (1.48 g, 12.98 mmol, 1 mL). The mixture was stirred at 25° C. for 1 h. LCMS showed the reaction was completed. The reaction mixture was poured into water, extracted with EtOAc (3×50 mL) and washed with NaHCO₃. The combined organic layer was dried over anhydrous Na₂SO₄ and filtered. The filtrate was concentrated in vacuum. The residue was purified by Prep-HPLC (Chromatographic columns: Xbridge 5 u C18 150×19 mm, Mobile Phase: MeCN—H₂O (0.1% FA), Gradient: 40-50) to afford N-[(3S)-1-[5-[2,6-dichloro-4-[6-(difluoromethyl)-3,5-dioxo-1,2,4-triazin-2-yl]phenoxy]-2-hydroxy-phenyl] sulfonyl pyrrolidin-3-yl]methanesulfonamide Compound 46 (2.5 mg, 9% yield) as a white solid. LCMS: [M+H]⁺=642.0. ¹H NMR (400 MHz, CD₃OD) δ 7.82 (s, 2H), 7.15 (d, J=3.2 Hz, 1H), 7.07 (dd, J=9.2, 2.4 Hz, 1H), 7.00 (d, J=9.2 Hz, 1H), 6.71 (t, J=52.8 Hz, 1H), 3.97-3.90 (m, 1H), 3.69-3.73 (m, 1H), 3.55-3.47 (m, 1H), 3.33-3.35 (m, 1H), 3.18-3.13 (m, 1H), 2.93 (s, 3H), 2.13-2.21 (m, 1H), 1.80-1.89 (m, 1H). ¹⁹F NMR (376 MHz, CD₃OD) δ–124.2 (s, 2F).

The compounds of Formula (I') or (I) in Table 9 below were made according to Example 23 of Compound 46.

TABLE 9

| Cmpd No. | LC-MS, $^1$H and $^{19}$F-NMR data |
|---|---|
| 47 | LCMS: [M + H]$^+$ = 642.0. $^1$H NMR (400 MHz, CD$_3$OD) δ 7.82 (s, 2H), 7.15 (d, J = 2.4 Hz, 1H), 7.07 (dd, J = 9.2, 2.4 Hz, 1H), 7.00 (d, J = 9.2 Hz, 1H), 6.70 (t, J = 52.8 Hz, 1H), 3.97-3.90 (m, 1H), 3.69-3.73 (m, 1H), 3.55-3.47 (m, 1H), 3.33-3.35 (m, 1H), 3.18-3.13 (m, 1H), 2.93 (s, 3H), 2.13-2.21 (m, 1H), 1.80-1.89 (m, 1H). $^{19}$F NMR (376 MHz, CD$_3$OD) δ-124.1 (s, 2F). |
| 48 | LCMS: [M + H]$^+$ = 668.1. $^1$H NMR (400 MHz, CD$_3$OD) δ 7.82 (s, 2H), 7.15 (d, J = 2.8 Hz, 1H), 7.11 (dd, J = 3.2 Hz, 9.2 Hz, 1H), 6.99 (d, J = 8.8 Hz, 1H), 6.71 (t, J = 52.8 Hz, 1H), 3.93-3.80 (m, 1H), 3.55-3.35 (m, 3H), 3.19-3.15 (m, 1H), 2.52-2.46 (m, 1H), 2.13-2.04 (m, 1H), 1.91-1.82 (m, 1H), 1.09-0.91 (m, 4H). $^{19}$F NMR (376 MHz, CD$_3$OD) δ-124.1 (s, 2F). |
| 49 | LCMS: [M + H]$^+$ = 668.1. $^1$H NMR (400 MHz, CD$_3$OD) δ 7.82 (s, 2H), 7.15 (d, J = 2.8 Hz, 1H), 7.11 (dd, J = 3.2 Hz, 9.2 Hz, 1H), 6.99 (d, J = 8.8 Hz, 1H), 6.71 (t, J = 52.8 Hz, 1H), 3.93-3.80 (m, 1H), 3.55-3.35 (m, 3H), 3.19-3.15 (m, 1H), 2.52-2.46 (m, 1H), 2.13-2.04 (m, 1H), 1.91-1.82 (m, 1H), 1.09-0.91 (m, 4H). |
| 50 | LCMS: [M + H]$^+$ = 642.0. $^1$H NMR (400 MHz, CD$_3$OD) δ 7.82 (s, 2H), 7.15 (d, J = 3.2 Hz, 1H), 7.09 (dd, J = 8.8, 3.2 Hz, 1H), 6.99 (d, J = 8.2 Hz, 1H), 6.69 (t, J = 53.2 Hz, 1H), 3.88-3.82 (m, 1H), 3.41-3.37 (m, 2H), 3.27-3.25 (m, 1H), 3.21-3.15 (m, 1H), 2.84 (s, 3H), 2.10-2.02 (m, 1H), 1.95-1.81 (m, 1H). $^{19}$F NMR (376 MHz, CD$_3$OD) δ-124.0 (s, 2F). |
| 51 | LCMS: [M + H]$^+$ = 642.0. $^1$H NMR (400 MHz, CD$_3$OD) δ 7.82 (s, 2H), 7.15 (d, J = 3.2 Hz, 1H), 7.09 (dd, J = 8.8, 3.2 Hz, 1H), 6.99 (d, J = 8.8 Hz, 1H), 6.69 (t, J = 53.2 Hz, 1H), 3.88-3.82 (m, 1H), 3.41-3.37 (m, 2H), 3.27-3.25 (m, 1H), 3.21-3.15 (m, 1H), 2.84 (s, 3H), 2.10-2.02 (m, 1H), 1.95-1.81 (m, 1H). $^{19}$F NMR (376 MHz, CD$_3$OD) δ-124.2 (s, 2F). |
| 52 | LCMS: [M + H]$^+$ = 618.1. $^1$H NMR (400 MHz, CD$_3$OD) δ 7.81 (s, 2H), 7.16 (d, J = 3.2 Hz, 1H), 7.06 (dd, J = 9.2, 3.2 Hz, 1H), 6.95 (d, J = 9.2 Hz, 1H), 6.68 (t, J = 53.6 Hz, 1H), 4.42 (t, J = 8.4 Hz, 1H), 4.27-4.23 (m, 1H), 4.14-4.00 (m, 2H), 3.76-3.72 (m, 1H), 1.48-1.43 (m, 1H), 0.82-0.72 (m, 4H). $^{19}$F NMR (376 MHz, CD$_3$OD) δ-123.8 (s, 2F). |
| 53 | LCMS: [M + H]$^+$ = 621.1. $^1$H NMR (400 MHz, CD$_3$OD) δ 7.82 (s, 2H), 7.13 (d, J = 3.2 Hz, 1H), 7.08 (dd, J = 8.8, 3.2 Hz, 1H), 6.98 (d, J = 8.8 Hz, 1H), 6.72 (t, J = 52.8 Hz, 1H), 4.17-4.09 (m, 1 H), 4.02 (t, J = 8.4 Hz, 2H), 3.76 (dd, J = 8.4, 5.6 Hz, 2H), 2.80 (s, 6H). $^{19}$F NMR (376 MHz, CD$_3$OD) δ-124.3 (s, 2F). |
| 54 | LCMS: [M + H]$^+$ = 628.0. $^1$H NMR (400 MHz, CD$_3$OD) δ 7.82 (s, 2H), 7.15 (d, J = 3.2 Hz, 1H), 7.07 (dd, J = 9.2, 3.2 Hz, 1H), 6.97 (d, J = 9.2 Hz, 1H), 6.69 (t, J = 52.8 Hz, 1H), 4.24-4.20 (m, 1H), 3.88-3.78 (m, 2H), 3.76-3.74 (m, 2H), 2.88 (s, 3H). $^{19}$F NMR (376 MHz, CD$_3$OD) δ-124.0 (s, 2F). |
| 55 | LCMS: [M + H] $^+$ = 656.0. $^1$H NMR (400 MHz, CD$_3$OD) δ 7.82 (s, 2H), 7.15 (d, J = 2.8 Hz, 1H), 7.07 (dd, J = 8.8, 2.8 Hz, 1H), 6.99 (d, J = 8.8 Hz, 1H), 6.71 (t, J = 52.8 Hz, 1H), 3.95-3.86 (m, 1H), 3.70 (dd, J = 10.0, 6.8 Hz, 1H), 3.56-3.47 (m, 1H), 3.35-3.32 (m, 1H), 3.14 (dd, J = 10.0, 6.4 Hz, 1H), 3.03 (q, J = 7.2 Hz, 2H), 2.20-2.12 (m, 1H), 1.89-1.80 (m, 1H), 1.29 (t, J = 7.6 Hz, 3H). $^{19}$F NMR (376 MHz, CD$_3$OD) δ-124.2 (s, 2F). |
| 56 | LCMS: [M + H] $^+$ = 632.0. $^1$H NMR (400 MHz, CD$_3$OD) δ 7.82 (s, 2H), 7.15 (d, J = 2.8 Hz, 1H), 7.07 (dd, J = 9.2, 3.2 Hz, 1H), 6.99 (d, J = 8.8 Hz, 1H), 6.71 (t, J = 52.8 Hz, 1H), 4.31-4.24 (m, 1H), 3.60 (dd, J = 10.2, 6.4 Hz, 1H), 3.56-3.50 (m, 1H), 3.44-3.38 (m, 1H), 3.17 (dd, J = 10.0, 5.2 Hz, 1H), 2.14-2.06 (m, 1H), 1.87-1.79 (m, 1H), 1.56-1.48 (m, 1H), 0.83-0.77 (m, 2H), 0.76-0.68 (m, 2H). $^{19}$F NMR (376 MHz, CD$_3$OD) δ-124.2 (s, 2F). |
| 57 | LCMS: [M + H]$^+$ = 607.1/609.1. $^1$H NMR (400 MHz, CD$_3$OD) δ 7.82 (s, 2H), 7.12 (d, J = 2.8 Hz, 1H), 7.06 (dd, J = 8.8, 2.8 Hz, 1H), 6.96 (d, J = 8.8 Hz, 1H), 6.69 (t, J = 53.2 Hz, 1H), 4.17-4.13 (m, 1H), 3.97-3.93 (m, 2H), 3.70-3.66 (m, 2H), 2.63 (s, 3H). $^{19}$F NMR (376 MHz, CD$_3$OD) δ-123.9 (s, 2F). |

Example 24: Synthesis of Compound 58

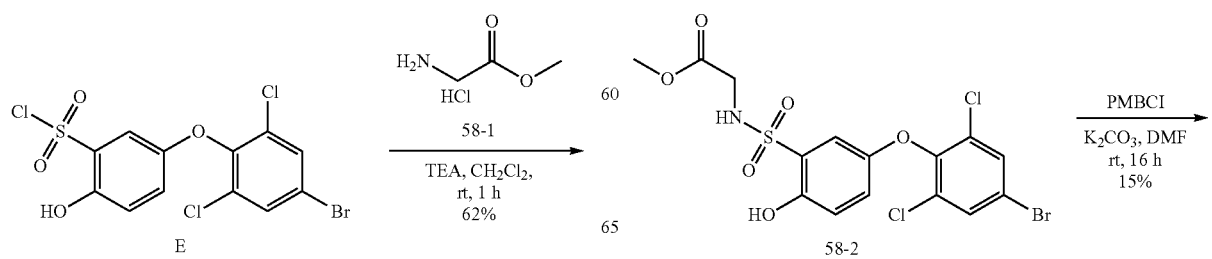

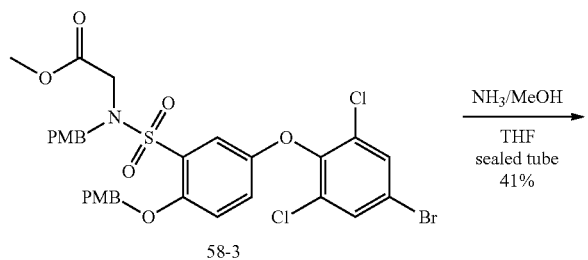

58-3

NH₃/MeOH
THF
sealed tube
41%

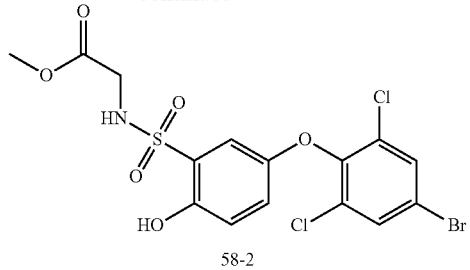

58-2

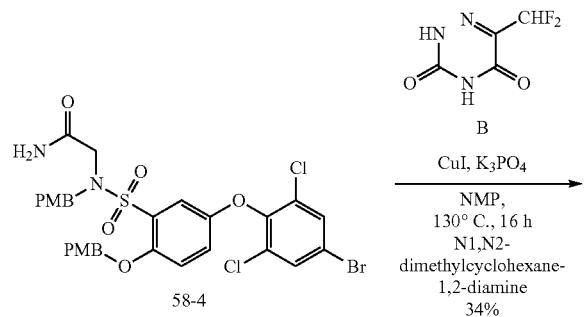

58-4

CuI, K₃PO₄
NMP,
130° C., 16 h
N1,N2-
dimethylcyclohexane-
1,2-diamine
34%

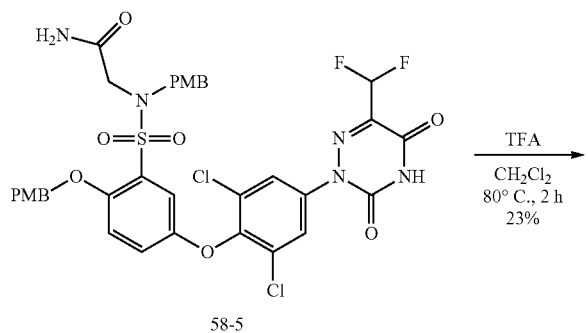

58-5

TFA
CH₂Cl₂
80° C., 2 h
23%

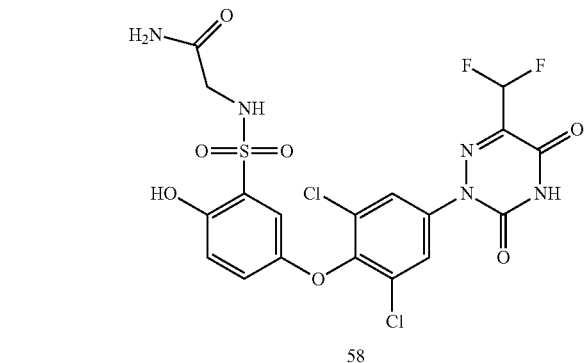

58

Step 1: 58-2

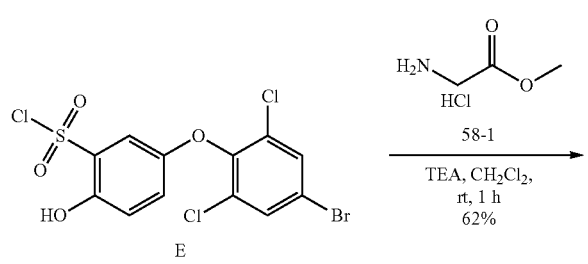

TEA, CH₂Cl₂,
rt, 1 h
62%

To a solution of methyl glycinate hydrochloride 58-1 (1.02 g, 8.09 mmol) and TEA (818.88 mg, 8.09 mmol) in CH₂Cl₂ (20 mL) was added 5-(4-bromo-2,6-dichloro-phenoxy)-2-hydroxy-benzenesulfonyl chloride Intermediate E (Example 5) (1 g, 2.31 mmol). The mixture was stirred at 25° C. for 1 h. LC-MS showed the reaction was completed. The reaction mixture was poured into water (50 mL) and extracted with CH₂Cl₂ (3×30 mL). The combined organic layer was washed with brine (50 mL), dried over anhydrous Na₂SO₄ and filtered. The filtrate was concentrated in vacuum. The residue was purified by silica gel chromatography (PE:EtOAc=2:1) to afford methyl 2-[[5-(4-bromo-2,6-dichloro-phenoxy)-2-hydroxy-phenyl]sulfonylamino]acetate 58-2 (700 mg, 62% yield) as a white solid. LCMS: [M+Na]=507.9.

Step 2: 58-3

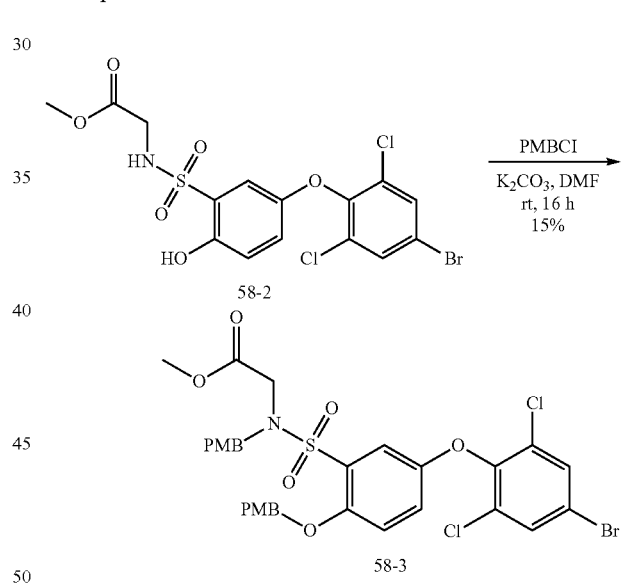

To a solution of methyl 2-[[5-(4-bromo-2,6-dichloro-phenoxy)-2-hydroxy-phenyl]sulfonylamino] acetate 58-2 (700 mg, 1.44 mmol) in DMF (7 mL) was added K₂CO₃ (398.83 mg, 2.89 mmol) and 1-(chloromethyl)-4-methoxy-benzene (316.36 mg, 2.02 mmol). The mixture was stirred at 25° C. for 16 h. LC-MS showed the reaction was completed. The reaction mixture was poured into water (50 mL) and extracted with CH₂Cl₂ (3×30 mL). The combined organic layer was washed with brine (3×20 mL), dried over anhydrous Na₂SO₄ and filtered. The filtrate was concentrated in vacuum. The residue was purified by silica gel chromatography (PE:EtOAc=5:1) to afford methyl 2-[[5-(4-bromo-2,6-dichloro-phenoxy)-2-[(4-methoxyphenyl)methoxy]phenyl]sulfonyl-[(4-methoxyphenyl)methyl] amino]acetate 58-3 (160 mg, 15% yield) as a white solid. LCMS: [M+Na]⁺=748.0.

Step 3: 58-4

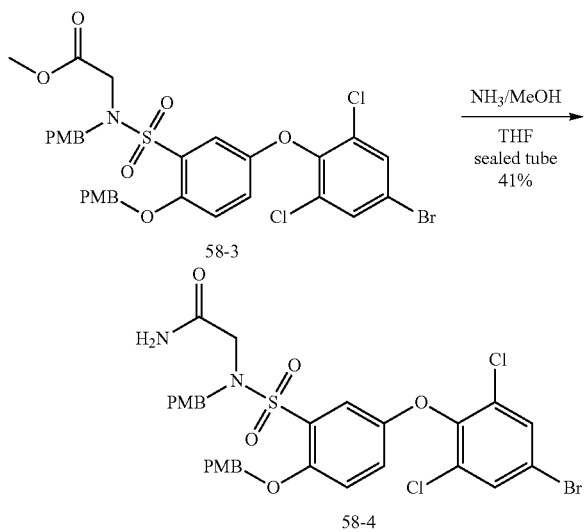

To a solution of methyl 2-[[5-(4-bromo-2,6-dichloro-phenoxy)-2-[(4-methoxyphenyl) methoxy]phenyl] sulfonyl-[(4-methoxyphenyl) methyl] amino]acetate 58-3 (160 mg, 220.56 umol) in THF (2 mL) was added $NH_3$ (6 M in MeOH, 5.83 mL). The mixture was sealed and stirred at 25° C. for 48 h. LC-MS showed the product was formed. The reaction mixture was concentrated in vacuum. The residue was purified by Prep-TLC (PE:EtOAc=1:1) to afford 2-[[5-(4-bromo-2,6-dichloro-phenoxy)-2-[(4-methoxyphenyl) methoxy]phenyl]sulfonyl-[(4-methoxyphenyl) methyl]amino]acetamide 58-4 (65 mg, 41% yield) as a white solid. LCMS: $[M+Na]^+=734.0$.

Step 4: 58-5

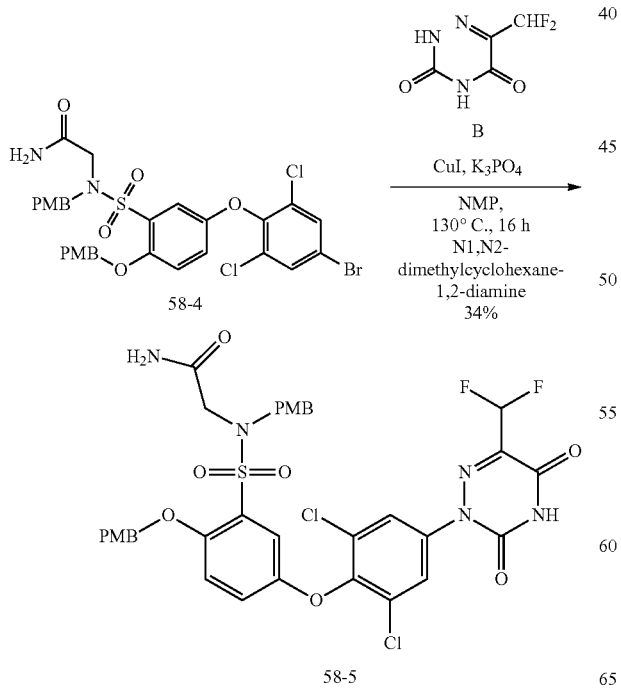

To a solution of 2-[[5-(4-bromo-2,6-dichloro-phenoxy)-2-[(4-methoxyphenyl)methoxy]phenyl]sulfonyl-[(4-methoxyphenyl)methyl]amino]acetamide 58-4 (65 mg, 91.50 umol) and 6-(difluoromethyl)-2H-1,2,4-triazine-3,5-dione Intermediate B (Example 2) (29.84 mg, 182.99 umol) in NMP (2 mL) was added N1,N2-dimethylcyclohexane-1,2-diamine (9.11 mg, 64.05 umol), CuI (34.85 mg, 182.99 umol) and $K_3PO_4$ (58.26 mg, 274.49 umol). The mixture was stirred in a sealed tube at 130° C. under $N_2$ (g) for 16 h. LC-MS showed the product was formed. The reaction mixture was diluted with EtOAc (80 mL), washed with aq. $NH_4Cl$ (3×50 mL) and brine (3×50 mL), dried over anhydrous $Na_2SO_4$ and filtered. The filtrate was concentrated in vacuum. The residue was purified by Prep-TLC ($CH_2Cl_2$: MeOH=10:1) to afford 2-[[5-[2,6-dichloro-4-[6-(difluoromethyl)-3,5-dioxo-1,2,4-triazin-2-yl] phenoxy]-2-[(4-methoxyphenyl) methoxy]phenyl]sulfonyl-[(4-methoxyphenyl)methyl]amino]acetamide 58-5 (25 mg, 34% yield) as a yellow solid. LCMS: $[M+Na]^+=814.0$.

Step 5: Compound 58

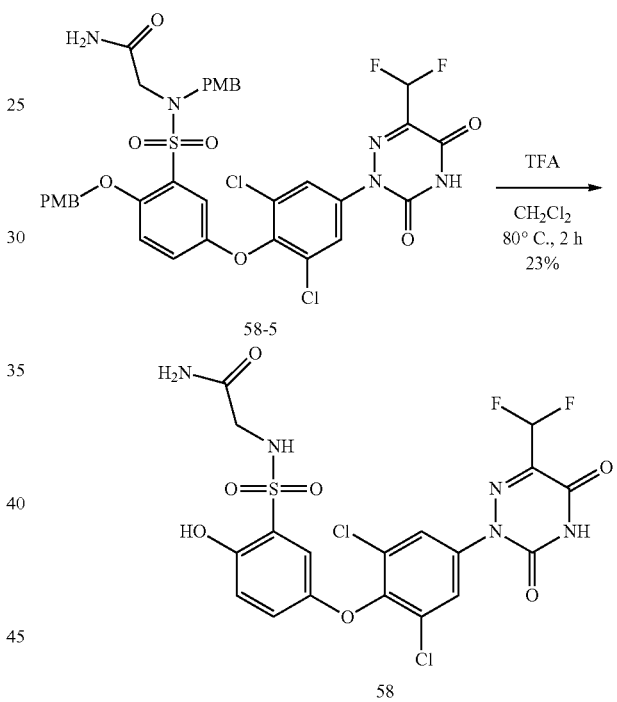

To a solution of 2-[[5-[2,6-dichloro-4-[6-(difluoromethyl)-3,5-dioxo-1,2,4-triazin-2-yl]phenoxy]-2-[(4-methoxyphenyl) methoxy] phenyl]sulfonyl-[(4-methoxyphenyl)methyl]amino]acetamide 58-5 (24 mg, 30.28 umol) in $CH_2Cl_2$ (2 mL) was added TFA (0.5 mL). The mixture was stirred at 80° C. under $N_2$ (g) for 2 h. LC-MS showed the reaction was completed. The reaction mixture was concentrated in vacuum. The residue was purified by Prep-HPLC(Chromatographic columns: Kromasil 100-5 C18 5 um 100×21.5 mm, Mobile Phase: MeCN—$H_2O$ (0.1% FA), Gradient: 30-40, Flow Rate: 25 ml/min) to afford 2-((5-(2,6-dichloro-4-(6-(difluoromethyl)-3,5-dioxo-4,5-dihydro-1,2,4-triazin-2(3H)-yl)phenoxy)-2-hydroxyphenyl)sulfonamido)acetamide Compound 58 (3.9 mg, 23% yield) as a white solid. LCMS: $[M+H]^+=552.0$. $^1H$ NMR (400 MHz, $CD_3OD$) δ 7.82 (s, 2H), 7.18 (d, J=3.2 Hz, 1H), 7.05 (dd, J=8.8, 2.8 Hz, 1H), 6.97 (d, J=8.4 Hz, 1H), 6.71 (t, J=52.8 Hz, 1H), 3.55 (s, 2H). $^{19}F$ NMR (376 MHz, $CD_3OD$) δ −124.3 (s, 2F).

The compounds of Formula (I') or (I) in Table 10 below were made according to Example 24 of Compound 58.

TABLE 10

| Cmpd No. | LC-MS, $^1$H and $^{19}$F-NMR data |
| --- | --- |
| 59 | LCMS: [M + H]$^+$ = 592.0. 1H NMR (400 MHz, CD$_3$OD) δ 7.80 (s, 2H), 7.19 (d, J = 3.2 Hz, 1H), 7.03 (dd, J = 9.2, 3.2 Hz, 1H), 6.96 (d, J = 8.8 Hz, 1H), 6.69 (t, J = 53.6 Hz,, 1H), 3.54 (s, 2H), 2.61-2.54 (m, 1H), 0.68-0.65 (m, 2H), 0.47-0.41 (m, 2H). $^{19}$F NMR (376 MHz, CD$_3$OD) δ-124.1 (s, 2F). |
| 60 | LCMS: [M + H]$^+$ = 566.0/568.0. 1H NMR (400 MHz, CD$_3$OD) δ 7.81 (s, 2H), 7.17 (d, J = 3.2 Hz, 1H), 7.05 (dd, J = 9.2, 3.2Hz, 1H), 6.98 (d, J = 8.8 Hz, 1H), 6.70 (t, J = 53.2 Hz, 1H), 3.53 (s, 2H), 2.71 (s, 3H). $^{19}$F NMR (376 MHz, CD$_3$OD) δ-124.1 (s, 2F). |
| 61 | LCMS: [M + H]$^+$ = 606.1/608.1. $^1$H NMR (400 MHz, CD$_3$OD) δ 7.81 (s, 2H), 7.09 (d, J = 2.8 Hz, 1H), 7.06 (dd, J = 8.8, 3.2 Hz, 1H), 6.95 (d, J = 8.8 Hz, 1H), 6.70 (t, J = 53.2 Hz, 1H), 4.02-3.94 (m, 1H), 2.84-2.78 (m, 1H), 2.67 (s, 3H), 2.26-2.20 (m, 2H), 2.18-2.10 (m, 2H). $^{19}$F NMR (376 MHz, CD$_3$OD) δ-124.1 (s, 2F). |
| 62 | LCMS: [M + H]$^+$ = 606.1. $^1$H NMR (400 MHz, CD$_3$OD) δ 7.81 (s, 2H), 7.19 (d, J = 2.8 Hz, 1H), 7.04 (dd, J = 2.8, 8.8 Hz, 1H), 6.97 (d, J = 8.8 Hz, 1H), 6.71 (t, J = 53.2 Hz, 1H), 4.25-4.17 (m, 1H), 3.54 (s, 2H), 2.26-2.18 (m, 2H), 1.93-1.88 (m, 2H), 1.74-1.67 (m, 2H). $^{19}$F NMR (376 MHz, CD$_3$OD) δ-124.2 (s, 2F). |

Example 25: Synthesis of Compound 63

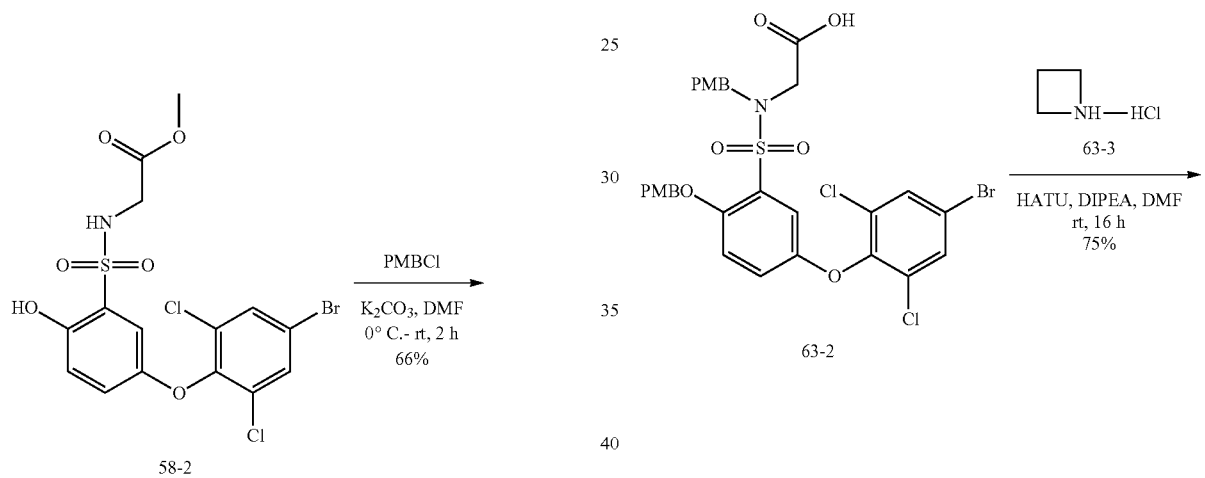

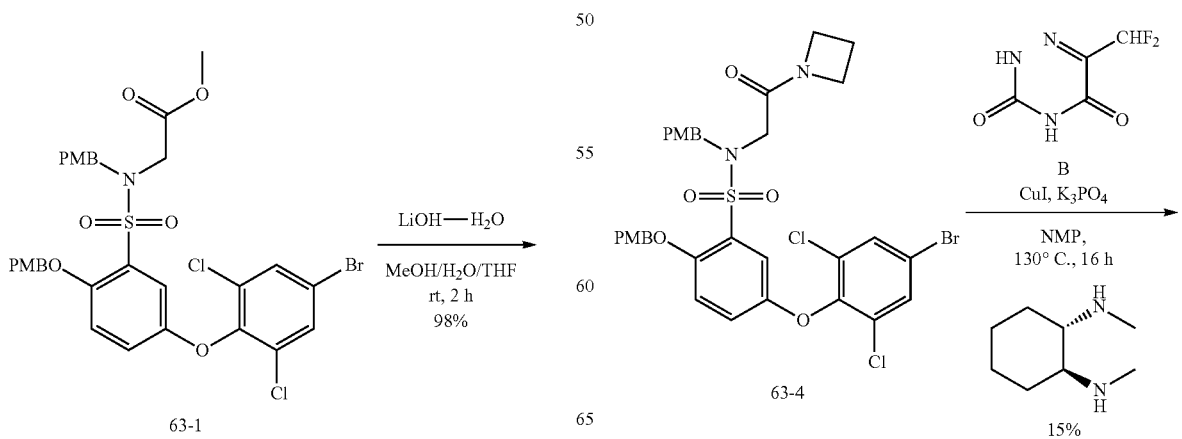

-continued

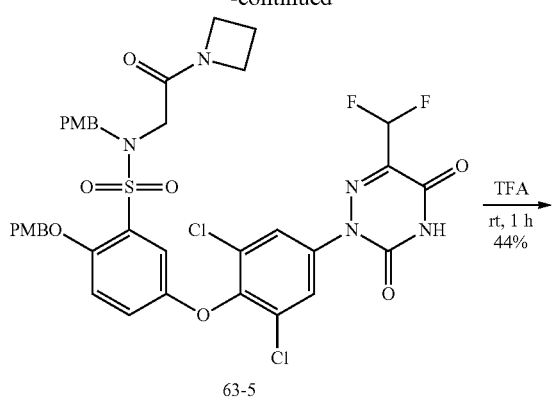
63-5

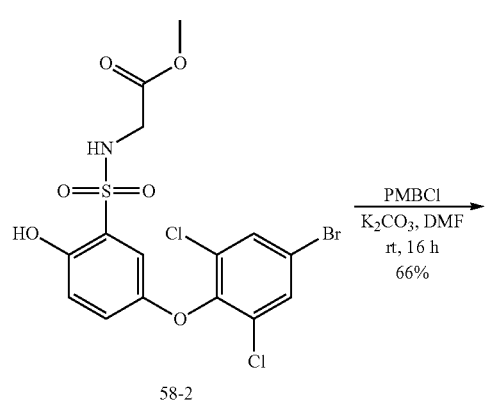
63

Step 1: 63-1

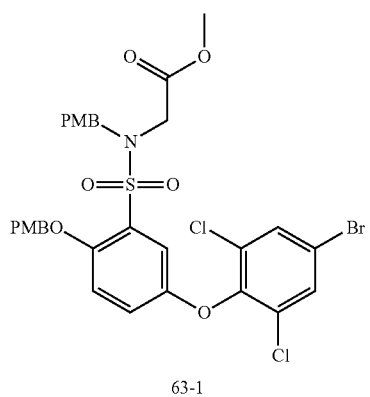
58-2

To a mixture of methyl 2-[[5-(4-bromo-2,6-dichloro-phenoxy)-2-hydroxy-phenyl] sulfonyl amino] acetate 58-2 (2.0 g, 4.12 mmol) and potassium carbonate (1.71 g, 12.37 mmol) in DMF (20 mL) at rt was added 1-(chloromethyl)-4-methoxy-benzene (1.29 g, 8.25 mmol). The reaction mixture was stirred at rt for 16 h. LC-MS showed the reaction worked. The reaction mixture was poured into water (50 mL) and extracted with EtOAc (3×20 mL). The combined organic layer was washed with brine (20 mL), dried over anhydrous Na$_2$SO$_4$ and filtered. The filtrate was concentrated in vacuum to afford a residue. The residue was purified by silica gel chromatography (PE:EtOAc=3:1) to afford methyl 2-[[5-(4-bromo-2,6-dichloro-phenoxy)-2-[(4-methoxyphenyl) methoxy] phenyl] sulfonyl-[(4-methoxyphenyl) methyl] amino] acetate 63-1 (2.0 g, 66% yield) as a light-yellow solid. LCMS: [M+Na]$^+$=745.9.

Step 2: 63-2

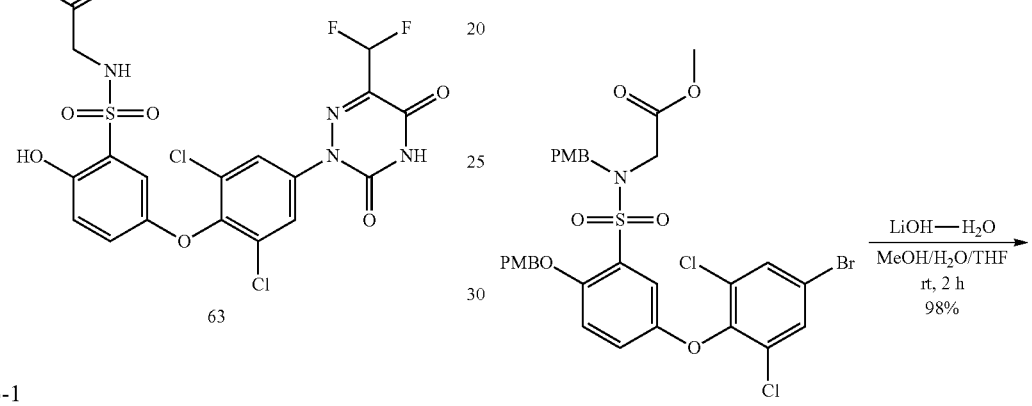
63-1

63-2

A mixture of methyl 2-[[5-(4-bromo-2,6-dichloro-phenoxy)-2-[(4-methoxyphenyl)methoxy]phenyl]sulfonyl-[(4-methoxyphenyl)methyl]amino]acetate 63-1 (1.5 g, 2.07 mmol) and LiOH—H$_2$O (260.54 mg, 6.20 mmol) in water (5 mL), MeOH (5 mL) and THF (5 mL) was stirred at rt for 2 h. LC-MS showed the reaction was completed. The reaction mixture was concentrated in vacuum. The residue was added into water (50 mL) and PH was adjusted to 2-3. The mixture was extracted with EtOAc (3×20 mL). The combined organic layer was washed with brine (20 mL), dried over anhydrous Na$_2$SO$_4$ and filtered. The filtrate was concentrated in vacuum to afford 2-[[5-(4-bromo-2,6-dichloro-phenoxy)-2-[(4-methoxyphenyl) methoxy] phenyl] sulfonyl-[(4-methoxyphenyl) methyl] amino] acetic acid 63-2 (1.45 g, 98% yield) as a light-yellow oil. LCMS: [M+Na]$^+$=732.2.

Step 3: 63-4

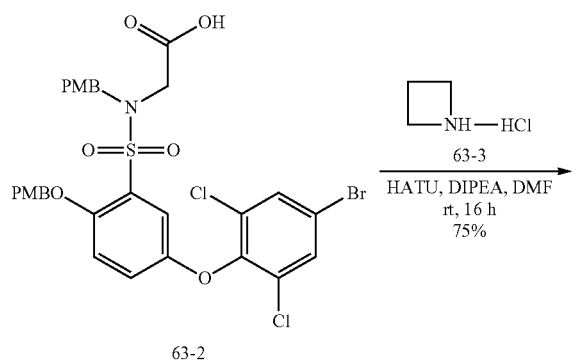

Step 4: 63-5

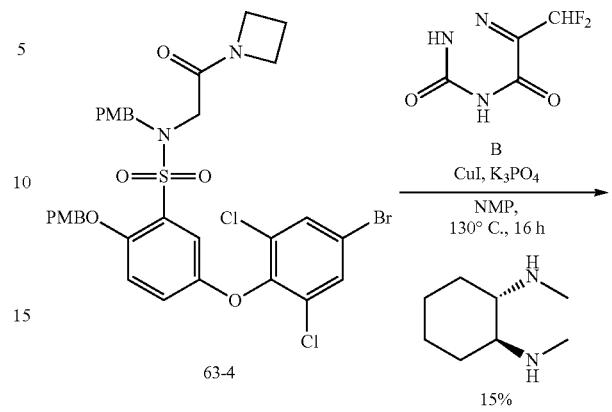

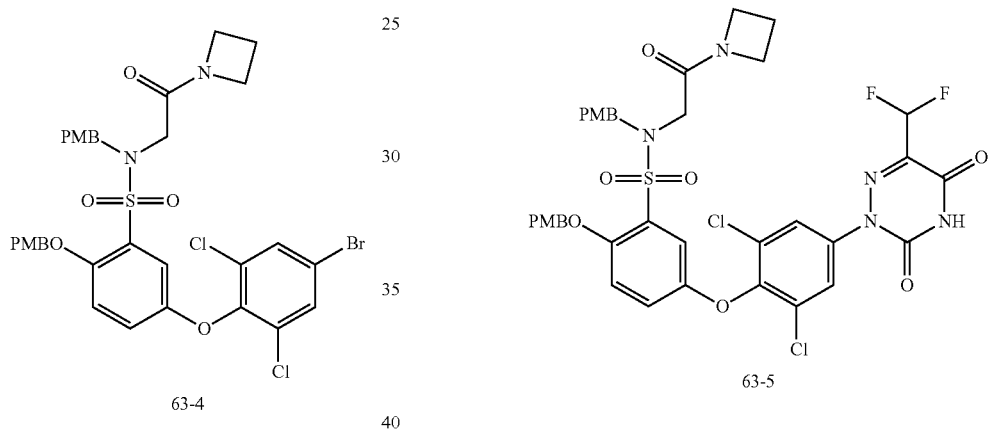

To a solution of 2-[[5-(4-bromo-2,6-dichloro-phenoxy)-2-[(4-methoxyphenyl)methoxy]phenyl]sulfonyl-[(4-methoxyphenyl)methyl]amino]acetic acid 63-2 (500 mg, 702.84 umol) in DMF (10 mL) at rt was added HATU (400.86 mg, 1.05 mmol) and azetidine hydrochloride 63-3 (197.26 mg, 2.11 mmol). The reaction mixture was stirred at rt for 10 mins. Then N, N-Diisopropylethylamine (272.51 mg, 2.11 mmol, 367.26 uL) was added into the reaction mixture. The reaction mixture was stirred for 16 h. LC-MS showed the reaction was completed. The reaction mixture was poured into water (50 mL) and extracted with EtOAc (3×20 mL). The combined organic layer was washed with brine (20 mL), dried over anhydrous $Na_2SO_4$ and filtered. The filtrate was concentrated in vacuum. The residue was purified by silica gel chromatography (PE:EtOAc=2:1) to afford N-[2-(azetidin-1-yl)-2-oxo-ethyl]-5-(4-bromo-2,6-dichloro-phenoxy)-2-[(4-methoxyphenyl)methoxy]-N-[(4-methoxyphenyl)methyl] benzene sulfonamide 63-4 (400 mg, 75% yield) as a light-yellow oil. LCMS: $[M+Na]^+=771.2$.

A mixture of N-[2-(azetidin-1-yl)-2-oxo-ethyl]-5-(4-bromo-2,6-dichloro-phenoxy)-2-[(4-methoxyphenyl)methoxy]-N-[(4-methoxyphenyl)methyl]benzenesulfonamide 63-4 (200 mg, 266.50 umol), 6-(difluoromethyl)-2H-1,2,4-triazine-3,5-dione Intermediate B (Example 2) (86.92 mg, 532.99 umol), cuprous iodide (126.89 mg, 666.24 umol), (1R,2R)—N1,N2-dimethylcyclohexane-1,2-diamine (30.33 mg, 213.20 umol) and potassium phosphate (169.70 mg, 799.49 umol) in NMP (4 mL) was stirred at 130° C. under $N_2$ (g) in a sealed tube for 16 h. LC-MS showed the reaction was completed. The reaction mixture was poured into water (50 mL) and extracted with EtOAc (3×20 mL). The combined organic layer was washed with brine (20 mL), dried over anhydrous $Na_2SO_4$ and filtered. The filtrate was concentrated in vacuum to afford a residue. The residue was purified by Prep-TLC ($CH_2Cl_2$:MeOH=20:1) to afford N-[2-(azetidin-1-yl)-2-oxo-ethyl]-5-[2,6-dichloro-4-[6-(difluoromethyl)-3,5-dioxo-1,2,4-triazin-2-yl]phenoxy]-2-[(4-methoxyphenyl)methoxy]benzenesulfonamide 63-5 (30 mg, 15% yield) as a light-yellow solid. LCMS: $[M+Na]^+=854.1$.

Step 5: Compound 63

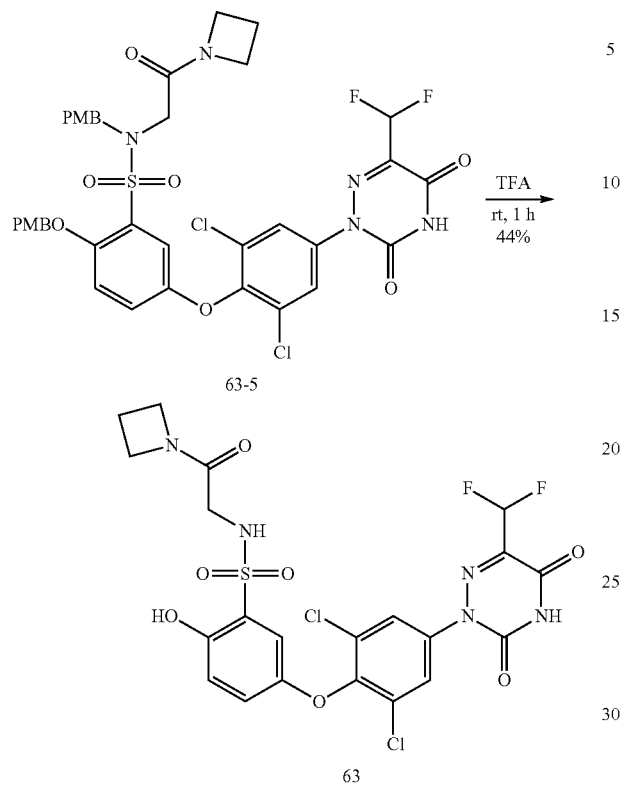

A mixture of N-[2-(azetidin-1-yl)-2-oxo-ethyl]-5-[2,6-dichloro-4-[6-(difluoromethyl)-3,5-dioxo-1,2,4-triazin-2-yl]phenoxy]-2-[(4-methoxyphenyl)methoxy]-N-[(4-methoxyphenyl)methyl]benzenesulfonamide 63-5 (30 mg, 36.03 umol) in TFA (4 mL) was stirred at rt for 2 h. LC-MS showed the reaction was completed. The reaction mixture was concentrated in vacuum. The residue was dissolved in CH$_2$Cl$_2$ (5 mL) and to the mixture was added NH$_3$ in MeOH (7 M/L, 1 mL). The reaction mixture was concentrated in vacuum. The residue was purified by Prep-HPLC (Chromatographic columns: Kromasil-C18 100×21.2 mm, 5 um Mobile Phase: MeCN—H$_2$O 0.1% FA), Gradient: 35-45) to afford N-[2-(azetidin-1-yl)-2-oxo-ethyl]-5-[2,6-dichloro-4-[6-(difluoromethyl)-3,5-dioxo-1,2,4-triazin-2-yl] phenoxy]-2-hydroxy-benzenesulfonamide Compound 63 (9.5 mg, 44% yield) as a white solid. LCMS: [M+H]$^+$=592.0. $^1$H NMR (400 MHz, CD$_3$OD) δ 7.82 (s, 2H), 7.18 (d, J=3.2 Hz, 1H), 7.06 (dd, J=9.2, 3.2 Hz, 1H), 6.97 (d, J=8.8 Hz, 1H), 6.71 (t, J=52.8 Hz, 1H), 4.19 (t, J=7.6 Hz, 2H), 3.93 (t, J=8.0 Hz, 2H), 3.56 (s, 2H), 2.32-2.22 (m, 2H). $^{19}$F NMR (376 MHz, CD$_3$OD) δ−124.1 (s, 2F).

Example 26: Synthesis of Compound 64

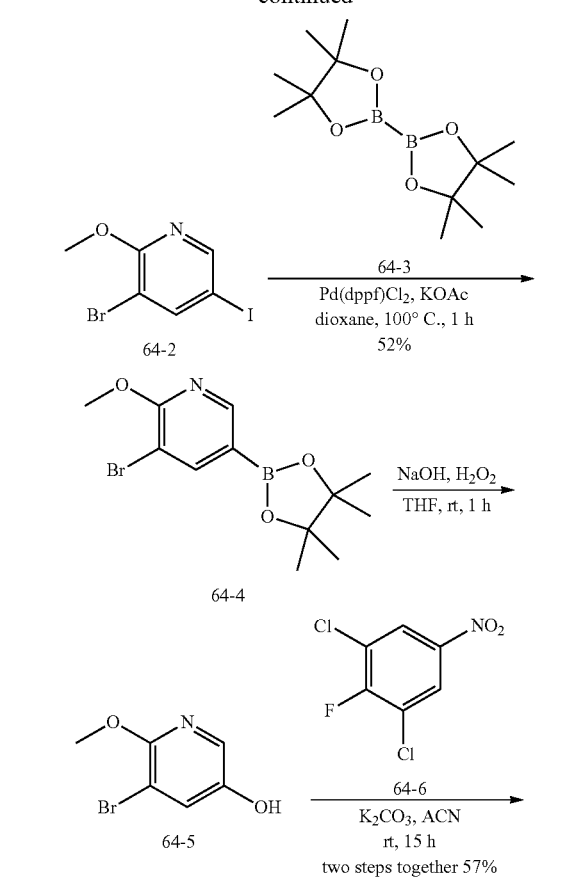

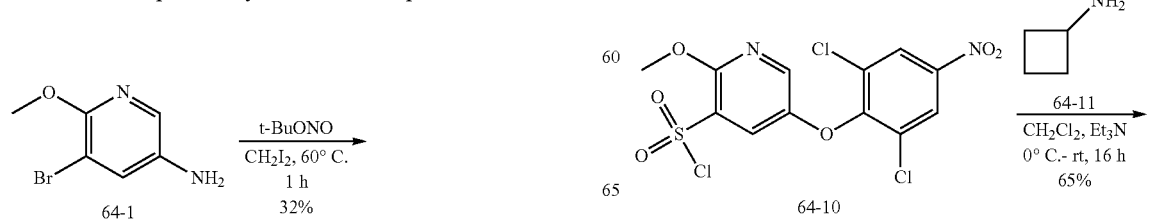

-continued

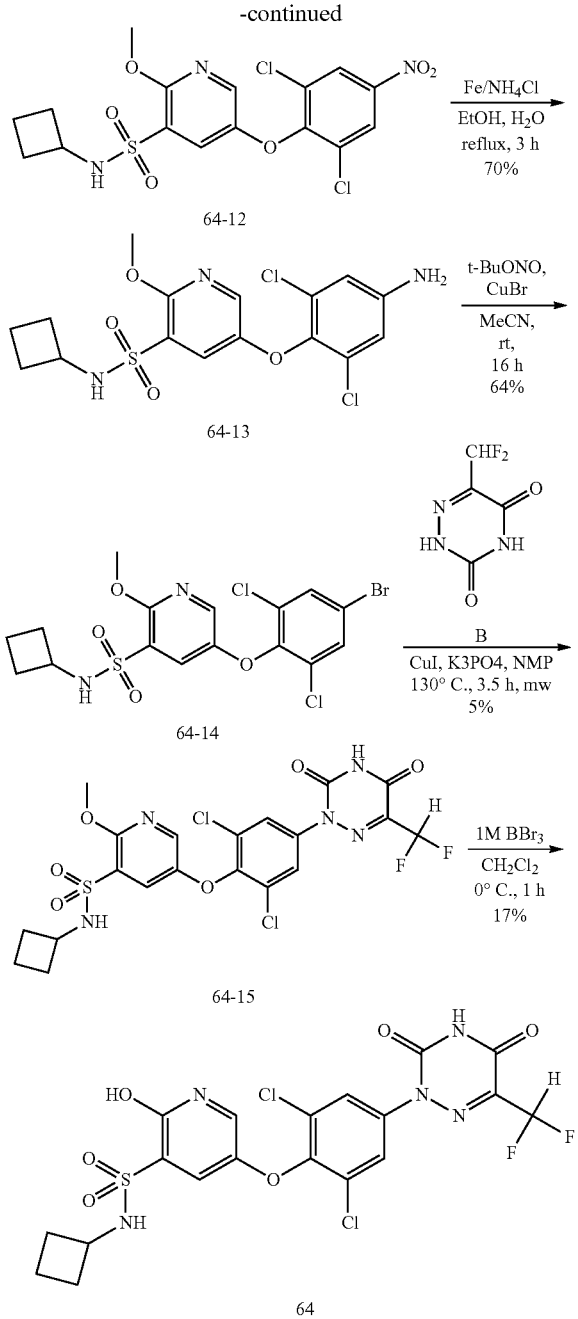

Step 1: 64-2

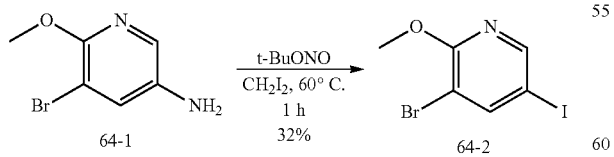

To a solution of 5-bromo-6-methoxy-pyridin-3-amine 64-1 (10 g, 49.25 mmol) in Diiodomethane (263.83 g, 985.05 mmol, 79.23 mL) was added ʹBuONO (11.16 g, 108.36 mmol) slowly. The mixture was stirred at 60° C. for 1 h. LCMS showed the product was formed. The reaction mixture was poured into water and extracted with EtOAc (3×100 mL). The combined organic layer was dried over anhydrous Na$_2$SO$_4$. The reaction mixture was filtered and concentrated in vacuum to afford a residue. The residue was purified by silica gel chromatography PE (100%) to afford 3-bromo-5-iodo-2-methoxy-pyridine 64-2 (5.0 g, 32% yield) as a yellow solid. LCMS: [M+H]$^+$=314.0/315.9.

Step 2: 64-4

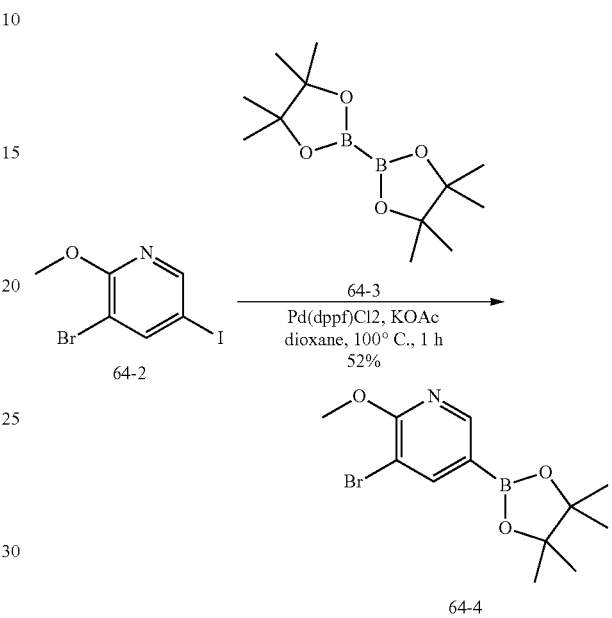

A solution of 3-bromo-5-iodo-2-methoxy-pyridine 64-2 (3.8 g, 12.11 mmol), 4,4,5,5-tetramethyl-2-(4,4,5,5-tetramethyl-1,3,2-dioxaborolan-2-yl)-1,3,2-dioxaborolane 64-3 (2.46 g, 9.68 mmol), Pd(dppf)Cl$_2$ (4.94 g, 6.76 mmol) and KOAc (3.56 g, 36.32 mmol) in dioxane (5 mL) under N$_2$ was stirred at 100° C. under microwave for 1 h. LCMS showed the reaction was completed. The reaction mixture was poured into water and extracted with EtOAc (3×50 mL). The combined organic layer was dried over anhydrous Na$_2$SO$_4$, filtered and concentrated in vacuum to afford a residue. The residue was purified by silica gel chromatography (PE: EtOAc=50:1) to afford 3-bromo-2-methoxy-5-(4,4,5,5-tetramethyl-1,3,2-dioxaborolan-2-yl) pyridine 64-4 (2.0 g, 52% yield) as a yellow solid. LCMS: [M+H]$^+$=314.1/316.1.

Step 3: 64-5

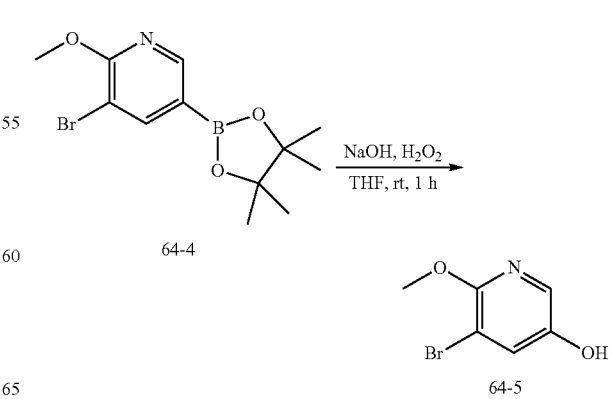

To a solution of 3-bromo-2-methoxy-5-(4,4,5,5-tetramethyl-1,3,2-dioxaborolan-2-yl) pyridine 64-4 (1.5 g, 4.78 mmol) in THF (20 mL) 2N NaOH (5 ml) and 30% H₂O₂ (3 ml) was added. The mixture was stirred at 25° C. for 1 h. LCMS showed the reaction was complete and the desired product was detected. The reaction was used for the next step without further work up. LCMS: [M+H]⁺=204.0/206.0.

Step 4: 64-7

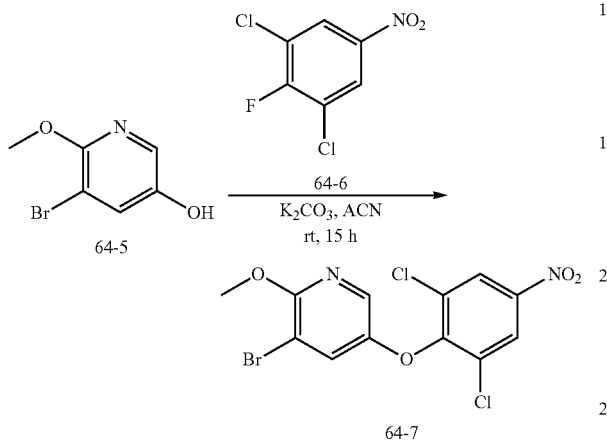

To a solution of 5-bromo-6-methoxy-pyridin-3-ol 64-5 (966 mg, 4.73 mmol) from previous step was added 1,3-dichloro-2-fluoro-5-nitro-benzene 64-6 (994.26 mg, 4.73 mmol) and K₂CO₃ (1.31 g, 9.47 mmol). The reaction was stirred at 25° C. for 15 h. LCMS showed the product was formed. The reaction mixture was poured into water and extracted with EtOAc (3×50 mL). The combined organic layer was dried over anhydrous Na₂SO₄, filtered and concentrated in vacuum to afford a residue. The residue was purified by silica gel chromatography (PE:EtOAc=50:1) to afford 3-bromo-5-(2,6-dichloro-4-nitro-phenoxy)-2-methoxy-pyridine 64-7 (1.08 g, 57% yield) as a yellow solid. LCMS: [M+H]⁺=392.9/394.9.

Step 5: 64-9

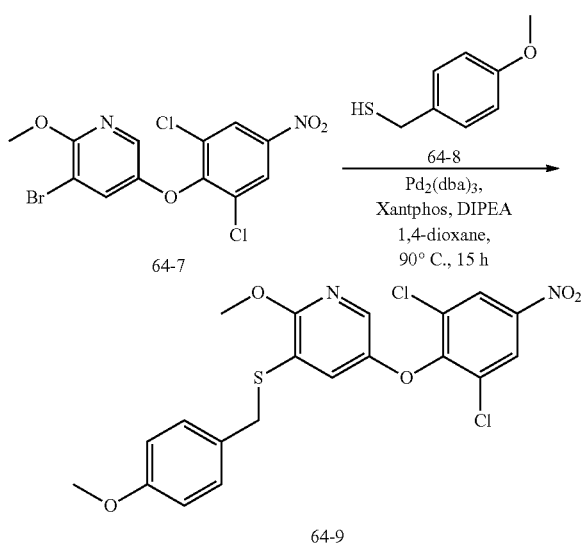

A mixture of 3-bromo-5-(2,6-dichloro-4-nitro-phenoxy)-2-methoxy-pyridine 64-7 (1.2 g, 3.05 mmol), (4-methoxyphenyl) methanethiol 64-8 (469.73 mg, 3.05 mmol), Pd₂(dba)₃ (139.34 mg, 152.28 umol), xantphos (44.0 mg, 76.1 umol) and DIPEA (785.78 mg, 6.09 mmol) in dioxane (10 mL) was stirred at 90° C. for 15 h under N₂ atmosphere. LCMS showed the reaction was completed. The residue was added into water (50 mL) and extracted with EtOAc (3×20 mL). The organic phase was washed with brine (50 mL), dried over anhydrous Na₂SO₄, filtered and concentrated in vacuum to afford a residue. The residue was purified by flash chromatography (PE:EtOAc=30:1) to afford 5-(2,6-dichloro-4-nitro-phenoxy)-2-methoxy-3-(4-methoxyphenyl) pyridine 64-9 (1.2 g, 93% yield) as a yellow oil. LCMS: [M+H]⁺=467.0/469.1.

Step 6: 64-10

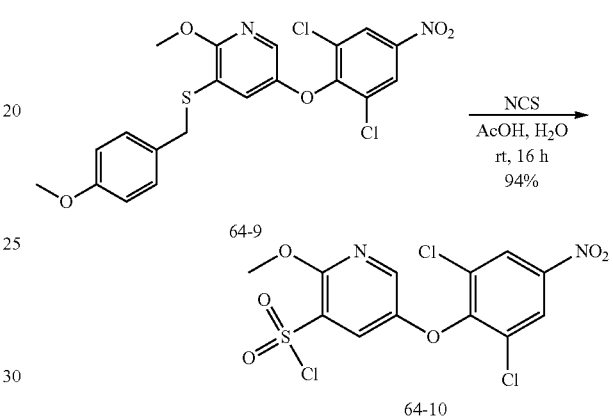

To a solution of 5-(2,6-dichloro-4-nitro-phenoxy)-2-methoxy-3-[(4-methoxyphenyl) methylsulfanyl] pyridine 64-9 (1.2 g, 2.57 mmol) in AcOH (3 mL) and H₂O (1 mL) was added NCS (1.37 g, 10.27 mmol) slowly at 0° C. The mixture was stirred at 25° C. for 16 h. LCMS showed the product was formed. The residue was added into water (50 mL) and extracted with EtOAc (3×100 mL). The combined organic layer was dried over anhydrous Na₂SO₄, filtered and concentrated in vacuum to afford a residue. The residue was purified by silica gel chromatography (PE:EtOAc=30:1) to afford 5-(2,6-dichloro-4-nitro-phenoxy)-2-methoxy-pyridine-3-sulfonyl chloride 64-10 (1 g, 94% yield) as a yellow solid.

Step 7: 64-12

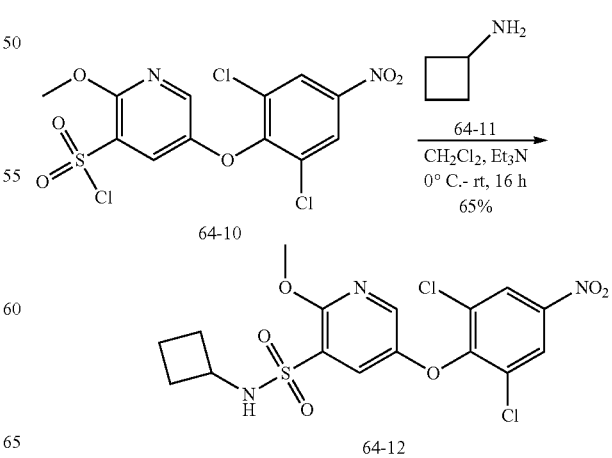

To a solution of 5-(2,6-dichloro-4-nitro-phenoxy)-2-methoxy-pyridine-3-sulfonyl chloride 64-10 (700 mg, 1.69 mmol) and cyclobutanamine 64-11 (180.55 mg, 2.54 mmol) in DCM (3 mL) was added TEA (342.50 mg, 3.38 mmol) at 0° C. The mixture was stirred at 25° C. for 16 h. LCMS showed the product was formed. The residue was added into water (50 mL) and extracted with EtOAc (3×100 mL). The combined organic layer was dried over anhydrous $Na_2SO_4$, filtered and concentrated in vacuum to afford a residue. The residue was purified by silica gel chromatography (PE: EtOAc=5:1) to afford N-cyclobutyl-5-(2,6-dichloro-4-nitro-phenoxy)-2-methoxy-pyridine-3-sulfonamide 64-12 (500 mg, 65% yield) as a yellow solid. LCMS: $[M+H]^+=448.0/450.0$.

Step 8: 64-13

To a mixture of $^tBuONO$ (162.52 mg, 1.58 mmol) and CuBr (169.76 mg, 1.18 mmol) in $CH_3CN$ (3 mL) was added 5-(4-amino-2,6-dichloro-phenoxy)-N-cyclobutyl-2-methoxy-pyridine-3-sulfonamide 64-13 (330 mg, 788.92 umol). The reaction was stirred at 25° C. for 15 h. LCMS showed the product was formed. The reaction mixture was poured into water and extracted with EtOAc (3×50 mL). The combined organic layer was dried over anhydrous $Na_2SO_4$, filtered and concentrated in vacuum to afford a residue. The residue was purified by silica gel chromatography (PE: EtOAc=5:1) to afford 5-(4-bromo-2,6-dichloro-phenoxy)-N-cyclobutyl-2-methoxy-pyridine-3-sulfonamide 64-14 (245 mg, 64% yield) as a yellow solid. LCMS: $[M+H]^+=481.0/483.0$.

Step 10: 64-15

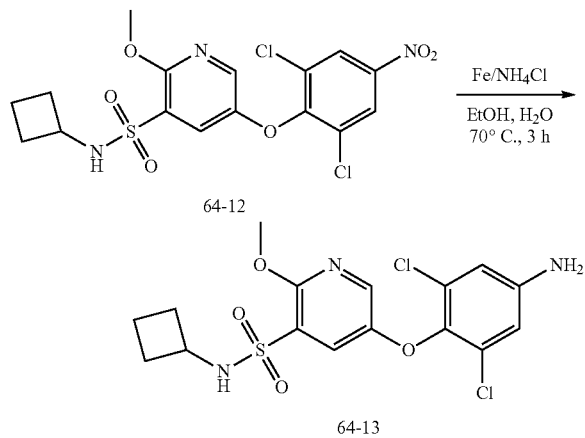

A solution of N-cyclobutyl-5-(2,6-dichloro-4-nitro-phenoxy)-2-methoxy-pyridine-3-sulfonamide 64-12 (500 mg, 1.12 mmol), Fe (622.88 mg, 11.15 mmol) and $NH_4Cl$ (301.15 mg, 5.58 mmol) in $H_2O$ (5 mL) and EtOH (5 mL) was stirred at 70° C. for 3 h. LCMS showed the reaction was completed. The reaction mixture was poured into water and extracted with EtOAc (3×100 mL). The combined organic layer was dried over anhydrous $Na_2SO_4$, filtered and concentrated in vacuum to afford a residue. The residue was used for next step without further purification. LCMS: $[M+H]^+=418.1/420.0$.

Step 9: 64-14

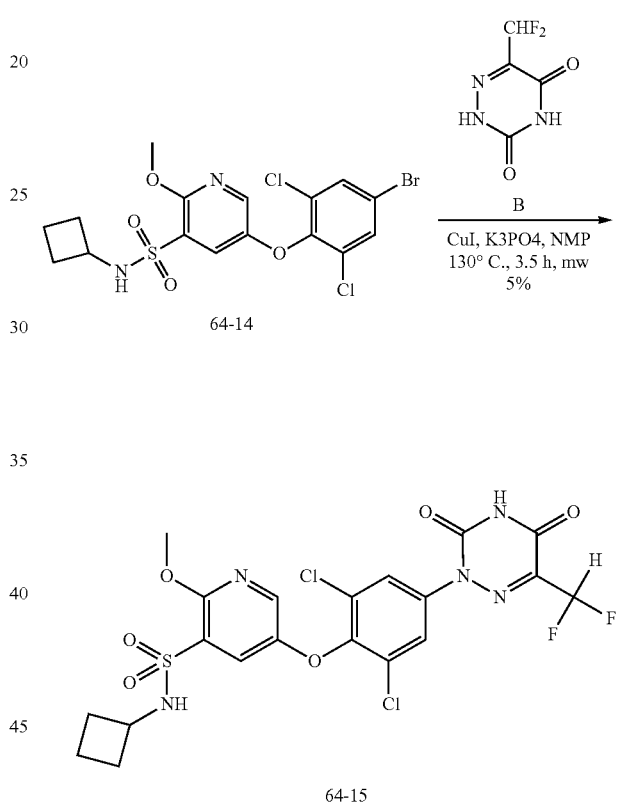

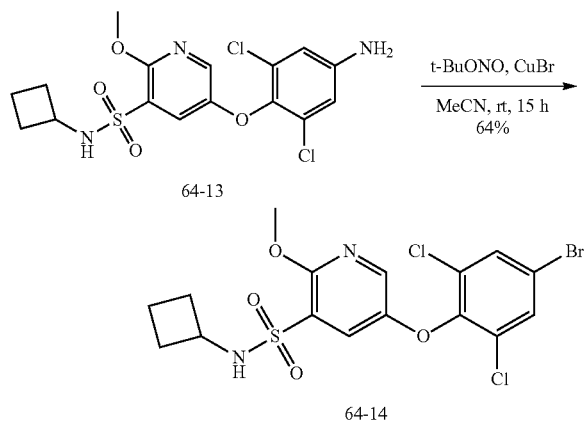

A mixture of 5-(4-bromo-2,6-dichloro-phenoxy)-N-cyclobutyl-2-methoxy-pyridine-3-sulfonamide 64-14 (100 mg, 207.39 umol), 6-(difluoromethyl)-2H-1,2,4-triazine-3,5-dione Intermediate B (Example 2) (67.64 mg, 414.79 umol), (1S,2S)-cyclohexane-1,2-diamine (18.95 mg, 165.91 umol), CuI (98.75 mg, 518.48 umol) and $K_3PO_4$ (131.90 mg, 622.18 umol) in NMP (2 mL) under $N_2$ was stirred at 130° C. under microwave for 3.5 h. LCMS showed the product was formed. The reaction mixture was poured into water and extracted with EtOAc (3×50 mL). The combined organic layer was dried over anhydrous $Na_2SO_4$, filtered and concentrated in vacuum to afford a residue. The residue was purified by prep-TLC ($CH_2Cl_2$:MeOH=20:1) to afford N-cyclobutyl-5-[2,6-dichloro-4-[6-(difluoromethyl)-3,5-dioxo-1,2,4-triazin-2-yl]phenoxy]-2-methoxy-pyridine-3-sulfonamide 64-15 (6 mg, 5% yield) as a yellow solid. LCMS: $[M+H]^+=564.0/566.0$.

Step 11: Compound 64

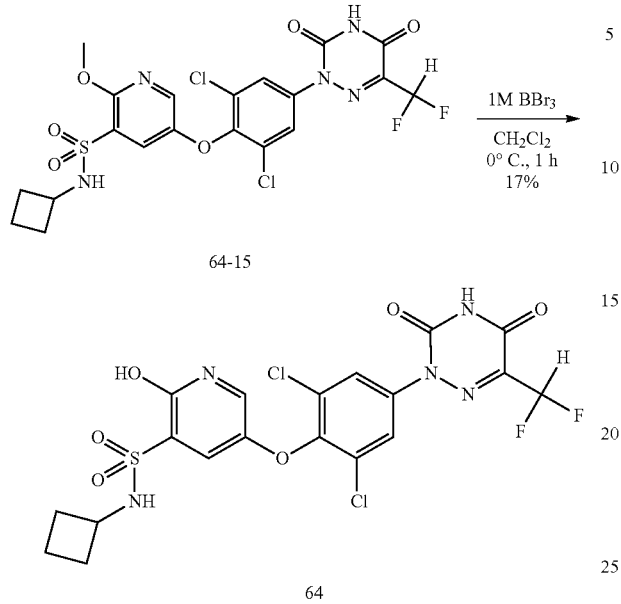

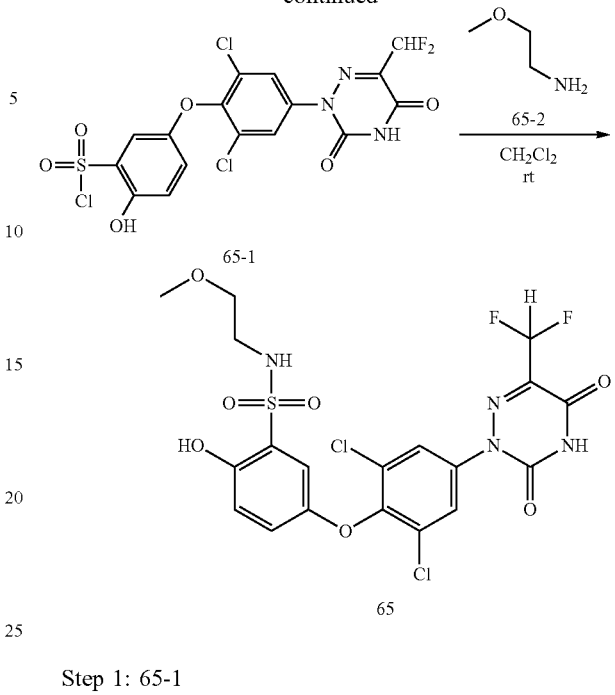

A solution of N-cyclobutyl-5-[2,6-dichloro-4-[6-(difluoromethyl)-3,5-dioxo-1,2,4-triazin-2-yl]phenoxy]-2-methoxy-pyridine-3-sulfonamide 64-15 (6 mg, 10.63 umol) and BBr$_3$ (79.74 mg, 318.95 umol) in CH$_2$Cl$_2$ (2 mL) was stirred at 0° C. for 1 h. LCMS showed the product was formed. The reaction mixture was poured into water and extracted with EtOAc (3×50 mL). The combined organic layer was dried over anhydrous Na$_2$SO$_4$, filtered and concentrated in vacuum to afford a residue. The residue was purified by Prep-HPLC (Xbridge 5 u C18 150×19 mm, Mobile Phase: MeCN—H$_2$O (0.1% FA), Gradient: 44-54) to afford N-cyclobutyl-5-[2,6-dichloro-4-[6-(difluoromethyl)-3,5-dioxo-1,2,4-triazin-2-yl] phenoxy]-2-hydroxy-pyridine-3-sulfonamide Compound 64 (6 mg, 17% yield) as a white solid. LCMS: [M+H]$^+$=550.0/552.0. $^1$H NMR (400 MHz, CD$_3$OD) δ 7.78 (s, 2H), 7.63 (d, J=3.2 Hz, 1H), 7.59 (d, J=2.8 Hz, 1H), 6.65 (t, J=54.0 Hz, 1H), 3.70-3.64 (m, 1H), 2.02-1.97 (m, 2H), 1.89-1.84 (m, 2H), 1.61-1.52 (m, 2H). $^{19}$F NMR (376 MHz, CD$_3$OD) δ −123.8 (s, 2F).

Example 27: Synthesis of Compound 65

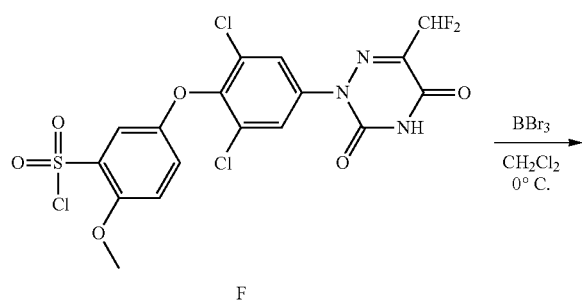

Step 1: 65-1

To a mixture of 5-[2,6-dichloro-4-[6-(difluoromethyl)-3,5-dioxo-1,2,4-triazin-2-yl] phenoxy]-2-methoxy-benzenesulfonyl chloride Intermediate F (Example 6) (10 mg, crude) in CH$_2$Cl$_2$ (1 mL) at 0° C. was added boron tribromide CH$_2$Cl$_2$ solution (1 M, 378.29 uL). The reaction mixture was stirred at 0° C. for 1.0 h. LC-MS showed the reaction worked. The reaction mixture was poured into water (50 mL) and extracted with EtOAc (3×20 mL). The combined organic layer was washed with brine (20 mL), dried over anhydrous Na$_2$SO$_4$ and filtered. The filtrate was concentrated in vacuum to afford 5-[2,6-dichloro-4-[6-(difluoromethyl)-3,5-dioxo-1,2,4-triazin-2-yl] phenoxy]-2-hydroxy-benzenesulfonyl chloride 65-1 (9 mg, crude) as a light-yellow oil. The crude product was used directly for next step without purification. LCMS: [M+H]$^+$=514.0/516.0.

Step 2: Compound 65

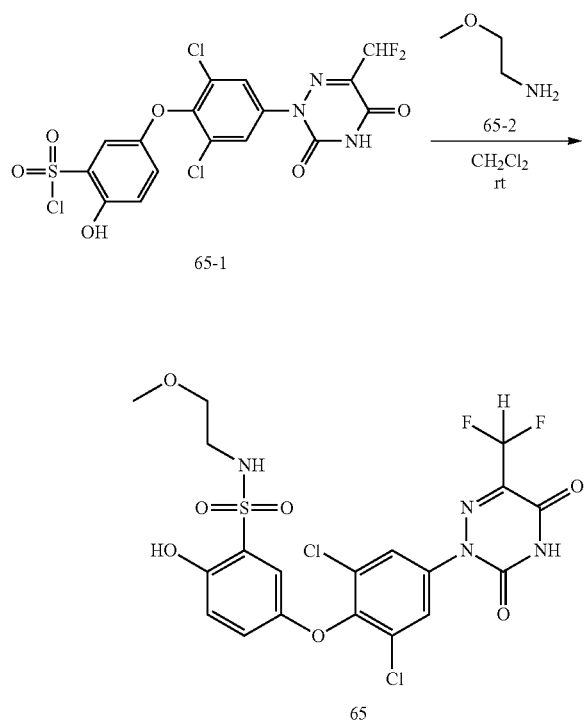

A mixture of 5-[2,6-dichloro-4-[6-(difluoromethyl)-3,5-dioxo-1,2,4-triazin-2-yl]phenoxy]-2-hydroxy-benzenesulfonyl chloride 65-1 (9 mg, crude) and 2-methoxyethan-1-amine 65-2 (6.13 mg, 81.61 umol, 7.09 uL) in $CH_2Cl_2$ (5 mL) was stirred at rt for 16 h. LC-MS showed the reaction was completed. The reaction mixture was concentrated in vacuum. The residue was purified by Prep-HPLC (Chromatographic columns: Kromasil-C18 100×21.2 mm 5 um, Mobile Phase: MeCN—$H_2O$ (0.1% TFA), Gradient: 39-49) The prepared solution was cooled to 0° C. and 1 M HCl (0.5 mL) was added. The mixture was freeze-dried to give 5-[2,6-dichloro-4-[6-(difluoromethyl)-3,5-dioxo-1,2,4-triazin-2-yl] phenoxy]-2-hydroxy-N-(2-methoxyethyl) benzenesulfonamide Compound 65 (1.3 mg, HCl salts, 8% yield three steps together) as a light-yellow solid. LCMS: $[M+H]^+=553.0$. $^1H$ NMR (400 MHz, $CD_3OD$) δ 7.80 (s, 2H), 7.16 (d, J=3.2 Hz, 1H), 7.09 (dd, J=9.2, 3.2 Hz, 1H), 6.97 (d, J=8.8 Hz, 1H), 6.68 (t, J=53.6 Hz, 1H), 3.37-3.35 (m, 2H), 3.22 (s, 3H), 3.06-3.02 (m, 2H). $^{19}F$ NMR (376 MHz, $CD_3OD$) δ−124.1 (s, 2F).

The compounds of Formula (I') or (I) in Table 11 below were made according to Example 27 of Compound 65.

Example 28: Synthesis of Compound 68

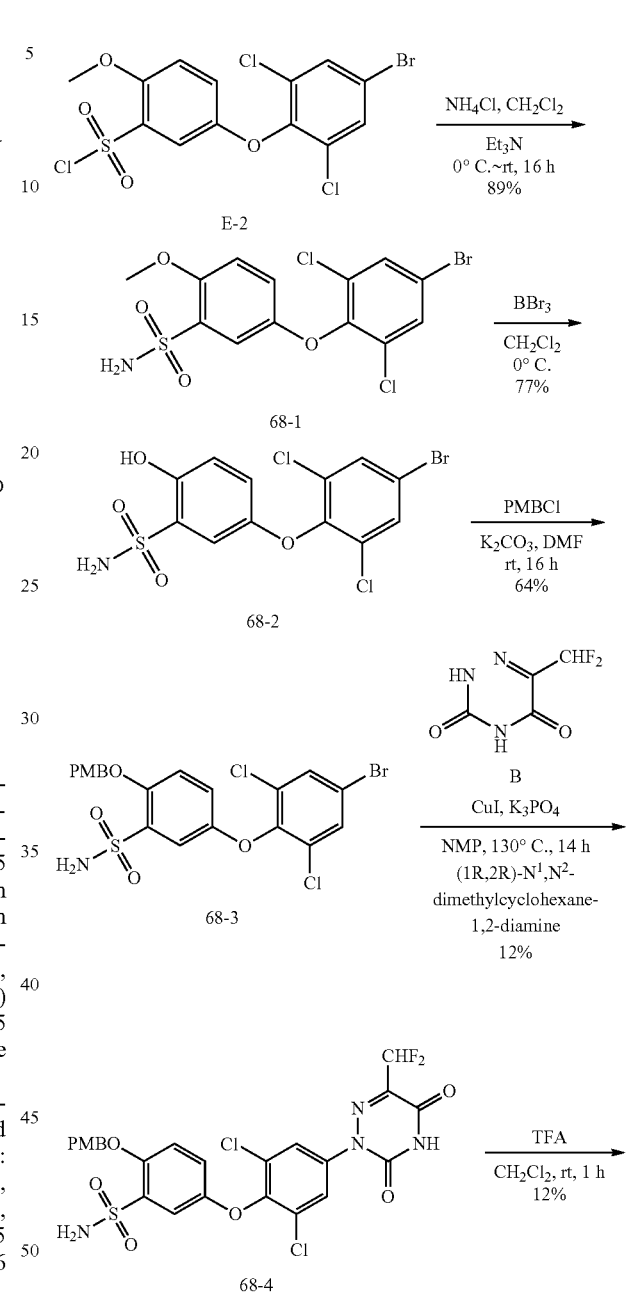

TABLE 11

| Cmpd No. | LC-MS, $^1H$ and $^{19}F$-NMR data |
|---|---|
| 66 | LCMS: $[M + H]^+$ = 579.3. $^1H$ NMR (400 MHz, CD3OD) δ 7.81 (s, 2H), 7.12 (d, J = 3.2 Hz, 1H), 7.07 (dd, J = 9.2, 3.2 Hz, 1H), 6.97 (d, J = 9.2 Hz, 1H), 6.71 (t, J = 52.8 Hz, 1H), 4.13-4.08 (m, 1H), 3.60-3.50 (m, 1H), 2.05-1.94 (m, 1H), 1.58-1.73 (m, 3H), 1.46-1.28 (m, 2H). $^{19}F$ NMR (376 MHz, $CD_3OD$) δ-124.2 (s, 2F). |
| 67 | LCMS: $[M + H]^+$ = 579.0. $^1H$ NMR (400 MHz, $CD_3OD$) δ 7.82 (s, 2H), 7.12 (d, J = 2.4 Hz, 1H), 7.07 (dd, J = 8.8, 2.8 Hz, 1H), 6.97 (d, J = 8.8 Hz, 1H), 6.71 (t, J = 52.8 Hz, 1H), 4.10 (s, 1H), 3.58-3.54 (m, 1H), 2.04-1.96 (m, 1H), 1.72-1.58 (m, 3H), 1.45-1.39 (m, 1H). $^{19}F$ NMR (376 MHz, $CD_3OD$) δ-124.2 (s, 2F). |

-continued

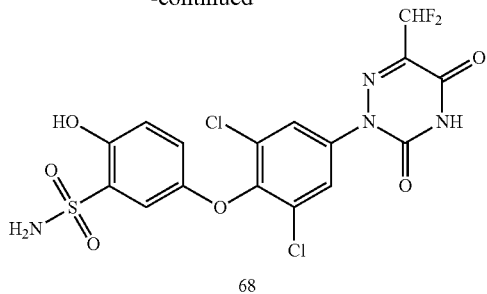

68

Step 1: 68-1

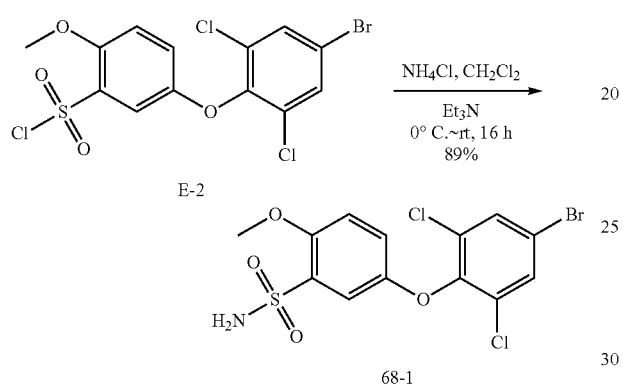

To a mixture of ammonium chloride (479.18 mg, 8.96 mmol) and triethylamine (1.36 g, 13.44 mmol, 1.87 mL) in CH$_2$Cl$_2$ (20 mL) was added a mixture of 5-(4-bromo-2,6-dichloro-phenoxy)-2-methoxy-benzenesulfonyl chloride E-2 (Example 5) (1.0 g, 2.24 mmol) in CH$_2$Cl$_2$ (20 mL). The reaction mixture was stirred at rt for 16 h. LC-MS showed the reaction was completed. The reaction mixture was poured into water (50 mL) and extracted with EtOAc (3×20 mL). The combined organic layer was washed with brine (20 mL), dried over anhydrous Na$_2$SO$_4$ and filtered. The filtrate was concentrated in vacuum. The residue was titrated with hexane (20 mL) to afford 5-(4-bromo-2,6-dichloro-phenoxy)-2-methoxy-benzenesulfonamide 68-1 (860 mg, 89% yield) as a white solid. LCMS: [M+H]$^+$=425.9/427.9.

Step 2: 68-2

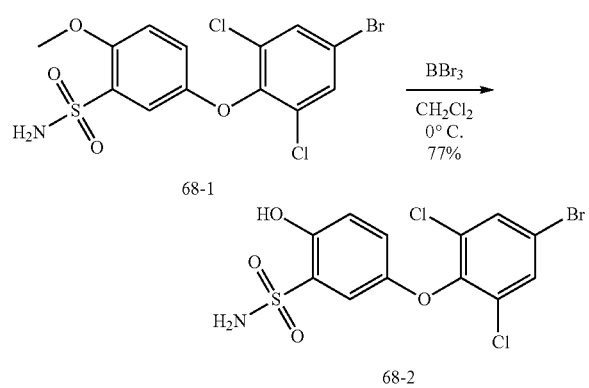

To a solution of 5-(4-bromo-2,6-dichloro-phenoxy)-2-methoxy-benzenesulfonamide 68-1 (200 mg, 468.28 umol) in CH$_2$Cl$_2$ (10 mL) at 0° C. was added a solution of boron tribromide (1.17 g, 4.68 mmol) in CH$_2$Cl$_2$ (2 mL) dropwise. The reaction mixture was stirred at 0° C. for 1 h. TLC (CH$_2$Cl$_2$:MeOH=10:1) showed the reaction was completed. The reaction mixture was poured into sat. NaHCO$_3$ (50 mL) solution and extracted with EtOAc (3×20 mL). The combined organic layer was washed with brine (20 mL), dried over anhydrous Na$_2$SO$_4$ and filtered. The filtrate was concentrated in vacuum to afford 5-(4-bromo-2,6-dichlorophenoxy)-2-hydroxybenzenesulfonamide 68-2 (150 mg, 77% yield) as a crude. The crude was used directly for next step without purification.

Step 3: 68-3

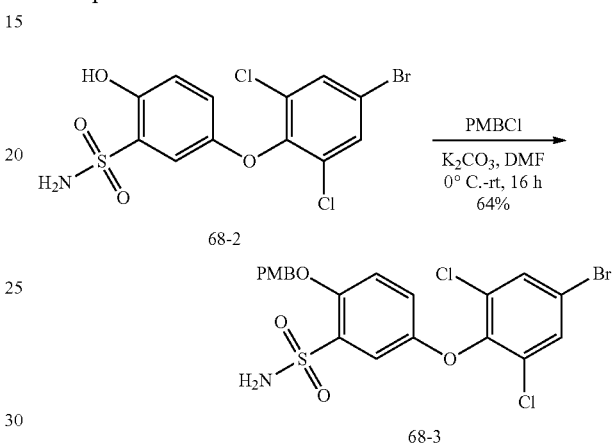

To a mixture of 5-(4-bromo-2,6-dichloro-phenoxy)-2-hydroxy-benzenesulfonamide 68-2 (600 mg, 1.45 mmol) and potassium carbonate (602.25 mg, 4.36 mmol) in DMF (50 mL) was added 1-(chloromethyl)-4-methoxybenzene (227.48 mg, 1.45 mmol). The reaction mixture was stirred at rt for 16 h. LC-MS showed the reaction was completed. The reaction mixture was poured into water (50 mL) and extracted with EtOAc (3×20 mL). The combined organic layer was washed with brine (20 mL), dried over anhydrous Na$_2$SO$_4$ and filtered. The filtrate was concentrated in vacuum. The residue was purified by silica gel chromatography (PE:EtOAc=5:1) to afford 5-(4-bromo-2,6-dichloro-phenoxy)-2-[(4-methoxyphenyl) methoxy] benzene sulfonamide 68-3 (500 mg, 64% yield) as a light-yellow solid. LCMS: [M+Na]$^+$=554.0/556.0.

Step 4: 68-4

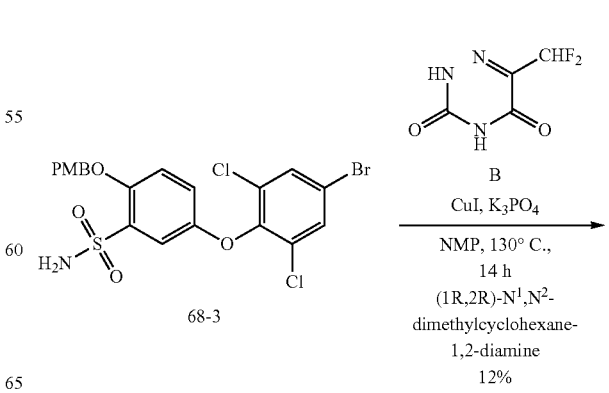

-continued

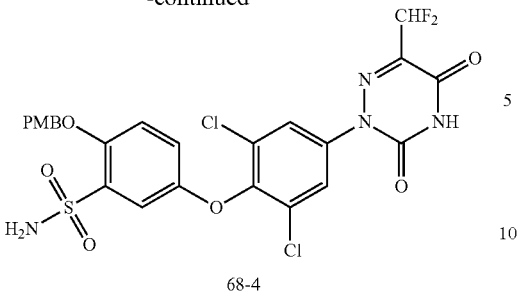

68-4

A mixture of 5-(4-bromo-2,6-dichloro-phenoxy)-2-[(4-methoxyphenyl)methoxy]benzenesulfonamide 68-3 (300 mg, 562.62 umol), 6-(difluoromethyl)-1,2,4-triazine-3,5 (2H,4H)-dione Intermediate B (Example 2) (183.51 mg, 1.13 mmol), cuprous iodide (267.88 mg, 1.41 mmol), potassium phosphate (358.28 mg, 1.69 mmol) and (1R,2R)—N1,N2-dimethylcyclohexane-1,2-diamine (64.02 mg, 450.10 umol) in NMP (4 mL) was stirred in a sealed tube at 130° C. under $N_2$ (g) for 14 h. LC-MS showed the reaction was completed. The reaction mixture was poured into water (50 mL) and extracted with EtOAc (3×20 mL). The combined organic layer was washed with brine (20 mL), dried over anhydrous $Na_2SO_4$ and filtered. The filtrate was concentrated in vacuum. The residue was purified by Prep-TLC ($CH_2Cl_2$:MeOH=10:1) to afford 5-[2,6-dichloro-4-[6-(difluoromethyl)-3,5-dioxo-1,2,4-triazin-2-yl] phenoxy]-2-[(4-methoxyphenyl) methoxy] benzene sulfonamide 68-4 (44 mg, 12% yield) as a light-yellow solid. LCMS: [M+Na]$^+$=637.0

Step 5: Compound 68

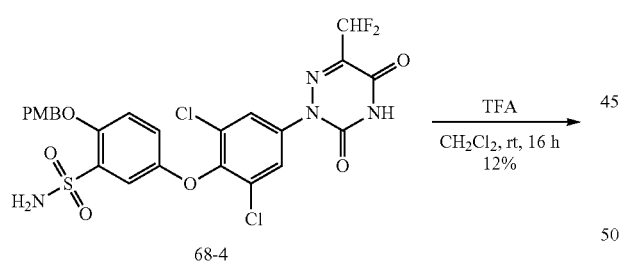

68-4

-continued

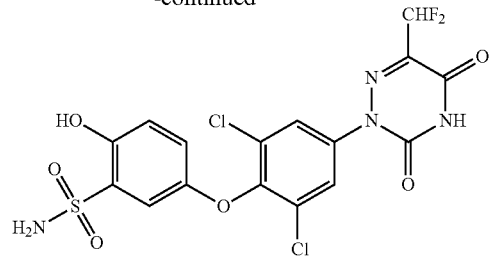

68

To a solution of 5-[2,6-dichloro-4-[6-(difluoromethyl)-3,5-dioxo-1,2,4-triazin-2-yl] phenoxy]-2-[(4-methoxyphenyl) methoxy] benzene sulfonamide 68-4 (54 mg, 87.75 umol) in $CH_2Cl_2$ (10 mL) at rt was added TFA (2 mL). The reaction mixture was stirred at rt for 16 h. LC-MS showed the reaction was completed. The reaction mixture was concentrated in vacuum. The residue was dissolved in EtOAc (10 mL) and washed with sat. $NaHCO_3$ solution (4 mL). The organic layer was washed with brine (10 mL), dried over anhydrous $Na_2SO_4$ and filtered. The filtrate was concentrated in vacuum. The residue was purified by Prep-TLC ($CH_2Cl_2$:MeOH=10:1) to afford a crude product as a light-yellow solid. The crude product was titrated with a mixture of solvent (hexane:$CH_2Cl_2$=1:1) to afford 5-[2,6-dichloro-4-[6-(difluoromethyl)-3,5-dioxo-1,2,4-triazin-2-yl] phenoxy]-2-hydroxy-benzene sulfonamide Compound 68 (5.4 mg, 12% yield) as a white solid. LCMS: [M–H]$^-$=493.0. $^1$H NMR (400 MHz, $CD_3OD$) δ 7.80 (s, 2H), 7.19 (d, J=3.2 Hz, 1H), 7.03 (dd, J=9.2, 3.2 Hz, 1H), 6.97 (d, J=9.2 Hz, 1H), 6.71 (t, J=52.8 Hz, 1H). $^{19}$F NMR (376 MHz, $CD_3OD$) δ–124.8 (s, 2F).

The compounds of Formula (I') or (I) in Table 12 below were made according to Example 28 of Compound 68.

TABLE 12

| Cmpd No. | LC-MS, $^1$H and $^{19}$F-NMR data |
|---|---|
| 69 | LCMS: [M + H]$^+$ = 574.0. $^1$H NMR (400 MHz, $CD_3OD$) δ 7.82 (s, 2H), 7.11 (d, J = 3.2 Hz, 1H), 7.08 (dd, J = 8.8, 3.2 Hz, 1H), 6.97 (d, J = 8.8 Hz, 1H), 6.71 (t, J = 52.8 Hz, 1H), 3.84-3.71 (m, 1H), 2.88-2.75 (m, 1H), 2.48-2.41 (m, 2H), 2.25-2.18 (m, 2H). $^{19}$F NMR (376 MHz, $CD_3OD$) δ-124.2 (s, 2F). NOE and SFC confirmed Compound 69 as a cis compound. |
| 70 | LCMS: [M + H]$^+$ = 565.0/566.9. $^1$H NMR (400 MHz, $CD_3OD$) δ 7.82 (s, 2H), 7.12 (d, J = 2.8 Hz, 1H), 7.05 (dd, J = 8.8, 3.2 Hz, 1H), 6.96 (d, J = 9.2 Hz, 1H), 6.71 (t, J = 53.2 Hz, 1H), 3.35 (s, 2H), 0.58-0.67 (m, 4H). $^{19}$F NMR (376 MHz, $CD_3OD$) δ-123.9 (s, 2F). |
| 102 | LCMS: [M + H]$^+$ = 485.0. $^1$H NMR (400 MHz, $CD_3OD$) δ 7.79 (s, 1H), 7.74 (s, 2H), 7.37 (s, 1H), 2.64 (s, 3H). |

Example 29: Synthesis of Compound 71

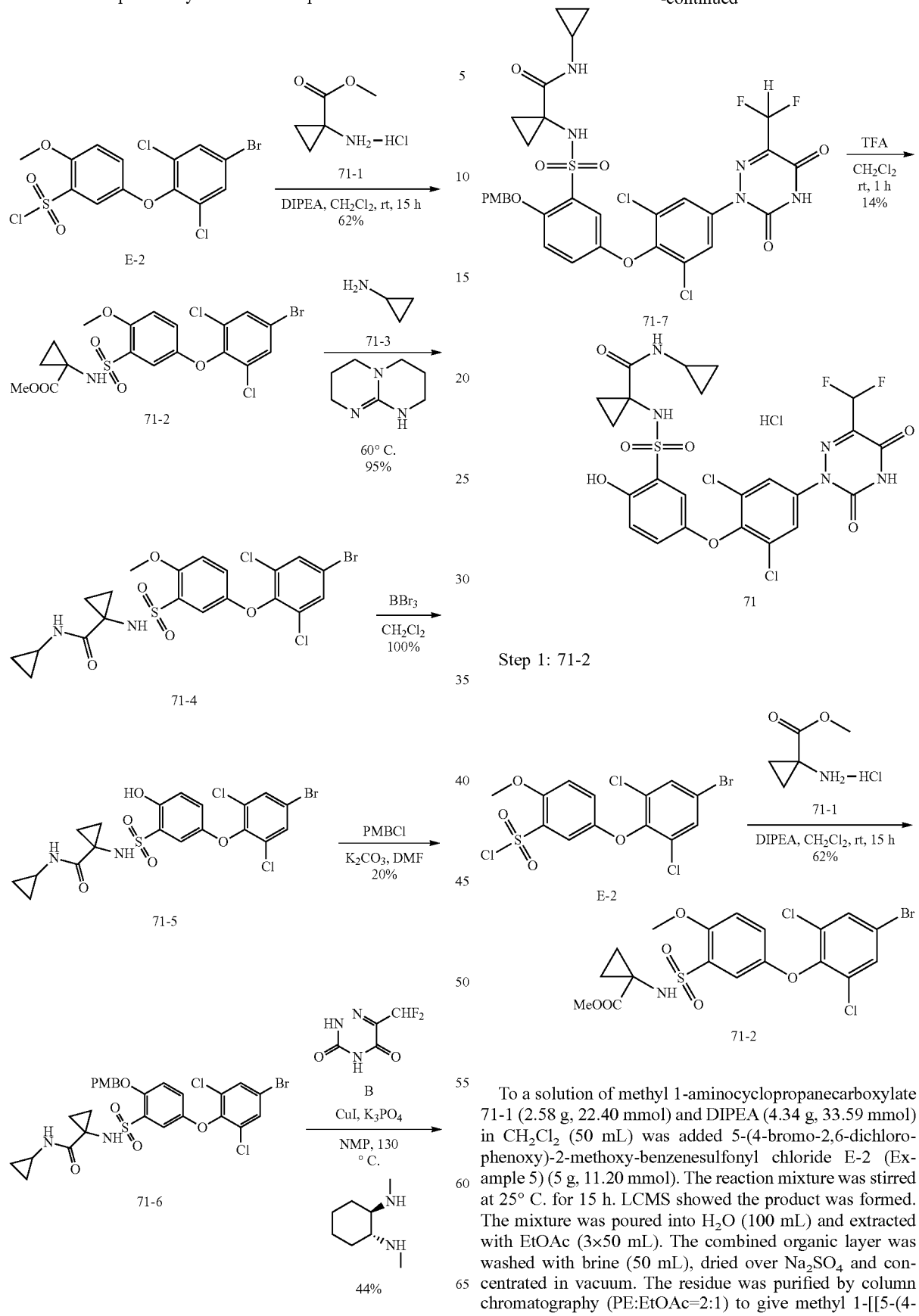

Step 1: 71-2

To a solution of methyl 1-aminocyclopropanecarboxylate 71-1 (2.58 g, 22.40 mmol) and DIPEA (4.34 g, 33.59 mmol) in CH$_2$Cl$_2$ (50 mL) was added 5-(4-bromo-2,6-dichloro-phenoxy)-2-methoxy-benzenesulfonyl chloride E-2 (Example 5) (5 g, 11.20 mmol). The reaction mixture was stirred at 25° C. for 15 h. LCMS showed the product was formed. The mixture was poured into H$_2$O (100 mL) and extracted with EtOAc (3×50 mL). The combined organic layer was washed with brine (50 mL), dried over Na$_2$SO$_4$ and concentrated in vacuum. The residue was purified by column chromatography (PE:EtOAc=2:1) to give methyl 1-[[5-(4-bromo-2,6-dichloro-phenoxy)-2-methoxy-phenyl] sulfonyl amino] cyclopropane carboxylate 71-2 (3.7 g, 62% yield) as a yellow solid. LCMS: [M+H]$^+$=523.9/525.9.

Step 2: 71-4

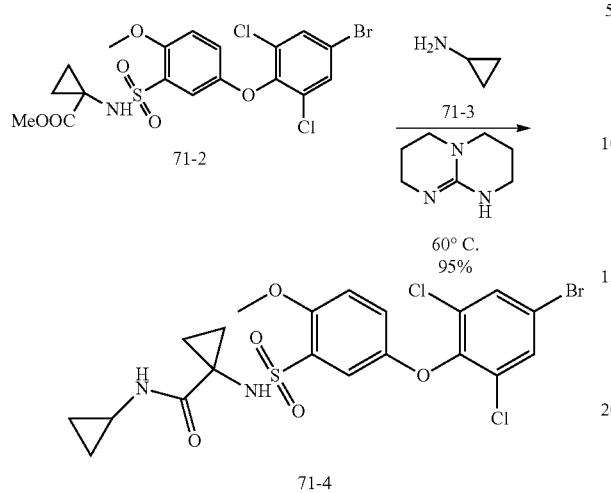

71-4

A solution of methyl 1-[[5-(4-bromo-2,6-dichloro-phenoxy)-2-methoxy-phenyl]sulfonylamino]cyclopropane carboxylate 71-2 (600 mg, 1.14 mmol) and 1,3,4,6,7,8-hexahydro-2H-pyrimido[1,2-a]pyrimidine (159.02 mg, 1.14 mmol) in cyclopropanamine 71-3 (14.13 g, 247.41 mmol, 17.14 mL) was stirred at 60° C. for 15 h. LCMS showed the product was formed. The reaction mixture was poured into water and extracted with EtOAc (3×50 mL). The combined organic layer was dried over anhydrous Na$_2$SO$_4$. The reaction mixture was filtered and concentrated in vacuum. The residue was purified by column chromatography (CH$_2$Cl$_2$: CH$_3$OH=20:1) to give 1-[[5-(4-bromo-2,6-dichloro-phenoxy)-2-methoxy-phenyl] sulfonyl amino]-N-cyclopropyl-cyclopropane carboxamide 71-4 (600 mg, 95% yield) as a yellow solid. LCMS: [M+H]$^+$=549.0/551.0.

Step 3: 71-5

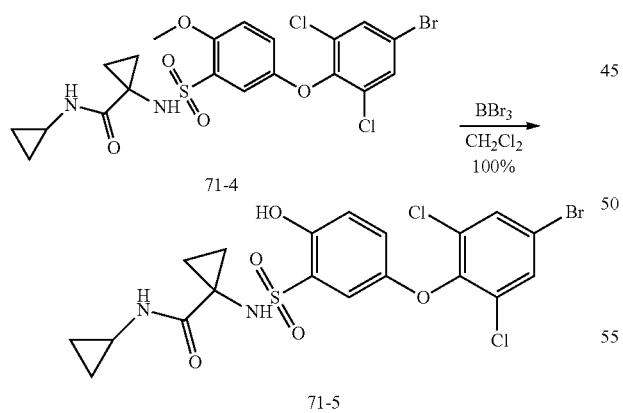

To a solution of 1-[[5-(4-bromo-2,6-dichloro-phenoxy)-2-methoxy-phenyl] sulfonylamino]-N-cyclopropyl-cyclopropanecarboxamide 71-4 (400 mg, 726.94 umol) in CH$_2$Cl$_2$ (5 ml) was added BBr$_3$ (5.45 g, 21.81 mmol) at 0° C. The mixture was stirred at 0° C. for 1 h. LCMS showed the product was formed. The reaction mixture was poured into water and extracted with EtOAc (3×50 mL). The combined organic layer was dried over anhydrous Na$_2$SO$_4$.

The reaction mixture was filtered and concentrated in vacuum to afford a residue. The crude product 1-[[5-(4-bromo-2,6-dichloro-phenoxy)-2-hydroxy-phenyl] sulfonyl amino]-N-cyclopropyl-cyclopropane carboxamide 71-5 (430 mg, crude) was used for next step without purification. LCMS: [M+H]$^+$=534.9/536.9.

Step 4: 71-6

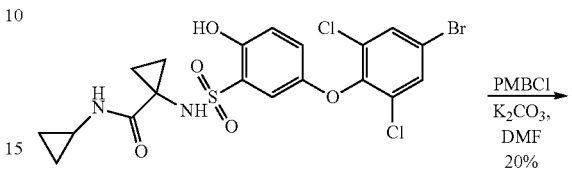

71-5

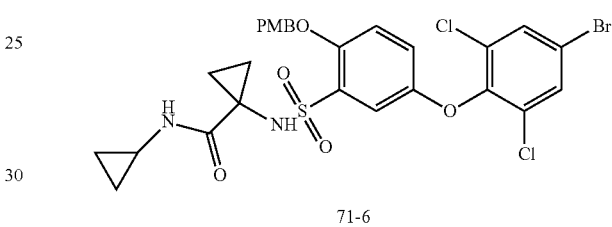

71-6

A solution of 1-[[5-(4-bromo-2,6-dichloro-phenoxy)-2-hydroxy-phenyl]sulfonylamino]-N-cyclopropyl-cyclopropanecarboxamide 71-5 (430 mg, 801.91 umol), PMBCl (182.86 mg, 1.20 mmol) and K$_2$CO$_3$ (221.33 mg, 1.60 mmol) in DMF (5 mL) was stirred at 25° C. for 16 h. LCMS showed the product was formed. The reaction mixture was poured into water and extracted with EtOAc (3×50 mL). The combined organic layer was dried over anhydrous Na$_2$SO$_4$. The reaction mixture was filtered and concentrated in vacuum. The residue was purified by column chromatography (PE:EtOAc=1:1) to give 1-[[5-(4-bromo-2,6-dichloro-phenoxy)-2-[(4-methoxyphenyl) methoxy] phenyl] sulfonylamino]-N-cyclopropyl-cyclopropanecarboxamide 71-6 (110 mg, 20% yield) as a white solid. LCMS: [M+Na]$^+$=677.0/678.9.

Step 5: 71-7

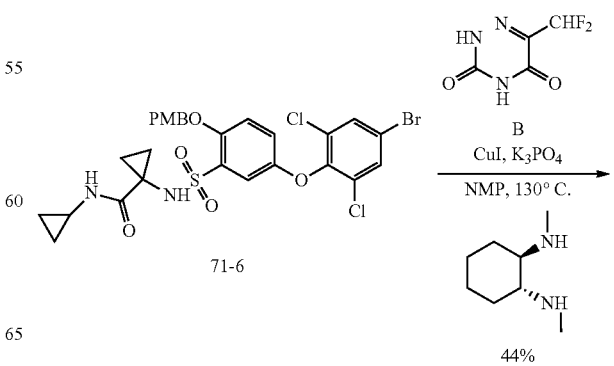

71-6

-continued

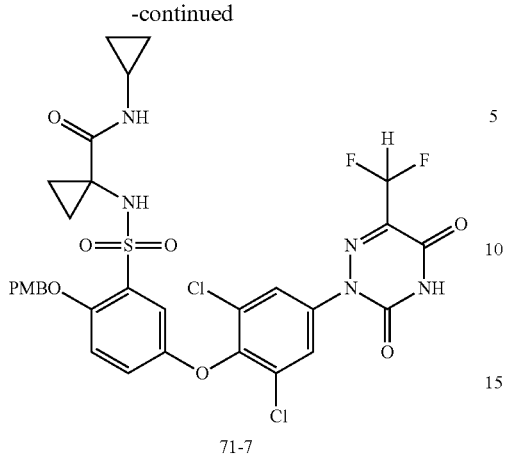

71-7

A mixture of 1-[[5-(4-bromo-2,6-dichloro-phenoxy)-2-[(4-methoxyphenyl) methoxy] phenyl]sulfonylamino]-N-cyclopropyl-cyclopropanecarboxamide 71-6 (110 mg, 167.59 umol), 6-(difluoromethyl)-2H-1,2,4-triazine-3,5-dione Intermediate B (Example 2) (54.66 mg, 335.18 umol), N1,N2-dimethylcyclohexane-1,2-diamine (19.07 mg, 134.07 umol), CuI (79.79 mg, 418.97 umol) and K$_3$PO$_4$ (106.59 mg, 502.76 umol) in NMP (2 mL) was stirred at 130° C. for 15 h. LCMS showed the product was formed. The mixture was poured into water (50 mL) and extracted with EtOAc (3×20 mL). The mixture was washed with brine (50 mL) and water (50 mL), dried over Na$_2$SO$_4$ and concentrated in vacuum. The residue was purified by Prep-TLC (CH$_2$Cl$_2$:CH$_3$OH=10:1) to give N-cyclopropyl-1-[[5-[2,6-dichloro-4-[6-(difluoromethyl)-3,5-dioxo-1,2,4-triazin-2-yl] phenoxy]-2-[(4-methoxyphenyl) methoxy] phenyl]sulfonyl amino] cyclopropane carboxamide 71-7 (55 mg, 44% yield) as a yellow solid. LCMS: [M+Na]$^+$=760.1/762.0.

Step 6: Compound 71

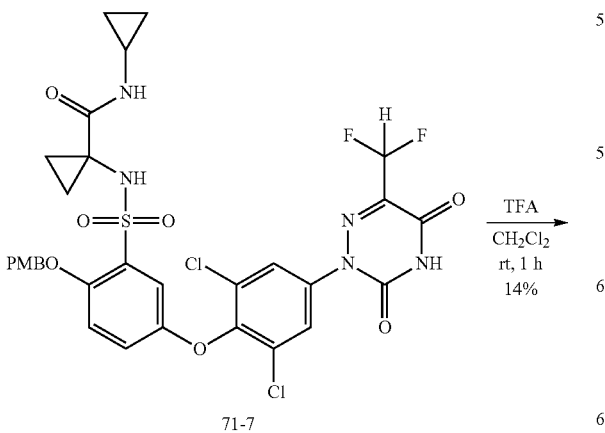

-continued

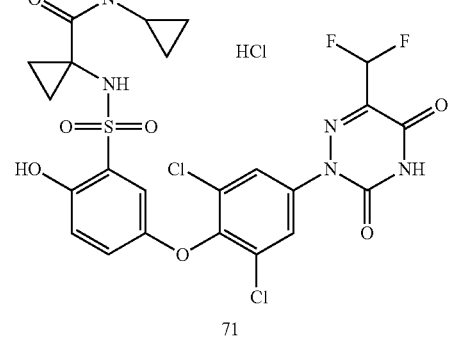

71

To a solution of N-cyclopropyl-1-[[5-[2,6-dichloro-4-[6-(difluoromethyl)-3,5-dioxo-1,2,4-triazin-2-yl]phenoxy]-2-[(4-methoxyphenyl) methoxy] phenyl] sulfonyl amino] cyclopropane carboxamide 71-7 (55 mg, 74.47 umol) in CH$_2$Cl$_2$ (5 mL) was added TFA (740.00 mg, 6.49 mmol, 0.5 mL). The mixture was stirred at 25° C. for 1 h. LCMS showed the product was formed. The mixture was washed with brine (50 mL) and water (50 mL) dried over Na$_2$SO$_4$ and concentrated in vacuum. The residue was purified by Prep-HPLC (Gemini 5 u C18 100×21.2 mm, Mobile Phase: MeCN—H$_2$O (0.1% TFA), Gradient: 43-53). The prepared solution was cooled to 0° C. and 1 M HCl (0.5 mL) was added. The mixture was freeze-dried to give N-cyclopropyl-1-[[5-[2,6-dichloro-4-[6-(difluoromethyl)-3,5-dioxo-1,2,4-triazin-2-yl] phenoxy]-2-hydroxy-phenyl] sulfonyl amino] cyclopropane carboxamide Compound 71 (6.6 mg, 14% yield) as a yellow solid. LCMS: [M+H]$^+$=618.0/620.0. $^1$H NMR (400 MHz, CD$_3$OD) δ 7.83 (s, 2H), 7.10 (m, 2H), 6.99 (dd, J=6.8, 2.8 Hz, 1H), 6.71 (t, J=52.8 Hz, 1H), 2.59-2.54 (m, 1H), 1.27 (dd, J=8.8, 4.8 Hz, 2H), 1.02 (dd, J=7.6, 4.8 Hz, 2H), 0.72-0.67 (m, 2H), 0.49-0.45 (m, 2H). $^{19}$F NMR (376 MHz, CD$_3$OD) δ−124.2 (s, 2F).

Example 30: Synthesis of Compound 72

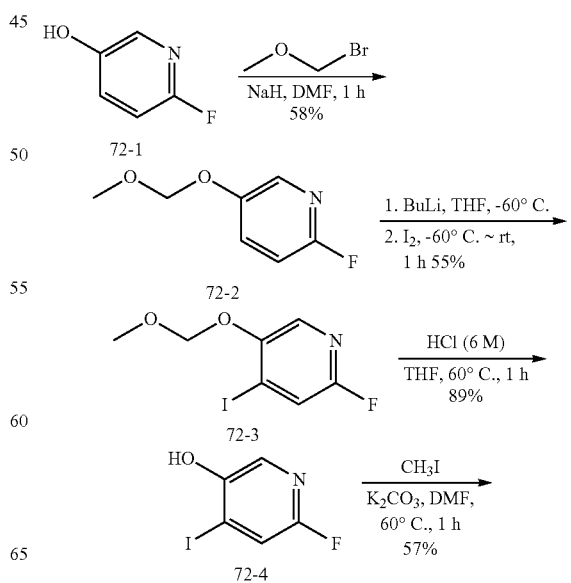

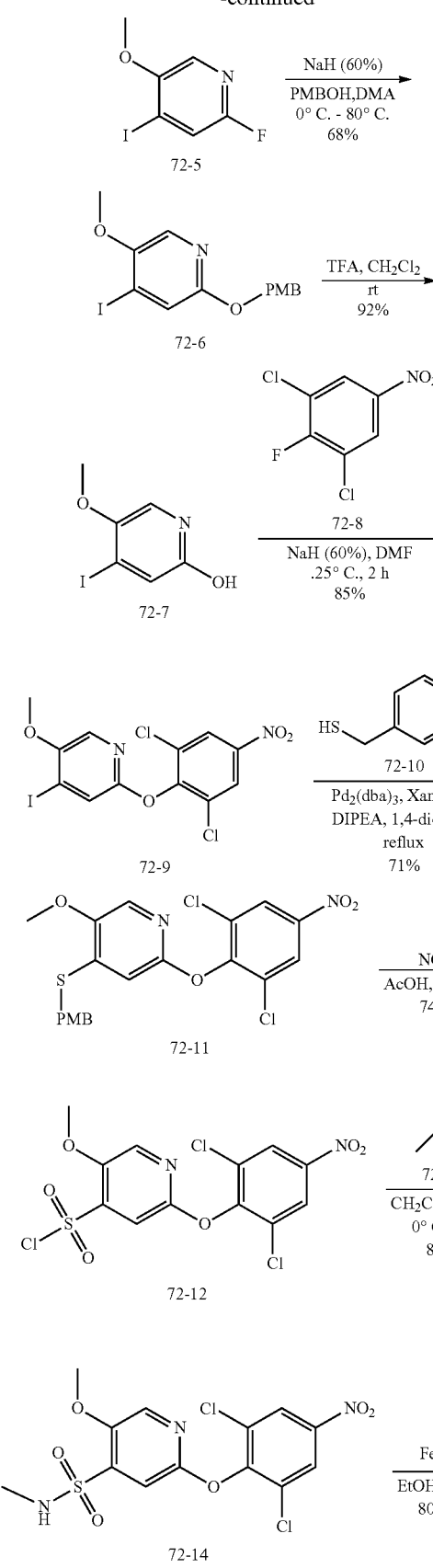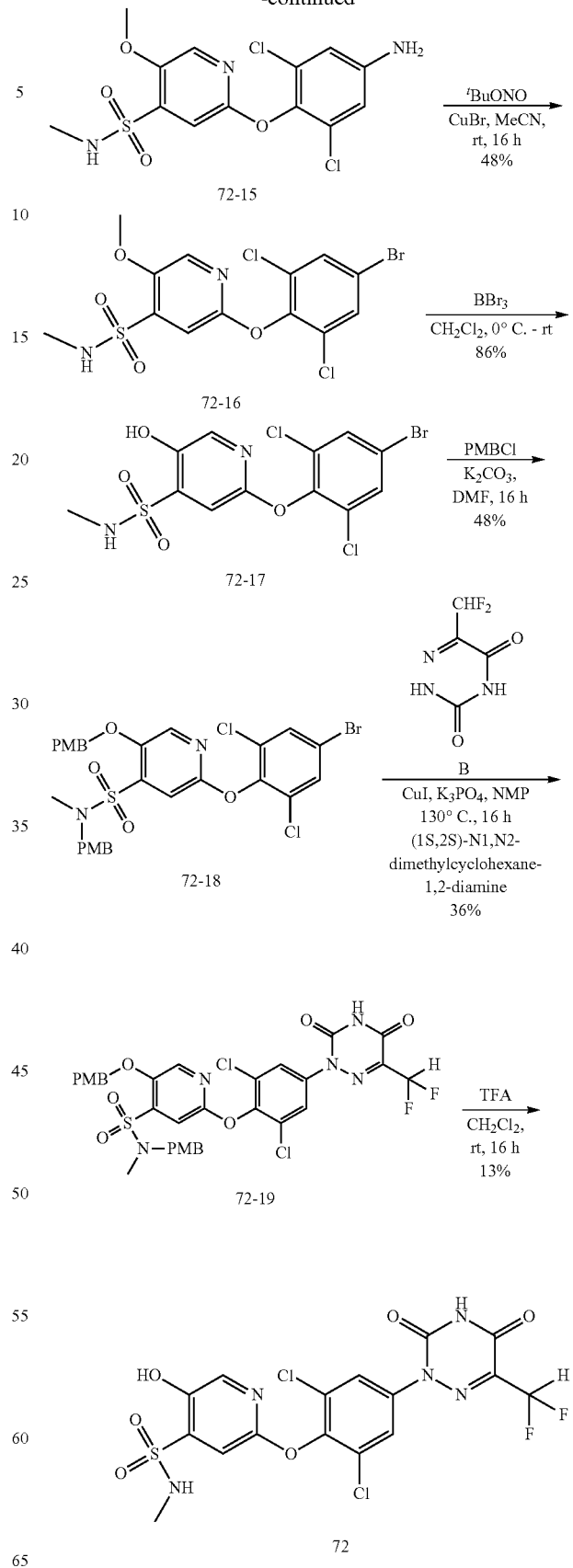

Step 1: 72-2

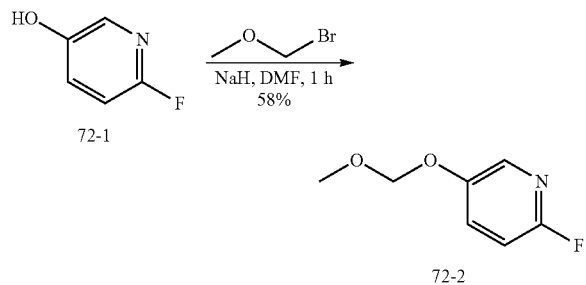

To a solution of 6-fluoropyridin-3-ol 72-1 (5.0 g, 44.21 mmol) in DMF (50 mL) was added sodium hydride (2.03 g, 50.83 mmol, 60% purity). The mixture was stirred at 0° C. for 0.5 h. Then bromo(methoxy)methane (6.08 g, 48.63 mmol) was added. The reaction mixture was stirred at rt for 1 h. TLC (PE:EtOAc=10:1) showed the reaction worked. The reaction mixture was poured into water (50 mL) and extracted with EtOAc (3×50 mL). The combined organic layer was washed with brine (20 mL), dried over anhydrous $Na_2SO_4$ and filtered. The filtrate was concentrated in vacuum. The residue was purified by silica gel chromatography (PE:EtOAc=20:1) to afford 2-fluoro-5-(methoxy methoxy) pyridine 72-2 (4.0 g, 5800 yield) as a colorless oil. LCMS: $[M+H]^+=158.0$.

Step 2: 72-3

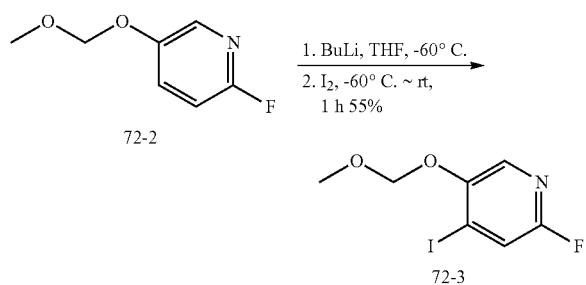

To a solution of 2-fluoro-5-(methoxy methoxy) pyridine 72-2 (2.0 g, 12.73 mmol) in THF (20 mL) was added n-Butyllithium hexane solution (2.4 M, 7.95 mL) dropwise at −60° C. The mixture was stirred at −60° C. for 0.5 h under $N_2$ protection. Then iodine (3.23 g, 12.73 mmol) was added. The reaction mixture was stirred from −60° C. to rt over 0.5 h. TLC (PE:EtOAc=5:1) showed the reaction worked. The reaction mixture was poured into water (50 mL) and extracted with EtOAc (3×20 mL). The combined organic layer was washed with brine (20 mL), dried over anhydrous $Na_2SO_4$ and filtered. The filtrate was concentrated in vacuum. The residue was purified by silica gel chromatography (PE:EtOAc=10:1) to afford 2-fluoro-4-iodo-5-(methoxy methoxy) pyridine 72-3 (2.0 g, 55% yield) as a white solid. LCMS: $[M+H]^+=284.0$.

Step 3: 72-4

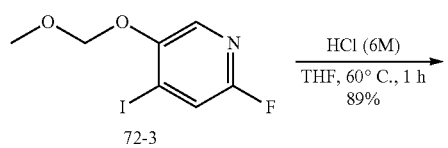

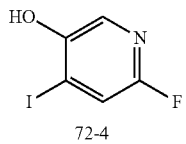

To a solution of 2-fluoro-4-iodo-5-(methoxy methoxy) pyridine 72-3 (0.8 g, 2.83 mmol) in THF (10 mL) was added 6M HCl in water (3 mL, 18 mmol). The reaction mixture was stirred at 60° C. for 1 h. TLC (PE:EtOAc=5:1, Rf=0.2) showed the reaction was completed. The reaction mixture was concentrated in vacuum to afford 6-fluoro-4-iodo-pyridin-3-ol 72-4 (600 mg, 89% yield) as a crude. The crude was used directly for next step without purification. LCMS: $[M+H]^+=240.0$.

Step 4: 72-5

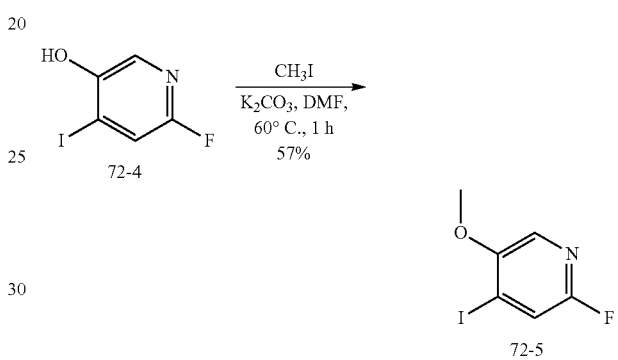

To a mixture of 6-fluoro-4-iodo-pyridin-3-ol 72-4 (0.5 g, 2.09 mmol), iodomethane (890.88 mg, 6.28 mmol) and potassium carbonate (867.45 mg, 6.28 mmol) in DMF (5 mL). The reaction mixture was stirred at 60° C. for 1 h. TLC (PE:EtOAc=10:1, $R_f=0.3$) showed the reaction was completed. The reaction mixture was poured into water (50 mL) and extracted with EtOAc (3×20 mL). The combined organic layer was washed with brine (20 mL), dried over anhydrous $Na_2SO_4$ and filtered. The filtrate was concentrated in vacuum. The residue was purified by silica gel chromatography (PE:EtOAc=10:1) to afford 2-fluoro-4-iodo-5-methoxy-pyridine 72-5 (0.3 g, 57% yield) as a colorless oil. LCMS: $[M+H]^+=254.0$.

Step 5: 72-6

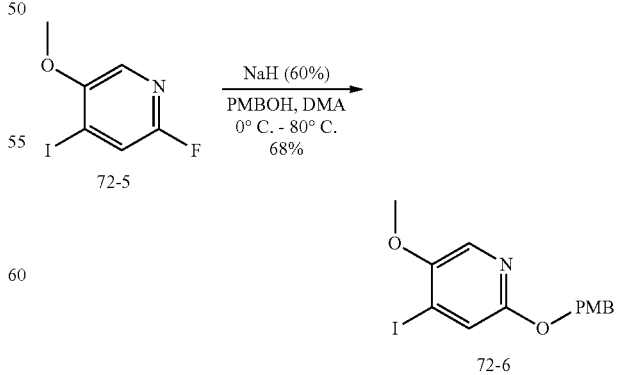

To a mixture of (4-methoxyphenyl) methanol (196.59 mg, 1.42 mmol) was added sodium hydride (66.39 mg, 1.66 mmol, 60%) in DMA (2.0 mL) at 0° C. The mixture was stirred at 0° C. for 0.5 h before 2-fluoro-4-iodo-5-methoxy-pyridine 72-5 (0.3 g, 1.19 mmol) was added. The mixture was stirred at 80° C. for 30 min. TLC (PE:EtOAc=10:1 R$_f$=0.4) showed the reaction was completed. The reaction mixture was poured into water (50 mL) and extracted with EtOAc (3×20 mL). The combined organic layer was washed with brine (20 mL), dried over anhydrous Na$_2$SO$_4$ and filtered. The filtrate was concentrated in vacuum. The residue was purified by silica gel chromatography (PE:EtOAc=5:1) to afford 4-iodo-5-methoxy-2-[(4-methoxyphenyl) methoxy] pyridine 72-6 (0.3 g, 68% yield) as a white solid. LCMS: [M+Na]$^+$=394.1.

Step 6: 72-7

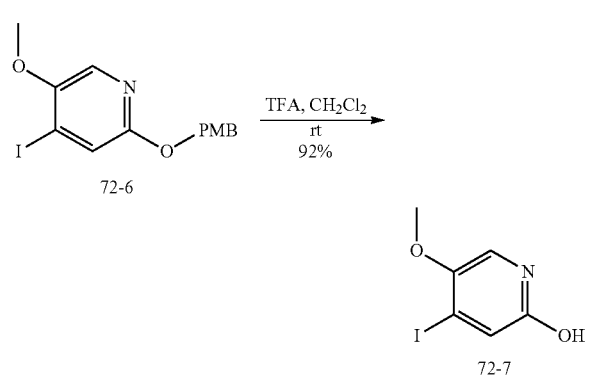

To a mixture of 4-iodo-5-methoxy-2-[(4-methoxyphenyl) methoxy] pyridine 72-6 (1.6 g, 4.31 mmol) in CH$_2$Cl$_2$ (5 mL) 2,2,2-trifluoroacetic acid (2.46 g, 21.55 mmol, 1.66 mL) was added. The mixture was stirred at 25° C. for 30 min. TLC (PE:EtOAc=2:1) showed the reaction was completed. The reaction mixture was concentrated in vacuum. The residue was purified by silica gel chromatography (PE:EtOAc=2:1) to afford 4-iodo-5-methoxy-pyridin-2-ol 72-7 (1.0 g, 92% yield) as a colorless oil. LCMS: [M+H]$^+$=252.0.

Step 7: 72-9

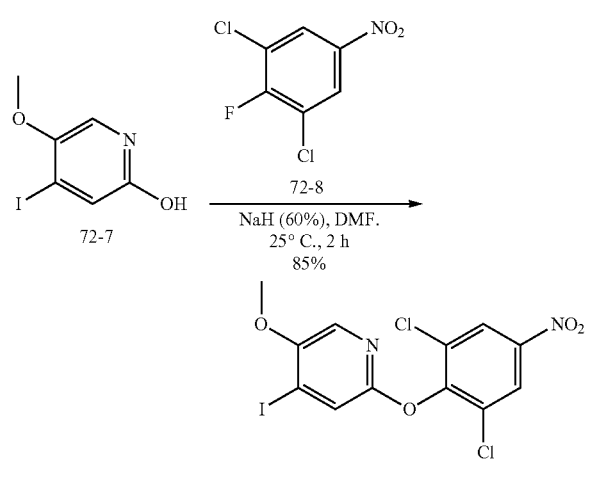

To a solution of 4-iodo-5-methoxy-pyridin-2-ol 72-7 (1.0 g, 3.98 mmol) in DMF (5 mL) was added sodium hydride (239.00 mg, 5.98 mmol, 60%). The mixture was stirred at 25° C. for 30 min. Then 1,3-dichloro-2-fluoro-5-nitro-benzene 72-8 (1.25 g, 5.98 mmol) was added and the mixture was stirred at 25° C. for 2 h. LC-MS showed the reaction was completed. The reaction mixture was poured into water (50 mL) and extracted with EtOAc (3×20 mL). The combined organic layer was washed with brine (20 mL), dried over anhydrous Na$_2$SO$_4$ and filtered. The filtrate was concentrated in vacuum. The residue was purified by silica gel chromatography (PE:EtOAc=5:1) to afford 2-(2,6-dichloro-4-nitro-phenoxy)-4-iodo-5-methoxy-pyridine 72-9 (1.5 g, 85% yield) as a light-yellow solid. LCMS: [M+H]$^+$=440.9.

Step 8: 72-11

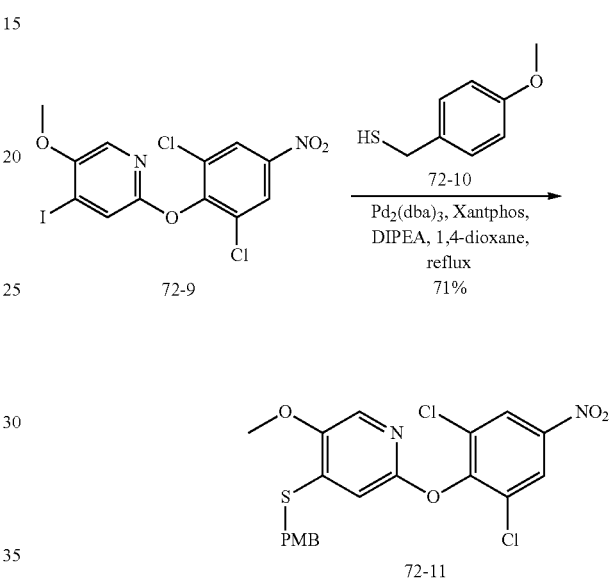

A mixture of 2-(2,6-dichloro-4-nitro-phenoxy)-4-iodo-5-methoxy-pyridine 72-9 (0.2 g, 453.51 umol), (4-methoxyphenyl) methanethiol 72-10 (104.92 mg, 680.26 umol), DIPEA (117.23 mg, 907.23 umol), (1E,4E)-1,5-diphenyl-penta-1,4-dien-3-one; palladium (41.53 mg, 45.35 umol) and (5-diphenylphosphanyl-9,9-dimethyl-xanthen-4-yl)-diphenyl-phosphane (52.48 mg, 90.70 umol) in dioxane (3 mL) was stirred at 110° C. for 16 h under N2. LC-MS showed the reaction was completed. The reaction mixture was poured into water (50 mL) and extracted with EtOAc (3×20 mL). The combined organic layer was washed with brine (20 mL), dried over anhydrous Na$_2$SO$_4$ and filtered. The filtrate was concentrated in vacuum. The residue was purified by silica gel chromatography (PE:EtOAc=5:1) to afford 2-(2,6-dichloro-4-nitro-phenoxy)-5-methoxy-4-[(4-methoxyphenyl) methyl sulfanyl] pyridine 72-11 (150 mg, 71% yield) as a light-yellow solid. LCMS: [M+H]$^+$=467.1.

Step 9: 72-12

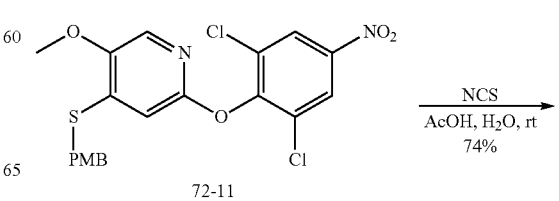

-continued

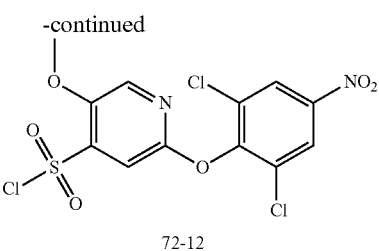

72-12

A mixture of 2-(2,6-dichloro-4-nitro-phenoxy)-5-methoxy-4-[(4-methoxyphenyl)methylsulfanyl]pyridine 72-11 (0.2 g, 427.97 umol) and 1-chloropyrrolidine-2,5-dione (285.74 mg, 2.14 mmol) in HOAc (3 mL) and water (1 mL) was stirred at rt for 16 h. LC-MS showed the reaction was completed. The reaction mixture was poured into water (50 mL) and extracted with EtOAc (3×20 mL). The combined organic layer was washed with brine (20 mL), dried over anhydrous Na$_2$SO$_4$ and filtered. The filtrate was concentrated in vacuum. The residue was purified by silica gel chromatography (PE:EtOAc=5:1) to afford 2-(2,6-dichloro-4-nitro-phenoxy)-5-methoxy-pyridine-4-sulfonyl chloride 72-12 (150 mg, 74% yield) as a light-yellow solid. LCMS: [M+H]$^+$=413.1.

Step 10: 72-14

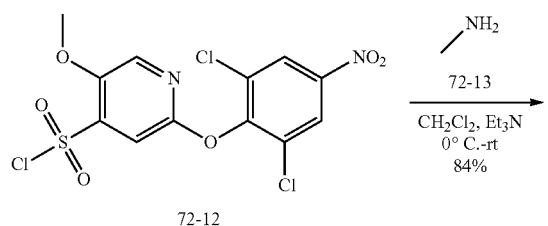

72-12

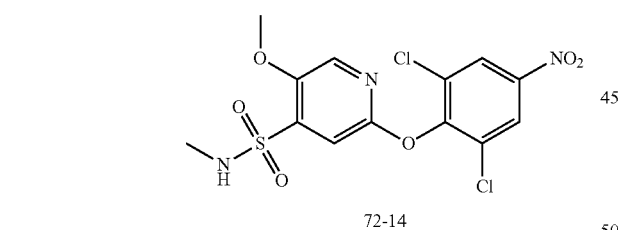

72-14

To a mixture of methanamine 72-13 (45.05 mg, 1.45 mmol) and N, N-diethylethanamine (293.57 mg, 2.90 mmol, 404.37 uL) in CH$_2$Cl$_2$ (5 mL) was added 2-(2,6-dichloro-4-nitro-phenoxy)-5-methoxy-pyridine-4-sulfonyl chloride 72-12 (0.12 g, 290.12 umol). The reaction mixture was stirred at rt for 16 h. LC-MS showed the reaction was completed. The reaction mixture was poured into water (50 mL) and extracted with EtOAc (3×20 mL). The combined organic layer was washed with brine (20 mL), dried over anhydrous Na$_2$SO$_4$ and filtered. The filtrate was concentrated in vacuum. The residue was purified by silica gel chromatography (PE:EtOAc=2:1) to afford 2-(2,6-dichloro-4-nitro-phenoxy)-5-methoxy-N-methyl-pyridine-4-sulfonamide 72-14 (100 mg, 84% yield) as a white solid. LCMS: [M+H]$^+$=408.0.

Step 11: 72-15

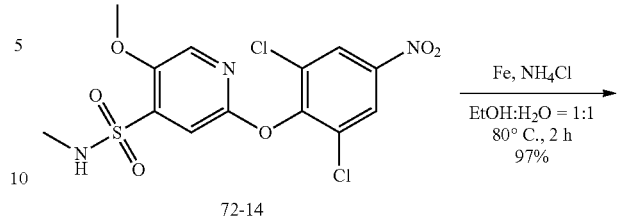

72-14

72-15

A mixture of 2-(2,6-dichloro-4-nitro-phenoxy)-5-methoxy-N-methyl-pyridine-4-sulfonamide 72-14 (0.1 g, 244.97 umol), Fe (136.80 mg, 2.45 mmol) and ammonium chloride (131.04 mg, 2.45 mmol, 85.65 uL) in ethanol (3 mL) and water (3 mL) was stirred at 80° C. for 2 h. LC-MS showed the reaction was completed. The reaction mixture was concentrated and poured into water (50 mL) and extracted with EtOAc (3×20 mL). The combined organic layer was washed with brine (20 mL), dried over anhydrous Na$_2$SO$_4$ and filtered. The filtrate was concentrated in vacuum. The residue was purified by silica gel chromatography (PE:EtOAc=2:1) to afford 2-(4-amino-2,6-dichloro-phenoxy)-5-methoxy-N-methyl-pyridine-4-sulfonamide 72-15 (90 mg, 97% yield) as a light-yellow solid. LCMS: [M+H]$^+$=378.0.

Step 12: 72-16

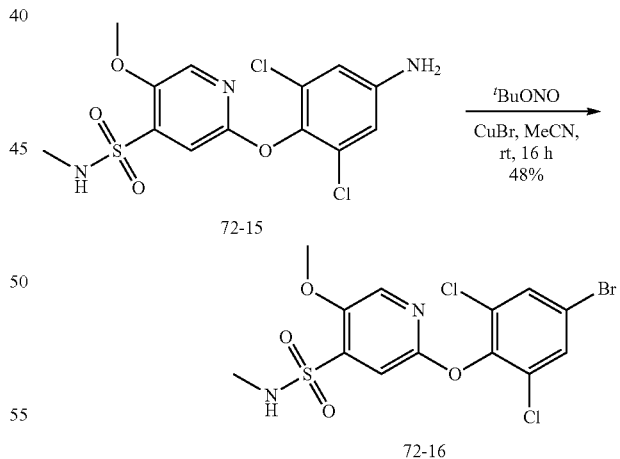

72-15

72-16

A mixture of 2-(4-amino-2,6-dichloro-phenoxy)-5-methoxy-N-methyl-pyridine-4-sulfonamide 72-15 (90 mg, 237.95 umol), CuBr (51.20 mg, 356.93 umol) and tert-butyl nitrite (49.07 mg, 475.90 umol) in CH$_3$CN (5 mL) was stirred at 25° C. under N$_2$ (g) for 16 h. LC-MS showed the reaction worked. The reaction mixture was poured into water (50 mL) and extracted with EtOAc (3×20 mL). The combined organic layer was washed with brine (20 mL), dried over anhydrous Na$_2$SO$_4$ and filtered. The filtrate was concentrated in vacuum. The residue was purified by silica gel chromatography (CH$_2$Cl$_2$:MeOH=20:1) to afford 2-(4-bromo-2,6-dichlorophenoxy)-5-methoxy-N-methylpyridine-4-sulfonamide 72-16 (50 mg, 48% yield) as a light-yellow solid. LCMS: [M+H]$^+$=441.0/443.0.

Step 13: 72-17

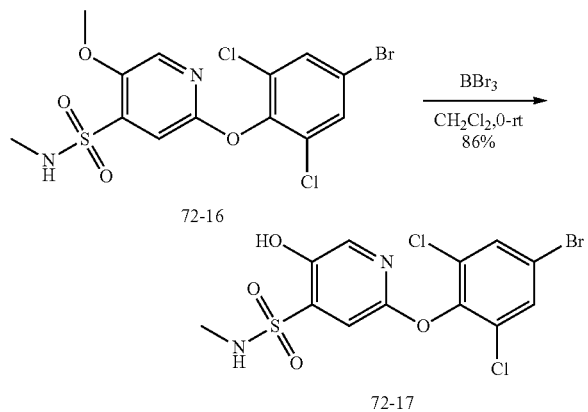

To a solution of 2-(4-bromo-2,6-dichlorophenoxy)-5-methoxy-N-methylpyridine-4-sulfonamide 72-16 (0.24 g, 542.85 umol) in CH$_2$Cl$_2$ (10 mL) at 0° C. was added a solution of boron tribromide (1.17 g, 4.68 mmol) in CH$_2$Cl$_2$ (2 mL) dropwise. The reaction mixture was stirred at 0° C. for 1 h. TLC (CH$_2$Cl$_2$:MeOH=10:1) showed the reaction was completed. The reaction mixture was poured into sat. NaHCO$_3$ (50 mL) solution and extracted with EtOAc (3×20 mL). The combined organic layer was washed with brine (20 mL), dried over anhydrous Na$_2$SO$_4$ and filtered. The filtrate was concentrated in vacuum to afford 2-(4-bromo-2,6-dichloro-phenoxy)-5-hydroxy-N-methyl-pyridine-4-sulfonamide 72-17 (200 mg, 86% yield) as a crude product which was used directly for next step without purification.

Step 14: 72-18

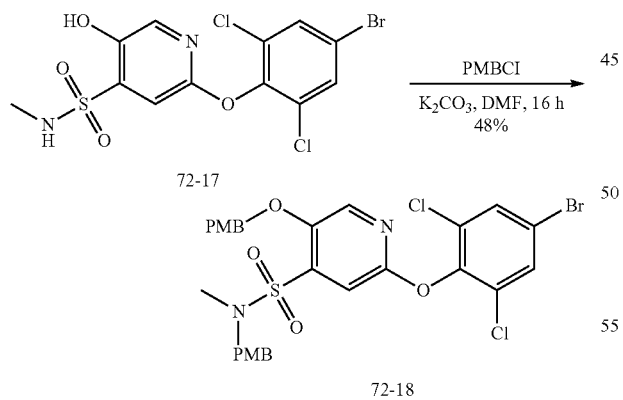

To a mixture of 2-(4-bromo-2,6-dichloro-phenoxy)-5-hydroxy-N-methyl-pyridine-4-sulfonamide 72-17 (0.20 g, 467.20 umol) and potassium carbonate (193.71 mg, 1.40 mmol) in DMF (5 mL) was added 1-(chloromethyl)-4-methoxy-benzene (87.80 mg, 560.64 umol). The reaction mixture was stirred at rt for 16 h. TLC (PE:EtOAc=5:1) showed the reaction was completed. The reaction mixture was poured into water (50 mL) and extracted with EtOAc (3×20 mL). The combined organic layer was washed with brine (20 mL), dried over anhydrous Na$_2$SO$_4$ and filtered. The filtrate was concentrated in vacuum. The residue was purified by silica gel chromatography (PE:EtOAc=5:1) to afford 2-(4-bromo-2,6-dichloro-phenoxy)-5-[(4-methoxyphenyl) methoxy]-N-[(4-methoxyphenyl) methyl]-N-methyl-pyridine-4-sulfonamide 72-18 (0.15 g, 48% yield) as a light-yellow solid. LCMS: [M+H]$^+$=667.0/669.0.

Step 15: 72-19

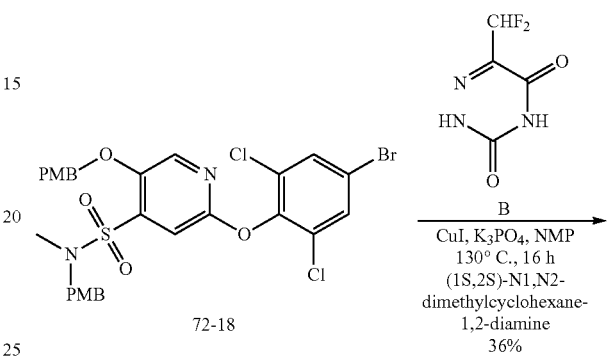

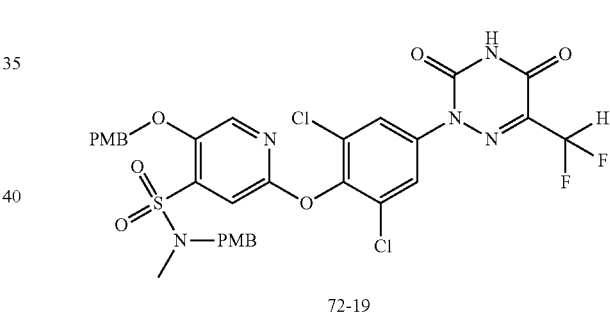

A mixture of 2-(4-bromo-2,6-dichloro-phenoxy)-5-[(4-methoxyphenyl)methoxy]-N-[(4-methoxyphenyl)methyl]-N-methyl-pyridine-4-sulfonamide 72-18 (0.1 g, 149.62 umol)), 6-(difluoromethyl)-2H-1,2,4-triazine-3,5-dione Intermediate B (Example 2) (48.80 mg, 299.23 umol), (1S,2S)—N1,N2-dimethylcyclohexane-1,2-diamine (17.03 mg, 119.69 umol, 18.87 uL), K$_3$PO$_4$ (95.27 mg, 448.85 umol) and copper iodide (71.24 mg, 374.04 umol) in NMP (4 mL) was stirred at 130° C. for 16 h. LC-MS showed the reaction was completed. The reaction mixture was poured into sat. NH$_4$Cl (50 mL) and extracted with EtOAc (3×20 mL). The combined organic layer was washed with brine (2×20 mL), dried over anhydrous Na$_2$SO$_4$ and filtered. The filtrate was concentrated in vacuum. The residue was purified by Prep-TLC (CH$_2$Cl$_2$:MeOH=10:1) to afford 2-[2,6-dichloro-4-[6-(difluoromethyl)-3,5-dioxo-1,2,4-triazin-2-yl]phenoxy]-5-[(4-methoxyphenyl)methoxy]-N-[(4-methoxyphenyl)methyl]-N-methyl-pyridine-4-sulfonamide 72-19 (40 mg, 36% yield) as a yellow solid. LCMS: [M+H]$^+$=750.9.

Step 16: Compound 72

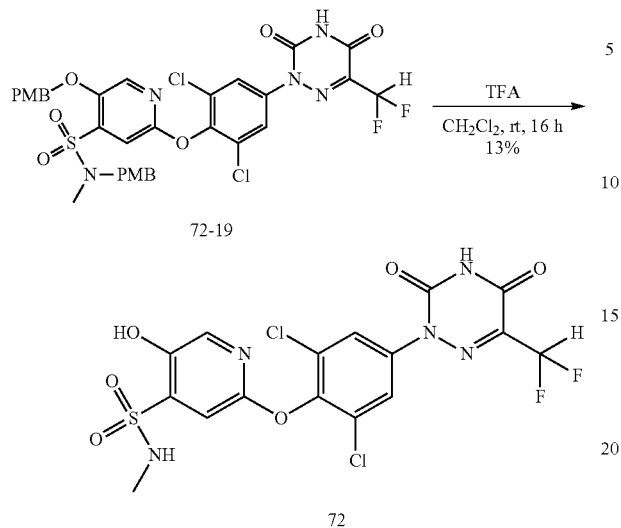

To a solution of 2-[2,6-dichloro-4-[6-(difluoromethyl)-3,5-dioxo-1,2,4-triazin-2-yl] phenoxy]-5-[(4-methoxyphenyl)methoxy]-N-methyl-pyridine-4-sulfonamide 72-19 (50 mg, 79.31 umol) in CH$_2$Cl$_2$ (5 mL) was added TFA (1 mL). The mixture was stirred at 25° C. for 1 h. LC-MS showed the reaction was completed. The reaction mixture was concentrated in vacuum. The residue was purified by Prep-TLC (CH$_2$Cl$_2$:MeOH=10:1) to afford a yellow solid. The yellow solid was further purified by Prep-HPLC (Chromatographic columns: Kromasil-C18 100×21.2 mm 5 um, Mobile Phase: MeCN—H$_2$O (0.1% FA), Gradient: 35-50) to afford 2-[2,6-dichloro-4-[6-(difluoromethyl)-3,5-dioxo-1,2,4-triazin-2-yl] phenoxy]-5-hydroxy-N-methyl-pyridine-4-sulfonamide Compound 72 (5.4 mg, 13% yield) as a white solid. LCMS: [M+H]$^+$=510.0. $^1$H NMR (400 MHz, CD$_3$OD) δ 7.78 (s, 1H), 7.77 (s, 2H), 7.37 (s, 1H), 6.70 (t, J=53.2 Hz, 1H), 2.63 (s, 3H). $^{19}$F NMR (376 MHz, CD$_3$OD) δ−124.1 (s, 2F).

Example 31: Synthesis of Compound 73

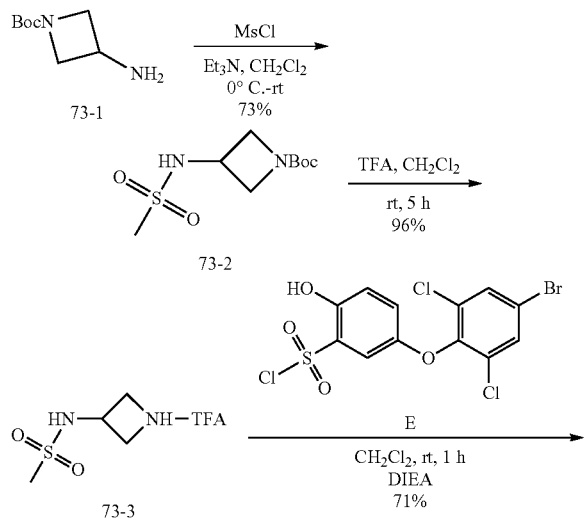

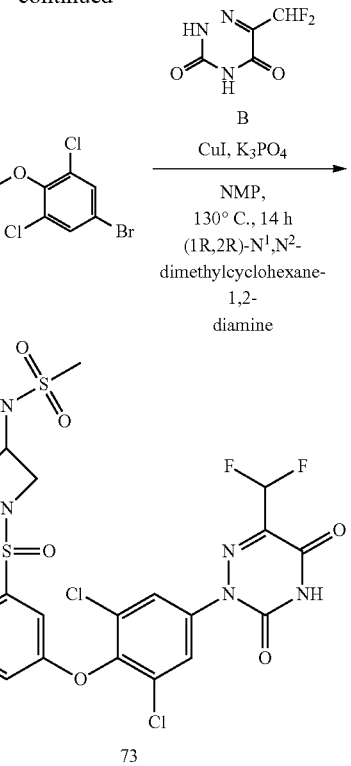

Step 1: 73-2

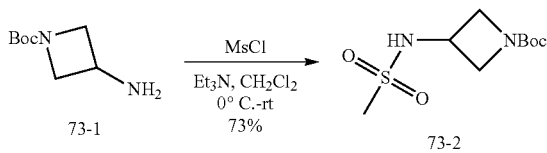 [SMILES: "MsCl" ; CC(C)(C)OC(=O)N1CC(N)C1 ; CC(C)(C)OC(=O)N1CC(NS(C)(=O)=O)C1]

To a solution of tert-butyl 3-aminoazetidine-1-carboxylate 73-1 (4.2 g, 24.39 mmol) and triethylamine (7.40 g, 73.16 mmol, 10.20 mL) in CH$_2$Cl$_2$ (50 mL) at 0° C. was added methanesulfonyl chloride (2.79 g, 24.39 mmol, 1.89 mL) dropwise. The reaction mixture was stirred at rt for 16 h. LC-MS showed the reaction was completed. The reaction mixture was poured into water (200 mL) and extracted with EtOAc (3×50 mL). The combined organic layer was washed with brine (100 mL), dried over anhydrous Na$_2$SO$_4$ and filtered. The filtrate was concentrated in vacuum. The residue was purified by silica gel chromatography (PE: EtOAc=2:1) to afford tert-butyl 3-(methanesulfonamido)azetidine-1-carboxylate 73-2 (4.5 g, 73% yield) as a light-yellow solid. LCMS: [M+Na]$^+$=273.1.

Step 2: 73-3

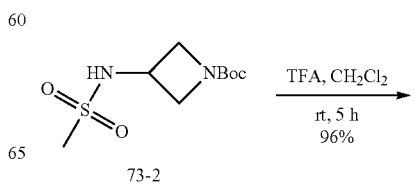

-continued

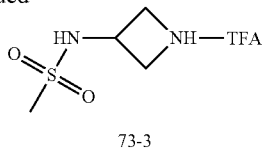

73-3

To a solution of tert-butyl 3-(methanesulfonamido) azetidine-1-carboxylate 73-2 (4.5 g, 17.98 mmol) in CH$_2$Cl$_2$ (20 mL) was added trifluoroacetic acid (10.25 g, 89.89 mmol, 6.93 mL). The reaction mixture was stirred at rt for 5 h. LC-MS showed the reaction was completed. The reaction mixture was concentrated in vacuum to afford N-(1-(2,2,2-trifluoroacetyl)-1λ$^4$-azetidin-3-yl)methanesulfonamide 73-3 (4.26 g, 96% yield) as a residue. The residue was used directly for next step without purification. LCMS: [M+H]$^+$=151.1.

Step 3: 73-4

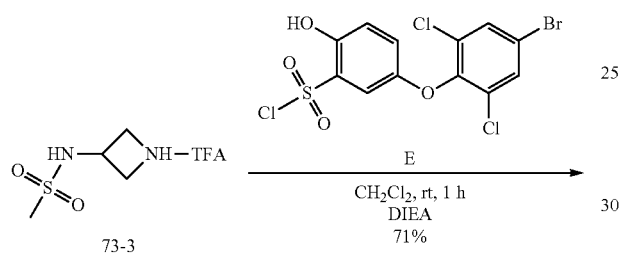

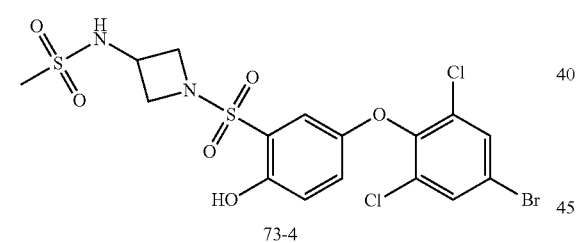

73-4

To a solution of N-(1-(2,2,2-trifluoroacetyl)-1λ$^4$-azetidin-3-yl)methanesulfonamide 73-3 (173.64 mg, 1.16 mmol) and N,N-Diisopropylethylamine (448 mg, 3.47 mmol) in CH$_2$Cl$_2$ (10 mL) was added 5-(4-bromo-2,6-dichloro-phenoxy)-2-hydroxy-benzenesulfonyl chloride Intermediate E (Example 5) (500 mg, 1.16 mmol). The reaction mixture was stirred at rt for 16 h. LC-MS showed the reaction was completed. The reaction mixture was poured into water (500 mL) and extracted with EtOAc (3×100 mL). The combined organic layer was washed with brine (200 mL), dried over anhydrous Na$_2$SO$_4$ and filtered. The filtrate was concentrated in vacuum. The residue was purified by silica gel chromatography (CH$_2$Cl$_2$:MeOH=20:1) to afford N-(1-((5-(4-bromo-2,6-dichlorophenoxy)-2-hydroxyphenyl)sulfonyl)azetidin-3-yl)methanesulfonamide 73-4 (450 mg, 71% yield) as a light-yellow solid. LCMS: [M+H]$^+$=545.1/547.1.

Step 4: Compound 73

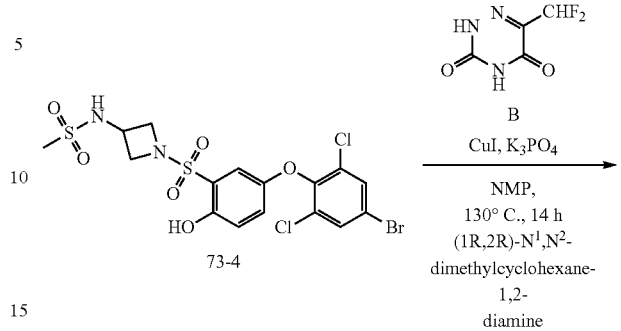

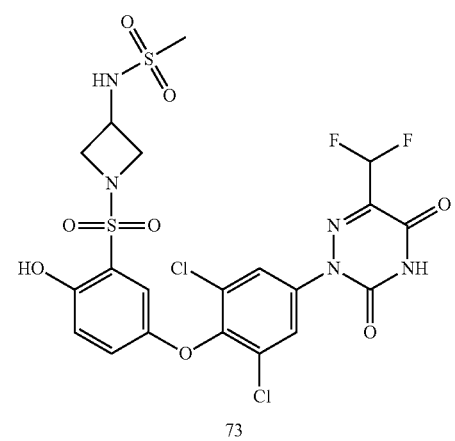

73

A mixture of N-(1-((5-(4-bromo-2,6-dichlorophenoxy)-2-hydroxyphenyl)sulfonyl)azetidin-3-yl)methanesulfonamide 73-4 (200 mg, 366.14 umol), 6-(difluoromethyl)-2H-1,2,4-triazine-3,5-dione Intermediate B (Example 2) (59.71 mg, 366.14 umol), cuprous iodide (174.33 mg, 915.35 umol), potassium phosphate (233.16 mg, 1.10 mmol) and (1R,2R)—N1,N2-dimethylcyclohexane-1,2-diamine (41.66 mg, 292.91 umol) in NMP (10 mL) was stirred at 130° C. for 14 h. LC-MS showed the reaction was completed. The reaction mixture was poured into sat. NH$_4$Cl (50 mL) and extracted with EtOAc (3×20 mL). The combined organic layer was washed with brine (2×20 mL), dried over anhydrous Na$_2$SO$_4$ and filtered. The filtrate was concentrated in vacuum to afford a residue. The residue was purified by Prep-TLC (CH$_2$Cl$_2$:MeOH=10:1) to afford a light-yellow solid. The light-yellow solid was purified by Prep-HPLC (Chromatographic columns: Kromasil-C18 100×21.2 mm 5 um, Mobile Phase: MeCN—H$_2$O (0.1% F A), Gradient: 25-35) to afford N-[1-[5-[2,6-dichloro-4-[6-(difluoromethyl)-3,5-dioxo-1,2,4-triazin-2-yl] phenoxy]-2-hydroxy-phenyl] sulfonylazetidin-3-yl] methane sulfonamide Compound 73 (2.8 mg, 1% yield) as a white solid. LCMS: [M+H]$^+$=628.0. $^1$H NMR (400 MHz, CD$_3$OD) δ 7.82 (s, 2H), 7.14-7.13 (m, 2H), 7.05 (dd, J=8.4, 3.2 Hz, 1H), 6.71 (t, J=52.8 Hz, 1H), 4.19-4.12 (m, 3H), 3.86-3.83 (m, 2H), 2.88 (s, 3H). $^{19}$F NMR (376 MHz, CD$_3$OD) δ−124.0 (s, 2F).

Example 32: Synthesis of Compound 74

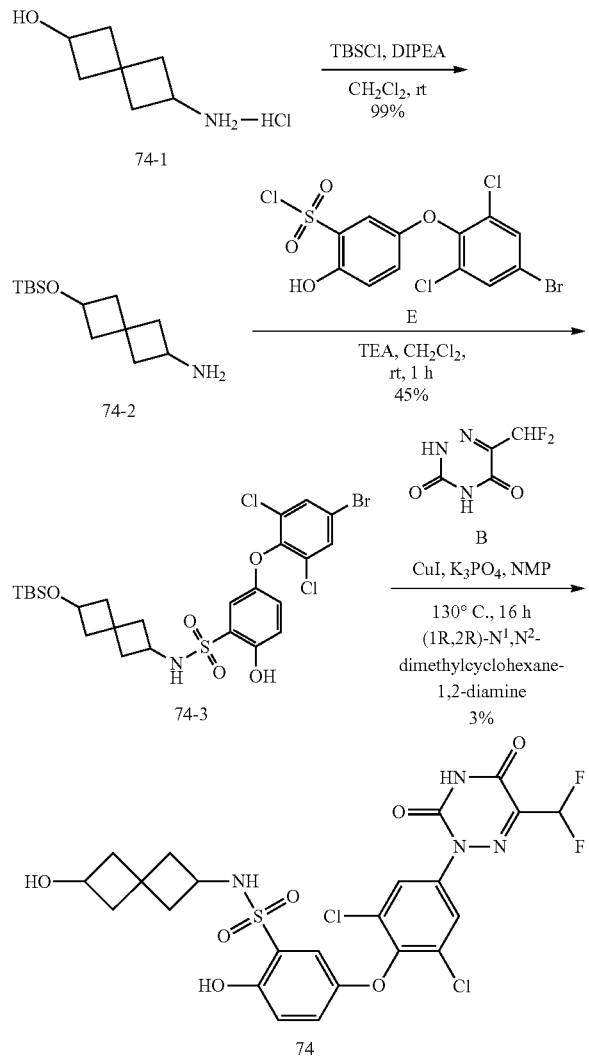

Step 1: 74-2

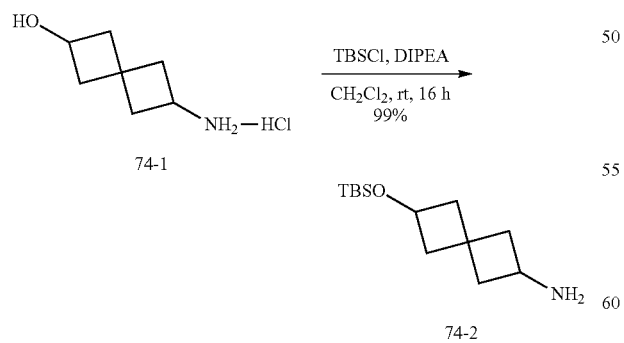

To a solution of 6-amino spiro [3.3] heptan-2-ol 74-1 (300 mg, 1.83 mmol, HC) in CH₂Cl₂ (6 mL) was added DIPEA (710.78 mg, 5.50 mmol, 957.93 uL) and tert-butyl-chloro-dimethyl-silane (552.61 mg, 3.67 mmol, 682.24 uL) at 0° C. The reaction mixture was stirred at rt for 16 h. LCMS showed the reaction was completed. The mixture was concentrated in vacuum to give 2-[tert-butyl(dimethyl) silyl] oxyspiro [3.3] heptan-6-amine 74-2 (440 mg, 99% yield) as a colorless oil which was used for next step without further purification. LCMS: [M+H]⁺=242.3.

Step 2: 74-3

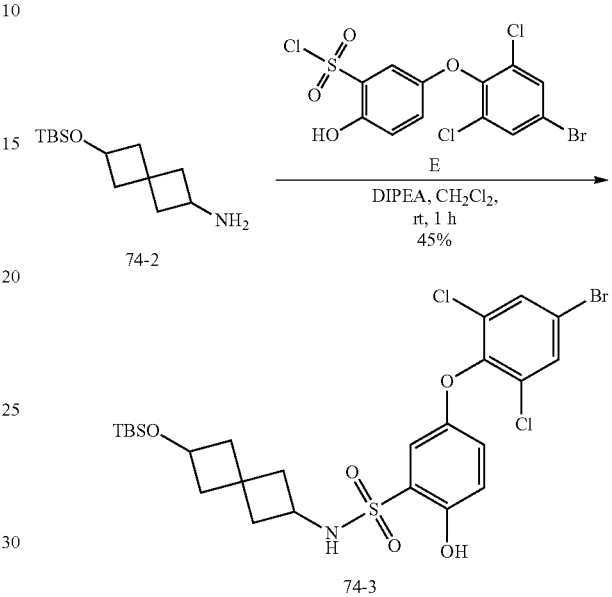

To a solution of 2-[tert-butyl(dimethyl)silyl] oxyspiro [3.3] heptan-6-amine 74-2 (1.67 g, 6.94 mmol) in CH₂Cl₂ (20 mL) was added DIPEA (6.94 mmol, 1.21 mL) and 5-(4-bromo-2,6-dichloro-phenoxy)-2-hydroxy-benzenesulfonyl chloride Intermediate E (Example 5) (600 mg, 1.39 mmol). The reaction mixture was stirred at rt for 1 h. LCMS showed the reaction was completed. After removing the solvent, 30 mL of water was added to the residue. The mixture was extracted with EtOAc (3×20 ml). The organic layer was dried and concentrated. The residue was purified by flash chromatography (EtOAc:PE=1:5) to give 5-(4-bromo-2,6-dichloro-phenoxy)-N-[2-[tert-butyl(dimethyl) silyl] oxyspiro [3.3] heptan-6-yl]-2-hydroxy-benzenesulfonamide 74-3 (400 mg, 45% yield) as a colorless oil. LCMS: [M+Na]⁺=658.0.

Step 3: Compound 74

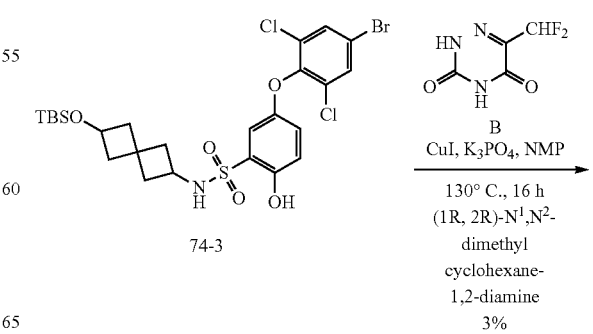

301
-continued

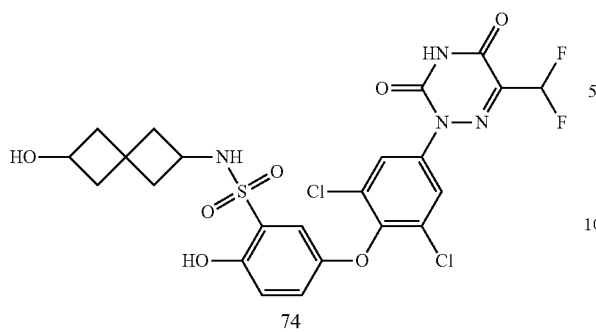

74

A mixture of 5-(4-bromo-2,6-dichloro-phenoxy)-N-[2-[tert-butyl(dimethyl) silyl] oxyspiro [3.3]heptan-6-yl]-2-hydroxy-benzenesulfonamide 74-3 (100 mg, 156.87 umol), 6-(difluoro methyl)-2H-1,2,4-triazine-3,5-dione Intermediate B (Example 2) (51.16 mg, 313.73 umol), (1S,2S)—N1,N2-dimethylcyclohexane-1,2-diamine (15.62 mg, 109.81 umol, 17.32 uL), tripotassium phosphate (99.89 mg, 470.60 umol) and copper iodide (74.69 mg, 392.17 umol) in NMP (2 mL) was stirred at 130° C. for 16 h. LCMS showed the reaction was completed. The reaction mixture was diluted with EtOAc (30 mL) and filtered over a pad of celite. 10 ml water was added to the filtrate which was extracted with EtOAc (3×10 mL). The combined organic phase was washed with brine (20 mL), dried over $Na_2SO_4$ and concentrated. The residue was purified by prep-HPLC (Chromatographic columns: Kromasil-C18 100×21.2 mm 5 um, Mobile Phase: MeCN—$H_2O$ (0.1% FA), Gradient: 50-60) to give 5-[2,6-dichloro-4-[6-(difluoromethyl)-3,5-dioxo-1,2,4-triazin-2-yl] phenoxy]-2-hydroxy-N-(2-hydroxyspiro [3.3] heptan-6-yl) benzene sulfonamide Compound 74 (2.7 mg, 3% yield) as a yellow solid. LCMS: [M+Na]$^+$=627.1. $^1$H NMR (400 MHz, CD$_3$OD) δ 7.82 (s, 2H), 7.10-7.06 (m, 2H), 6.96 (d, J=8.8 Hz, 1H), 6.71 (t, J=52.8 Hz, 1H), 4.02-3.95 (m, 1H), 3.60-3.52 (m, 1H), 3.32-3.26 (m, 1H), 2.17-2.10 (m, 1H), 2.04-2.01 (m, 1H), 1.97-1.91 (m, 1H), 1.88-1.77 (m, 4H). $^{19}$F NMR (376 MHz, CD$_3$OD) δ −124.2 (s, 2F).

The compounds of Formula (I') or (I) in Table 13 below were made according to Example 32 of Compound 74.

TABLE 13

| Cmpd No. | LC-MS, $^1$H and $^{19}$F-NMR data |
|---|---|
| 75 | LCMS : [M + H] $^+$ = 579.0. $^1$H NMR (400 MHZ, CD$_3$OD) δ 7.82 (s, 2H), 7.14-7.03 (m, 2H), 6.97 (d, J = 9.2 Hz, 1H), 6.71 (t, J = 52.8 Hz, 1H), 4.15-4.06 (m,1H), 3.61-3.51 (m, 1H), 2.03-1.94 (m, 1H), 1.77-1.53 (m, 4H), 1.45-1.36 (m, 1H). $^{19}$F NMR (376 MHZ, CD$_3$OD) δ −124.2 (s, 2F). |
| 76 | LCMS: [M + H]$^+$ = 565.0/567.0. $^1$H NMR (400 MHZ, CD$_3$OD) δ 7.81 (s, 2H), 7.14 (d, J = 3.2 Hz, 1H), 7.04 (dd, J = 9.2, 3.2 Hz, 1H), 6.98 (d, J = 9.2 Hz, 1H), 6.70 (t, J = 52.8 Hz,, 1H), 4.39-4.31 (m, 1H), 3.51-3.43 (m, 3H), 3.22-3.20 (m, 1H), 1.92-1.89 (m, 1H), 1.86-1.78 (m, 1H). $^{19}$F NMR (376 MHz, CD$_3$OD) δ −124.1 (s, 2F). |
| 77 | LCMS: [M + H]$^+$ = 565.0. $^1$H NMR (400 MHZ, CD$_3$OD) δ 7.82 (s, 2H), 7.14 (d, J = 2.8 Hz, 1H), 7.06 (dd, J = 9.2, 3.2 Hz 1H), 6.98 (d, J = 8.8 Hz, 1H), 6.71 (t, J = 53.2 Hz, 1H), 4.37-4.32 (m, 1H), 3.44-3.49 (m, 3H), 3.20-3.23 (m, 1H), 1.96-1.90 (m, 1H), 1.85-1.76 (m, 1H). $^{19}$F NMR (376 MHz, CD$_3$OD) δ −124.2 (s, 2F). |

302

Example 33: Synthesis of Compound 78

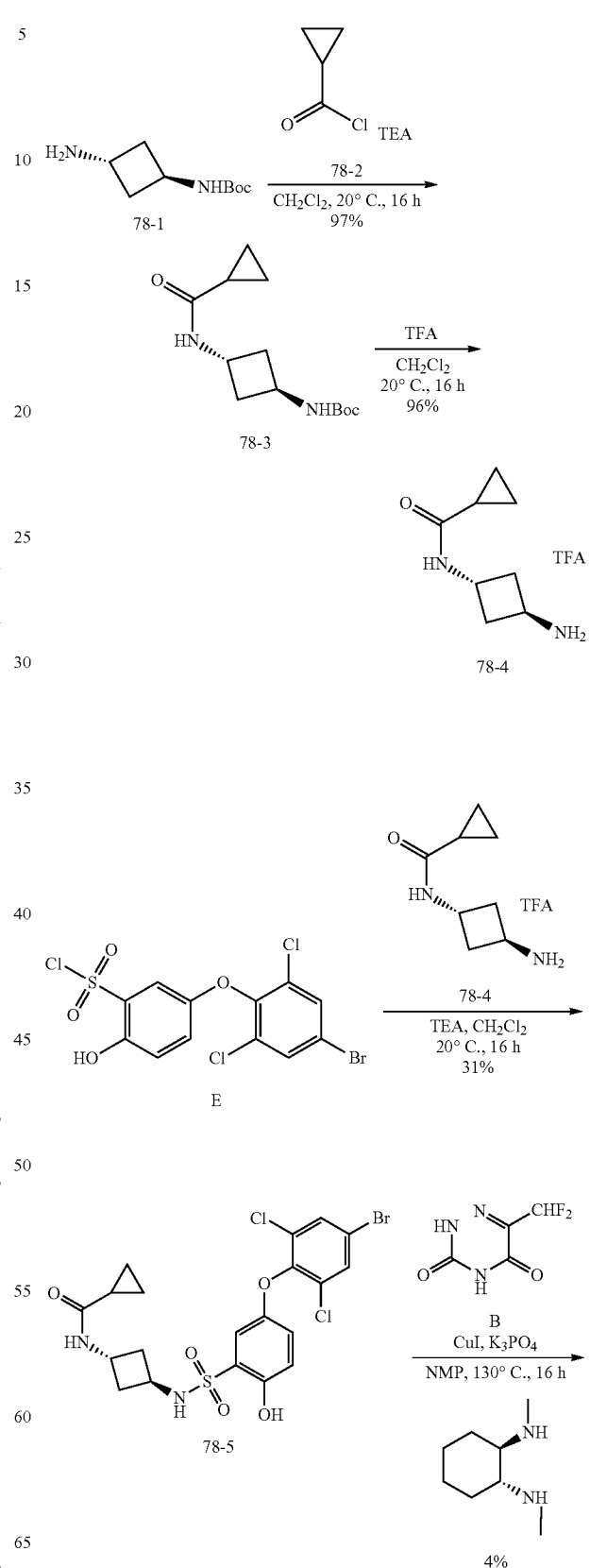

-continued

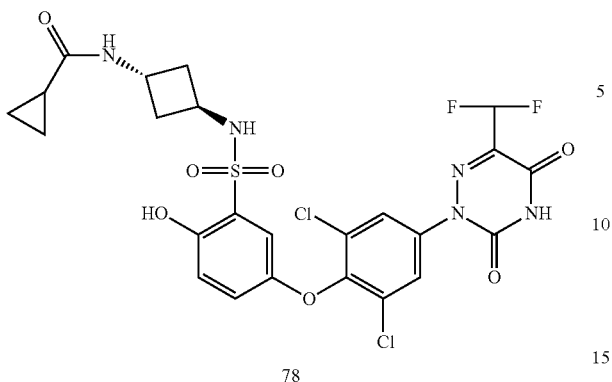

78

Step 1: 78-3

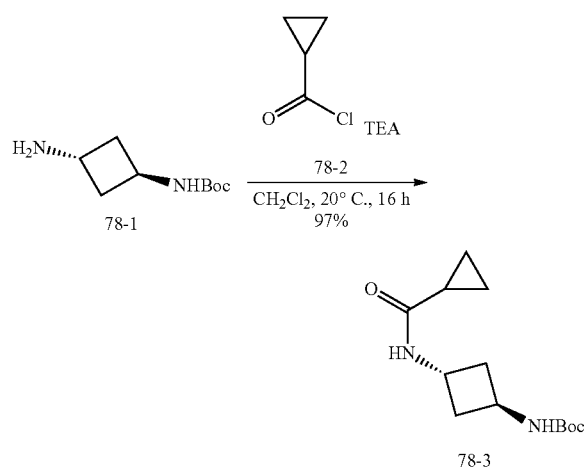 [SMILES: O=C(Cl)C1CC1 ; CC(C)(C)OC(=O)N[C@H]1C[C@H](N)C1 ; CC(C)(C)OC(=O)N[C@H]1C[C@H](NC(=O)C2CC2)C1]

To a mixture of tert-butyl N-(3-aminocyclobutyl) carbamate 78-1 (200 mg, 1.07 mmol) in CH$_2$Cl$_2$ (2 mL) was added TEA (325.98 mg, 3.22 mmol) and cyclopropane carbonyl chloride 78-2 (112.25 mg, 1.07 mmol). The mixture was stirred at 20° C. for 16 h. LCMS showed the material was consumed and the product was formed. The reaction mixture was washed with water (2 mL) and extracted with EtOAc (3×5 mL). The combined organic layer was washed with brine (5 mL), dried over anhydrous Na$_2$SO$_4$, filtered and concentrated in vacuum to afford tert-butyl N-[3-(cyclopropane carbonyl amino)-cyclobutyl]-carbamate 78-3 (280 mg, 97% yield) as a yellow solid. LCMS: [M+H−56]$^+$=199.1.

Step 2: 78-4

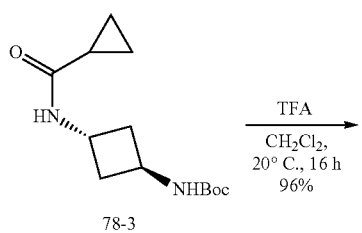

-continued

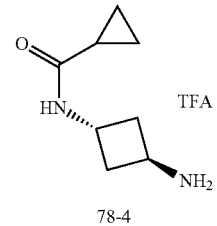

To a mixture of tert-butyl N-[3-(cyclopropane carbonyl amino)-cyclobutyl]-carbamate 78-3 (200 mg, 786.40 umol) in CH$_2$Cl$_2$ (2 mL) was added TFA (448.32 mg, 3.93 mmol) and was stirred at 20° C. for 16 h. LCMS showed the product was formed. The reaction mixture was concentrated in vacuum to afford a N-[3-[(2,2,2-trifluoroacetyl)-amino]-cyclobutyl]-cyclopropanecarboxamide 78-4 (200 mg, 96% yield) as a light yellow solid, which was used to the next step without further purification. LCMS: [M+H]$^+$=155.2.

Step 3: 78-5

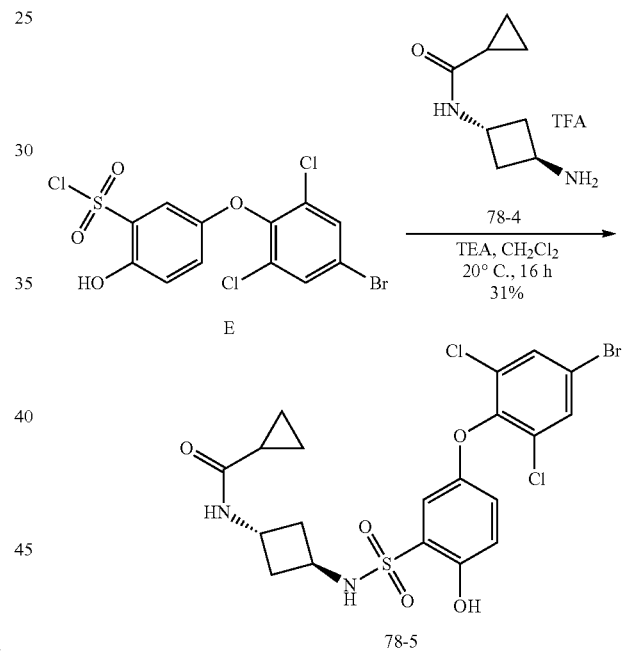

To a mixture of N-(3-amino-cyclobutyl)-cyclopropane carboxamide 78-4 (178.28 mg, 1.16 mmol) in CH$_2$Cl$_2$ (5 mL) was added TEA (350.95 mg, 3.47 mmol) and 5-(4-bromo-2,6-dichloro-phenoxy)-2-hydroxy-benzenesulfonyl chloride Intermediate E (Example 5) (500 mg, 1.16 mmol). The reaction mixture was stirred at 20° C. for 16 h. LCMS showed the starting material was consumed and the product was formed. The reaction mixture was washed with water (5 mL) and extracted with EtOAc (3×5 mL). The combined organic layer was washed with brine (5 mL), dried over anhydrous Na$_2$SO$_4$, filtered and concentrated in vacuum. The residue was purified by prep-TLC (CH$_2$Cl$_2$: CH$_3$OH=10:1) to afford N-[3-[[5-(4-bromo-2,6-dichloro-phenoxy)-2-hydroxy-phenyl]-sulfonylamino]-cyclobutyl]-cyclopropanecarboxamide 78-5 (200 mg, 31% yield) as a yellow solid. LCMS: [M+H]$^+$=548.9/550.9.

Step 4: Compound 78

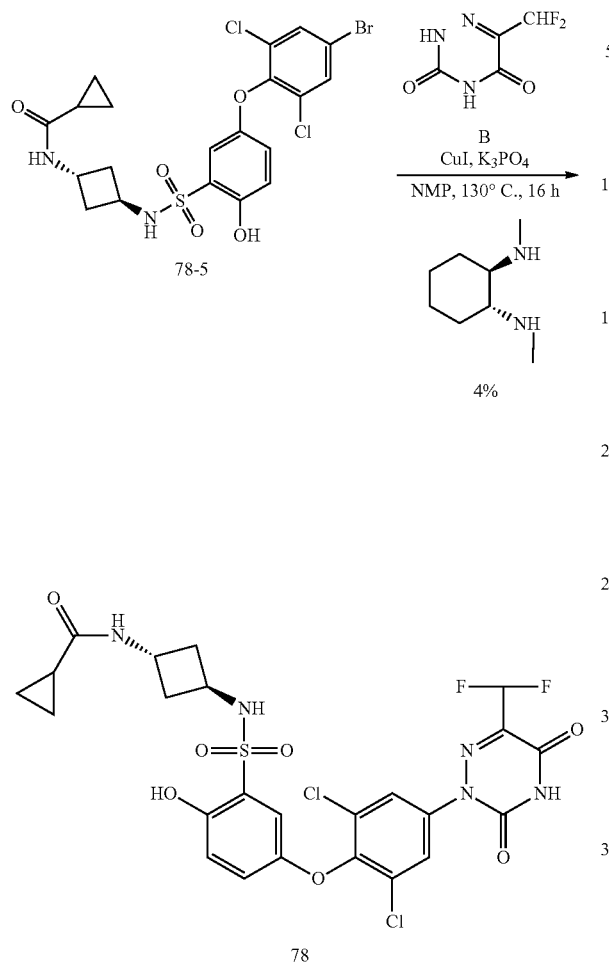

To mixture of N-[3-[[5-(4-bromo-2,6-dichloro-phenoxy)-2-hydroxy-phenyl]sulfonyl amino]cyclobutyl] cyclopropane carboxamide 78-5 (200 mg, 363.47 umol) in NMP (3 mL) was added 6-(difluoromethyl)-2H-1,2,4-triazine-3,5-dione Intermediate B (Example 2) (118.55 mg, 726.94 umol), (1R,2R)—N1,N2-dimethylcyclohexane-1,2-diamine (41.36 mg, 290.78 umol), $K_3PO_4$ (231.17 mg, 1.09 mmol) and CuI (173.06 mg, 908.68 umol). The mixture was stirred at 130° C. for 16 h under $N_2$ atmosphere. LCMS showed the product was formed. The reaction mixture was washed with water (2 mL) and extracted with EtOAc (3×4 mL). The combined organic layer was washed with brine (4 mL), dried over anhydrous $Na_2SO_4$, filtered and concentrated in vacuum. The residue was purified by Prep-HPLC (Kromasil-C18 100×21.2 mm 5 um, Mobile Phase: MeCN—$H_2O$ (0.1% FA), Gradient: 40-50) to afford N-[3-[[5-[2,6-dichloro-4-[6-(difluoromethyl)-3,5-dioxo-1,2,4-triazin-2-yl]-phenoxy]-2-hydroxy-phenyl]-sulfonylamino]-cyclobutyl]-cyclopropanecarboxamide Compound 78 (1.1 mg, 4% yield). LCMS: $[M+H]^+$=631.9. 1H NMR (400 MHz, $CD_3OD$) δ 7.71 (s, 2H), 7.01 (d, J=3.2 Hz, 1H), 6.96 (dd, J=8.8 Hz, 3.2 Hz, 1H), 6.86 (d, J=9.2 Hz, 1H), 6.60 (t, J=53.2 Hz, 1H), 4.00-3.97 (m, 1H), 3.83-3.79 (m, 1H), 2.11-2.09 (m, 2H), 1.95-1.85 (m, 2H), 1.42-1.43 (m, 1H), 0.69-0.68 (m, 2H), 0.61-0.63 (m, 2H). $^{19}F$ NMR (376 MHz, $CD_3OD$) δ−124.2 (s, 2F).

Example 34: Synthesis of Compound 79

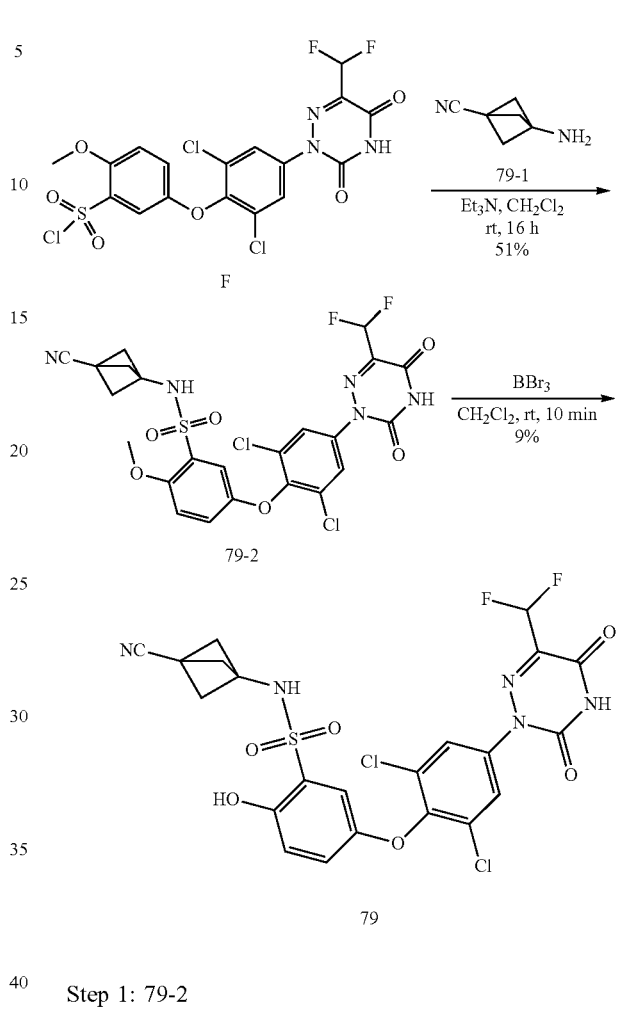

Step 1: 79-2

To a solution of 3-aminobicyclo [1.1.1] pentane-1-carbonitrile 79-1 (20.45 mg, 189.14 umol) and N, N-diethylethanamine (24.45 mg, 189.14 umol) in CH$_2$Cl$_2$ (5 mL) was added 5-(2,6-dichloro-4-(6-(difluoromethyl)-3,5-dioxo-4,5-dihydro-1,2,4-triazin-2(3H)-yl)phenoxy)-2-methoxybenzenesulfonyl chloride Intermediate F (Example 6) (50 mg, 94.57 umol) at 0° C. The mixture was stirred at rt for 16 h. LC-MS showed the reaction was completed. The reaction was concentrated in vacuum and purified by prep-TLC (CH$_2$Cl$_2$:CH$_3$OH=10:1) to afford N-(3-cyanobicyclo[1.1.1]pentan-1-yl)-5-(2,6-dichloro-4-(6-(difluoromethyl)-3,5-dioxo-4,5-dihydro-1,2,4-triazin-2(3H)-yl) phenoxy)-2-methoxybenzenesulfonamide 79-2 (29 mg, 51%) as a yellow solid. LCMS: [M+H]$^+$=600.0.

Step 2: Compound 79

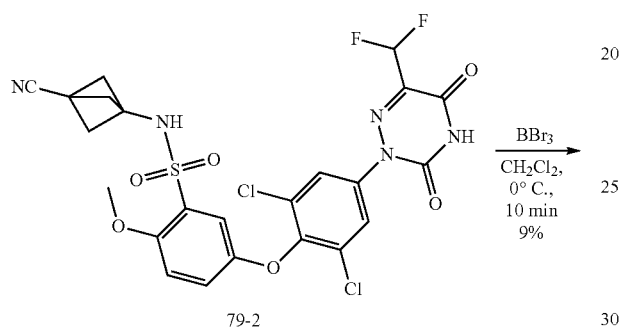

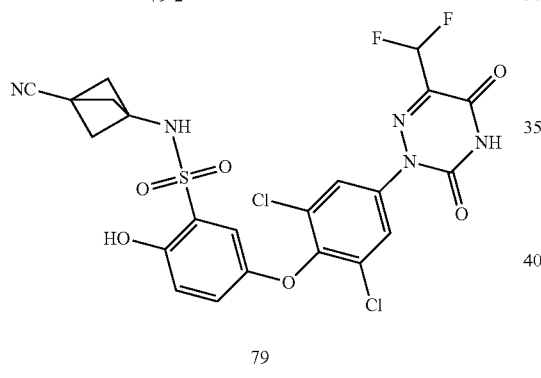

To a solution of N-(3-cyanobicyclo[1.1.1]pentan-1-yl)-5-(2,6-dichloro-4-(6-(difluoromethyl)-3,5-dioxo-4,5-dihydro-1,2,4-triazin-2(3H)-yl)phenoxy)-2-methoxy benzene sulfonamide 79-2 (26 mg, 43.31 umol) in CH$_2$Cl$_2$ (2 mL) was added BBr$_3$ (0.5 mL) at 0° C. The reaction was stirred at 0° C. for 10 min. TLC showed the reaction was completed. The reaction was quenched by adding water (0.1 mL) and concentrated in vacuum. Then the resulting mixture was purified by prep-HPLC (Chromatographic columns: Xbridge 5 u C18 150×19 mm, Mobile Phase: MeCN—H$_2$O (0.1% FA), Gradient: 40-50) to afford N-(3-cyanobicyclo[1.1.1]pentan-1-yl)-5-(2,6-dichloro-4-(6-(difluoromethyl)-3,5-dioxo-4,5-dihydro-1,2,4-triazin-2(3H)-yl)phenoxy)-2-hydroxybenzenesulfonamide Compound 79 (2.4 mg, 9% yield) as a white solid. LCMS: [M+Na]$^+$=607.9. $^1$H NMR (400 MHz, CD$_3$OD) δ 7.84 (s, 2H), 7.15 (dd, J=8.8, 3.2 Hz, 1H), 7.08 (d, J=3.2 Hz, 1H), 6.99 (d, J=8.8 Hz, 1H), 6.71 (t, J=52.8 Hz, 1H), 2.19 (s, 6H). $^{19}$F NMR (376 MHz, CD$_3$OD) δ −124.2 (s, 2F).

The compounds of Formula (I) or (I) in Table 14 below were made according to Example 34 of Compound 79.

TABLE 14

| Cmpd No. | LC-MS, $^1$H and $^{19}$F-NMR data |
| --- | --- |
| 80 | LCMS: [M + H]$^+$ = 565.0 $^1$H NMR (400 MHZ, CD$_3$OD) δ 7.81 (s, 2H), 7.14 (d, J = 3.2 Hz, 1H), 7.05 (dd, J = 8.8, 2.8Hz, 1H), 6.97 (d, J = 8.8 Hz, 1H), 6.71 (t, J = 52.8 Hz, 1H), 2.97 (s, 2H), 0.65-0.62 (m, 2H), 0.51-0.48 (m, 2H). $^{19}$F NMR (376 MHZ, CD$_3$OD) δ −124.2 (s, 2F). |
| 81 | LCMS: [M + H]$^+$ = 577.0. $^1$H NMR (400 MHZ, CD$_3$OD) δ 7.83 (s, 2H), 7.16-7.06 (m, 2H), 6.97 (d, J = 8.8 Hz, 1H), 6.72 (t, J = 52.8 Hz, 1H), 3.30 (s, 6H). $^{19}$F NMR (376 MHz, CD$_3$OD) δ −124.2 (s, 2F). |
| 82 | LCMS: [M + H] $^+$ = 627.0. $^1$H NMR (400 MHZ, CD$_3$OD) δ 7.82 (s, 2H), 7.14-7.04 (m, 2H), 6.97 (d, J = 8.8 Hz, 1H), 6.71 (t, J = 52.8 Hz, 1H), 4.12-3.99 (m, 1H), 3.73-3.61 (m, 1H), 2.84 (s, 3H), 2.50-2.57 (m, 2H), 2.47-2.33 (m, 2H). $^{19}$F NMR (376 MHz, CD$_3$OD) δ −124.2 (s, 2F). |
| 83 | LCMS: [M + H] $^+$ = 598.9. $^1$H NMR (400 MHZ, CD$_3$OD) δ 7.27 (s, 2H), 7.06 (d, J = 3.2 Hz, 1H), 7.00 (dd, J = 9.2, 3.2 Hz, 1H), 6.91 (d, J = 8.8 Hz, 1H), 6.62 (t, J = 52.8 Hz, 1H), 4.20-4.15 (m, 2H), 4.11-4.05 (m, 1H), 3.96-3.91(m, 2H). $^{19}$F NMR (376 MHz, CD$_3$OD) δ −124.3 (s, 2F). |

Example 35: Synthesis of Compound 84

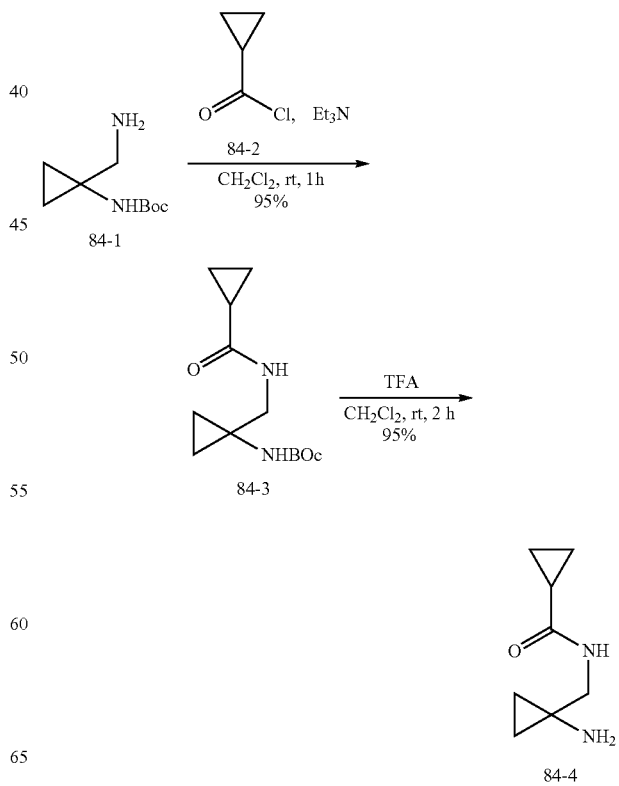

-continued

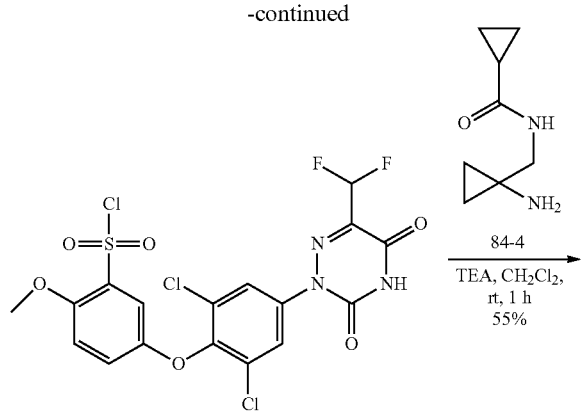

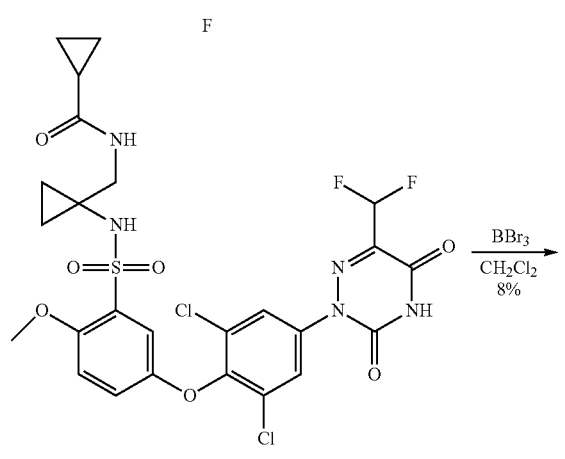

84-5

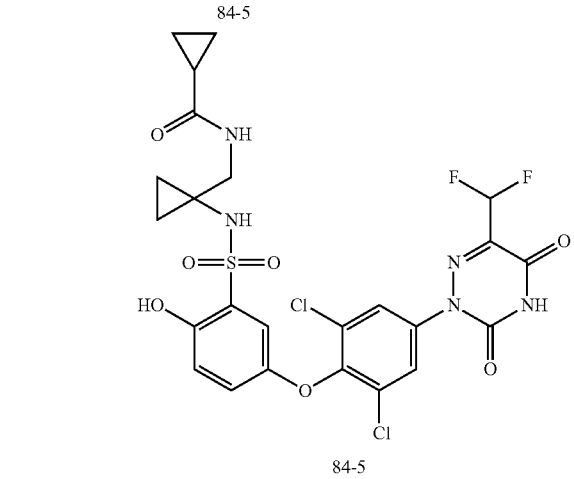

84-5

Step 1: 84-3

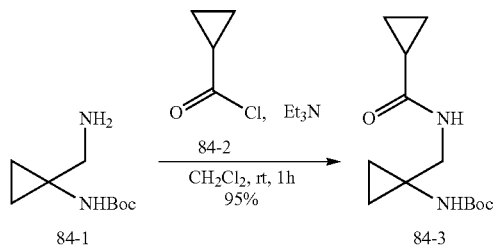 [SMILES: "Et3N" ; CC(C)(C)OC(=O)NC1(CN)CC1 ; O=C(Cl)C1CC1 ; CC(C)(C)OC(=O)NC1(CNC(=O)C2CC2)CC1]

A mixture of cyclopropane carbonyl chloride 84-2 (145.93 mg, 1.40 mmol, 126.89 uL), tert-butyl N-[1-(amino methyl) cyclopropyl] carbamate 84-1 (200 mg, 1.07 mmol) and TEA (325.98 mg, 3.22 mmol, 449.01 uL) in CH$_2$Cl$_2$ (3 mL) was stirred at 25° C. for 1 h. LCMS showed the reaction was completed. Water (15 mL) was added and the mixture was extracted with EtOAc (3×15 mL). The combined organic layers were washed with brine, dried over Na$_2$SO$_4$ and concentrated in vacuum to give tert-butyl N-[1-[(cyclopropane carbonyl amino) methyl]cyclopropyl] carbamate 84-3 (260 mg, 95% yield) as a yellow solid. LCMS: [M+Na]$^+$=255.1.

Step 2: 84-4

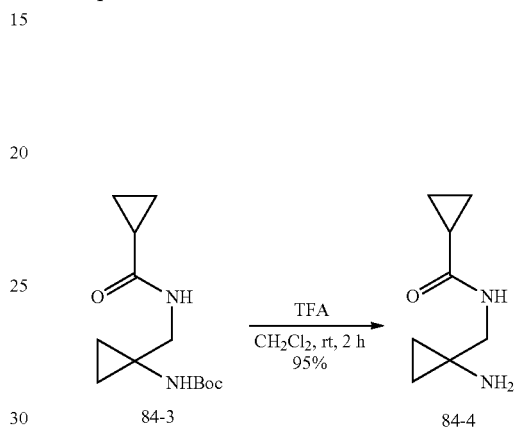

A mixture of tert-butyl N-[1-[(cyclopropane carbonyl amino) methyl] cyclopropyl] carbamate 84-3 (260 mg, 1.02 mmol) and TFA (1.48 g, 12.98 mmol, 1 mL) in CH$_2$Cl$_2$ (5 mL) was stirred at 25° C. for 1 h. LCMS showed the reaction was completed. The mixture was concentrated to give N-[(1-aminocyclopropyl) methyl] cyclopropane carboxamide 84-4 (150 mg, 95% yield) as a yellow solid. LCMS: [M+H]$^+$=155.1.

Step 3: 84-5

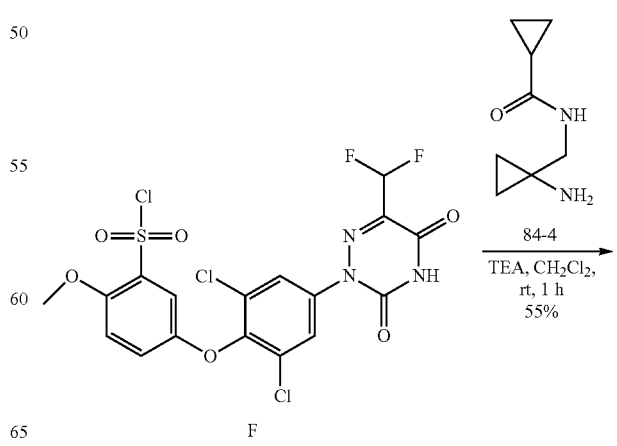

-continued

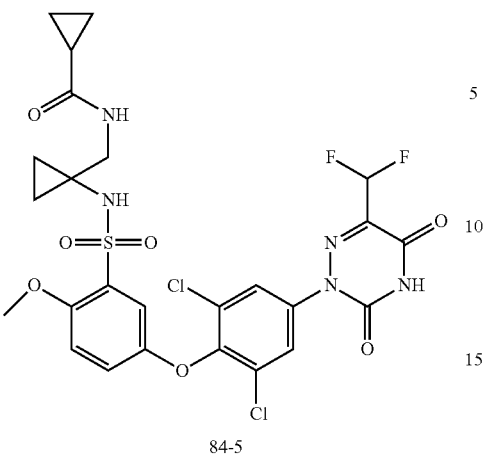

84-5

A mixture of 5-[2,6-dichloro-4-[6-(difluoromethyl)-3,5-dioxo-1,2,4-triazin-2-yl]phenoxy]-2-methoxy-benzene-sulfonyl chloride F (60 mg, 113.49 umol), N-[(1-aminocyclopropyl) methyl]cyclopropane carboxamide 84-4 (35.00 mg, 226.97 umol) and TEA (34.45 mg, 340.46 umol, 47.45 uL) in CH$_2$Cl$_2$ (2 mL) was stirred at 25° C. for 1 h. LCMS showed the reaction was completed. Water (15 mL) was added and the mixture was extracted with EtOAc (3×15 mL). The combined organic layers were washed with brine, dried over Na$_2$SO$_4$ and concentrated in vacuum. The residue was purified by flash chromatography (CH$_2$Cl$_2$:MeOH=10:1) to give N-[[1-[[5-[2,6-dichloro-4-[6-(difluoromethyl)-3,5-dioxo-1,2,4-triazin-2-yl]phenoxy]-2-methoxy-phenyl]sulfonyl amino]cyclopropyl]methyl]cyclopropane carboxamide 84-5 (40 mg, 55% yield) as a yellow solid. LCMS: [M+H]$^+$=646.0.

Step 4: Compound 84

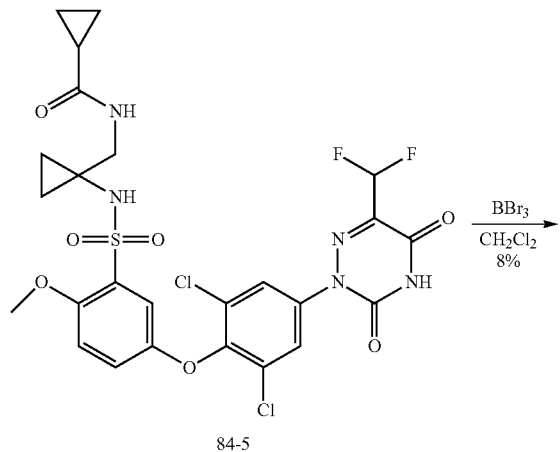

84-5

-continued

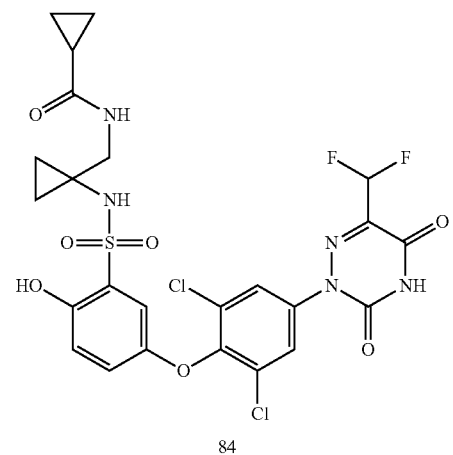

84

To a solution of N-[[1-[[5-[2,6-dichloro-4-[6-(difluoromethyl)-3,5-dioxo-1,2,4-triazin-2-yl]phen oxy]-2-methoxy-phenyl]sulfonyl amino]cyclopropyl]methyl] cyclopropane carboxamide 84-5 (40 mg, 61.88 umol) in CH$_2$Cl$_2$ (2 mL) was added boron tribromide (15.50 mg, 61.88 umol) at 0° C. The mixture was stirred at 0° C. for 0.5 h. LCMS showed the reaction was completed. Water (15 mL) was added and the mixture was extracted with EtOAc (3×13 mL). The combined organic layers were washed with brine, dried over Na$_2$SO$_4$ and concentrated in vacuum. The residue was purified by prep-HPLC (Xbridge 5 u C18 150×19 mm, Mobile Phase: MeCN—H$_2$O (0.1% TFA), Gradient: 40-50). The prepared solution was cooled to 0° C. and 1 M HCl (0.5 mL) was added. The mixture was freeze-dried to give N-[[1-[[5-[2,6-dichloro-4-[6-(difluoromethyl)-3,5-dioxo-1,2,4-triazin-2-yl] phenoxy]-2-hydroxy-phenyl] sulfonyl amino] cyclopropyl] methyl]cyclopropane carboxamide Compound 84 (3.2 mg, 8% yield) as a yellow solid. LCMS: [M+H]$^+$=632.1. $^1$H NMR (400 MHz, CD$_3$OD) δ 7.82 (s, 2H), 7.07-7.10 (m, 2H), 6.96 (d, J=8.8 Hz, 1H), 6.72 (t, J=52.8 Hz, 1H), 3.21 (s, 2H), 1.54-1.57 (m, 1H), 0.85-0.71 (m, 4H), 0.70-0.58 (m, 4H). $^{19}$F NMR (376 MHz, CD$_3$OD) δ−124.3 (s, 2F).

The compounds of Formula (I') or (I) in Table 15 below were made according to Example 35 of Compound 84.

TABLE 15

| Cmpd No. | LC-MS, $^1$H and $^{19}$F-NMR data |
|---|---|
| 85 | LCMS: [M + H]$^+$ = 644.0. $^1$H NMR (400 MHZ, CD$_3$OD) δ 7.82 (s, 2H), 7.15-7.05 (m, 2H), 6.97 (d, J = 8.8 Hz, 1H), 6.70 (t, J = 53.2 Hz, 1H), 1.99 (s,6H), 1.47-1.40 (m, 1H), 0.79-0.73 (m, 2H), 0.73-0.66 (m, 2H). $^{19}$F NMR (376 MHz, CD$_3$OD) δ −124.1 (s, 2F). |
| 86 | LCMS: [M + H]$^+$ = 632.0. $^1$H NMR (400 MHZ, CD$_3$OD) δ 7.82 (s, 2H), 7.13-7.02 (m, 2H), 6.97 (d, J = 8.8 Hz, 1H), 6.71 (t, J = 52.8 Hz, 1H), 3.86-3.74 (m, 1H), 3.45-3.36 (m, 1H), 2.46-2.34 (m, 2H), 1.86-1.74 (m, 2H), 1.52-1.42 (m, 1H), 0.81-0.62 (m, 4H). $^{19}$F NMR (375 MHz, CD$_3$OD) δ −124.2 (s, 2F). |

Example 36: Synthesis of Compound 87
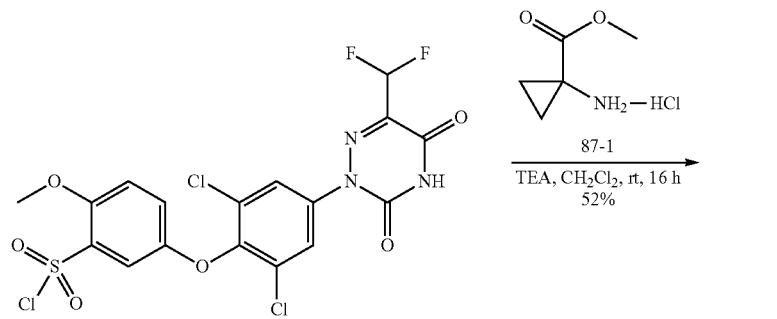
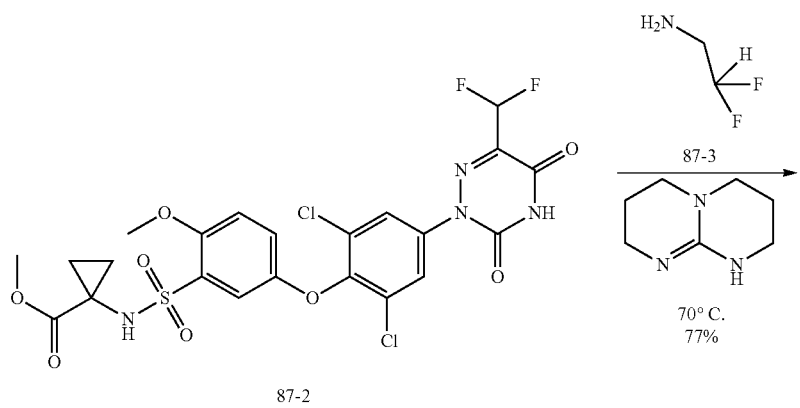
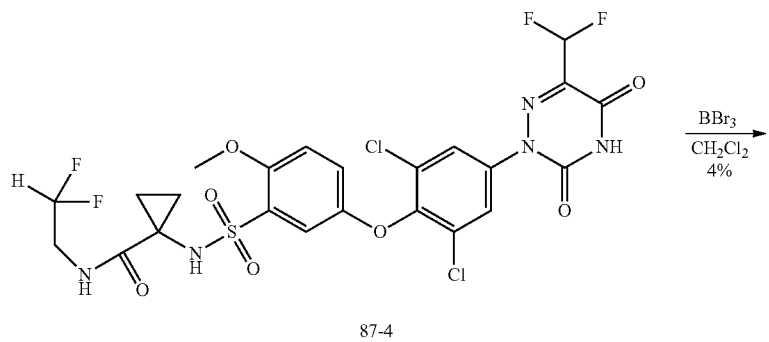
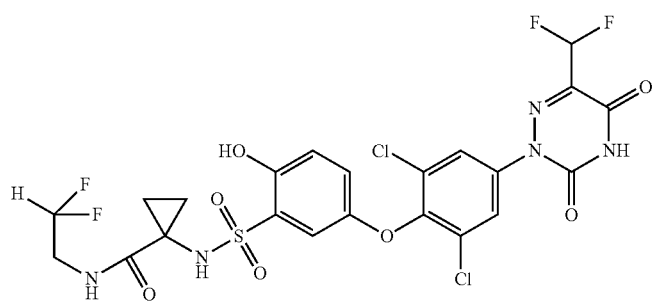

Step 1: 87-2

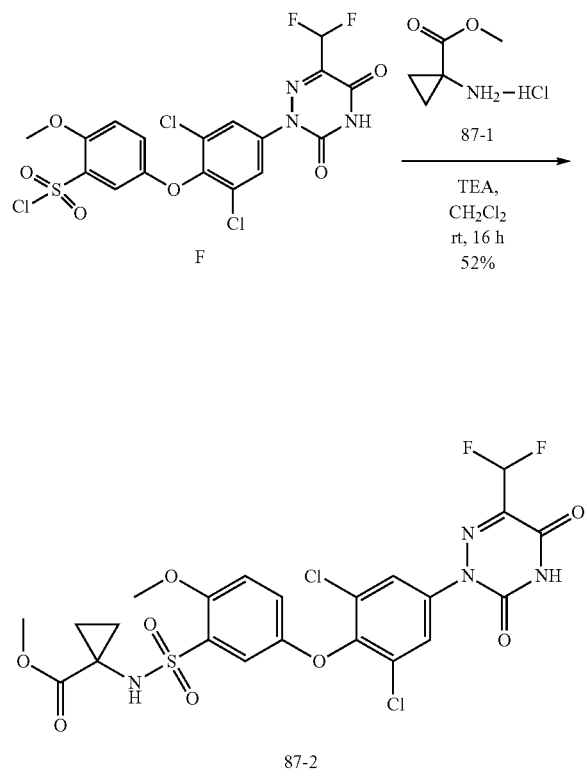

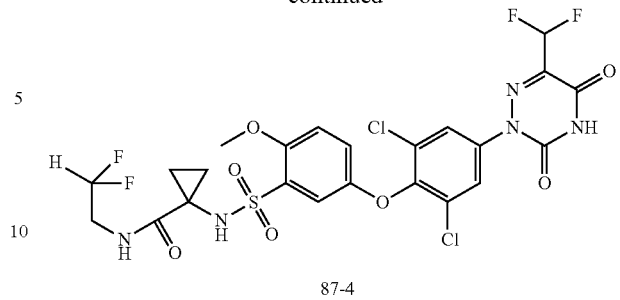

A solution of methyl 1-[[5-[2,6-dichloro-4-[6-(difluoromethyl)-3,5-dioxo-1,2,4-triazin-2-yl]phenoxy]-2-methoxyphenyl]sulfonylamino]cyclopropanecarboxylate 87-2 (60 mg, 98.79 umol) and TBD (41.25 mg, 296.36 umol) in 2,2-difluoroethanamine 87-3 (1.15 g, 14.19 mmol, 1 mL) was stirred at 70° C. for 15 h. LCMS showed the product was formed. The reaction mixture was poured into water and extracted with EtOAc (3×50 mL). The combined organic layer was dried over anhydrous Na$_2$SO$_4$, filtered and concentrated in vacuum. The residue was purified by column chromatography (PE:EtOAc=1:1) to give 1-[[5-[2,6-dichloro-4-[6-(difluoromethyl)-3,5-dioxo-1,2,4-triazin-2-yl]phenoxy]-2-methoxy-phenyl] sulfonylamino]-N-(2,2-difluoroethyl)cyclopropane carboxamide 87-4 (50 mg, 77% yield) as a yellow oil. LCMS: [M+H]$^+$=655.9.

Step 3: Compound 87

To a solution of methyl 1-aminocyclopropanecarboxylate; hydrochloride 87-1 (86.02 mg, 567.43 umol) and TEA (57.42 mg, 567.43 umol, 79.09 uL) in CH$_2$Cl$_2$ (5 mL) was added 5-[2,6-dichloro-4-[6-(difluoromethyl)-3,5-dioxo-1,2,4-triazin-2-yl] phenoxy]-2-methoxy-benzenesulfonyl chloride Intermediate F (Example 6) (100 mg, 189.14 umol). The mixture was stirred at 25° C. for 16 h. LCMS showed the product was formed. The reaction mixture was poured into water and extracted with EtOAc (3×50 mL). The combined organic layer was dried over anhydrous Na$_2$SO$_4$, filtered and concentrated in vacuum. The residue was purified by column chromatography (CH$_2$Cl$_2$:CH$_3$OH=20:1) to give methyl 1-[[5-[2,6-dichloro-4-[6-(difluoromethyl)-3,5-dioxo-1,2,4-triazin-2-yl] phenoxy]-2-methoxy-phenyl] sulfonylamino] cyclopropane carboxylate 87-2 (60 mg, 52% yield) as a yellow oil. LCMS: [M+H]$^+$=607.0.

Step 2: 87-4

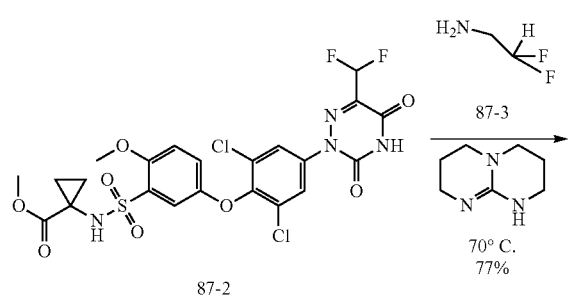

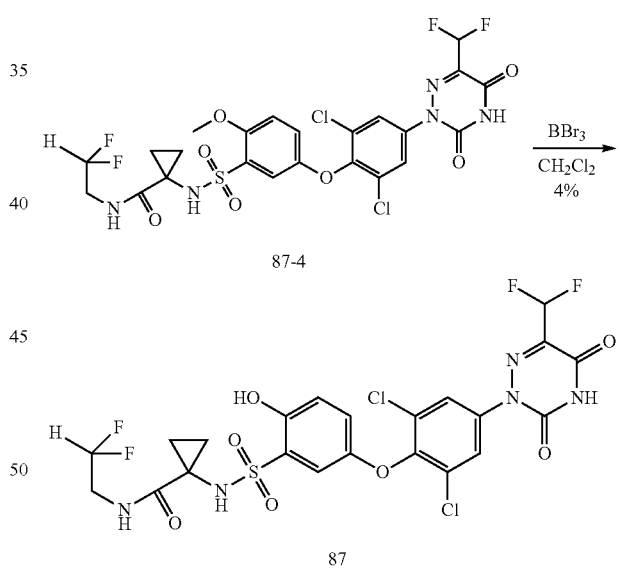

To a solution of 1-[[5-[2,6-dichloro-4-[6-(difluoromethyl)-3,5-dioxo-1,2,4-triazin-2-yl]phenoxy]-2-methoxyphenyl]sulfonylamino]-N-(2,2-difluoroethyl)cyclopropanecarboxamide 87-4 (50 mg, 76.17 umol) in CH$_2$Cl$_2$ (3 mL) was added BBr$_3$ (190.44 mg, 761.74 umol) at 0° C. The mixture was stirred at 0° C. for 15 min. LCMS showed the product was formed. The reaction mixture was poured into water and extracted with EtOAc (3×50 mL). The combined organic layer was dried over anhydrous Na$_2$SO$_4$, filtered and concentrated in vacuum. The residue was purified by Prep-HPLC (Chromatographic columns: Kromasil 100-5 C18 5 um 100×21.5 mm, Mobile Phase: MeCN—H$_2$O (0.10%

FA), Gradient: 40-50) to give 1-[[5-[2,6-dichloro-4-[6-(difluoromethyl)-3,5-dioxo-1,2,4-triazin-2-yl] phenoxy]-2-hydroxy-phenyl] sulfonyl amino]-N-(2,2-difluoroethyl) cyclopropanecarboxamide Compound 87 (2.0 mg, 4 0 yield) as a white solid. LCMS: [M+H]⁺=642.2. ¹H NMR (400 MHz, CD₃OD) δ 7.82 (s, 2H), 7.13-7.09 (m, 2H), 6.98 (d, J=8.4 Hz, 1H), 6.70 (t, J=53.2 Hz, 1H), 5.84 (tt, J=56.1, 4.0 Hz, 1H), 3.56 (td, J=14.8, 4.0 Hz, 2H), 1.28-1.25 (i, 2H), 1.01-0.98 (in, 2H). ¹⁹F NMR (376 MHz, CD₃OD) δ−124.2 (s, 2F),−124.2 (s, 2F).

The compounds of Formula (I') or (I) in Table 16 below were made according to Example 36 of Compound 87.

TABLE 16

| Cmpd No. | LC-MS, ¹H and ¹⁹F-NMR data |
|---|---|
| 88 | LCMS: [MS + H]⁺ = 616.1. ¹H NMR (400 MHZ, CD₃OD) δ 7.81 (s, 2H), 7.19 (d, J = 2.8 Hz, 1H), 7.04 (dd, J = 8.8, 3.2 Hz, 1H), 6.97 (d, J = 8.8 Hz, 1H), 6.71 (t, J = 52.8 Hz, 1H), 5.83 (tt, J = 56.0, 4.0 Hz, 1H), 3.62 (s, 2H), 3.53 (td, J = 15.2, 4.4 Hz, 2H). ¹⁹F NMR (376 MHZ, CD₃OD) δ −124.3 (s, 2F), −124.3 (s, 2F). |
| 89 | LCMS: [M + H] ⁺ = 632.0. ¹H NMR (400 MHZ, CD₃OD) δ 7.82 (s, 2H), 7.13-7.10 (m, 2H), 7.10 (d, J = 8.4 Hz, 1H), 6.72 (t, J = 53.2 Hz, 1H), 4.23-4.18 (m, 1H), 2.27-2.20 (m, 2H), 1.98-1.88 (m, 2H), 1.74-1.65 (m, 2H), 1.26-1.23 (m, 2H), 1.05-1.02 (m, 2H). ¹⁹F NMR (376 MHz, CD₃OD) δ −124.2 (s, 2F). |
| 90 | LCMS: [M + H]⁺ = 646.3. ¹H NMR (400 MHZ, CD₃OD) δ 7.83 (s, 2H), 7.11-7.08 (m, 2H), 6.99 (d, J = 8.4 Hz, 1H), 6.71 (t, J = 52.8 Hz, 1H), 4.04-4.01 (m, 1H), 1.90-1.87 (m, 2H), 1.73-1.70 (m, 2H), 1.60-1.57 (m, 2H), 1.42-1.37 (m, 2H), 1.27-1.24 (m, 2H), 1.02-0.99 (m, 2H). ¹⁹F NMR (376 MHz, CD₃OD) δ −124.3 (s, 2F). |
| 91 | LCMS: [M + H]⁺ = 632.3. ¹H NMR (400 MHZ, CD₃OD) δ 7.81 (s, 2H), 7.18 (d, J = 3.2 Hz, 1H), 7.03-7.00 (dd, J = 8.8, 3.2 Hz, 1H), 6.94 (d, J = 9.2 Hz, 1H), 6.71 (t, J = 52.8 Hz, 1H), 3.75-3.71 (m, 1H), 3.48-3.46 (m, 1H), 3.22-3.19 (m, 1H), 3.14-3.12 (m, 1H), 1.93-1.88 (m, 2H), 1.77-1.74 (m, 2H), 1.14-1.11 (m, 2H), 0.91-0.88 (m, 2H). ¹⁹F NMR (376 MHz, CD₃OD) δ −124.3 (s, 2F). |
| 92 | LCMS: [M + H]⁺ = 632.5. ¹H NMR (400 MHZ, CD₃OD) δ 7.81 (s, 2H), 7.12 (d, J = 3.2 Hz, 1H), 7.07 (dd, J = 8.8, 3.2 Hz, 1H), 6.99 (d, J = 8.8 Hz, 1H), 6.71 (t, J = 52.8 Hz, 1H), 2.59-2.50 (m, 1H), 2.43-2.31 (m, 2H), 2.16-2.08 (m, 2H), 1.86-1.67 (m, 2H), 0.72-0.67 (m, 2H), 0.50-0.42 (m, 2H). ¹⁹F NMR (376 MHz, CD₃OD) δ −124.2 (s, 2F) |
| 93 | LCMS: [M + H]⁺ = 636.0. ¹H NMR (400 MHZ, CD₃OD) δ 7.80 (s, 2H), 7.13 (d, J = 3.2 Hz, 1H), 7.10 (dd, J = 8.8, 3.2 Hz, 1H), 6.99 (d, J = 8.8 Hz, 1H), 2.60-2.55 (m, 1H), 1.27 (dd, J = 8.4, 4.8 Hz, 2H), 1.03 (dd, J = 7.6, 4.4 Hz, 2H), 0.72-0.68 (m, 2H), 0.49-0.45 (m, 2H). ¹⁹F NMR (376 MHz, CD₃OD) δ −69.3 (s, 3F). |

Example 37: Synthesis of Intermediate G

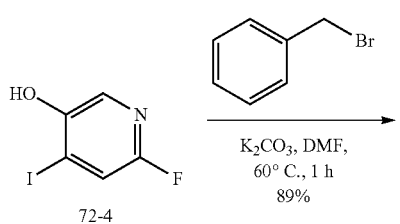

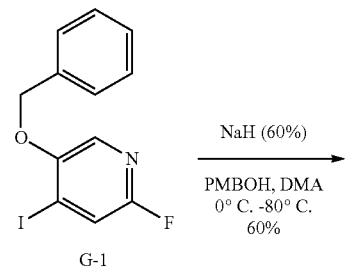

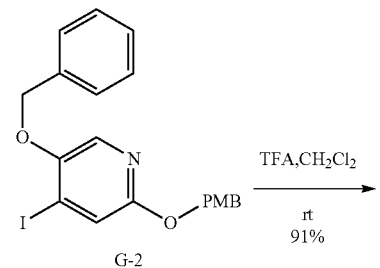

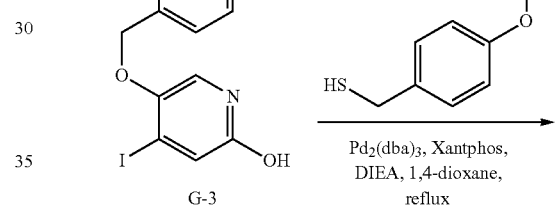

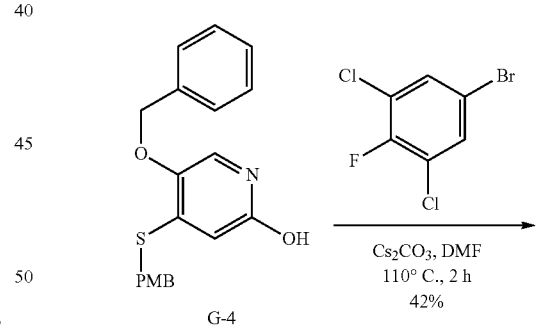

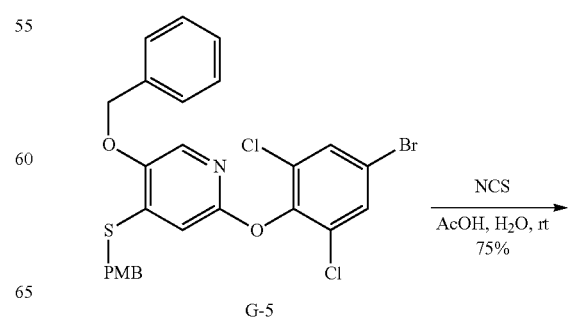

319

-continued

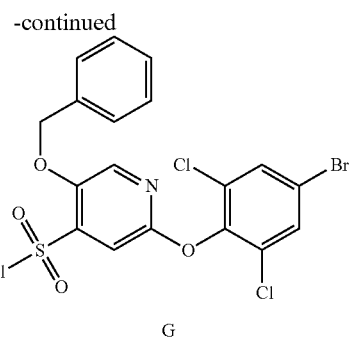

G

Step 1: G-1

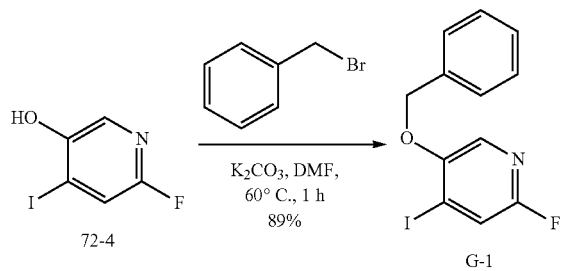 [SMILES: Oc1cnc(F)cc1I ; BrCc1ccccc1 ; Fc1cc(I)c(OCc2ccccc2)cn1]

A mixture of 6-fluoro-4-iodo-pyridin-3-ol 72-4 (4.4 g, 18.41 mmol), bromomethylbenzene (3.15 g, 18.41 mmol, 2.19 mL) and K₂CO₃ (2.54 g, 18.41 mmol) in DMF (40 mL) was stirred at 60° C. for 1 h. LCMS showed the product was formed. The mixture was poured into water (20 mL) and extracted with EtOAc (2×20 mL). The combined organic layer was washed successively with brine (50 mL) and water (50 mL). The organic layer was dried over Na₂SO₄ and concentrated in vacuum. The residue was purified by silica gel chromatography (PE:EA=10:1) to afford 5-benzyloxy-2-fluoro-4-iodo-pyridine G-1 (5.45 g, 89% yield) as a yellow solid. LCMS: [M+H]⁺=329.9

Step 2: G-2

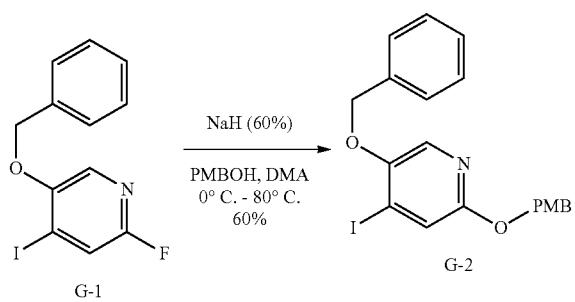

To a mixture of (4-methoxyphenyl) methanol (2.74 g, 19.88 mmol) in DMA (50 mL) was added NaH (60%) (889.26 mg, 23.20 mmol) at 0° C. The mixture was stirred at 0° C. for 0.5 h. Then 5-benzyloxy-2-fluoro-4-iodo-pyridine G-1 (5.45 g, 16.57 mmol) was added and the mixture was stirred at 80° C. for 0.5 h. LCMS showed the product was formed. The reaction mixture was extracted with EtOAc (50 mL) and washed with brine (3×50 mL). The combined organic layer was dried over anhydrous Na₂SO₄. The reaction mixture was filtered and concentrated in vacuum to afford a residue. The residue was purified by column chromatography (PE:EtOAc=10:1) to give 5-(benzyloxy)-4-iodo-2-((4-methoxybenzyl) oxy) pyridine G-2 (4.5 g, 60% yield) as a yellow solid. LCMS: [M+Na]⁺=470.1

Step 3: G-3

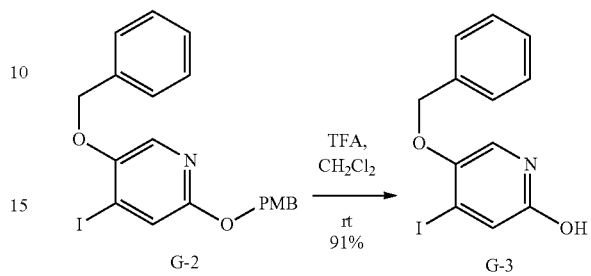

To a mixture of 5-benzyloxy-4-iodo-2-[(4-methoxyphenyl) methoxy] pyridine G-2 (4.5 g, 10.06 mmol) in CH₂Cl₂ (5 mL) was added TFA (1.15 g, 10.06 mmol, 775.14 uL). The mixture was stirred at rt for 1 h. LCMS showed the reaction was completed. The mixture was poured into water (20 mL) and extracted with EtOAc (2×20 mL). The combined organic layer was washed successively with brine (50 mL) and water (50 mL). The organic layer was dried over Na₂SO₄ and concentrated in vacuum. The residue was purified by flash chromatography (CH₂Cl₂:CH₃OH=30:1) to give 5-benzyloxy-4-iodo-pyridin-2-ol G-3 (3.0 g, 91% yield) as a yellow solid. LCMS: [M+H]⁺=328.0

Step 4: G-4

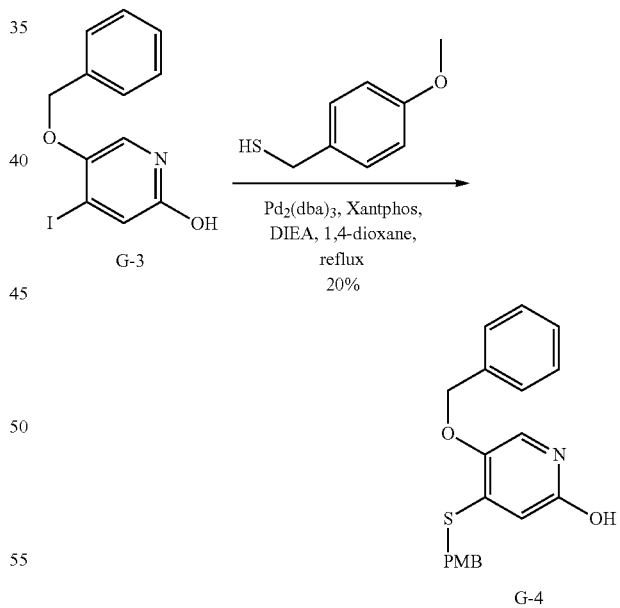

A mixture of 4-iodo-5-phenoxy-pyridin-2-ol G-3 (3.0 g, 9.58 mmol), (4-methoxyphenyl)methanethiol (2.22 g, 14.37 mmol), Pd₂(dba)₃ (876.74 mg, 958.19 umol), xantphos (1.11 g, 1.92 mmol) and DIEA (2.47 g, 19.16 mmol) in dioxane (30 mL) was refluxed for 15 h under N₂ atmosphere. LCMS showed the reaction was completed. The mixture was poured into water (20 mL) and extracted with EtOAc (2×20 mL). The combined organic layer was washed successively with brine (50 mL) and water (50 mL). The organic layer was dried over Na₂SO₄ and concentrated in vacuum. The residue was purified by flash chromatography (CH₂Cl₂:CH₃OH=20:1) to give 5-(4-methoxyphenyl)-6-phenoxy-pyridin-3-ol G-4 (585 mg, 20% yield) as a yellow solid. LCMS: [M+H]⁺=354.1

Step 5: G-5

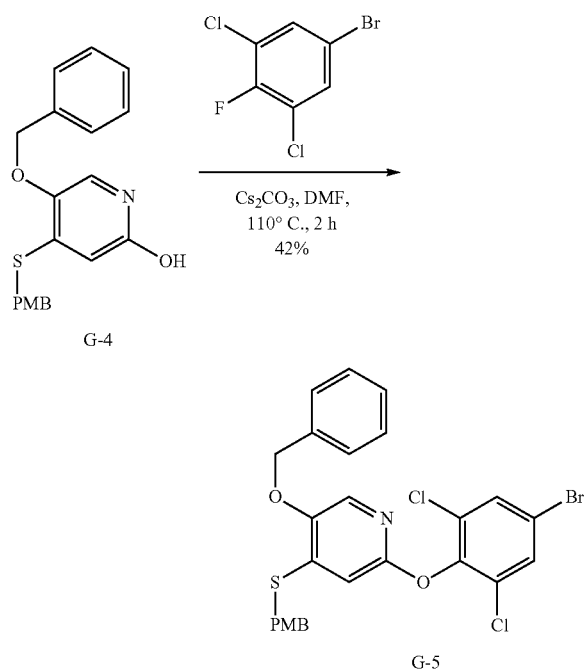

G-4

G-5

A mixture of 5-benzyloxy-4-[(4-methoxyphenyl) methylsulfanyl] pyridin-2-ol G-4 (585 mg, 1.66 mmol), 5-bromo-1,3-dichloro-2-fluoro-benzene (605.52 mg, 2.48 mmol) and Cs₂CO₃ (1.62 g, 4.97 mmol) in DMF (30 mL) was stirred at 110° C. for 2 h. LCMS showed the reaction was completed. The mixture was poured into water (20 mL) and extracted with EtOAc (2×20 mL). The combined organic layer was washed successively with brine (50 mL) and water (50 mL). The organic layer was dried over Na₂SO₄ and concentrated in vacuum. The residue was purified by flash chromatography (PE:EtOAc=10:1) to give 5-benzyloxy-2-(4-bromo-2,6-dichloro-phenoxy)-4-[(4-methoxyphenyl) methylsulfanyl] pyridine G-5 (410 mg, 42% yield) as a yellow solid. LCMS: [M+H]⁺=575.9/578.0

Step 6: G

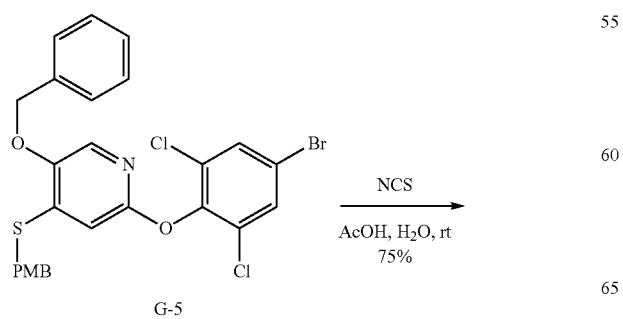

G-5

-continued

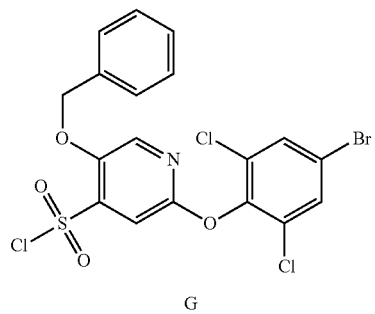

G

A mixture of 5-benzyloxy-2-(4-bromo-2,6-dichloro-phenoxy)-4-[(4-methoxyphenyl) methylsulfanyl] pyridine G-5 (410 mg, 710.18 umol) and NCS (379.33 mg, 2.84 mmol) in AcOH (6 mL) and water (2 mL) was stirred at rt for 15 h. LCMS showed the reaction was completed. The mixture was poured into water (20 mL) and extracted with EtOAc (2×20 mL). The combined organic layer was washed successively with brine (50 mL) and water (50 mL). The organic layer was dried over Na₂SO₄ and concentrated in vacuum. The residue was purified by flash chromatography (PE:EtOAc=10:1) to give 5-benzyloxy-2-(4-bromo-2,6-dichloro-phenoxy) pyridine-4-sulfonyl chloride G (280 mg, 75% yield) as a yellow solid. LCMS: [M+H]⁺=521.8/523.8

Example 38: Synthesis of Intermediate H

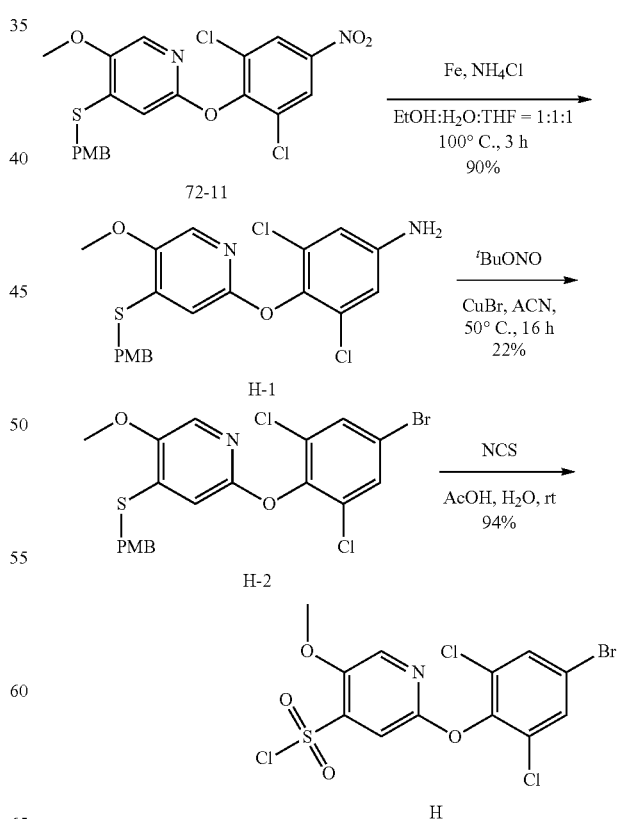

Step 1: H-1

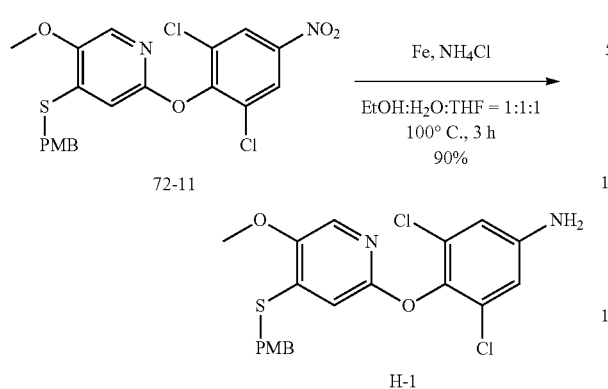

72-11

H-1

Step 3: H

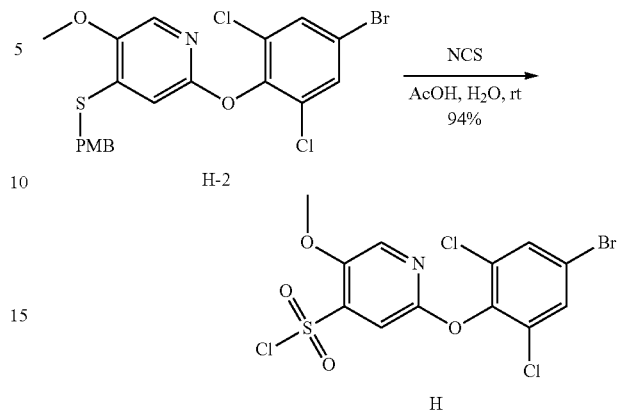

H-2

H

A mixture of 2-(2,6-dichloro-4-nitro-phenoxy)-5-methoxy-4-[(4-methoxyphenyl) methylsulfanyl] pyridine 72-11 (2.5 g, 5.35 mmol), Fe (2.99 g, 53.50 mmol) and NH$_4$Cl (1.44 g, 26.75 mmol) in water (10 mL), THF (10 mL) and ethanol (10 mL) was stirred at 100° C. for 3 h. LCMS showed the product was formed. The mixture was extracted with EtOAc (3×50 mL). The combined organic layer was dried over anhydrous Na$_2$SO$_4$, filtered and concentrated in vacuum to afford a residue. The residue purified by silica gel chromatography (PE:EtOAc=2:1) to give crude 3,5-dichloro-4-[[5-methoxy-4-[(4-methoxyphenyl) methylsulfanyl]-2-pyridyl]oxy] aniline H-1 (2.6 g) as a yellow solid. LCMS: [M+H]$^+$=437.1

Step 2: H-2

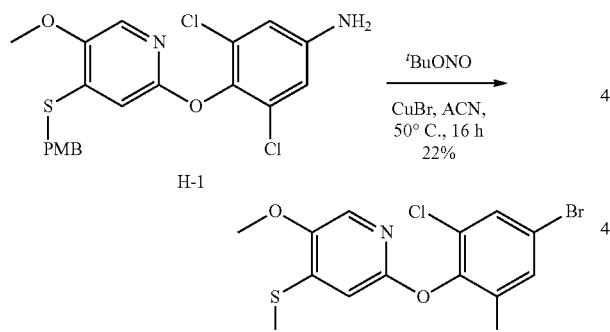

H-1

H-2

To a mixture of $^t$BuONO (1.10 g, 10.70 mmol) and CuBr (1.15 g, 8.03 mmol) in CH$_3$CN (30 mL) was added 3,5-dichloro-4-[[5-methoxy-4-[(4-methoxyphenyl) methylsulfanyl]-2-pyridyl]oxy] aniline H-1 (2.6 g, 5.35 mmol). The reaction was stirred at 50° C. for 16 h. LCMS showed the product was formed. The reaction mixture was poured into water and extracted with EtOAc (3×50 mL). The combined organic layer was dried over anhydrous Na$_2$SO$_4$, filtered and concentrated in vacuum to afford a residue. The residue was purified by silica gel chromatography (PE:EtOAc=10:1) to give 2-(4-bromo-2,6-dichloro-phenoxy)-5-methoxy-4-[(4-methoxyphenyl) methylsulfanyl] pyridine H-2 (590 mg, 22% yield) as a yellow solid. LCMS: [M+H]$^+$=500.0/502.0

To a solution of 2-(4-bromo-2,6-dichloro-phenoxy)-5-methoxy-4-[(4-methoxyphenyl) methylsulfanyl] pyridine H-2 (590.00 mg, 1.18 mmol) in AcOH (6 mL) and H$_2$O (2 mL) was added NCS (628.73 mg, 4.71 mmol) at 0° C. The mixture was stirred at rt for 16 h. LCMS showed the product was formed. The mixture was extracted with EtOAc (3×50 mL). The combined organic layer was dried over anhydrous Na$_2$SO$_4$, filtered and concentrated in vacuum to afford a residue. The residue was purified by silica gel chromatography (PE:EtOAc=10:1) to afford 2-(4-bromo-2,6-dichloro-phenoxy)-5-methoxy-pyridine-4-sulfonyl chloride H (500 mg, 94% yield) as a yellow solid. LCMS: [M+H]$^+$=445.9/447.8

Example 39: Synthesis of Intermediate I

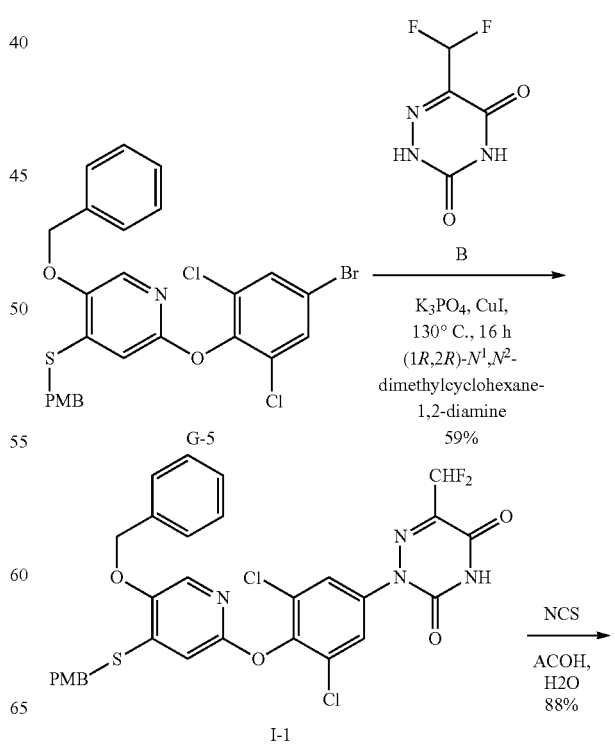

G-5

B

I-1

Step 1: I-1

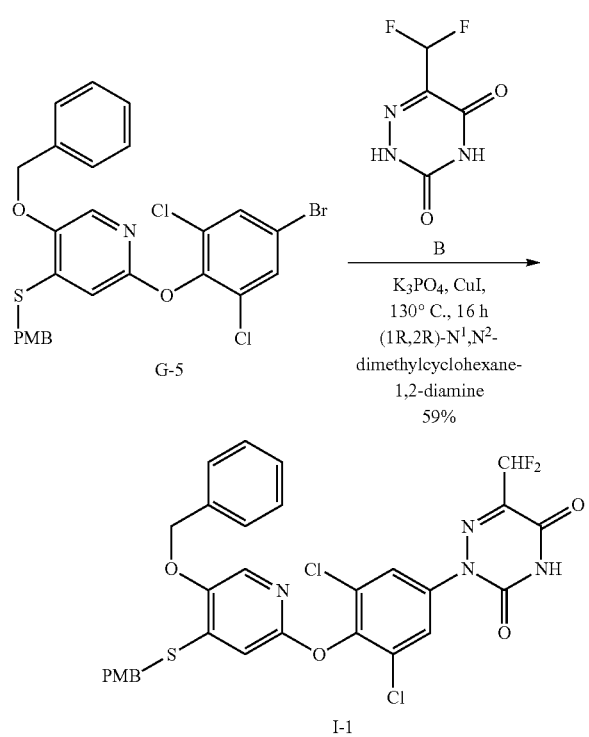

A mixture of 5-benzyloxy-2-(4-bromo-2,6-dichloro-phenoxy)-4-[(4-methoxyphenyl)methylsulfanyl]pyridine G-5 (7 g, 12.13 mmol), (1R,2R)—N1,N2-dimethylcyclohexane-1,2-diamine (1.21 g, 8.49 mmol, 1.34 mL), 6-(difluoromethyl)-2H-1,2,4-triazine-3,5-dione B (3.95 g, 24.25 mmol), CuI (5.77 g, 30.31 mmol, 1.03 mL) and $K_3PO_4$ (12.87 g, 60.63 mmol) in NMP (70 mL) was stirred at 130° C. for 16 h under N2. LC/MS showed the reaction was complete. EA (200 mL) and 1 M HCl (50 mL) was added into the reaction. The solids were filtered off. The filtrate was washed with brine (2×60 mL), dried over $Na_2SO_4$ and concentrated in vacuum. The resulting mixture was purified by silica gel chromatography (DCM/MeOH=50:1) to afford 2-(4-((5-(benzyloxy)-4-((4-methoxybenzyl)thio)pyridin-2-yl)oxy)-3,5-dichlorophenyl)-6-(difluoromethyl)-1,2,4-triazine-3,5(2H,4H)-dione I-1 (4.75 g, 59%) as yellow solid. LCMS: $[M+H]^+=659.0/660.9$

Step 2: I

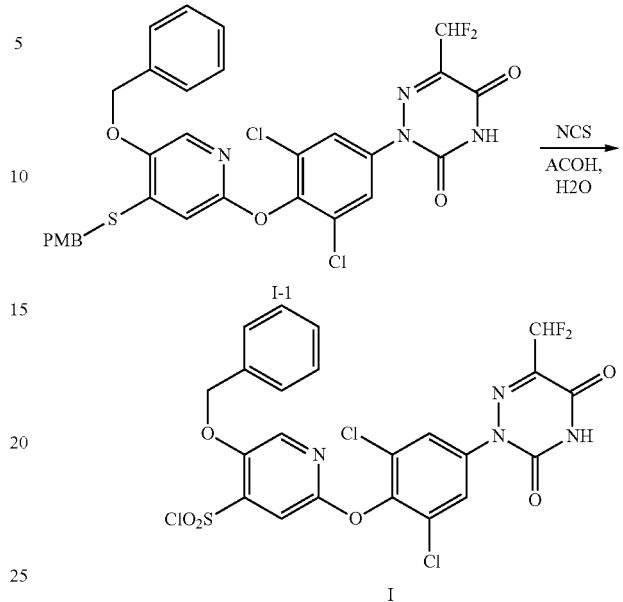

To a solution of 2-[4-[[5-benzyloxy-4-[(4-methoxyphenyl)methylsulfanyl]-2-pyridyl]oxy]-3,5-dichloro-phenyl]-6-(difluoromethyl)-1,2,4-triazine-3,5-dione I-1 (1.97 g, 2.99 mmol) in water (10 mL) and AcOH (30 mL) was added NCS (1.99 g, 14.94 mmol, 1.21 mL). The mixture was stirred at rt for 16 h. LCMS showed the reaction was complete. EA (150 mL) was added into the reaction. The mixture was washed with aqueous $NaHCO_3$ (5×100 mL) and brine (2×50 mL), dried over $Na_2SO_4$ and concentrated in vacuum. The resulting mixture was purified by silica gel chromatography (PE:EA=3:1) to afford 5-(benzyloxy)-2-(2,6-dichloro-4-(6-(difluoromethyl)-3,5-dioxo-4,5-dihydro-1,2,4-triazin-2(3H)-yl)phenoxy)pyridine-4-sulfonyl chloride I (1.6 g, 88% yield) as yellow solid. LCMS: $[M+H]^+=605.0/607.0$

Example 40: Synthesis of Intermediate J

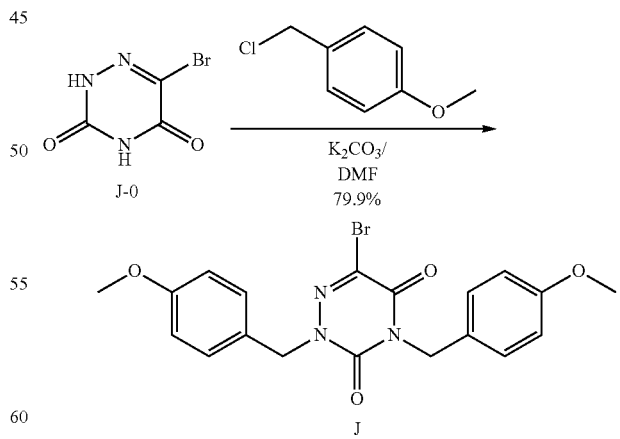

To a mixture of 6-bromo-2H-1,2,4-triazine-3,5-dione J-0 (5 g, 26.05 mmol) and 1-(chloromethyl)-4-methoxy-benzene (10.20 g, 65.11 mmol) in DMF (50 mL) was added $K_2CO_3$ (10.80 g, 78.14 mmol) at rt. The reaction solution was stirred for 8 h at 100° C. TLC (EA/PE=1/1) showed a new spot and the starting material was consumed completely. The solution was concentrated in vacuum. The crude product was purified by silica gel chromatography (petroleum ether/ethylacetate=10:1-1:1, v/v) to afford 6-bromo-2,4-bis[(4-methoxyphenyl)methyl]-1,2,4-triazine-3,5-dione J (9 g, 20.82 mmol, 79.94% yield) as white solid. LCMS: [M+Na]⁺=454.1/456.1
Example 41: Synthesis of Compound 94
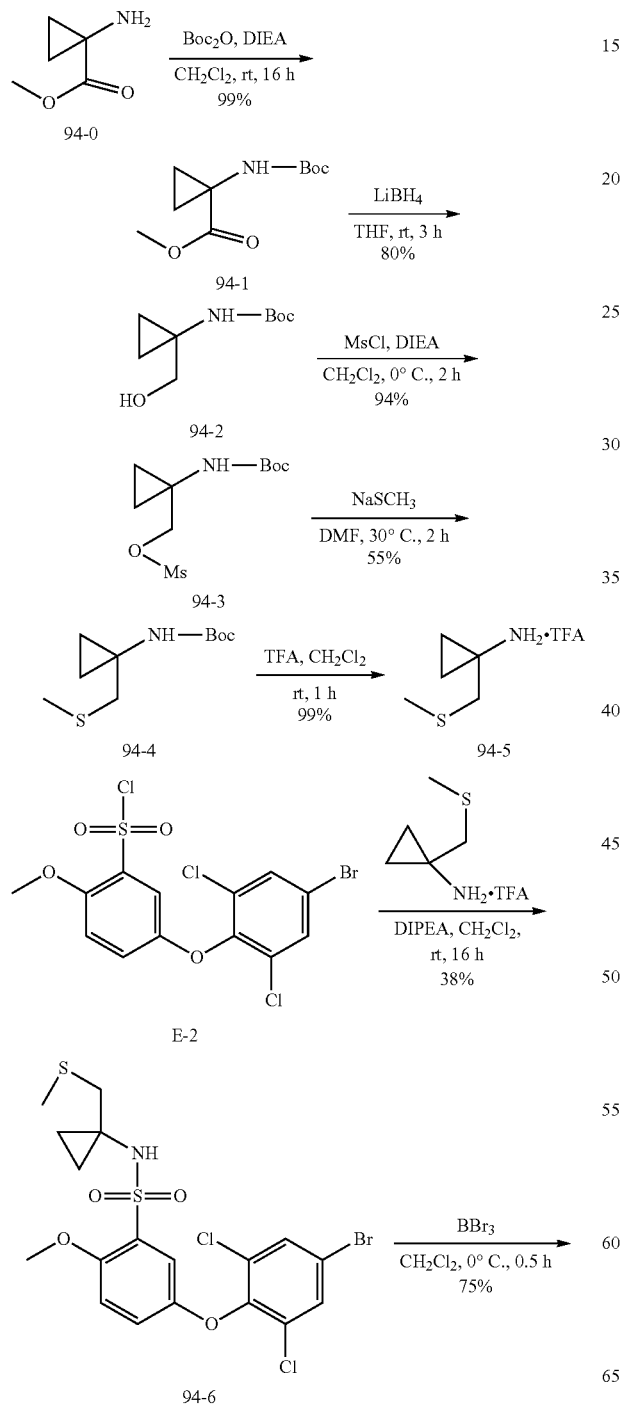
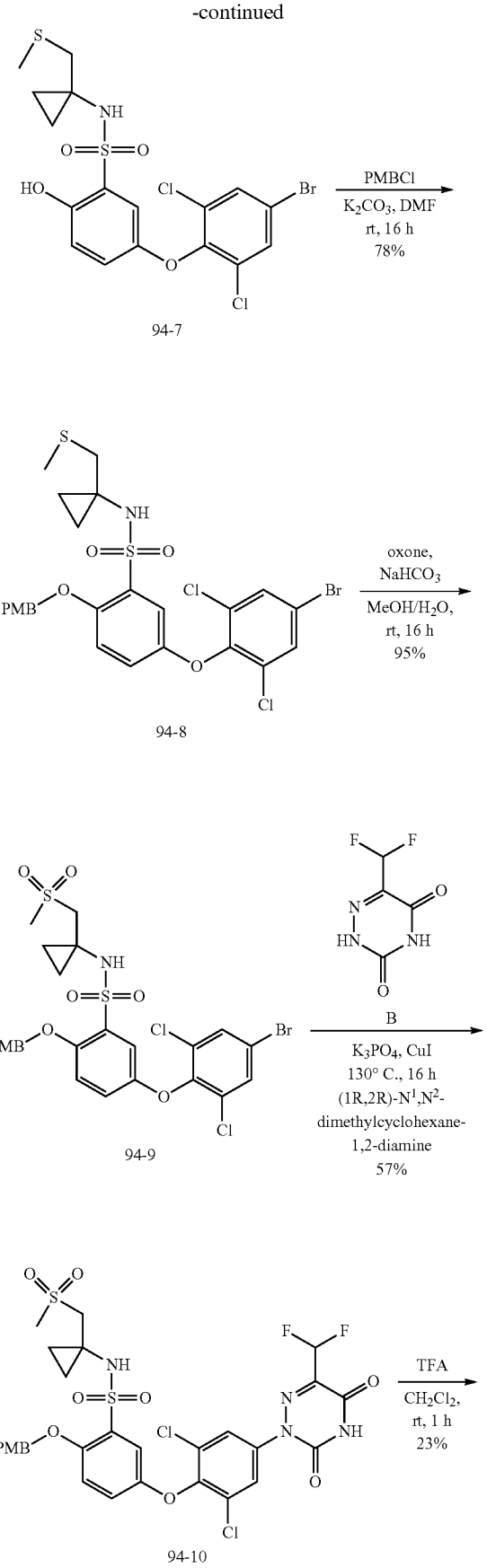

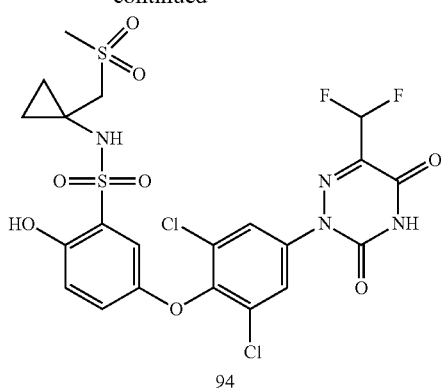

94

Step 1: 94-1

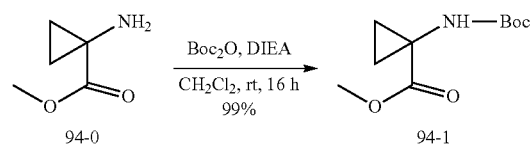

To a solution of methyl 1-aminocyclopropanecarboxylate hydrochloride 94-0 (3.45 g, 22.76 mmol) in CH$_2$Cl$_2$ (50 mL) was added DIPEA (8.82 g, 68.28 mmol, 11.89 mL) followed by Boc$_2$O (5.46 g, 25.03 mmol, 5.75 mL) at 0° C. The resulting mixture was stirred at rt for 16 h. LCMS showed the reaction was completed. The reaction mixture was transferred into the separatory funnel and washed with water (100 mL), brine (100 mL) and dried over Na$_2$SO$_4$. The solvent was removed in vacuum to give methyl 1-(tert-butoxycarbonyl amino) cyclopropane carboxylate 94-1 (4.9 g, 99% yield) as a colorless oil which was used for the next step without any purification. LCMS: [M+Na]$^+$=238.2

Step 2: 94-2

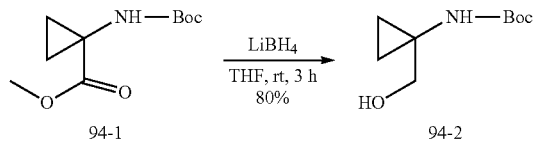

To a solution of methyl 1-(tert-butoxycarbonyl amino) cyclopropane carboxylate 94-1 (5.0 g, 23.23 mmol) in THF (50 mL) was added dropwise a suspension of lithium boronhydride (2 M, 18.58 mL) in THF at 0° C. The reaction mixture was stirred at rt for 3 h. LCMS showed the reaction was completed. The reaction was quenched by slow addition of MeOH (18 mL). After being stirred overnight, the reaction mixture was poured into an equal volume of sat. NH$_4$Cl (54 mL). The aqueous layer was extracted with EtOAc (4×20 mL). The combined organic layer was dried and concentrated. The residue was purified by flash chromatography (EtOAc:PE=1:1) to give tert-butyl N-[1-(hydroxymethyl) cyclopropyl] carbamate 94-2 (3.5 g, 80% yield) as a white solid. LCMS: [M+Na]$^+$=210.2.

Step 3: 94-3

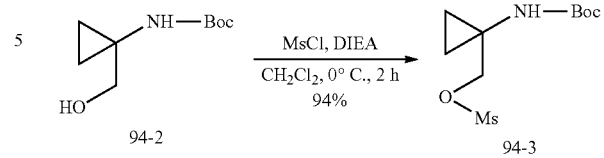

To a solution of tert-butyl N-[1-(hydroxymethyl) cyclopropyl] carbamate 94-2 (2 g, 10.68 mmol) in CH$_2$Cl$_2$ (10 mL) was added N-ethyl-N-isopropyl-propan-2-amine (1.79 g, 13.89 mmol, 2.42 mL) followed by MsCl (1.35 g, 11.75 mmol, 909.43 uL) at 0° C. The resulting mixture was stirred at 0° C. for 2 h. LCMS showed the reaction was completed. The reaction mixture was transferred into the separatory funnel and washed with sat. NaHCO$_3$ (10 mL), brine (10 mL) and dried over Na$_2$SO$_4$. Solvent was removed in vacuum to give [1-(tert-butoxycarbonylamino) cyclopropyl] methyl methanesulfonate 94-3 (2.66 g, 94% yield) as a crude product which was used for the next step without any purification. LCMS: [M+Na]$^+$=288.2

Step 4: 94-4

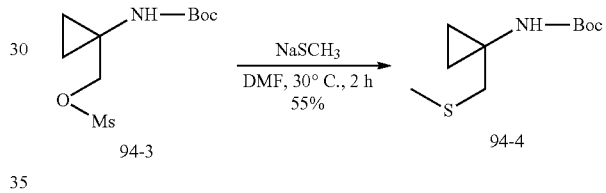

To a solution of [1-(tert-butoxycarbonyl amino) cyclopropyl] methyl methanesulfonate 94-3 (2.66 g, 10.03 mmol) in DMF (10 mL) was added sodium methanethiolate (913.49 mg, 13.03 mmol). The reaction mixture was stirred at 30° C. for 2 h. LCMS showed the reaction was completed. The reaction mixture was diluted with EtOAc (50 mL) and washed with water (3×100 mL) and brine (100 mL) and dried over Na$_2$SO$_4$. Solvent was removed in vacuum. The residue was purified by flash chromatography (EtOAc:PE=1:5) to give tert-butyl N-[1-(methyl sulfanyl methyl) cyclopropyl] carbamate 94-4 (1.2 g, 55% yield) as a yellow oil. LCMS: [M+Na]$^+$=240.2

Step 5: 94-5

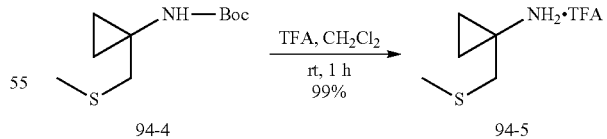

To a solution of tert-butyl N-[1-(methylsulfanylmethyl) cyclopropyl] carbamate 94-4 (1.2 g, 5.52 mmol) in CH$_2$Cl$_2$ (10 mL) was added TFA (5.92 g, 51.92 mmol, 4 mL). The reaction mixture was stirred at rt for 1 h. LCMS showed the reaction was completed. Solvent was removed in vacuum to give 1-(methyl sulfanyl methyl) cyclopropane amine 94-5 (640 mg, 99% yield) as a yellow oil which was used for the next step without any purification. LCMS: [M+H]$^+$=118.2

Step 6: 94-6

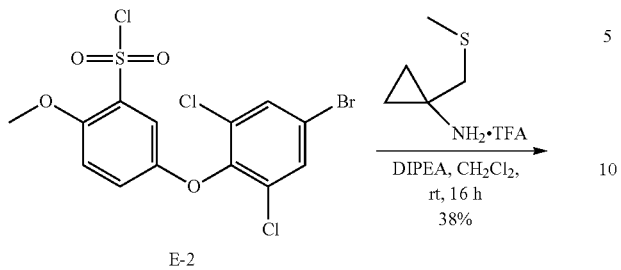

To a solution of 1-(methyl sulfanyl methyl) cyclopropane amine (1.50 g, 12.80 mmol) in CH₂Cl₂ (10 mL) was added DIPEA (5.57 g, 43.06 mmol, 7.50 mL) and 5-(4-bromo-2,6-dichloro-phenoxy)-2-methoxy-benzenesulfonyl chloride E-2 (300 mg, 671.85 umol). The reaction mixture was stirred at rt for 16 h. LCMS showed the reaction was completed. After removing the solvent, to the residue was added water (30 mL) and extracted with EtOAc (3×20 ml). The organic layer was dried over Na₂SO₄ and concentrated. The residue was purified by flash chromatography on silica gel chromatography (EtOAc:PE=2:3) to give 5-(4-bromo-2,6-dichloro-phenoxy)-2-methoxy-N-[1-(methylsulfanylmethyl)cyclopropyl] benzene sulfonamide 94-6 (136 mg, 38% yield) as a white solid. LCMS: [M+H]⁺=526.0/528.0

Step 7: 94-7

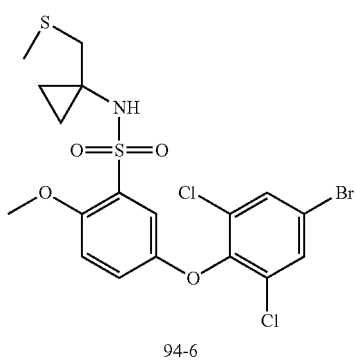

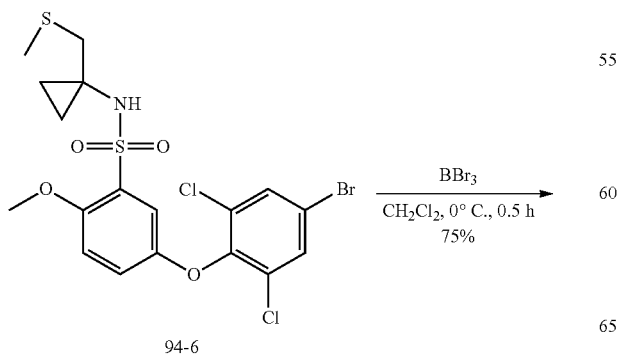

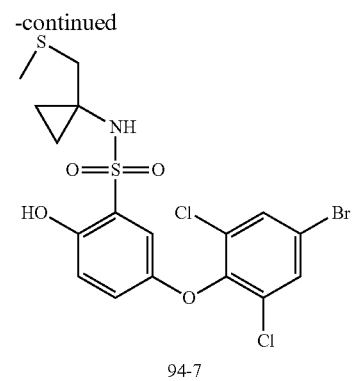

To a solution of 5-(4-bromo-2,6-dichloro-phenoxy)-2-methoxy-N-[1-(methyl sulfanyl methyl) cyclopropyl] benzene sulfonamide 94-6 (136 mg, 257.93 umol) in CH₂Cl₂ (3 mL) was added tribromoborane (795.00 mg, 3.17 mmol, 0.3 mL) at 0° C. The reaction mixture was stirred at 0° C. for 0.5 h. LCMS showed the reaction was completed. 10 ml of ice-water was added to reaction mixture at 0° C. and the mixture was extracted with EtOAc (2×10 mL). The organic phase was washed with brine (10 mL), dried and concentrated to give 5-(4-bromo-2,6-dichloro-phenoxy)-2-hydroxy-N-[1-(methyl sulfanyl methyl) cyclopropyl] benzene sulfonamide 94-7 (100 mg, 75% yield) as a yellow oil which was used in next step without any purification. LCMS: [M+H]⁺=512.0/514.0

Step 8: 94-8

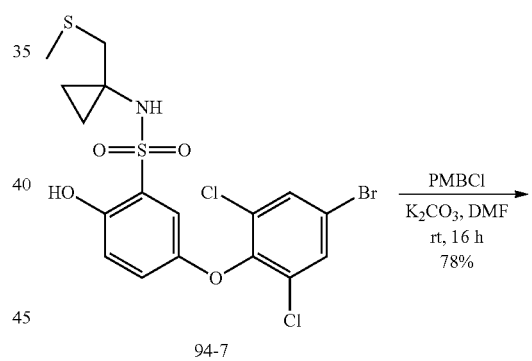

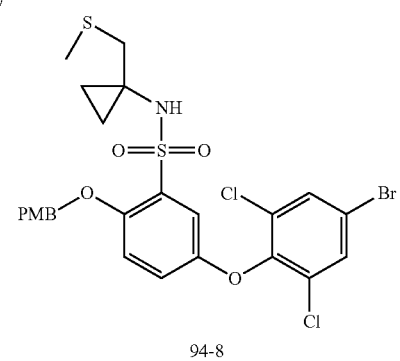

A mixture of 5-(4-bromo-2,6-dichloro-phenoxy)-2-hydroxy-N-[1-(methylsulfanylmethyl)cyclopropyl] benzenesulfonamide 94-7 (100 mg, 194.84 umol), dipotassium carbonate (53.86 mg, 389.67 umol) and 1-(chloromethyl)-4-methoxy-benzene (45.77 mg, 292.25 umol) in DMF (3 mL) was stirred at rt for 16 h. LCMS showed the reaction was completed. The mixture was added to water (30 mL) and extracted with EtOAc (3×20 ml). The organic layer was washed with brine (3×50 mL), dried and concentrated. The residue was purified by flash chromatography (PE: EtOAc=1:1) to give 5-(4-bromo-2,6-dichloro-phenoxy)-N-[3-[tert-butyl(dimethyl)silyl] oxycyclobutyl]-2-[(4-methoxyphenyl) methoxy] benzene sulfonamide 94-8 (96 mg, 78% yield) as a white solid. LCMS: [M+Na]$^+$=654.0/656.0.

Step 9: 94-9

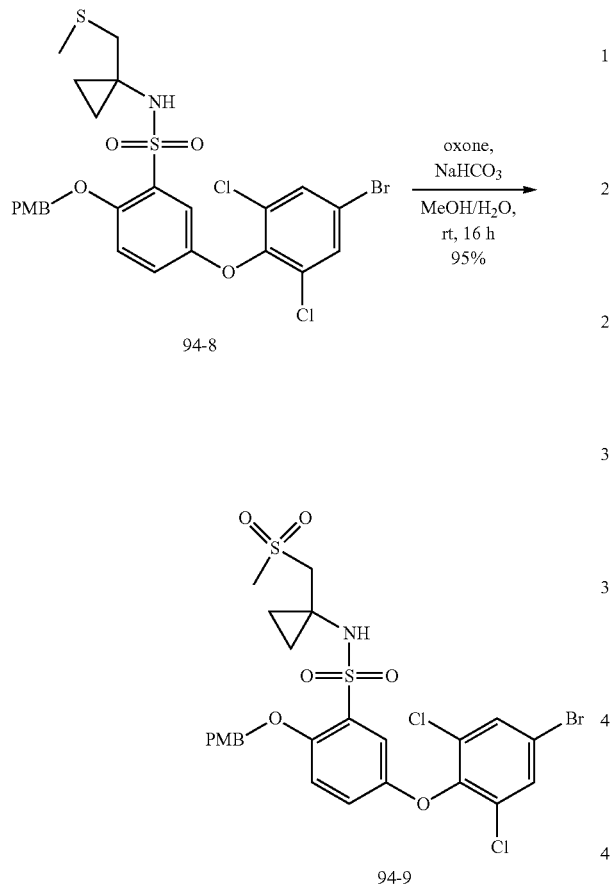

To a solution of 5-(4-bromo-2,6-dichloro-phenoxy)-2-[(4-methoxyphenyl)methoxy]-N-[1-(methylsulfanylmethyl)cyclopropyl]benzenesulfonamide 94-8 (40 mg, 63.15 umol) in methanol (2 mL) and water (0.5 mL) was added sodium hydrogen carbonate (26.53 mg, 315.76 umol) and oxone (58.23 mg, 94.73 umol). The reaction mixture was stirred at rt for 16 h. LCMS showed the reaction was completed. Solvent was removed in vacuum and the crude was dissolved in EtOAc (20 mL). The organic layer was washed with water (20 mL) and brine (20 mL), dried and concentrated. The residue was purified by prep-TLC (EtOAc:PE=1:1) to give 5-(4-bromo-2,6-dichloro-phenoxy)-2-[(4-methoxyphenyl) methoxy]-N-[1-(methyl sulfonylmethyl) cyclopropyl]Benzene sulfonamide 94-9 (40 mg, 95% yield) as a yellow solid. LCMS: [M+Na]$^+$=686.0/687.9

Step 10: 94-10

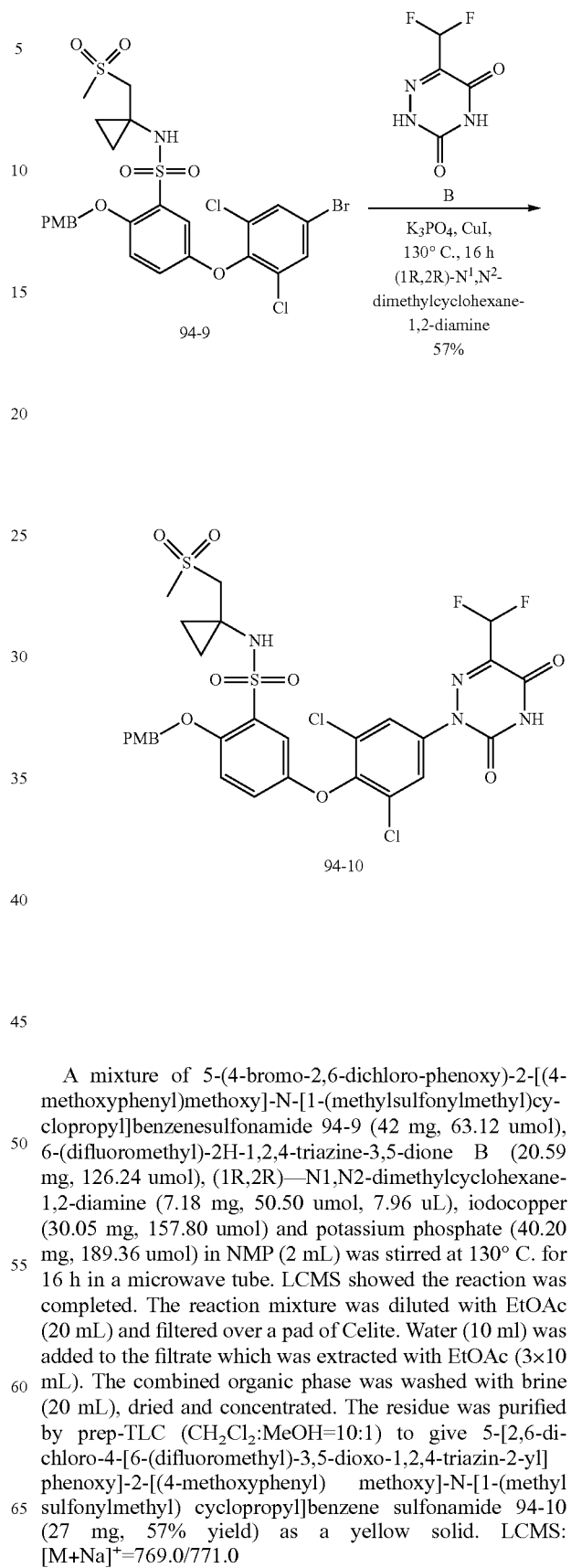

A mixture of 5-(4-bromo-2,6-dichloro-phenoxy)-2-[(4-methoxyphenyl)methoxy]-N-[1-(methylsulfonylmethyl)cyclopropyl]benzenesulfonamide 94-9 (42 mg, 63.12 umol), 6-(difluoromethyl)-2H-1,2,4-triazine-3,5-dione B (20.59 mg, 126.24 umol), (1R,2R)—N1,N2-dimethylcyclohexane-1,2-diamine (7.18 mg, 50.50 umol, 7.96 uL), iodocopper (30.05 mg, 157.80 umol) and potassium phosphate (40.20 mg, 189.36 umol) in NMP (2 mL) was stirred at 130° C. for 16 h in a microwave tube. LCMS showed the reaction was completed. The reaction mixture was diluted with EtOAc (20 mL) and filtered over a pad of Celite. Water (10 ml) was added to the filtrate which was extracted with EtOAc (3×10 mL). The combined organic phase was washed with brine (20 mL), dried and concentrated. The residue was purified by prep-TLC (CH$_2$Cl$_2$:MeOH=10:1) to give 5-[2,6-dichloro-4-[6-(difluoromethyl)-3,5-dioxo-1,2,4-triazin-2-yl] phenoxy]-2-[(4-methoxyphenyl) methoxy]-N-[1-(methyl sulfonylmethyl) cyclopropyl]benzene sulfonamide 94-10 (27 mg, 57% yield) as a yellow solid. LCMS: [M+Na]$^+$=769.0/771.0

Step 11: 94

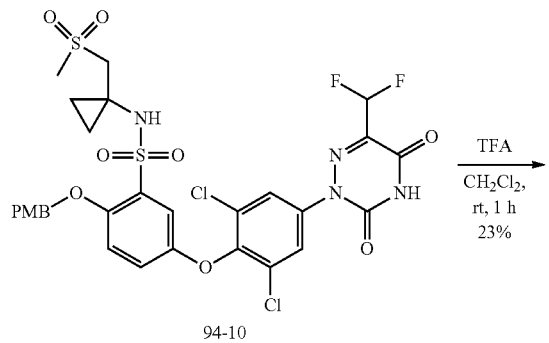

94-10

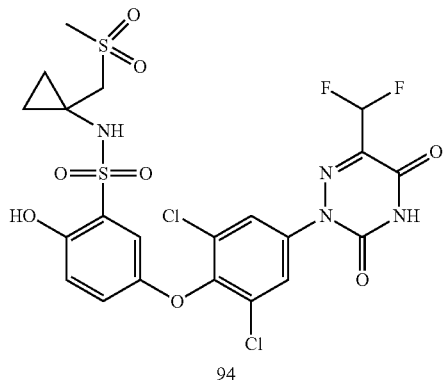

94

To a mixture of 5-[2,6-dichloro-4-[6-(difluoromethyl)-3,5-dioxo-1,2,4-triazin-2-yl]phenoxy]-2-[(4-methoxyphenyl)methoxy]-N-[1-(methylsulfonylmethyl)cyclopropyl]benzenesulfonamide 94-10 (27 mg, 36.12 umol) in $CH_2Cl_2$ (3 mL) was added TFA (1.48 g, 12.98 mmol, 1 mL). The reaction mixture was stirred at rt for 1 h. LCMS showed the reaction was completed. The solvent was evaporated under vacuum. EtOAc (20 mL) was added to the residue and the mixture was washed with aqueous $NaHCO_3$ (20 mL), dried and concentrated. The residue was purified by prep-HPLC (Kromasil-C18 100×21.2 mm 5 um, MeCN—$H_2O$ (0.1% FA) Gradient: 50-60%) to give 5-[2,6-dichloro-4-[6-(difluoromethyl)-3,5-dioxo-1,2,4-triazin-2-yl] phenoxy]-2-hydroxy-N-[1-(methyl sulfonylmethyl)cyclopropyl] benzene sulfonamide 94 (5.2 mg, 23% yield) as a yellow solid. LCMS: [M+H]$^+$=627.0. $^1$H NMR (400 MHz, $CD_3OD$) δ 7.83 (s, 2H), 7.14-7.09 (m, 2H), 6.96 (d, J=8.8 Hz, 1H), 6.70 (t, J=53.2 Hz, 1H), 3.34 (s, 2H), 3.06 (s, 3H), 0.86-0.76 (m, 4H). $^{19}$F NMR (376 MHz, $CD_3OD$) δ−124.257 (s, 2F).

Example 42: Synthesis of Compound 95

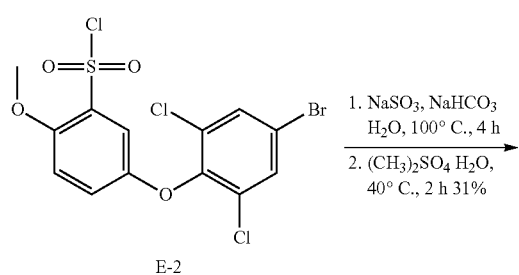

E-2

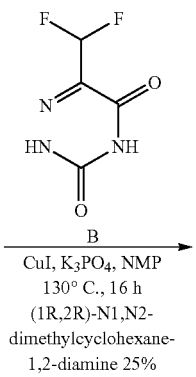

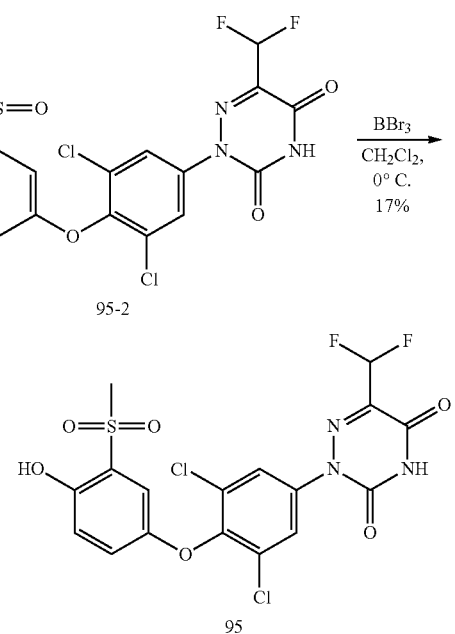

Step 1: 95-1

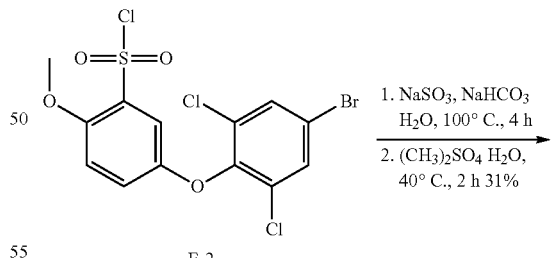

E-2

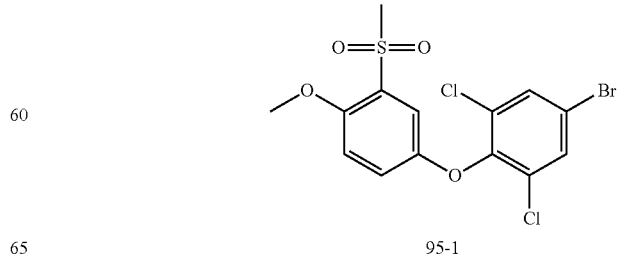

95-1

To a mixture of Na₂SO₃ (230.79 mg, 2.24 mmol) and NaHCO₃ (118.13 mg, 2.24 mmol) in water (10 mL) was added 5-(4-bromo-2,6-dichloro-phenoxy)-2-methoxy-benzenesulfonyl chloride E-2 (0.5 g, 1.12 mmol) at 25° C. The mixture was stirred at 100° C. for 4 h. Then dimethyl sulfate (211.85 mg, 1.68 mmol) was added and the mixture was stirred at 40° C. for 2 h. LCMS showed the reaction was completed. EtOAc (50 mL) was added into the reaction. The mixture was washed with brine (2×30 mL), dried over Na₂SO₄ and concentrated in vacuum. The residue was purified by flash chromatography (PE:EtOAc=2:1) to give 5-bromo-1,3-dichloro-2-(4-methoxy-3-methylsulfonyl-phenoxy) benzene 95-1 (150 mg, 31% yield) as a colorless oil. LCMS: [M+H]⁺=425.0/426.9

Step 2: 95-2

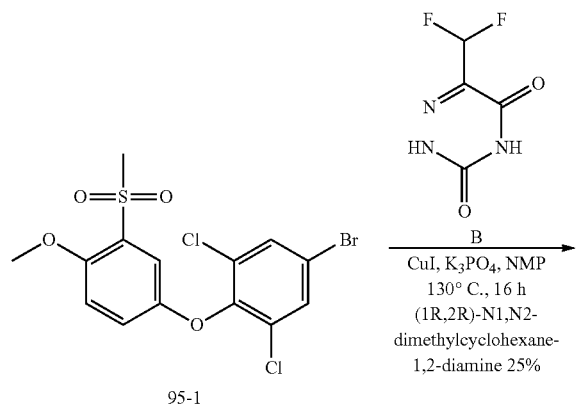

A mixture of 5-bromo-1,3-dichloro-2-(4-methoxy-3-methylsulfonyl-phenoxy)benzene 95-1 (0.1 g, 234.68 umol), 6-(difluoromethyl)-2H-1,2,4-triazine-3,5-dione B (76.54 mg, 469.36 umol), (1R,2R)—N1,N2-dimethylcyclohexane-1,2-diamine (26.71 mg, 187.75 umol), copper(I) iodide (111.74 mg, 586.7 umol) and potassium phosphate (149.44 mg, 704.04 umol) in NMP (1 mL) was stirred at 130° C. for 16 h. LCMS showed the reaction was complete. EtOAc (20 mL) was added into the reaction. Solids were filtrated off and the filtrate was washed with water (20 mL), brine (4×20 mL), dried over anhydrous Na₂SO₄ and filtered. The filtrate was concentrated in vacuum to afford a residue which was purified by silica gel chromatography (CH₂Cl₂:CH₃OH=20:1) to give dichloro-4-(4-methoxy-3-methylsulfonyl-phenoxy) phenyl]-6-(difluoromethyl)-1,2,4-triazine-3,5-dione 95-2 (30 mg, 25% yield) as a yellow solid. LCMS: [M+H]⁺=508.1/510.1

Step 3: 95

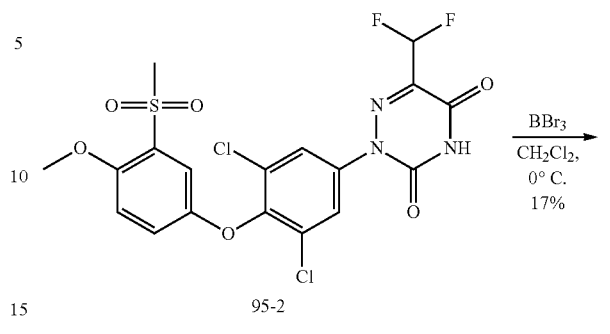

To a mixture of 2-[3,5-dichloro-4-[(5-methoxy-4-methylsulfonyl-2-pyridyl) oxy]phenyl]-6-(difluoromethyl)-1,2,4-triazine-3,5-dione 95-2 (30 mg, 58.91 umol) in CH₂Cl₂ (5 mL) was added BBr₃ (0.5 mL) at 0° C. The mixture was stirred at 0° C. for 1 h. LCMS showed the reaction was complete. The reaction was quenched by aqueous NaHCO₃ solution (20 mL). Then the mixture was extracted with EtOAc (2×50 mL). The organic layer was washed with brine (2×20 mL), dried over anhydrous Na₂SO₄ and filtered. The filtrate was concentrated in vacuum and purified by prep-HPLC (Xbridge 5 u C18 150×19 mm, MeCN—H₂O (0.1% FA), Gradient: 37-47%) to give 2-[3,5-dichloro-4-[(5-hydroxy-4-methylsulfonyl-2-pyridyl) oxy]phenyl]-6-(difluoromethyl)-1,2,4-triazine-3,5-dione 95 (5 mg, 17% yield) as a white solid. LCMS: [M+H]⁺=493.9/495.9. ¹H NMR (400 MHz, DMSO-d₆) δ 12.87 (s, 1H), 10.99 (s, 1H), 7.86 (s, 2H), 7.20 (dd, J=8.8, 3.2 Hz, 1H), 7.08 (d, J=8.8 Hz, 1H), 7.05 (d, J=3.2 Hz, 1H), 6.91 (t, J=52.4 Hz, 1H), 3.26 (s, 3H). ¹⁹F NMR (376 MHz, DMSO-d₆) δ−122.05 (s, 2F).

Example 43: Synthesis of Compound 96

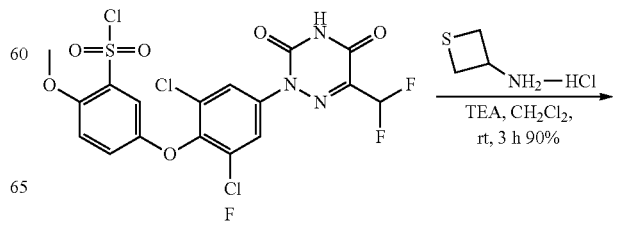

-continued

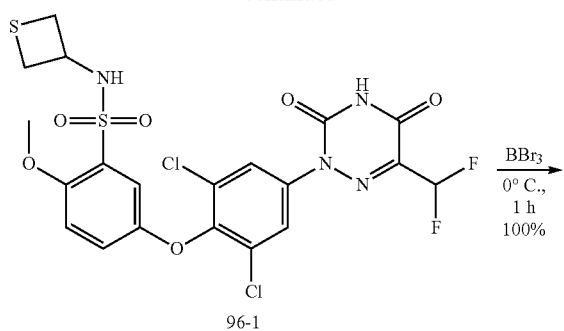

96-1

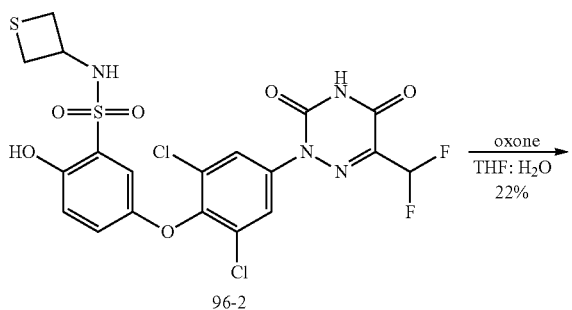

96-2

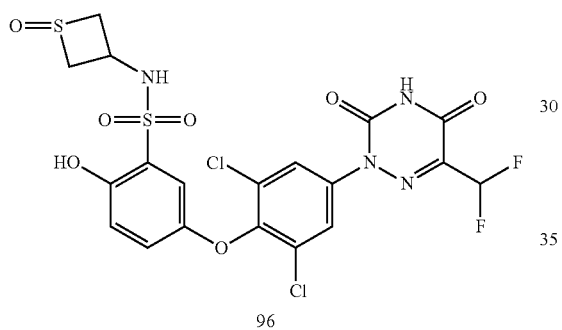

96

Step 1: 96-1

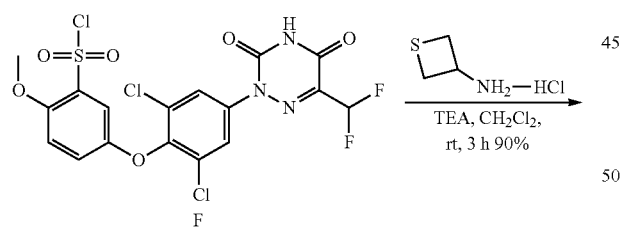

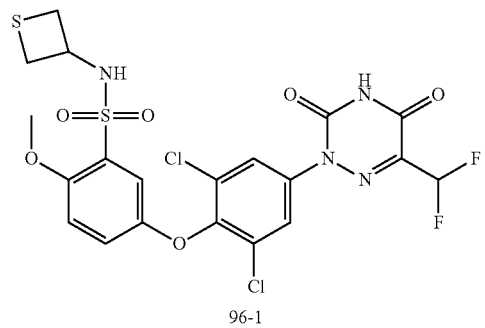

96-1

To a solution of thietan-3-amine hydrochloride (38.02 mg, 302.63 umol) and TEA (45.93 mg, 453.95 umol, 63.27 uL) in $CH_2Cl_2$ (3 mL) was added 5-[2,6-dichloro-4-[6-(difluoromethyl)-3,5-dioxo-1,2,4-triazin-2-yl]phenoxy]-2-methoxy-benzenesulfonyl chloride F (80 mg, 151.32 umol). The mixture was stirred at rt for 3 h. LCMS showed the product was formed. The reaction mixture was poured into water and extracted with EtOAc (3×30 mL). The combined organic layer was dried over anhydrous $Na_2SO_4$ and filtered. The filtrate was concentrated in vacuum to afford a residue. The residue was purified by silica gel chromatography ($CH_2Cl_2$:$CH_3OH$=20:1) to afford 5-[2,6-dichloro-4-[6-(difluoromethyl)-3,5-dioxo-1,2,4-triazin-2-yl] phenoxy]-2-methoxy-N-(thietan-3-yl) benzenesulfonamide 96-1 (80 mg, 90% yield) as a yellow solid. LCMS: $[M+Na]^+$=603.0/605.0.

Step 2: 96-2

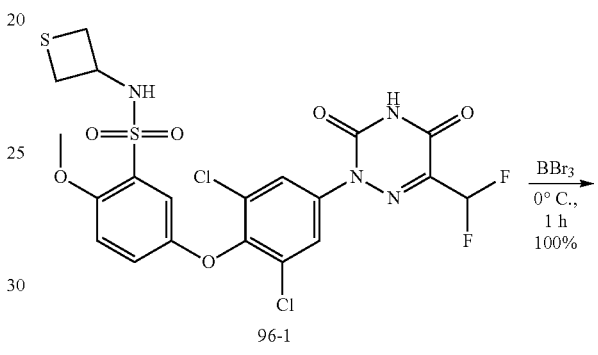

96-1

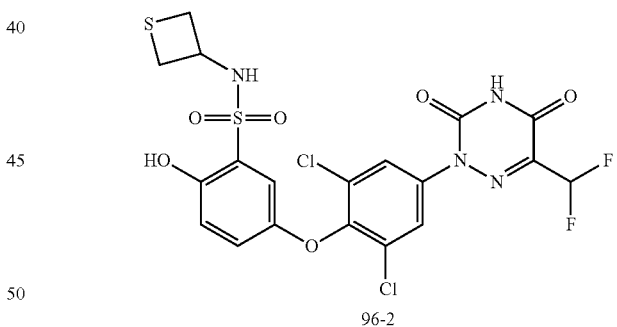

96-2

To a mixture of 5-[2,6-dichloro-4-[6-(difluoromethyl)-3,5-dioxo-1,2,4-triazin-2-yl] phenoxy]-2-methoxy-N-(thietan-3-yl) benzenesulfonamide 96-1 (80 mg, 137.60 umol) in $CH_2Cl_2$ (3 mL) was added $BBr_3$ (34.40 mg, 137.60 umol, 0.3 mL) at 0° C. The mixture was stirred at 0° C. for 1 h. LCMS showed the product was formed. The reaction mixture was poured into water and extracted with EtOAc (3×30 mL). The combined organic layer was dried over anhydrous $Na_2SO_4$ and filtered. The filtrate was concentrated in vacuum to afford 5-(2,6-dichloro-4-(6-(difluoromethyl)-3,5-dioxo-4,5-dihydro-1,2,4-triazin-2(3H)-yl)phenoxy)-2-hydroxy-N-(thietan-3-yl)benzenesulfonamide 96-2 as a residue. The residue was used for the next step without further purification. LCMS: $[M+Na]^+$=589.0/590.9.

Step 3: 96

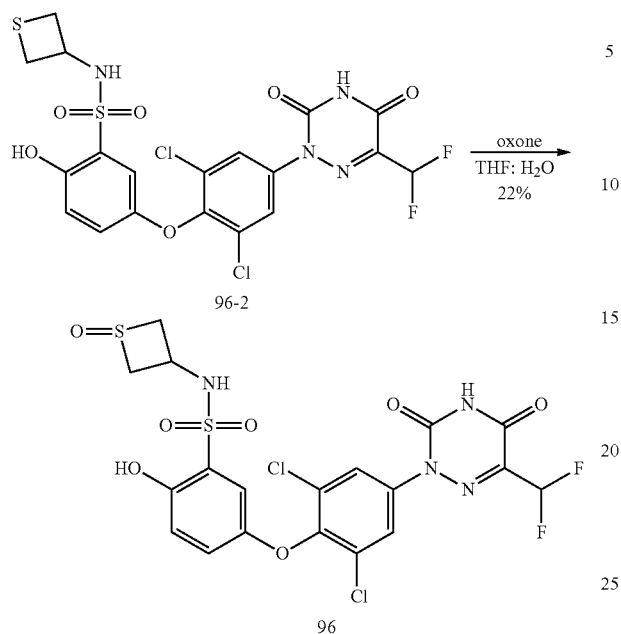

To a mixture of 5-[2,6-dichloro-4-[6-(difluoromethyl)-3,5-dioxo-1,2,4-triazin-2-yl] phenoxy]-2-hydroxy-N-(thietan-3-yl) benzenesulfonamide 96-2 (80 mg, 141.00 umol) in THF (2 mL) and H$_2$O (2 mL) was added oxone (86.68 mg, 141.00 umol). The mixture was stirred at rt for 3 h. LCMS showed the product was formed. The reaction mixture was poured into water and extracted with EtOAc (3×30 mL). The combined organic layer was dried over anhydrous Na$_2$SO$_4$ and filtered. The filtrate was concentrated in vacuum to afford a residue. The residue was purified by Prep-HPLC (Xbridge 5 u C18 150×19 mm, MeCN—H$_2$O (0.1% FA), Gradient: 36-40%) to afford 5-[2,6-dichloro-4-[6-(difluoromethyl)-3,5-dioxo-1,2,4-triazin-2-yl] phenoxy]-2-hydroxy-N-(1-oxothietan-3-yl) benzenesulfonamide 96 (18.4 mg, 22% yield) as a white solid. LCMS: [M+H]$^+$=583.0/584.9. $^1$H NMR (400 MHz, CD$_3$OD) δ 7.82 (s, 2H), 7.15 (d, J=3.2 Hz, 1H), 7.08 (dd, J=9.2, 3.2 Hz, 1H), 6.98 (d, J=8.9 Hz, 1H), 6.71 (t, J=52.8 Hz, 1H), 3.90-3.82 (m, 3H), 3.20-3.13 (m, 2H). $^{19}$F NMR (376 MHz, CD$_3$OD) δ −124.26 (s, 2F).

Example 44: Synthesis of Compound 97

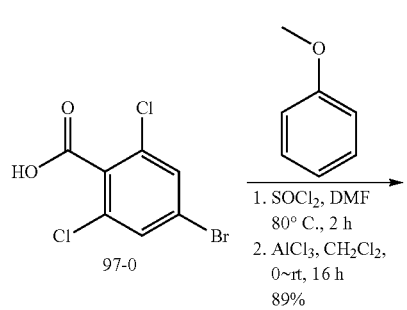

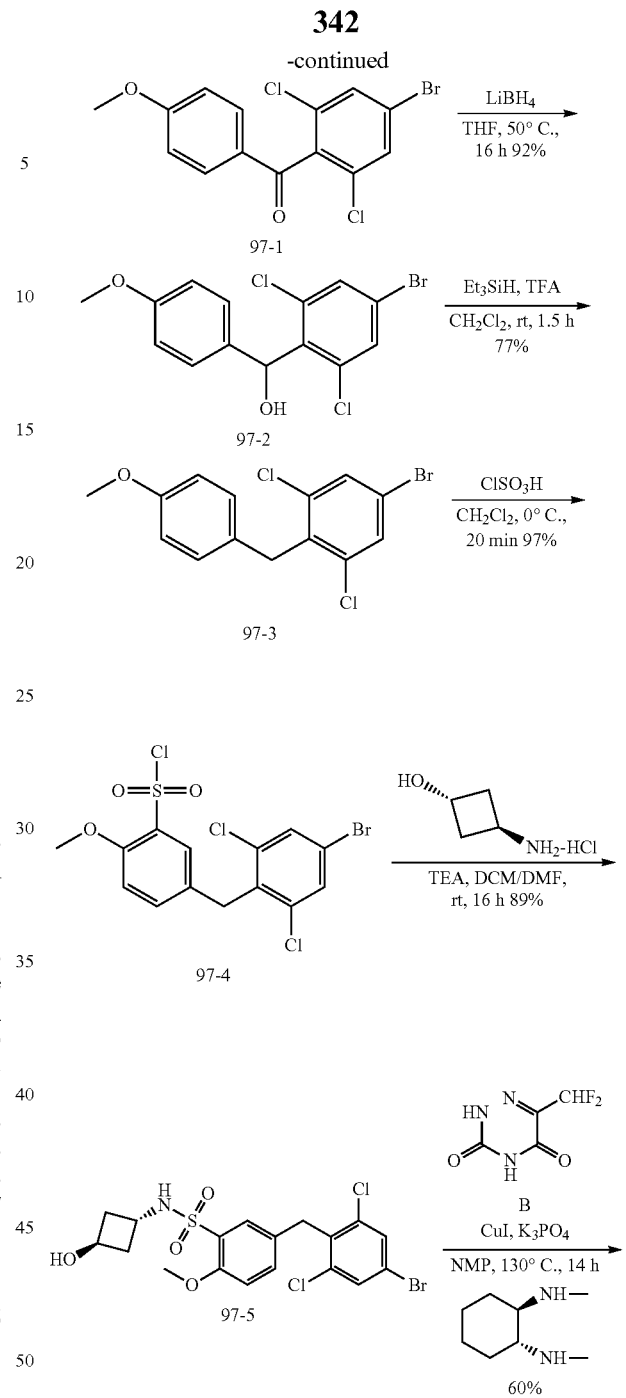

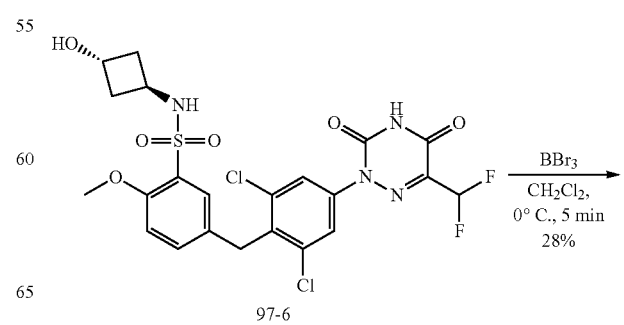

-continued

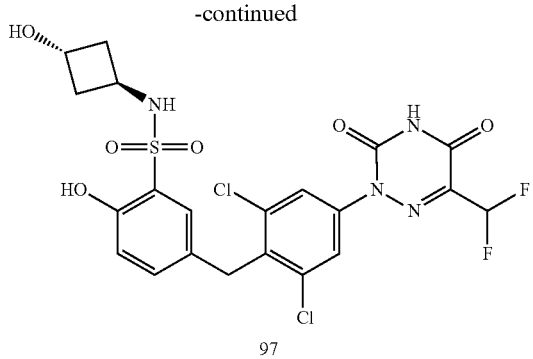

97

Step 1: 97-1

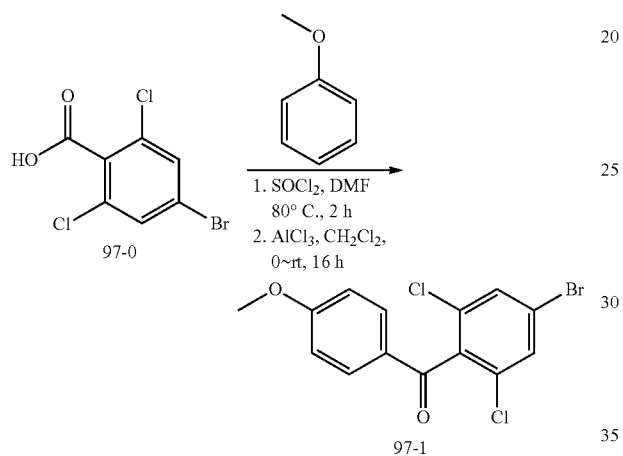

To a solution of 4-bromo-2,6-dichloro-benzoic acid 97-0 (500 mg, 1.85 mmol) in SOCl₂ (5 mL) was added DMF (0.05 mL). The mixture was stirred at 80° C. for 2 hr. Then it's concentrated to remove SOCl₂ under reduced pressure. The residue was dissolved in CH₂Cl₂ (5 mL) and anisole (300.49 mg, 2.78 mmol) was added. The solution was cooled to 0° C. and AlCl₃ (370.52 mg, 2.78 mmol) was added slowly. The mixture was slowly warmed to rt and stirred under N₂ (g) for 16 hr. TLC (PE:EtOAc=20:1) and LCMS showed the reaction was complete. The reaction mixture was poured into ice-water (50 mL) and extracted with CH₂Cl₂ (3×20 mL). The combined organic layer was washed with brine (20 mL), dried over anhydrous Na₂SO₄, filtered and concentrated in vacuum to afford a residue. The residue was purified by flash column chromatography (PE:EtOAc=100:1) to afford (4-bromo-2,6-dichloro-phenyl)-(4-methoxyphenyl) methanone 97-1 (600 mg, 89% yield) as a white solid. LCMS: [M+H]⁺=361.0

Step 2: 97-2

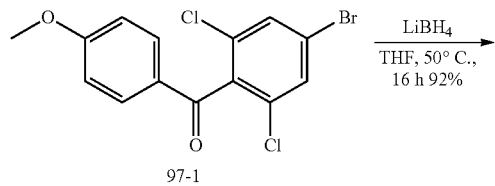

-continued

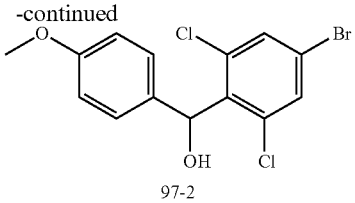

To a solution of (4-bromo-2,6-dichloro-phenyl)-(4-methoxyphenyl) methanone 97-1 (300 mg, 833.26 umol) in THF (10 mL) was added LiBH₄ (2 M, 1.25 mL). The mixture was stirred at 50° C. under N₂ (g) for 16 h. TLC (PE:EtOAc=20:1) showed the reaction was completed. CH₃OH (10 mL) was added dropwise. Then the mixture was poured into aqueous NH₄Cl (30 mL) and extracted with EtOAc (3×20 mL). The combined organic layer was washed with brine (20 mL), dried over anhydrous Na₂SO₄ and filtered. The filtrate was concentrated in vacuum to afford a residue. The residue was purified by flash column chromatography (PE:EtOAc=20:1) to afford (4-bromo-2,6-dichloro-phenyl)-(4-methoxyphenyl) methanol 97-2 (280 mg, 92% yield) as a white solid.

Step 3: 97-3

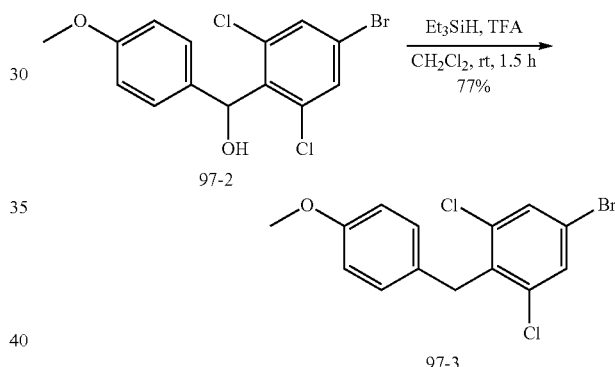

To a solution of (4-bromo-2,6-dichloro-phenyl)-(4-methoxyphenyl) methanol 97-2 (540 mg, 1.49 mmol) in CH₂Cl₂ (10 mL) were added TFA (1 mL) and Et₃SiH (1 mL). The mixture was stirred at rt under N₂ (g) for 1.5 h. TLC (PE:EtOAc=20:1) showed the reaction was completed. The reaction mixture was poured into saturated aqueous NaHCO₃ (30 mL) and extracted with CH₂Cl₂ (3×20 mL). The combined organic layer was washed with brine (20 mL), dried over anhydrous Na₂SO₄ and filtered. The filtrate was concentrated in vacuum to afford a residue. The residue was purified by flash column chromatography to afford 5-bromo-1,3-dichloro-2-[(4-methoxyphenyl) methyl] benzene 97-3 (400 mg, 77% yield) as a white solid.

Step 4: 97-4

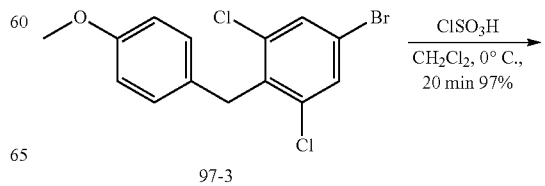

-continued

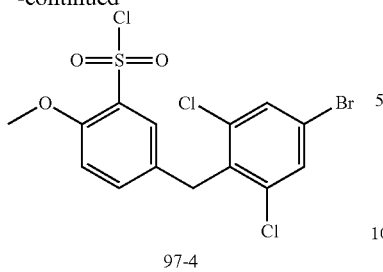

97-4

To a solution of 5-bromo-1,3-dichloro-2-[(4-methoxyphenyl) methyl] benzene 97-3 (320 mg, 924.73 umol) in $CH_2Cl_2$ (35 mL) was added $ClSO_3H$ (2.5 mL) at 0° C. The mixture was stirred at 0° C. under $N_2$ (g) for 20 min. TLC (PE:EtOAc=10:1) showed the reaction was completed. The reaction mixture was poured into ice water (50 mL) slowly and extracted with EtOAc (3×50 mL). The combined organic layer was washed with brine (50 mL), dried over anhydrous $Na_2SO_4$ and filtered. The filtrate was concentrated in vacuum to afford a residue. The residue was crude 5-[(4-bromo-2,6-dichloro-phenyl) methyl]-2-methoxy-benzenesulfonyl chloride 97-4 (400 mg, 97% yield). It's a yellow solid and used in the next step directly without further purification.

Step 5: 97-5

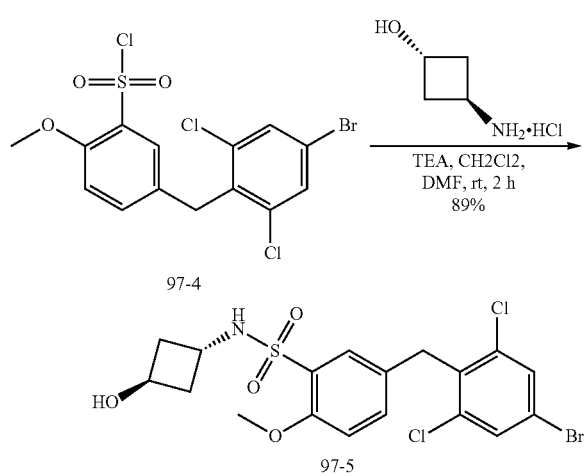

A solution of 5-[(4-bromo-2,6-dichloro-phenyl)methyl]-2-methoxy-benzenesulfonyl chloride 97-4 (400 mg, 899.78 umol) in $CH_2Cl_2$ (10 mL) was added into the mixture of 3-aminocyclobutanol; hydrochloride 7 (222.39 mg, 1.80 mmol) and TEA (455.24 mg, 4.50 mmol) in DMF (2 mL). The mixture was stirred at rt for 2 h. LC-MS showed the reaction was completed. The reaction mixture was concentrated and the residue was poured into water (50 mL) and extracted with EtOAc (3×30 mL). The combined organic layer was washed with brine (3×20 mL), dried over anhydrous $Na_2SO_4$ and filtered. The filtrate was concentrated in vacuum to afford a residue. The residue was purified by column chromatography (PE:EtOAc=7:3) to afford 5-[(4-bromo-2,6-dichloro-phenyl) methyl]-N-(3-hydroxycyclobutyl)-2-methoxy-benzenesulfonamide 97-5 (400 mg, 89% yield) as a yellow solid. LCMS: $[M+H]^+=493.9496.0$ Step 6: 97-6

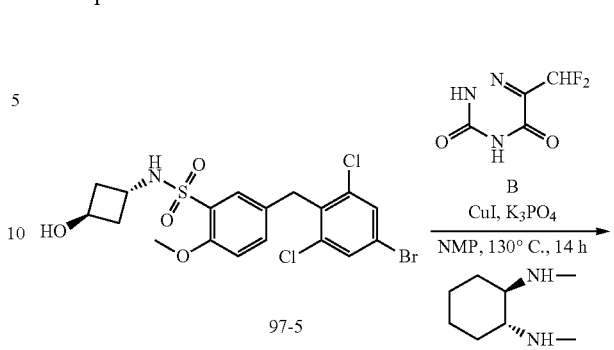

To a solution of 5-[(4-bromo-2,6-dichloro-phenyl) methyl]-N-(3-hydroxycyclobutyl)-2-methoxy-benzenesulfonamide 97-5 (100 mg, 201.93 umol) and 6-(difluoromethyl)-2H-1,2,4-triazine-3,5-dione B (65.86 mg, 403.87 umol) in NMP (2 mL) were added (1R,2R)—N1,N2-dimethylcyclohexane-1,2-diamine (20.11 mg, 141.35 umol), CuI (96.15 mg, 504.83 umol) and $K_3PO_4$ (128.59 mg, 605.80 umol). The mixture was stirred at 130° C. in a sealed tube for 14 h. LC-MS showed product was formed. The reaction mixture was diluted with EtOAc (50 mL) and water (50 mL). Then HCl (2 M) was added to adjusted pH to 5-6. The mixture was filtered and the filtrate was extracted with EtOAc (3×50 mL), washed with brine (3×20 mL), dried over anhydrous $Na_2SO_4$ and filtered. The filtrate was concentrated in vacuum to afford a residue. The residue was purified by flash column chromatography ($CH_2Cl_2$: $CH_3OH$=20:1) to afford 5-[[2,6-dichloro-4-[6-(difluoromethyl)-3,5-dioxo-1,2,4-triazin-2-yl]phenyl]methyl]-N-(3-hydroxycyclobutyl)-2-methoxy-benzenesulfonamide 97-6 (70 mg, 60% yield) as a yellow solid. LCMS: $[M+H]^+=576.9/579.1$ Step 7: 97

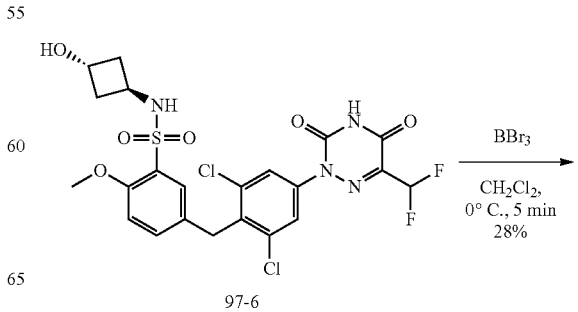

347
-continued

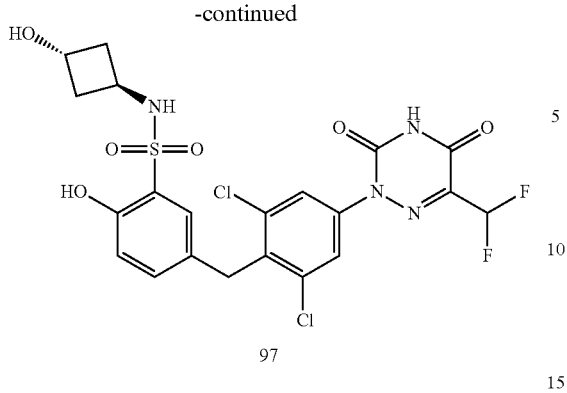

97

348
-continued

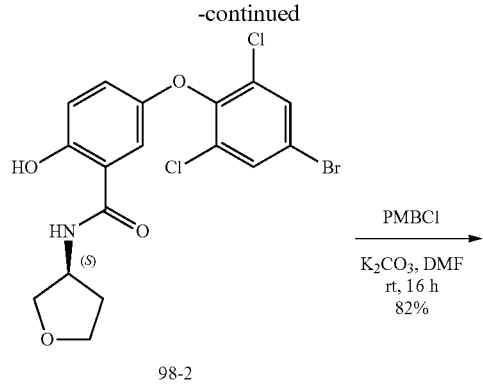

98-2

To a solution of 5-[[2,6-dichloro-4-[6-(difluoromethyl)-3,5-dioxo-1,2,4-triazin-2-yl]phenyl]methyl]-N-(3-hydroxycyclobutyl)-2-methoxy-benzenesulfonamide 97-6 (70 mg, 121.24 umol) in CH$_2$Cl$_2$ (2 mL) was added BBr$_3$ (303.73 mg, 1.21 mmol) at 0° C. The mixture was stirred at 0° C. for 5 min. LC-MS showed product was formed. The reaction mixture was poured into saturated aqueous NaHCO$_3$ (30 mL). The mixture was extracted with EtOAc (3×30 mL), washed with brine (20 mL), dried over anhydrous Na$_2$SO$_4$ and filtered. The filtrate was concentrated in vacuum to afford a residue. The residue was purified by Prep-HPLC (Xbridge 5 u C18 150×19 mm, MeCN—H$_2$O (0.1% FA), Gradient: 35-95%, 20 ml/min) to afford 5-[[2,6-dichloro-4-[6-(difluoromethyl)-3,5-dioxo-1,2,4-triazin-2-yl]phenyl]methyl]-2-hydroxy-N-(3-hydroxycyclobutyl)benzenesulfonamide 97 (19.4 mg, 28% yield) as a white solid. LCMS: [M+H]$^+$=563.1/565.0. $^1$H NMR (400 MHz, CD$_3$OD) δ 7.74 (s, 2H), 7.53 (d, J=2.4 Hz, 1H), 7.29 (dd, J=8.4, 2.4 Hz, 1H), 6.89 (d, J=8.8 Hz, 1H), 6.70 (t, J=52.8 Hz, 1H), 4.33 (s, 2H), 4.27-4.20 (m, 1H), 3.89-3.81 (m, 1H), 2.17-2.08 (m, 2H), 2.02-1.94 (m, 2H). $^{19}$F NMR (376 MHz, CD$_3$OD) δ−124.21 (s, 2F).

Example 45: Synthesis of Compound 98

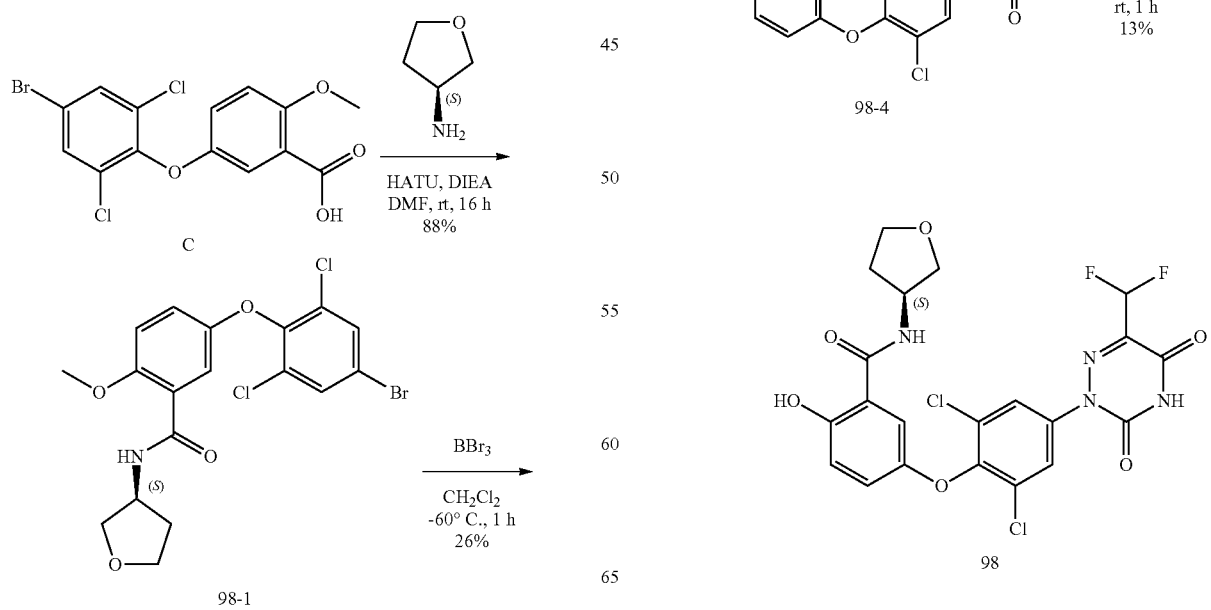

Step 1: 98-1

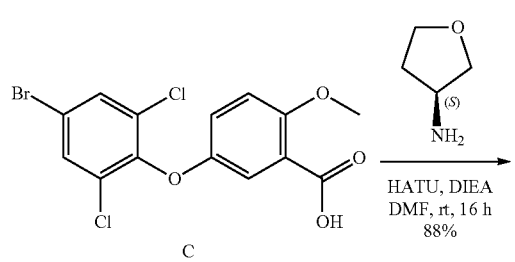

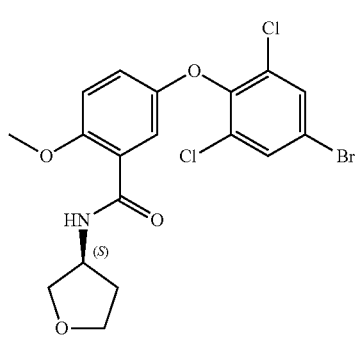

98-1

To a mixture of 5-(4-bromo-2,6-dichlorophenoxy)-2-methoxybenzoic acid C (500 mg, 1.28 mmol), (S)-tetrahydrofuran-3-amine hydrochloride (222.23 mg, 1.80 mmol) and HATU (727.43 mg, 1.91 mmol) in DMF (10 mL) was added N-ethyldiisopropylamine (659.35 mg, 5.10 mmol). The mixture was stirred at rt for 16 h. LC-MS showed the reaction was complete. EtOAc (50 mL) was added into the reaction. Then the mixture was washed with brine (2×30 mL), dried over $Na_2SO_4$ and concentrated in vacuum. The resulting mixture was purified by silica gel chromatography (PE:EtOAc=3:1) to afford (S)-5-(4-bromo-2,6-dichlorophenoxy)-2-methoxy-N-(tetrahydrofuran-3-yl) benzamide 98-1 (520 mg, 88% yield) as colorless oil. LCMS: $[M+H]^+$=460.0/462.0.

Step 2: 98-2

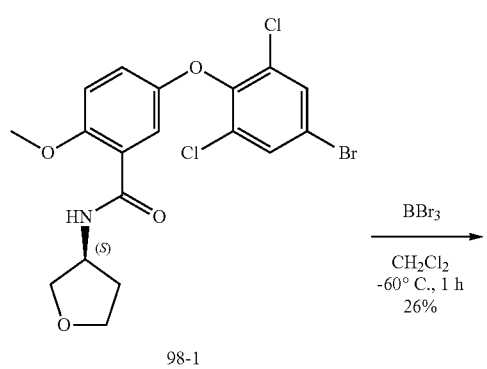

98-1

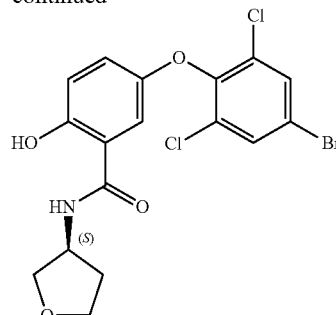

98-2

To a solution of (S)-5-(4-bromo-2,6-dichlorophenoxy)-2-methoxy-N-(tetrahydrofuran-3-yl) benzamide 98-1 (420 mg, 910.80 umol) in $CH_2Cl_2$ (10 mL) was added $BBr_3$ (2 mL) at −60° C. The mixture was stirred at −60° C. for 1 h. LC-MS showed the reaction was completed. The reaction was poured into ice-water. Then the mixture was extracted with EtOAc (2×30 mL). The combined organic layer was washed with brine (2×20 mL), dried over $Na_2SO_4$ and concentrated in vacuum. The resulting mixture was purified by silica gel chromatography (PE:EtOAc=3:1) to afford (S)-5-(4-bromo-2,6-dichlorophenoxy)-2-hydroxy-N-(tetrahydrofuran-3-yl) benzamide 98-2 (106 mg, 26% yield) as a colorless oil. LCMS: $[M+H]^+$=445.9/448.0.

Step 3: 98-3

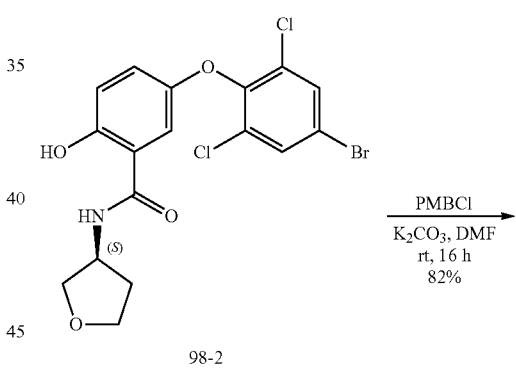

98-2

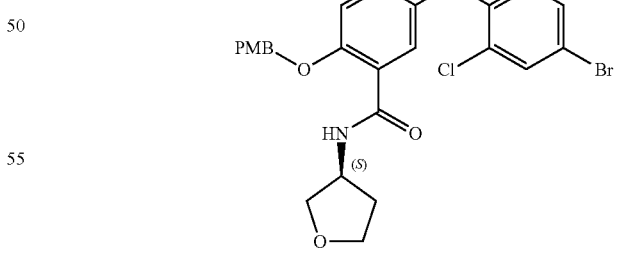

98-3

A mixture of (S)-5-(4-bromo-2,6-dichlorophenoxy)-2-hydroxy-N-(tetrahydrofuran-3-yl) benzamide 98-2 (106 mg, 237.08 umol), potassium carbonate (65.53 mg, 474.16 umol) and 1-(chloromethyl)-4-methoxy-benzene (55.69 mg, 355.62 umol) in DMF (5 mL) was stirred at rt for 16 h. LC-MS showed the reaction was complete. EtOAc (30 mL)

was added into the reaction. Then the mixture was washed with brine (2×20 mL), dried over Na₂SO₄ and concentrated in vacuum. The resulting mixture was purified by silica gel chromatography (PE:EtOAc=3:1) to afford (S)-5-(4-bromo-2,6-dichlorophenoxy)-2-((4-methoxybenzyl) oxy)-N-(tetrahydrofuran-3-yl) benzamide 98-3 (110 mg, 82% yield) as a white solid. LCMS: [M+Na]⁺=587.9/590.1.

Step 4: 98-4

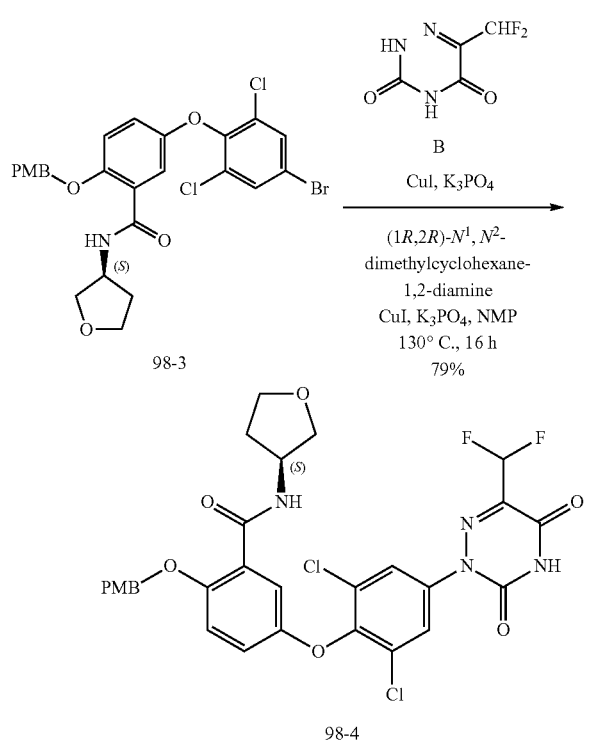

A mixture of (S)-5-(4-bromo-2,6-dichlorophenoxy)-2-((4-methoxybenzyl) oxy)-N-(tetrahydrofuran-3-yl) benzamide 98-3 (110 mg, 193.92 umol), 6-(difluoromethyl)-2H-1,2,4-triazine-3,5-dione B (63.25 mg, 387.83 umol), (1R, 2R)—N1,N2-dimethylcyclohexane-1,2-diamine (19.31 mg, 135.74 umol), copper (I) iodide (92.33 mg, 484.79 umol) and potassium phosphate (123.49 mg, 581.75 umol) in NMP (2 mL) was stirred at 130° C. for 16 h. LC-MS showed the reaction was ok. EtOAc (10 mL) was added into the reaction. Solids were filtrated off and the filtrate was washed with brine (2×10 mL), dried over Na₂SO₄ and concentrated in vacuum. The resulting mixture was purified by silica gel chromatography (CH₂Cl₂:CH₃OH=30:1) to afford (S)-5-(2,6-dichloro-4-(6-(difluoromethyl)-3,5-dioxo-4,5-dihydro-1,2,4-triazin-2(3H)-yl)phenoxy)-2-((4-methoxybenzyl)oxy)-N-(tetrahydrofuran-3-yl)benzamide 98-4 (100 mg, 79% yield) as a yellow oil. LCMS: [M+Na]⁺=671.1/672.9.

Step 5: 98

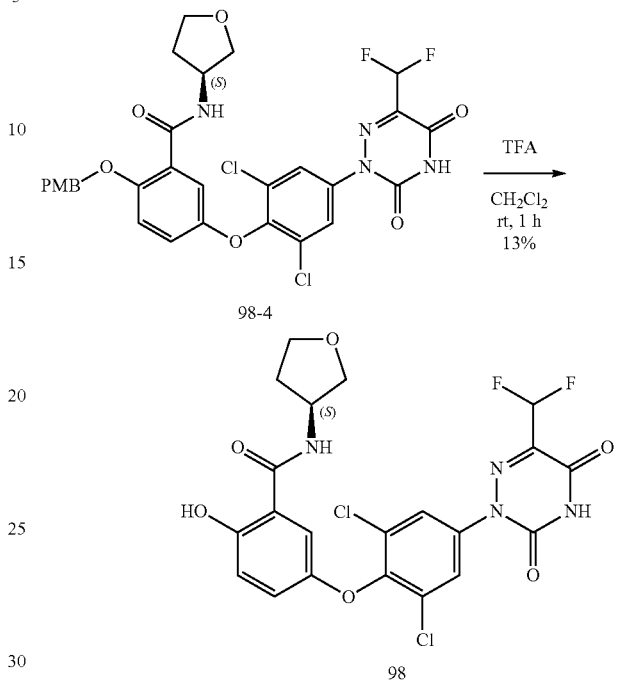

A mixture of(S)-5-(2,6-dichloro-4-(6-(difluoromethyl)-3,5-dioxo-4,5-dihydro-1,2,4-triazin-2(3H)-yl) phenoxy)-2-((4-methoxybenzyl)oxy)-N-(tetrahydrofuran-3-yl)benzamide 98-4 (100 mg, 153.98 umol) and TFA (0.5 mL) in CH₂Cl₂ (5 mL) was stirred at rt for 1 h. LC-MS showed the reaction was complete. EtOAc (30 mL) was added into the reaction. The mixture was washed with brine (2×30 mL), dried over Na₂SO₄ and concentrated in vacuum. The resulting mixture was purified by prep-HPLC (Xbridge 5 u C18 150×19 mm, MeCN—H₂O (0.1% TFA), Gradient: 40-70%) to afford (S)-5-(2,6-dichloro-4-(6-(difluoromethyl)-3,5-dioxo-4,5-dihydro-1,2,4-triazin-2(3H)-yl) phenoxy)-2-hydroxy-N-(tetrahydrofuran-3-yl) benzamide 98 (10.4 mg, 13% yield) as a white solid. LCMS: [M+H]⁺=529.0/530.9. ¹H NMR (400 MHz, CD₃OD) δ 7.79 (s, 2H), 7.40 (d, J=3.2 Hz, 1H), 6.94 (dd, J=8.8, 2.8 Hz, 1H), 6.89 (d, J=8.8 Hz, 1H), 6.72 (t, J=52.8 Hz, 1H), 4.60-4.55 (m, 1H), 3.98-3.91 (m, 2H), 3.85-3.79 (m, 1H), 3.72-3.69 (m, 1H), 2.34-2.25 (m, 1H), 1.98-1.92 (m, 1H). ¹⁹F NMR (376 MHz, CD₃OD) δ−124.34 (s, 2F).

Example 46: Synthesis of Compound 99

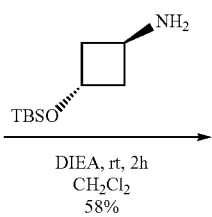

-continued
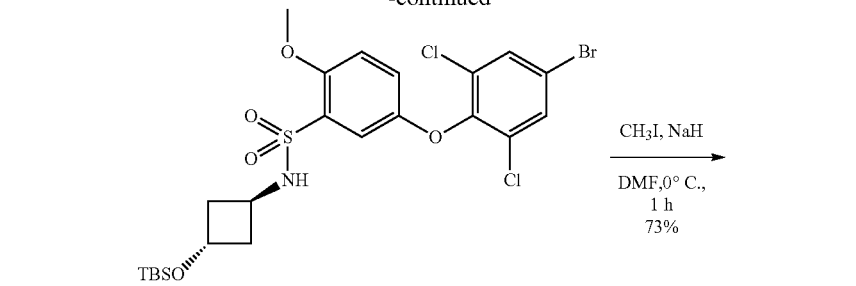
99-1
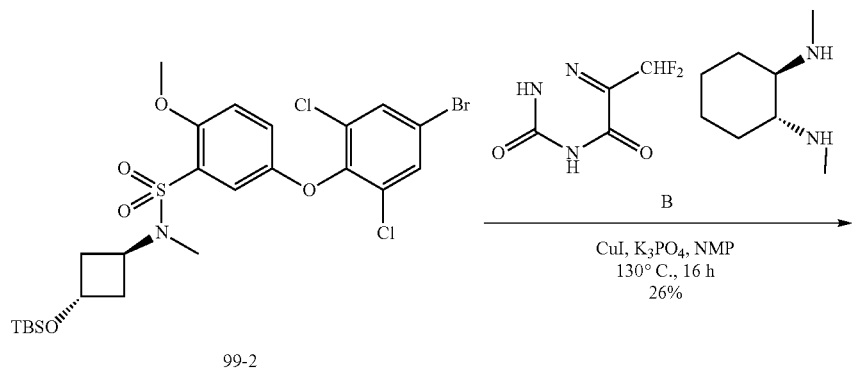
99-2
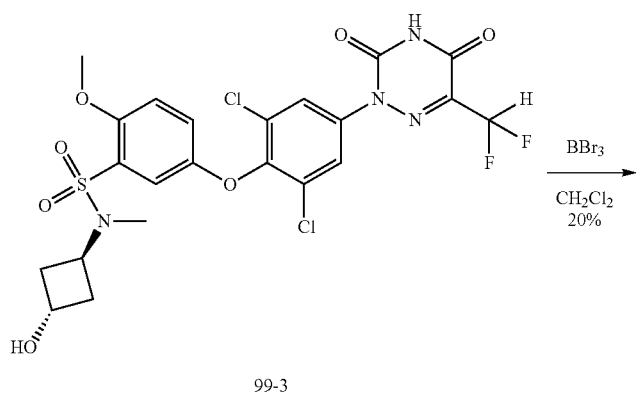
99-3
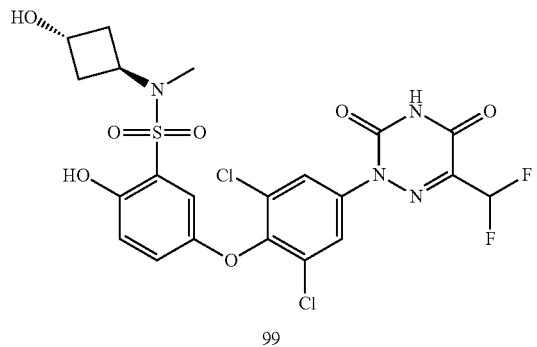
99

Step 1: 99-1

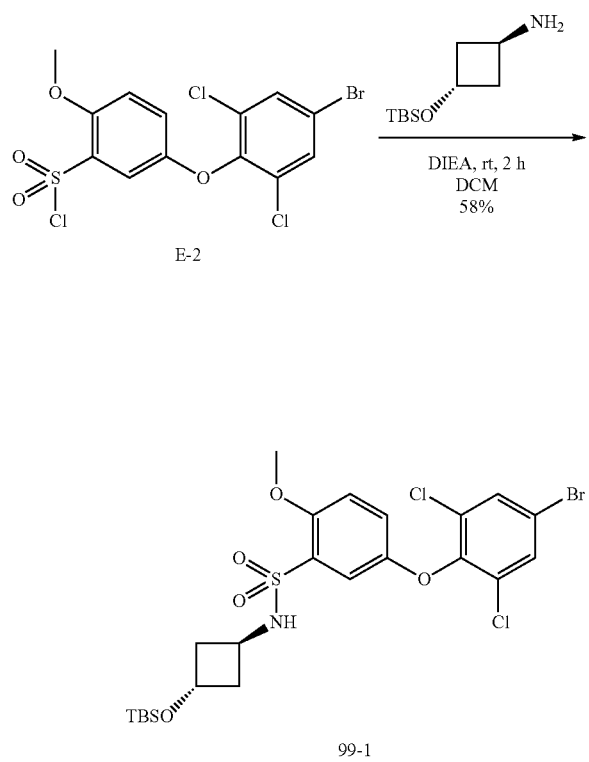

Step 2: 99-2

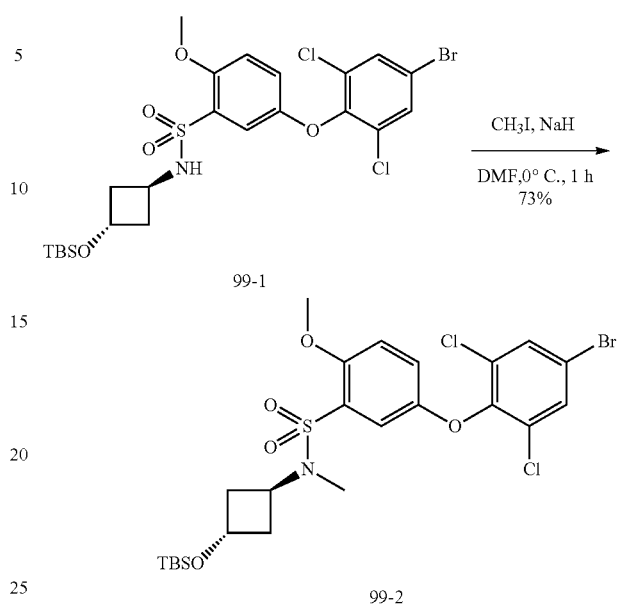

To a mixture of 3-[tert-butyl(dimethyl)silyl]oxycyclobutanamine (270.59 mg, 1.34 mmol) in CH₂Cl₂ (5 mL) was added DIEA (434.16 mg, 3.36 mmol, 585.12 uL) and 5-(4-bromo-2,6-dichloro-phenoxy)-2-methoxy-benzenesulfonyl chloride E-2 (500 mg, 1.12 mmol). The mixture was stirred at rt for 2 h. LCMS showed the starting material was consumed and the product was found. The reaction mixture was poured into water (20 mL) and extracted with EtOAc (3×20 mL). The combined organic layer was dried over anhydrous Na₂SO₄ and filtered. The filtrate was concentrated in vacuum to afford a residue. The residue was purified by silica gel chromatography (PE:EtOAc=3:1) to afford 5-(4-bromo-2,6-dichloro-phenoxy)-N-[3-[tert-butyl(dimethyl)silyl]oxycyclobutyl]-2-methoxy-benzenesulfonamide 99-1 (400 mg, 58% yield) as a white solid. LCMS: $[M+H]^+=610.1/612.1$ To a cooled mixture of 5-(4-bromo-2,6-dichloro-phenoxy)-N-[3-[tert-butyl(dimethyl)silyl]oxycyclobutyl]-2-methoxy-benzenesulfonamide 99-1 (400 mg, 654.19 umol) in DMF (4 mL) was added NaH (23.55 mg, 981.28 umol) and the mixture was stirred at 0° C. for 30 min. CH₃I (185.66 mg, 1.31 mmol) was added to the above mixture slowly and the mixture was stirred at 0° C. for 30 min. TLC (PE: EtOAc=3:1) showed the starting material was consumed and a new spot was formed. The reaction mixture was poured into water (10 mL) and extracted with EtOAc (3×20 mL). The combined organic layer was washed with brine (20 mL), dried over anhydrous Na₂SO₄ and filtered. The filtrate was concentrated in vacuum to afford a residue which was purified by prep-TLC (PE:EtOAc=3:1) to afford 5-(4-bromo-2,6-dichloro-phenoxy)-N-[3-[tert-butyl(dimethyl)silyl]oxycyclobutyl]-2-methoxy-N-methyl-benzenesulfonamide 99-2 (300 mg, 73% yield) as a white solid. LCMS: $[M+H]^+=624.1/626.1$ Step 3: 99-3

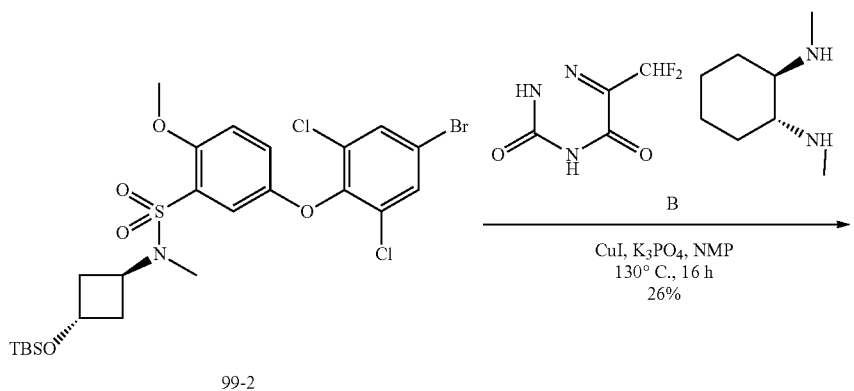

-continued

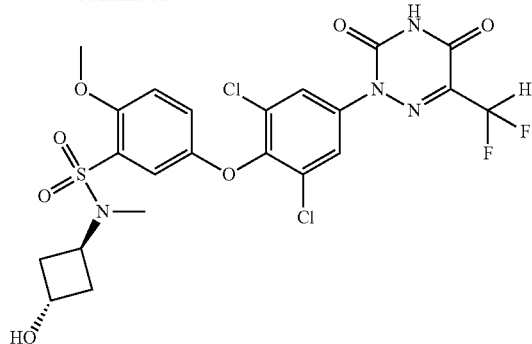

99-3

To a mixture of 5-(4-bromo-2,6-dichloro-phenoxy)-N-[3-[tert-butyl(dimethyl)silyl]oxycyclobutyl]-2-methoxy-N-methyl-benzenesulfonamide 99-2 (200 mg, 319.76 umol) in NMP (2 mL) was added 6-(difluoromethyl)-2H-1,2,4-triazine-3,5-dione B (104.29 mg, 639.52 umol), (1R,2R)—N1,N2-dimethylcyclohexane-1,2-diamine (36.39 mg, 255.81 umol, 40.34 uL), $K_3PO_4$ (203.37 mg, 959.27 umol) and CuI (152.24 mg, 799.39 umol). The mixture was stirred at 130° C. for 16 h. LCMS showed the starting material was consumed and the product was found. The reaction mixture was added into EtOAc (10 mL) and the mixture was washed with 0.2N HCl (10 mL). The mixture was filtered and the filtrate was extracted with EtOAc (20 mL*3). The combined organic layers were washed with brine (20 mL), dried over anhydrous $Na_2SO_4$ and filtered. The filtrate was concentrated in vacuum to afford a residue. The residue was purified by prep-TLC ($CH_2Cl_2$:$CH_3OH$=10:1) to afford 5-[2,6-dichloro-4-[6-(difluoromethyl)-3,5-dioxo-1,2,4-triazin-2-yl]phenoxy]-N-(3-hydroxycyclobutyl)-2-methoxy-N-methyl-benzenesulfonamide 99-3 (50 mg, 26% yield) as a yellow solid. LCMS: $[M+H]^+$=593.1/595.1

Step 4: 99

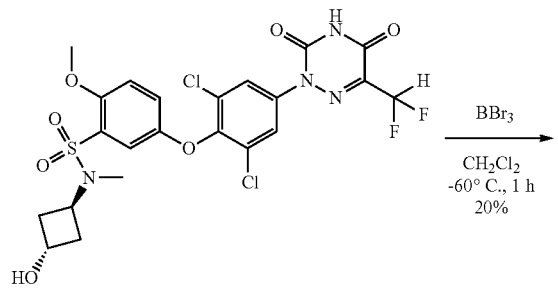

99-3

$\xrightarrow{\text{BBr}_3}{\text{CH}_2\text{Cl}_2 \; -60°\text{C., 1 h} \; 20\%}$ -continued

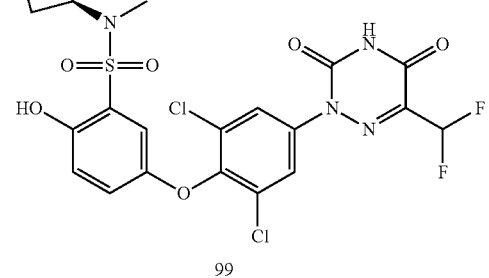

99

To a mixture of 5-[2,6-dichloro-4-[6-(difluoromethyl)-3,5-dioxo-1,2,4-triazin-2-yl]phenoxy]-N-(3-hydroxycyclobutyl)-2-methoxy-N-methyl-benzenesulfonamide 99-3 (50 mg, 84.26 umol) in $CH_2Cl_2$ (2 mL) was added $BBr_3$ (212.78 mg, 842.62 umol) slowly at −60° C. The mixture was stirred at −60° C. for 1 h. LCMS showed the starting material was consumed and the product was found. The reaction mixture was poured into saturated aqueous $NaHCO_3$ (20 mL) and extracted with EtOAc (3×20 mL). The combined organic layer was washed with brine (20 mL), dried over anhydrous $Na_2SO_4$ and filtered. The filtrate was concentrated in vacuum to afford a residue. The residue was purified by prep-HPLC (Daisogel-C18 250×50 mm 10 um, MeCN—$H_2O$ (0.1% FA), Gradient: 35-55%) to afford 5-[2,6-dichloro-4-(3-oxo-4,5-dihydro-1,2,4-triazin-2-yl)phenoxy]-2-hydroxy-N-(3-hydroxycyclobutyl)-N-methyl-benzenesulfonamide 99 (8.9 mg, 20% yield) as a white solid. LCMS: $[M+H]^+$=579.1/581.1. $^1$H NMR (400 MHz, $CD_3OD$) δ 7.82 (s, 2H), 7.07 (d, J=2.8 Hz, 1H), 7.05 (s, 1H), 6.97-6.95 (m, 1H), 6.71 (t, J=52.8 Hz, 1H), 4.61-4.56 (m, 1H), 4.22-4.20 (m, 1H), 2.81 (s, 3H), 2.41-2.37 (m, 2H), 2.00-1.97 (m, 2H). $^{19}$F NMR (376 MHz, $CD_3OD$) δ−122.18 (s, 2F).

Example 47: Synthesis of Compound 100

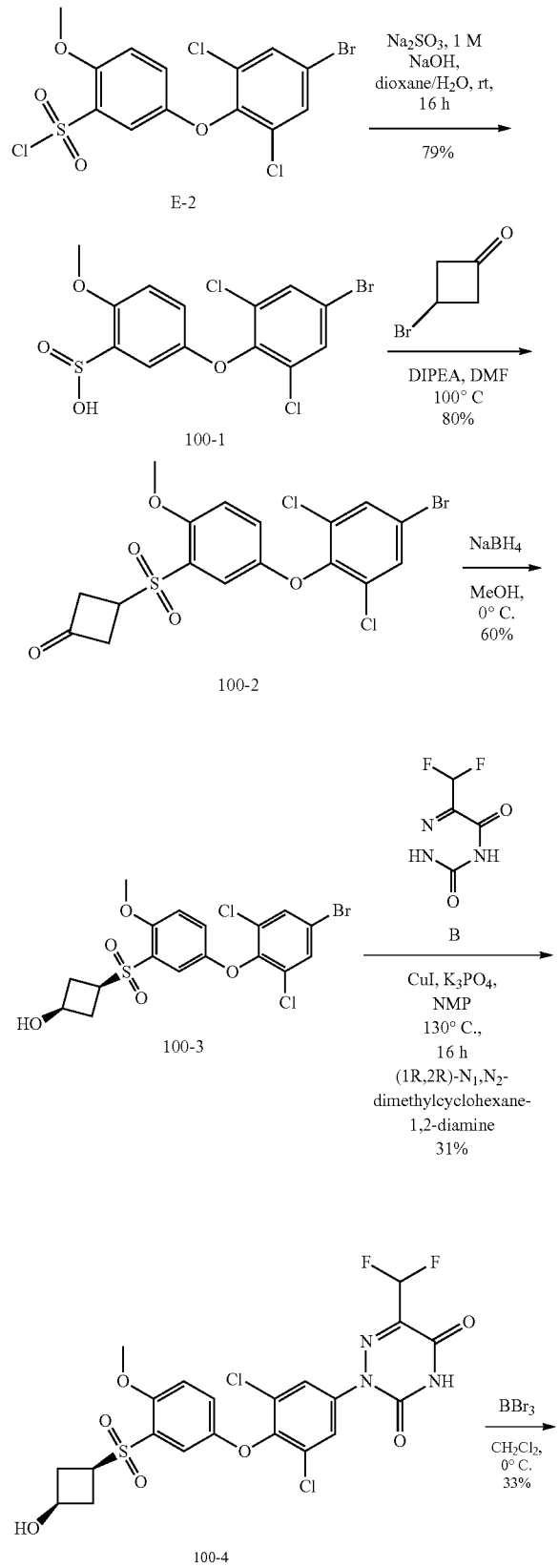

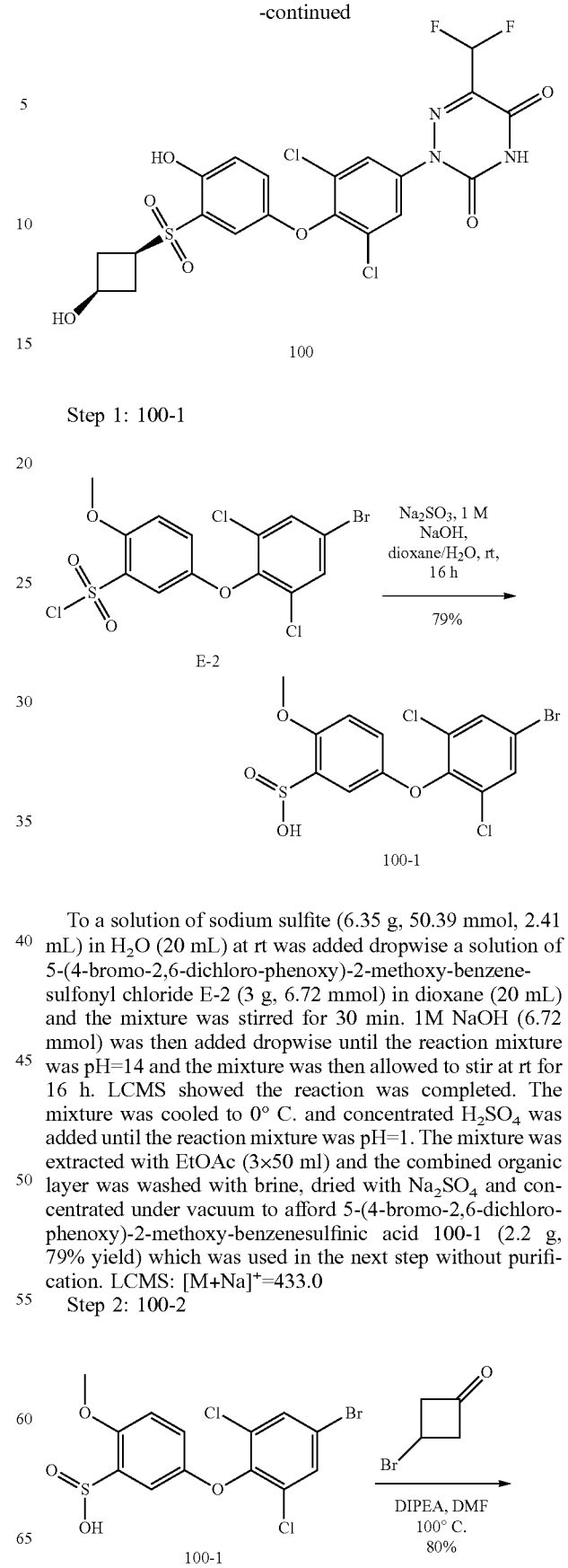

Step 1: 100-1

To a solution of sodium sulfite (6.35 g, 50.39 mmol, 2.41 mL) in $H_2O$ (20 mL) at rt was added dropwise a solution of 5-(4-bromo-2,6-dichloro-phenoxy)-2-methoxy-benzene-sulfonyl chloride E-2 (3 g, 6.72 mmol) in dioxane (20 mL) and the mixture was stirred for 30 min. 1M NaOH (6.72 mmol) was then added dropwise until the reaction mixture was pH=14 and the mixture was then allowed to stir at rt for 16 h. LCMS showed the reaction was completed. The mixture was cooled to 0° C. and concentrated $H_2SO_4$ was added until the reaction mixture was pH=1. The mixture was extracted with EtOAc (3×50 ml) and the combined organic layer was washed with brine, dried with $Na_2SO_4$ and concentrated under vacuum to afford 5-(4-bromo-2,6-dichloro-phenoxy)-2-methoxy-benzenesulfinic acid 100-1 (2.2 g, 79% yield) which was used in the next step without purification. LCMS: $[M+Na]^+=433.0$ Step 2: 100-2

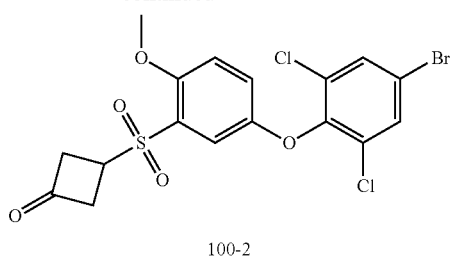

100-2

A solution of 5-(4-bromo-2,6-dichloro-phenoxy)-2-methoxy-benzenesulfinic acid 100-1 (700 mg, 1.70 mmol), 3-bromocyclobutanone (1.27 g, 8.49 mmol) and DIPEA (658.63 mg, 5.10 mmol, 887.64 uL) in DMF (3 mL) was stirred at 100° C. for 16 h. LCMS showed the product was formed. The reaction mixture was poured into water and extracted with EtOAc (3×50 mL). The combined organic layer was dried over anhydrous $Na_2SO_4$, filtered and concentrated in vacuum to afford a residue. The residue was purified by flash chromatography (PE:EtOAc=1:1) to afford 3-[5-(4-bromo-2,6-dichloro-phenoxy)-2-methoxy-phenyl]sulfonyl cyclobutanone 100-2 (660 mg, 80% yield) as a white solid. LCMS: $[M+Na]^+=501.0/502.8$ Step 3: 100-3

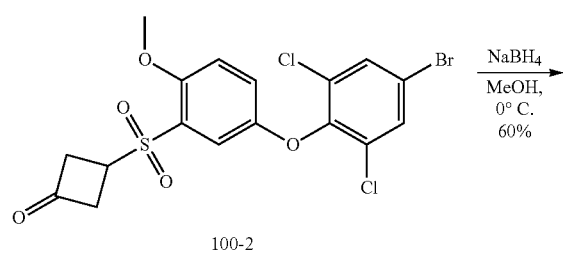

To a solution of 3-[5-(4-bromo-2,6-dichloro-phenoxy)-2-methoxy-phenyl]sulfonylcyclobutanone 100-2 (660 mg, 1.37 mmol) in $CH_3OH$ (5 mL) was added $NaBH_4$ (266.48 mg, 7.01 mmol) at 0° C. The mixture was stirred at 0° C. for 2 h. LCMS showed the product was formed. The reaction mixture was poured into water and extracted with EtOAc (3×30 mL). The combined organic layer was dried over anhydrous $Na_2SO_4$, filtered and concentrated in vacuum to afford a residue. The residue was purified by flash chromatography (PE:EtOAc=1:1) to afford (1s,3s)-3-((5-(4-bromo-2,6-dichlorophenoxy)-2-methoxyphenyl) sulfonyl) cyclobutan-1-ol 100-3 (400 mg, 60% yield) as a yellow solid. LCMS: $[M+H]^+=480.9/482.9$ Step 4: 100-4

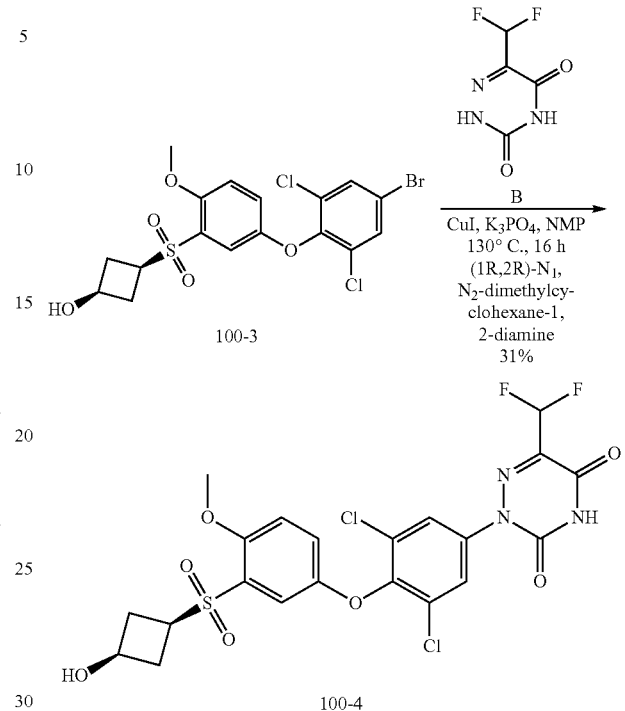

A solution of (1s,3s)-3-((5-(4-bromo-2,6-dichlorophenoxy)-2-methoxyphenyl) sulfonyl) cyclobutan-1-ol 100-3 (260 mg, 539.23 umol), 6-(difluoromethyl)-2H-1,2,4-triazine-3,5-dione B (175.88 mg, 1.08 mmol), (1R,2R)—N1,N2-dimethylcyclohexane-1,2-diamine (61.36 mg, 431.38 umol), CuI (256.74 mg, 1.35 mmol) and $K_3PO_4$ (342.95 mg, 1.62 mmol) in NMP (3 mL) was stirred in a sealed tube at 130° C. for 16 h. LCMS showed the product was formed. The reaction mixture was added into EtOAc (50 mL) and the mixture was washed with 0.2N HCl (50 mL). The mixture was filtered and the filtrate was extracted with EtOAc (50 mL). The combined organic layers were washed with brine (50 mL), dried over anhydrous $Na_2SO_4$, filtered and concentrated in vacuum to afford a residue. The residue was purified by column chromatography ($CH_2Cl_2$:$CH_3OH$=20:1) to afford 2-(3,5-dichloro-4-(3-(((1s,3s)-3-hydroxycyclobutyl) sulfonyl)-4-methoxyphenoxy) phenyl)-6-(difluoromethyl)-1,2,4-triazine-3,5(2H,4H)-dione 100-4 (95 mg, 31% yield) as a yellow solid. LCMS: $[M+H]^+=564.0/566.0$.

Step 5:100

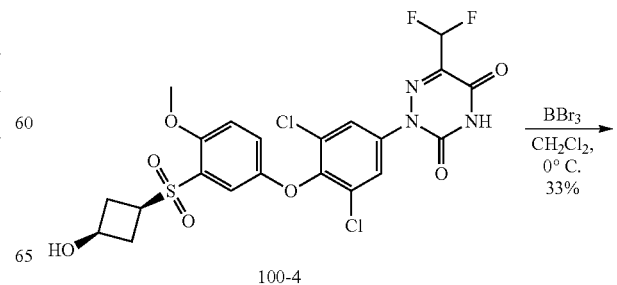

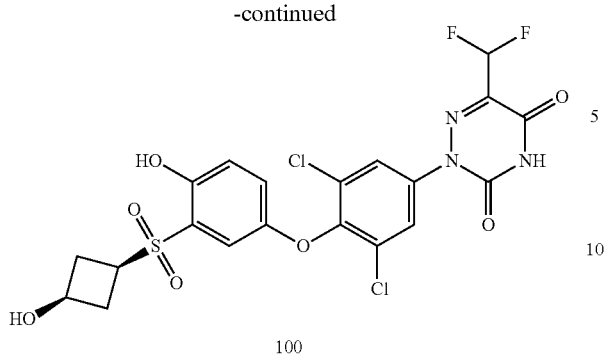

100

To a mixture of 2-(3,5-dichloro-4-(3-(((1s,3s)-3-hydroxy-cyclobutyl) sulfonyl)-4-methoxyphenoxy) phenyl)-6-(difluoromethyl)-1,2,4-triazine-3,5(2H,4H)-dione 100-4 (95 mg, 168.34 umol) in $CH_2Cl_2$ (3 mL) was added $BBr_3$ (168.34 umol, 1 mL) at 0° C. The mixture was stirred at 0° C. for 0.5 h. LCMS showed the reaction was completed. The mixture was washed successively with brine (50 mL) and water (50 mL). The organic layer was dried over $Na_2SO_4$ and concentrated in vacuum. The residue was purified by flash chromatography ($CH_2Cl_2$:$CH_3OH$=20:1) to give the crude product. The crude product was purified by C18 column (MeCN:$H_2O$=37%) to give 2-(3,5-dichloro-4-(4-hydroxy-3-(((1s,3s)-3-hydroxycyclobutyl) sulfonyl) phenoxy) phenyl)-6-(difluoromethyl)-1,2,4-triazine-3,5(2H,4H)-dione 100 (30.7 mg, 33% yield) as a white solid. The cis structure was confirmed through NOE. LCMS: $[M+H]^+$=550.1. $^1H$ NMR (400 MHz, DMSO-$d_6$) δ 8.29 (s, 1H), 7.84 (s, 2H), 7.16 (dd, J=8.8, 3.2 Hz, 1H), 7.05 (d, J=8.8 Hz, 1H), 7.01 (d, J=2.8 Hz, 1H), 6.78 (t, J=53.6 Hz, 1H), 4.00-3.97 (m, 1H), 3.85-3.81 (m, 1H), 2.33-2.28 (m, 2H), 2.17-2.04 (m, 2H). $^{19}F$ NMR (376 MHz, DMSO-$d_6$)) δ−121.67 (s, 2F).

Example 48: Synthesis of Compound 101

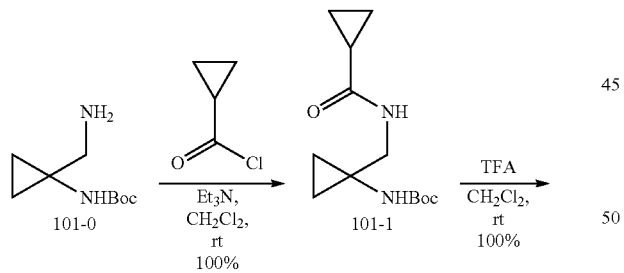

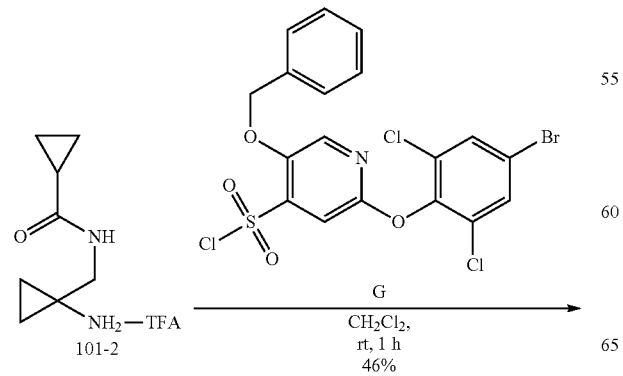

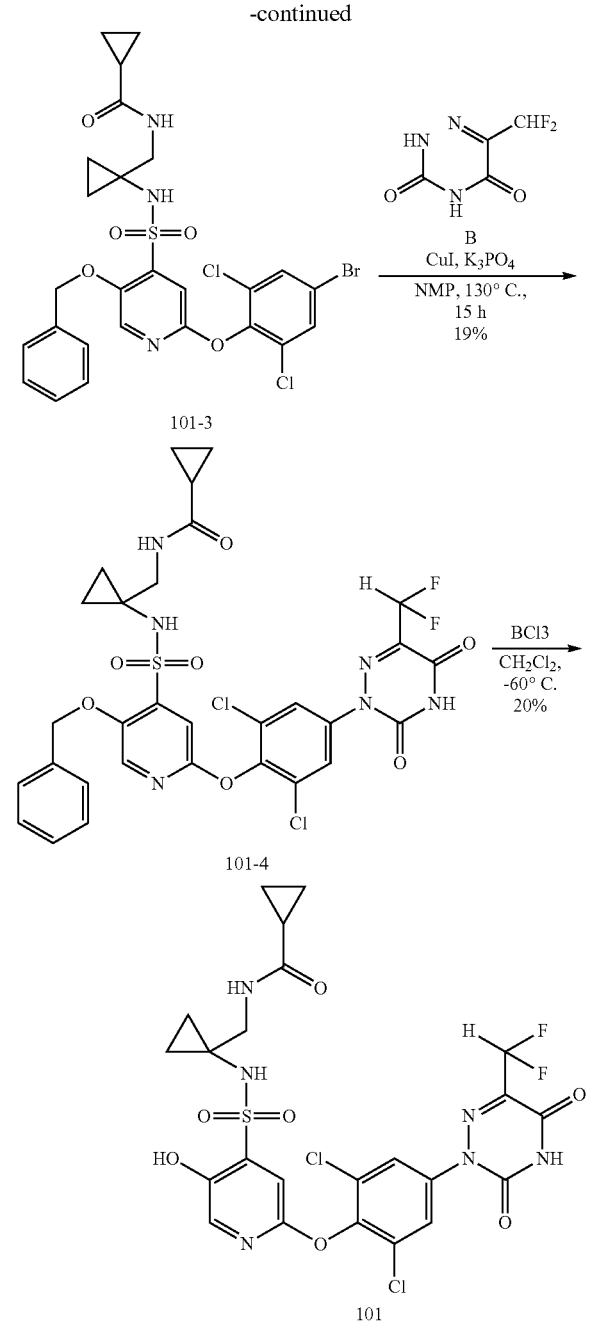

Step 1: 101-1

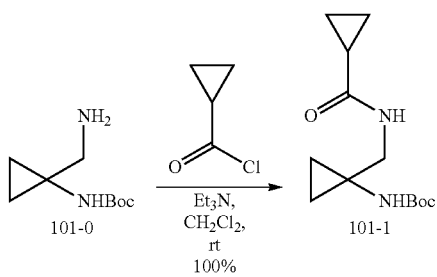 [SMILES: CC(C)(C)OC(=O)NC1(CN)CC1 ; O=C(Cl)C1CC1 ; CC(C)(C)OC(=O)NC1(CNC(=O)C2CC2)CC1]

365

To a mixture of tert-butyl N-[1-(aminomethyl) cyclopropyl] carbamate 101-0 (200 mg, 1.07 mmol) and TEA (325.98 mg, 3.22 mmol, 449.01 uL) in CH₂Cl₂ (5 mL) was added cyclopropanecarbonyl chloride (134.70 mg, 1.29 mmol, 117.13 uL) at rt. The mixture was stirred at rt for 1 h. LCMS showed the reaction was completed. The mixture was poured into water (20 mL) and extracted with EtOAc (2×20 mL). The combined organic layer was washed successively with brine (50 mL) and water (50 mL). The organic layer was dried over Na₂SO₄ and concentrated in vacuum. The crude residue tert-butyl N-[1-[(cyclopropanecarbonylamino) methyl] cyclopropyl] carbamate 101-1 (285 mg), was used for the next step without further purification. LCMS: [M+Na]⁺=277.1

Step 2: 101-2

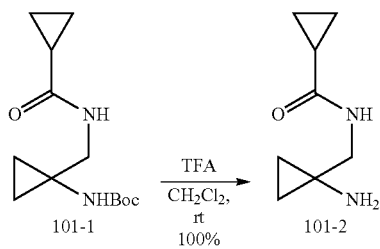 [SMILES: CC(C)(C)OC(=O)NC1(CNC(=O)C2CC2)CC1 ; NC1(CNC(=O)C2CC2)CC1 ; "TFA"]

To a mixture of tert-butyl N-[1-[(cyclopropanecarbonylamino) methyl] cyclopropyl] carbamate 101-1 (285 mg, 1.10 mmol) in CH₂Cl₂ (5 mL) was added TFA (3.19 g, 27.96 mmol, 2.15 mL) at rt. The mixture was stirred at rt for 1 h. LCMS showed the reaction was completed. The mixture was concentrated in vacuum. The crude residue N-[(1-aminocyclopropyl) methyl]cyclopropanecarboxamide 101-2 (400 mg), was used for the next step without further purification. LCMS: [M+H]⁺=155.2

Step 3: 101-3

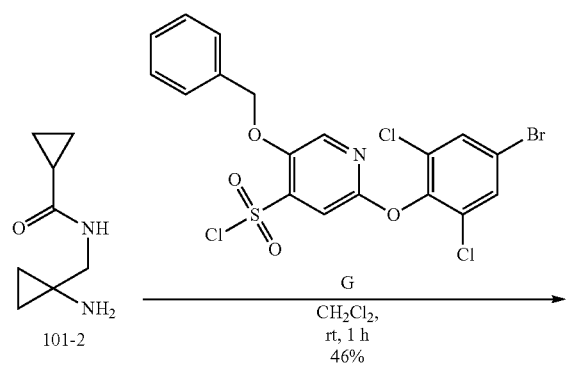

366

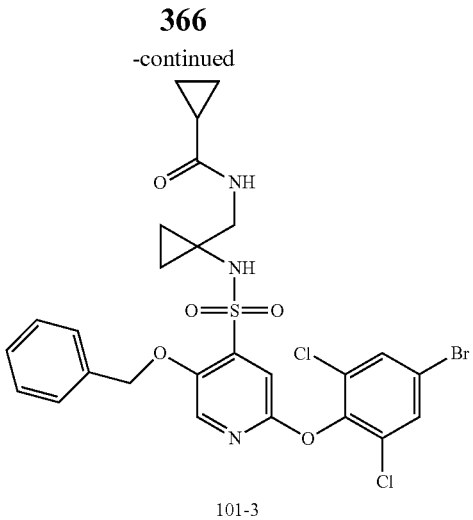

101-3

To a mixture of N-[[1-[(2,2,2-trifluoroacetyl) amino] cyclopropyl] methyl]cyclopropanecarboxamide 101-2 (219.82 mg, 878.51 umol) and TEA (133.35 mg, 1.32 mmol, 183.67 uL) in CH₂Cl₂ (3 mL) was added 5-benzyloxy-2-(4-bromo-2,6-dichloro-phenoxy)pyridine-4-sulfonyl chloride G (230 mg, 439.26 umol). The mixture was stirred at rt for 1 h. LCMS showed the reaction was completed. The mixture was poured into water (20 mL) and extracted with EtOAc (2×20 mL). The combined organic layer was washed successively with brine (50 mL) and water (50 mL). The organic layer was dried over Na₂SO₄ and concentrated in vacuum. The residue was purified by flash chromatography (PE:EtOAc=2:1) to give N-[[1-[[5-benzyloxy-2-(4-bromo-2,6-dichloro-phenoxy)-4-pyridyl] sulfonylamino] cyclopropyl] methyl]cyclopropanecarboxamide 101-3 (130 mg, 46% yield) as a yellow solid. LCMS: [M+H]⁺=639.8/641.9

Step 4: 101-4

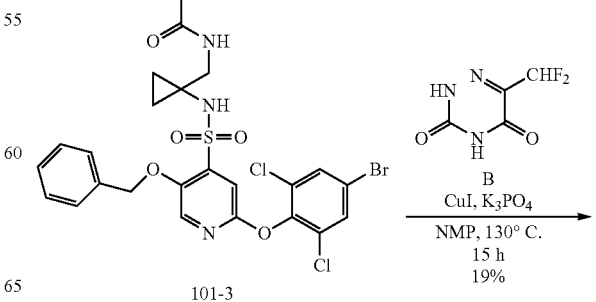

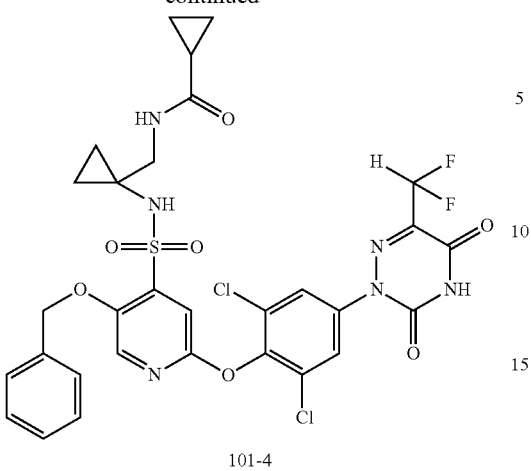

101-4

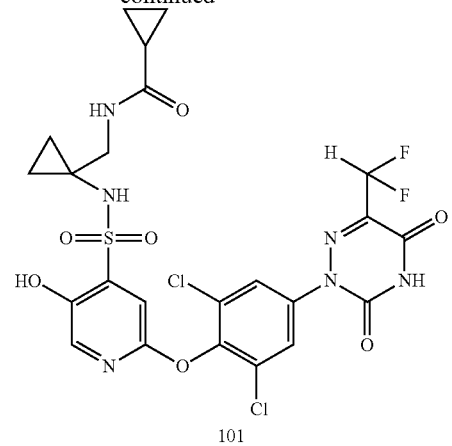

101

A mixture of N-[[1-[[5-benzyloxy-2-(4-bromo-2,6-dichloro-phenoxy)-4-pyridyl] sulfonylamino]cyclopropyl] methyl] cyclopropanecarboxamide 101-3 (130 mg, 202.69 umol), 6-(difluoromethyl)-2H-1,2,4-triazine-3,5-dione B (66.11 mg, 405.39 umol), (1R,2R)—N1,N2-dimethylcyclohexane-1,2-diamine (23.07 mg, 162.16 umol, 25.57 uL), CuI (96.51 mg, 506.74 umol) and K₃PO₄ (128.91 mg, 608.08 umol) in NMP (3 mL) was stirred at 130° C. for 15 h. LCMS showed the product was formed. The mixture was poured into water (20 mL) and extracted with EtOAc (2×20 mL). The combined organic layer was washed successively with brine (50 mL) and water (50 mL). The organic layer was dried over Na₂SO₄ and concentrated in vacuum. The residue was purified by Prep-TLC (CH₂Cl₂:CH₃OH=10:1) to give N-[[1-[[5-benzyloxy-2-[2,6-dichloro-4-[3,5-dioxo-6-(trifluoromethyl)-1,2,4-triazin-2-yl] phenoxy]-4-pyridyl] sulfonylamino] cyclopropyl] methyl] cyclopropanecarboxamide 101-4 (30 mg, 19% yield) as a yellow solid. LCMS: [M+H]⁺=722.9/724.8

Step 5:101

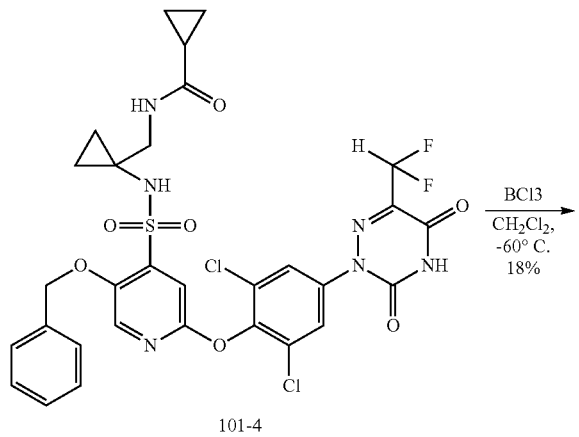

101-4

To a mixture of N-[[1-[[5-benzyloxy-2-[2,6-dichloro-4-[3,5-dioxo-6-(trifluoromethyl)-1,2,4-triazin-2-yl] phenoxy]-4-pyridyl] sulfonylamino] cyclopropyl]methyl] cyclopropanecarboxamide 101-4 (30 mg, 40.46 umol) in CH₂Cl₂ (3 mL) was added BCl₃ (25.73 mg, 219.92 umol, 0.5 mL) at −60° C. The mixture was stirred at −60° C. for 0.5 h. LCMS showed the product was formed. The mixture was poured into water (20 mL) and extracted with EtOAc (2×20 mL). The combined organic layer was washed successively with brine (50 mL) and water (50 mL). The organic layer was dried over Na₂SO₄ and concentrated in vacuum. The residue was purified by Prep-HPLC (Xbridge 5 u C18 150×19 mm, MeCN—H₂O (0.1% FA), Gradient: 35-45%) to give N-[[1-[[2-[2,6-dichloro-4-[3,5-dioxo-6-(trifluoromethyl)-1,2,4-triazin-2-yl] phenoxy]-5-hydroxy-4-pyridyl] sulfonylamino] cyclopropyl] methyl] cyclopropanecarboxamide 101 (5.0 mg, 18% yield) as a yellow solid. LCMS: [M+H]⁺=632.9/635.0. ¹H NR (400 MHz, CD₃OD) δ 7.77 (s, 2H), 7.76 (s, 1H), 7.39 (s, 1H), 6.71 (t, J=53.2 Hz, 1H), 3.31 (s, 2H), 1.59-1.56 (i, 1H), 0.83-0.80 (m, 2H), 0.76-0.71 (m, 6H). ¹⁹F NMR (376 MHz, CD₃OD) δ−124.2 (s, 2F).

The compounds of Formula (I') or (I) in Table 17 below were made according to Example 48 of Compound 101.

TABLE 17

| Cmpd No. | LC-MS, ¹H and ¹⁹F-NMR data |
|---|---|
| 103 | LCMS: [M + H]⁺ = 580.0/582.0. ¹H NMR (400 MHZ, CD₃OD) δ 7.78 (s, 1H), 7.77 (s, 2H), 7.41 (s, 1H), 6.71 (t, J = 52.8 Hz, 1H), 3.19 (s, 2H), 3.01 (s,3H), 0.94 (m, 2H), 0.70 (m, 2H). ¹⁹F NMR (376 MHz, CD₃OD) δ −124.2 (s, 2F). |
| 104 | LCMS: [M + H]⁺ = 565.9/567.9. ¹H NMR (400 MHZ, CD₃OD) δ 7.78 (s, 1H), 7.77 (s, 2H), 7.40 (s, 1H), 6.70 (t, J = 53.2 Hz, 1H), 4.08-4.02 (m, 1H), 3.86 (m, 1H), 3.78-3.70 (m, 2H), 3.57 (m 1H), 2.14-2.05 (m, 1H), 1.87-1.80 (m, 1H). ¹⁹F NMR (376 MHZ, CD₃OD) δ −124.1 (s, 2F). |
| 105 | LCMS: [M + H]⁺ = 585.9. ¹H NMR (400 MHZ, CD₃OD) δ 7.78 (s, 1H), 7.77 (s, 2H), 7.39 (s, 1H), 6.70 (t, J = 52.8 Hz, 1H), 3.87-3.83 (m, 1H), 2.80-2.71 (m, 2H), 2.64-2.48 (m, 2H). ¹⁹F NMR (376 MHZ, CD₃OD) δ-85.6 (d, J = 200.3 Hz, 1F), −101.8 (d, J = 200.3 Hz, 1F), −124.2 (s, 2F). |
| 106 | LCMS: [M + H]⁺ = 565.8/567.8. ¹H NMR (400 MHZ, CD₃OD) δ 7.79 (s, 1H), 7.77 (s, 2H), 7.41 (s, 1H), 6.70 (t, J = 53.2 Hz, 1H), 4.07-4.04 (m, 1H), 3.86 (m, 1H), 3.78-3.70 (m, 2H), 3.57 (m, 1H), 2.12-2.07 (m, 1H), 1.85-1.82 (m, 1H). ¹⁹F NMR (376 MHz, CD₃OD) δ −124.2 (s, 2F). |
| 107 | LCMS: [M + H]⁺ = 552.0/553.9. ¹H NMR (400 MHZ, CD₃OD) δ 7.83 (s, 1H), 7.77 (s, 2H), 7.33 (s, 1H), 6.69 (t, J = 53.2 Hz, 1H), 4.52-4.46 (m, 1H), 4.18 (m, 2H), 3.85 (m, 2H). ¹⁹F NMR (376 MHZ, CD₃OD) δ −124.0 (s, 2F). |

TABLE 17-continued

| Cmpd No. | LC-MS, $^1$H and $^{19}$F-NMR data |
|---|---|
| 108 | LCMS: [M + H]$^+$ = 566.0/568.0. $^1$H NMR (400 MHZ, CD$_3$OD) δ 7.80 (s, 1H), 7.77 (s, 2H), 7.41 (s, 1H), 6.71 (t, J = 52.8 Hz, 1H), 4.39-4.37 (m, 1H), 3.61-3.54 (m, 4H), 2.03-1.96 (m, 1H), 1.90-1.86 (m, 1H). $^{19}$F NMR (376 MHz, CD$_3$OD) δ -124.2 (s, 2F). |
| 109 | LCMS: [M + H]$^+$ = 572.0/574.0. $^1$H NMR (400 MHZ, CD$_3$OD) δ 7.85 (s, 1H), 7.77 (s, 2H), 7.42 (s, 1H), 6.71 (t, J = 52.8 Hz, 1H), 4.52-4.46 (t, J = 12 Hz , 4H). $^{19}$F NMR (376 MHZ, CD$_3$OD) δ -124.23 (s, 2F), -102.01 (s, 2F). |
| 110 | LCMS: [M + H]$^+$ = 538.1. $^1$H NMR (400 MHZ, CD$_3$OD) δ 7.77 (s, 1H), 7.77 (s, 2H), 7.39 (s, 1H), 6.70 (t, J = 52.8 Hz, 1H), 3.62-3.48 (m, 1H), 1.11 (d, J = 6.8 Hz, 6H). $^{19}$F NMR (376 MHZ, CD$_3$OD) δ -124.19 (s, 2F). |
| 111 | LCMS: [M + H]$^+$ = 560.1/562.0. $^1$H NMR (400 MHZ, DMSO-d$_6$) δ 7.89 (s, 1H), 7.78 (s, 2H), 7.36 (s, 1H), 6.89 (t, J = 52.4 Hz, 1H), 6.01 (tt, J = 55.2, 3.6 Hz, 1H), 3.49 (td, J = 15.6, 3.6 Hz, 2H). $^{19}$F NMR (376 MHz, DMSO-d$_6$) δ -122.09 (s, 2F), -122.20 (s, 2F). |
| 112 | LCMS: [M + H]$^+$ = 526.0. $^1$H NMR (400 MHZ, DMSO-d6) δ 7.88 (s, 1H), 7.78 (s, 2H), 7.34 (s, 1H), 6.88 (t, J = 52.4 Hz, 1H), 3.01-2.90 (m, 2H), 1.01 (t, J = 7.2 Hz, 3H). $^{19}$F NMR (376.5 MHz, DMSO-d6) δ -122.06 (s, 2F) |
| 113 | LCMS: [M + H]$^+$ = 524.0/526.0. $^1$H NMR (400 MHZ, DMSO-d$_6$) δ 12.86 (s, 1H), 10.99 (s, 1H), 7.93 (s, 1H), 7.79 (s, 2H), 7.37 (s, 1H), 6.91 (t, J = 52.4 Hz, 1H), 2.84 (s, 6H). $^{19}$F NMR (376 MHZ, DMSO-d$_6$) δ -122.16 (s, 2F). |
| 114 | LCMS: [M + H]$^+$ = 511.0. $^1$H NMR (400 MHZ, CD$_3$OD) δ 7.80 (s, 1H), 7.74 (s, 2H), 7.42 (s, 1H), 2.33-2.27 (m, 1H), 0.58-0.57 (m, 4H). |

Example 49: Synthesis of Compound 115

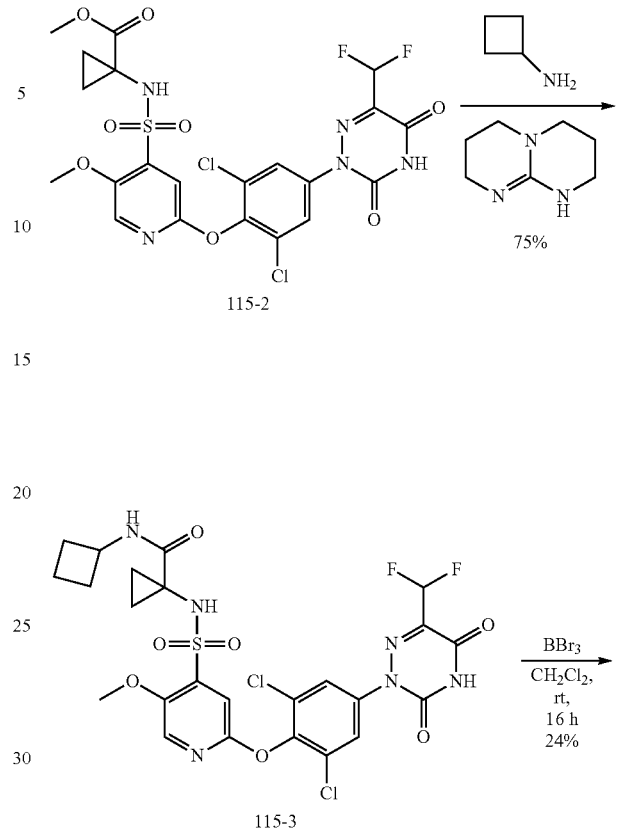

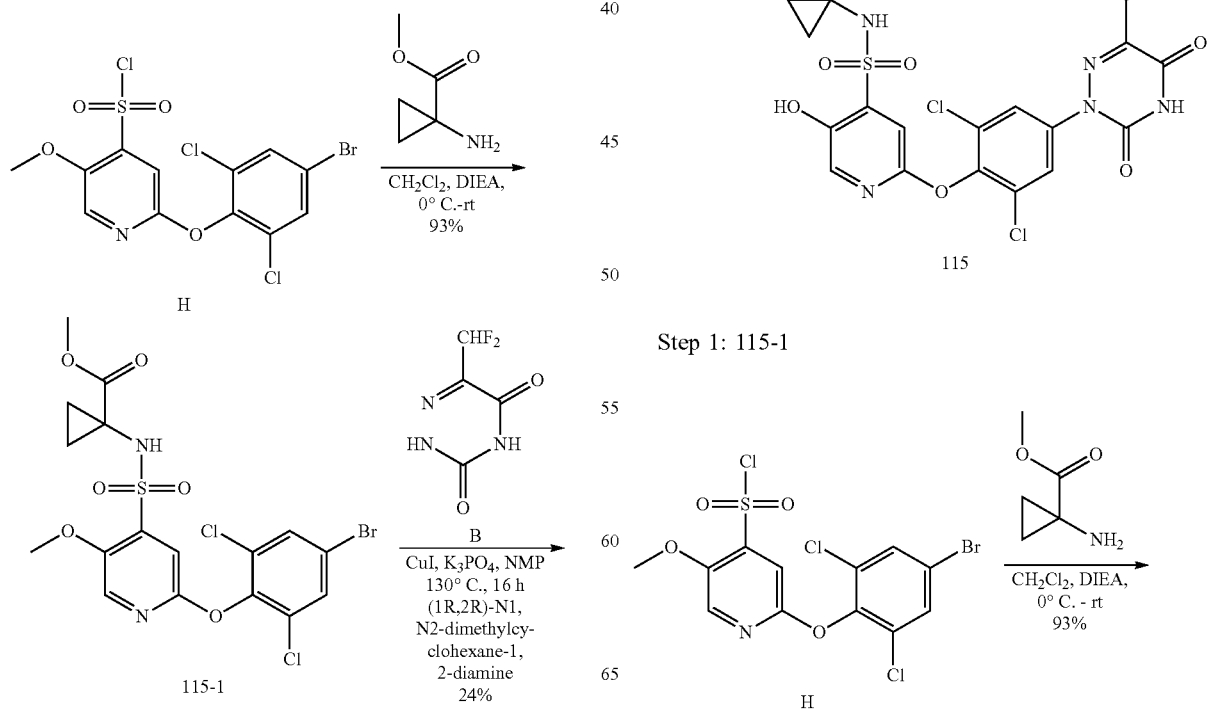

Step 1: 115-1

-continued

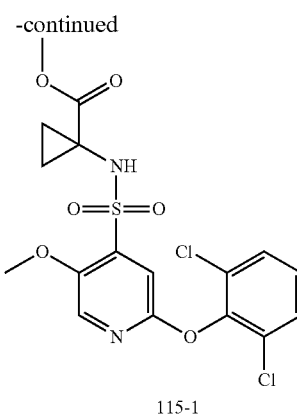

115-1

To a solution of methyl 1-aminocyclopropanecarboxylate hydrochloride (162.59 mg, 1.07 mmol) in $CH_2Cl_2$ (10 mL) were added DIPEA (277.25 mg, 2.15 mmol) and 2-(4-bromo-2,6-dichloro-phenoxy)-5-methoxy-pyridine-4-sulfonyl chloride H (400 mg, 715.06 umol) at 0° C. The mixture was stirred at rt under $N_2$ (g) for 1 h. LC-MS showed the reaction was completed. The reaction mixture was poured into water (30 mL) and extracted with $CH_2Cl_2$ (3×30 mL). The combined organic layer was washed with brine (3×20 mL), dried over anhydrous $Na_2SO_4$ and filtered. The filtrate was concentrated in vacuum to afford a residue. The residue was purified by silica gel chromatography (PE:EtOAc=2:1) to afford methyl 1-[[2-(4-bromo-2,6-dichloro-phenoxy)-5-methoxy-4-pyridyl]sulfonylamino]cyclopropanecarboxylate 115-1 (350 mg, 93% yield) as a white solid. LCMS: $[M+H]^+=524.9$ Step 2: 115-2

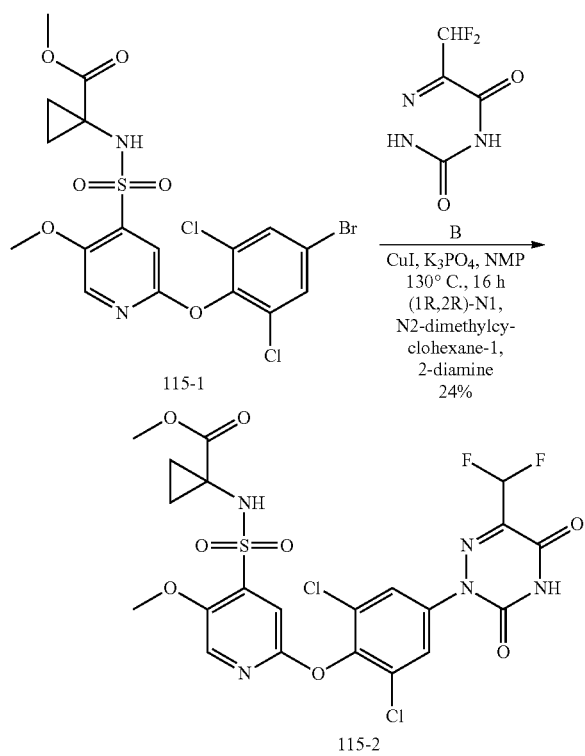

To a mixture of methyl 1-[[2-(4-bromo-2,6-dichloro-phenoxy)-5-methoxy-4-pyridyl]sulfonylamino]cyclopropanecarboxylate 115-1 (350 mg, 665.17 umol) and 6-(difluoromethyl)-2H-1,2,4-triazine-3,5-dione B (216.95 mg, 1.33 mmol) in NMP (6 mL) were added (1R,2R)—N1,N2-dimethylcyclohexane-1,2-diamine (66.23 mg, 465.62 umol), CuI (253.36 mg, 1.33 mmol) and $K_3PO_4$ (423.58 mg, 2.00 mmol). The mixture was stirred at 130° C. for 16 h. LC-MS showed product was formed. The reaction mixture was diluted with EtOAc (50 mL), washed with aq. $NH_4Cl$ (3×20 mL) and brine (3×20 mL), dried over anhydrous $Na_2SO_4$ and filtered. The filtrate was concentrated in vacuum to afford a residue. The residue was purified by flash column chromatography ($CH_2Cl_2$:$CH_3OH$=10:1) to afford methyl 1-[[2-[2,6-dichloro-4-[6-(difluoromethyl)-3,5-dioxo-1,2,4-triazin-2-yl] phenoxy]-5-methoxy-4-pyridyl] sulfonylamino] cyclopropanecarboxylate 115-2 (100 mg, 24% yield) as a yellow oil. LCMS: $[M+H]^+=608.0$ Step 3: 115-3

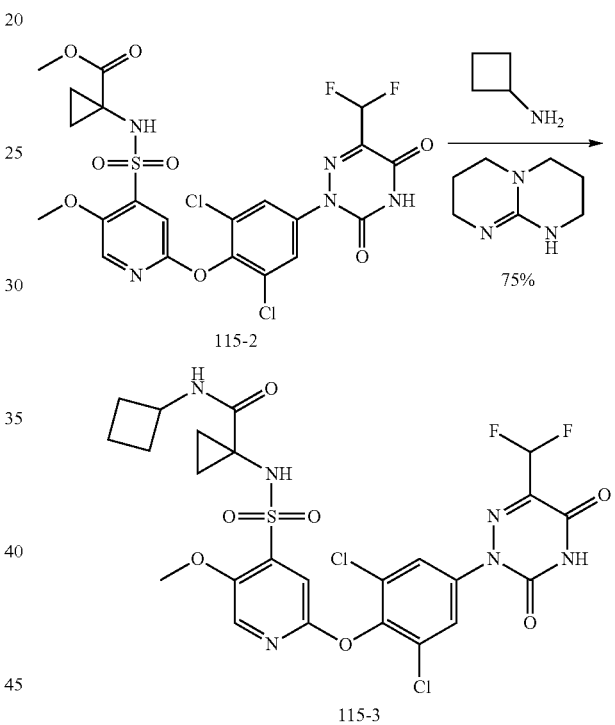

To a solution of methyl 1-[[2-[2,6-dichloro-4-[6-(difluoromethyl)-3,5-dioxo-1,2,4-triazin-2-yl]phenoxy]-5-methoxy-4-pyridyl]sulfonylamino]cyclopropanecarboxylate 115-2 (50 mg, 82.19 umol) in THF (0.5 mL) were added cyclobutanamine (29.23 mg, 410.94 umol) and 3,4,6,7,8,9-hexahydro-2H-pyrimido[1,2-a]pyrimidine (34.32 mg, 246.57 umol). The mixture was stirred at 70° C. under $N_2$ (g) for 16 h. LC-MS showed the reaction was completed. The reaction mixture was poured into water (20 mL) and extracted with EtOAc (3×20 mL). The combined organic layer was washed with brine (3×10 mL), dried over anhydrous $Na_2SO_4$ and filtered. The filtrate was concentrated in vacuum to afford a residue. The residue was crude N-cyclobutyl-1-[[2-[2,6-dichloro-4-[6-(difluoromethyl)-3,5-dioxo-1,2,4-triazin-2-yl] phenoxy]-5-methoxy-4-pyridyl] sulfonylamino] cyclopropanecarboxamide 115-3 (40 mg, 75% yield). It's a yellow oil and used in the next step directly without further purification. LCMS: $[M+H]^+=647.0$ Step 4: 115

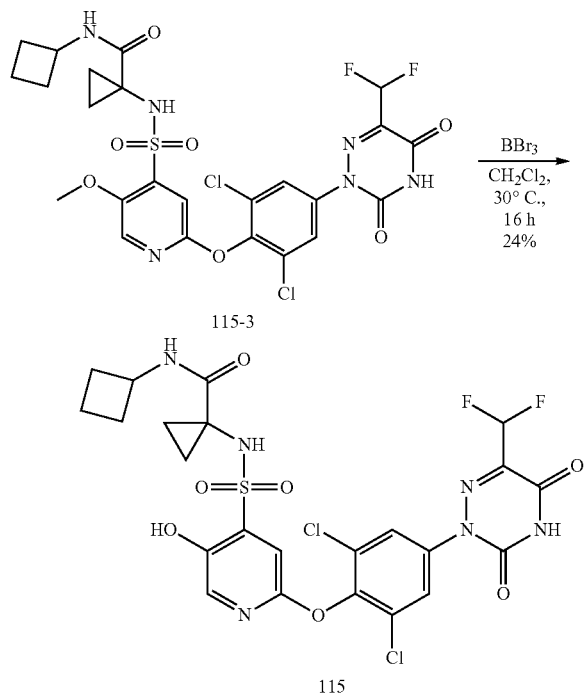

To a solution of N-cyclobutyl-1-[[2-[2,6-dichloro-4-[6-(difluoromethyl)-3,5-dioxo-1,2,4-triazin-2-yl]phenoxy]-5-methoxy-4-pyridyl]sulfonylamino]cyclopropanecarboxamide 115-3 (30 mg, 46.34 umol) in CH₂Cl₂ (2.5 mL) was added BBr₃ (1.06 g, 4.23 mmol, 0.4 mL). The mixture was stirred at 30° C. for 16 h. LC-MS showed the reaction was completed. The reaction mixture was poured into saturated NaHCO₃ (20 mL) and extracted with EtOAc (3×10 mL). The combined organic layer was washed with brine (10 mL), dried over anhydrous Na₂SO₄ and filtered. The filtrate was concentrated in vacuum to afford a residue. The residue was purified by Prep-HPLC (Xbridge 5 u C18 150×19 mm, MeCN—H₂O (0.1% FA), Gradient: 38-48%, 20 ml/min) to afford N-cyclobutyl-1-[[2-[2,6-dichloro-4-[6-(difluoromethyl)-3,5-dioxo-1,2,4-triazin-2-yl]phenoxy]-5-hydroxy-4-pyridyl]sulfonylamino]cyclopropanecarboxamide 115 (7.2 mg, 24% yield) as a white solid. LCMS: [M+H]⁺=633.0. ¹H NMR (400 MHz, CD₃OD) δ 7.81 (s, 1H), 7.77 (s, 2H), 7.40 (s, 1H), 6.71 (t, J=52.8 Hz, 1H), 4.22-4.16 (m, 1H), 2.27-2.20 (m, 2H), 1.93-1.85 (m, 2H), 1.75-1.67 (m, 2H), 1.35-1.30 (m, 2H), 1.16-1.08 (m, 2H). ¹⁹F NMR (376.5 MHz, CD₃OD) δ−124.2 (s, 2F).

The compounds of Formula (I') or (I) in Table 18 below were made according to Example 49 of Compound 115.

TABLE 18

| Cmpd No. | LC-MS, ¹H and ¹⁹F-NMR data |
|---|---|
| 116 | LCMS: [M + H]⁺ = 647.0. ¹H NMR (400 MHZ, CD₃OD) δ 7.80 (s, 1H), 7.77 (s, 2H), 7.40 (s, 1H), 6.71 (t, J = 52.8 Hz, 1H), 4.06-3.99 (m, 1H), 1.93-1.84 (m, 2H), 1.76-1.67 (m, 2H), 1.64-1.53 (m, 2H), 1.41-1.31 (m, 4H), 1.15-1.08 (m, 2H). ¹⁹F NMR (376.5 MHZ, CD₃OD) δ -124.2 (s, 2F). |
| 117 | LCMS: [M + H]⁺ = 644.9. ¹H NMR (400 MHZ, CD₃OD) δ 7.79 (s, 1H), 7.77 (s, 2H), 7.37 (s, 1H), 6.70 (t, J = 52.8 Hz, 1H), 5.85 (tt, J = 4.0,56.0 Hz, 1H), 3.56 (m, 2H), 1.37-1.32 (m, 2H), 1.10-1.03 (m, 2H). ¹⁹F NMR (376.5 MHz, CD₃OD) δ -124.17 (s, 2F), -124.24 (s, 2F). |
| 118 | LCMS: [M + H]⁺ = 633.0. ¹H NMR (400 MHZ, CD₃OD) δ 7.77 (s, 2H), 7.76 (s, 1H), 7.40 (s, 1H), 6.71 (t, J = 52.0 Hz, 1H), 3.76-3.73 (m, 2H), 3.16-3.12 (m, 2H), 1.94-1.88 (m, 2H), 1.79-1.73 (m, 2H), 1.20-1.17 (m, 2H), 1.03-1.00 (m, 2H). ¹⁹F NMR (376 MHz, CD₃OD) δ -124.2 (s, 2F). |
| 121 | LCMS: [M + H]⁺ = 633.0. ¹H NMR (400 MHZ, CD₃OD) 7.76 (s, 2H), 7.73 (s, 1H), 7.22 (s, 1H), 6.68 (t, J = 53.2 Hz, 1H), 2.55-2.50 (m, 1H), 2.48-2.39 (m, 2H), 2.26-2.16 (m, 2H), 1.85-1.78 (m, 2H), 0.71-0.66 (m, 2H), 0.50-0.46 (m, 2H). ¹⁹F NMR (376 MHz, CD₃OD) δ -123.90 (s, 2F). |

Example 50: Synthesis of Compound 119

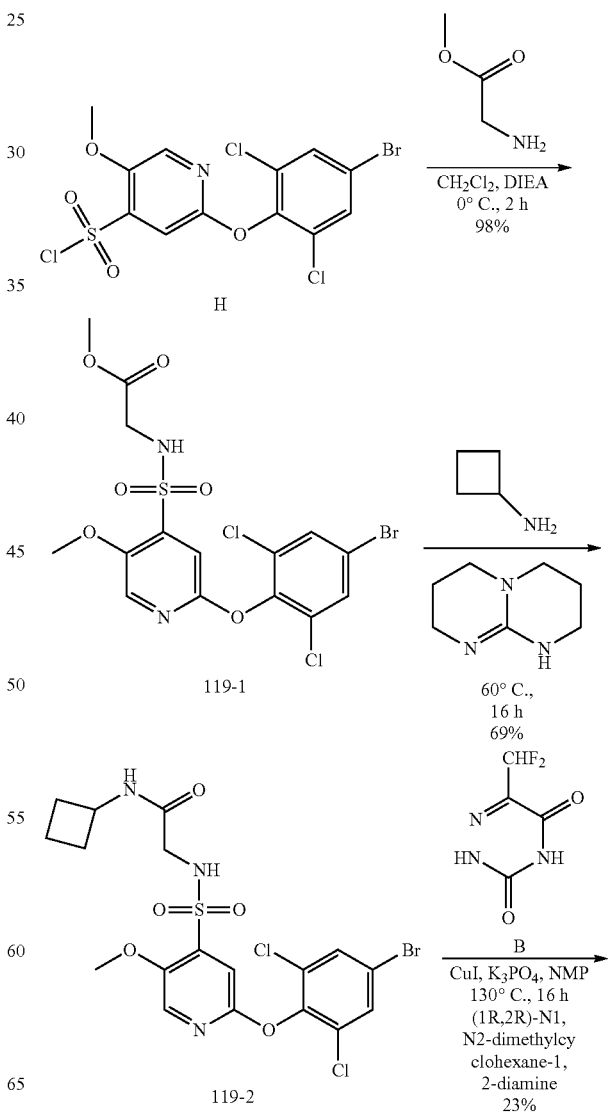

-continued

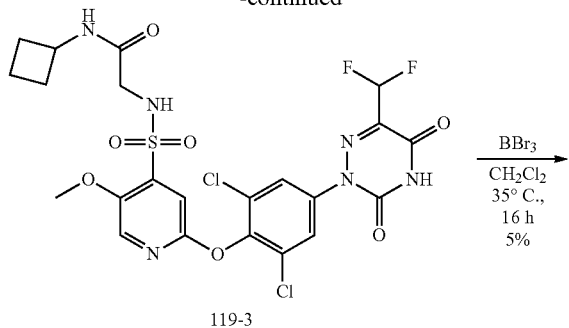

119-3

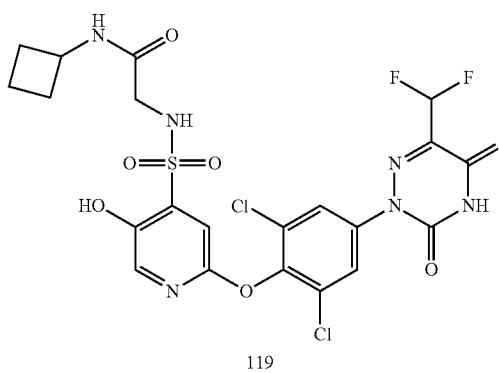

119

Step 1: 119-1

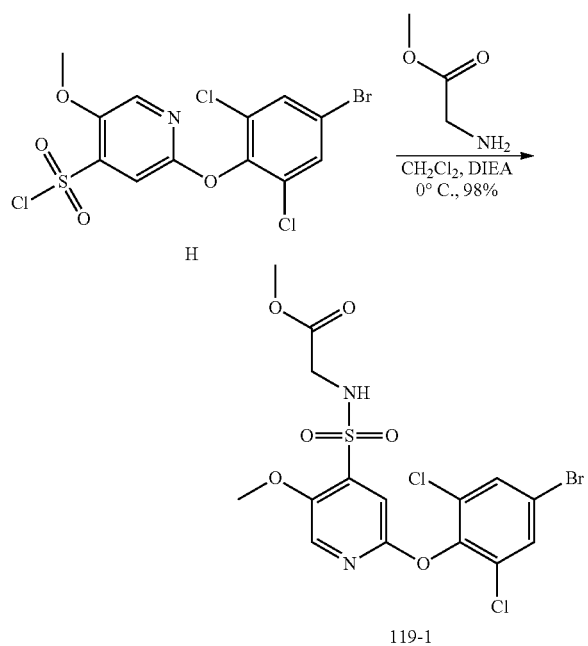

To a mixture of methyl 2-aminoacetate (248.85 mg, 2.79 mmol) in CH$_2$Cl$_2$ (5 mL) was added DIEA (433.19 mg, 3.35 mmol) and 2-(4-bromo-2,6-dichloro-phenoxy)-5-methoxy-pyridine-4-sulfonyl chloride H (500 mg, 1.12 mmol). The mixture was stirred at 0° C. for 2 h. LCMS showed the starting material was consumed and the product was found. Water was added into the reaction. The mixture was extracted with EtOAc (3×10 mL). The combined organic layer was dried over anhydrous Na$_2$SO$_4$ and concentrated in vacuum to afford methyl 2-[[2-(4-bromo-2,6-dichloro-phenoxy)-5-methoxy-4-pyridyl]-sulfonylamino]-acetate 119-1 (580 mg, 98% yield) which was used in the next step without further purification. LCMS: [M+H]$^+$=498.9/500.9

Step 2: 119-2

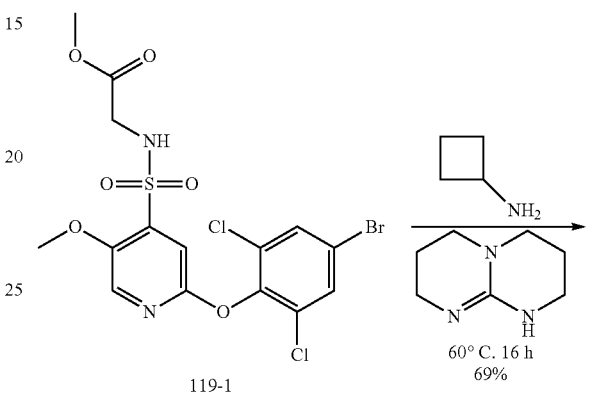

To a mixture of methyl 2-[[2-(4-bromo-2,6-dichloro-phenoxy)-5-methoxy-4-pyridyl]sulfonylamino]acetate 119-1 (200 mg, 399.88 umol) in cyclobutanamine (142.20 mg, 2.00 mmol, 170.71 uL) was added 3,4,6,7,8,9-hexahydro-2H-pyrimido[1,2-a]pyrimidine (111.33 mg, 799.76 umol). The mixture was stirred at 60° C. for 16 h in a steal tube. LCMS showed the starting material was consumed and the product was found. Water was added into the reaction. The mixture was extracted with EtOAc (3×10 mL). The combined organic layer was dried over anhydrous Na$_2$SO$_4$ and concentrated in vacuum to afford a residue. The residue was purified by silica gel chromatography (CH$_2$Cl$_2$:CH$_3$OH=10:1) to afford 2-[[2-(4-bromo-2,6-dichloro-phenoxy)-5-methoxy-4-pyridyl]-sulfonylamino]-N-cyclobutyl-acetamide 119-2 (150 mg, 69% yield) as a light white solid. LCMS: [M+H]$^+$=537.9/539.9

Step 3: 119-3

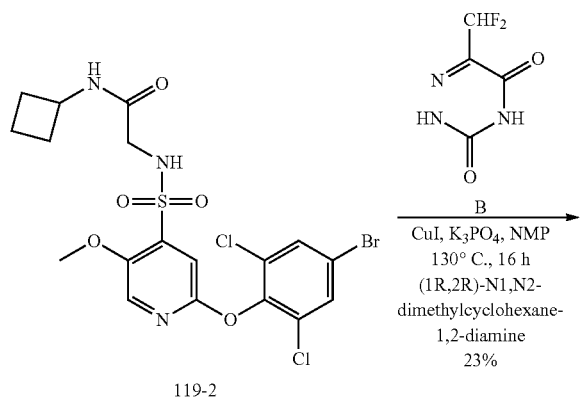

Step 4: 119

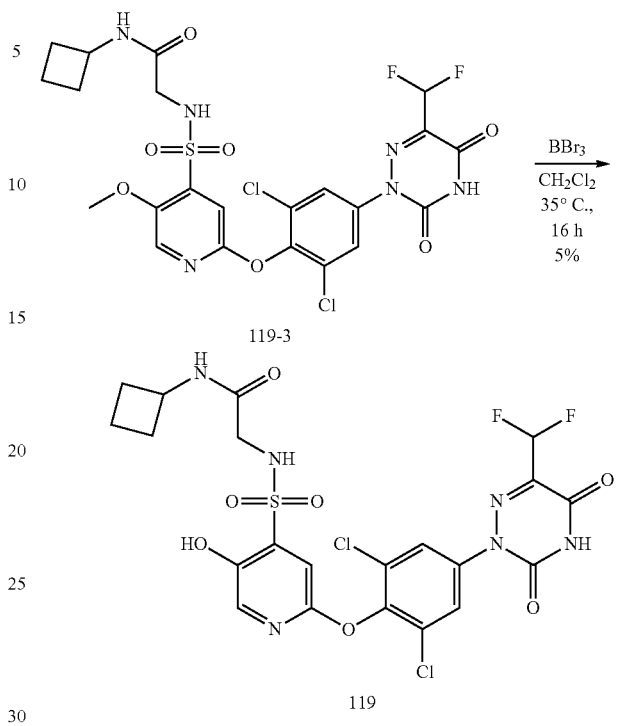

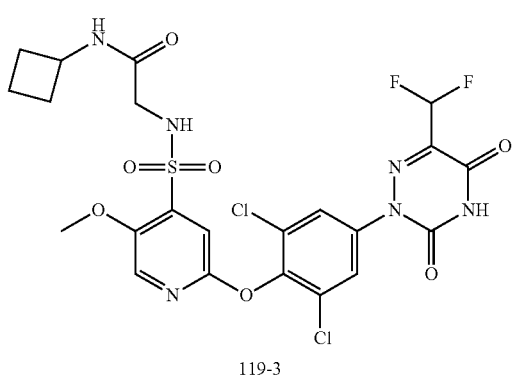

To a mixture of 2-[[2-(4-bromo-2,6-dichloro-phenoxy)-5-methoxy-4-pyridyl]sulfonylamino]-N-cyclobutyl-acetamide 119-2 (150 mg, 278.18 umol) in NMP (2 mL) was added 6-(difluoromethyl)-2H-1,2,4-triazine-3,5-dione B (90.73 mg, 556.35 umol), (1R,2R)—N1,N2-dimethylcyclohexane-1,2-diamine (31.65 mg, 222.54 umol, 35.09 uL), CuI (132.45 mg, 695.44 umol) and $K_3PO_4$ (176.92 mg, 834.53 umol). The mixture was stirred at 130° C. for 16 h. LCMS showed the starting material was consumed and the product was found. Water was added into the reaction. The mixture was extracted with EtOAc (3×10 mL). the combined organic layer was dried over anhydrous $Na_2SO_4$ and concentrated in vacuum to afford a residue. The residue was purified by Prep-TLC ($CH_2Cl_2$:$CH_3OH$=10:1) to afford N-cyclobutyl-2-[[2-[2,6-dichloro-4-[6-(difluoromethyl)-3,5-dioxo-1,2,4-triazin-2-yl]-phenoxy]-5-methoxy-4-pyridyl]-sulfonylamino]-acetamide 119-3 (40 mg, 23% yield) as a yellow solid. LCMS: [M+H]$^+$=621.0/623.0

To a mixture of N-cyclobutyl-2-[[2-[2,6-dichloro-4-[6-(difluoromethyl)-3,5-dioxo-1,2,4-triazin-2-yl]phenoxy]-5-methoxy-4-pyridyl]sulfonylamino]acetamide 119-3 (40 mg, 64.37 umol) in $CH_2Cl_2$ (2 mL) was added $BBr_3$ (161.26 mg, 643.71 umol) at 0° C. and the mixture was stirred at 35° C. for 16 h in a steal tube. LCMS showed the starting material was consumed and the product was found. The reaction mixture was poured into saturated aqueous $NaHCO_3$ (5 mL) and extracted with EtOAc (3×5 mL). The combined organic layer was washed with brine (5 mL), dried over anhydrous $Na_2SO_4$ and filtered. The filtrate was concentrated in vacuum to afford a residue. The residue was purified by Prep-HPLC (Kromasil-C18 100×21.2 mm 5 um, MeCN—$H_2O$ (0.1% TFA), Gradient: 45-555%) to give N-cyclobutyl-2-[[2-[2,6-dichloro-4-[6-(difluoromethyl)-3,5-dioxo-1,2,4-triazin-2-yl]-phenoxy]-5-hydroxy-4-pyridyl]-sulfonylamino]-acetamide 119 (2.2 mg, 5% yield) as a light white solid. LCMS: [M+H]$^+$=607.0/608.9. $^1$H NMR (400 MHz, $CD_3OD$) δ 7.78 (s, 1H), 7.76 (s, 2H), 7.40 (s, 1H), 6.71 (t, J=52.8 Hz, 1H), 4.23-4.18 (m, 1H), 3.70 (s, 2H), 2.19-2.23 (m, 2H), 1.95-1.88 (m, 2H), 1.74-1.69 (m, 2H). $^{19}$F NMR (376 MHz, $CD_3OD$) δ−124.5 (s, 2F).

The compounds of Formula (I') or (I) in Table 19 below were made according to Example 50 of Compound 119.

TABLE 19

| Cmpd No. | LC-MS, $^1$H and $^{19}$F-NMR data |
|---|---|
| 120 | LCMS: [M + H]$^+$ = 593.0. $^1$H NMR (400 MHZ, $CD_3OD$) δ 7.78 (s, 3H), 7.39 (s, 1H), 6.71 (t, J = 52.8, 1H), 3.72 (s, 2H), 2.57-2.62 (m, 1H), 0.68-0.73 (m, 2H), 0.55-0.41 (m, 2H). $^{19}$F NMR (376 MHz, $CD_3OD$) δ −124.1(s, 2F). |

Example 51: Synthesis of Compound 122

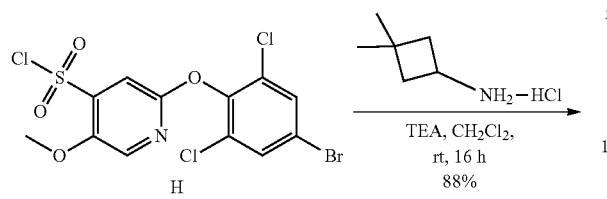

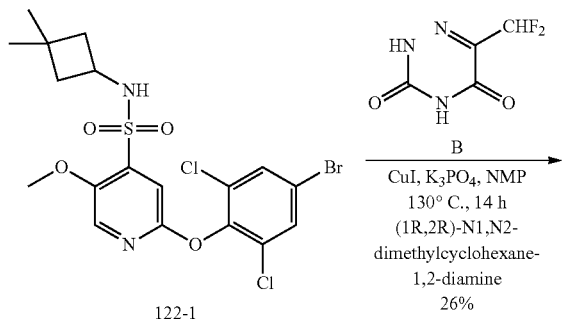

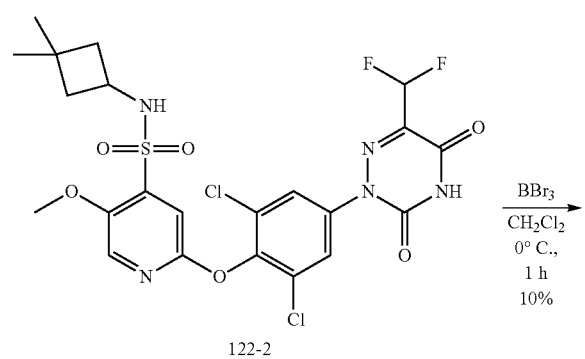

Step 1: 122-1

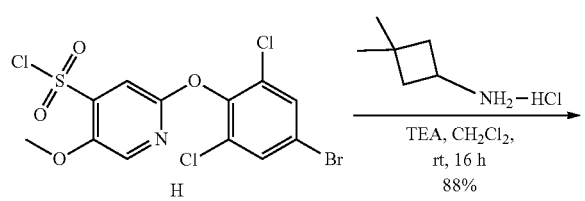

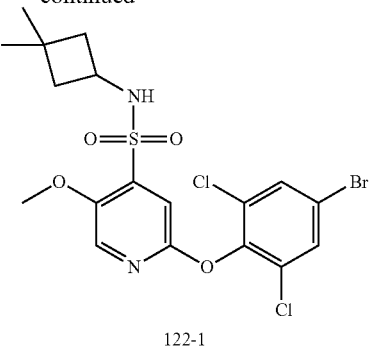

122-1

To a mixture of 3,3-dimethylcyclobutanamine (44.32 mg, 446.91 umol) and TEA (226 mg, 2.23 mmol) in CH$_2$Cl$_2$ (5 mL), was added 2-(2,6-dichloro-4-nitro-phenoxy)-5-methoxy-pyridine-4-sulfonyl chloride H (0.1 g, 223.46 umol). The reaction mixture was stirred at rt for 16 h. LC-MS showed the reaction was completed. The reaction mixture was poured into water (50 mL) and extracted with EtOAc (3×20 mL). The combined organic layer was washed with brine (20 mL), dried over anhydrous Na$_2$SO$_4$ and filtered. The filtrate was concentrated in vacuum. The residue was purified by silica gel chromatography (PE: EtOAc=2:1) to afford 2-(4-bromo-2,6-dichloro-phenoxy)-N-(3,3-dimethylcyclobutyl)-5-methoxy-pyridine-4-sulfonamide 122-1 (100 mg, 88% yield) as a white solid. LCMS: [M+H]$^+$=509.0/511.0.

Step 2: 122-2

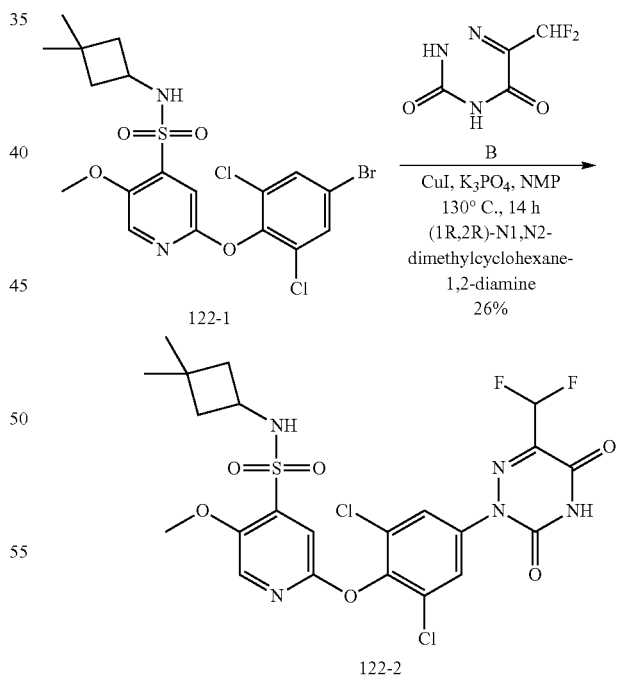

A mixture of 2-(4-bromo-2,6-dichloro-phenoxy)-N-(3,3-dimethylcyclobutyl)-5-methoxy-pyridine-4-sulfonamide 122-1 (0.1 g, 195.99 umol), 6-(difluoromethyl)-2H-1,2,4-triazine-3,5-dione B (63.93 mg, 391.98 umol), (1R,2R)—N1,N2-dimethylcyclohexane-1,2-diamine (22.30 mg, 156.79 umol), K$_3$PO$_4$ (124.81 mg, 587.97 umol) and iodocopper (93.32 mg, 489.98 umol) in NMP (4 mL) was stirred at 130° C. for 14 h. LC-MS showed the reaction was completed. The reaction mixture was poured into sat. NH$_4$Cl (50 mL) and extracted with EtOAc (3×20 mL). The combined organic layer was washed with brine (2×20 mL), dried over anhydrous Na$_2$SO$_4$ and filtered. The filtrate was concentrated in vacuum. The residue was purified by Prep-TLC (CH$_2$Cl$_2$:MeOH=10:1) to afford 2-[2,6-dichloro-4-[6-(difluoromethyl)-3,5-dioxo-1,2,4-triazin-2-yl] phenoxy]-N-(3,3-dimethylcyclobutyl)-5-methoxy-pyridine-4-sulfonamide 122-2 (30 mg, 26% yield) as a yellow solid. LCMS: [M+H]$^+$=592.0594.0.

Step 3: 122

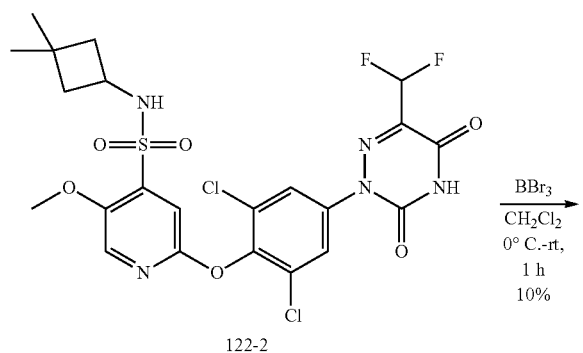

To a solution of 2-[2,6-dichloro-4-[6-(difluoromethyl)-3,5-dioxo-1,2,4-triazin-2-yl] phenoxy]-N-(3,3-dimethylcyclobutyl)-5-methoxy-pyridine-4-sulfonamide 122-2 (30 mg, 50.64 umol) in CH$_2$Cl$_2$ (3 mL) was added BBr$_3$ (1 mL) at 0° C. The mixture was stirred at rt for 1 h. LC-MS showed the reaction was completed. The reaction mixture was concentrated in vacuum. The residue was purified by C18 chromatography (MeCN:H$_2$O=1:9-1:1) to give 2-[2,6-dichloro-4-[6-(difluoromethyl)-3,5-dioxo-1,2,4-triazin-2-yl] phenoxy]-5-hydroxy-N-methyl-pyridine-4-sulfonamide 122 (3.0 mg, 10% yield) as a white solid. LCMS: [M+H]$^+$=578.0. $^1$H NMR (400 MHz, CD$_3$OD) δ 7.77 (s, 3H), 7.36 (s, 1H), 6.71 (t, J=52.8 Hz, 1H), 3.88-3.79 (m, 1H), 1.95-1.88 (m, 2H), 1.78-1.69 (m, 2H), 1.06 (s, 3H), 1.05 (s, 3H). $^{19}$F NMR (376 MHz, CD$_3$OD) δ −124.2 (s, 2F).

The compounds of Formula (I') or (I) in Table 20 below were made according to Example 51 of Compound 122.

TABLE 20

| Cmpd No. | LC-MS, $^1$H and $^{19}$F-NMR data |
|---|---|
| 123 | LCMS: [M + H]$^+$ = 550.0. $^1$H NMR (400 MHZ, CD$_3$OD) δ 7.77 (s, 3H), 7.37 (s, 1H), 6.71 (t, J = 52.8 Hz, 1H), 3.87-3.82 (m, 1H), 2.10-2.03 (m, 2H), 1.97-1.92 (m, 2H), 1.63-1.56 (m, 2H). $^{19}$F NMR (376 MHz, CD$_3$OD) δ −124.26 (s, 2F). |
| 124 | LCMS: [M + H]$^+$ = 564.0. $^1$H NMR (400 MHZ, CD$_3$OD) δ 7.78 (s, 1H), 7.77 (s, 2H), 7.39 (s, 1H), 6.71 (t, J = 52.8, 1H), 3.63-3.71 (m, 1H), 1.84-1.72 (m, 2H), 1.65-1.68 (m, 2H), 1.44-1.52 (m, 4H). $^{19}$F NMR (376 MHZ, CD$_3$OD) δ −124.2 (s, 2F). |
| 125 | LCMS: [M + H]$^+$ = 575.0. $^1$H NMR (400 MHZ, CD$_3$OD) δ 7.78 (s, 1H), 7.77 (s, 2H), 7.38 (s, 1H), 6.70 (t, J = 52.8 Hz, 1H), 4.02-3.89 (m, 1H), 2.95-2.80 (m, 1H), 2.59-2.53 (m, 2H), 2.34-2.26 (m, 2H). $^{19}$F NMR (376 MHZ, CD$_3$OD) δ −124.2 (s, 2F) |
| 126 | LCMS: [M + H]$^+$ = 565.9. $^1$H NMR (400 MHZ, CD$_3$OD) δ 7.77(s, 3H), 7.32 (s, 1H), 6.70 (t, J = 49.6 Hz, 1H), 4.31-4.25 (m, 1H), 4.07-4.00 (m, 1H), 2.26-2.17 (m, 2H), 2.13-2.05 (m, 2H). $^{19}$F NMR (376 MHz, CD$_3$OD) δ −124.2 (s, 2F). |
| 127 | LCMS: [M + H]$^+$ = 524.0. $^1$H NMR (400 MHZ, DMSO-d$_6$) δ 12.86 (s, 1H), 8.16 (s, 1H), 7.81 (s, 2H), 7.68-7.66 (m, 1H), 7.44 (s, 1H), 6.91 (t, J = 52.4 Hz, 1H), 3.92 (s, 3H), 2.56 (d, J = 4.8 Hz, 3H). $^{19}$F NMR (376 MHZ, DMSO-d$_6$) δ −122.11 (s, 2F). |

Example 52: Synthesis of Compound 128

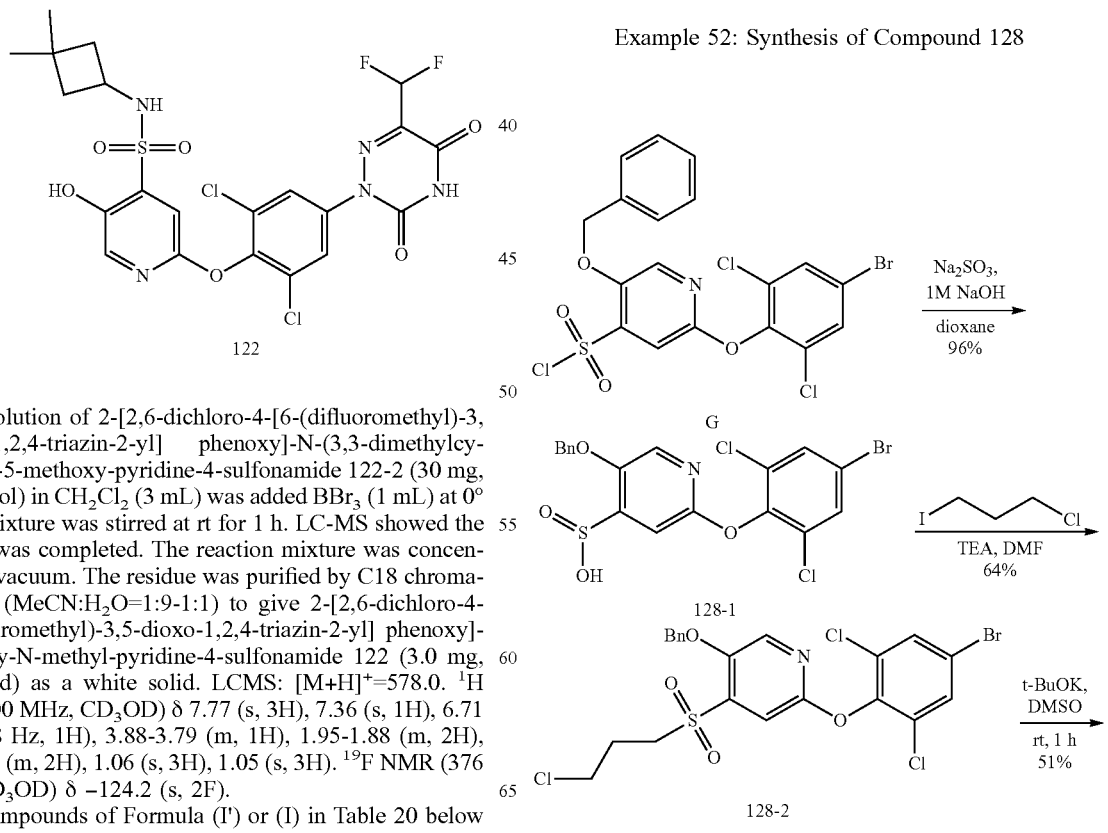

-continued

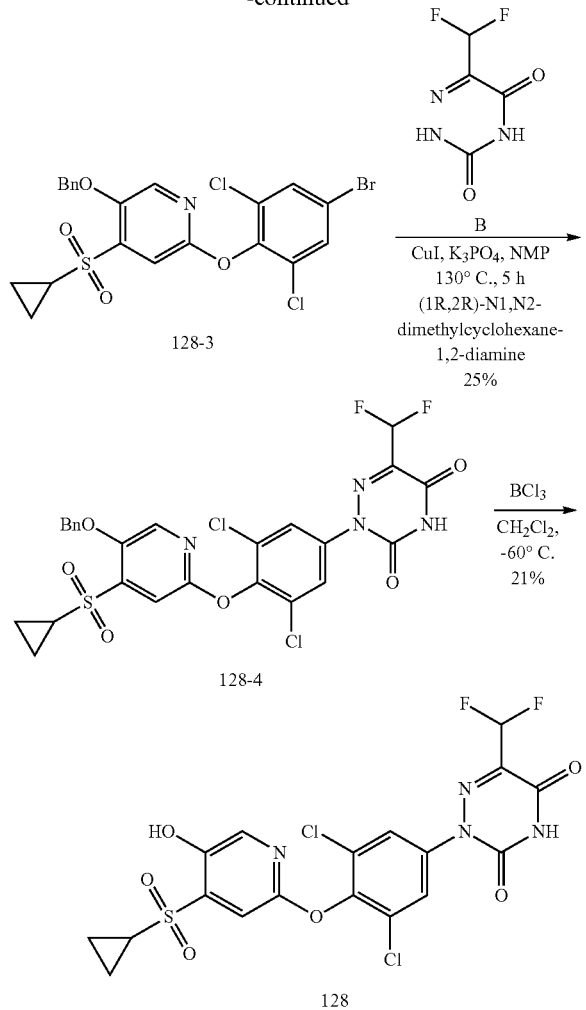

Step 1: 128-1

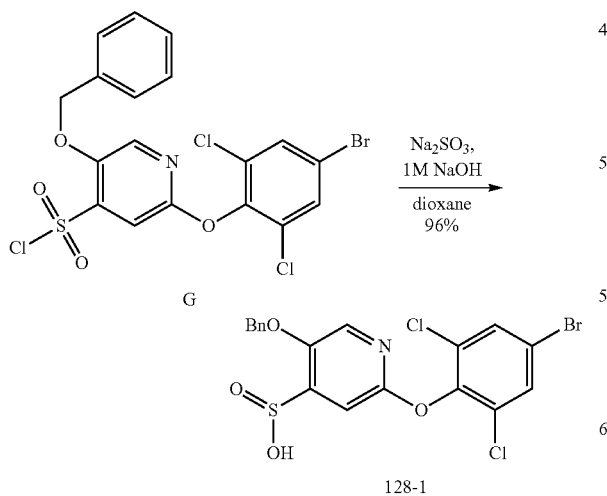

sulfonyl chloride G (2.0 g, 3.82 mmol) in dioxane (10 mL) and the mixture was stirred at rt for 30 min. 1N NaOH (3.82 mmol) was then added dropwise until the reaction mixture was pH=14 and the mixture was then allowed to stirred at rt for 16 h. LCMS showed the reaction was completed. The mixture was cooled to 0° C. and concentrated $H_2SO_4$ was added until the reaction mixture was pH=1. The mixture was extracted with EtOAc (3×50 ml) and the combined organic layers were washed with brine and dried over $Na_2SO_4$ and concentrated in vacuum to afford 5-benzyloxy-2-(4-bromo-2,6-dichloro-phenoxy) pyridine-4-sulfinic acid 128-1 (1.8 g, 96% yield). It's used in the next step without purification. LCMS: $[M+H]^+$=487.9/489.9.

Step 2: 128-2

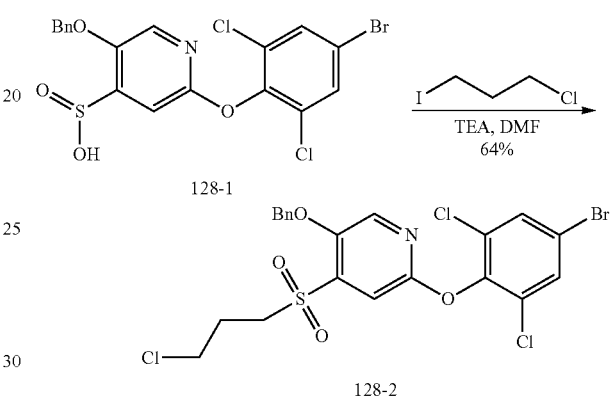

To a solution of 5-benzyloxy-2-(4-bromo-2,6-dichloro-phenoxy) pyridine-4-sulfinic acid 128-1 (700 mg, 1.43 mmol) in DMF (5 mL) was added TEA (188.24 mg, 1.86 mmol, 259.29 uL) and 1-chloro-3-iodo-propane (585.10 mg, 2.86 mmol, 307.95 uL). The mixture was stirred at rt for 15 h. LCMS showed the reaction was completed. The mixture was poured into water (50 mL), extracted with EtOAc (50 ml) and washed with bine (3×50 ml). The organic layer was dried over $Na_2SO_4$ and concentrated in vacuum. The residue was purified by flash chromatography (PE:EtOAc=10:1) to give 5-benzyloxy-2-(4-bromo-2,6-dichloro-phenoxy)-4-(3-chloropropylsulfonyl) pyridine 128-2 (520 mg, 64% yield) as a yellow solid. LCMS: $[M+H]^+$=564.1/566.1/567.9

Step 3: 128-3

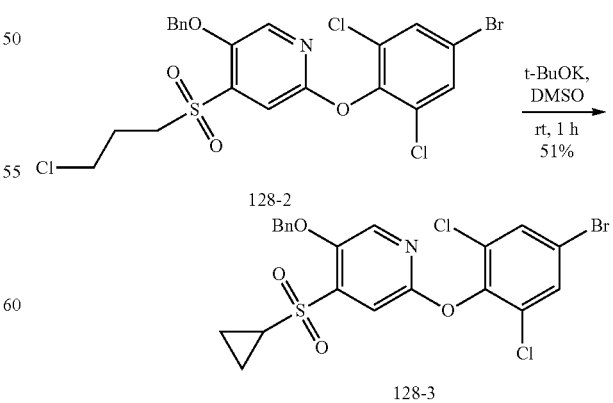

A solution of 5-benzyloxy-2-(4-bromo-2,6-dichloro-phenoxy)-4-(3-chloropropylsulfonyl) pyridine 128-2 (520 mg, To a solution of sodium sulfite (3.61 g, 28.65 mmol, 1.37 mL) in $H_2O$ (20 mL) was added dropwise a solution of 5-benzyloxy-2-(4-bromo-2,6-dichloro-phenoxy) pyridine-4-

919.23 umol) and t-BuOK (205.91 mg, 1.84 mmol) in DMSO (5 mL) was stirred at rt under N₂ for 1 h. LCMS showed the reaction was completed. The reaction mixture was poured into water and extracted with EtOAc (3×50 mL). The combined organic layer was dried over anhydrous Na₂SO₄, filtered and concentrated in vacuum to afford a residue. The residue was purified by silica gel chromatography (PE:EtOAc=3:1) to afford 5-benzyloxy-2-(4-bromo-2,6-dichloro-phenoxy)-4-cyclopropylsulfonyl-pyridine 128-3 (250 mg, 51% yield) as a yellow oil. LCMS: [M+H]⁺=527.9/529.9.

Step 4: 128-4

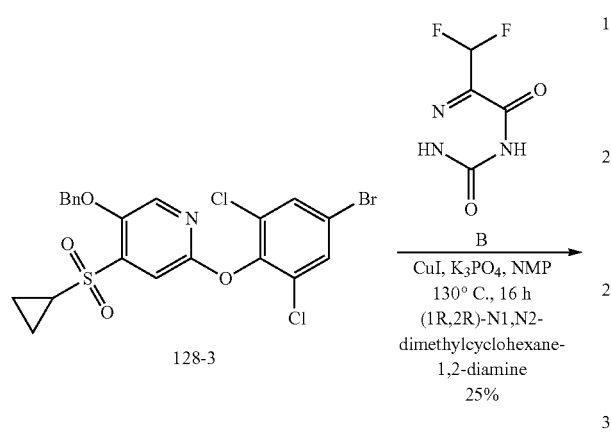

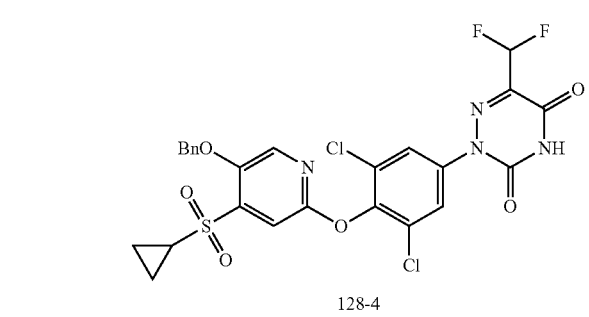

A mixture of 5-benzyloxy-2-(4-bromo-2,6-dichloro-phenoxy)-4-cyclopropylsulfonyl-pyridine 128-3 (100 mg, 188.95 umol), 6-(difluoromethyl)-2H-1,2,4-triazine-3,5-dione B (61.63 mg, 377.91 umol), (1R,2R)—N1,N2-dimethylcyclohexane-1,2-diamine (21.50 mg, 151.16 umol), CuI (89.97 mg, 472.38 umol) and K₃PO₄ (120.17 mg, 566.86 umol) in NMP (3 mL) was stirred in a sealed tube at 130° C. for 16 h. LCMS showed the product was formed. The reaction mixture was added into EtOAc (50 mL) and the mixture was washed with 0.2N HCl (50 mL). The mixture was filtered and the filtrate was extracted with EtOAc (50 mL). The combined organic layers were washed with brine (50 mL), dried over anhydrous Na₂SO₄, filtered and concentrated in vacuum to afford a residue. The residue was purified by column chromatography (CH₂Cl₂:CH₃OH=20:1) to afford 2-[4-[(5-benzyloxy-4-cyclopropylsulfonyl-2-pyridyl)oxy]-3,5-dichloro-phenyl]-6-(difluoromethyl)-1,2,4-triazine-3,5-dione 128-4 (30 mg, 25% yield) as a yellow solid. LCMS: [M+H]⁺=611.1

Step 5: 128

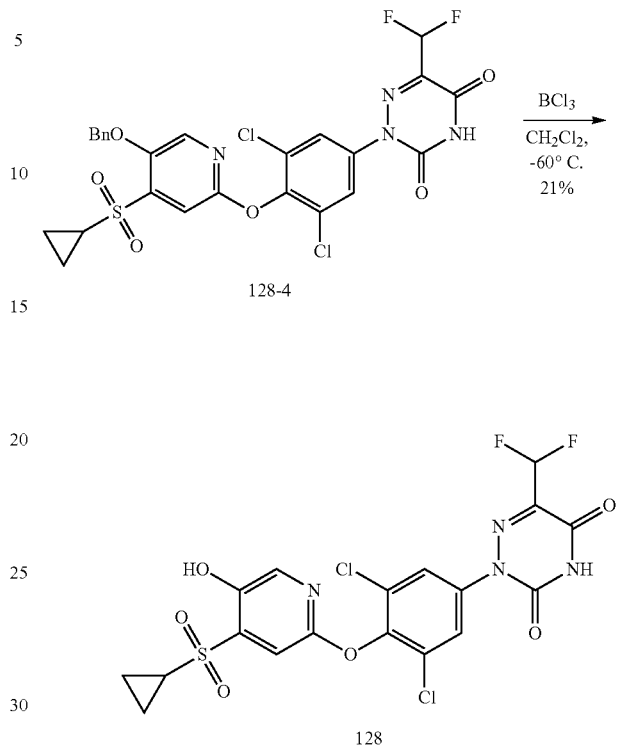

To a solution of 2-[4-[(5-benzyloxy-4-cyclopropylsulfonyl-2-pyridyl)oxy]-3,5-dichloro-phenyl]-6-(difluoromethyl)-1,2,4-triazine-3,5-dione 128-4 (30 mg, 49.07 umol) in CH₂Cl₂ (3 mL) was added BCl₃ (1M in CH₂Cl₂) (0.5 mL) at −60° C. The mixture was stirred at −60° C. for 1h. LCMS showed the product was formed. The reaction mixture was poured into water and extracted with EtOAc (3×30 mL). The combined organic layer was dried over anhydrous Na₂SO₄, filtered and concentrated in vacuum to afford a residue. The residue was purified by Prep-HPLC (Xbridge 5 u C18 150×19 mm, MeCN—H₂O (0.1% FA), Gradient: 30-60%) to afford 2-[3,5-dichloro-4-[(4-cyclopropylsulfonyl-5-hydroxy-2-pyridyl) oxy] phenyl]-6-(difluoromethyl)-1,2,4-triazine-3,5-dione 128 (5.5 mg, 21% yield) as a white solid. LCMS: [M+H]⁺=520.9/523.1. ¹H NMR (400 MHz, DMSO-d₆) δ 12.86 (s, 1H), 11.35 (s, 1H), 7.98 (s, 1H), 7.79 (s, 2H), 7.36 (s, 1H), 6.91 (t, J=52.4, 1H), 3.21-3.14 (m, 1H), 1.15-1.13 (m, 4H). ¹⁹F NMR (376 MHz, DMSO-d₆) δ−122.13 (s, 2F).

The compounds of Formula (I') or (I) in Table 21 below were made according to Example 52 of Compound 128.

TABLE 21

| Cmpd No. | LC-MS, ¹H and ¹⁹F-NMR data |
| --- | --- |
| 129 | LCMS: [M + H]⁺ = 496.0. ¹H NMR (400 MHZ, CD₃OD) δ 7.83 (s, 1H), 7.74 (s, 2H), 7.38 (s, 1H), 3.18-3.13 (m, 1H), 1.29-1.25 (m, 2H), 1.17-1.10 (m, 2H). |

Example 53: Synthesis of Compound 130

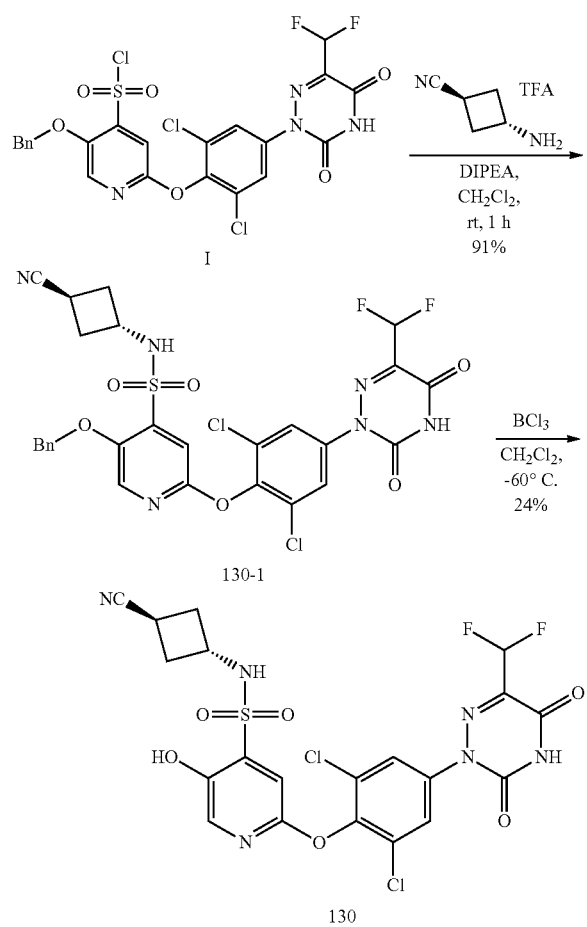

Step 1: 130-1

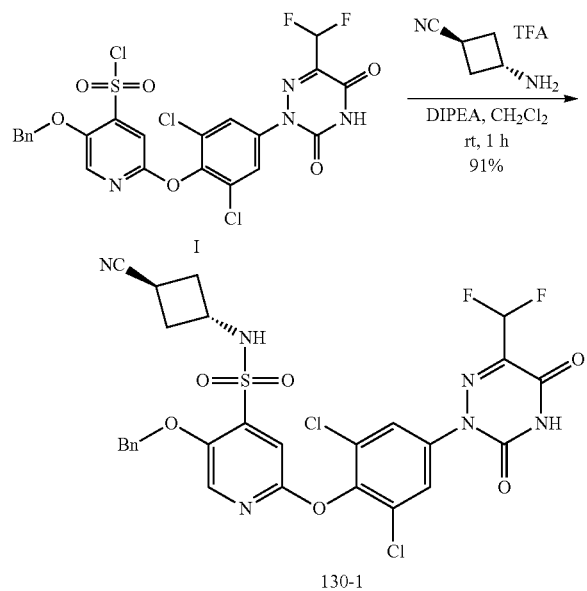

To a solution of (1r,3r)-3-aminocyclobutane-1-carbonitrile trifluoroacetic acid salt (155.36 mg, 742.84 umol) and DIPEA (192.01 mg, 1.49 mmol) in $CH_2Cl_2$ (5 mL) was added 5-benzyloxy-2-[2,6-dichloro-4-[6-(difluoromethyl)-3,5-dioxo-1,2,4-triazin-2-yl]phenoxy]pyridine-4-sulfonyl chloride I (300 mg, 495.23 umol). The mixture was stirred at rt for 1 h. LC-MS showed the reaction was completed. The reaction mixture was poured into water (20 mL) and extracted with $CH_2Cl_2$ (3×20 mL). The combined organic layer was washed with brine (20 mL), dried over anhydrous $Na_2SO_4$ and filtered. The filtrate was concentrated in vacuum. The residue was purified by column chromatography ($CH_2Cl_2:CH_3OH=10:1$) to afford 5-benzyloxy-N-(3-cyanocyclobutyl)-2-[2,6-dichloro-4-[6-(difluoromethyl)-3,5-dioxo-1,2,4-triazin-2-yl]phenoxy]pyridine-4-sulfonamide 130-1 (300 mg, 91% yield) as a yellow solid. LCMS: $[M+H]^+=665.2$ Step 2: 130

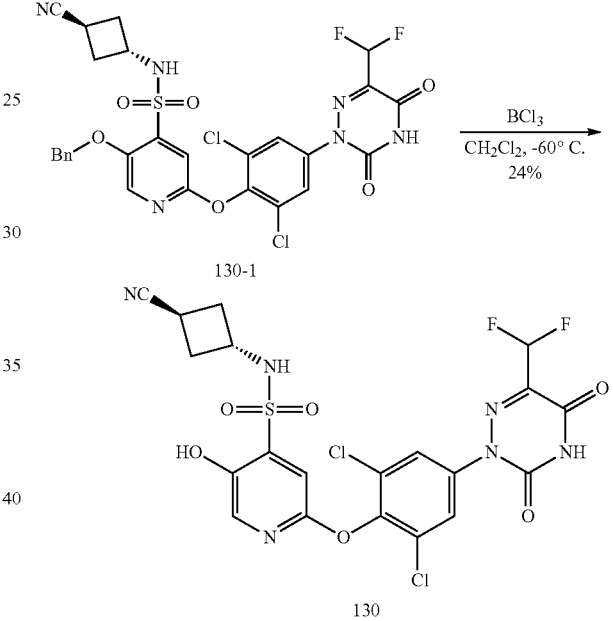

To a solution of 5-benzyloxy-N-(3-cyanocyclobutyl)-2-[2,6-dichloro-4-[6-(difluoromethyl)-3,5-dioxo-1,2,4-triazin-2-yl]phenoxy]pyridine-4-sulfonamide 130-1 (300 mg, 450.82 umol) in $CH_2Cl_2$ (5 mL) was added $BCl_3$ (1 M in $CH_2Cl_2$, 9.02 mL) at −60° C. and the mixture was stirred for 1 h at −60° C. LC-MS showed the reaction was completed. The reaction mixture was poured into saturated aqueous $NaHCO_3$ (50 mL) and extracted with EtOAc (3×30 mL). The combined organic layer was washed with brine (20 mL), dried over anhydrous $Na_2SO_4$ and filtered. The filtrate was concentrated in vacuum. The residue was purified by flash column chromatography ($CH_2Cl_2:CH_3OH=20:1$) to afford a crude product. The crude product was purified with Prep-TLC ($CH_2Cl_2:CH_3OH$ 10:1) to afford N-(3-cyanocyclobutyl)-2-[2,6-dichloro-4-[6-(difluoromethyl)-3,5-dioxo-1,2,4-triazin-2-yl]phenoxy]-5-hydroxy-pyridine-4-sulfonamide 130 (64.2 mg, 240 yield) as a white solid. LCMS: $[M+H]^+=575.0$. $^1H$ NR (400 MHz, DMSO-$d_6$) δ 7.92 (s, 1H), 7.78 (s, 2H), 7.35 (s, 1H), 6.84 (t, J=53.2 Hz, 1H), 4.22 (4.12 (m, 1H), 3.23-3.17 (m, 1H), 2.40-2.31 (n, 4H). $^{19}F$ NMR (376.5 MHz, DMSO-$d_6$) δ−124.21 (s, 2F).

The compounds of Formula (I') or (I) in Table 22 below were made according to Example 53 of Compound 130.

TABLE 22

| Cmpd No. | LC-MS, ¹H and ¹⁹F-NMR data |
|---|---|
| 131 | LCMS: [M + H]⁺ = 536.0/538.0. ¹H NMR (400 MHZ, CD₃OD) δ 7.83 (s, 1H), 7.79 (s, 2H), 7.43 (s, 1H), 6.73 (t, J = 53.2, 1H), 2.35-2.30 (m, 1H), 0.61-0.59 (m, 4H). ¹⁹F NMR (376 MHZ, CD₃OD) δ −124.2 (s, 2F). |
| 132 | LCMS: [M + H]⁺ = 565.9. ¹H NMR (400 MHZ, CD₃OD) δ 7.78 (s, 1H), 7.77 (s, 2H), 7.37 (s, 1H), 6.71 (t, J = 52.8 Hz, 1H), 3.87-3.80 (m, 1H), 3.46-3.36 (m, 1H), 2.48-2.42 (m, 2H), 1.87-1.75 (m, 2H). ¹⁹F NMR (376 MHZ, CD₃OD) δ −124.22 (s, 2F). |
| 133 | LCMS: [M + H]⁺ = 579.9. ¹H NMR (400 MHZ, CD₃OD) δ 7.78 (s, 1H), 7.77 (s, 2H), 7.38 (s, 1H), 6.71 (t, J = 52.8 Hz, 1H), 4.27-4.23 (m, 1H), 3.06 (d, J = 7.6 Hz, 2H), 2.29-2.27 (m, 1H), 2.09-2.03 (m, 2H), 1.99-1.93 (m, 2H). ¹⁹F NMR (376 MHz, CD₃OD) δ −124.25 (s, 2F). |
| 134 | LCMS: [M + H]⁺ = 579.9. ¹H NMR (400 MHZ,CD₃OD) δ 7.78 (s, 1H), 7.76 (s, 2H) 7.38 (s, 1H), 6.71 (t, J = 52.8 Hz, 1H),4.00-3.96 (m, 1H), 3.30 (d, J = 7.6 Hz, 2H), 2.29-2.27 (m, 2H), 1.89-1.77 (m, 1H), 1.56-1.49 (m, 2H). ¹⁹F NMR (376 MHz, CD₃OD) δ −124.18 (s, 2F). |
| 135 | LCMS: [M + H]⁺ = 561.0. ¹H NMR (400 MHZ, CD₃OD) δ 7.82 (s, 1H), 7.76 (s, 2H), 7.44 (s, 1H), 6.70 (t, J = 52.8 Hz, 1H), 1.49-1.40 (m, 4H). ¹⁹F NMR (376 MHz, CD₃OD) δ −124.17 (s, 2F). |
| 136 | LCMS: [M + H]⁺ = 580.0. ¹H NMR (400 MHZ, CD₃OD) δ 7.77 (s, 1H), 7.76 (s, 2H), 7.40 (s, 1H), 6.71 (t, J = 52.8 Hz, 1H), 3.87-3.84 (m, 2H), 3.51-3.46 (m, 1H), 3.41-3.34 (m, 2H), 1.73-1.70 (m, 2H), 1.61-1.55 (m, 2H). ¹⁹F NMR (376 MHz, CD₃OD) δ −124.24 (s, 2F). |
| 137 | LCMS: [M + H]⁺ = 568.1. ¹H NMR (400 MHZ, CD₃OD) δ 7.78 (s, 1H), 7.76 (s, 2H), 7.39 (s, 1H), 6.71 (t, J = 52.8 Hz, 1H), 2.94 (s, 2H), 1.19 (s, 6H). ¹⁹F NMR (376 MHZ, CD₃OD) δ −124.25 (s, 2F). |
| 138 | LCMS: [M + H]⁺ = 580.1/582.1. ¹H NMR (400 MHZ, Methanol-d₄) δ 7.68 (s, 1H), 7.67 (s, 2H), 7.28 (s, 1H), 6.61 (t, J = 52.8 Hz, 1H), 3.46-3.33 (m, 1H), 2.14-2.04 (m, 2H), 1.96-1.86 (m, 2H), 1.14 (s,3H). |
| 139 | LCMS: [M + H]⁺ = 580.0. ¹H NMR (400 MHZ, DMSO-d₆) δ 12.85 (s, 1H), 11.01 (s, 1H), 8.19 (d, J = 8.2 Hz, 1H), 7.88 (s, 1H), 7.79 (s, 2H), 7.33 (s, 1H), 6.92 (t, J = 52.8 Hz, 1H), 3.96-3.78 (m, 2H), 3.06 (s, 3H), 2.13-2.00 (m, 4H). ¹⁹F NMR (376 MHz, DMSO-d₆) δ −122.17 (s, 2F). |
| 140 | LCMS: [M + H]⁺ = 580.0 ¹H NMR (400 MHZ, CD₃OD) δ 7.78 (s, 1H), 7.77 (s, 2H), 7.38 (s, 1H), 6.71 (t, J = 52.8 Hz, 1H), 3.52-3.48 (m, 2H), 3.16 (s,3H), 2.46-2.43 (m, 2H), 1.85-1.78 (m, 2H). ¹⁹F NMR (376 MHz, CD₃OD) δ −124.2 (s, 2F). |
| 141 | LCMS: [M + H]⁺ = 566.1. ¹HNMR (400 MHZ, DMSO-d₆) δ 12.84 (brs, 1H), 11.05 (brs, 1H), 7.91 (s, 1H), 7.78 (s, 2H), 7.40 (s, 1H), 6.90 (t, J = 52.8 Hz, 1H), 5.25-4.92 (brs, 1H), 4.28 (s, 1H), 3.52-3.47 (m, 2H), 3.46-3.40 (m, 1H), 3.24-3.19 (m, 1H), 1.92-1.85 (m, 1H), 1.78 (s, 1H). ¹⁹F NMR (376 MHz, DMSO-d₆) δ −122.14 (s, 2F). |
| 142 | LCMS: [M + H]⁺ = 578.0. ¹H NMR (400 MHZ, CD₃OD) δ 7.79 (s, 1H), 7.78 (s, 2H), 7.38 (s, 1H),6.71 (t, J = 52.8 Hz, 1H), 1.90 (s, 6H). ¹⁹F NMR (376 MHZ, CD₃OD) δ −124.2 (s, 2F). |
| 143 | LCMS: [M + H]⁺ = 594.0. ¹H NMR (400 MHZ, CD₃OD) δ 7.78 (s, 1H), 7.77 (s, 2H), 7.39 (s, 1H), 6.71 (t, J = 52.8 Hz, 1H), 3.49-3.44 (m, 1H), 3.24-3.16 (m, 1H), 1.88-1.79 (m, 4H), 1.39-1.20 (m, 4H). ¹⁹F NMR (376 MHz, CD₃OD) δ −124.2 (s, 2F). |
| 144 | LCMS: [M + H]⁺ = 594.0. ¹H NMR (400 MHZ,CD₃OD) δ 7.78 (s, 1H), 7.77 (s, 2H), 7.39 (s, 1H), 6.71 (t, J = 52.8 Hz, 1H), 3.78-3.72 (m, 1H), 3.27-3.21 (m, 1H), 1.71-1.65 (m, 4H), 1.57-1.54 (m, 4H). ¹⁹F NMR (376 MHz, CD₃OD) δ −124.2 (s, 2F). |
| 158 | LCMS: [M + H]⁺ = 552.0/554.0. ¹H NMR (400 MHZ, Methanol-d₄) δ 7.67 (s, 3H), 7.29 (s, 1H), 6.61 (t, J = 52.9 Hz, 1H), 4.63 (s, J = 3.1 Hz, 2H), 4.49-4.44 (m, 3H). |
| 159 | LCMS: [M + H]⁺ = 592.0/594.1. ¹H NMR (400 MHZ, Methanol-d₄) δ 7.69 (s, 1H), 7.68 (s, 2H), 7.29 (s, 1H), 6.61 (t, J = 52.8 Hz, 1H), 1.68-1.64 (m, 2H), 1.53 (t, J = 2.4 Hz, 2H), 1.48 (ddd, J = 6.1, 3.7, 1.7 Hz, 2H), 1.43 (dd, J = 3.7, 1.7 Hz, 2H). |
| 160 | LCMS: [M + H]⁺ = 606.1/608.1. ¹H NMR (400 MHZ, Methanol-d₄) δ 7.69 (s,1H), 7.68(s, 2H), 7.29(s, 1H), 6.61 (t, J = 52.8 Hz, 1H), 1.80-1.72 (m, 2H), 1.65-1.50 (m, 8H) |

Example 54: Synthesis of Compound 145

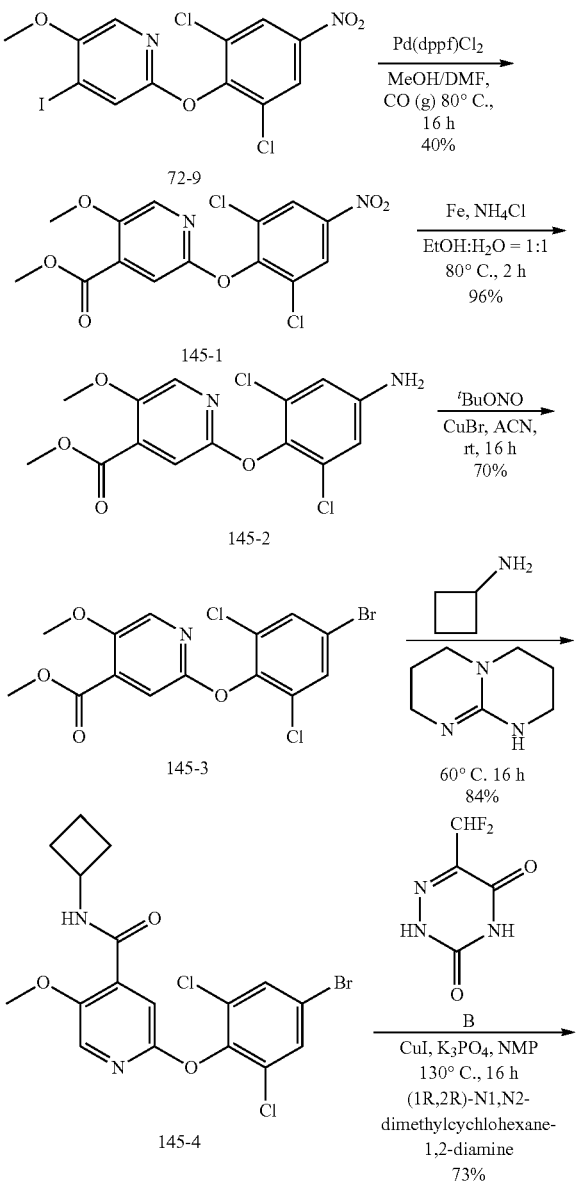

-continued

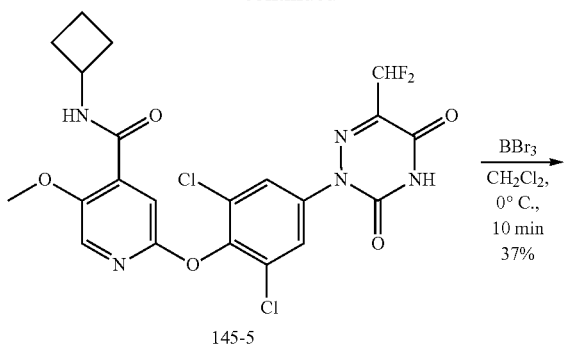

Step 2: 145-2

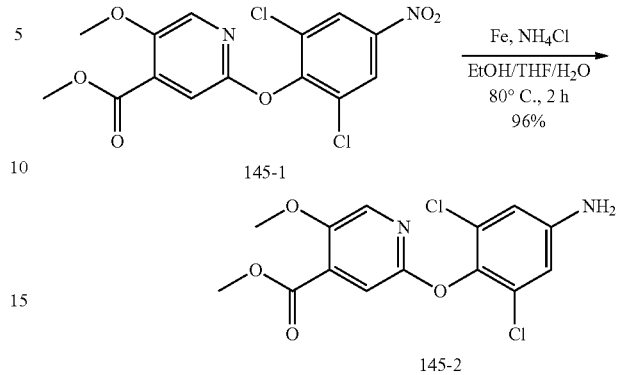

To a solution of methyl 2-(2,6-dichloro-4-nitro-phenoxy)-5-methoxy-pyridine-4-carboxylate 145-1 (430 mg, 1.15 mmol) in THF (5 mL), EtOH (10 mL) and H$_2$O (5 mL) were added Fe (321.77 mg, 5.76 mmol) and NH$_4$Cl (308.21 mg, 5.76 mmol). The mixture was stirred at 80° C. under N$_2$ (g) for 2 h. LC-MS showed the reaction was completed. The reaction mixture was concentrated and the residue was diluted with water (20 mL) and extracted with EtOAc (3×30 mL). The combined organic layer was washed with brine (20 mL), dried over anhydrous Na$_2$SO$_4$ and filtered. The filtrate was concentrated in vacuum to afford a residue. The residue was crude methyl 2-(4-amino-2,6-dichloro-phenoxy)-5-methoxy-pyridine-4-carboxylate 145-2 (380 mg, 96% yield). It's a yellow oil and used in the next step directly without further purification. LCMS: [M+H]$^+$=343.0

Step 3: 145-3

Step 1: 145-1

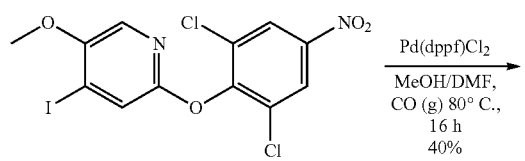

To a solution of 2-(2,6-dichloro-4-nitro-phenoxy)-4-iodo-5-methoxy-pyridine 72-9 (1.4 g, 3.17 mmol) in methanol (35 mL) and DMF (8 mL) were added TEA (963.70 mg, 9.52 mmol, 1.33 mL) and cyclopentyl(diphenyl)phosphane-dichloromethane-dichloropalladium-iron (259.25 mg, 317.46 umol). The mixture was stirred at 80° C. under CO (balloon) for 16 h. LC-MS showed the reaction was completed. The reaction mixture was concentrated and the residue was poured into water (50 mL) and extracted with EtOAc (3×30 mL). The combined organic layer was washed with brine (3×20 mL), dried over anhydrous Na$_2$SO$_4$ and filtered. The filtrate was concentrated in vacuum to afford a residue. The residue was purified by silica gel column chromatography (PE:EtOAc=50:1-10:1) to afford methyl 2-(2,6-dichloro-4-nitro-phenoxy)-5-methoxy-pyridine-4-carboxylate 145-1 (480 mg, 40% yield) as a yellow solid. LCMS: [M+H]$^+$=373.0

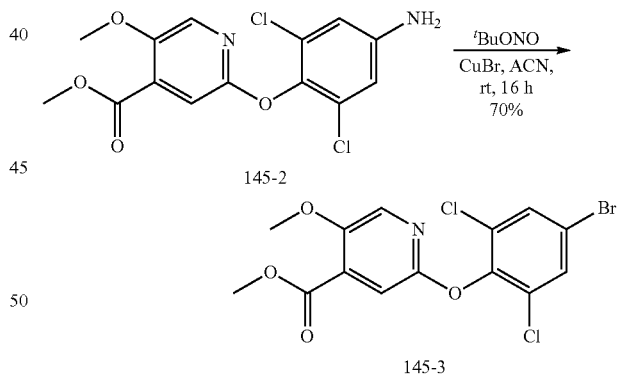

To a solution of methyl 2-(4-amino-2,6-dichloro-phenoxy)-5-methoxy-pyridine-4-carboxylate 145-2 (380 mg, 1.11 mmol) and CuBr (317.70 mg, 2.21 mmol, 67.45 uL) in CH$_3$CN (50 mL) was added $^t$BuONO (228.38 mg, 2.21 mmol). The mixture was stirred at rt under N$_2$ (g) for 16 h. LCMS showed the reaction was completed. The reaction mixture was concentrated in vacuum to afford a residue. The residue was purified by silica gel column chromatography (PE:EtOAc=10:1) to afford methyl 2-(4-bromo-2,6-dichloro-phenoxy)-5-methoxy-pyridine-4-carboxylate 145-3 (320 mg, 70% yield) as a yellow solid. LCMS: [M+H]$^+$=406.0

Step 4: 145-4

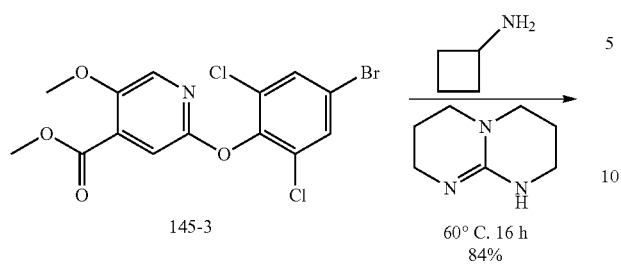

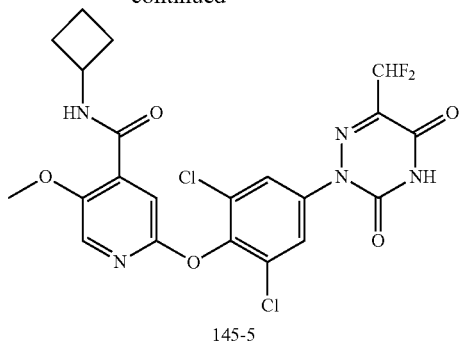

145-5

To a solution of 2-(4-bromo-2,6-dichloro-phenoxy)-N-cyclobutyl-5-methoxy-pyridine-4-carboxamide 145-4 (46.26 mg, 103.70 umol) and 6-(difluoromethyl)-2H-1,2,4-triazine-3,5-dione B (33.82 mg, 207.39 umol) in NMP (2 mL) was added (1R,2R)—N1,N2-dimethylcyclohexane-1,2-diamine (10.32 mg, 72.59 umol), CuI (49.37 mg, 259.24 umol) and $K_3PO_4$ (66.03 mg, 311.09 umol). The mixture was stirred at 130° C. for 16 h. LC-MS showed product was formed. The reaction mixture was diluted with EtOAc (50 mL), washed with aq. $NH_4Cl$ (3×20 mL) and brine (3×20 mL), dried over anhydrous $Na_2SO_4$ and filtered. The filtrate was concentrated in vacuum to afford a residue. The residue was purified by Prep-TLC ($CH_2Cl_2$:$CH_3OH$=10:1) to afford N-cyclobutyl-2-[2,6-dichloro-4-[6-(difluoromethyl)-3,5-dioxo-1,2,4-triazin-2-yl] phenoxy]-5-methoxy-pyridine-4-carboxamide 145-5 (40 mg, 73% yield) as a yellow solid. LCMS: $[M+Na]^+$=528.0

Step 6: 145

To a solution of methyl 2-(4-bromo-2,6-dichloro-phenoxy)-5-methoxy-pyridine-4-carboxylate 145-3 (300 mg, 737.02 umol) in THF (1 mL) were added cyclobutanamine (104.83 mg, 1.47 mmol) and 3,4,6,7,8,9-hexahydro-2H-pyrimido[1,2-a]pyrimidine (307.78 mg, 2.21 mmol). The mixture was stirred at 60° C. in a sealed tube for 16 h. LC-MS showed the reaction was completed. The reaction mixture was diluted with water (20 mL) and extracted with EtOAc (3×10 mL). The combined organic layer was washed with brine (10 mL), dried over anhydrous $Na_2SO_4$ and filtered. The filtrate was concentrated in vacuum to afford a residue. The residue was purified by silica gel chromatography (PE:EtOAc=5:1) to give 2-(4-bromo-2,6-dichloro-phenoxy)-N-cyclobutyl-5-methoxy-pyridine-4-carboxamide 145-4 (280 mg, 84% yield) as a yellow solid. LCMS: $[M+H]^+$=445.0

Step 5: 145-5

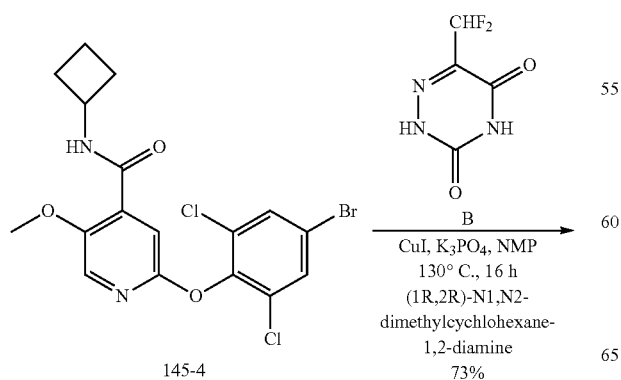

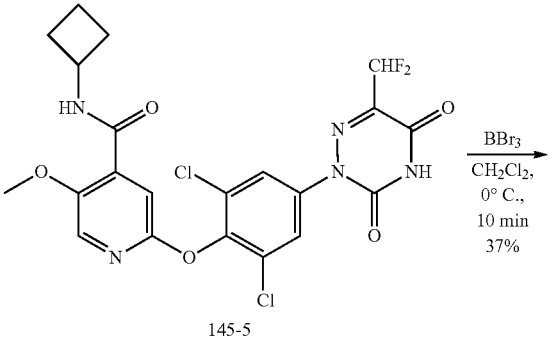

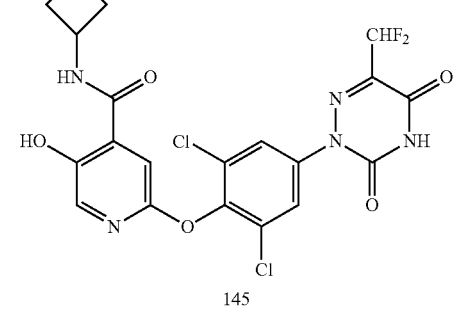

To a solution of N-cyclobutyl-2-[2,6-dichloro-4-[6-(difluoromethyl)-3,5-dioxo-1,2,4-triazin-2-yl]phenoxy]-5-methoxy-pyridine-4-carboxamide 145-5 (40 mg, 75.72 umol) in $CH_2Cl_2$ (3 mL) was added $BBr_3$ (189.69 mg, 757.16 umol) at 0° C. and the mixture was stirred for 10 min. LC-MS showed the reaction was completed. The reaction mixture was poured into water (20 mL) and extracted with CH$_2$Cl$_2$ (3×20 mL). The combined organic layer was washed with brine (20 mL), dried over anhydrous Na$_2$SO$_4$ and filtered. The filtrate was concentrated in vacuum to afford a residue. The residue was purified by Prep-HPLC (Kromasil 100-5 C18 5 um 100×21.5 mm, MeCN—H$_2$O (0.1% FA), Gradient: 50-100%, 25 ml/min) to afford N-cyclobutyl-2-[2,6-dichloro-4-[6-(difluoromethyl)-3,5-dioxo-1,2,4-triazin-2-yl]phenoxy]-5-hydroxy-pyridine-4-carboxamide 145 (14.6 mg, 37% yield) as a light yellow solid. LCMS: [M+H]$^+$=514.0. $^1$H NMR (400 MHz, CD$_3$OD) δ 7.76 (s, 3H), 7.50 (s, 1H), 6.71 (t, J=52.8 Hz, 1H), 4.57-4.48 (m, 1H), 2.43-2.34 (m, 2H), 2.18-2.07 (m, 2H), 1.86-1.76 (m, 2H). $^{19}$F NMR (376.5 MHz, CD$_3$OD) δ−124.2 (s, 2F).

Example 55: Synthesis of Compound 146

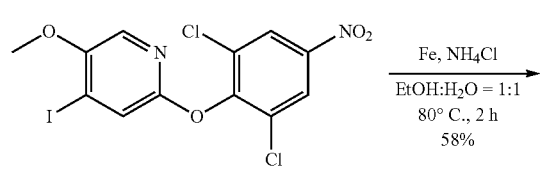

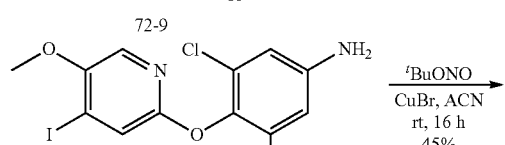

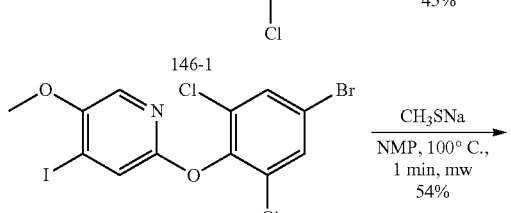

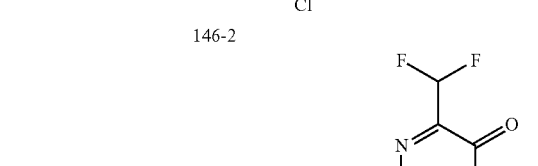

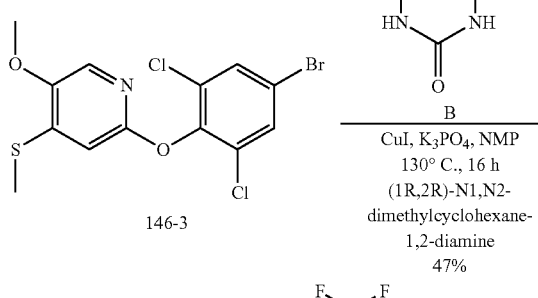

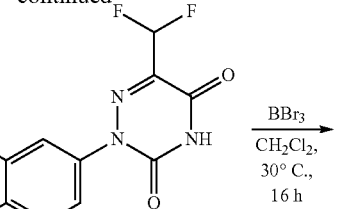

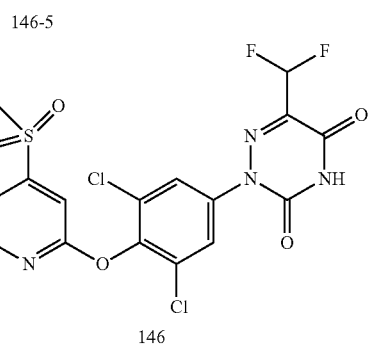

Step 1: 146-1

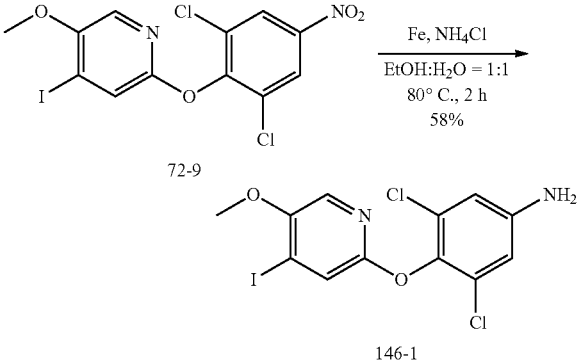

A mixture of 2-(2,6-dichloro-4-nitrophenoxy)-4-iodo-5-methoxypyridine 72-9 (2.5 g, 5.67 mmol), Fe (3.17 g, 56.69 mmol) and ammonium chloride (1.52 g, 28.34 mmol) in water (20 mL) and EtOH (20 mL) was stirred at 80° C. for 2 h. LCMS showed the reaction was completed. Water (30 mL) was added and the mixture was extracted with EtOAc (3×30 mL). The combined organic layers were washed with brine, dried over Na$_2$SO$_4$ and concentrated to give 3,5-dichloro-4-[(4-iodo-5-methoxy-2-pyridyl) oxy] aniline 146-1 (1.52 g, 58% yield) as a yellow solid. LCMS: [M+H]$^+$=410.9.

Step 2: 146-2

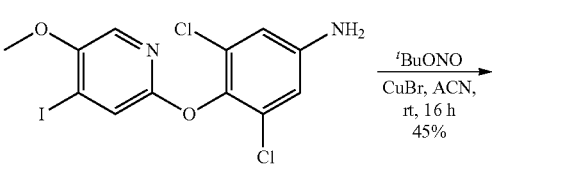

-continued

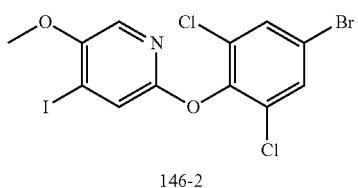

146-2

A mixture of tert-butyl nitrite (762.70 mg, 7.40 mmol) and CuBr (795.74 mg, 5.55 mmol) in MeCN (10 mL) was stirred at rt for 10 min. Then to the mixture was added 3,5-dichloro-4-[(4-iodo-5-methoxy-2-pyridyl) oxy] aniline 146-1 (1.52 g, 3.70 mmol) at rt. The mixture was stirred at rt for 16 h. LCMS showed the reaction was completed. Water (30 mL) was added and the mixture was extracted with EtOAc (3×30 mL). The combined organic layers were washed with brine, dried over $Na_2SO_4$ and concentrated in vacuum. The residue was purified by flash chromatography (eluent: PE:EtOAc=5:1) to give 2-(4-bromo-2,6-dichloro-phenoxy)-4-iodo-5-methoxy-pyridine 146-2 (1 g, 45% yield) as a yellow solid. LCMS: $[M+H]^+=473.9$.

Step 3: 146-3

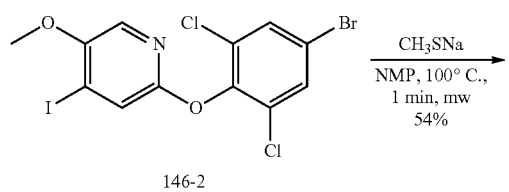

146-2

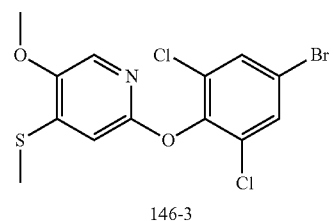

146-3

A mixture of 2-(4-bromo-2,6-dichloro-phenoxy)-4-iodo-5-methoxy-pyridine 146-2 (300 mg, 631.71 umol) and sodium methyl mercaptide (88.55 mg, 1.26 mmol) in NMP (5 mL) was stirred at 100° C. for 1 min under microwave. LCMS showed the reaction was completed. Water (15 mL) was added and the mixture was extracted with EtOAc (3×13 mL). The combined organic layers were washed with brine, dried over $Na_2SO_4$ and concentrated in vacuum. The residue was purified by flash chromatography (PE:EtOAc=5:1) to give 2-(4-bromo-2,6-dichloro-phenoxy)-5-methoxy-4-methylsulfanyl-pyridine 146-3 (150 mg, 54% yield, 90% purity) as a yellow solid. LCMS: $[M+H]^+=393.9$.

Step 4: 146-4

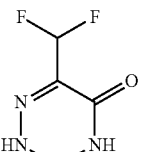

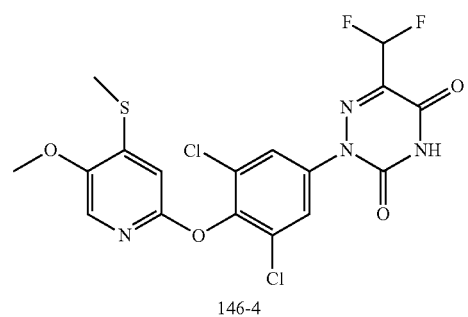

146-4

A mixture of 2-(4-bromo-2,6-dichloro-phenoxy)-5-methoxy-4-methylsulfanyl-pyridine 146-3 (50 mg, 126.55 umol), 6-(difluoromethyl)-2H-1,2,4-triazine-3,5-dione B (41.28 mg, 253.10 umol), CuI (60.25 mg, 316.38 umol), potassium phosphate (80.59 mg, 379.65 umol) and (1R, 2R)—N1,N2-dimethylcyclohexane-1,2-diamine (12.60 mg, 88.59 umol) in NMP (2 mL) was stirred at 130° C. for 16 h. LCMS showed the reaction was completed. Water (15 mL) was added and the mixture was extracted with EtOAc (3×13 mL). The combined organic layers were washed with brine, dried over $Na_2SO_4$ and concentrated in vacuum. The residue was purified by flash chromatography ($CH_2Cl_2$:MeOH=10:1) to give 2-[3,5-dichloro-4-[(5-methoxy-4-methylsulfanyl-2-pyridyl) oxy] phenyl]-6-(difluoro methyl)-1,2,4-triazine-3,5-dione 146-4 (32 mg, 47% yield) as a yellow solid. LCMS: $[M+H]^+=477.0$.

Step 5:146-5

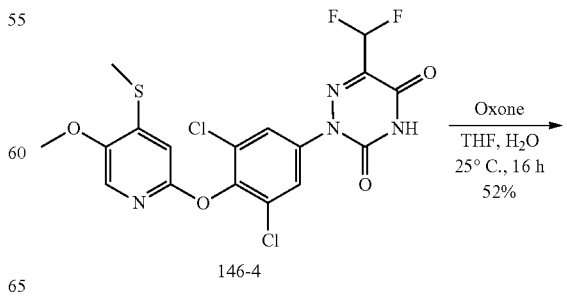

146-4

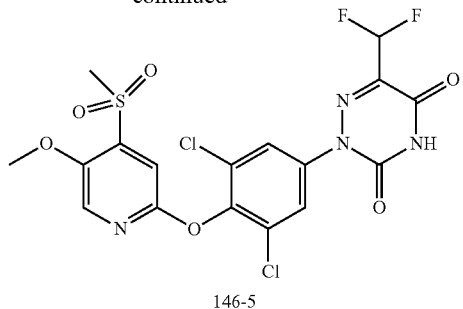

146-5

A mixture of 2-[3,5-dichloro-4-[(5-methoxy-4-methylsulfanyl-2-pyridyl)oxy]phenyl]-6-(difluoro methyl)-1,2,4-triazine-3,5-dione 146-4 (32 mg, 67.05 umol) and oxone (123.66 mg, 201.14 umol) in water (1 mL) and THF (1 mL) was stirred at 25° C. for 16 h. LCMS showed the reaction was completed. Water (15 mL) was added and the mixture was extracted with EtOAc (3×13 mL). The combined organic layers were washed with brine, dried over Na$_2$SO$_4$ and concentrated in vacuum. The residue was purified by flash chromatography (CH$_2$Cl$_2$:MeOH=10:1) to give 2-[3,5-dichloro-4-[(5-methoxy-4-methylsulfonyl-2-pyridyl) oxy] phenyl]-6-(difluoromethyl)-1,2,4-triazine-3,5-dione 146-5 (20 mg, 52% yield) as a yellow solid. LCMS: [M+H]$^+$=509.0.

Step 6: 146

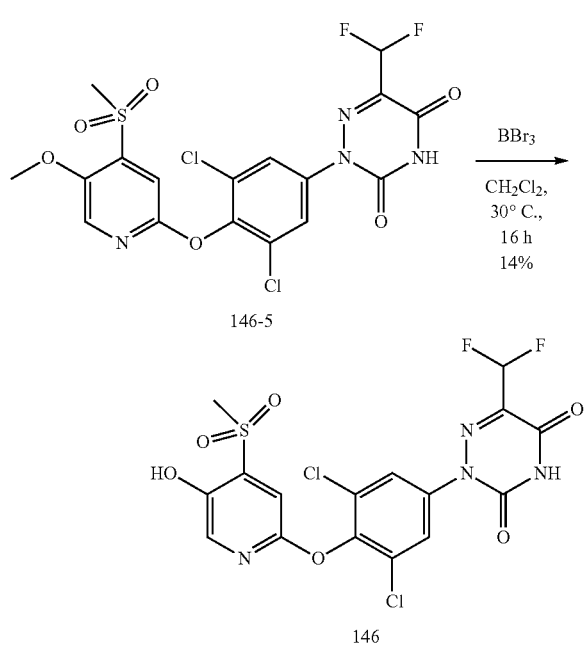

To a solution of 2-[3,5-dichloro-4-[(5-methoxy-4-methylsulfonyl-2-pyridyl) oxy] phenyl]-6-(difluoro methyl)-1,2,4-triazine-3,5-dione 146-5 (18 mg, 35.34 umol) in CH$_2$Cl$_2$ (2 mL) was added boron tribromide (88.55 mg, 353.45 umol) at 0° C. The mixture was stirred at 30° C. for 16 h. LCMS showed the reaction was completed. Water (1 mL) was added and the mixture was concentrated in vacuum. The residue was purified by prep-HPLC (Kromasil-C18 100× 21.2 mm 5 um, MeCN—H$_2$O (0.1% FA) Gradient: 40-50%) to give 2-[3,5-dichloro-4-[(5-hydroxy-4-methylsulfonyl-2-pyridyl) oxy] phenyl]-6-(difluoro methyl)-1,2,4-triazine-3,5-dione 146 (2.5 mg, 14% yield) as a yellow solid. LCMS: [M+H]$^+$=495.0. $^1$H NMR (400 MHz, CD$_3$OD) δ 7.83 (s, 1H), 7.77 (s, 2H), 7.47 (s, 1H), 6.71 (t, J=52.8 Hz, 1H), 3.35 (s, 3H). $^{19}$F NMR (376 MHz, CD$_3$OD) δ−124.2 (s, 2F).

Example 56: Synthesis of Compound 147

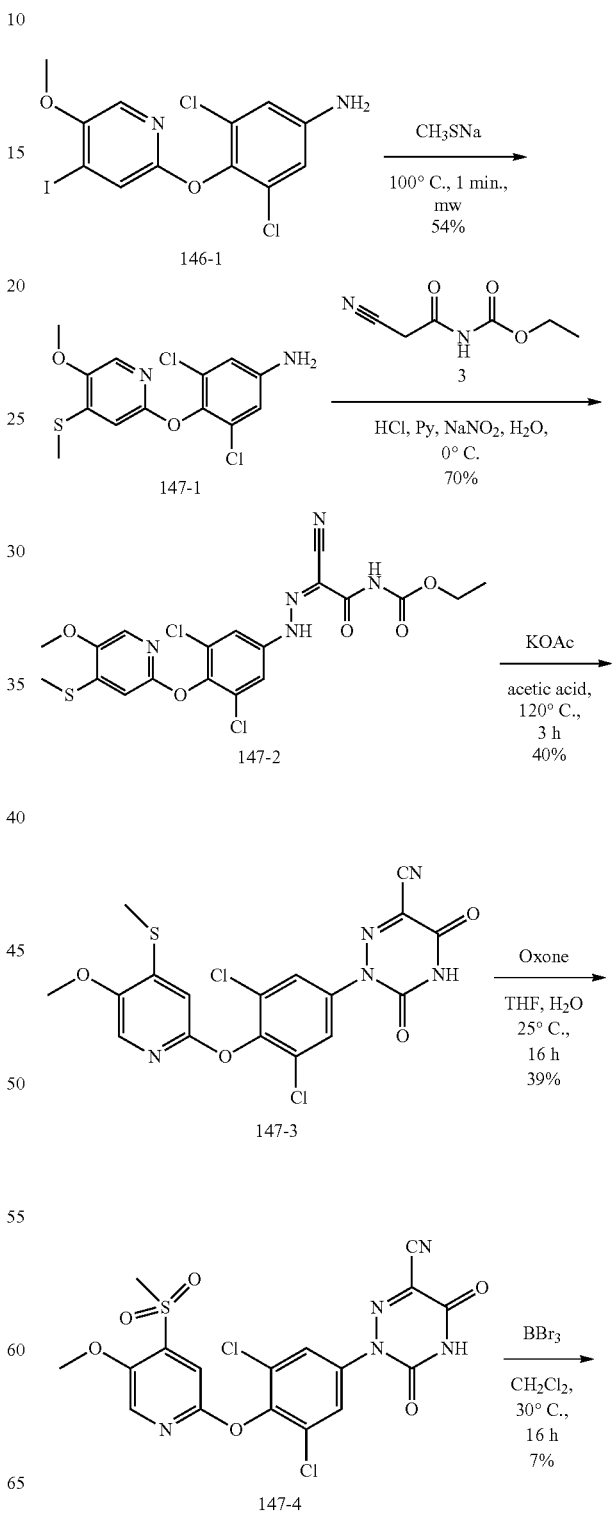

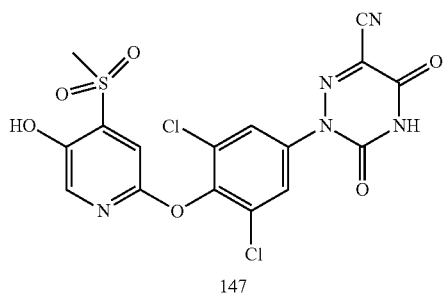

147

Step 1: 147-1

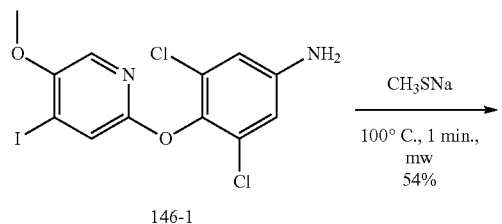

A mixture of 3,5-dichloro-4-[(4-iodo-5-methoxy-2-pyridyl) oxy] aniline 146-1 (250 mg, 608.24 umol) and sodium methyl mercaptide (85.26 mg, 1.22 mmol) in NMP (3 mL) was stirred at 100° C. for 1 min under microwave. LCMS showed the reaction was completed. Water (15 mL) was added and the mixture was extracted with EtOAc (3×13 mL). The combined organic layers were washed with brine, dried over Na₂SO₄ and concentrated in vacuum. The residue was purified by flash chromatography (PE:EtOAc=2:1) to give 3,5-dichloro-4-[(5-methoxy-4-methylsulfanyl-2-pyridyl) oxy] aniline 147-1 (120 mg, 54% yield) as a yellow solid. LCMS: [M+H]⁺=331.0/333.0.

Step 2: 147-2

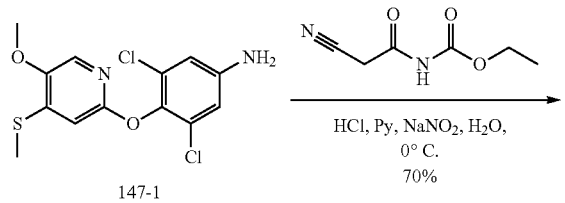

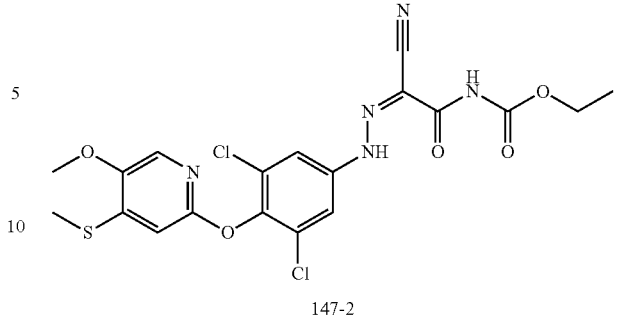

147-2

To a solution of 3,5-dichloro-4-[(5-methoxy-4-methylsulfanyl-2-pyridyl)oxy]aniline 147-1 (85 mg, 256.63 umol) in water (1 mL) was added HCl (1.50 g, 41.06 mmol, 1.87 mL) and sodium nitrite (26.56 mg, 384.94 umol) at 0° C. The mixture was stirred at 0° C. for 0.5 h. Then ethyl N-(2-cyanoacetyl) carbamate (48.08 mg, 307.96 umol) and pyridine (1.62 g, 20.53 mmol, 1.66 mL) in water (1 mL) were added at 0° C. After addition, the mixture was stirred at 0° C. for 30 min. LCMS showed the starting material was consumed. The mixture was quenched with H₂O (20 mL) and extracted with EtOAc (2×20 mL). The combined organic layers were dried over Na₂SO₄, filtered and concentrated to give ethyl N-[(2Z)-2-cyano-2-[[3,5-dichloro-4-[(5-methoxy-4-methylsulfanyl-2-pyridyl) oxy] phenyl]hydrazono] acetyl] carbamate 147-2 (100 mg, 70% yield) as a yellow solid. LCMS: [M+H]⁺=498.0/450.0.

Step 3: 147-3

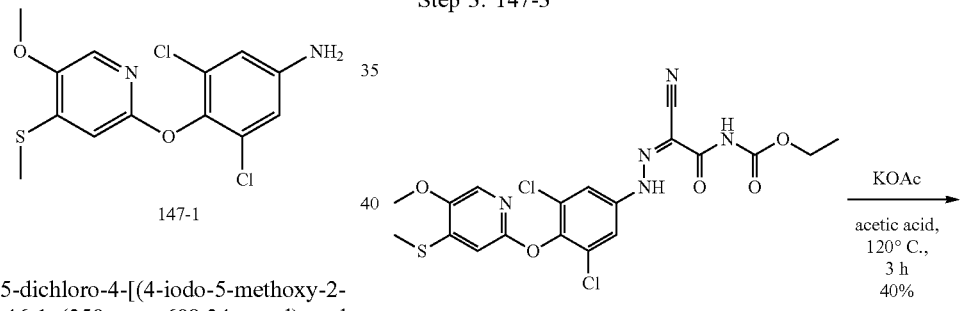

A mixture of ethyl N-[(2Z)-2-cyano-2-[[3,5-dichloro-4-[(5-methoxy-4-methylsulfanyl-2-pyridyl) oxy]phenyl]hydrazono]acetyl]carbamate 147-2 (100 mg, 200.67 umol) and potassium acetate (59.08 mg, 602.00 umol) in acetic acid (3 mL) was stirred at 120° C. for 3 h. LCMS showed the reaction was completed. Water (15 mL) was added and the mixture was extracted with EtOAc (3×13 mL). The combined organic layers were washed with brine, dried over Na₂SO₄, and concentrated in vacuum. The residue was purified by flash chromatography (eluent: CH₂Cl₂:

MeOH=10:1) to give 2-[3,5-dichloro-4-[(5-methoxy-4-methylsulfanyl-2-pyridyl) oxy] phenyl]-3,5-dioxo-1,2,4-triazine-6-carbonitrile 147-3 (40 mg, 40% yield) as a yellow solid. LCMS: [M+H]$^+$=452.0/454.0.

Step 4: 147-4

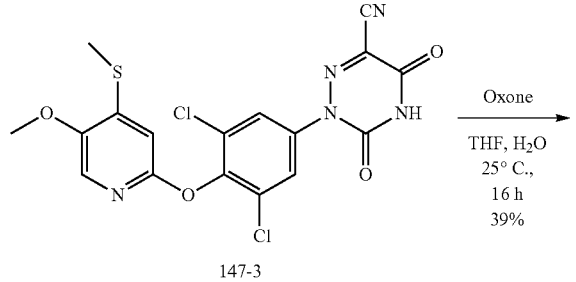

147-3

Step 5: 147

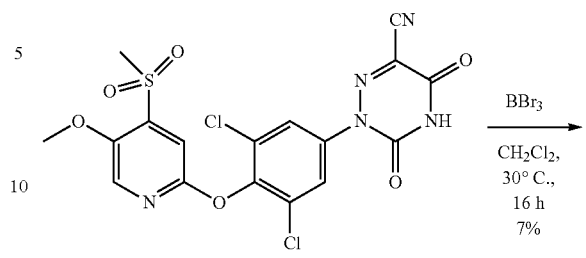

147-4

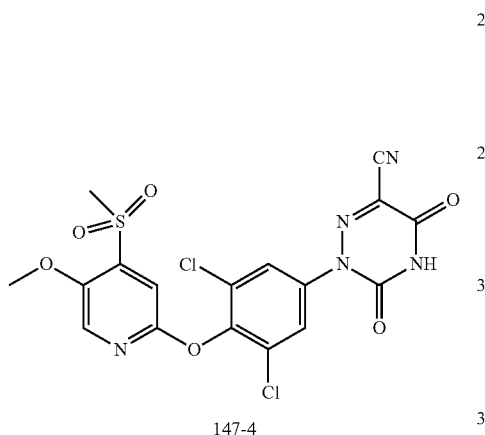

147-4

A mixture of 2-[3,5-dichloro-4-[(5-methoxy-4-methylsulfanyl-2-pyridyl)oxy]phenyl]-3,5-dioxo-1,2,4-triazine-6-carbonitrile 147-3 (90 mg, 199.00 umol) and oxone (367.01 mg, 596.99 umol) in THF (2 mL) and water (2 mL) was stirred at 25° C. for 16 h. LCMS showed the reaction was completed. Water (15 mL) was added and the mixture was extracted with EtOAc (3×13 mL). The combined organic layers were washed with brine, dried over Na$_2$SO$_4$ and concentrated in vacuum. The residue was purified by flash chromatography (CH$_2$Cl$_2$:MeOH=10:1) to give 2-[3,5-dichloro-4-[(5-methoxy-4-methylsulfonyl-2-pyridyl) oxy] phenyl]-3,5-dioxo-1,2,4-triazine-6-carbonitrile 147-4 (40 mg, 39% yield) as a yellow solid. LCMS: [M+H]$^+$=484.3/486.3.

147

To a solution of 2-[3,5-dichloro-4-[(5-methoxy-4-methylsulfonyl-2-pyridyl)oxy]phenyl]-3,5-dioxo-1,2,4-triazine-6-carbonitrile 147-4 (20 mg, 41.30 umol) in CH$_2$Cl$_2$ (5 mL) was added boron tribromide (103.46 mg, 412.99 umol) at 0° C. The mixture was stirred at 30° C. for 16 h. LCMS showed the starting material was consumed. The mixture was cooled to 0° C. and quenched with H$_2$O (20 mL) and extracted with EtOAc (2×20 mL). The combined organic layers were dried over Na$_2$SO$_4$, filtered and concentrated to obtain a residue. The residue was purified by prep-HPLC (Kromasil-C18 100×21.2 mm 5 um, MeCN—H$_2$O (0.1% FA), Gradient: 35-45%) to give 2-[3,5-dichloro-4-[(5-hydroxy-4-methylsulfonyl-2-pyridyl) oxy]phenyl]-3,5-dioxo-1,2,4-triazine-6-carbonitrile 147 (1.4 mg, 7% yield) as a yellow solid. LCMS: [M+H]$^+$=469.8. $^1$H NMR (400 MHz, CD$_3$OD) δ 7.83 (s, 1H), 7.74 (s, 2H), 7.47 (s, 1H), 3.35 (s, 3H).

Example 57: Synthesis of Compound 148

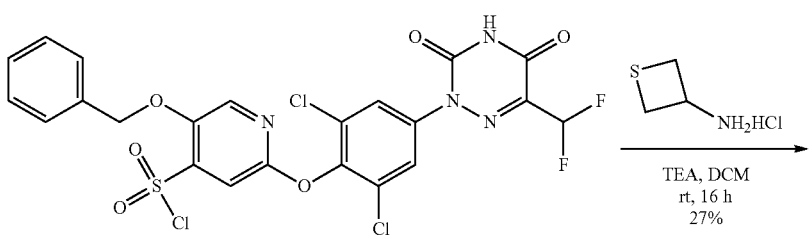

-continued
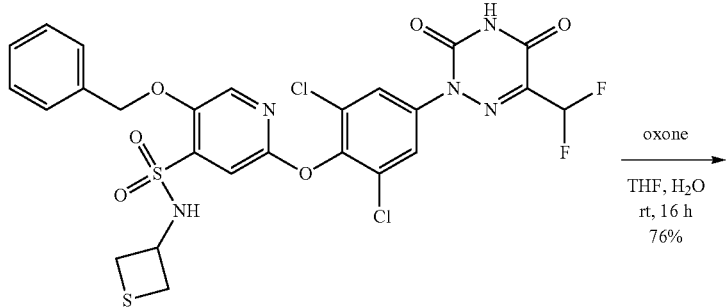
148-1
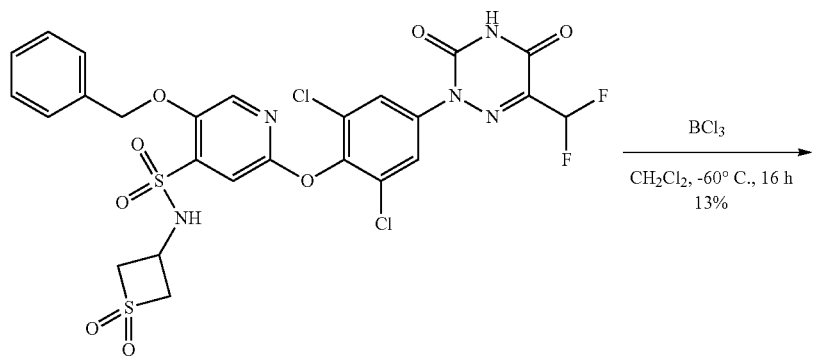
148-2
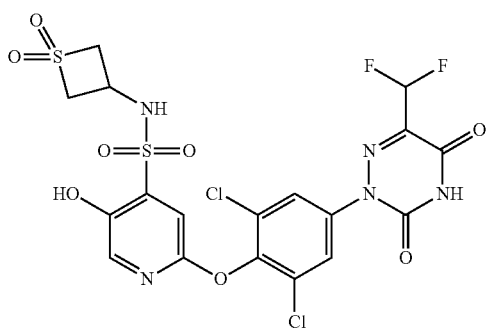
148
Step 1: 148-1
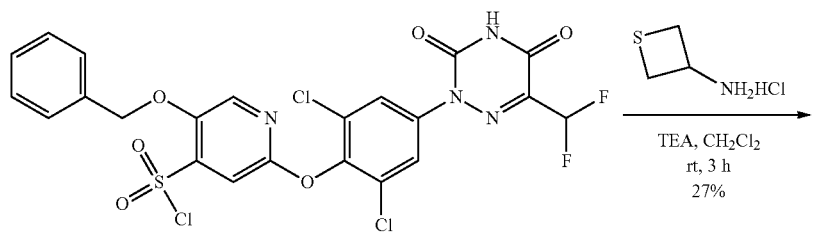
I

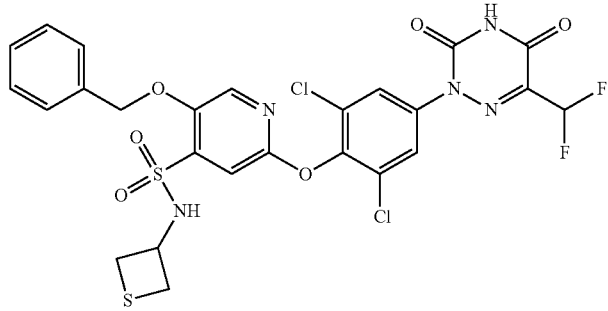

148-1

To a mixture of thietan-3-amine hydrochloride (29.44 mg, 330.15 umol) and TEA (83.52 mg, 825.38 umol, 115.04 uL) in $CH_2Cl_2$ (3 mL) was added 5-benzyloxy-2-[2,6-dichloro-4-[6-(difluoromethyl)-3,5-dioxo-1,2,4-triazin-2-yl]phenoxy]pyridine-4-sulfonyl chloride I (100 mg, 165.08 umol) at rt. The mixture was stirred at rt for 3 h. LCMS showed the reaction was complete. The reaction mixture was poured into water (50 mL) and extracted with EtOAc (3×10 mL). The combined organic layer was washed with brine (50 mL), dried over anhydrous $Na_2SO_4$, filtered and concentrated in vacuum to afford a residue. The residue was purified by silica gel chromatography ($CH_2Cl_2$:$CH_3OH$=20:1) to afford 5-benzyloxy-2-[2,6-dichloro-4-[6-(difluoromethyl)-3,5-dioxo-1,2,4-triazin-2-yl]-phenoxy]-N-(thietan-3-yl)-pyridine-4-sulfonamide 148-1 (30 mg, 27% yield) as a yellow solid. LCMS: $[M+H]^+$=658.0/660.0.

Step 2: 148-2

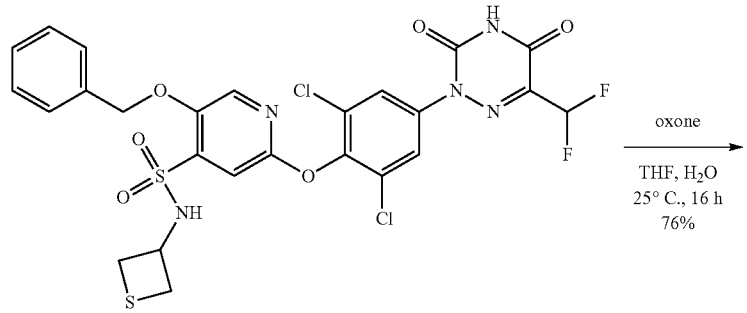

148-1

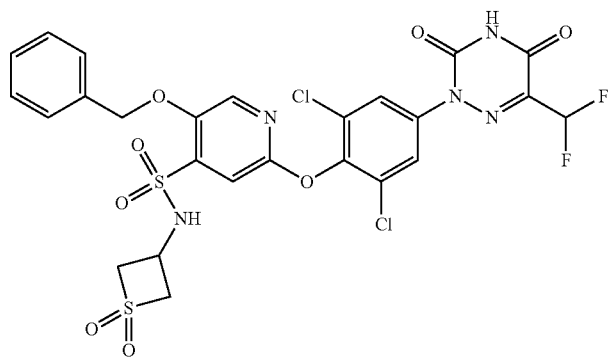

148-2

To a mixture of 5-benzyloxy-2-[2,6-dichloro-4-[6-(difluoromethyl)-3,5-dioxo-1,2,4-triazin-2-yl]-phenoxy]-N-(thietan-3-yl)-pyridine-4-sulfonamide 148-1 (50 mg, 75.93 umol) in THF (1 mL) and H₂O (1 mL) was added oxone (140.04 mg, 227.80 umol). The mixture was stirred at 25° C. for 16 h. LCMS showed the starting material was consumed and the product was found. The reaction mixture was poured into water (30 mL) and extracted with EtOAc (3×30 mL). The combined organic layer was washed with brine (30 mL), dried over anhydrous Na₂SO₄, filtered and concentrated in vacuum to afford a residue. The residue was purified by Prep-TLC (CH₂Cl₂:CH₃OH=10:1) to afford 5-benzyloxy-2-[2,6-dichloro-4-[6-(difluoromethyl)-3,5-dioxo-1,2,4-triazin-2-yl]-phenoxy]-N-(1,1-dioxothietan-3-yl)-pyridine-4-sulfonamide 148-2 (40 mg, 76% yield) as a yellow solid. LCMS: [M+H]⁺=689.9/691.9.

Step 3: 148

148 (4.8 mg, 13% yield) as a white solid. LCMS: [M+H]⁺=600.0/602.0. ¹H NMR (400 MHz, CD₃OD) δ 7.80 (s, 1H), 7.77 (s, 2H), 7.42 (s, 1H), 6.70 (t, J=52.8 Hz, 1H), 4.37-4.38 (m, 2H), 4.10-4.13 (m, 2H), 3.30-3.34 (m, 1H). ¹⁹F NMR (376 MHz, CD₃OD) δ –124.17 (s, 2F).

Example 58: Synthesis of Compound 149

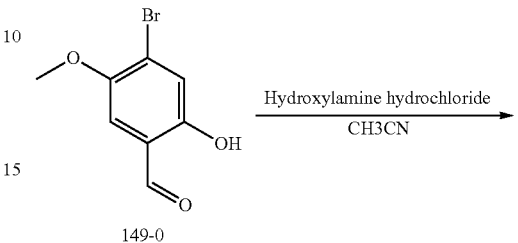

149-0

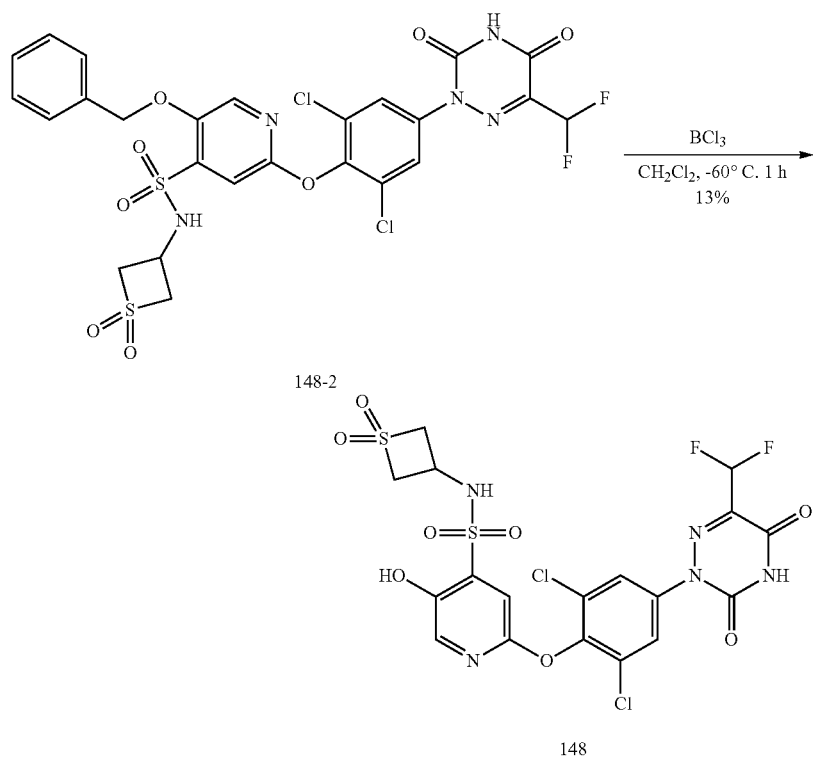

To a solution of 5-benzyloxy-2-[2,6-dichloro-4-[6-(difluoromethyl)-3,5-dioxo-1,2,4-triazin-2-yl]phenoxy]-N-(1,1-dioxothietan-3-yl)pyridine-4-sulfonamide 148-2 (40 mg, 57.93 umol) in CH₂Cl₂ (1 mL) was added BCl₃ (1M in CH₂Cl₂) (579.31 umol) slowly at –60° C. The mixture was stirred at –60° C. for 1 h. LCMS showed the starting material was consumed and the product was found. The reaction mixture was poured into aqueous NaHCO₃ (20 mL) and extracted with CH₂Cl₂ (3×30 mL). The combined organic layer was washed with brine (30 mL), dried over anhydrous Na₂SO₄, filtered and concentrated in vacuum to afford a residue. The residue was purified by Prep-HPLC (Kromasil-C18 100×21.2 mm 5 um, MeCN—H₂O (0.1% FA), Gradient: 35-45%) to afford 2-[2,6-dichloro-4-[6-(difluoromethyl)-3,5-dioxo-1,2,4-triazin-2-yl]-phenoxy]-N-(1,1-dioxothietan-3-yl)-5-hydroxy-pyridine-4-sulfonamide -continued

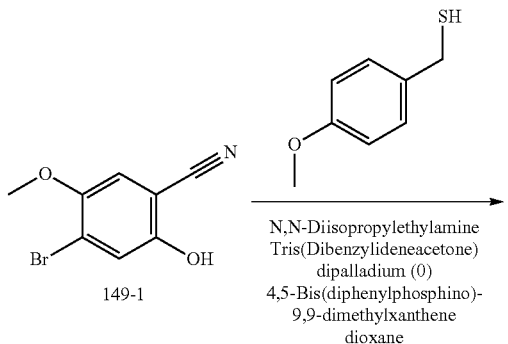

149-1

411
-continued

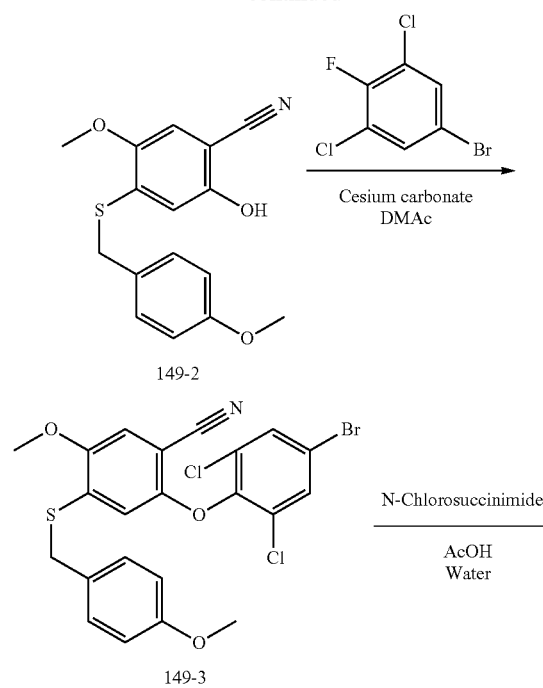

412
-continued

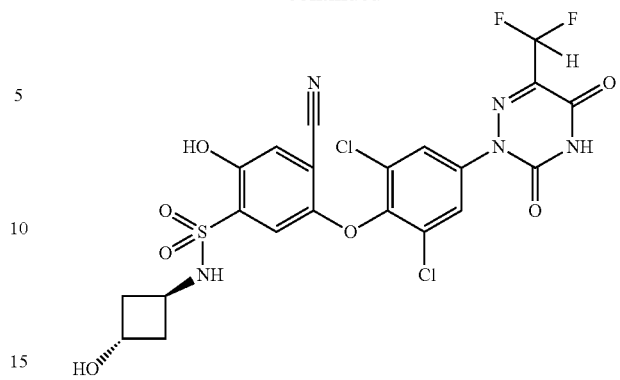

Step 1: 149-1

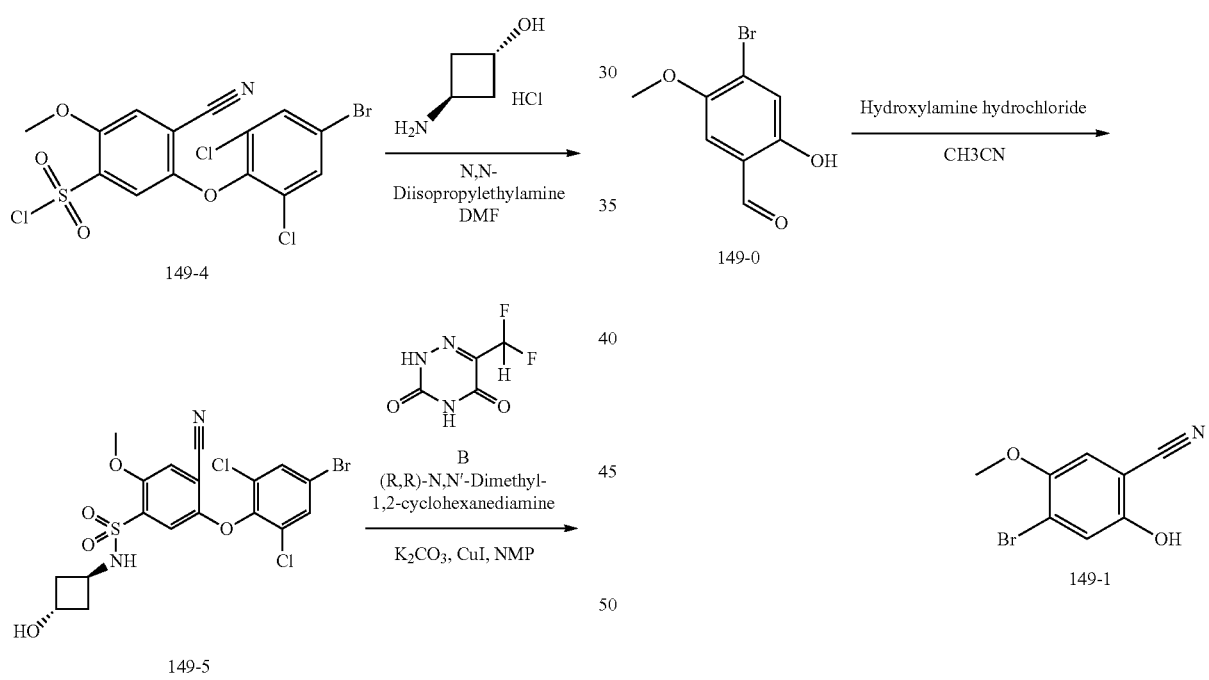

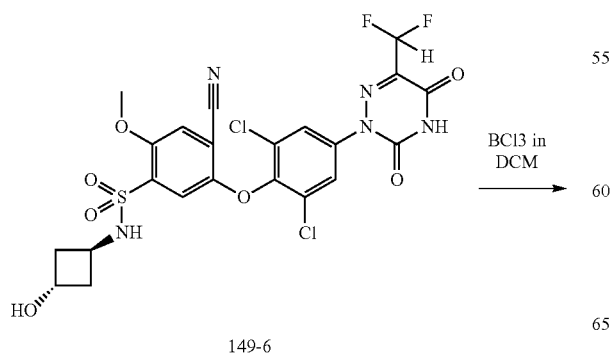

A mixture of 4-bromo-2-hydroxy-5-methoxy-benzaldehyde 149-0 (1 g, 4.33 mmol) and hydroxylamine hydrochloride (902.31 mg, 12.98 mmol, 540.31 uL) in CH$_3$CN (15 mL) was stirred at 80° C. for 16 hr. LCMS showed the reaction was complete. The mixture was poured into water (100 mL), extracted with EtOAc (80 mL*2), washed by brine (40 mL), dried over Na$_2$SO$_4$ and filtered. The filtrate was concentrated. The residue was purified by FCC (EtOAc in PE, 0-30%, v/v) to afford a crude, which was slurried in DCM/PE and filtered. The cake was dried under vacuum to afford 4-bromo-2-hydroxy-5-methoxy-benzonitrile 2 (890 mg, 3.90 mmol, 90.17% yield) as off-white solids. LCMS: [M+H]$^+$=228.0/230.0

Step 2: 149-2

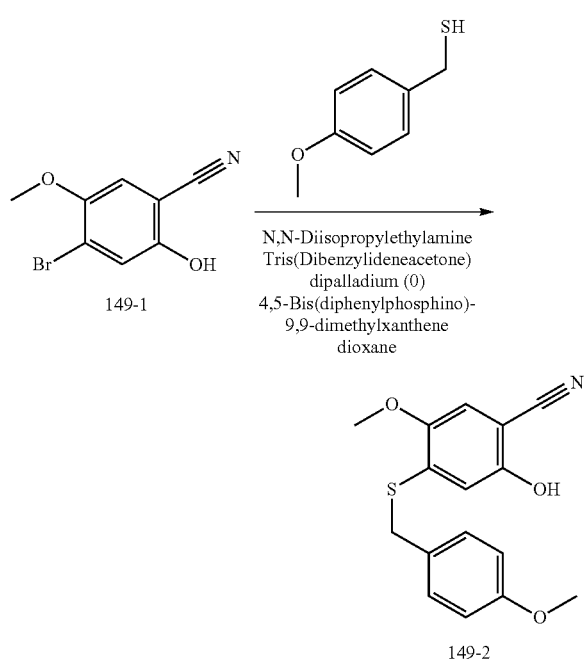

A mixture of 4-bromo-2-hydroxy-5-methoxy-benzonitrile 149-1 (850 mg, 3.73 mmol), (4-methoxyphenyl)methanethiol (603.61 mg, 3.91 mmol), N,N-Diisopropylethylamine (963.45 mg, 7.45 mmol, 1.30 mL), Tris(Dibenzylideneacetone)dipalladium (0) (170.66 mg, 186.37 umol), 4,5-Bis(diphenylphosphino)-9,9-dimethylxanthene (215.67 mg, 372.74 umol) and dioxane (10 mL) was stirred at 105° C. for 16 hr. LCMS showed the reaction was complete. The mixture was poured into a mixture of aqueous NaHCO₃ (100 mL) and EtOAc (100 mL). The mixture was filtered. The filtrate was extracted with EtOAc (50 mL*2), washed by brine (30 mL), dried over Na₂SO₄ and filtered. The filtrate was concentrated. The residue was purified by FCC (EtOAc in PE, 0~60%, v/v) to afford 2-hydroxy-5-methoxy-4-[(4-methoxyphenyl)methylsulfanyl]benzonitrile 4 (650 mg, 2.16 mmol, 57.87% yield) as a yellow solid. LCMS: [M+H]$^+$=302.1

Step 3: 149-3

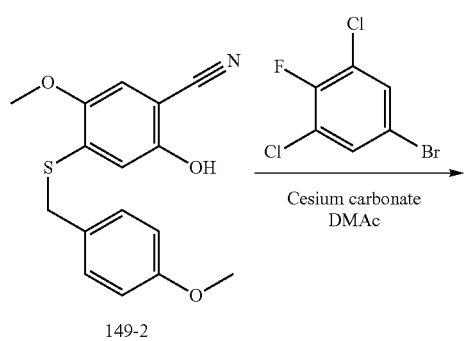

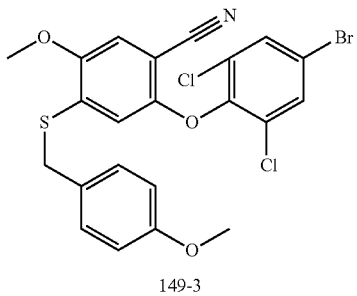

A mixture of 5-bromo-1,3-dichloro-2-fluoro-benzene (535.10 mg, 2.19 mmol), 2-hydroxy-5-methoxy-4-[(4-methoxyphenyl)methylsulfanyl]benzonitrile 149-2 (551 mg, 1.83 mmol), cesium carbonate (1.19 g, 3.66 mmol) and DMAc (8 mL) was stirred at 120° C. for 16 hr under N2. LCMS showed the starting material was consumed. The mixture was poured into water (100 mL), extracted with EtOAc (80 mL*3), washed with brine (40 mL*2), dried over Na₂SO₄ and filtered. The filtrate was concentrated. The residue was purified by FCC (EtOAc in PE, 0~15%, v/v) to afford 2-(4-bromo-2,6-dichloro-phenoxy)-5-methoxy-4-[(4-methoxyphenyl)methylsulfanyl]benzonitrile 149-3 (700 mg, 1.33 mmol, 72.89% yield) as yellow oil. LCMS: [M+H]$^+$=524.0.

Step 4: 149-4

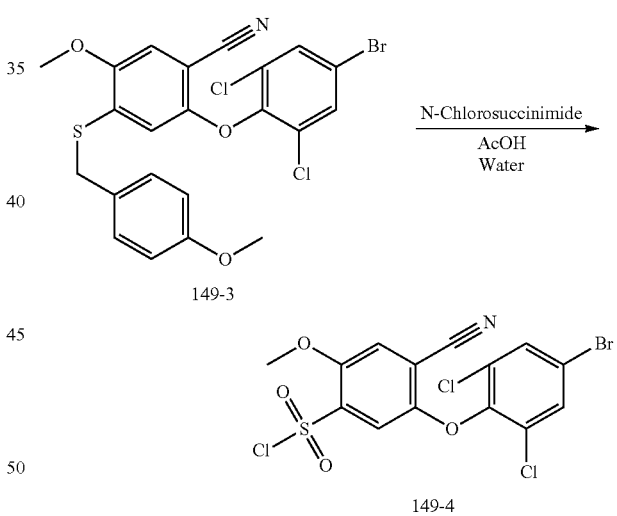

To a mixture of 2-(4-bromo-2,6-dichloro-phenoxy)-5-methoxy-4-[(4-methoxyphenyl)methylsulfanyl]benzonitrile 149-3 (300 mg, 571.17 umol), water (2 mL) and AcOH (8 mL) was added N-chlorosuccinimide (381.35 mg, 2.86 mmol, 231.12 uL) at 20° C. The mixture was stirred at 20° C. for 16 hr. LCMS showed the reaction was complete. The mixture was poured into water (100 mL), extracted with EtOAc (60 mL*3), washed by brine (40 mL), dried over Na₂SO₄ and filtered. The filtrate was concentrated. The residue was purified by FCC (EtOAc in PE, 0~20%, v/v) to afford 5-(4-bromo-2,6-dichloro-phenoxy)-4-cyano-2-methoxy-benzenesulfonyl chloride (260 mg, crude) as a white solid. LCMS: [M+Na]$^+$=491.9.

Step 5:149-5

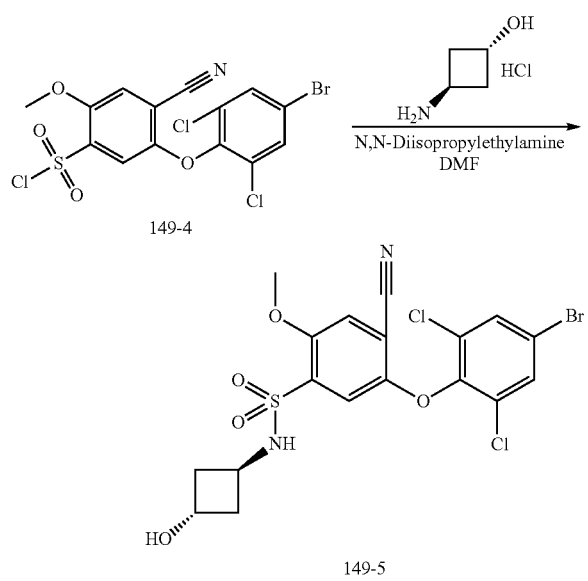

To a mixture of 3-aminocyclobutanol hydrochloride (102.21 mg, 827.08 umol), N,N-Diisopropylethylamine (356.32 mg, 2.76 mmol, 480.21 uL) in DMF (5 mL) was added 5-(4-bromo-2,6-dichloro-phenoxy)-4-cyano-2-methoxy-benzenesulfonyl chloride 149-4 (260 mg, 551.39 umol) at 20° C. The mixture was stirred at 20° C. for 2 hr. The mixture was poured into aqueous NaHCO₃ (100 mL), extracted with EtOAc (60 mL*3), washed by brine (40 mL), dried over Na₂SO₄ and filtered. The filtrate was concentrated. The residue was purified by FCC (EtOAc in PE, 10%~90%, v/v) to afford 5-(4-bromo-2,6-dichloro-phenoxy)-4-cyano-N-(3-hydroxycyclobutyl)-2-methoxy-benzenesulfonamide (220 mg, 421.30 umol, 76.41% yield) as an off-white solid. LCMS: [M+H]⁺=521.0.

Step 6: 149-6

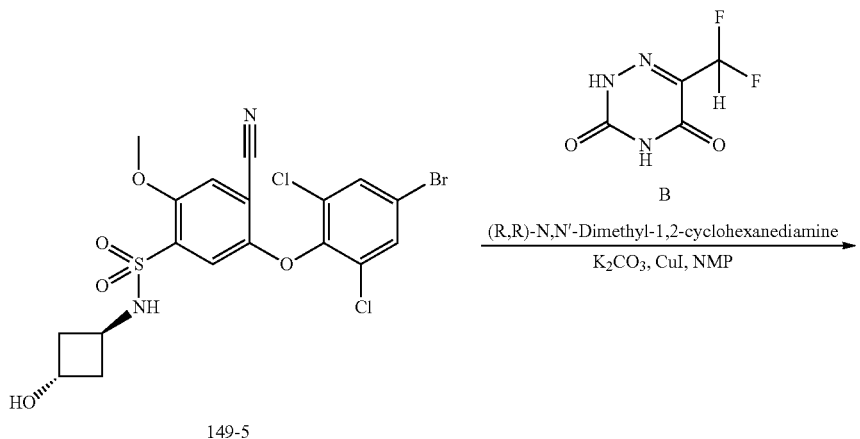

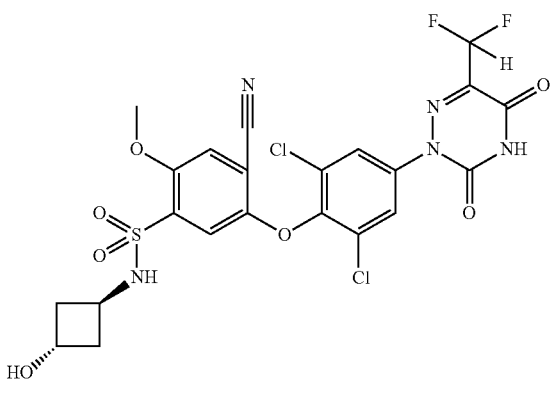

A mixture of 5-(4-bromo-2,6-dichlorophenoxy)-4-cyano-N-((1r,3r)-3-hydroxycyclobutyl)-2-methoxybenzenesulfonamide 149-5 (170 mg, 325.55 umol), 6-(difluoromethyl)-2H-1,2,4-triazine-3,5-dione B (106.18 mg, 651.10 umol), (R,R)—N,N'-dimethyl-1,2-cyclohexanediamine (23.15 mg, 162.77 umol), CuI (155.00 mg, 813.87 umol, 27.58 uL), potassium carbonate (224.97 mg, 1.63 mmol, 98.24 uL) in NMP (3.5 mL) was stirred at 133° C. for 6 hr. The mixture was poured into a mixture of 0.2N HCl (50 mL) and EtOAc (40 mL) and filtered. The filtrate was extracted with EtOAc (50 mL*3), washed by brine (30 mL), dried over $Na_2SO_4$ and filtered. The filtrate was concentrated. The crude was purified by FCC (MeOH in DCM, 0~8%, v/v) to afford 4-cyano-5-(2,6-dichloro-4-(6-(difluoromethyl)-3,5-dioxo-4,5-dihydro-1,2,4-triazin-2(3H)-yl)phenoxy)-N-((1r,3r)-3-hydroxycyclobutyl)-2-methoxybenzenesulfonamide 149-6 (18 mg, crude) as a yellow solid. LCMS: $[M+H]^+$=604.1.

Step 7: 149

Methanol-d4) δ 7.81 (s, 2H), 7.25 (s, 1H), 6.83 (s, 1H), 6.63 (t, J=52.8 Hz, 1H), 4.19-4.09 (m, 1H), 3.85-3.74 (m, 1H), 2.09-1.98 (m, 2H), 1.96-1.85 (m, 2H). LCMS: $[M+H]^+$=590.1.

Example 59: Synthesis of Compound 150

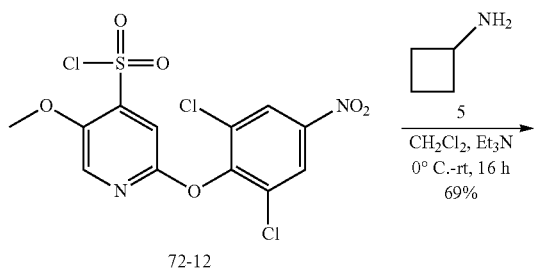

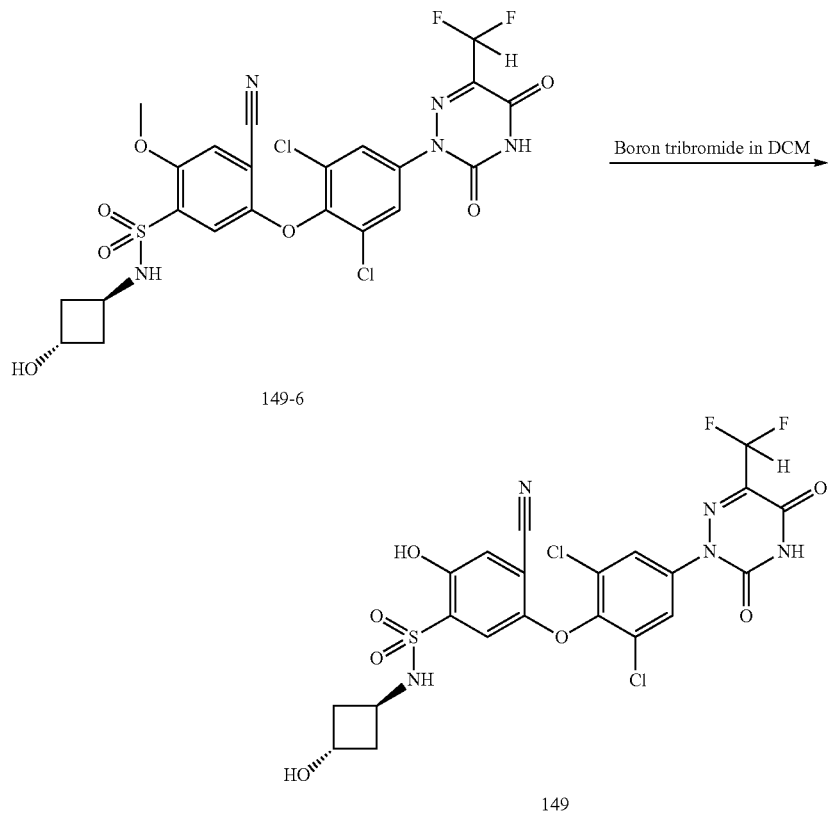

A mixture of 4-cyano-5-[2,6-dichloro-4-[6-(difluoromethyl)-3,5-dioxo-1,2,4-triazin-2-yl]phenoxy]-N-(3-hydroxycyclobutyl)-2-methoxy-benzenesulfonamide 149-6 (18 mg, 29.78 umol) and boron tribromide (1M in DCM, 3 mL) was stirred at 20° C. for 3 hr. The mixture was poured into ice and left to warm to about 10° C. The mixture was extracted with EtOAc (30 mL*3), washed by water (10 mL) and concentrated. The residue was purified by FCC (MeOH in EtOAc, 0~15%, v/v) to afford a crude product which was purified by prep-HPLC (HCOOH/$CH_3$CN/water) to give 4-cyano-5-[2,6-dichloro-4-[6-(difluoromethyl)-3,5-dioxo-1,2,4-triazin-2-yl]phenoxy]-2-hydroxy-N-(3-hydroxycyclobutyl)benzenesulfonamide 149 (3.6 mg, 6.10 umol, 20.48% yield) as a white solid. $^1$H NMR (400 MHz, -continued

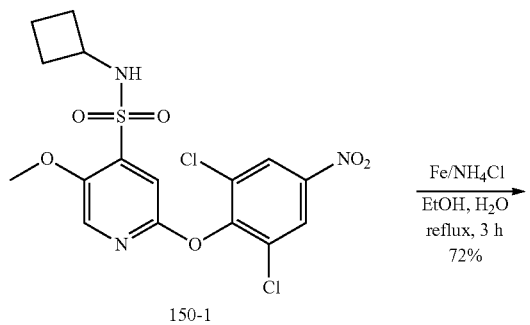

-continued

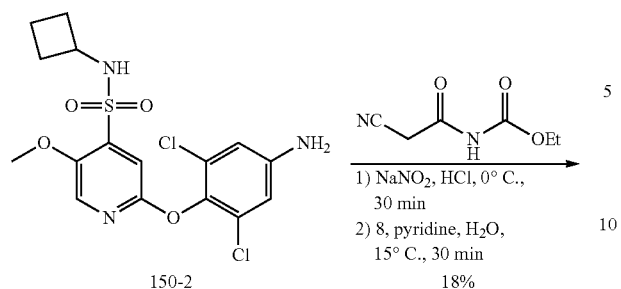
150-2

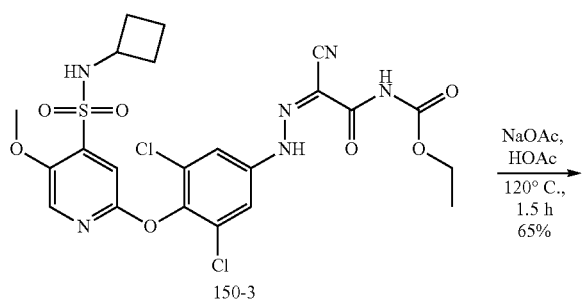
150-3

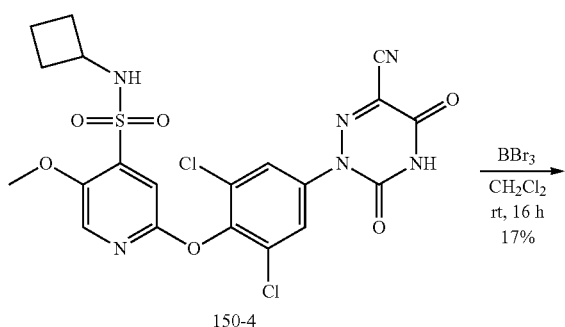
150-4

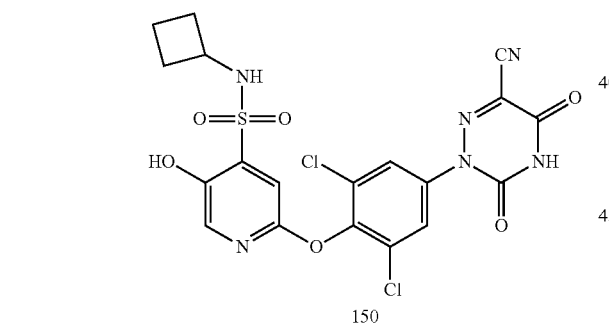
150

Step 1: 150-1

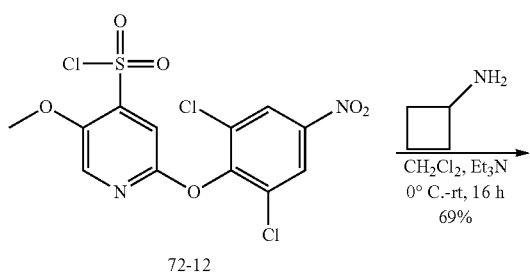
72-12

-continued

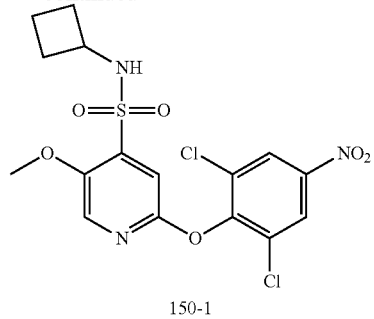
150-1

A solution of 2-(2,6-dichloro-4-nitro-phenoxy)-5-methoxy-pyridine-4-sulfonyl chloride 72-12 (400 mg, 967.08 umol), cyclobutanamine (68.78 mg, 967.08 umol) and TEA (489.29 mg, 4.84 mmol) in CH₂Cl₂ (3 mL) was stirred at rt for 16 h. LCMS showed the product was formed. The reaction mixture was poured into water and extracted with EtOAc (3×10 mL). The combined organic layer was dried over anhydrous Na₂SO₄, filtered and concentrated in vacuum to afford a residue. The residue was purified by silica gel chromatography (PE:EtOAc=2:1) to afford N-cyclobutyl-2-(2,6-dichloro-4-nitro-phenoxy)-5-methoxy-pyridine-4-sulfonamide 150-1 (300 mg, 69% yield) as a white solid. LCMS: [M+H]⁺=448.0

Step 2: 150-2

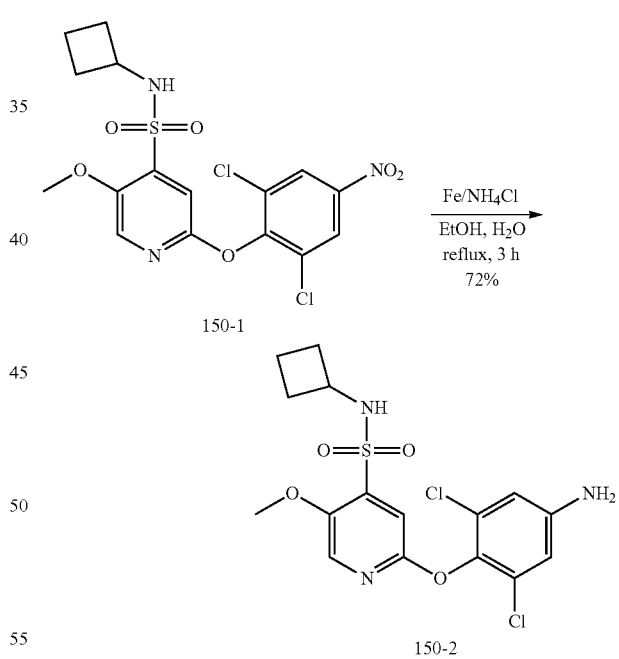

To a solution of N-cyclobutyl-2-(2,6-dichloro-4-nitro-phenoxy)-5-methoxy-pyridine-4-sulfonamide 150-1 (0.3 g, 669.23 umol) in EtOH (5 mL) and water (2 mL) was added NH₄Cl (178.99 mg, 3.35 mmol) and Fe (186.87 mg, 3.35 mmol). The mixture was refluxed under N₂ for 3 h. TLC: (EtOAc:PE=2:1 Rf=0.5) showed the reaction was completed. The mixture was filtered and the filtrate was concentrated in vacuum to afford 2-(4-amino-2,6-dichloro-phenoxy)-N-cyclobutyl-5-methoxy-pyridine-4-sulfonamide 150-2 (0.2 g, 72% yield) as a crude.

Step 3: 150-3

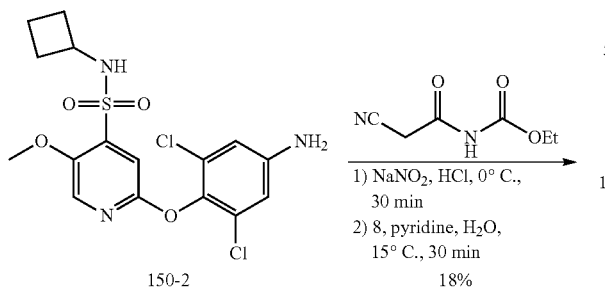

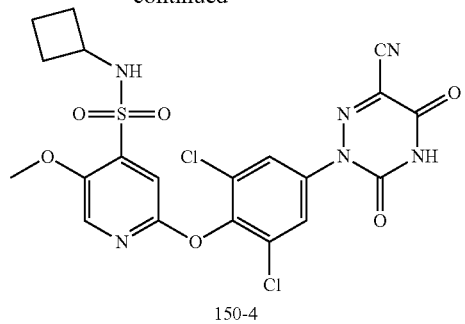

To a solution of ethyl N-[(2Z)-2-cyano-2-[[3,5-dichloro-4-[[4-(cyclobutylsulfamoyl)-5-methoxy-2-pyridyl]oxy]phenyl]hydrazono]acetyl]carbamate 150-3 (50 mg, 85.41 umol) in HOAc (5 mL) was added NaOAc (147.93 mg, 969.08 umol). The mixture was stirred at 120° C. for 1.5 h. LC-MS showed the reaction was completed. The reaction mixture was poured into saturated aqueous NaHCO$_3$ (50 mL) and extracted with EtOAc (3×20 mL). The combined organic layer was washed with brine (20 mL), dried over anhydrous Na$_2$SO$_4$ and filtered. The filtrate was concentrated in vacuum to afford a residue. The residue was purified by silica gel chromatography (CH$_2$Cl$_2$:CH$_3$OH=20:1-10:1) to afford N-cyclobutyl-2-[2,6-dichloro-4-(6-cyano-3,5-dioxo-1,2,4-triazin-2-yl)phenoxy]-5-methoxy-pyridine-4-sulfonamide 150-4 (30 mg, 65% yield) as a yellow solid. LCMS: [M+H]$^+$=539.1/541.1.

Step 5: 150

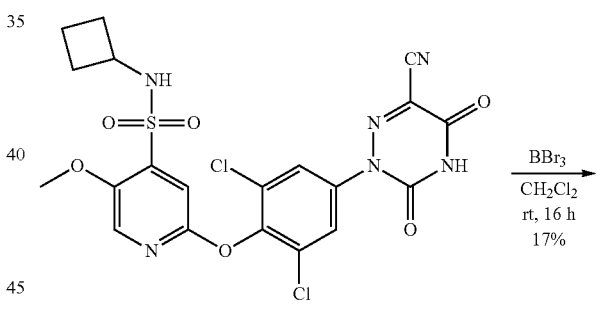

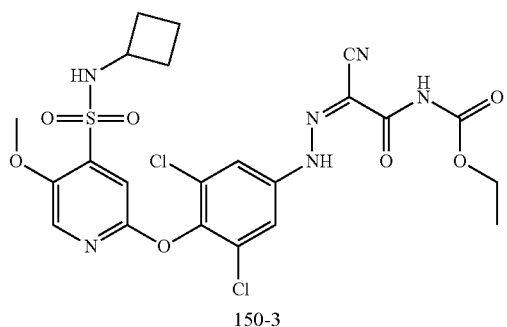

To a solution of 2-(4-amino-2,6-dichloro-phenoxy)-N-cyclobutyl-5-methoxy-pyridine-4-sulfonamide 150-2 (0.2 g, 478.13 umol) in HCl (12N in water, 2 mL) and AcOH (2 mL) was added the solution of NaNO$_2$ (42.89 mg, 624.57 umol) in H$_2$O (0.2 mL) at 0° C. The mixture was stirred at 0° C. for 30 min. Then ethyl N-(2-cyanoacetyl) carbamate (82.12 mg, 525.95 umol) in pyridine (3.91 g, 49.46 mmol) was added. The solution was warmed to 15° C. and stirred for 0.5 hour. LCMS showed the reaction was completed. The reaction mixture was filtered and the solid was dried in vacuum to afford ethyl N-[(2Z)-2-cyano-2-[[3,5-dichloro-4-[[4-(cyclobutylsulfamoyl)-5-methoxy-2-pyridyl] oxy] phenyl] hydrazono] acetyl] carbamate 150-3 (50 mg, 18% yield) as a crude. It's a red solid and used in the next step directly without further purification. LCMS: [M+H]$^+$=585.1/587.1.

Step 4: 150-4

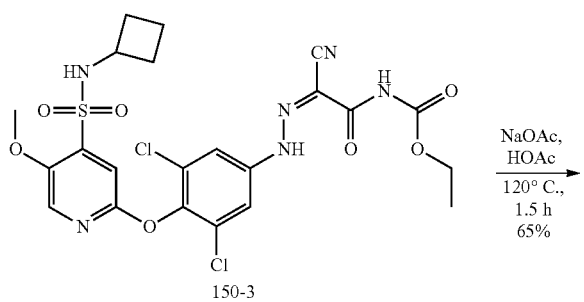

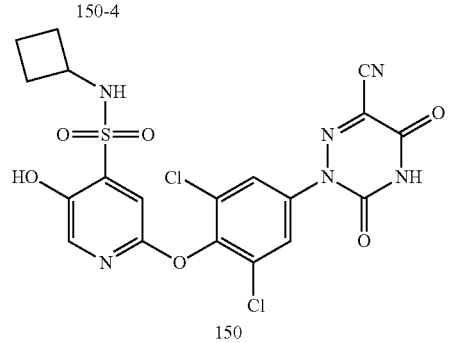

To a solution of N-cyclobutyl-2-[2,6-dichloro-4-(6-cyano-3,5-dioxo-1,2,4-triazin-2-yl)phenoxy]-5-methoxy-pyridine-4-sulfonamide 150-4 (30 mg, 55.62 umol) in CH$_2$Cl$_2$ (3 mL) was added BBr$_3$ (14.07 mg, 120.05 umol). The mixture was stirred at rt for 16 h. LCMS showed the product was formed. The reaction mixture was poured into water and extracted with EtOAc (3×100 mL). The combined organic layer was dried over anhydrous Na$_2$SO$_4$, filtered and concentrated in vacuum to afford a residue. The residue was purified by Prep-HPLC (Xbridge 5 u C18 150×19 mm, MeCN—H$_2$O (0.1% FA), Gradient: 47-577%) to give N-cyclopropyl-2-[2,6-dichloro-4-[6-(difluoromethyl)-3,5-dioxo-1,2,4-triazin-2-yl] phenoxy]-5-hydroxy-pyridine-4-sulfonamide 150 (4.9 mg, 17% yield) as a white solid. LCMS: [M+H]$^+$=524.9. $^1$H NMR (400 MHz, DMSO-d$_6$) δ 10.93 (s, 1H), 8.12-8.08 (m, 2H), 7.86 (s, 1H), 7.74 (s, 2H), 7.29 (s, 1H), 3.80-3.74 (m, 1H), 1.98-1.87 (m, 4H), 1.53-1.44 (m, 2H).

Example 60: Synthesis of Compound 151

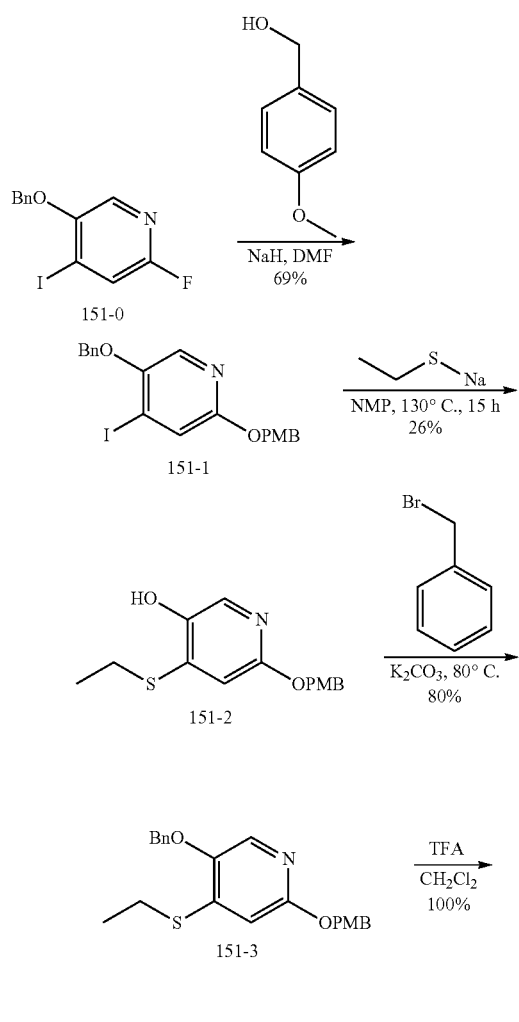

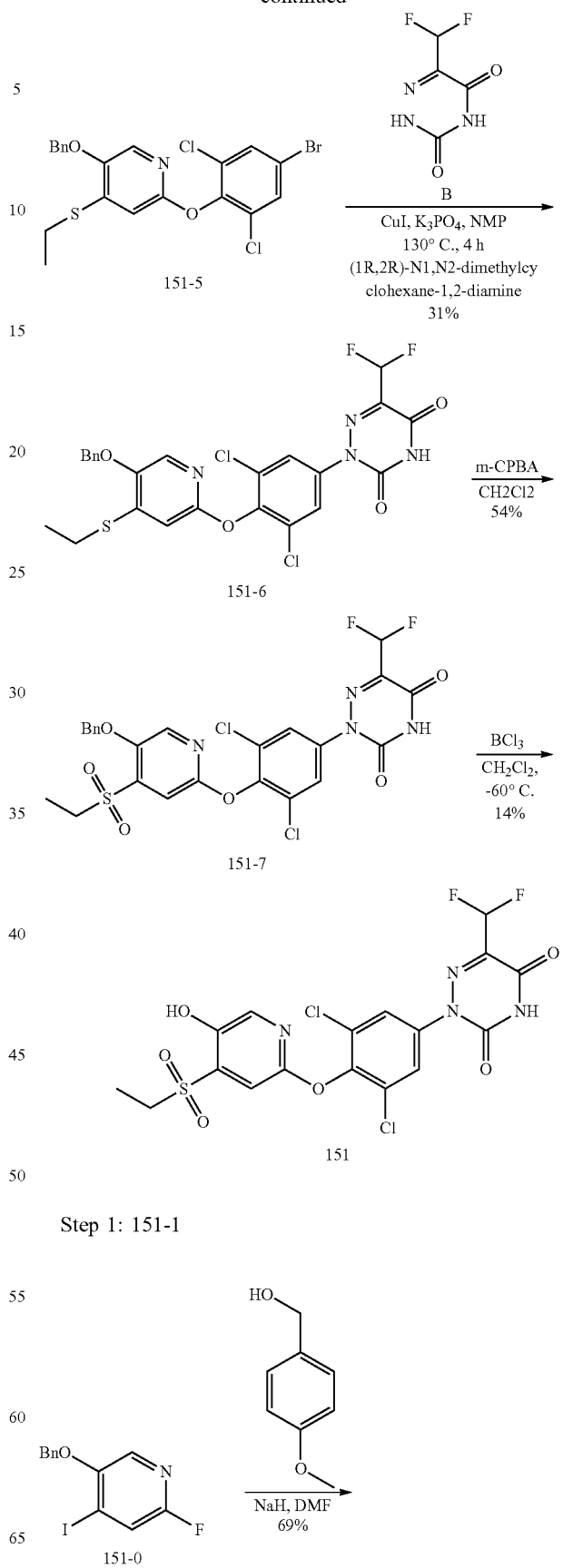

Step 1: 151-1

-continued

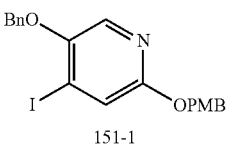
151-1

To a mixture of (4-methoxyphenyl) methanol (1.01 g, 7.29 mmol, 907.70 uL) in DMF (20 mL) was added NaH (60% in mineral oil) (204.17 mg, 8.51 mmol) at 0° C. The mixture was stirred at 0° C. for 0.5 h. Then 5-benzyloxy-2-fluoro-4-iodo-pyridine 151-0 (2.0 g, 6.08 mmol) was added and the mixture was stirred at 80° C. for 0.5 h. LCMS showed the product was formed. The reaction mixture was poured into water, extracted with EtOAc (50 mL) and washed with brine (3×50 mL). The combined organic layer was dried over anhydrous $Na_2SO_4$, filtered and concentrated in vacuum to afford a residue. The residue was purified by column chromatography (PE:EtOAc=10:1) to give 5-benzyloxy-4-iodo-2-[(4-methoxyphenyl) methoxy] pyridine 151-1 (1.88 g, 69% yield) as a yellow solid. LCMS: $[M+Na]^+=470.1$ Step 2: 151-2

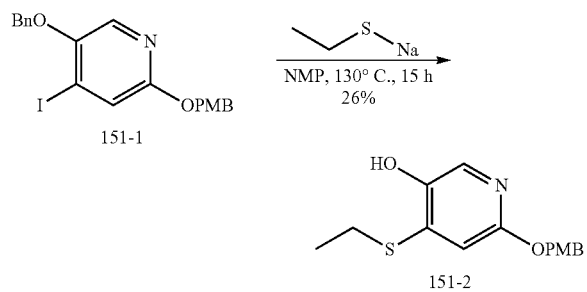

A mixture of 5-benzyloxy-4-iodo-2-[(4-methoxyphenyl) methoxy]pyridine 151-1 (1.2 g, 2.68 mmol) and sodium ethanethiolate (1.13 g, 13.41 mmol) in NMP (10 mL) was stirred at 130° C. for 15 h. LCMS showed the product was formed. The reaction mixture was poured into water, extracted with EtOAc (50 mL) and washed with brine (3×50 mL). The organic layer was dried over $Na_2SO_4$ and concentrated in vacuum. The residue was purified by flash chromatography (PE:EtOAc=3:1) to give 4-ethylsulfanyl-6-[(4-methoxyphenyl) methoxy] pyridin-3-ol 151-2 (210 mg, 26% yield) as a yellow solid. LCMS: $[M+H]^+=292.2$ Step 3: 151-3

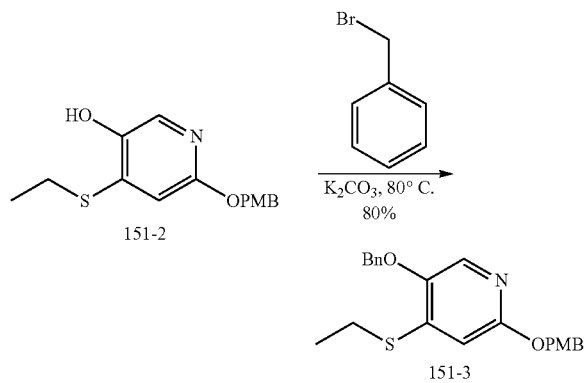

A mixture of 4-ethylsulfanyl-6-[(4-methoxyphenyl) methoxy]pyridin-3-ol 151-2 (200 mg, 686.42 umol), benzyl bromide (129.14 mg, 755.07 umol, 89.68 uL) and $K_2CO_3$ (189.45 mg, 1.37 mmol) in DMF (3 mL) was stirred at 80° C. for 3 h. LCMS showed the product was formed. The reaction mixture was poured into water, extracted with EtOAc (50 mL) and washed with brine (3×50 mL). The organic layer was dried over $Na_2SO_4$ and concentrated in vacuum. The residue was purified by flash chromatography (PE:EtOAc=10:1) to give 5-benzyloxy-4-ethylsulfanyl-2-[(4-methoxyphenyl) methoxy] pyridine 151-3 (210 mg, 80% yield) as a yellow solid. LCMS: $[M+H]^+=382.1$ Step 4: 151-4

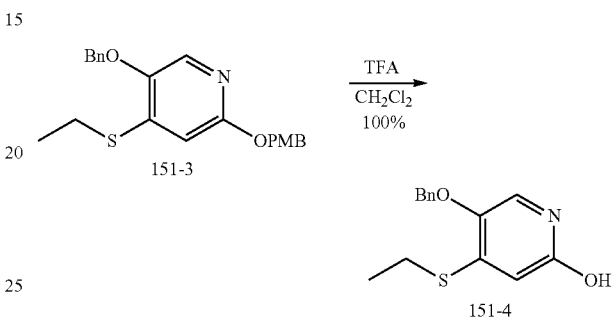

To a solution of 5-benzyloxy-4-ethylsulfanyl-2-[(4-methoxyphenyl) methoxy] pyridine 151-3 (210 mg, 550.48 umol) in $CH_2Cl_2$ (3 mL) was added TFA (1.48 g, 12.98 mmol, 1 mL). The mixture was stirred at rt for 0.5 h. LCMS showed the product was formed. The mixture was poured into saturated $NaHCO_3$ (50 mL) and extracted with EtOAc (3×50 mL). The organic layer was dried over $Na_2SO_4$ and concentrated in vacuum. The residue was used in next step without purification. LCMS: $[M+H]^+=262.2$ Step 5: 151-5

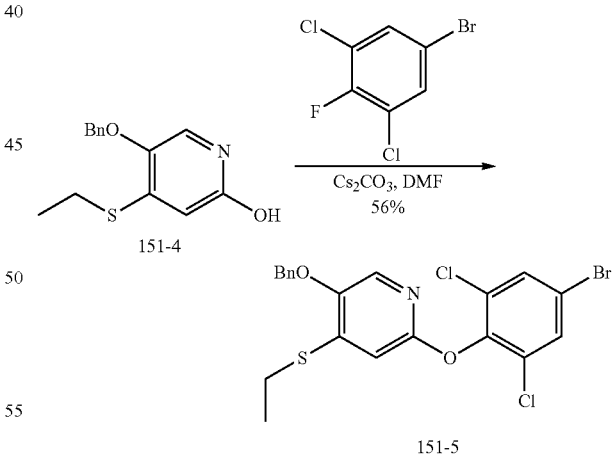

A mixture of 5-benzyloxy-4-ethylsulfanyl-pyridin-2-ol 151-4 (180 mg, 688.76 umol), 5-bromo-1,3-dichloro-2-fluoro-benzene (201.58 mg, 826.51 umol) and $Cs_2CO_3$ (449.07 mg, 1.38 mmol) in DMF (5 mL) was stirred at 120° C. for 3 h. LCMS showed the reaction was completed. The reaction mixture was poured into water, extracted with EtOAc (50 mL) and washed with brine (3×50 mL). The organic layer was dried over $Na_2SO_4$ and concentrated in vacuum. The residue was purified by flash chromatography (PE:EtOAc=20:1) to give 5-benzyloxy-2-(4-bromo-2,6-dichloro-phenoxy)-4-ethylsulfanyl-pyridine 151-5 (190 mg, 56% yield) as a yellow solid. LCMS: [M+H]⁺=484.0/486.1/488.0

Step 6: 151-6

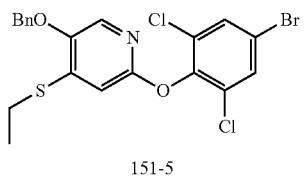

151-5

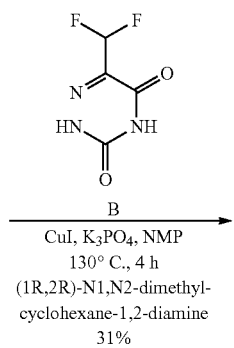

B
CuI, K₃PO₄, NMP
130° C., 4 h
(1R,2R)-N1,N2-dimethyl-cyclohexane-1,2-diamine
31%

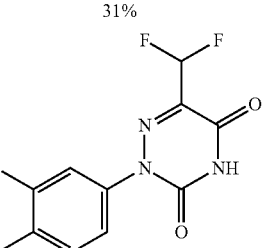

151-6

A mixture of 5-benzyloxy-2-(4-bromo-2,6-dichloro-phenoxy)-4-ethylsulfanyl-pyridine 151-5 (190 mg, 391.57 umol), 6-(difluoromethyl)-2H-1,2,4-triazine-3,5-dione B (127.72 mg, 783.15 umol), (1R,2R)—N1,N2-dimethylcyclohexane-1,2-diamine (44.56 mg, 313.26 umol), CuI (186.44 mg, 978.94 umol) and K₃PO₄ (249.04 mg, 1.17 mmol, 116.92 uL) in NMP (10 mL) was stirred in a sealed tube at 130° C. for 4 h. LCMS showed the product was formed. The reaction mixture was added into EtOAc (50 mL) and to the resulting mixture was added 0.2N HCl (50 mL). The mixture was filtered and the filtrate was extracted with EtOAc (50 mL*2). The combined organic layers were washed with brine (50 mL), dried over anhydrous Na₂SO₄, filtered and concentrated in vacuum to afford a residue. The residue was purified by column chromatography (CH₂Cl₂:CH₃OH=20:1) to afford 2-[4-[(5-benzyloxy-4-ethylsulfanyl-2-pyridyl)oxy]-3,5-dichloro-phenyl]-6-(difluoromethyl)-1,2,4-triazine-3,5-dione 151-6 (70 mg, 31% yield) as a yellow solid. LCMS: [M+H]⁺=567.0/569.0

Step 7: 151-7

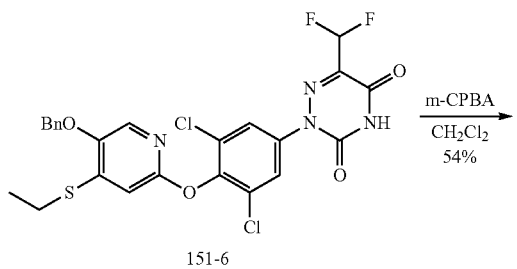

151-6

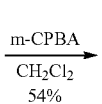

m-CPBA
CH₂Cl₂
54%

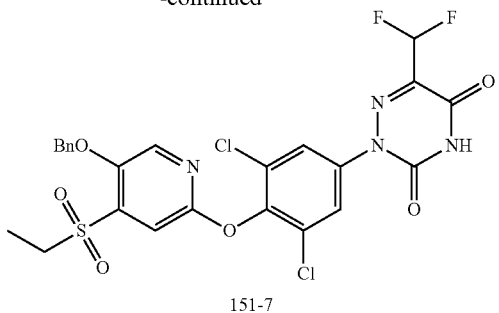

151-7

To a solution of 2-[4-[(5-benzyloxy-4-ethylsulfanyl-2-pyridyl)oxy]-3,5-dichloro-phenyl]-6-(difluoromethyl)-1,2,4-triazine-3,5-dione 151-6 (70 mg, 123.37 umol) in CH₂Cl₂ (3 mL) was added m-CPBA (78.46 mg, 456.16 umol). The mixture was stirred at rt for 1 h. LCMS showed the product was formed. The reaction mixture was poured into water and extracted with EtOAc (3×10 mL). The combined organic layer was dried over anhydrous Na₂SO₄, filtered and concentrated in vacuum to afford a residue. The residue was purified by column chromatography (CH₂Cl₂:CH₃OH=20:1) to afford 2-[4-[(5-benzyloxy-4-ethylsulfonyl-2-pyridyl)oxy]-3,5-dichloro-phenyl]-6-(difluoromethyl)-1,2,4-triazine-3,5-dione 151-7 (40 mg, 54% yield) as a yellow solid. LCMS: [M+H]⁺=599.0/600.9

Step 8: 151

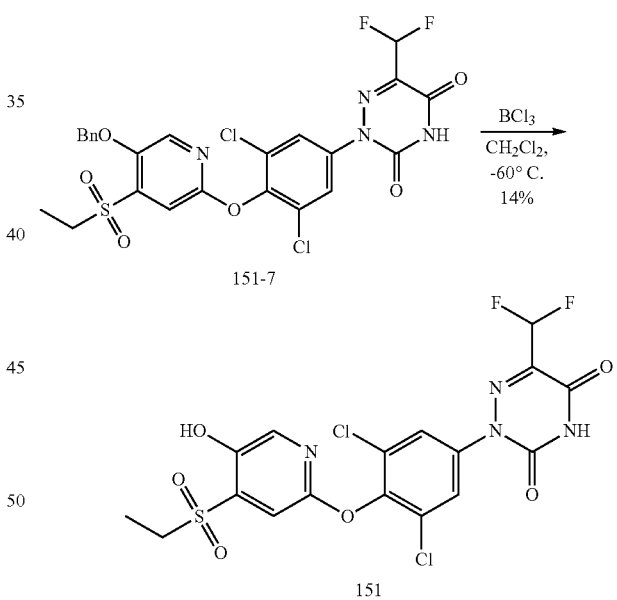

To a solution of 2-[4-[(5-benzyloxy-4-ethylsulfonyl-2-pyridyl)oxy]-3,5-dichloro-phenyl]-6-(difluoromethyl)-1,2,4-triazine-3,5-dione 151-7 (40 mg, 66.73 umol) in CH₂Cl₂ (3 mL) was added BCl₃ (1M in CH₂Cl₂) (0.5 mmol, 0.5 mL) at −60° C. The mixture was stirred at −60° C. for 1 h. LCMS showed the product was formed. The reaction mixture was poured into saturated aqueous NaHCO₃ (30 mL) and extracted with EtOAc (3×10 mL). The combined organic layer was dried over anhydrous Na₂SO₄, filtered and concentrated in vacuum to afford a residue. The residue was purified by Prep-HPLC (Xbridge 5 u C18 150×19 mm, MeCN—H₂O (0.1% FA), Gradient: 43-53%) to afford 2-[3, 5-dichloro-4-[(4-ethylsulfonyl-5-hydroxy-2-pyridyl) oxy]phenyl]-6-(difluoromethyl)-1,2,4-triazine-3,5-dione 151 (4.8 mg, 14% yield) as a white solid. LCMS: [M+H]$^+$=509.0/511.0. $^1$H NMR (400 MHz, DMSO-d$_6$) δ 12.82 (brs, 1H), 11.41 (brs, 1H), 7.98 (s, 1H), 7.80 (s, 2H), 7.42 (s, 1H), 6.91 (t, J=52.4 Hz, 1H), 3.54 (q, J=7.4 Hz, 2H), 1.17 (t, J=7.4 Hz, 3H). $^{19}$F NMR (376 MHz, DMSO-d$_6$)) δ−122.15 (s, 2F).
Example 61: Synthesis of Compound 152
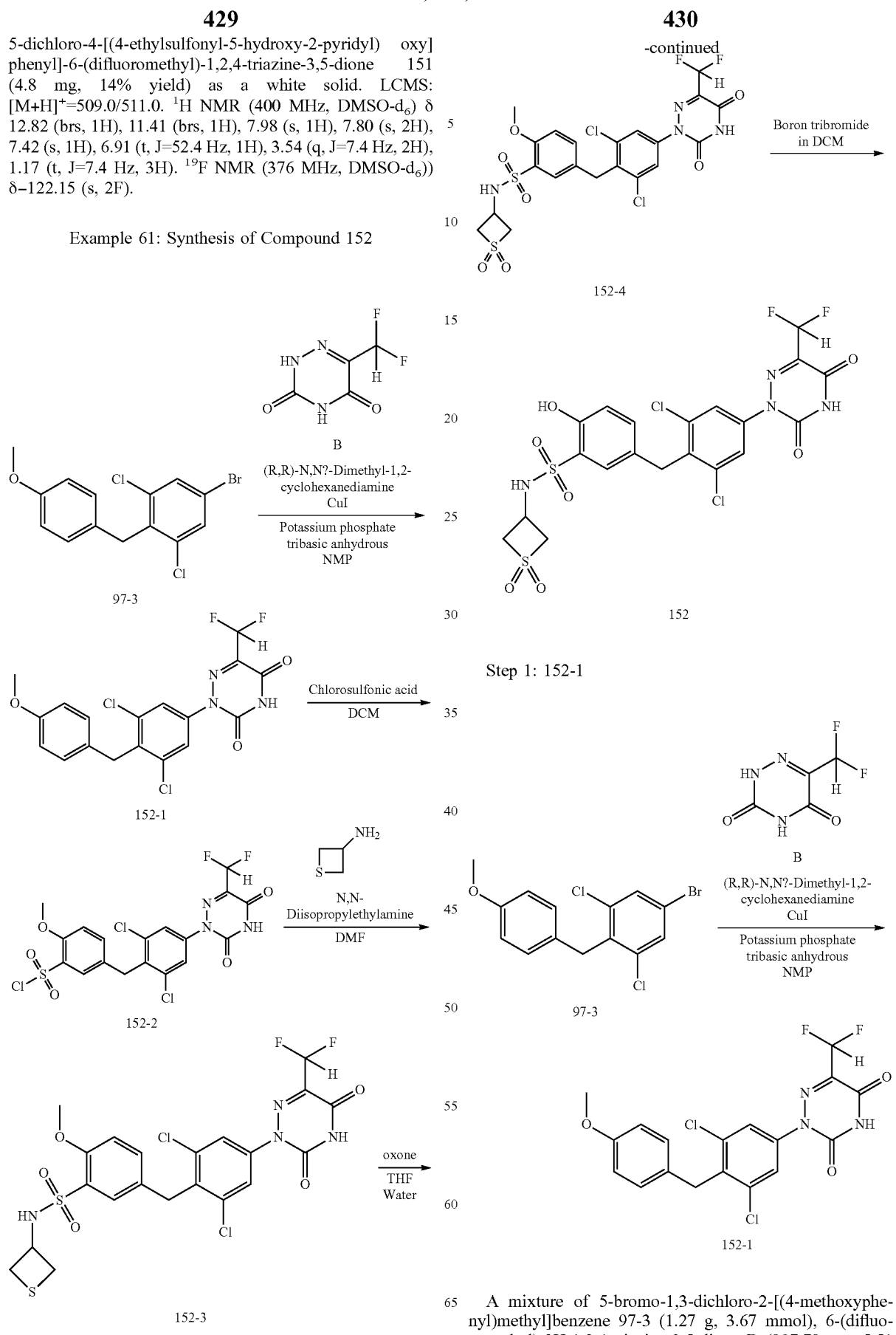
Step 1: 152-1
A mixture of 5-bromo-1,3-dichloro-2-[(4-methoxyphenyl)methyl]benzene 97-3 (1.27 g, 3.67 mmol), 6-(difluoromethyl)-2H-1,2,4-triazine-3,5-dione B (897.78 mg, 5.51 mmol), (R,R)—N,N'-Dimethyl-1,2-cyclohexanediamine (261.01 mg, 1.84 mmol), CuI (1.75 g, 9.18 mmol, 310.92 uL), anhydrous potassium phosphate (1.56 g, 7.34 mmol) and NMP (13 mL) was stirred at 130° C. for 2 hr. The mixture was poured into aq. NH₄Cl (300 mL), extracted with EtOAc (150 mL*3), washed by brine (50 mL), dried over Na₂SO₄ and filtered. The filtrate was concentrated. The residue was purified by FCC (MeOH in DCM, 0-2%, v/v) to afford 2-[3,5-dichloro-4-[(4-methoxyphenyl)methyl]phenyl]-6-(difluoromethyl)-1,2,4-triazine-3,5-dione 152-1 (1.5 g, crude) as yellow oil. LCMS: [M+H]⁺=428.0/430.0.

Step 2: 152-2

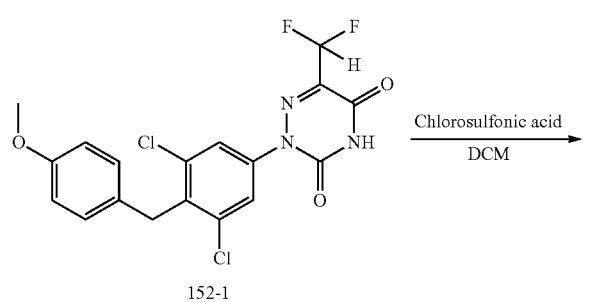

152-1

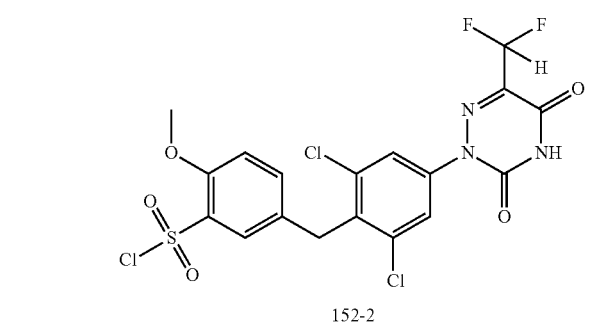

152-2

To a solution of 2-[3,5-dichloro-4-[(4-methoxyphenyl)methyl]phenyl]-6-(difluoromethyl)-1,2,4-triazine-3,5-dione 152-1 (1.2 g, 2.80 mmol) in DCM (100 mL) was added chlorosulfonic acid (21.00 g, 180.22 mmol, 12.00 mL) at 0° C. The mixture was stirred at 0° C. for 15 min. The mixture was poured into ice water, extracted with DCM (20 mL*2), washed by water (20 mL), diluted with EtOAc (30 mL), dried over Na₂SO₄ and filtered. The filtrate was concentrated to afford crude 5-[[2,6-dichloro-4-[6-(difluoromethyl)-3,5-dioxo-1,2,4-triazin-2-yl]phenyl]methyl]-2-methoxy-benzenesulfonyl chloride 152-2 (1.5 g) as yellow oil.

Step 3: 152-3

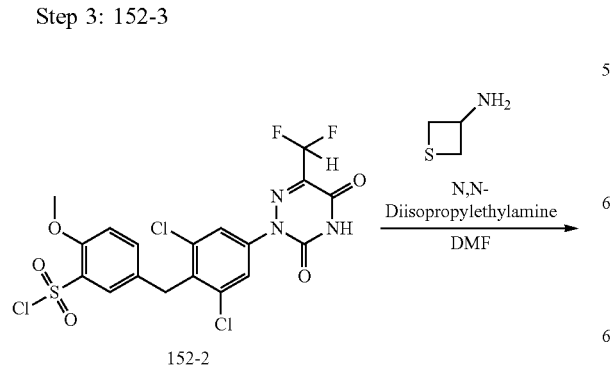

152-2

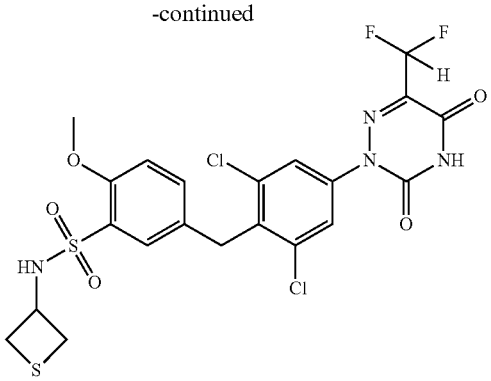

152-3

To a mixture of N,N-Diisopropylethylamine (1.48 g, 11.48 mmol, 2 mL) and thietan-3-amine hydrochloride (381.59 mg, 3.04 mmol) in DMF (25 mL) was added 5-[[2,6-dichloro-4-[6-(difluoromethyl)-3,5-dioxo-1,2,4-triazin-2-yl]phenyl]methyl]-2-methoxy-benzenesulfonyl chloride 152-2 (800 mg, 1.52 mmol). The mixture was stirred at rt for 1 hr. Then the mixture was poured into aq. NaHCO₃ (100 mL), extracted with EtOAc (60 mL*3), washed by brine (30 mL), dried over Na₂SO₄, filtered and concentrated. The residue was purified by FCC (MeOH in DCM, 0-10%, v/v) to afford 5-[[2,6-dichloro-4-[6-(difluoromethyl)-3,5-dioxo-1,2,4-triazin-2-yl]phenyl]methyl]-2-methoxy-N-(thietan-3-yl)benzenesulfonamide 152-3 (562 mg, crude) as a white solid. LCMS: [M+H]⁺=579.1/581.1.

Step 4: 152-4

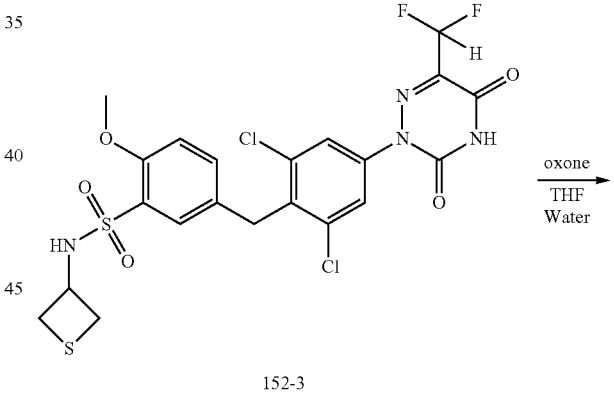

152-3

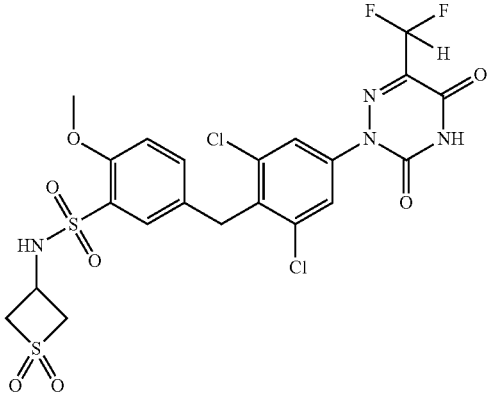

152-4

A mixture of 5-[[2,6-dichloro-4-[6-(difluoromethyl)-3,5-dioxo-1,2,4-triazin-2-yl]phenyl]methyl]-2-methoxy-N-(thietan-3-yl)benzenesulfonamide 152-3 (562 mg, 969.93 umol) and oxone (2.39 g, 3.88 mmol) in THF (8 mL) and water (8 mL) was stirred at rt for 16 hr. The mixture was poured into water (50 mL), extracted with EtOAc (50 mL*2), washed with brine (40 mL), dried over Na$_2$SO$_4$ and filtered. The filtrate was concentrated to afford crude 5-[[2,6-dichloro-4-[6-(difluoromethyl)-3,5-dioxo-1,2,4-triazin-2-yl]phenyl]methyl]-N-(1,1-dioxothietan-3-yl)-2-methoxy-benzenesulfonamide 152-4 (576 mg) as a white solid. LCMS: [M+H]$^+$=611.1/613.1.

Step 5:152

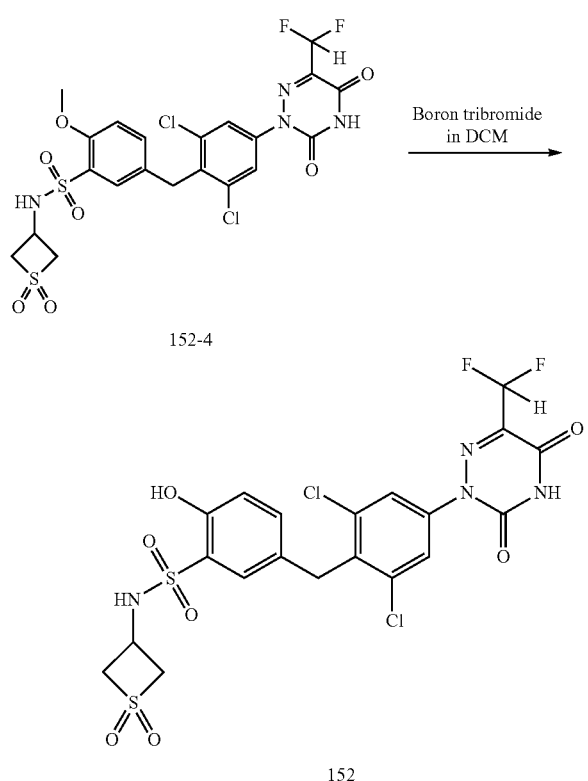

A mixture of 5-[[2,6-dichloro-4-[6-(difluoromethyl)-3,5-dioxo-1,2,4-triazin-2-yl]phenyl]methyl]-N-(1,1-dioxothietan-3-yl)-2-methoxy-benzenesulfonamide 152-4 (576 mg, 942.07 umol) and boron tribromide (1 M in DCM, 30 mL) was stirred at 45° C. for 2 hr. LCMS showed the product formed. The mixture was concentrated, diluted with DCM (20 mL) and quenched with MeOH (5 mL) at −78° C. The mixture was concentrated to give a residue which was purified by FCC (ODS column, CH$_3$CN/0.1% HCOOH in water) to afford 5-[[2,6-dichloro-4-[6-(difluoromethyl)-3,5-dioxo-1,2,4-triazin-2-yl]phenyl]methyl]-N-(1,1-dioxothietan-3-yl)-2-hydroxy-benzenesulfonamide 152 (83 mg, 132.30 umol, 14.04% yield) as a white solid. LCMS: [M+H]$^+$=597.1/599.1. $^1$H NMR (400 MHz, Methanol-d$_4$) δ 7.64 (s, 2H), 7.48 (d, J=2.4 Hz, 1H), 7.23 (dd, J=8.5, 2.4 Hz, 1H), 6.83 (d, J=8.5 Hz, 1H), 6.60 (t, J=52.9 Hz, 1H), 4.24 (s, 2H), 4.18-4.06 (m, 2H), 4.06-3.96 (m, 1H), 3.96-3.86 (m, 2H)

Example 62: Synthesis of Compound 153

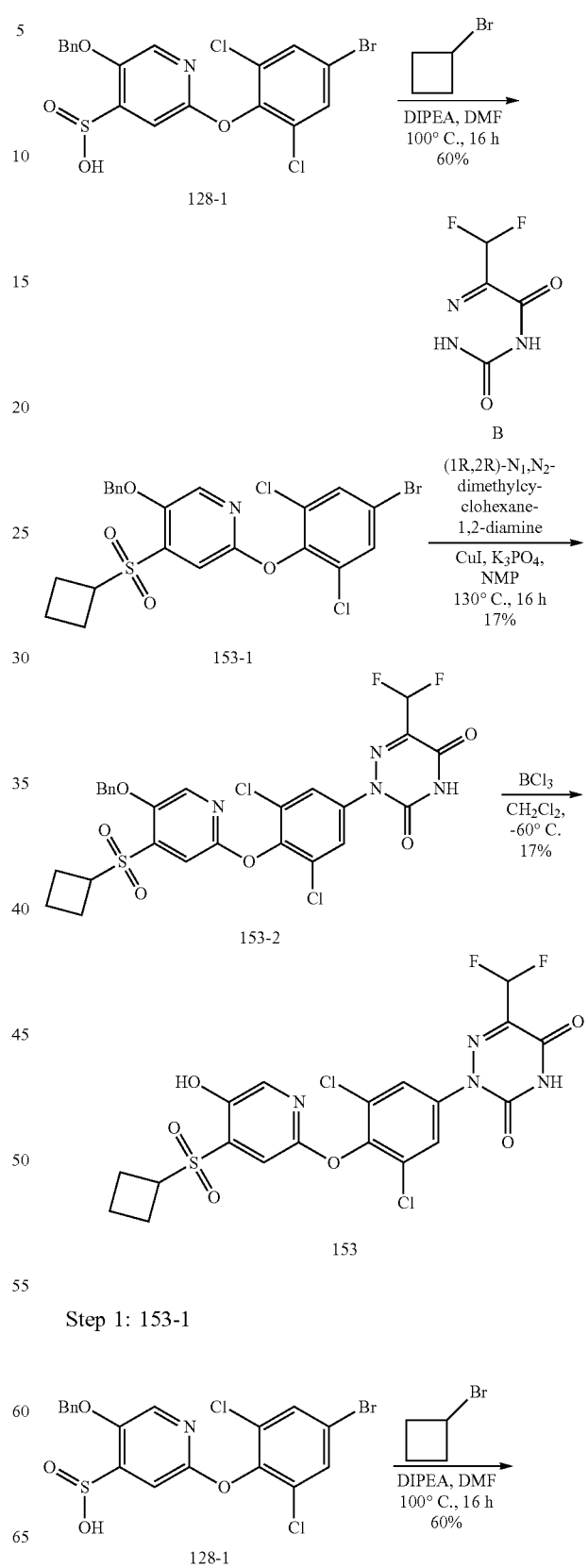

Step 1: 153-1

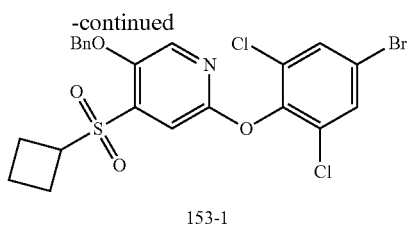

153-1

To a mixture of 5-benzyloxy-2-(4-bromo-2,6-dichloro-phenoxy)-pyridine-4-sulfinic acid 128-1 (300 mg, 613.29 umol) in DMF (5 mL) was added bromocyclobutane (1.24 g, 9.20 mmol) and DIPEA (118.89 mg, 919.93 umol, 160.23 uL). The mixture was stirred at 100° C. for 16 h in a steal tube. LCMS showed the starting material was consumed and the product was found. The reaction mixture was washed with water (5 mL) and extracted with EtOAc (3×10 mL). The combined organic layer was washed with brine (5 mL), dried over anhydrous $Na_2SO_4$, filtered and concentrated in vacuum to afford a residue. The residue was purified by silica gel chromatography (PE:EtOAc=5:1) to afford 5-benzyloxy-2-(4-bromo-2,6-dichloro-phenoxy)-4-cyclobutylsulfonyl-pyridine 153-1 (200 mg, 60% yield) as a yellow oil. LCMS: $[M+H]^+$=542.0/544.0

Step 2: 153-2

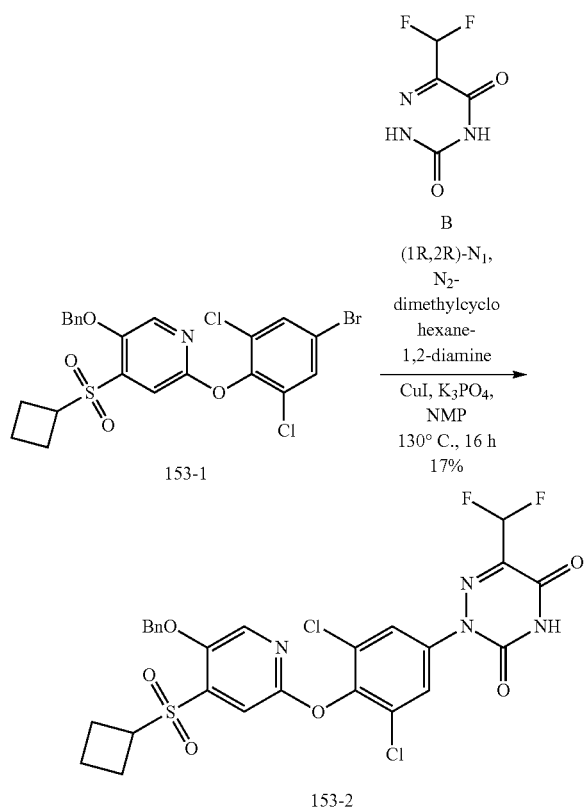

To a mixture of 5-benzyloxy-2-(4-bromo-2,6-dichloro-phenoxy)-4-cyclobutylsulfonyl-pyridine 153-1 (200 mg, 368.15 umol) in NMP (3 mL) was added 6-(difluoromethyl)-2H-1,2,4-triazine-3,5-dione B (120.08 mg, 736.30 umol), (1R,2R)—N1,N2-dimethylcyclohexane-1,2-diamine (41.89 mg, 294.52 umol, 46.44 uL), $K_3PO_4$ (234.14 mg, 1.10 mmol) and CuI (175.29 mg, 920.37 umol). The mixture was stirred at 130° C. for 16 h. LCMS showed the starting material was consumed and the product was found. The reaction mixture was added into EtOAc (10 mL) and to the mixture was added 0.2N HCl (10 mL). The mixture was filtered and the filtrate was extracted with EtOAc (10 mL*2). The combined organic layers were washed with brine (10 mL), dried over anhydrous $Na_2SO_4$, filtered and concentrated in vacuum to afford a residue. The residue was purified by silica gel chromatography ($CH_2Cl_2$:$CH_3OH$=10:1) to afford 2-[4-[(5-benzyloxy-4-cyclobutylsulfonyl-2-pyridyl)oxy]-3,5-dichloro-phenyl]-6-(difluoromethyl)-1,2,4-triazine-3,5-dione 153-2 (40 mg, 17% yield) as a yellow solid. LCMS: $[M+H]^+$=625.1/627.1

Step 3: 153

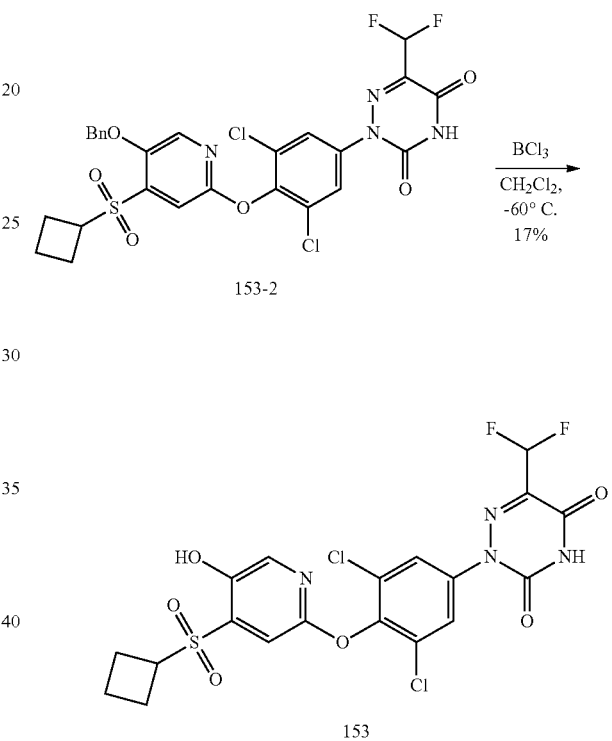

To a mixture of 2-[4-[(5-benzyloxy-4-cyclobutylsulfonyl-2-pyridyl)oxy]-3,5-dichloro-phenyl]-6-(difluoromethyl)-1,2,4-triazine-3,5-dione 153-2 (40 mg, 63.96 umol) in $CH_2Cl_2$ (2 mL) was added $BCl_3$ (1 M in $CH_2Cl_2$) (0.64 mL, 0.64 mmol) slowly at −60° C. The mixture was stirred at −60° C. for 1 h. LCMS showed the starting material was consumed and the product was found. The reaction mixture was poured into Sat. $NaHCO_3$ (5 mL) and extracted with EtOAc (3×10 mL). The combined organic layer was washed with brine (5 mL), dried over anhydrous $Na_2SO_4$, filtered and concentrated in vacuum to afford a residue. The residue was purified by prep-HPLC (Xbridge 5 u C18 150×19 mm, MeCN—$H_2O$ (0.1% FA), Gradient: 36-46%) to afford 2-[3,5-dichloro-4-[(4-cyclobutylsulfonyl-5-hydroxy-2-pyridyl)oxy]phenyl]-6-(difluoromethyl)-1,2,4-triazine-3,5-dione (6.0 mg, 17% yield) 153 as a white solid. LCMS: $[M+H]^+$=534.9/536.9. $^1$H NMR (400 MHz, $CD_3OD$) δ 7.80 (s, 1H), 7.77 (s, 1H), 7.45 (s, 1H), 6.71 (t, J=52.8 Hz, 1H), 4.50-4.46 (m, 1H), 2.54-2.49 (m, 2H), 2.27-2.25 (m, 2H), 2.08-2.06 (m, 2H). $^{19}$F NMR (376 MHz, $CD_3OD$) δ−124.2 (s, 2F).

Example 63: Synthesis of Compound 154
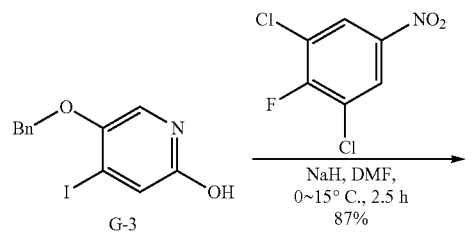
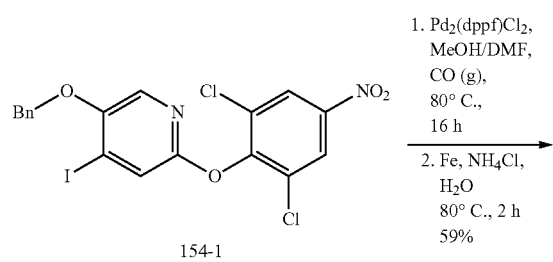
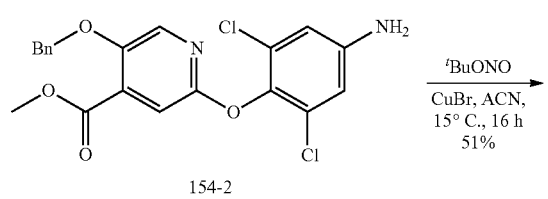
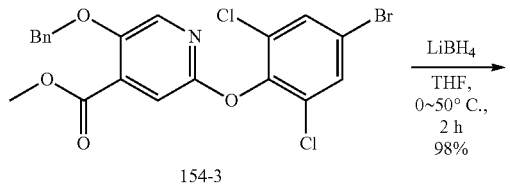
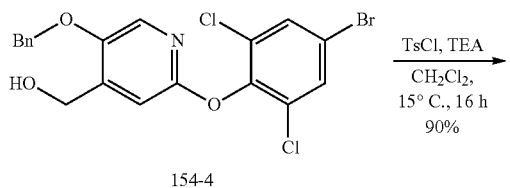
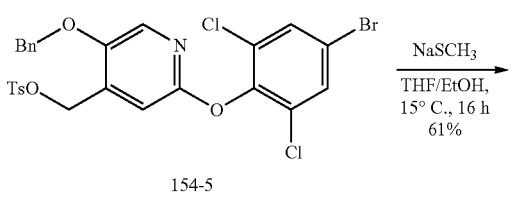
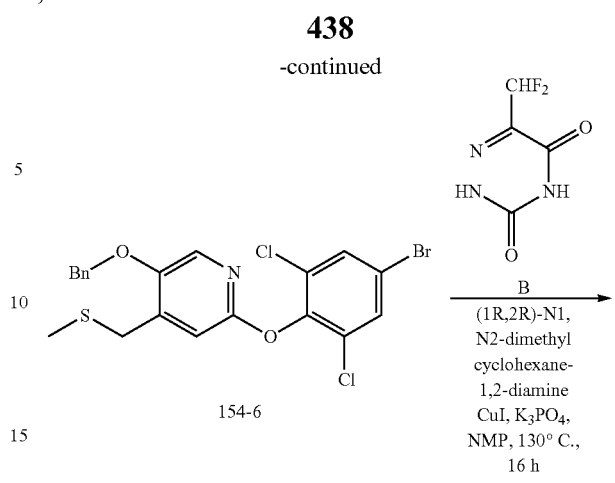
Step 1: 154-1

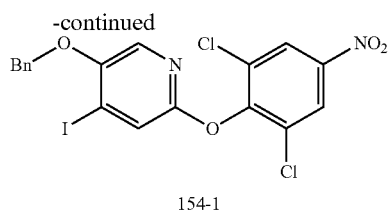

154-1

To a solution of 5-benzyloxy-4-iodo-pyridin-2-ol G-3 (1 g, 3.06 mmol) in DMF (20 mL) was added NaH (183.40 mg, 4.59 mmol, 60% in mineral oil) at 0° C. and the mixture was stirred for 30 min. Then 1,3-dichloro-2-fluoro-5-nitro-benzene (834.52 mg, 3.97 mmol) was added and the mixture was stirred at 15° C. under $N_2$ (g) for 2 h. LC-MS) showed the reaction was completed. The reaction mixture was poured into water (50 mL) and extracted with EtOAc (3×40 mL). The combined organic layer was washed with brine (20 mL), dried over anhydrous $Na_2SO_4$ and filtered. The filtrate was concentrated in vacuum to afford a residue. The residue was purified by flash column chromatography (PE: EtOAc=10:1 to 5:1) to afford 5-benzyloxy-2-(2,6-dichloro-4-nitro-phenoxy)-4-iodo-pyridine 154-1 (1.38 g, 87% yield) as a yellow solid. LCMS: $[M+H]^+=517.0/519.0$.

Step 2: 154-2

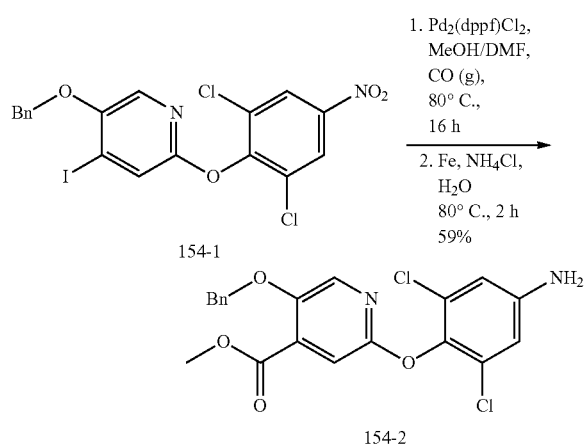

To a solution of 5-benzyloxy-2-(2,6-dichloro-4-nitro-phenoxy)-4-iodo-pyridine 154-1 (1.38 g, 2.67 mmol) in methanol (20 mL) and DMF (46 mL) were added TEA (810.15 mg, 8.01 mmol) and cyclopentyl(diphenyl)phosphane; dichloromethane; dichloropalladium iron (217.94 mg, 266.87 umol). The mixture was stirred at 80° C. under CO (balloon) for 16 h. LC-MS showed the starting material was consumed. The mixture was cooled and diluted with $H_2O$ (40 mL). Then $NH_4Cl$ (713.77 mg, 13.34 mmol) and Fe (745.18 mg, 13.34 mmol) were added. The mixture was stirred at 80° C. for 2 h. LC-MS showed the reaction was completed. The reaction mixture was filtered and concentrated. The residue was diluted with water (50 mL) and extracted with EtOAc (3×30 mL). The combined organic layer was washed with brine (3×20 mL), dried over anhydrous $Na_2SO_4$ and filtered. The filtrate was concentrated in vacuum to afford a residue. The residue was purified by flash column chromatography (PE:EtOAc=2:1) to afford methyl 2-(4-amino-2,6-dichloro-phenoxy)-5-benzyloxy-pyridine-4-carboxylate 154-2 (670 mg, 59% yield) as a yellow solid. LCMS: $[M+H]^+=419.0/421.0$.

Step 3: 154-3

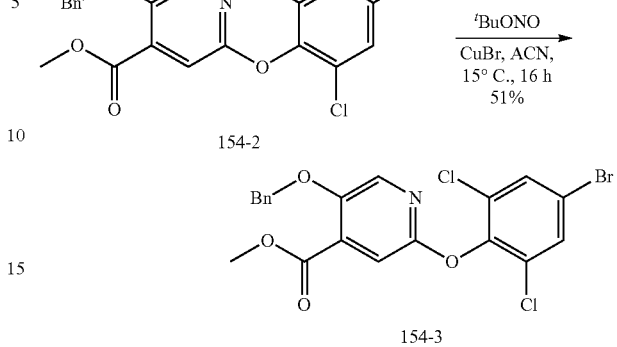

To a suspension of methyl 2-(4-amino-2,6-dichloro-phenoxy)-5-benzyloxy-pyridine-4-carboxylate 154-2 (670 mg, 1.60 mmol) and CuBr (458.48 mg, 3.20 mmol) in MeCN (20 mL) was added $^t$BuONO (329.58 mg, 3.20 mmol). The mixture was stirred at 15° C. under $N_2$ (g) for 16 h. LCMS showed the reaction was completed. The reaction mixture was concentrated in vacuum to afford a residue. The residue was purified by flash column chromatography (PE: EtOAc=15:1) to afford methyl 5-benzyloxy-2-(4-bromo-2,6-dichloro-phenoxy)pyridine-4-carboxylate 154-3 (400 mg, 51% yield) as a yellow solid. LCMS: $[M+H]^+=482.4/484.0/486.0$.

Step 4: 154-4

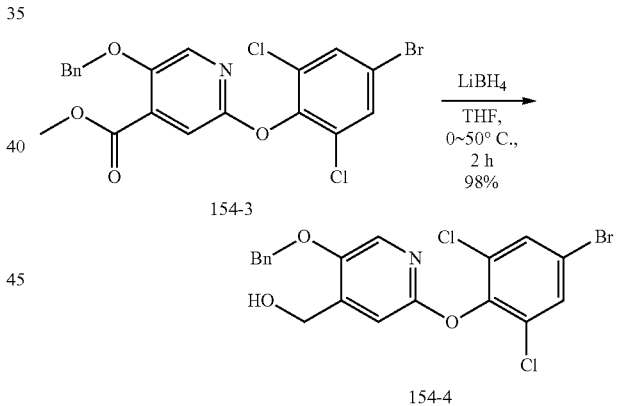

To a solution of methyl 5-benzyloxy-2-(4-bromo-2,6-dichloro-phenoxy)pyridine-4-carboxylate 154-3 (400 mg, 827.92 umol) in THF (5 mL) was added $LiBH_4$ (2 M in THF, 827.92 uL) at 0° C. The mixture was stirred at 50° C. under $N_2$ (g) for 2 h. LC-MS showed the reaction was completed. MeOH (10 mL) was added dropwise. The mixture was poured into saturated aqueous $NH_4Cl$ (50 mL) and extracted with EtOAc (3×50 mL). The combined organic layer was washed with brine (3×20 mL), dried over anhydrous $Na_2SO_4$ and filtered. The filtrate was concentrated in vacuum to afford a residue. The residue was crude [5-benzyloxy-2-(4-bromo-2,6-dichloro-phenoxy)-4-pyridyl]methanol 154-4 (370 mg, 98% yield). It's a yellow solid and used in the next step directly without further purification. LCMS: $[M+H]^+=454.0/456.0/458.0$.

Step 5: 154-5

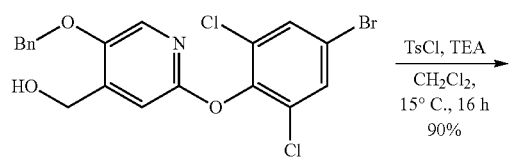

To a solution of [5-benzyloxy-2-(4-bromo-2,6-dichloro-phenoxy)-4-pyridyl]methanol 154-4 (370 mg, 812.96 umol) and TEA (164.53 mg, 1.63 mmol) in CH₂Cl₂ (10 mL) were added 4-methylbenzenesulfonyl chloride (232.48 mg, 1.22 mmol) and N,N-dimethylpyridin-4-amine (9.93 mg, 81.30 umol). The mixture was stirred at 15° C. under N₂ (g) for 16 h. LC-MS showed the reaction was completed. The reaction mixture was poured into water (50 mL) and extracted with EtOAc (3×30 mL). The combined organic layer was washed with brine (30 mL), dried over anhydrous Na₂SO₄ and filtered. The filtrate was concentrated in vacuum to afford a residue. The residue was crude [5-benzyloxy-2-(4-bromo-2,6-dichloro-phenoxy)-4-pyridyl]methyl 4-methylbenzenesulfonate 154-5 (450 mg, 90% yield). It's a yellow solid and used in the next step directly without further purification. LCMS: [M+H]⁺=608.0/610.0/612.0.

Step 6: 154-6

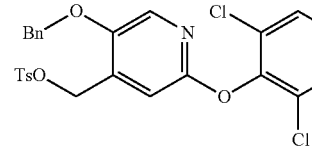

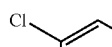

To a solution of sodium methanethiolate (181.82 mg, 2.41 mmol) in EtOH (15 mL) was added [5-benzyloxy-2-(4-bromo-2,6-dichloro-phenoxy)-4-pyridyl]methyl 4-methyl-benzenesulfonate 154-5 (490 mg, 804.18 umol) in THF (10 mL). The mixture was stirred at 15° C. for 16 h. LC-MS showed the reaction was completed. The reaction mixture was poured into water (50 mL) and extracted with EtOAc (3×30 mL). The combined organic layer was washed with brine (30 mL), dried over anhydrous Na₂SO₄ and filtered. The filtrate was concentrated in vacuum to afford a residue. The residue was purified by silica gel chromatography (PE:EtOAc=20:1) to afford 5-benzyloxy-2-(4-bromo-2,6-dichloro-phenoxy)-4-(methylsulfanylmethyl)pyridine 154-6 (240 mg, 61% yield) as a white solid. LCMS: [M+H]⁺=484.0/486.0/488.0.

Step 7: 154-7

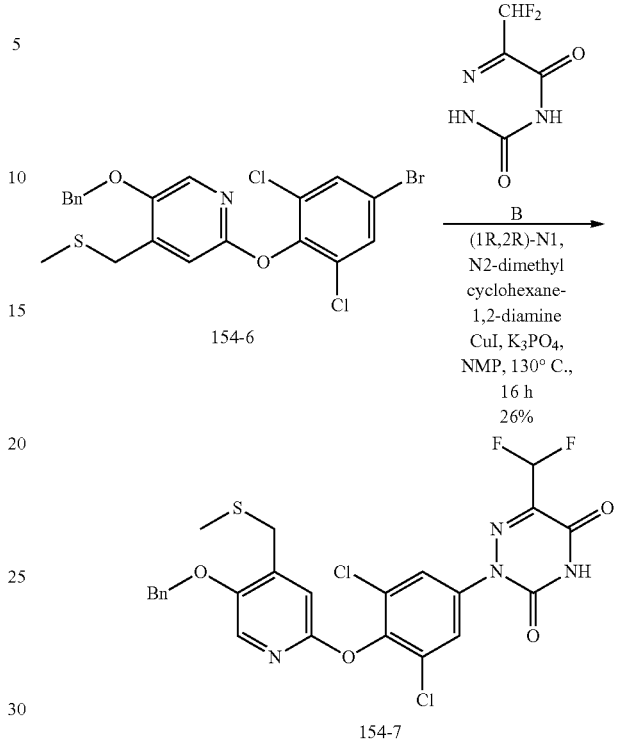

To a solution of 5-benzyloxy-2-(4-bromo-2,6-dichloro-phenoxy)-4-(methylsulfanylmethyl)pyridine 154-6 (100 mg, 206.09 umol) and 6-(difluoromethyl)-2H-1,2,4-triazine-3,5-dione B (67.22 mg, 412.18 umol) in NMP (2 mL) were added (1R,2R)—N1,N2-dimethylcyclohexane-1,2-diamine (20.52 mg, 144.26 umol), CuI (98.13 mg, 515.23 umol) and K₃PO₄ (131.24 mg, 618.27 umol). The mixture was stirred at 130° C. in a sealed tube for 16 h. LC-MS showed the product was formed. The reaction mixture was diluted with EtOAc (50 mL) and water (50 mL). Then 2N HCl was added to adjust pH to 5-6. The mixture was filtered through celite. The filtrate was extracted with EtOAc (3×50 mL), washed with brine (3×20 mL), dried over anhydrous Na₂SO₄ and filtered. The filtrate was concentrated in vacuum to afford a residue. The residue was purified by flash column chromatography (CH₂Cl₂:CH₃OH=20:1) to afford 2-[4-[[5-benzy-loxy-4-(methylsulfanylmethyl)-2-pyridyl]oxy]-3,5-di-chloro-phenyl]-6-(difluoromethyl)-1,2,4-triazine-3,5-dione 154-7 (30 mg, 26% yield) as a yellow solid. LCMS: [M+H]⁺=567.1/569.1.

Step 8: 154-8

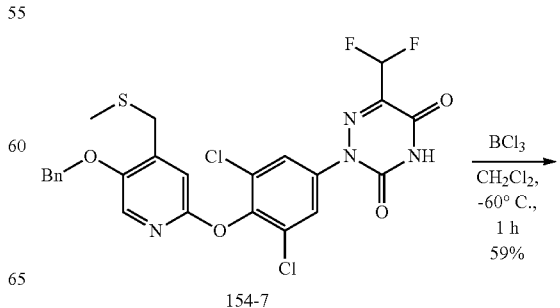

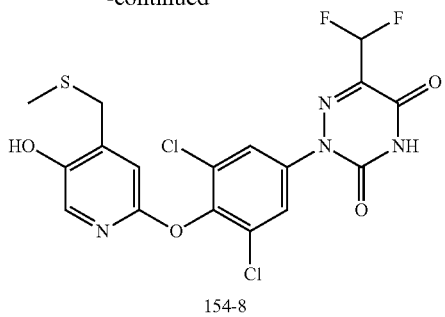

154-8

To a solution of 2-[4-[[5-benzyloxy-4-(methylsulfanylmethyl)-2-pyridyl]oxy]-3,5-dichloro-phenyl]-6-(difluoromethyl)-1,2,4-triazine-3,5-dione 154-7 (30 mg, 52.87 umol) in CH₂Cl₂ (1 mL) was added boron trichloride (1 M in CH₂Cl₂, 528.74 uL) at −60° C. and the mixture was stirred at −60° C. for 1 h. LC-MS showed product was formed. The reaction mixture was poured into saturated aqueous NaHCO₃ (20 mL). The mixture was extracted with EtOAc (3×20 mL), washed with brine (3×20 mL), dried over anhydrous Na₂SO₄ and filtered. The filtrate was concentrated in vacuum to afford a residue. The residue was crude 2-[3,5-dichloro-4-[[5-hydroxy-4-(methylsulfanylmethyl)-2-pyridyl]oxy]phenyl]-6-(difluoromethyl)-1,2,4-triazine-3,5-dione 154-8 (25 mg, 59% yield, 60% purity). It's a yellow oil and used to the next step directly without further purification. LCMS: [M+H]⁺=477.0/479.0.

Step 9: 154

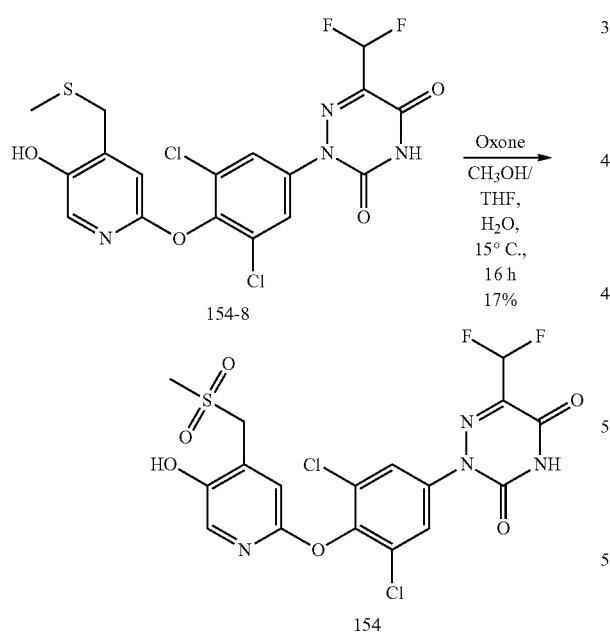

To a solution of 2-[3,5-dichloro-4-[[5-hydroxy-4-(methylsulfanylmethyl)-2-pyridyl]oxy]phenyl]-6-(difluoromethyl)-1,2,4-triazine-3,5-dione 154-8 (25 mg, 31.43 umol, 60% purity) in water (1 mL), CH₃OH (1 mL) and THF (3 mL) was added NaHCO₃ (13.20 mg, 157.14 umol) and oxone (28.98 mg, 47.14 umol). The mixture was stirred at 15° C. for 16 h. LC-MS showed the reaction was completed. The reaction mixture was diluted with water (10 mL) and extracted with EtOAc (3×10 mL). The combined organic layer was washed with brine (20 mL), dried over anhydrous Na₂SO₄ and filtered. The filtrate was concentrated in vacuum to afford a residue. The residue was purified by Prep-TLC (CH₂Cl₂:CH₃OH=10:1) to give a crude product. The crude product was purified with reversed flash column chromatography (C18 spherical 40-60 um 100 A, MeCN—H₂O (0.1% FA), Gradient: 30-40%, 20 ml/min) to afford 2-[3,5-dichloro-4-[[5-hydroxy-4-(methylsulfonylmethyl)-2-pyridyl]oxy]phenyl]-6-(difluoromethyl)-1,2,4-triazine-3,5-dione 154 (2.8 mg, 17% yield) as a white solid. LCMS: [M+H]⁺=509.0/511.0. ¹H NMR (400 MHz, CD₃OD) δ 7.75 (s, 2H), 7.65 (s, 1H), 7.13 (s, 1H), 6.70 (t, J=53.2 Hz, 1H), 4.57-4.52 (d, J=16 Hz, 2H), 2.95 (s, 3H). ¹⁹F NMR (376 MHz, CD₃OD) δ−124.14 (s, 2F).

Example 64: Synthesis of Compound 156

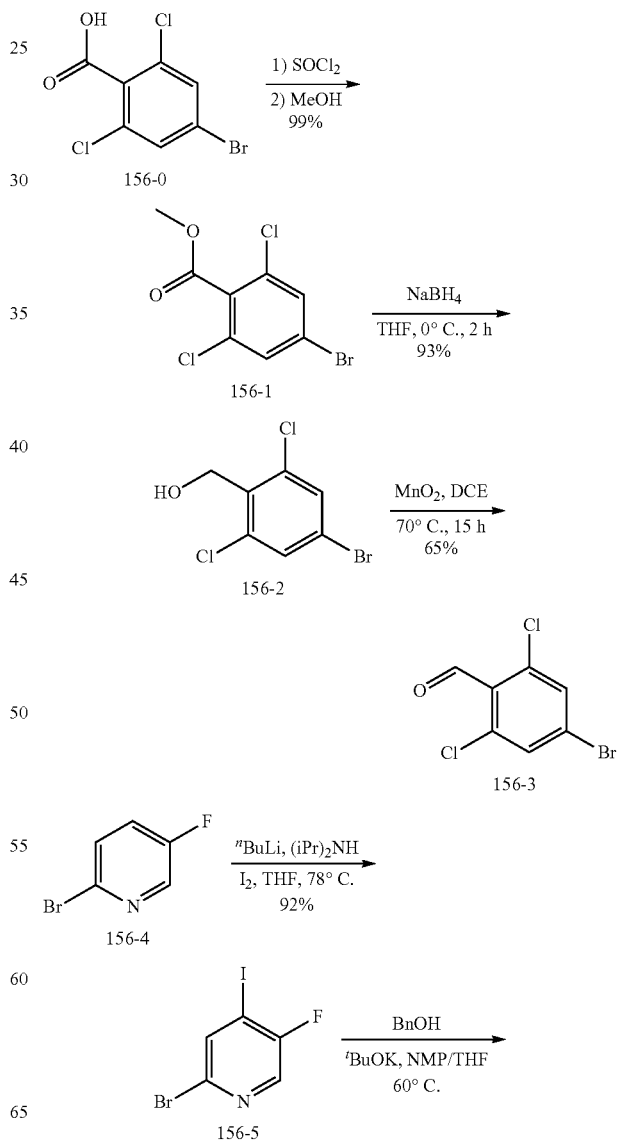

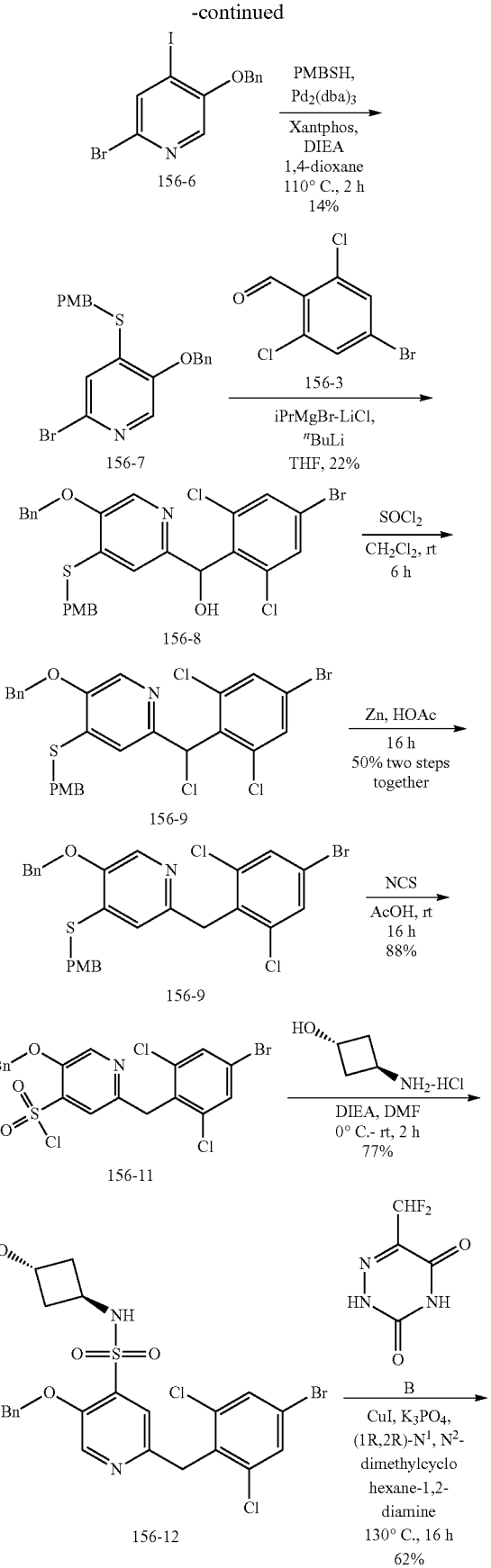
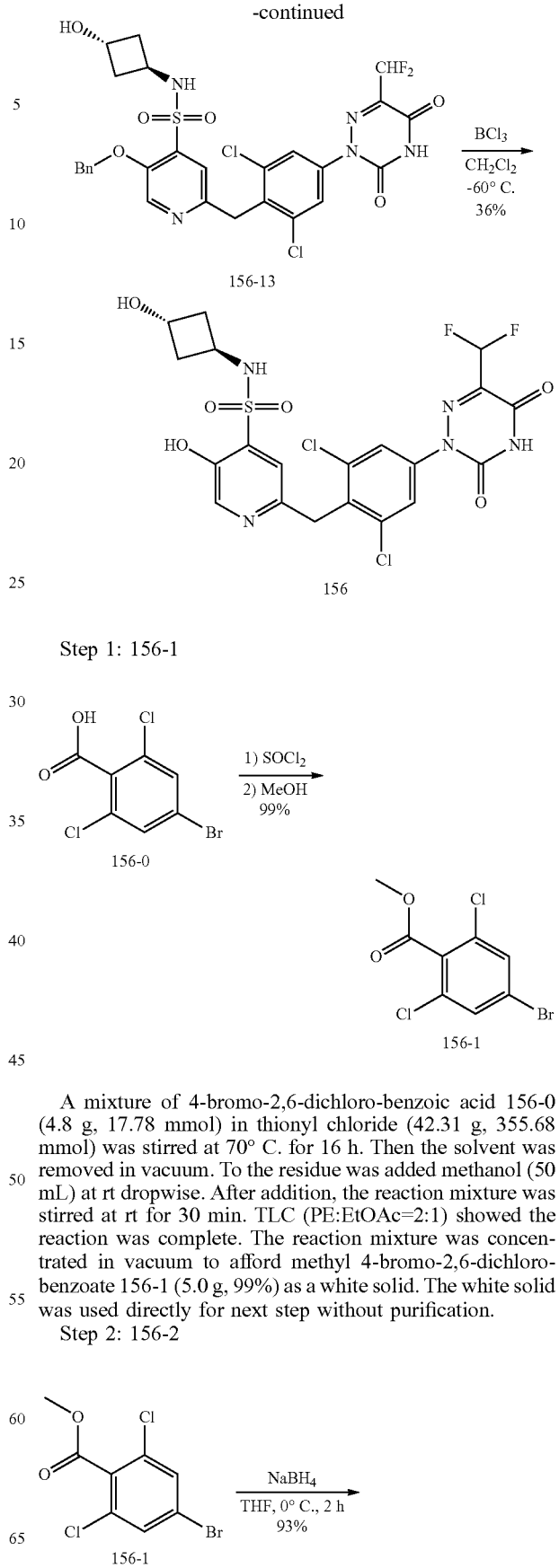

Step 1: 156-1

A mixture of 4-bromo-2,6-dichloro-benzoic acid 156-0 (4.8 g, 17.78 mmol) in thionyl chloride (42.31 g, 355.68 mmol) was stirred at 70° C. for 16 h. Then the solvent was removed in vacuum. To the residue was added methanol (50 mL) at rt dropwise. After addition, the reaction mixture was stirred at rt for 30 min. TLC (PE:EtOAc=2:1) showed the reaction was complete. The reaction mixture was concentrated in vacuum to afford methyl 4-bromo-2,6-dichloro-benzoate 156-1 (5.0 g, 99%) as a white solid. The white solid was used directly for next step without purification.

Step 2: 156-2

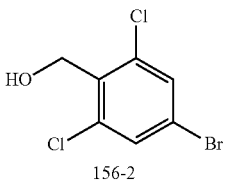

To a mixture of methyl 4-bromo-2,6-dichloro-benzoate 156-1 (5.0 g, 17.61 mmol) in THF (50 mL) at 0° C. was added NaBH₄ (2.01 g, 52.83 mmol) portion wise. The reaction mixture was stirred at 0° C. for 2 h. TLC (PE: EtOAc=2:1) showed the reaction was complete. The reaction mixture was poured into water (50 mL) and extracted with EtOAc (3×20 mL). The combined organic layer was washed with brine (20 mL), dried over anhydrous Na₂SO₄ and filtered. The filtrate was concentrated in vacuum to afford (4-bromo-2,6-dichloro-phenyl) methanol 156-2 (4.2 g, 93%) as a white solid. The white solid was used directly in next step without purification.

Step 3: 156-3

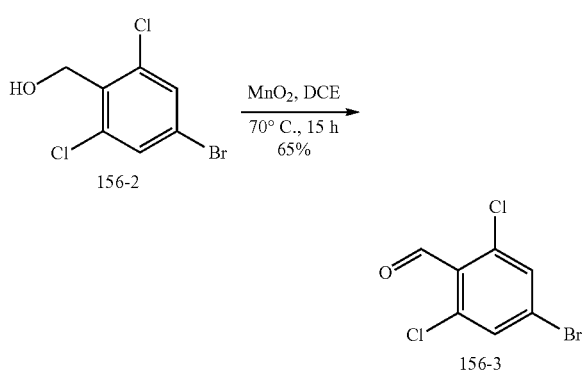

A mixture of (4-bromo-2,6-dichloro-phenyl)methanol 156-2 (9.3 g, 36.34 mmol) and manganese dioxide (63.18 g, 726.78 mmol) in dichloroethane (100 mL) was stirred at 70° C. for 15 h. TLC (PE:EtOAc=6:1) showed the reaction was complete. The solid was filtered through celite and washed with CH₂Cl₂ (3×30 mL). The combined filtrate was concentrated in vacuum. The residue was purified by column chromatography (PE:EtOAc=10:1) to afford 4-bromo-2,6-dichloro-benzaldehyde 156-3 (6.0 g, 65%) as a white solid.

Step 4: 156-5

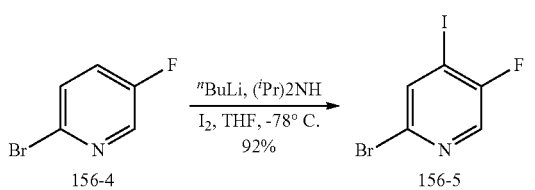 [SMILES: Fc1ccc(Br)nc1 ; Fc1cnc(Br)cc1I]

To a solution of diisopropyl amine (1.26 g, 12.50 mmol, 1.76 mL) in anhydrous THF (10 mL) at 0° C. was added n-butyllithium (2.5 M, 4.55 mL) dropwise. The reaction mixture was stirred at 0° C. for 30 min and then cooled to −78° C. A solution of 2-bromo-5-fluoro-pyridine 156-4 (2.0 g, 11.36 mmol) in anhydrous THF (10 mL) was added dropwise. The reaction mixture was stirred for 15 min and then a solution of iodine (3.17 g, 12.50 mmol) in anhydrous THF (10 mL) was added at −78° C. The reaction mixture was stirred for another 10 min. LC-MS showed the reaction was complete. Water (200 mL) was added to the reaction mixture at −78° C. which was then extracted with EtOAc (3×20 mL). The combined organic layer was washed with brine (20 mL), dried over anhydrous Na₂SO₄ and filtered. The filtrate was concentrated in vacuum. The residue was purified by silica gel chromatography (PE:EtOAc=100:1) to afford 2-bromo-5-fluoro-4-iodo-pyridine 156-5 (3.18 g, 92%) as a light-yellow solid. LCMS: [M+H]⁺=302.0/304.0.

Step 5: 156-6

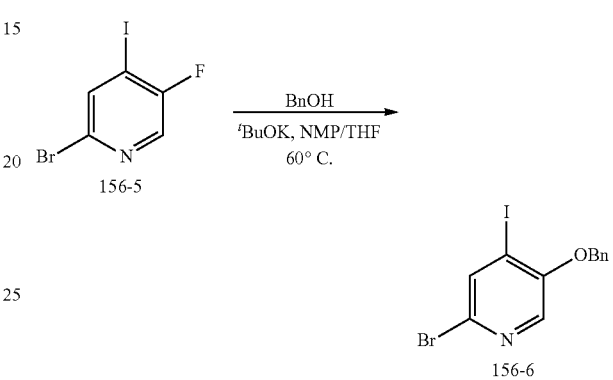

A mixture of 2-bromo-5-fluoro-4-iodo-pyridine 156-5 (4.0 g, 13.25 mmol), phenylmethanol (7.16 g, 66.25 mmol, 6.82 mL) and potassium tert-butoxide (1.49 g, 13.25 mmol) in THF (60 mL) and NMP (30 mL) was stirred at 60° C. for 6 h. TLC (PE:EtOAc=10:1) showed the reaction was complete. The reaction mixture was poured into sat. NH₄Cl (100 mL) and extracted with EtOAc (3×50 mL). The combined organic layer was washed with brine (20 mL), dried over anhydrous Na₂SO₄ and filtered. The filtrate was concentrated in vacuum. The residue was purified by silica gel chromatography (PE:EtOAc=50: 1-20:1) to afford 5-benzyloxy-2-bromo-4-iodo-pyridine 156-6 (2.0 g, crude) as a white solid. LCMS: [M+H]⁺=390.0/392.0.

Step 6: 156-7

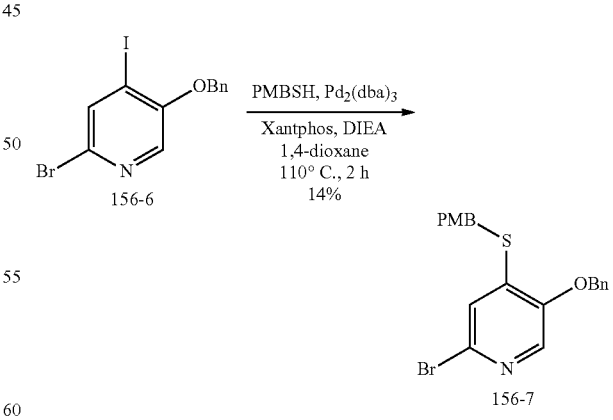

A mixture of 5-benzyloxy-2-bromo-4-iodo-pyridine 156-6 (8.48 g, 21.74 mmol), (4-methoxyphenyl) methanethiol (1.68 g, 10.87 mmol), N,N-Diisopropylethylamine (5.62 g, 43.49 mmol, 7.57 mL), (1E,4E)-1,5-diphenylpenta-1,4-dien-3-one; palladium (625.11 mg, 1.09 mmol) and (5-diphenylphosphanyl-9,9-dimethyl-xanthen-4-yl)-diphenyl-phosphane (1.26 g, 2.17 mmol) in 1,4-dioxane (150 mL) was stirred at 110° C. for 2 h. LC-MS showed the reaction was complete. The reaction mixture was poured into water (100 mL) and extracted with EtOAc (3×20 mL). The combined organic layer was washed with brine (20 mL), dried over anhydrous Na$_2$SO$_4$ and filtered. The filtrate was concentrated in vacuum. The residue was purified by silica gel chromatography (PE:EtOAc=10:1) to afford 5-(benzyloxy)-2-bromo-4-((4-methoxybenzyl) thio) pyridine 156-7 (1.34 g, 14%) as a light-yellow solid. LCMS: [M+H]$^+$=416.0/418.0.

Step 7: 156-8

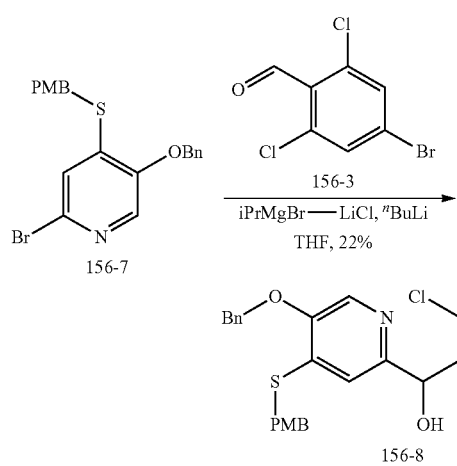

To a solution of 5-benzyloxy-2-bromo-4-[(4-methoxyphenyl) methyl sulfanyl] pyridine 156-7 (500 mg, 1.20 mmol) in THF (10 mL) at 0° C. was added isopropyl magnesium chloride-lithium chloride complex (1.3 M in THF, 923.82 uL). The reaction mixture was stirred for 30 min. Then n-Butyllithium (2.4 M, 500.40 uL) was added into the reaction mixture. The reaction mixture was stirred for 30 min. Then 4-bromo-2,6-dichlorobenzaldehyde (304.94 mg, 1.20 mmol) in THF (3 mL) was added into the reaction mixture at −10° C. The reaction mixture was stirred at rt for 2 h. LC-MS showed the reaction worked. The reaction mixture was poured into sat. NH$_4$Cl (50 mL) and extracted with EtOAc (3×20 mL). The combined organic layer was washed with brine (20 mL), dried over anhydrous Na$_2$SO$_4$ and filtered. The filtrate was concentrated in vacuum. The residue was purified by silica gel chromatography (PE: EtOAc=5:1~ EtOAc:MeOH=12:1) to afford [5-benzyloxy-4-[(4-methoxyphenyl)methylsulfanyl]-2-pyridyl]-(4-bromo-2,6-dichloro-phenyl) methanol 156-8 (162 mg, 22%) as a light-yellow solid. LCMS: [M+H]$^+$=590.0/592.0.

Step 8: 156-9

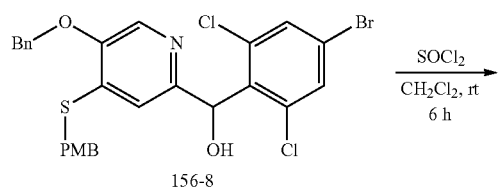

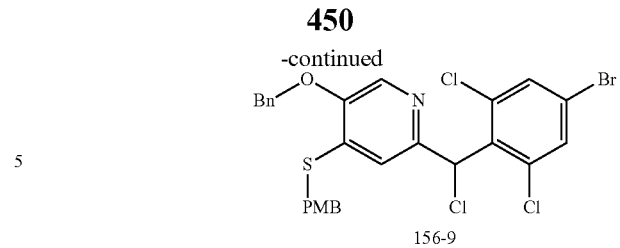

To a solution of [5-benzyloxy-4-[(4-methoxyphenyl) methyl sulfanyl]-2-pyridyl]-(4-bromo-2,6-dichloro-phenyl) methanol 156-8 (167 mg, 282.41 umol) in CH$_2$Cl$_2$ (5 mL) at rt was added SOCl$_2$ (4 mL). The reaction mixture was stirred at rt for 6 h. LC-MS showed the reaction was complete. The reaction mixture was concentrated in vacuum to afford 5-benzyloxy-2-[(4-bromo-2,6-dichloro-phenyl)-chloro-methyl]-4-[(4-methoxyphenyl) methylsulfanyl] pyridine 156-9 (167 mg, crude) as a yellow solid. It was used directly for next step without purification. LCMS: [M+H]$^+$=608.0/610.0.

Step 9: 156-10

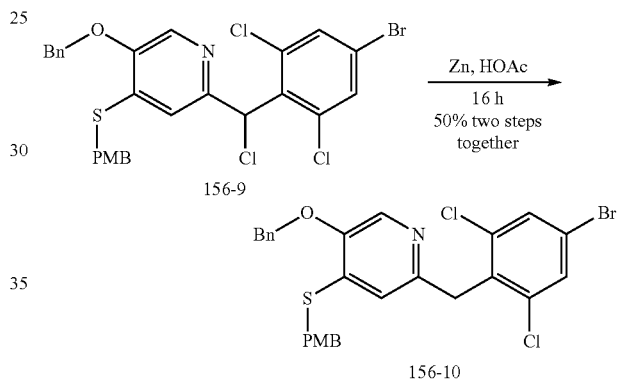

To a solution of 5-benzyloxy-2-[(4-bromo-2,6-dichloro-phenyl)-chloro-methyl]-4-[(4-methoxyphenyl) methylsulfanyl] pyridine 156-9 (167 mg, 273.87 umol) in HOAc (5 mL) at rt was added Zn (179.05 mg, 2.74 mmol). The reaction mixture was stirred at rt for 16 h. LC-MS showed the reaction was complete. The reaction mixture was poured into sat. NaHCO$_3$ (50 mL) and extracted with EtOAc (3×20 mL). The combined organic layer was washed with brine (20 mL), dried over anhydrous Na$_2$SO$_4$ and filtered. The filtrate was concentrated in vacuum. The residue was purified by silica gel chromatography (PE:EtOAc=10:1) to afford 5-benzyloxy-2-[(4-bromo-2,6-dichloro-phenyl) methyl]-4-[(4-methoxyphenyl) methylsulfanyl] pyridine 156-10 (79 mg, 50% for steps 8&9 together) as a light-yellow solid. LCMS: [M+H]$^+$=574.0/576.0.

Step 10: 156-11

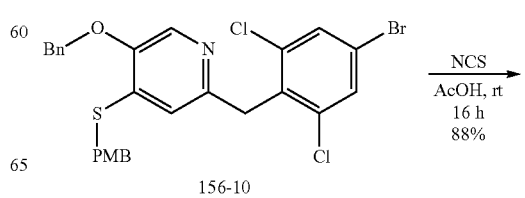

-continued

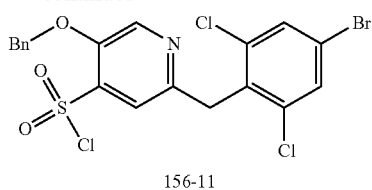

156-11

To a mixture of 5-(benzyloxy)-2-(4-bromo-2,6-dichlorobenzyl)-4-((4-methoxybenzyl) thio) pyridine 156-10 (230 mg, 399.76 umol) in water (3 mL) and HOAc (9 mL) at rt was added NCS (213.52 mg, 1.60 mmol). The reaction mixture was stirred at rt for 16 h. LC-MS showed the reaction was complete. The reaction mixture was poured into sat. NaHCO₃ (200 mL) and extracted with EtOAc (3×20 mL). The combined organic layer was washed with brine (20 mL), dried over anhydrous Na₂SO₄ and filtered. The filtrate was concentrated in vacuum. The residue was purified by silica gel chromatography (PE:EtOAc=10:1) to afford 5-(benzyloxy)-2-(4-bromo-2,6-dichlorobenzyl) pyridine-4-sulfonyl chloride 156-11 (185 mg, 88% yield) as a light-yellow solid. LCMS: [M+H]⁺=520.0/522.0.

Step 11: 156-12

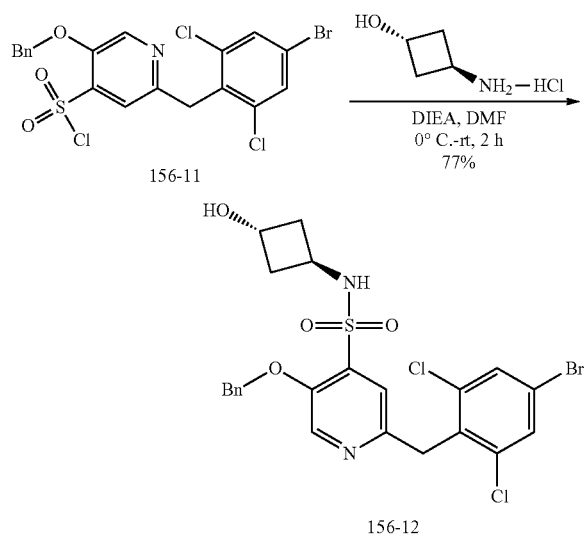

To a solution of 3-aminocyclobutanol hydrochloride 156-11 (65.74 mg, 531.98 umol) and N,N-Diisopropylethylamine (137.51 mg, 1.06 mmol, 185.32 uL) in DMF (5 mL) at rt was added 5-benzyloxy-2-[(4-bromo-2,6-dichloro-phenyl)methyl]pyridine-4-sulfonyl chloride 156-11 (185 mg, 354.65 umol). The reaction mixture was stirred at rt for 2 h. LC-MS showed the reaction was complete. The reaction mixture was poured into water (50 mL) and extracted with EtOAc (3×20 mL). The combined organic layer was washed with brine (20 mL), dried over anhydrous Na₂SO₄ and filtered. The filtrate was concentrated in vacuum. The residue was purified by silica gel chromatography (PE: EtOAc=1:1) to afford 5-benzyloxy-2-[(4-bromo-2,6-dichloro-phenyl) methyl]-N-(3-hydroxycyclobutyl) pyridine-4-sulfonamide 156-12 (157 mg, 77%) as a light-yellow solid. LCMS: [M+H]⁺=571.0/573.0.

Step 12: 156-13

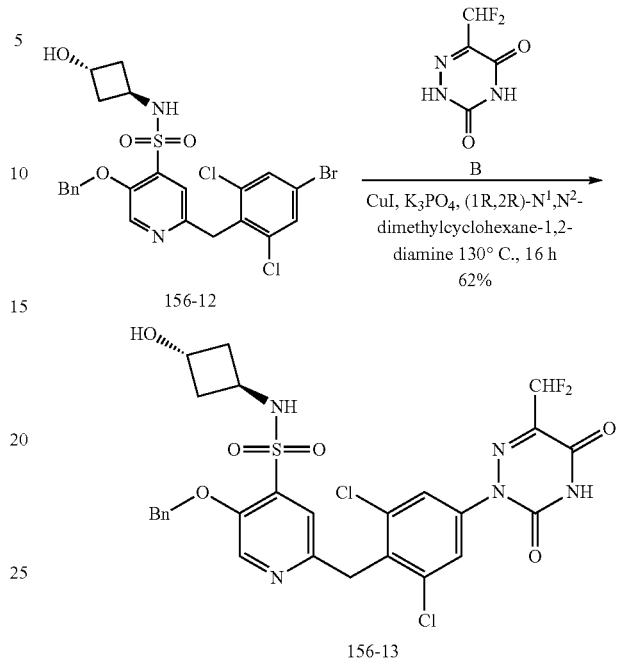

A mixture of 5-benzyloxy-2-[(4-bromo-2,6-dichloro-phenyl)methyl]-N-(3-hydroxycyclobutyl)pyridine-4-sulfonamide 156-12 (67 mg, 117.07 umol), 6-(difluoromethyl)-3H-1,2,2,4-triazine-3,5(4H)-dione B (37.95 mg, 234.14 umol), cuprous iodide (66.89 mg, 351.22 umol), potassium phosphate (124.25 mg, 585.36 umol) and (1R,2R)—N1,N2-dimethylcyclohexane-1,2-diamine (19.98 mg, 140.49 umol) in NMP (3 mL) was stirred at 130° C. for 16 h. LC-MS showed the reaction worked. The reaction mixture was poured into 1N HCl (50 mL) and extracted with EtOAc (3×20 mL). The combined organic layer was washed with brine (20 mL), dried over anhydrous Na₂SO₄ and filtered. The filtrate was concentrated in vacuum. The residue was purified by Prep-TLC (CH₂Cl₂:MeOH=10:1) to afford 5-benzyloxy-2-[[2,6-dichloro-4-[6-(difluoromethyl)-3,5-di-oxo-1,2,4-triazin-2-yl]phenyl]methyl]-N-(3-hydroxycyclobutyl)pyridine-4-sulfonamide 156-13 (48.0 mg, 62%) as a light-yellow solid. LCMS: [M+H]⁺=654.0/656.0.

Step 13: 156

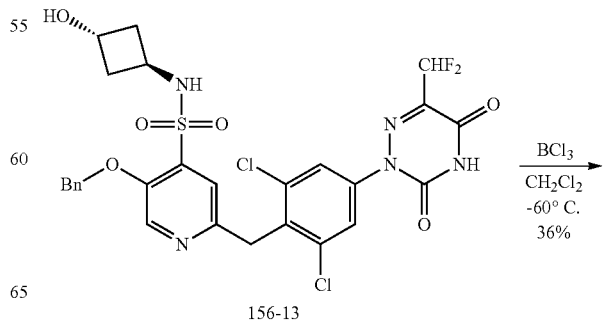

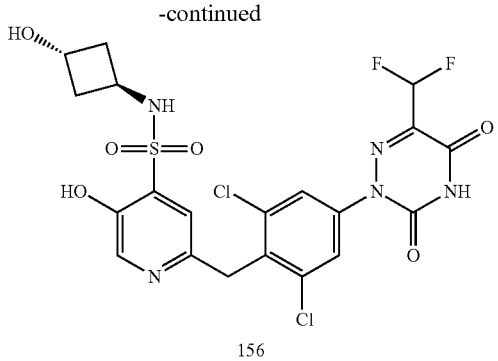

156

To a mixture of 5-benzyloxy-2-[[2,6-dichloro-4-[6-(difluoromethyl)-3,5-dioxo-1,2,4-triazin-2-yl]phenyl]methyl]-N-(3-hydroxycyclobutyl)pyridine-4-sulfonamide 156-13 (48 mg, 73.34 umol) in $CH_2Cl_2$ (4 mL) at −60° C. was added $BCl_3$ (1 M in $CH_2Cl_2$, 1.47 mL). The reaction mixture was stirred at −60° C. for 1 h. LC-MS showed the reaction was complete. The reaction mixture was poured into water (50 mL) and extracted with EtOAc (3×20 mL). The combined organic layer was washed with brine (20 mL), dried over anhydrous $Na_2SO_4$ and filtered. The filtrate was concentrated in vacuum. The residue was purified by C18 chromatography (MeCN:$H_2O$=55%) to afford 2-(2,6-dichloro-4-(6-(difluoromethyl)-3,5-dioxo-4,5-dihydro-1,2,4-triazin-2 (3H)-yl)benzyl)-5-hydroxy-N-((1r,3r)-3-hydroxycyclobutyl)pyridine-4-sulfonamide 156 (15 mg, 36%) as a white solid. LCMS: [M+H]$^+$=564.0/566.0. $^1$H NMR (400 MHz, $CD_3OD$) δ 8.21 (s, 1H), 7.75 (s, 2H), 7.33 (s, 1H), 6.70 (t, J=52.8 Hz, 1H), 4.51 (s, 2H), 4.23-4.21 (m, 1H), 3.94-3.90 (m, 1H), 2.15-2.10 (m, 2H), 2.15-1.98 (m, 2H). $^{19}$F NMR (376 MHz, $CD_3OD$) δ−124.18 (s, 2F).

Example 65: Synthesis of Compound 161

Compound 161 was synthesized using same route as that for intermediate I and compound 130 by substituting 6-(difluoromethyl)-1,2,4-triazine-3,5(2H,4H)-dione and (1r,3r)-3-aminocyclobutane-1-carbonitrile with 6-methyl-1,2,4-triazine-3,5(2H,4H)-dione and (1r,3r)-3-aminocyclobutan-1-ol hydrochloride respectively. For Compound 161, LCMS: [M+H]$^+$=530.0/532.0. $^1$H NMR (400 MHz, Methanol-d$_4$) δ 7.68 (s, 1H), 7.67 (s, 2H), 7.25 (s, 1H), 4.20 (dt, J=6.8, 3.4 Hz, 1H), 3.96 (t, J=7.2 Hz, 1H), 2.17 (s, 3H), 2.16-2.09 (m, 2H), 2.05-1.96 (m, 2H).

The compounds of Formula (I') or (I) in Table 23 below were made according to Example 65 of Compound 161.

TABLE 23

| Cmpd No. | LC-MS, $^1$H and $^{19}$F-NMR data |
|---|---|
| 162 | LCMS: [M + H]$^+$ = 530.0/532.0. $^1$H NMR (400 MHZ, Methanol-d$_4$) δ 7.68 (s, 1H), 7.68 (s, 2H), 7.25 (s, 1H), 3.77-3.69 (m, 1H), 3.33-3.26 (m, 1H), 2.39-2.33 (m, 2H), 2.17 (s, 3H), 1.78-1.69 (m, 2H). |
| 163 | LCMS: [M + H]$^+$ = 530.0/532.0. $^1$H NMR (400 MHZ, Methanol-d$_4$) δ 7.69 (s, 1H), 7.67 (s, 2H), 7.28 (s, 1H), 3.97-3.94 (m, 1H), 3.82-3.73 (m, 1H), 3.68-3.61 (m, 2H), 3.48 (dd, J = 9.2, 4.4 Hz, 1H), 2.17 (s, 3H), 2.05-1.96 (m, 1H), 1.80-1.70 (m, 1H). |
| 164 | LCMS: [M + H]$^+$ = 530.0/532.0. $^1$H NMR (400 MHZ, Methanol-d$_4$) δ 7.70 (s, 1H), 7.68 (s, 2H), 7.29 (s, 1H), 3.97-3.93 (m, 1H), 3.80-3.74 (m, 1H), 3.68-3.60 (m, 2H), 3.48 (dd, J = 9.2, 4.4 Hz, 1H), 2.17 (s, 3H), 2.05-1.96 (m, 1H), 1.77-1.69 (m, 1H). |
| 165 | LCMS: [M + H]$^+$ = 516.0/518.0. $^1$H NMR (400 MHz, CD$_3$OD) δ 7.78 (s, 1H), 7.77 (s, 2H), 7.58 (s, 1H), 7.35 (s, 1H), 4.30 (tt, J = 7.0, 3.6 Hz, 1H), 4.06 (tt, J = 8.1, 6.4 Hz, 1H), 2.29-2.18 (m, 2H), 2.15-2.06 (m, 2H). |

Example 66: Synthesis of Compounds 166 and 167

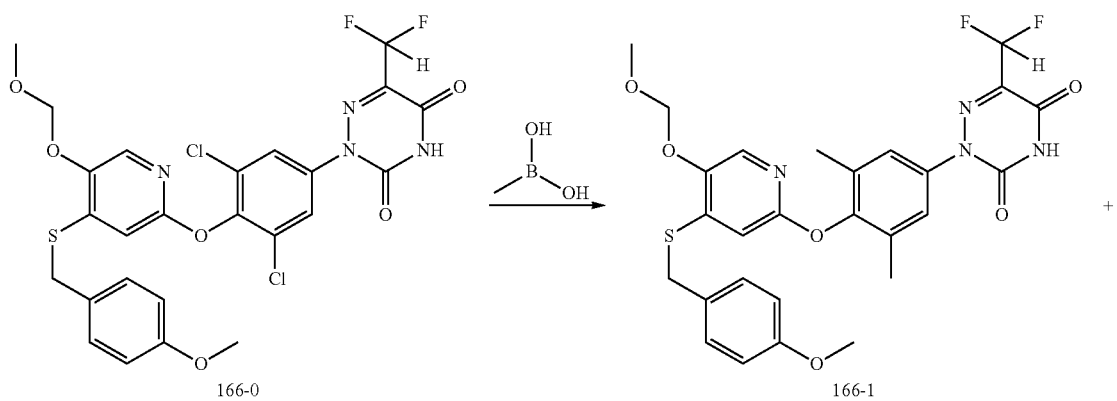

166-0      166-1

455
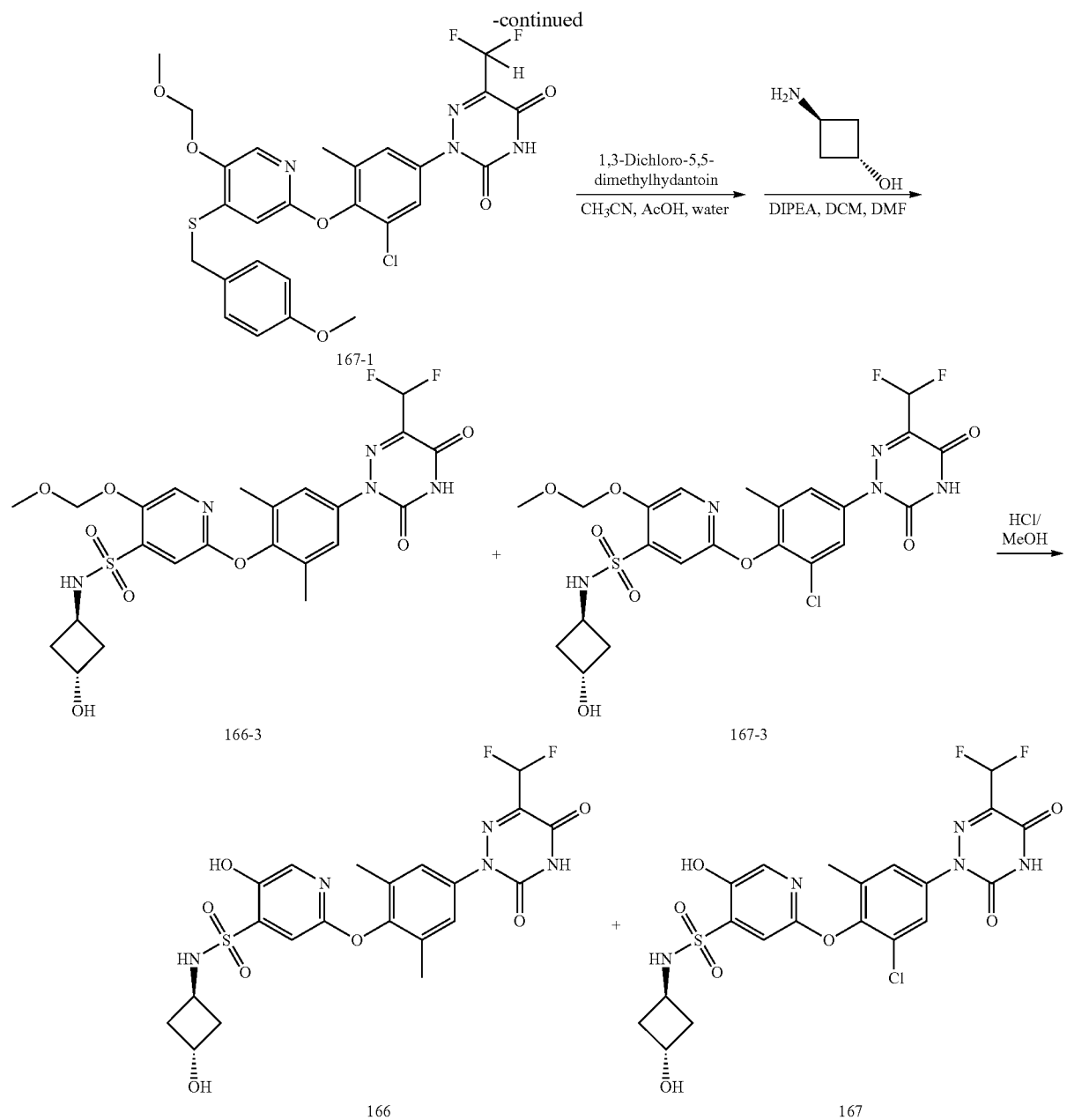
456
Step 1: 166-1 & 167-1
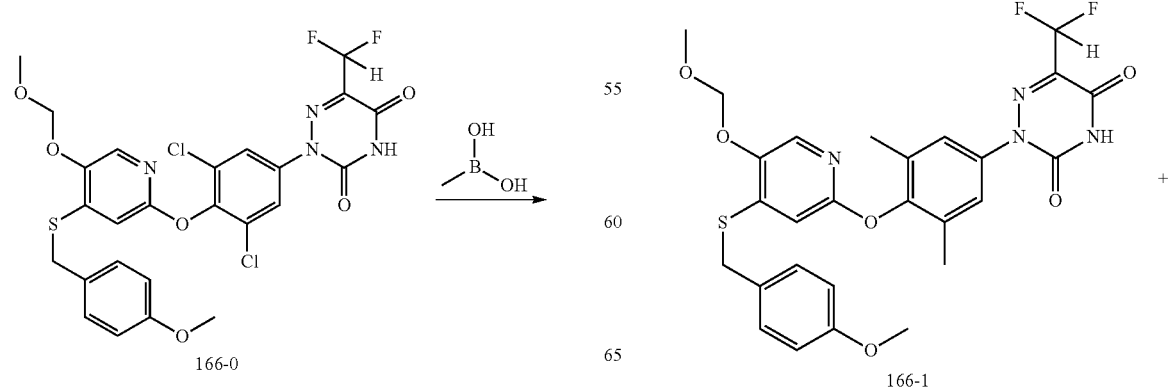

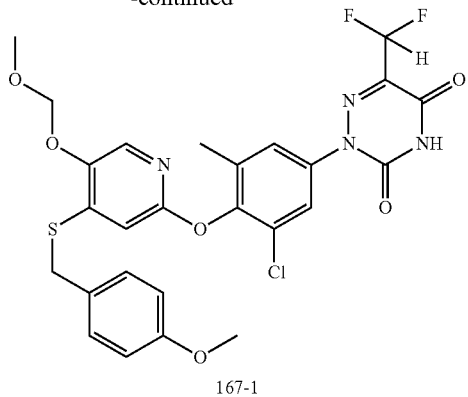

167-1

A mixture of methylboronic acid (209.81 mg, 3.50 mmol, 22.79 uL), 2-[3,5-dichloro-4-[[5-(methoxymethoxy)-4-[(4-methoxyphenyl)methylsulfanyl]-2-pyridyl]oxy]phenyl]-6-(difluoromethyl)-1,2,4-triazine-3,5-dione 166-0 (215 mg, 350.50 umol) (166-0 was synthesized in a similar manner as intermediate I-1), bis(di-tert-butyl(4-dimethylaminophenyl)phosphine)dichloropalladium(II) (49.64 mg, 70.10 umol), cesium carbonate (570.99 mg, 1.75 mmol) and dioxane (4 mL) was stirred at 100° C. for 16 hr. LCMS showed the starting material was consumed. The mixture was poured into saturated aqueous NH₄Cl (50 mL), extracted with EtOAc (50 mL*3), washed by brine (40 mL*1), dried over Na₂SO₄ and filtered. The filtrate was concentrated. The residue was purified by FCC (EtOAc in PE, 0~50%, v/v) to afford a mixture of 6-(difluoromethyl)-2-[4-[[5-(methoxymethoxy)-4-[(4-methoxyphenyl)methylsulfanyl]-2-pyridyl]oxy]-3,5-dimethyl-phenyl]-1,2,4-triazine-3,5-dione 166-1 and 2-[3-chloro-4-[[5-(methoxymethoxy)-4-[(4-methoxyphenyl)methylsulfanyl]-2-pyridyl]oxy]-5-methyl-phenyl]-6-(difluoromethyl)-1,2,4-triazine-3,5-dione 167-1 (180 mg, crude) as off-white solids. LCMS: [M+H]⁺=573.2 (compound 166-1), 593.1 (compound 167-1).

Steps 2 & 3: 166-3 & 167-3

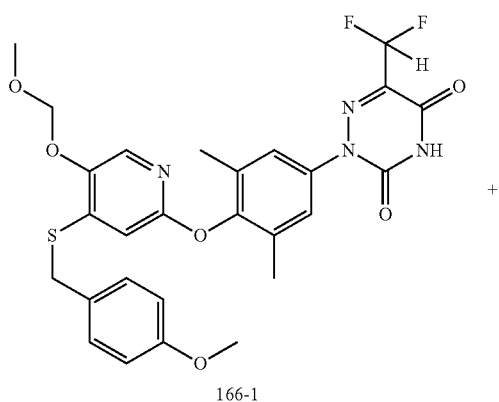

166-1

+

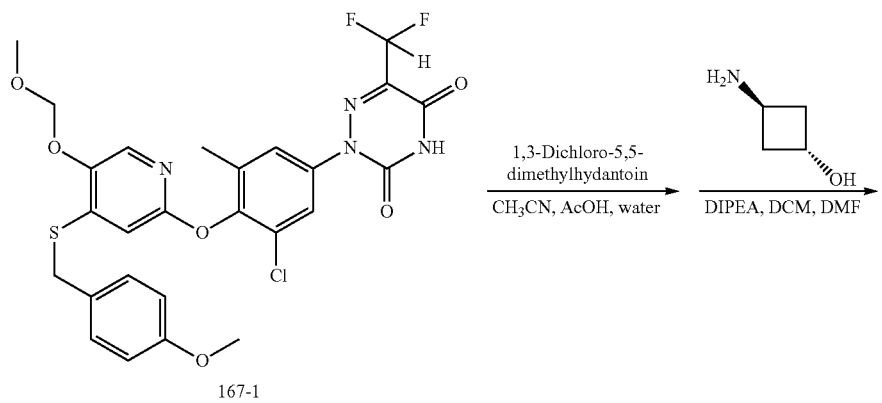

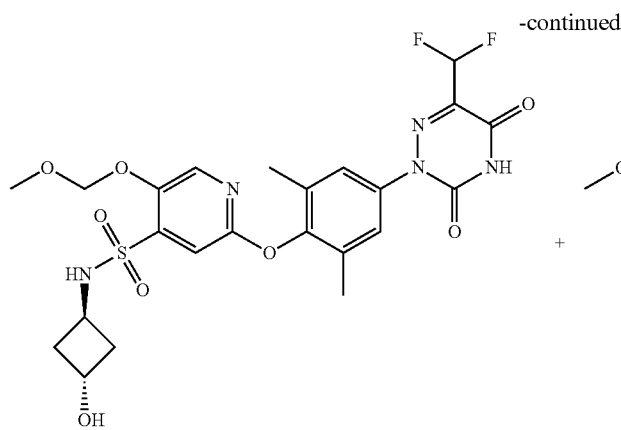

166-3

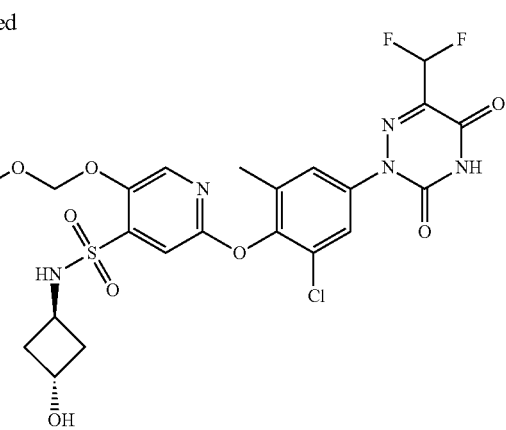

167-3

-continued

Steps 4: 166 & 167

A mixture of 6-(difluoromethyl)-2-[4-[[5-(methoxymethoxy)-4-[(4-methoxyphenyl)methylsulfanyl]-2-pyridyl]oxy]-3,5-dimethyl-phenyl]-1,2,4-triazine-3,5-dione 166-1 and 2-[3-chloro-4-[[5-(methoxymethoxy)-4-[(4-methoxyphenyl)methylsulfanyl]-2-pyridyl]oxy]-5-methyl-phenyl]-6-(difluoromethyl)-1,2,4-triazine-3,5-dione 167-1 (180 mg, crude) was dissolved in CH$_3$CN (4 mL). The mixture was cooled with ice salt bath. AcOH (0.05 mL) and H$_2$O (0.2 mL) was added with cooling. 1,3-Dichloro-5,5-dimethylhydantoin (185.81 mg, 943.10 umol, 123.87 uL) in CH$_3$CN (2 mL) was added slowly. The mixture was stirred for 10 min with ice salt bath cooling. TLC (DCM/EtOAc=5/1) showed the reaction was complete. The mixture was poured into saturated NaHCO$_3$ solution (50 mL), extracted with DCM (40 mL*2), dried over Na$_2$SO$_4$ and filtered. The filtrate was concentrated. The residue was dissolved in DCM (4 mL) and added to the mixture of 3-aminocyclobutanol hydrochloride (58.27 mg, 471.55 umol), N,N-Diisopropylethylamine (40.63 mg, 314.37 umol, 54.76 uL) and DMF (4 mL) drop wise at 0° C. The mixture was then stirred at 25° C. for 1 h. LCMS showed the reaction was complete. The mixture was poured into saturated NaHCO$_3$ solution (100 mL) and filtered. The filtrate was extracted with EtOAc (50 mL*3), washed by brine (40 mL), dried over Na$_2$SO$_4$ and filtered. The filtrate was concentrated and purified by FCC (EtOAc in PE, 0-50%, v/v) to afford a mixture of 2-[4-[6-(difluoromethyl)-3,5-dioxo-1,2,4-triazin-2-yl]-2,6-dimethyl-phenoxy]-N-(3-hydroxycyclobutyl)-5-(methoxymethoxy)pyridine-4-sulfonamide 166-3 and 2-[2-chloro-4-[6-(difluoromethyl)-3,5-dioxo-1,2,4-triazin-2-yl]-6-methyl-phenoxy]-N-(3-hydroxycyclobutyl)-5-(methoxymethoxy)pyridine-4-sulfonamide 167-3 (100 mg) as off-white solids. LCMS: [M+H]$^+$=570.2 (compound 166-3), 590.2 (compound 167-3).

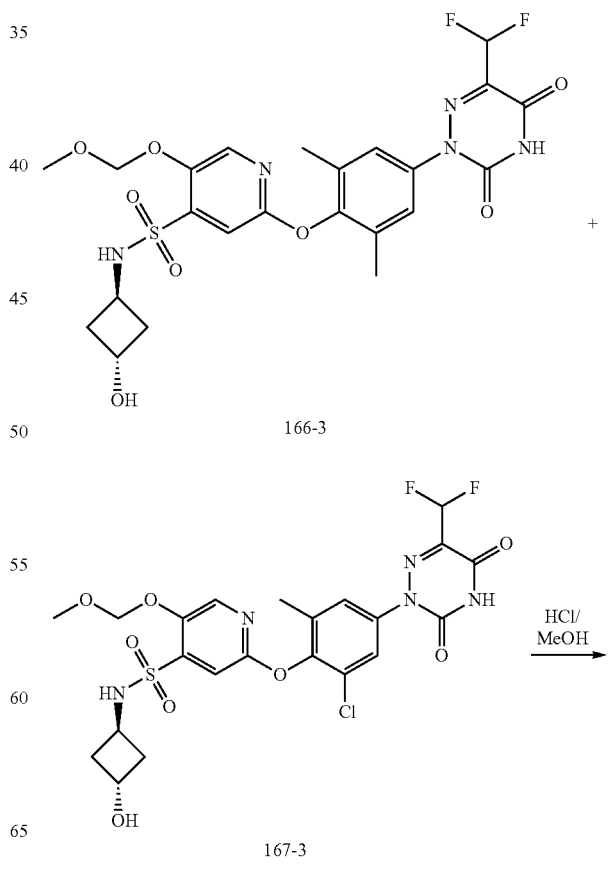

166-3

167-3

HCl/ MeOH

-continued

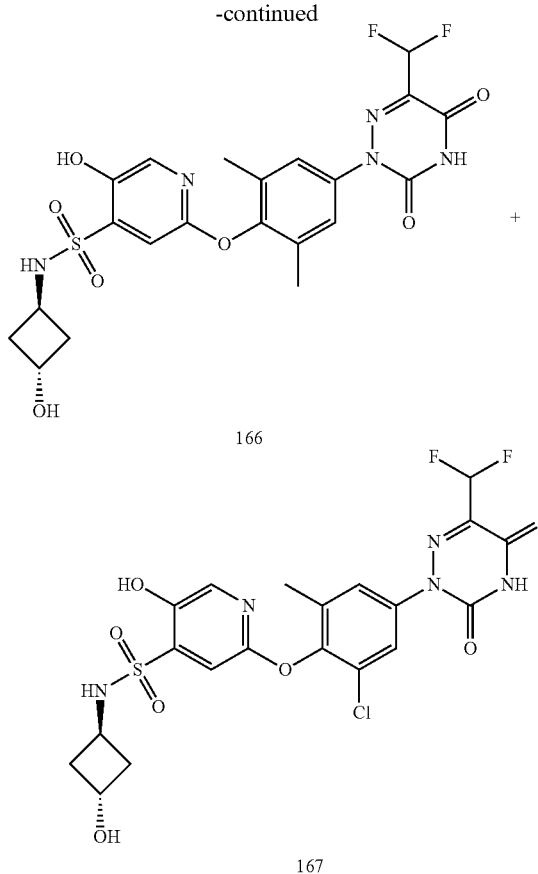

166

167

To a mixture of 2-[4-[6-(difluoromethyl)-3,5-dioxo-1,2,4-triazin-2-yl]-2,6-dimethyl-phenoxy]-N-(3-hydroxycyclobutyl)-5-(methoxymethoxy)pyridine-4-sulfonamide 166-3 and 2-[2-chloro-4-[6-(difluoromethyl)-3,5-dioxo-1,2,4-triazin-2-yl]-6-methyl-phenoxy]-N-(3-hydroxycyclobutyl)-5-(methoxymethoxy)pyridine-4-sulfonamide 167-3 (100 mg, crude) was added HCl in MeOH (4 M, 3 mL). The mixture was stirred at 30° C. for 4 hr. LCMS showed the reaction was complete. The mixture was diluted with EtOAc (100 mL), washed by water (20 mL*3) and concentrated. The residue was purified by prep-HPLC (column: XBridge® Prep C18 5 μm 19×150 mm; A: 0.1% HCO$_2$H water, B: acetonitrile; gradient: 5-95% B; GT: 25 min; flow rate: 17 mL/min) to afford 2-[4-[6-(difluoromethyl)-3,5-dioxo-1,2,4-triazin-2-yl]-2,6-dimethyl-phenoxy]-5-hydroxy-N-(3-hydroxycyclobutyl)pyridine-4-sulfonamide 166 (4 mg, 7.57 umol, 4.31% yield) as white solids and 2-[2-chloro-4-[6-(difluoromethyl)-3,5-dioxo-1,2,4-triazin-2-yl]-6-methyl-phenoxy]-5-hydroxy-N-(3-hydroxycyclobutyl)pyridine-4-sulfonamide 167 (24 mg, 43.96 umol, 25.04% yield) as white solids. For 166: LCMS: [M+H]$^+$=526.2. $^1$H NMR (400 MHz, Methanol-d$_4$) δ 7.72 (s, 1H), 7.21 (s, 2H), 7.09 (s, 1H), 6.59 (t, J=52.8 Hz, 1H), 4.24-4.14 (m, 1H), 4.00-3.88 (m, 1H), 2.18-2.07 (m, 2H), 2.04 (s, 6H), 2.03-1.89 (m, 2H). For 167: LCMS: [M+H]$^+$=546.1. $^1$H NMR (400 MHz, Methanol-d$_4$) δ 7.78 (s, 1H), 7.58 (d, J=2.6 Hz, 1H), 7.47 (d, J=2.6 Hz, 1H), 7.29 (s, 1H), 6.69 (t, J=52.8 Hz, 1H), 4.33-4.25 (m, 1H), 4.10-3.99 (m, 1H), 2.28-2.16 (m, 5H), 2.15-2.03 (m, 2H).

Example 67: Synthesis of Compound 168

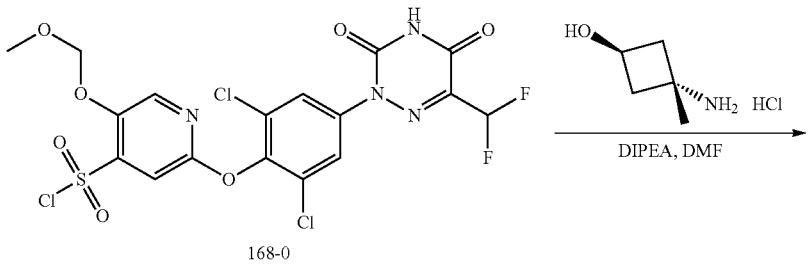

168-0

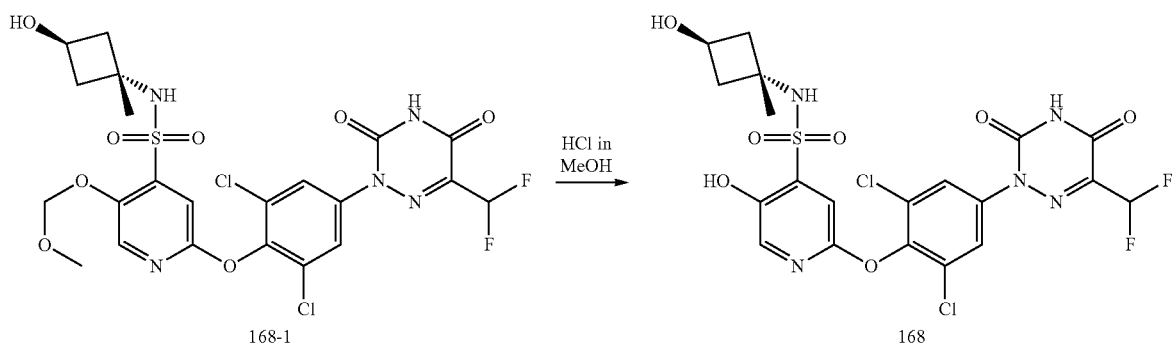

168-1        168

Step 1: 168-1

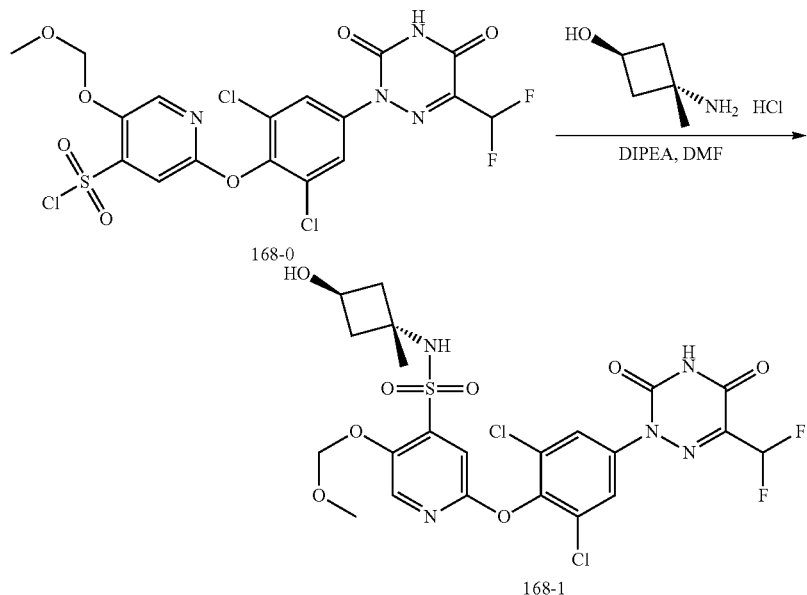

To a solution of 3-amino-3-methyl-cyclobutanol (55.32 mg, 401.99 umol, HCl salt) in DMF (3 mL) was added N,N-Diisopropylethylamine (103.91 mg, 803.98 umol, 140.04 uL). The mixture was cooled to 0° C. Then 2-[2,6-dichloro-4-[6-(difluoromethyl)-3,5-dioxo-1,2,4-triazin-2-yl]phenoxy]-5-(methoxymethoxy)pyridine-4-sulfonyl chloride 168-0 (synthesized using similar route as intermediate I) (150.00 mg, 267.99 umol) was added and the mixture was stirred at 25° C. for 1 hr. LC-MS showed the reaction was complete. The reaction mixture was poured into saturated aqueous $NH_4Cl$ (50 mL), extracted with EA (50 mL*3), washed by brine (30 mL), dried over anhydrous $Na_2SO_4$ and concentrated. The residue was purified by FCC (EtOAc in PE, 0~80%, v/v) to afford 2-[2,6-dichloro-4-[6-(difluoromethyl)-3,5-dioxo-1,2,4-triazin-2-yl]phenoxy]-N-(3-hydroxy-1-methyl-cyclobutyl)-5-(methoxymethoxy)pyridine-4-sulfonamide 168-1 (160 mg, 256.25 umol, 95.62% yield) as colorless film. LCMS: $[M+H]^+$=624.1.

Step 2: 168

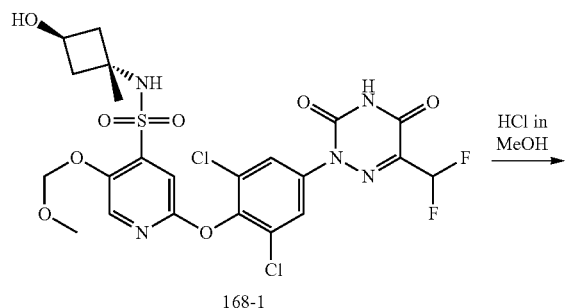

-continued

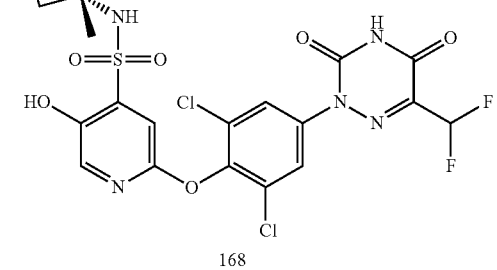

A mixture of 2-[2,6-dichloro-4-[6-(difluoromethyl)-3,5-dioxo-1,2,4-triazin-2-yl]phenoxy]-N-(3-hydroxy-1-methyl-cyclobutyl)-5-(methoxymethoxy)pyridine-4-sulfonamide 168-1 (160 mg, 256.25 umol) and hydrochloric acid in MeOH (4 M, 5 mL) was stirred at 30° C. for 16 hr. LCMS showed the reaction was complete. The mixture was diluted with EtOAc (100 mL), washed by water (15 mL×3) and concentrated. The residue was purified by prep-HPLC (column: XBridge® Prep C18 5 m 19×150 mm; A: 0.1% $HCO_2H$ water, B: acetonitrile; gradient: 5-95% B; GT: 25 min; flow rate: 17 mL/min) to afford 2-[2,6-dichloro-4-[6-(difluoromethyl)-3,5-dioxo-1,2,4-triazin-2-yl]phenoxy]-5-hydroxy-N-(3-hydroxy-1-methyl-cyclobutyl)pyridine-4-sulfonamide 168 (76 mg, 130.28 umol, 50.84% yield) as white solids. LCMS: $[M+H]^+$=580.1. $^1$H NMR (400 MHz, $CD_3OD$) δ 7.69 (s, 1H), 7.67 (s, 2H), 7.28 (s, 1H), 6.61 (t, J=52.9 Hz, 1H), 4.12-4.01 (m, 1H), 2.60-2.50 (m, 2H), 1.78-1.67 (m, 2H), 1.29 (s, 3H).

The compounds of Formula (I') or (I) in Table 24 below were made according to Example 67 of Compound 168.

TABLE 24

| Cmpd No. | LC-MS, $^1$H and $^{19}$F-NMR data |
|---|---|
| 169 | LCMS: [M + H]$^+$ = 565.1 . $^1$H NMR (400 MHZ, CD$_3$OD) δ 7.67 (s, 1H), 7.66 (s, 2H), 7.26 (s, 1H), 6.60 (t, J = 53.0 Hz, 1H), 4.31-4.24 (m, 1H), 3.98-3.93 (m, 2H), 3.60-3.48 (m, 2H), 2.58 (s, 3H). |
| 170 | LCMS: [M + H] $^+$ = 566.0. $^1$H NMR (400 MHZ, CD$_3$OD) δ 7.68 (s, 1H), 7.67 (s, 2H), 7.29 (s, 1H), 6.61 (t, J = 52.8 Hz, 1H), 4.23-4.18(m, 1H), 3.86-3.78 (m, 1H), 2.00-1.84 (m, 3H), 1.75-1.64 (m, 1H). |
| 171 | LCMS: [M + H] $^+$ = 566.0. $^1$H NMR (400 MHZ, Methanol-d$_4$) δ 7.67 (s, 1H), 7.67 (s, 2H), 7.31 (s, 1H), 6.61 (t, J = 52.9 Hz, 1H), 3.86-3.80(m, 1H), 3.53-3.45 (m, 1H), 1.92-1.85(m, 1H), 1.65 (dd, J = 10.3, 8.4 Hz, 1H), 1.42-1.25 (m, 1H), 1.23-1.12 (m, 1H). |

Example 68: TR-FRET Thyroid Receptor α/β Coactivator Assay

A time-resolved FRET (TR-FRET) assay was used to test representative compounds of the application.

THR-β Coactivator Peptide Recruitment Assay

THR-β Coactivator Peptide Recruitment Assay were conducted by using Invitrogen's LanthaScreen™ TR-FRET Thyroid Receptor beta Assay Kit (Catalog no. PV4686). Binding of an agonist to the nuclear receptor causes a subsequent binding of a coactivator peptide, resulting in fluorescence energy transfer from the labelled nuclear receptor to the proximal coactivator peptide, which reflects the binding affinity of the agonist and the nuclear receptor. The assay was conducted by following the manufacturer's instructions. Briefly, THR beta-LBD (the final concentration is 0.5 nM) was added to the 384-well assay plate containing test compounds, followed by addition of Fluorescein-SRC2-2 coactivator peptide and terbium (Tb)-labeled anti-GST antibody. The final concentration of THR beta-LBD, Fluorescein-SRC2-2 coactivator peptide and terbium (Tb)-labeled anti-GST antibody is 0.5 nM, 0.1 nM and 2 nM, respectively. After a gentle mix and incubation at room temperature for 2 h, the signal was read on the EnVision Multilabel Plate Reader at wavelengths of 520 nm and 495 nm. TR-FRET ratio was calculated by dividing the emission signal at 520 nm and the emission signal at 495 nm, and then was plotted against a sigmoidal dose response curve (four parameters, GraphPad™ Prism 8) to determine the EC$_{50}$ value.

THR-α Coactivator Peptide Recruitment Assay

THR-α Coactivator Peptide Recruitment Assay were conducted by using Invitrogen's LanthaScreen™ TR-FRET Thyroid Receptor alpha Assay Kit (Catalog no. PV4687), following the same method described above except that THR alpha-LBD of a final concentration 0.25 nM was used.

As shown in the Table below, the tested compounds are thyroid hormone receptor agonists, with EC$_{50}$ and E$_{max}$ values from the THRα/β recruitment assay.

TABLE 25

| | Classification Criteria | | | |
|---|---|---|---|---|
| Classes | THRα EC$_{50}$ (nM) | THRβ EC$_{50}$ (nM) | THRα E$_{max}$ (% of T3) | THRβ E$_{max}$ (% of T3) |
| A | <2 | <2 | 85~110 | 90~110 |
| B | 2~200 | 2~20 | 40~85 | 75~90 |
| C | 200~1000 | 20~100 | <40 | <75 |
| D | >1000 | >100 | — | — |

TABLE 26

| | Activities of Compounds in TR-FRET Assay | | | |
|---|---|---|---|---|
| Cmpd No. | THRα EC$_{50}$ (nM) | THRα E$_{max}$ (% of T3) | THRβ EC$_{50}$ (nM) | THRβ E$_{max}$ (% of T3) |
| T3 | A | A | A | A |
| MGL3196 | C | B | C | C |
| 1 | B | B | B | A |
| 2 | C | B | B | B |
| 3 | D | B | C | A |
| 4 | C | B | C | A |
| 5 | D | B | C | A |
| 6 | D | B | C | B |
| 7 | B | A | A | A |
| 8 | B | B | A | B |
| 9 | C | B | D | A |
| 10 | D | C | D | B |
| 11 | D | B | D | A |
| 12 | A | A | A | A |
| 13 | A | A | A | A |
| 14 | A | A | A | A |
| 15 | A | B | A | B |
| 16 | B | A | A | B |
| 17 | B | A | A | A |
| 18 | C | B | B | B |
| 19 | B | A | A | A |
| 20 | B | A | B | A |
| 21 | B | B | B | A |
| 22 | C | B | B | B |
| 23 | B | A | A | A |
| 24 | B | A | A | A |
| 25 | D | C | C | B |
| 26 | B | A | A | A |
| 27 | A | A | A | B |
| 28 | A | A | A | B |
| 29 | B | A | A | A |
| 30 | A | A | A | A |
| 31 | B | B | B | C |
| 32 | B | C | B | C |
| 33 | B | B | A | C |
| 34 | C | B | C | C |
| 35 | C | B | C | C |
| 36 | B | B | B | B |
| 37 | B | A | B | B |
| 38 | B | A | B | B |
| 39 | B | B | A | C |
| 40 | B | A | A | B |
| 41 | B | A | A | B |
| 42 | B | A | A | A |
| 43 | B | A | B | A |
| 44 | B | A | B | B |
| 45 | B | A | A | B |
| 46 | B | B | A | B |
| 47 | B | B | B | C |
| 48 | C | B | B | B |
| 49 | C | C | B | C |
| 50 | C | B | B | C |
| 51 | C | B | B | C |
| 52 | D | B | C | B |
| 53 | D | B | B | B |
| 54 | C | B | C | C |
| 55 | B | B | A | B |
| 56 | B | B | A | C |
| 57 | D | C | C | C |
| 58 | B | A | A | B |
| 59 | C | B | B | A |
| 60 | B | B | B | B |

TABLE 26-continued

Activities of Compounds in TR-FRET Assay

| Cmpd No. | THRα EC$_{50}$ (nM) | THRα E$_{max}$ (% of T3) | THRβ EC$_{50}$ (nM) | THRβ E$_{max}$ (% of T3) |
|---|---|---|---|---|
| 61 | D | B | B | B |
| 62 | C | B | B | B |
| 63 | D | B | C | B |
| 64 | D | C | D | B |
| 65 | B | B | A | B |
| 66 | B | B | B | C |
| 67 | B | B | B | B |
| 68 | B | A | B | B |
| 69 | B | A | A | A |
| 70 | B | B | B | B |
| 71 | B | B | B | A |
| 72 | B | B | B | A |
| 73 | B | B | B | C |
| 74 | C | B | C | B |
| 75 | C | B | B | C |
| 76 | B | A | A | B |
| 77 | B | A | B | B |
| 78 | C | B | C | C |
| 79 | B | A | A | B |
| 80 | B | A | B | A |
| 81 | B | A | B | A |
| 82 | D | B | C | B |
| 83 | B | A | A | A |
| 84 | B | A | A | A |
| 85 | D | C | D | C |
| 86 | C | C | B | C |
| 87 | C | B | A | B |
| 88 | C | B | C | B |
| 89 | B | A | A | B |
| 90 | B | A | A | B |
| 91 | C | B | B | A |
| 92 | C | B | B | B |
| 93 | D | C | C | B |
| 94 | C | B | B | B |
| 95 | A | A | A | A |
| 96 | C | A | C | A |
| 97 | B | A | A | A |
| 98 | B | B | B | B |
| 99 | B | A | B | B |
| 100 | B | A | A | A |
| 101 | C | B | B | B |
| 102 | C | A | B | B |
| 103 | D | B | B | C |
| 104 | B | B | A | B |
| 105 | B | A | A | B |
| 106 | B | A | B | B |
| 107 | B | B | B | B |
| 108 | B | B | B | B |
| 109 | B | A | A | B |
| 110 | B | A | A | A |
| 111 | B | A | A | A |
| 112 | B | A | A | A |
| 113 | B | A | A | B |
| 114 | B | A | A | A |
| 115 | D | B | B | C |
| 116 | D | B | C | C |
| 117 | D | C | C | C |
| 118 | D | C | D | B |
| 119 | D | C | D | C |
| 120 | D | C | D | C |
| 121 | D | C | D | C |
| 122 | C | B | B | C |
| 123 | B | A | A | A |
| 124 | B | B | A | B |
| 125 | C | B | B | B |
| 126 | B | A | B | A |
| 127 | C | C | C | C |
| 128 | B | A | A | B |
| 129 | B | B | B | A |
| 130 | C | B | B | B |
| 131 | B | A | A | A |
| 132 | C | B | B | A |
| 133 | D | B | C | B |
| 134 | D | B | C | B |
| 135 | B | A | B | A |
| 136 | B | B | B | B |
| 137 | D | B | C | C |
| 138 | D | C | D | C |
| 139 | C | B | B | B |
| 140 | C | B | C | B |
| 141 | B | B | B | B |
| 142 | C | B | C | B |
| 143 | C | B | B | B |
| 144 | D | C | C | C |
| 145 | B | B | B | B |
| 146 | B | A | B | A |
| 147 | C | B | C | A |
| 148 | B | A | B | B |
| 149 | D | C | D | C |
| 150 | B | A | B | A |
| 151 | B | A | A | A |
| 152 | A | A | A | A |
| 153 | B | A | A | A |
| 154 | C | B | B | B |
| 156 | D | B | B | A |
| 158 | B | A | A | A |
| 159 | C | B | C | B |
| 160 | D | B | C | B |
| 161 | C | B | C | B |
| 162 | D | C | D | B |
| 163 | C | B | C | B |
| 164 | C | B | C | B |
| 165 | D | B | C | C |
| 166 | D | B | D | B |
| 167 | C | A | B | A |
| 168 | B | A | B | A |
| 169 | D | C | D | C |
| 170 | C | B | C | C |
| 171 | C | C | C | C |

Example 69: Pharmacodynamics Study of MGL3196, Compound 23, 42, 72 & 126 in PTU Induced Hypothyroidism SD Rat Model Thyroid hormones (THs) affect growth, metabolism, and the physiological function of nearly all organs. Biological activity arises from activation of nuclear hormone receptors (Thyroid hormone receptors, THRs), which in turn modulate the expression of numerous target genes. Therefore, the expression of target gene in liver and heart can be used to determine tissue selective THR activation. PTU induced hypothyroidism SD rats were treated with a single dose of THR agonists, mRNA levels for select THR-responsive genes in liver (DIO1) and heart tissue (α-MIC) were measured at 24h (FIG. 1), with ED$_{50}$ and E$_{max}$ shown in Table 27 below.

TABLE 27

ED$_{50}$ and Emax of Representative Compounds

| Compounds | Liver DIO1 absolute ED$_{50}$ (mg/kg) | Liver DIO1 Emax* (%) | Heart α-MHC Emax* (%, high dose) |
|---|---|---|---|
| T3 | — | 100 | — |
| MGL3196 | 20.5 | 59 | <5 |
| Compound 23 | 5.4 | ≥80 | <5 |
| Compound 42 | 4.6 | ≥80 | <5 |
| Compound 72 | 16.8 | ≥80 | <5 |
| Compound 126 | 21.0 | ≥80 | <5 |

*Assumed Emax.

Male SD rats (~180 g) were housed 3 per cage under standard vivarium conditions and were fed a normal chow diet for 5-7 days of acclimation. Before starting the treatment, rats body weight was recorded, and animals were randomly divided into several groups (n=4-6 per group), including vehicle group, compound treatment groups, all compounds were administrated by gavage, except T3 by intraperitoneal administration (i.p.), T3 and MGL3196 as positive control, 4 representative and active compounds (Compound 23, Compound 42, Compound 72, Compound 126) were tested in the same batch or different batches of this hypothyroidism SD rat model and one i.p. group: T3 group (i.p., 0.12 mg/kg). PTU were administered via drinking water to a final concentration of 0.05% (0.05g/100 ml water) for all PTU groups for 18 days. At ~3 pm of day 17, the body weight of rats was recorded, and then animals were administered via intraperitoneal injection or gavage of compounds at indicated dosages. At 24h after compound dosing, rats will be euthanized by CO2 inhaling, and liver and heart were collected for gene expression analysis. RNA was extracted from each tissue and was used for first strand cDNA with iScript cDNA Synthesis reagents (Biorad, #1708891). The RT-PCRs for rat GAPDH, α-MHC and DIO1 genes are conducted using primers listed in Table 28.

TABLE 28

Primers for Selected THR-sensitive Genes.

| Gene | | Sequences |
|---|---|---|
| GAPDH | Forward | 5'-AGTGCCAGCCTCGTCTCATA-3' (SEQ ID NO. 1) |
| | Reverse | 5'-GAAGGGGTCGTTGATGGCAA-3' (SEQ ID NO. 2) |
| α-MHC | Forward | 5'-CAACCTGTCCAAGTTCCGCA-3' (SEQ ID NO. 3) |
| | Reverse | 5'-CTCATCGTGCATTTTCTGCTTGG-3' (SEQ ID NO. 4) |
| DIO1 | Forward | 5'-GTGGACACAATGCAGAACCAG-3' (SEQ ID NO. 5) |
| | Reverse | 5'-ACTTCCTCAGGATTGTAGTTC-3' (SEQ ID NO. 6) |

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:

1. A compound of Formula (I') or (I):

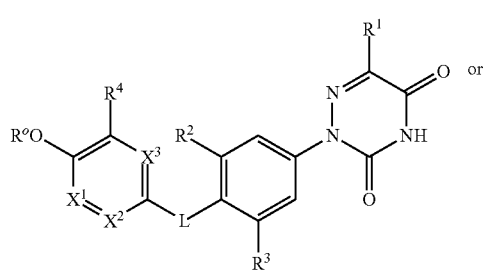

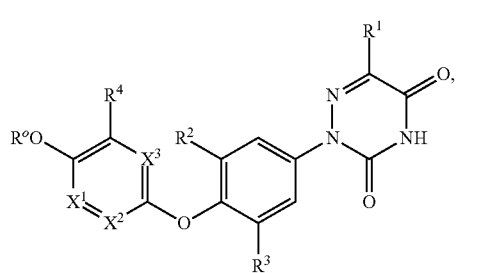

or a pharmaceutically acceptable salt, solvate, prodrug, stereoisomer, or tautomer thereof, wherein:

$R^O$ is H or $(C_1$-$C_4)$ alkyl;

each of $X^1$, $X^2$, and $X^3$ is $CR^X$ or $X^2$ is N, and $X^1$ and $X^3$ are each $CR^X$;

each $R^X$ is independently H, $(C_1$-$C_4)$ alkyl, CN, F, Cl, or $(C_3$-$C_5)$ cycloalkyl, wherein the alkyl or cycloalkyl is optionally substituted with one or more $R^8$, wherein when $X^2$ is N and L is $CH_2$, then $R^X$ is not $(C_3$-$C_8)$ cycloalkyl;

L is $CH_2$, NH, N$((C_1$-$C_4)$ alkyl), $S(O)_2$, or O;

$R^1$ is $CH_2F$, $CHF_2$, $CF_3$, Cl, $NH_2$, or CN, or when $X^2$ is N, $R^1$ is H, $(C_1$-$C_4)$ alkyl, $CH_2F$, $CHF_2$, $CF_3$, Cl, $NH_2$, or CN;

$R^2$ and $R^3$ are each independently H, F, Cl, or $CH_3$;

$R^4$ is $(CH_2)_{0\text{-}3}S(O)_2R^{4'}$, $S(O)_2NR^{4'}R^{4''}$, $C(O)NR^{4'}R^{4''}$, $(C_1$-$C_4)$ alkyl, or $(C_3$-$C_6)$ cycloalkyl, wherein when $X^2$ is N and L is $CH_2$, then $R^4$ is not $(C_3$-$C_6)$ cycloalkyl, and wherein when $R^1$ is CN, then $R^4$ is not $(C_1$-$C_4)$ alkyl;

$R^{4'}$ and $R^{4''}$ are each independently H, $(C_1$-$C_4)$ alkyl, $(C_3$-$C_{15})$ cycloalkyl, or 3- to 10-membered heterocyclyl comprising 1 to 3 heteroatoms selected from N, O, and S, wherein the alkyl, cycloalkyl, or heterocyclyl is optionally substituted with one or more $(CH_2)_yR^5$, wherein when $R^4$ is $S(O)_2R^{4'}$, $R^{4'}$ is not H; or $R^{4'}$ and $R^{4''}$, together with the nitrogen atom to which they are attached, form a 3- to 10-membered heterocyclic ring optionally comprising 1 to 3 additional heteroatoms selected from N, O, and S and optionally substituted with one or more $(CH_2)_yR^5$;

each $R^5$ is independently F, Cl, OH, $(C_1$-$C_4)$ alkyl, $(C_1$-$C_4)$ alkoxy, oxo, CN, $(C_3$-$C_6)$ cycloalkyl, heterocyclyl comprising one 3- to 6-membered ring and 1 to 3 heteroatoms selected from N, O, and S, $NR^6R^{6'}$, $NR^6S(O)_2R^7$, $NR^6C(O)R^7$, $C(O)R^7$, $C(O)NR^6R^{6'}$, $S(O)_2R^7$, or S(O)$_2$NR$^6$R$^{6'}$, wherein each cycloalkyl or heterocyclyl is optionally substituted with F, Cl, OH, (C$_1$-C$_4$) alkyl, (C$_1$-C$_4$) alkoxy, CN, NR$^6$R$^{6'}$, NR$^6$S(O)$_2$R$^7$, NR$^6$C(O)R$^7$, C(O)R$^7$, C(O)NR$^6$R$^{6'}$, S(O)$_2$R$^7$, or S(O)$_2$NR$^6$R$^{6'}$; or when y is 0, two R$^5$, together with the atom or atoms to which they are attached, may optionally form a 3- to 6-membered ring optionally substituted with F, Cl, OH, (C$_1$-C$_4$) alkyl, (C$_1$-C$_4$) alkoxy, CN, NR$^6$R$^{6'}$, NR$^6$S(O)$_2$R$^7$, NR$^6$C(O)R$^7$, C(O)R$^7$, C(O)NR$^6$R$^{6'}$, S(O)$_2$R$^7$, or S(O)$_2$NR$^6$R$^{6'}$;

each R$^6$ and R$^{6'}$ is independently H, (C$_1$-C$_5$) alkyl, or (C$_3$-C$_{10}$) cycloalkyl, wherein each alkyl or cycloalkyl is optionally substituted with one or more R$^8$; or R$^6$ and R$^{6'}$, together with the nitrogen atom to which they are attached, form a 3- to 6-membered heterocyclic ring optionally comprising one additional heteroatom selected from N, O, and S and optionally substituted with one or more R$^8$;

each R$^7$ is independently H, (C$_1$-C$_5$) alkyl, or (C$_3$-C$_{10}$) cycloalkyl, wherein each alkyl or cycloalkyl is optionally substituted with one or more R$^8$, wherein when R$^5$ is S(O)$_2$R$^7$ or NR$^6$S(O)$_2$R$^7$, R$^7$ is not H;

each R$^8$ is independently halogen, NO$_2$, NH$_2$, CN, NH((C$_1$-C$_4$) alkyl), N((C$_1$-C$_4$) alkyl)$_2$, OH, oxo, (C$_1$-C$_4$) alkyl, or (C$_1$-C$_4$) alkoxy, wherein when R$^x$, R$^6$, or R$^{6'}$ is alkyl, R$^8$ is not oxo; and y is 0, 1, 2, 3, or 4.

2. The compound of claim 1, wherein X$^2$ is N, and X$^1$ and X$^3$ are each CR$^x$.

3. The compound of claim 1, wherein X$^1$, X$^2$, and X$^3$ are each CR$^x$.

4. The compound of claim 1, wherein L is S(O)$_2$ or O.

5. The compound of claim 1, wherein L is CH$_2$, NH, or N((C$_1$-C$_4$) alkyl)).

6. The compound of claim 1, wherein R$^1$ is CH$_2$F, CHF$_2$, CF$_3$, Cl, or NH$_2$.

7. The compound of claim 1, wherein R$^1$ is CN.

8. The compound of claim 1, wherein R$^1$ is H or (C$_1$-C$_4$) alkyl when X$^2$ is N.

9. The compound of claim 1, wherein R$^2$ and R$^3$ are each H.

10. The compound of claim 1, wherein one of R$^2$ and R$^3$ is H, and the other is F, Cl, or CH$_3$.

11. The compound of claim 1, wherein R$^2$ and R$^3$ are each independently F, Cl, or CH$_3$.

12. The compound of claim 1, wherein R$^2$ and R$^3$ are each Cl.

13. The compound of claim 1, wherein R$^4$ is (CH$_2$)$_{0-3}$S(O)$_2$R$^{4'}$, S(O)$_2$NR$^4$R$^{4''}$, or C(O)NR$^4$R$^{4''}$.

14. The compound of claim 1, wherein R$^4$ is (C$_1$-C$_4$) alkyl or (C$_3$-C$_6$) cycloalkyl.

15. A compound selected from the table below:

| Structure | Chemical Name |
|---|---|
| 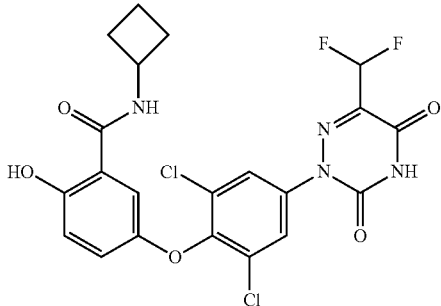 [SMILES: O=C(NC1CCC1)c1cc(Oc2c(Cl)cc(-n3nc(C(F)F)c(=O)[nH]c3=O)cc2Cl)ccc1O] | N-cyclobutyl-5-(2,6-dichloro-4-(6-(difluoromethyl)-3,5-dioxo-4,5-dihydro-1,2,4-triazin-2(3H)-yl)phenoxy)-2-hydroxybenzamide |
| 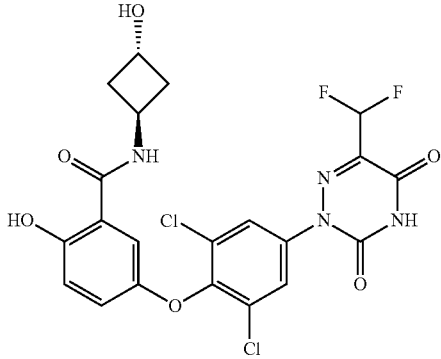 [SMILES: O=C(N[C@H]1C[C@H](O)C1)c1cc(Oc2c(Cl)cc(-n3nc(C(F)F)c(=O)[nH]c3=O)cc2Cl)ccc1O] | 5-(2,6-dichloro-4-(6-(difluoromethyl)-3,5-dioxo-4,5-dihydro-1,2,4-triazin-2(3H)-yl)phenoxy)-2-hydroxy-N-((1r,3r)-3-hydroxycyclobutyl)benzamide |

-continued

| Structure | Chemical Name |
|---|---|
| 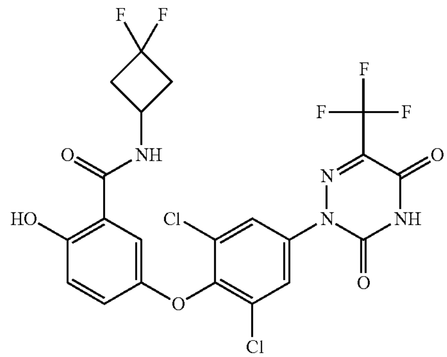 [SMILES: O=C(NC1CC(F)(F)C1)c1cc(Oc2c(Cl)cc(-n3nc(C(F)(F)F)c(=O)[nH]c3=O)cc2Cl)ccc1O] | 5-(2,6-dichloro-4-(3,5-dioxo-6-(trifluoromethyl)-4,5-dihydro-1,2,4-triazin-2(3H)-yl)phenoxy)-N-(3,3-difluorocyclobutyl)-2-hydroxybenzamide, |
| 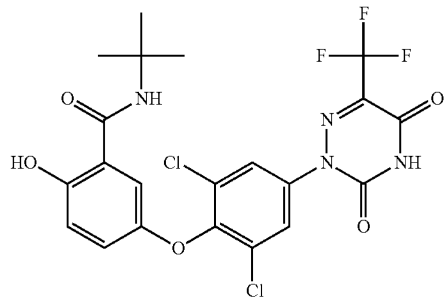 [SMILES: CC(C)(C)NC(=O)c1cc(Oc2c(Cl)cc(-n3nc(C(F)(F)F)c(=O)[nH]c3=O)cc2Cl)ccc1O] | N-(tert-butyl)-5-(2,6-dichloro-4-(3,5-dioxo-6-(trifluoromethyl)-4,5-dihydro-1,2,4-triazin-2(3H)-yl)phenoxy)-2-hydroxybenzamide, |
| 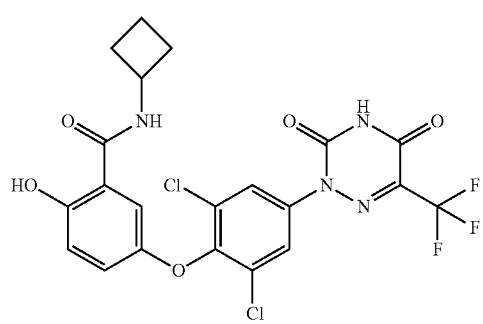 [SMILES: O=C(NC1CCC1)c1cc(Oc2c(Cl)cc(-n3nc(C(F)(F)F)c(=O)[nH]c3=O)cc2Cl)ccc1O] | N-cyclobutyl-5-(2,6-dichloro-4-(3,5-dioxo-6-(trifluoromethyl)-4,5-dihydro-1,2,4-triazin-2(3H)-yl)phenoxy)-2-hydroxybenzamide, |
| 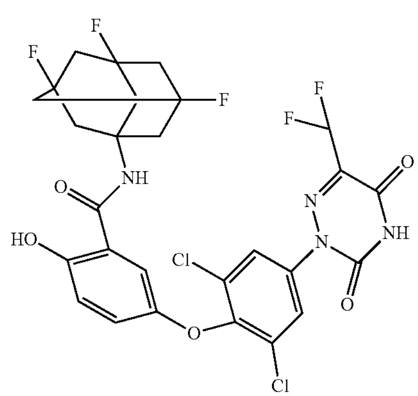 [SMILES: O=C(NC12CC3(F)CC(F)(CC(F)(C3)C1)C2)c1cc(Oc2c(Cl)cc(-n3nc(C(F)F)c(=O)[nH]c3=O)cc2Cl)ccc1O] | 5-(2,6-dichloro-4-(6-(difluoromethyl)-3,5-dioxo-4,5-dihydro-1,2,4-triazin-2(3H)-yl)phenoxy)-2-hydroxy-N-(3,5,7-trifluoroadamantan-1-yl)benzamide, |

-continued

| Structure | Chemical Name |
|---|---|
| | 2-(4-(3-((1R,4S)-2-azabicyclo[2.2.1]heptane-2-carbonyl)-4-hydroxyphenoxy)-3,5-dichlorophenyl)-6-chloro-1,2,4-triazine-3,5(2H,4H)-dione |
| | 2-(4-(3-((1S,4R)-2-azabicyclo[2.2.1]heptane-2-carbonyl)-4-hydroxyphenoxy)-3,5-dichlorophenyl)-6-chloro-1,2,4-triazine-3,5(2H,4H)-dione |
| | 2-(3,5-dichloro-4-((3-cyclobutyl-4-hydroxyphenyl)sulfonyl)phenyl)-6-(trifluoromethyl)-1,2,4-triazine-3,5(2H,4H)-dione |
| | N-cyclobutyl-5-(2,6-dichloro-4-(3,5-dioxo-6-(trifluoromethyl)-4,5-dihydro-1,2,4-triazin-2(3H)-yl)phenoxy)-4-fluoro-2-hydroxybenzamide |
| | N-cyclobutyl-5-(2,6-dichloro-4-(6-(difluoromethyl)-3,5-dioxo-4,5-dihydro-1,2,4-triazin-2(3H)-yl)phenoxy)-4-fluoro-2-hydroxybenzamide |

-continued

| Structure | Chemical Name |
|---|---|
| 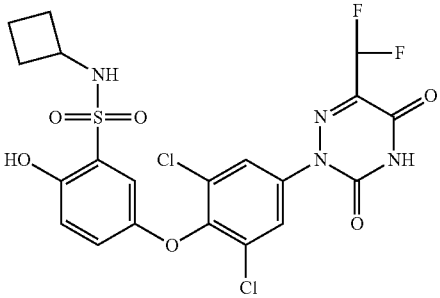 [SMILES: O=c1[nH]c(=O)n(-c2cc(Cl)c(Oc3ccc(O)c(S(=O)(=O)NC4CCC4)c3)c(Cl)c2)nc1C(F)F] | N-cyclobutyl-5-(2,6-dichloro-4-(6-(difluoromethyl)-3,5-dioxo-4,5-dihydro-1,2,4-triazin-2(3H)-yl)phenoxy)-2-hydroxybenzenesulfonamide, |
| 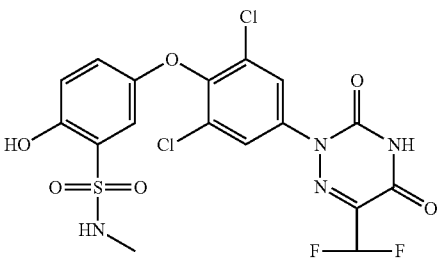 [SMILES: CNS(=O)(=O)c1cc(Oc2c(Cl)cc(-n3nc(C(F)F)c(=O)[nH]c3=O)cc2Cl)ccc1O] | 5-(2,6-dichloro-4-(6-(difluoromethyl)-3,5-dioxo-4,5-dihydro-1,2,4-triazin-2(3H)-yl)phenoxy)-2-hydroxy-N-methylbenzenesulfonamide, |
| 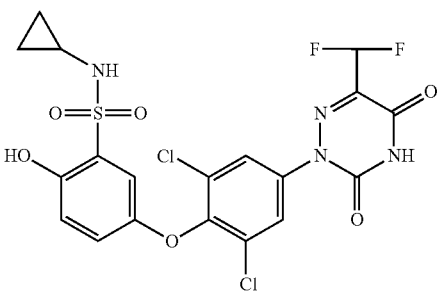 [SMILES: O=c1[nH]c(=O)n(-c2cc(Cl)c(Oc3ccc(O)c(S(=O)(=O)NC4CC4)c3)c(Cl)c2)nc1C(F)F] | N-cyclopropyl-5-(2,6-dichloro-4-(6-(difluoromethyl)-3,5-dioxo-4,5-dihydro-1,2,4-triazin-2(3H)-yl)phenoxy)-2-hydroxybenzenesulfonamide, |
| 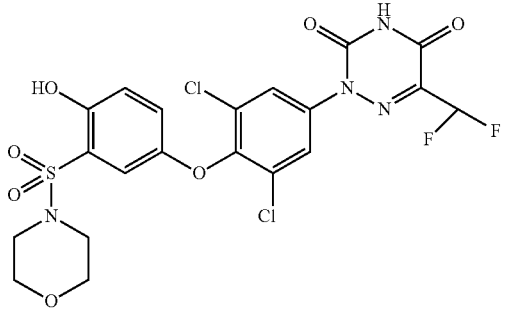 [SMILES: O=c1[nH]c(=O)n(-c2cc(Cl)c(Oc3ccc(O)c(S(=O)(=O)N4CCOCC4)c3)c(Cl)c2)nc1C(F)F] | 2-(3,5-dichloro-4-(4-hydroxy-3-(morpholinosulfonyl)phenoxy)phenyl)-6-(difluoromethyl)-1,2,4-triazine-3,5(2H,4H)-dione, |
| 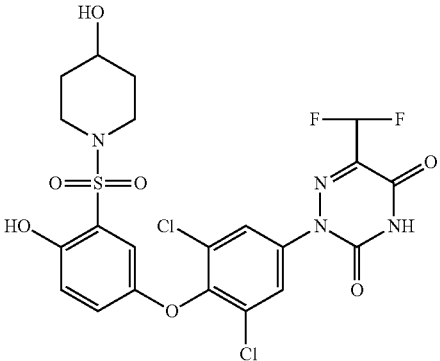 [SMILES: O=c1[nH]c(=O)n(-c2cc(Cl)c(Oc3ccc(O)c(S(=O)(=O)N4CCC(O)CC4)c3)c(Cl)c2)nc1C(F)F] | 2-(3,5-dichloro-4-(4-hydroxy-3-((4-hydroxypiperidin-1-yl)sulfonyl)phenoxy)phenyl)-6-(difluoromethyl)-1,2,4-triazine-3,5(2H,4H)-dione, |

| Structure | Chemical Name |
|---|---|
| 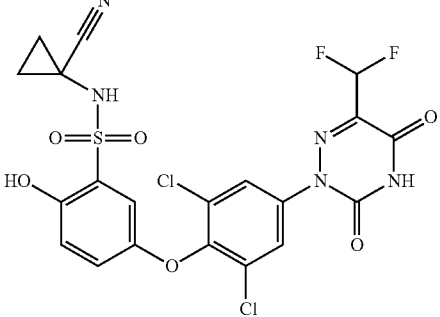 | N-(1-cyanocyclopropyl)-5-(2,6-dichloro-4-(6-(difluoromethyl)-3,5-dioxo-4,5-dihydro-1,2,4-triazin-2(3H)-yl)phenoxy)-2-hydroxybenzenesulfonamide |
| 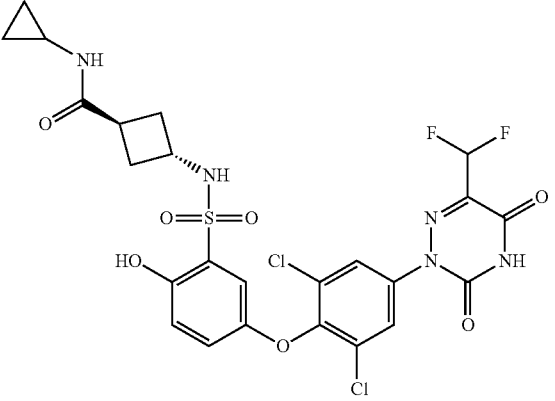 [SMILES: O=c1[nH]c(=O)n(-c2cc(Cl)c(Oc3ccc(O)c(S(=O)(=O)N[C@H]4C[C@H](C(=O)NC5CC5)C4)c3)c(Cl)c2)nc1C(F)F] | (1r,3r)-N-cyclopropyl-3-((5-(2,6-dichloro-4-(6-(difluoromethyl)-3,5-dioxo-4,5-dihydro-1,2,4-triazin-2(3H)-yl)phenoxy)-2-hydroxyphenyl)sulfonamido)cyclobutane-1-carboxamide |
| 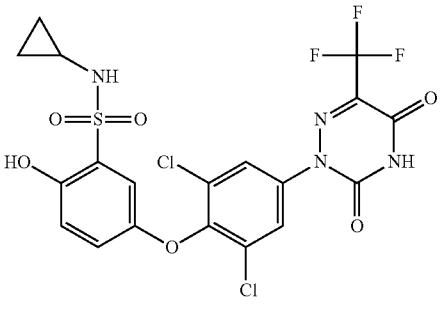 [SMILES: O=c1[nH]c(=O)n(-c2cc(Cl)c(Oc3ccc(O)c(S(=O)(=O)NC4CC4)c3)c(Cl)c2)nc1C(F)(F)F] | N-cyclopropyl-5-(2,6-dichloro-4-(3,5-dioxo-6-(trifluoromethyl)-4,5-dihydro-1,2,4-triazin-2(3H)-yl)phenoxy)-2-hydroxybenzenesulfonamide |
| 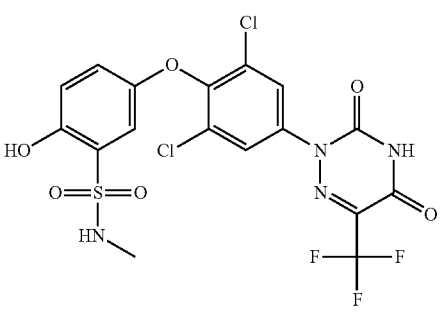 [SMILES: CNS(=O)(=O)c1cc(Oc2c(Cl)cc(-n3nc(C(F)(F)F)c(=O)[nH]c3=O)cc2Cl)ccc1O] | 5-(2,6-dichloro-4-(3,5-dioxo-6-(trifluoromethyl)-4,5-dihydro-1,2,4-triazin-2(3H)-yl)phenoxy)-2-hydroxy-N-methylbenzenesulfonamide |

| Structure | Chemical Name |
|---|---|
| 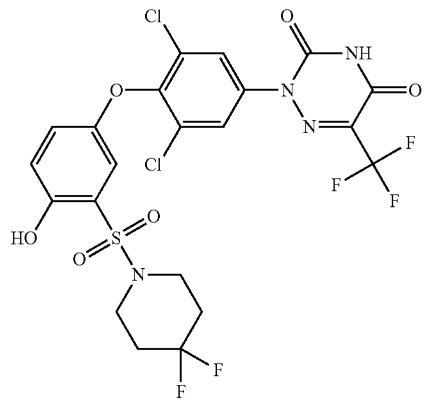 [SMILES: O=c1[nH]c(=O)n(-c2cc(Cl)c(Oc3ccc(O)c(S(=O)(=O)N4CCC(F)(F)CC4)c3)c(Cl)c2)nc1C(F)(F)F] | 2-(3,5-dichloro-4-(3-((4,4-difluoropiperidin-1-yl)sulfonyl)-4-hydroxyphenoxy)phenyl)-6-(trifluoromethyl)-1,2,4-triazine-3,5(2H,4H)-dione , |
| 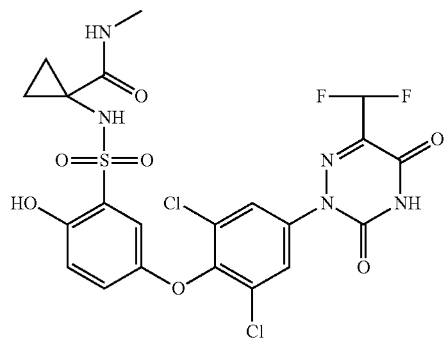 [SMILES: CNC(=O)C1(NS(=O)(=O)c2cc(Oc3c(Cl)cc(-n4nc(C(F)F)c(=O)[nH]c4=O)cc3Cl)ccc2O)CC1] | 1-((5-(2,6-dichloro-4-(6-(difluoromethyl)-3,5-dioxo-4,5-dihydro-1,2,4-triazin-2(3H)-yl)phenoxy)-2-hydroxyphenyl)sulfonamido)-N-methylcyclopropane-1-carboxamide , |
| 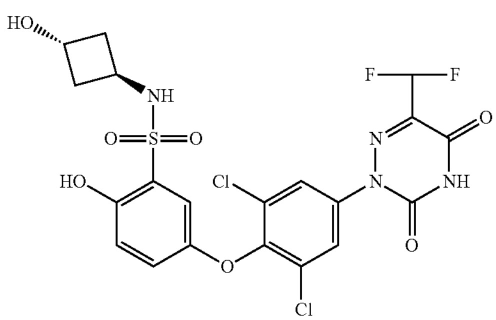 | 5-(2,6-dichloro-4-(6-(difluoromethyl)-3,5-dioxo-4,5-dihydro-1,2,4-triazin-2(3H)-yl)phenoxy)-2-hydroxy-N-((1r,3r)-3-hydroxycyclobutyl)benzenesulfonamide , |
| 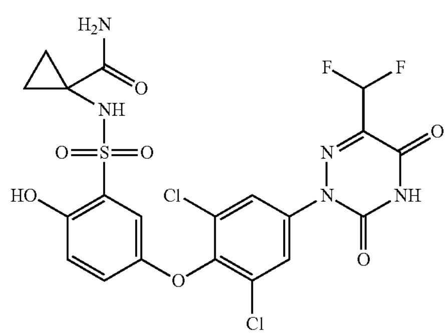 [SMILES: NC(=O)C1(NS(=O)(=O)c2cc(Oc3c(Cl)cc(-n4nc(C(F)F)c(=O)[nH]c4=O)cc3Cl)ccc2O)CC1] | 1-((5-(2,6-dichloro-4-(6-(difluoromethyl)-3,5-dioxo-4,5-dihydro-1,2,4-triazin-2(3H)-yl)phenoxy)-2-hydroxyphenyl)sulfonamido)cyclopropane-1-carboxamide , |

| Structure | Chemical Name |
|---|---|
| 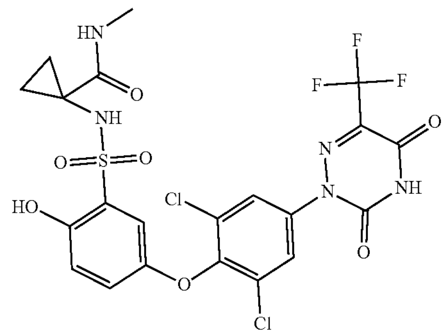 [SMILES: CNC(=O)C1(NS(=O)(=O)c2cc(Oc3c(Cl)cc(-n4nc(C(F)(F)F)c(=O)[nH]c4=O)cc3Cl)ccc2O)CC1] | 1-((5-(2,6-dichloro-4-(3,5-dioxo-6-(trifluoromethyl)-4,5-dihydro-1,2,4-triazin-2(3H)-yl)phenoxy)-2-hydroxyphenyl)sulfonamido)-N-methylcyclopropane-1-carboxamide, |
| 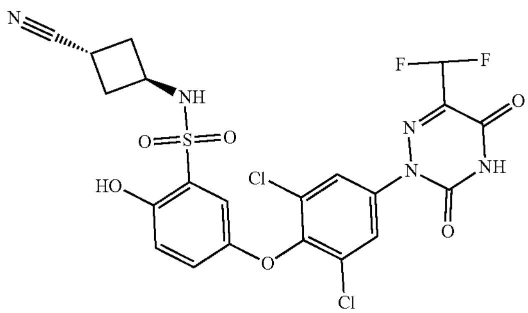 [SMILES: N#C[C@H]1C[C@H](NS(=O)(=O)c2cc(Oc3c(Cl)cc(-n4nc(C(F)F)c(=O)[nH]c4=O)cc3Cl)ccc2O)C1] | N-((1r,3r)-3-cyanocyclobutyl)-5-(2,6-dichloro-4-(6-(difluoromethyl)-3,5-dioxo-4,5-dihydro-1,2,4-triazin-2(3H)-yl)phenoxy)-2-hydroxybenzenesulfonamide, |
| 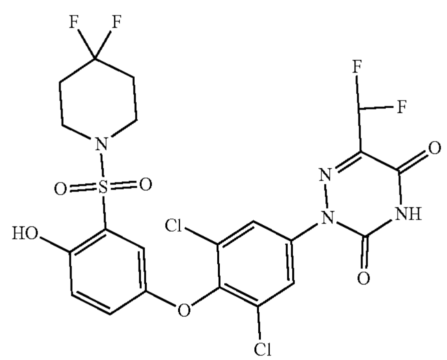 [SMILES: O=c1[nH]c(=O)n(-c2cc(Cl)c(Oc3ccc(O)c(S(=O)(=O)N4CCC(F)(F)CC4)c3)c(Cl)c2)nc1C(F)F] | 2-(3,5-dichloro-4-(3-((4,4-difluoropiperidin-1-yl)sulfonyl)-4-hydroxyphenoxy)phenyl)-6-(difluoromethyl)-1,2,4-triazine-3,5(2H,4H)-dione, |
| 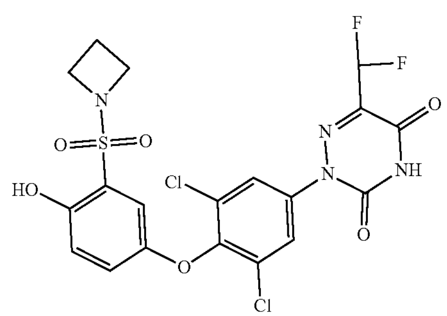 [SMILES: O=c1[nH]c(=O)n(-c2cc(Cl)c(Oc3ccc(O)c(S(=O)(=O)N4CCC4)c3)c(Cl)c2)nc1C(F)F] | 2-(4-(3-(azetidin-1-ylsulfonyl)-4-hydroxyphenoxy)-3,5-dichlorophenyl)-6-(difluoromethyl)-1,2,4-triazine-3,5(2H,4H)-dione, |
| 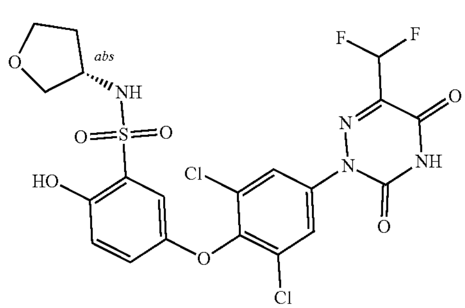 [SMILES: O=c1[nH]c(=O)n(-c2cc(Cl)c(Oc3ccc(O)c(S(=O)(=O)N[C@H]4CCOC4)c3)c(Cl)c2)nc1C(F)F] | (S)-5-(2,6-dichloro-4-(6-(difluoromethyl)-3,5-dioxo-4,5-dihydro-1,2,4-triazin-2(3H)-yl)phenoxy)-2-hydroxy-N-(tetrahydrofuran-3-yl)benzenesulfonamide, |

-continued

| Structure | Chemical Name |
|---|---|
| | (R)-5-(2,6-dichloro-4-(6-(difluoromethyl)-3,5-dioxo-4,5-dihydro-1,2,4-triazin-2(3H)-yl)phenoxy)-2-hydroxy-N-(tetrahydrofuran-3-yl)benzenesulfonamide |
| | 2-(3,5-dichloro-4-(4-hydroxy-3-(piperazin-1-ylsulfonyl)phenoxy)phenyl)-6-(difluoromethyl)-1,2,4-triazine-3,5(2H,4H)-dione |
| | 2-(3,5-dichloro-4-(3-((4-(cyclopropanecarbonyl)piperazin-1-yl)sulfonyl)-4-hydroxyphenoxy)phenyl)-6-(difluoromethyl)-1,2,4-triazine-3,5(2H,4H)-dione |
| | 2-(3,5-dichloro-4-(4-hydroxy-3-((4-methyl-3-oxopiperazin-1-yl)sulfonyl)phenoxy)phenyl)-6-(difluoromethyl)-1,2,4-triazine-3,5(2H,4H)-dione |

-continued

| Structure | Chemical Name |
|---|---|
|  | (S)-5-(2,6-dichloro-4-(6-(difluoromethyl)-3,5-dioxo-4,5-dihydro-1,2,4-triazin-2(3H)-yl)phenoxy)-2-hydroxy-N-(1-methyl-5-oxopyrrolidin-3-yl)benzenesulfonamide |
|  | (R)-5-(2,6-dichloro-4-(6-(difluoromethyl)-3,5-dioxo-4,5-dihydro-1,2,4-triazin-2(3H)-yl)phenoxy)-2-hydroxy-N-(1-methyl-5-oxopyrrolidin-3-yl)benzenesulfonamide |
|  | 5-(2,6-dichloro-4-(6-(difluoromethyl)-3,5-dioxo-4,5-dihydro-1,2,4-triazin-2(3H)-yl)phenoxy)-2-hydroxy-N-((1r,3r)-3-methoxycyclobutyl)benzenesulfonamide |
|  | 5-(2,6-dichloro-4-(6-(difluoromethyl)-3,5-dioxo-4,5-dihydro-1,2,4-triazin-2(3H)-yl)phenoxy)-2-hydroxy-N-((1s,3s)-3-methoxycyclobutyl)benzenesulfonamide |

| Structure | Chemical Name |
|---|---|
| | N-(1-(azetidine-1-carbonyl)cyclopropyl)-5-(2,6-dichloro-4-(6-(difluoromethyl)-3,5-dioxo-4,5-dihydro-1,2,4-triazin-2(3H)-yl)phenoxy)-2-hydroxybenzenesulfonamide |
| | (S)-2-(3,5-dichloro-4-(4-hydroxy-3-((3-(methylsulfonyl)pyrrolidin-1-yl)sulfonyl)phenoxy)phenyl)-6-(difluoromethyl)-1,2,4-triazine-3,5(2H,4H)-dione |
| | 2-(3,5-dichloro-4-(4-hydroxy-3-((3-hydroxyazetidin-1-yl)sulfonyl)phenoxy)phenyl)-6-(difluoromethyl)-1,2,4-triazine-3,5(2H,4H)-dione |
| | (S)-5-(2,6-dichloro-4-(6-(difluoromethyl)-3,5-dioxo-4,5-dihydro-1,2,4-triazin-2(3H)-yl)phenoxy)-2-hydroxy-N-(1-hydroxypropan-2-yl)benzenesulfonamide |

-continued

| Structure | Chemical Name |
|---|---|
| | 5-(2,6-dichloro-4-(6-(difluoromethyl)-3,5-dioxo-4,5-dihydro-1,2,4-triazin-2(3H)-yl)phenoxy)-2-hydroxy-N-((1s,3s)-3-hydroxycyclobutyl)benzenesulfonamide |
| | 5-(2,6-dichloro-4-(6-(difluoromethyl)-3,5-dioxo-4,5-dihydro-1,2,4-triazin-2(3H)-yl)phenoxy)-2-hydroxy-N-(((1r,3r)-3-hydroxycyclobutyl)methyl)benzenesulfonamide |
| | 5-(2,6-dichloro-4-(6-(difluoromethyl)-3,5-dioxo-4,5-dihydro-1,2,4-triazin-2(3H)-yl)phenoxy)-2-hydroxy-N-(((1s,3s)-3-hydroxycyclobutyl)methyl)benzenesulfonamide |
| | (R)-5-(2,6-dichloro-4-(6-(difluoromethyl)-3,5-dioxo-4,5-dihydro-1,2,4-triazin-2(3H)-yl)phenoxy)-2-hydroxy-N-(1-hydroxypropan-2-yl)benzenesulfonamide |

| Structure | Chemical Name |
|---|---|
| 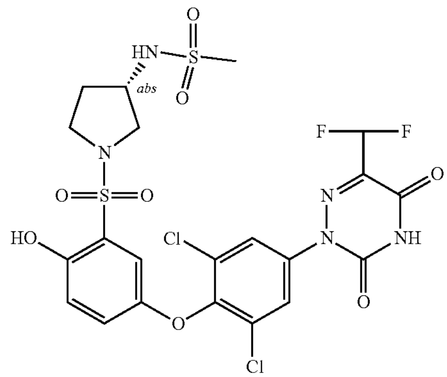 [SMILES: CS(=O)(=O)N[C@H]1CCN(S(=O)(=O)c2cc(Oc3c(Cl)cc(-n4nc(C(F)F)c(=O)[nH]c4=O)cc3Cl)ccc2O)C1] | (S)-N-(1-((5-(2,6-dichloro-4-(6-(difluoromethyl)-3,5-dioxo-4,5-dihydro-1,2,4-triazin-2(3H)-yl)phenoxy)-2-hydroxyphenyl)sulfonyl)pyrrolidin-3-yl)methanesulfonamide, |
| 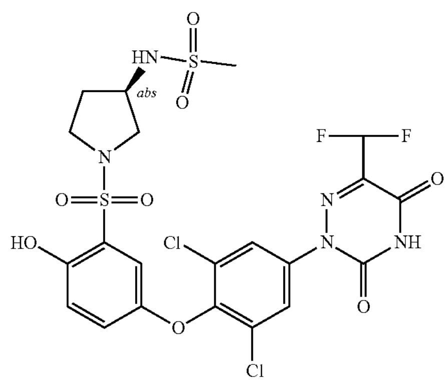 [SMILES: CS(=O)(=O)N[C@@H]1CCN(S(=O)(=O)c2cc(Oc3c(Cl)cc(-n4nc(C(F)F)c(=O)[nH]c4=O)cc3Cl)ccc2O)C1] | (R)-N-(1-((5-(2,6-dichloro-4-(6-(difluoromethyl)-3,5-dioxo-4,5-dihydro-1,2,4-triazin-2(3H)-yl)phenoxy)-2-hydroxyphenyl)sulfonyl)pyrrolidin-3-yl)methanesulfonamide, |
| 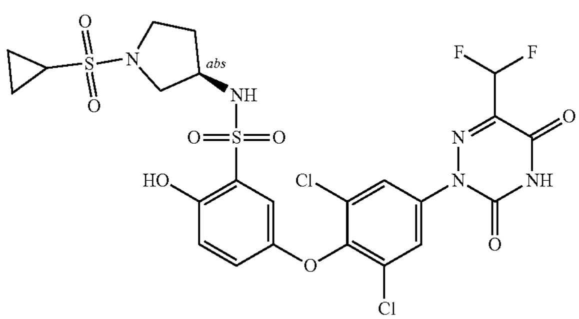 [SMILES: O=c1[nH]c(=O)n(-c2cc(Cl)c(Oc3ccc(O)c(S(=O)(=O)N[C@@H]4CCN(S(=O)(=O)C5CC5)C4)c3)c(Cl)c2)nc1C(F)F] | (R)-N-(1-(cyclopropylsulfonyl)pyrrolidin-3-yl)-5-(2,6-dichloro-4-(6-(difluoromethyl)-3,5-dioxo-4,5-dihydro-1,2,4-triazin-2(3H)-yl)phenoxy)-2-hydroxybenzenesulfonamide, |
| 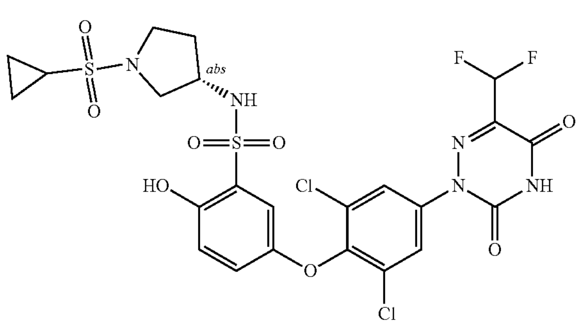 [SMILES: O=c1[nH]c(=O)n(-c2cc(Cl)c(Oc3ccc(O)c(S(=O)(=O)N[C@H]4CCN(S(=O)(=O)C5CC5)C4)c3)c(Cl)c2)nc1C(F)F] | (S)-N-(1-(cyclopropylsulfonyl)pyrrolidin-3-yl)-5-(2,6-dichloro-4-(6-(difluoromethyl)-3,5-dioxo-4,5-dihydro-1,2,4-triazin-2(3H)-yl)phenoxy)-2-hydroxybenzenesulfonamide, |

| Structure | Chemical Name |
|---|---|
| 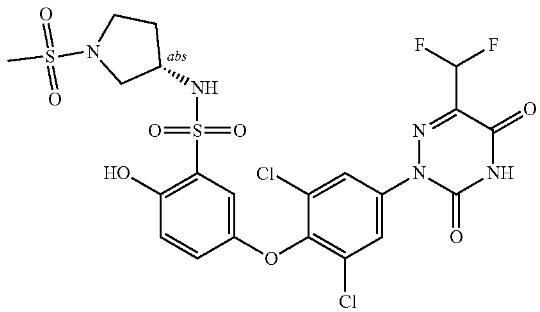 [SMILES: CS(=O)(=O)N1CC[C@H](NS(=O)(=O)c2cc(Oc3c(Cl)cc(-n4nc(C(F)F)c(=O)[nH]c4=O)cc3Cl)ccc2O)C1] | (S)-5-(2,6-dichloro-4-(6-(difluoromethyl)-3,5-dioxo-4,5-dihydro-1,2,4-triazin-2(3H)-yl)phenoxy)-2-hydroxy-N-(1-(methylsulfonyl)pyrrolidin-3-yl)benzenesulfonamide, |
| 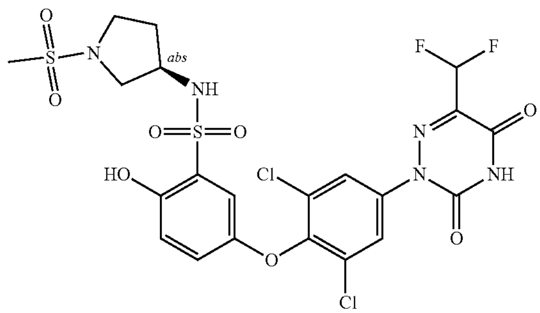 [SMILES: CS(=O)(=O)N1CC[C@@H](NS(=O)(=O)c2cc(Oc3c(Cl)cc(-n4nc(C(F)F)c(=O)[nH]c4=O)cc3Cl)ccc2O)C1] | (R)-5-(2,6-dichloro-4-(6-(difluoromethyl)-3,5-dioxo-4,5-dihydro-1,2,4-triazin-2(3H)-yl)phenoxy)-2-hydroxy-N-(1-(methylsulfonyl)pyrrolidin-3-yl)benzenesulfonamide, |
| 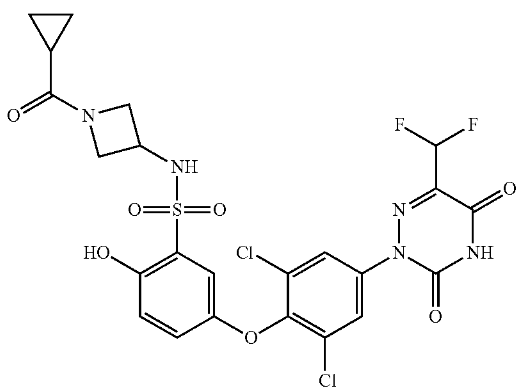 [SMILES: O=C(C1CC1)N1CC(NS(=O)(=O)c2cc(Oc3c(Cl)cc(-n4nc(C(F)F)c(=O)[nH]c4=O)cc3Cl)ccc2O)C1] | N-(1-(cyclopropanecarbonyl)azetidin-3-yl)-5-(2,6-dichloro-4-(6-(difluoromethyl)-3,5-dioxo-4,5-dihydro-1,2,4-triazin-2(3H)-yl)phenoxy)-2-hydroxybenzenesulfonamide, |
| 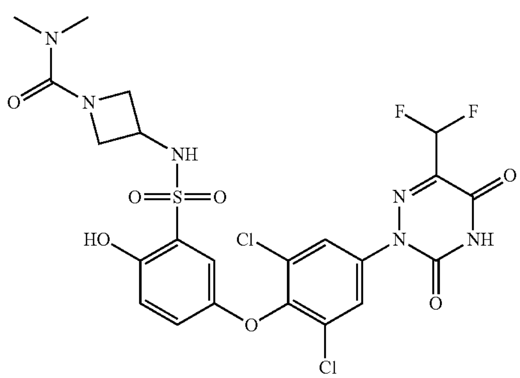 [SMILES: CN(C)C(=O)N1CC(NS(=O)(=O)c2cc(Oc3c(Cl)cc(-n4nc(C(F)F)c(=O)[nH]c4=O)cc3Cl)ccc2O)C1] | 3-((5-(2,6-dichloro-4-(6-(difluoromethyl)-3,5-dioxo-4,5-dihydro-1,2,4-triazin-2(3H)-yl)phenoxy)-2-hydroxyphenyl)sulfonamido)-N,N-dimethylazetidine-1-carboxamide, |

| Structure | Chemical Name |
|---|---|
| 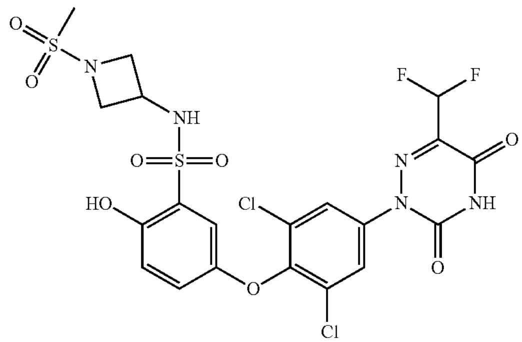 [SMILES: CS(=O)(=O)N1CC(NS(=O)(=O)c2cc(Oc3c(Cl)cc(-n4nc(C(F)F)c(=O)[nH]c4=O)cc3Cl)ccc2O)C1] | 5-(2,6-dichloro-4-(6-(difluoromethyl)-3,5-dioxo-4,5-dihydro-1,2,4-triazin-2(3H)-yl)phenoxy)-2-hydroxy-N-(1-(methylsulfonyl)azetidin-3-yl)benzenesulfonamide, |
| 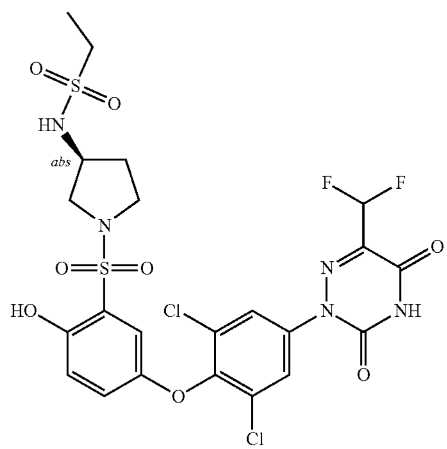 [SMILES: CCS(=O)(=O)N[C@H]1CCN(S(=O)(=O)c2cc(Oc3c(Cl)cc(-n4nc(C(F)F)c(=O)[nH]c4=O)cc3Cl)ccc2O)C1] | (S)-N-(1-((5-(2,6-dichloro-4-(6-(difluoromethyl)-3,5-dioxo-4,5-dihydro-1,2,4-triazin-2(3H)-yl)phenoxy)-2-hydroxyphenyl)sulfonyl)pyrrolidin-3-yl)ethanesulfonamide, |
| 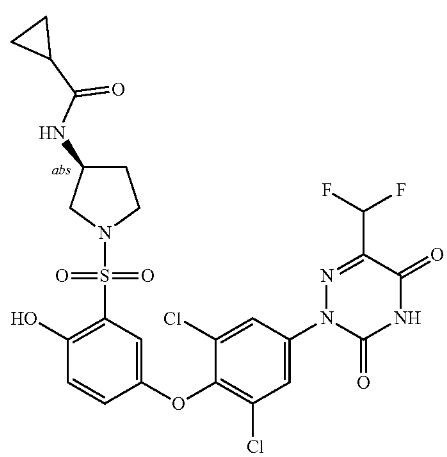 [SMILES: O=C(N[C@H]1CCN(S(=O)(=O)c2cc(Oc3c(Cl)cc(-n4nc(C(F)F)c(=O)[nH]c4=O)cc3Cl)ccc2O)C1)C1CC1] | (S)-N-(1-((5-(2,6-dichloro-4-(6-(difluoromethyl)-3,5-dioxo-4,5-dihydro-1,2,4-triazin-2(3H)-yl)phenoxy)-2-hydroxyphenyl)sulfonyl)pyrrolidin-3-yl)cyclopropanecarboxamide, |
| 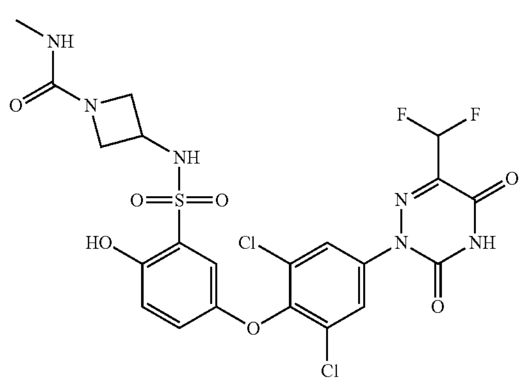 [SMILES: CNC(=O)N1CC(NS(=O)(=O)c2cc(Oc3c(Cl)cc(-n4nc(C(F)F)c(=O)[nH]c4=O)cc3Cl)ccc2O)C1] | 3-((5-(2,6-dichloro-4-(6-(difluoromethyl)-3,5-dioxo-4,5-dihydro-1,2,4-triazin-2(3H)-yl)phenoxy)-2-hydroxyphenyl)sulfonamido)-N-methylazetidine-1-carboxamide, |

| Structure | Chemical Name |
|---|---|
| | 2-((5-(2,6-dichloro-4-(6-(difluoromethyl)-3,5-dioxo-4,5-dihydro-1,2,4-triazin-2(3H)-yl)phenoxy)-2-hydroxyphenyl)sulfonamido)acetamide |
| | N-cyclopropyl-2-((5-(2,6-dichloro-4-(6-(difluoromethyl)-3,5-dioxo-4,5-dihydro-1,2,4-triazin-2(3H)-yl)phenoxy)-2-hydroxyphenyl)sulfonamido)acetamide |
| | 2-((5-(2,6-dichloro-4-(6-(difluoromethyl)-3,5-dioxo-4,5-dihydro-1,2,4-triazin-2(3H)-yl)phenoxy)-2-hydroxyphenyl)sulfonamido)-N-methylacetamide |
| | (1r,3r)-3-((5-(2,6-dichloro-4-(6-(difluoromethyl)-3,5-dioxo-4,5-dihydro-1,2,4-triazin-2(3H)-yl)phenoxy)-2-hydroxyphenyl)sulfonamido)-N-methylcyclobutane-1-carboxamide |

| Structure | Chemical Name |
|---|---|
| 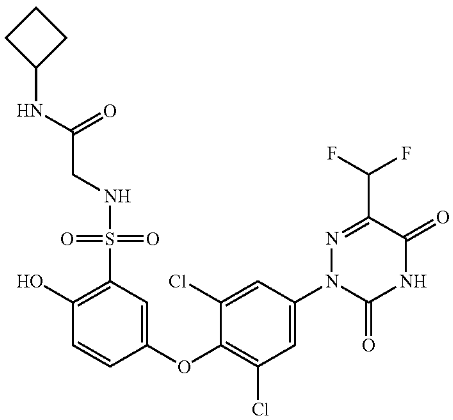 [SMILES: O=C(CNS(=O)(=O)c1cc(Oc2c(Cl)cc(-n3nc(C(F)F)c(=O)[nH]c3=O)cc2Cl)ccc1O)NC1CCC1] | N-cyclobutyl-2-((5-(2,6-dichloro-4-(6-(difluoromethyl)-3,5-dioxo-4,5-dihydro-1,2,4-triazin-2(3H)-yl)phenoxy)-2-hydroxyphenyl)sulfonamido)acetamide , |
| 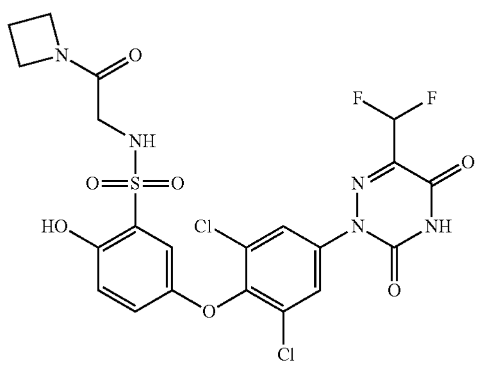 [SMILES: O=C(CNS(=O)(=O)c1cc(Oc2c(Cl)cc(-n3nc(C(F)F)c(=O)[nH]c3=O)cc2Cl)ccc1O)N1CCC1] | N-(2-(azetidin-1-yl)-2-oxoethyl)-5-(2,6-dichloro-4-(6-(difluoromethyl)-3,5-dioxo-4,5-dihydro-1,2,4-triazin-2(3H)-yl)phenoxy)-2-hydroxybenzenesulfonamide , |
| 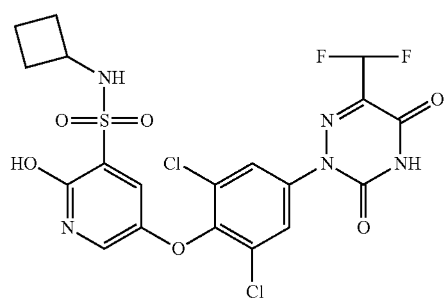 [SMILES: O=c1[nH]c(=O)n(-c2cc(Cl)c(Oc3cnc(O)c(S(=O)(=O)NC4CCC4)c3)c(Cl)c2)nc1C(F)F] | N-cyclobutyl-5-(2,6-dichloro-4-(6-(difluoromethyl)-3,5-dioxo-4,5-dihydro-1,2,4-triazin-2(3H)-yl)phenoxy)-2-hydroxypyridine-3-sulfonamide , |
| 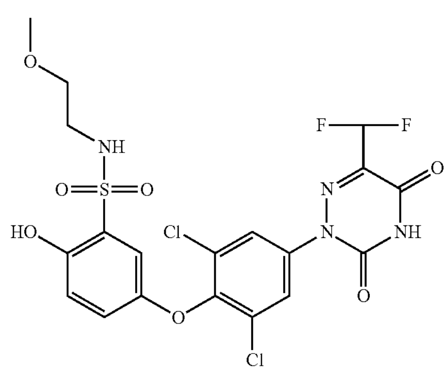 [SMILES: COCCNS(=O)(=O)c1cc(Oc2c(Cl)cc(-n3nc(C(F)F)c(=O)[nH]c3=O)cc2Cl)ccc1O] | 5-(2,6-dichloro-4-(6-(difluoromethyl)-3,5-dioxo-4,5-dihydro-1,2,4-triazin-2(3H)-yl)phenoxy)-2-hydroxy-N-(2-methoxyethyl)benzenesulfonamide , |

| Structure | Chemical Name |
|---|---|
| | 5-(2,6-dichloro-4-(6-(difluoromethyl)-3,5-dioxo-4,5-dihydro-1,2,4-triazin-2(3H)-yl)phenoxy)-2-hydroxy-N-((1R,3S)-3-hydroxycyclopentyl)benzenesulfonamide |
| | 5-(2,6-dichloro-4-(6-(difluoromethyl)-3,5-dioxo-4,5-dihydro-1,2,4-triazin-2(3H)-yl)phenoxy)-2-hydroxy-N-((1S,3R)-3-hydroxycyclopentyl)benzenesulfonamide |
| | 5-(2,6-dichloro-4-(6-(difluoromethyl)-3,5-dioxo-4,5-dihydro-1,2,4-triazin-2(3H)-yl)phenoxy)-2-hydroxybenzenesulfonamide |
| | N-((1s,3s)-3-cyanocyclobutyl)-5-(2,6-dichloro-4-(6-(difluoromethyl)-3,5-dioxo-4,5-dihydro-1,2,4-triazin-2(3H)-yl)phenoxy)-2-hydroxybenzenesulfonamide |
| | 5-(2,6-dichloro-4-(6-(difluoromethyl)-3,5-dioxo-4,5-dihydro-1,2,4-triazin-2(3H)-yl)phenoxy)-2-hydroxy-N-(1-(hydroxymethyl)cyclopropyl)benzenesulfonamide |

| Structure | Chemical Name |
|---|---|
| 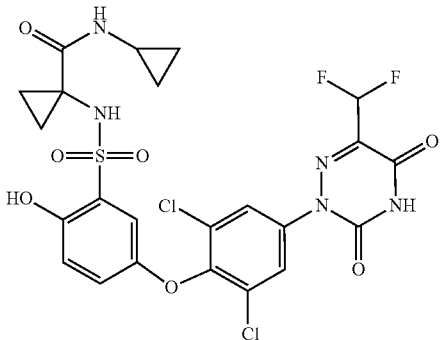 [SMILES: O=C(NC1CC1)C1(NS(=O)(=O)c2cc(Oc3c(Cl)cc(-n4nc(C(F)F)c(=O)[nH]c4=O)cc3Cl)ccc2O)CC1] | N-cyclopropyl-1-((5-(2,6-dichloro-4-(6-(difluoromethyl)-3,5-dioxo-4,5-dihydro-1,2,4-triazin-2(3H)-yl)phenoxy)-2-hydroxyphenyl)sulfonamido)cyclopropane-1-carboxamide, |
| 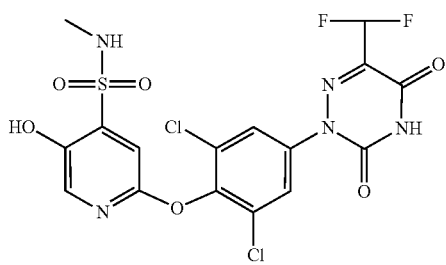 [SMILES: CNS(=O)(=O)c1cc(Oc2c(Cl)cc(-n3nc(C(F)F)c(=O)[nH]c3=O)cc2Cl)ncc1O] | 2-(2,6-dichloro-4-(6-(difluoromethyl)-3,5-dioxo-4,5-dihydro-1,2,4-triazin-2(3H)-yl)phenoxy)-5-hydroxy-N-methylpyridine-4-sulfonamide, |
| 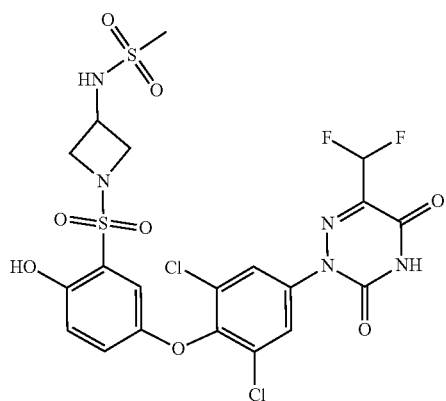 [SMILES: CS(=O)(=O)NC1CN(S(=O)(=O)c2cc(Oc3c(Cl)cc(-n4nc(C(F)F)c(=O)[nH]c4=O)cc3Cl)ccc2O)C1] | N-(1-((5-(2,6-dichloro-4-(6-(difluoromethyl)-3,5-dioxo-4,5-dihydro-1,2,4-triazin-2(3H)-yl)phenoxy)-2-hydroxyphenyl)sulfonyl)azetidin-3-yl)methanesulfonamide, |
| 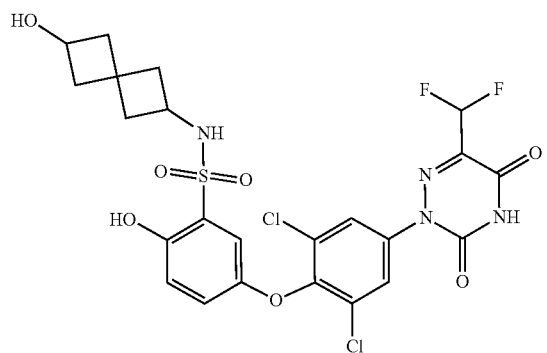 [SMILES: O=c1[nH]c(=O)n(-c2cc(Cl)c(Oc3ccc(O)c(S(=O)(=O)NC4CC5(CC(O)C5)C4)c3)c(Cl)c2)nc1C(F)F] | 5-(2,6-dichloro-4-(6-(difluoromethyl)-3,5-dioxo-4,5-dihydro-1,2,4-triazin-2(3H)-yl)phenoxy)-2-hydroxy-N-(6-hydroxyspiro[3.3]heptan-2-yl)benzenesulfonamide, |

-continued

| Structure | Chemical Name |
|---|---|
| 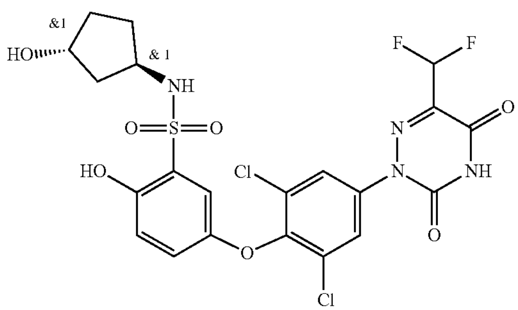 [SMILES: O=c1[nH]c(=O)n(-c2cc(Cl)c(Oc3ccc(O)c(S(=O)(=O)N[C@@H]4CC[C@@H](O)C4)c3)c(Cl)c2)nc1C(F)F] | 5-(2,6-dichloro-4-(6-(difluoromethyl)-3,5-dioxo-4,5-dihydro-1,2,4-triazin-2(3H)-yl)phenoxy)-2-hydroxy-N-((1R,3R)-3-hydroxycyclopentyl)benzenesulfonamide , |
| 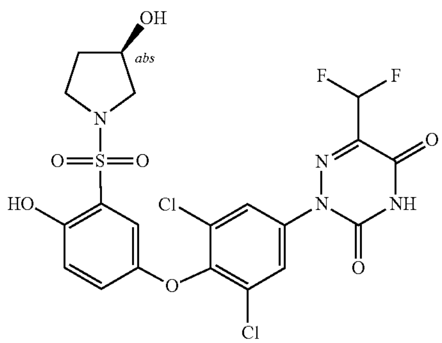 [SMILES: O=c1[nH]c(=O)n(-c2cc(Cl)c(Oc3ccc(O)c(S(=O)(=O)N4CC[C@@H](O)C4)c3)c(Cl)c2)nc1C(F)F] | (R)-2-(3,5-dichloro-4-(4-hydroxy-3-((3-hydroxypyrrolidin-1-yl)sulfonyl)phenoxy)phenyl)-6-(difluoromethyl)-1,2,4-triazine-3,5(2H,4H)-dione , |
| 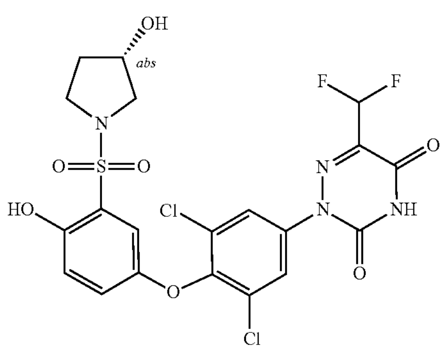 | (S)-2-(3,5-dichloro-4-(4-hydroxy-3-((3-hydroxypyrrolidin-1-yl)sulfonyl)phenoxy)phenyl)-6-(difluoromethyl)-1,2,4-triazine-3,5(2H,4H)-dione , |
| 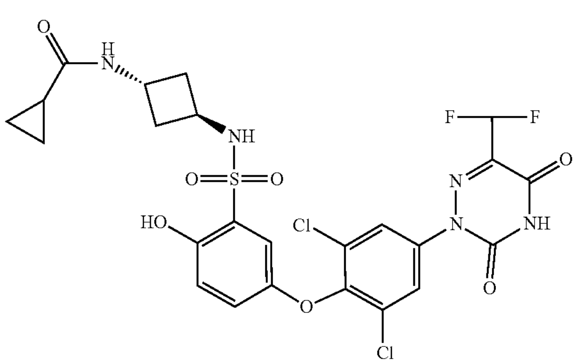 [SMILES: O=C(N[C@H]1C[C@H](NS(=O)(=O)c2cc(Oc3c(Cl)cc(-n4nc(C(F)F)c(=O)[nH]c4=O)cc3Cl)ccc2O)C1)C1CC1] | N-((1r,3r)-3-((5-(2,6-dichloro-4-(6-(difluoromethyl)-3,5-dioxo-4,5-dihydro-1,2,4-triazin-2(3H)-yl)phenoxy)-2-hydroxyphenyl)sulfonamido)cyclobutyl)cyclopropanecarboxamide , |

-continued

| Structure | Chemical Name |
|---|---|
| | N-(3-cyanobicyclo[1.1.1]pentan-1-yl)-5-(2,6-dichloro-4-(6-(difluoromethyl)-3,5-dioxo-4,5-dihydro-1,2,4-triazin-2(3H)-yl)phenoxy)-2-hydroxybenzenesulfonamide |
| | 5-(2,6-dichloro-4-(6-(difluoromethyl)-3,5-dioxo-4,5-dihydro-1,2,4-triazin-2(3H)-yl)phenoxy)-2-hydroxy-N-((1-hydroxycyclopropyl)methyl)benzenesulfonamide |
| | 5-(2,6-dichloro-4-(6-(difluoromethyl)-3,5-dioxo-4,5-dihydro-1,2,4-triazin-2(3H)-yl)phenoxy)-2-hydroxy-N-(3-hydroxybicyclo[1.1.1]pentan-1-yl)benzenesulfonamide |
| | 5-(2,6-dichloro-4-(6-(difluoromethyl)-3,5-dioxo-4,5-dihydro-1,2,4-triazin-2(3H)-yl)phenoxy)-2-hydroxy-N-((1r,3r)-3-(methylsulfonyl)cyclobutyl)benzenesulfonamide |
| | 5-(2,6-dichloro-4-(6-(difluoromethyl)-3,5-dioxo-4,5-dihydro-1,2,4-triazin-2(3H)-yl)phenoxy)-N-(1,1-dioxidothietan-3-yl)-2-hydroxybenzenesulfonamide |

-continued

| Structure | Chemical Name |
|---|---|
| 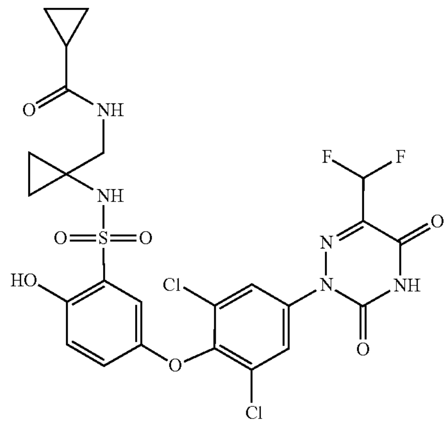 [SMILES: O=C(NCC1(NS(=O)(=O)c2cc(Oc3c(Cl)cc(-n4nc(C(F)F)c(=O)[nH]c4=O)cc3Cl)ccc2O)CC1)C1CC1] | N-((1-((5-(2,6-dichloro-4-(6-(difluoromethyl)-3,5-dioxo-4,5-dihydro-1,2,4-triazin-2(3H)-yl)phenoxy)-2-hydroxyphenyl)sulfonamido)cyclopropyl)methyl)cyclopropanecarboxamide, |
| 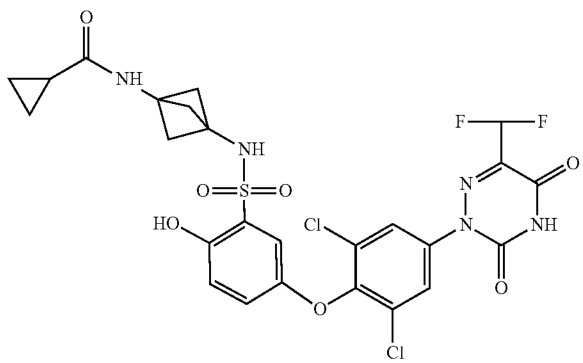 [SMILES: O=C(NC12CC(NS(=O)(=O)c3cc(Oc4c(Cl)cc(-n5nc(C(F)F)c(=O)[nH]c5=O)cc4Cl)ccc3O)(C1)C2)C1CC1] | N-(3-((5-(2,6-dichloro-4-(6-(difluoromethyl)-3,5-dioxo-4,5-dihydro-1,2,4-triazin-2(3H)-yl)phenoxy)-2-hydroxyphenyl)sulfonamido)bicyclo[1.1.1]pentan-1-yl)cyclopropanecarboxamide, |
| 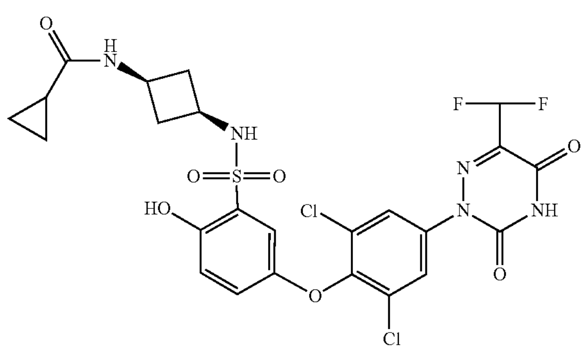 [SMILES: O=C(N[C@H]1C[C@@H](NS(=O)(=O)c2cc(Oc3c(Cl)cc(-n4nc(C(F)F)c(=O)[nH]c4=O)cc3Cl)ccc2O)C1)C1CC1] | N-((1s,3s)-3-((5-(2,6-dichloro-4-(6-(difluoromethyl)-3,5-dioxo-4,5-dihydro-1,2,4-triazin-2(3H)-yl)phenoxy)-2-hydroxyphenyl)sulfonamido)cyclobutyl)cyclopropanecarboxamide, |
| 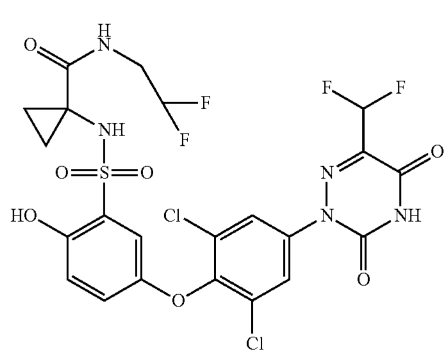 [SMILES: O=C(NCC(F)F)C1(NS(=O)(=O)c2cc(Oc3c(Cl)cc(-n4nc(C(F)F)c(=O)[nH]c4=O)cc3Cl)ccc2O)CC1] | 1-((5-(2,6-dichloro-4-(6-(difluoromethyl)-3,5-dioxo-4,5-dihydro-1,2,4-triazin-2(3H)-yl)phenoxy)-2-hydroxyphenyl)sulfonamido)-N-(2,2-difluoroethyl)cyclopropane-1-carboxamide, |

| Structure | Chemical Name |
|---|---|
| 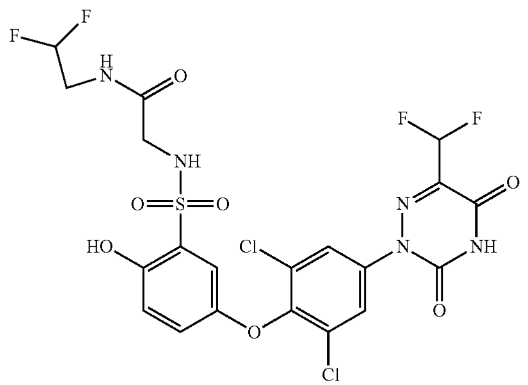 [SMILES: O=C(CNS(=O)(=O)c1cc(Oc2c(Cl)cc(-n3nc(C(F)F)c(=O)[nH]c3=O)cc2Cl)ccc1O)NCC(F)F] | 2-((5-(2,6-dichloro-4-(6-(difluoromethyl)-3,5-dioxo-4,5-dihydro-1,2,4-triazin-2(3H)-yl)phenoxy)-2-hydroxyphenyl)sulfonamido)-N-(2,2-difluoroethyl)acetamide , |
| 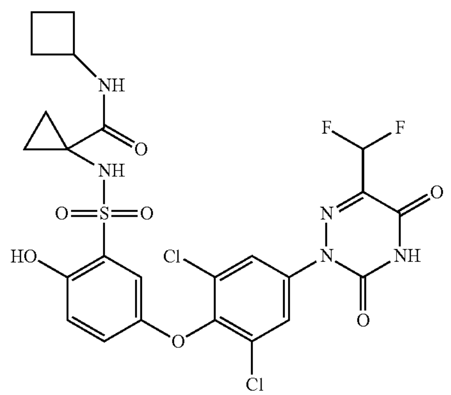 [SMILES: O=C(NC1CCC1)C1(NS(=O)(=O)c2cc(Oc3c(Cl)cc(-n4nc(C(F)F)c(=O)[nH]c4=O)cc3Cl)ccc2O)CC1] | N-cyclobutyl-1-((5-(2,6-dichloro-4-(6-(difluoromethyl)-3,5-dioxo-4,5-dihydro-1,2,4-triazin-2(3H)-yl)phenoxy)-2-hydroxyphenyl)sulfonamido)cyclopropane-1-carboxamide , |
| 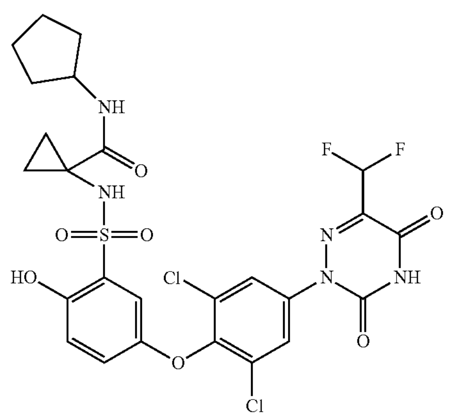 [SMILES: O=C(NC1CCCC1)C1(NS(=O)(=O)c2cc(Oc3c(Cl)cc(-n4nc(C(F)F)c(=O)[nH]c4=O)cc3Cl)ccc2O)CC1] | N-cyclopentyl-1-((5-(2,6-dichloro-4-(6-(difluoromethyl)-3,5-dioxo-4,5-dihydro-1,2,4-triazin-2(3H)-yl)phenoxy)-2-hydroxyphenyl)sulfonamido)cyclopropane-1-carboxamide , |
| 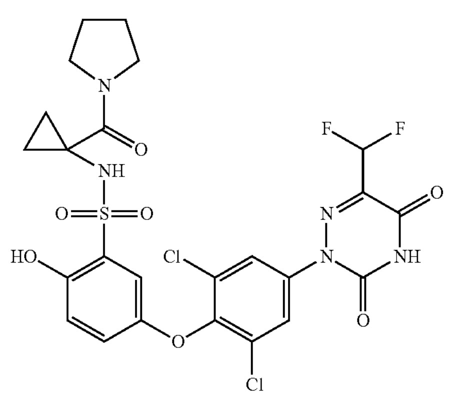 | 5-(2,6-dichloro-4-(6-(difluoromethyl)-3,5-dioxo-4,5-dihydro-1,2,4-triazin-2(3H)-yl)phenoxy)-2-hydroxy-N-(1-(pyrrolidine-1-carbonyl)cyclopropyl)benzenesulfonamide , |

| Structure | Chemical Name |
|---|---|
| 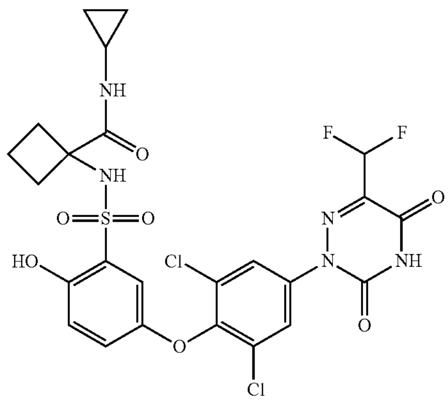 [SMILES: O=C(NC1CC1)C1(NS(=O)(=O)c2cc(Oc3c(Cl)cc(-n4nc(C(F)F)c(=O)[nH]c4=O)cc3Cl)ccc2O)CCC1] | N-cyclopropyl-1-((5-(2,6-dichloro-4-(6-(difluoromethyl)-3,5-dioxo-4,5-dihydro-1,2,4-triazin-2(3H)-yl)phenoxy)-2-hydroxyphenyl)sulfonamido)cyclobutane-1-carboxamide, |
| 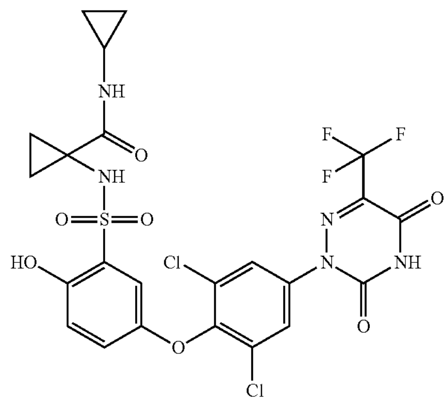 [SMILES: O=C(NC1CC1)C1(NS(=O)(=O)c2cc(Oc3c(Cl)cc(-n4nc(C(F)(F)F)c(=O)[nH]c4=O)cc3Cl)ccc2O)CC1] | N-cyclopropyl-1-((5-(2,6-dichloro-4-(3,5-dioxo-6-(trifluoromethyl)-4,5-dihydro-1,2,4-triazin-2(3H)-yl)phenoxy)-2-hydroxyphenyl)sulfonamido)cyclopropane-1-carboxamide, |
| 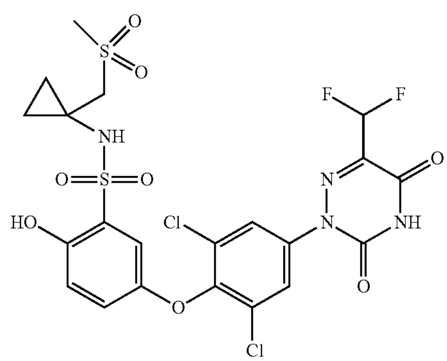 [SMILES: CS(=O)(=O)CC1(NS(=O)(=O)c2cc(Oc3c(Cl)cc(-n4nc(C(F)F)c(=O)[nH]c4=O)cc3Cl)ccc2O)CC1] | 5-(2,6-dichloro-4-(6-(difluoromethyl)-3,5-dioxo-4,5-dihydro-1,2,4-triazin-2(3H)-yl)phenoxy)-2-hydroxy-N-(1-((methylsulfonyl)methyl)cyclopropyl)benzenesulfonamide, |
| 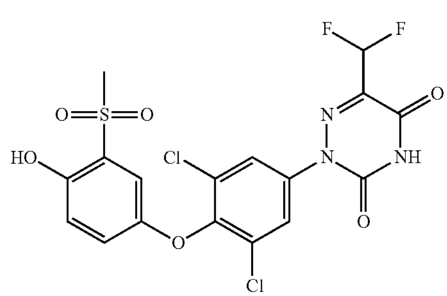 [SMILES: CS(=O)(=O)c1cc(Oc2c(Cl)cc(-n3nc(C(F)F)c(=O)[nH]c3=O)cc2Cl)ccc1O] | 2-(3,5-dichloro-4-(4-hydroxy-3-(methylsulfonyl)phenoxy)phenyl)-6-(difluoromethyl)-1,2,4-triazine-3,5(2H,4H)-dione, |

| Structure | Chemical Name |
|---|---|
| | 5-(2,6-dichloro-4-(6-(difluoromethyl)-3,5-dioxo-4,5-dihydro-1,2,4-triazin-2(3H)-yl)phenoxy)-2-hydroxy-N-(1-oxidothietan-3-yl)benzenesulfonamide |
| | 5-(2,6-dichloro-4-(6-(difluoromethyl)-3,5-dioxo-4,5-dihydro-1,2,4-triazin-2(3H)-yl)benzyl)-2-hydroxy-N-((1r,3r)-3-hydroxycyclobutyl)benzenesulfonamide |
| | (S)-5-(2,6-dichloro-4-(6-(difluoromethyl)-3,5-dioxo-4,5-dihydro-1,2,4-triazin-2(3H)-yl)phenoxy)-2-hydroxy-N-(tetrahydrofuran-3-yl)benzamide |
| | 5-(2,6-dichloro-4-(6-(difluoromethyl)-3,5-dioxo-4,5-dihydro-1,2,4-triazin-2(3H)-yl)phenoxy)-2-hydroxy-N-((1r,3r)-3-hydroxycyclobutyl)-N-methylbenzenesulfonamide |
| | 2-(3,5-dichloro-4-(4-hydroxy-3-(((1s,3s)-3-hydroxycyclobutyl)sulfonyl)phenoxy)phenyl)-6-(difluoromethyl)-1,2,4-triazine-3,5(2H,4H)-dione |

| Structure | Chemical Name |
|---|---|
| 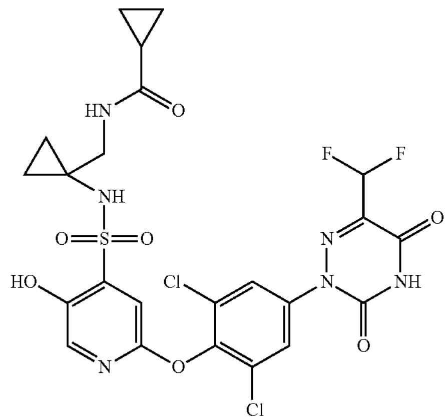 [SMILES: O=C(NCC1(NS(=O)(=O)c2cc(Oc3c(Cl)cc(-n4nc(C(F)F)c(=O)[nH]c4=O)cc3Cl)ncc2O)CC1)C1CC1] | N-((1-((2-(2,6-dichloro-4-(6-(difluoromethyl)-3,5-dioxo-4,5-dihydro-1,2,4-triazin-2(3H)-yl)phenoxy)-5-hydroxypyridine)-4-sulfonamido)cyclopropyl)methyl)cyclopropanecarboxamide , |
| 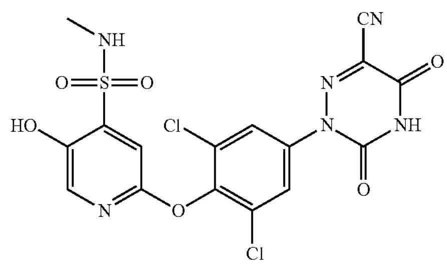 [SMILES: CNS(=O)(=O)c1cc(Oc2c(Cl)cc(-n3nc(C#N)c(=O)[nH]c3=O)cc2Cl)ncc1O] | 2-(2,6-dichloro-4-(6-cyano-3,5-dioxo-4,5-dihydro-1,2,4-triazin-2(3H)-yl)phenoxy)-5-hydroxy-N-methylpyridine-4-sulfonamide , |
| 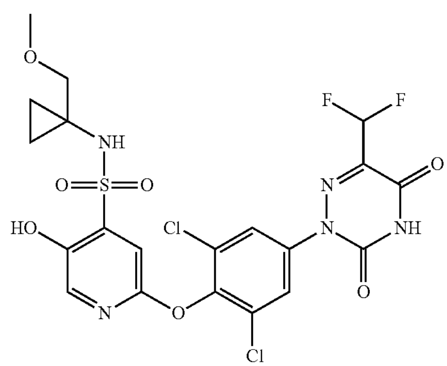 [SMILES: COCC1(NS(=O)(=O)c2cc(Oc3c(Cl)cc(-n4nc(C(F)F)c(=O)[nH]c4=O)cc3Cl)ncc2O)CC1] | 2-(2,6-dichloro-4-(6-(difluoromethyl)-3,5-dioxo-4,5-dihydro-1,2,4-triazin-2(3H)-yl)phenoxy)-5-hydroxy-N-(1-(methoxymethyl)cyclopropyl)pyridine-4-sulfonamide , |
| 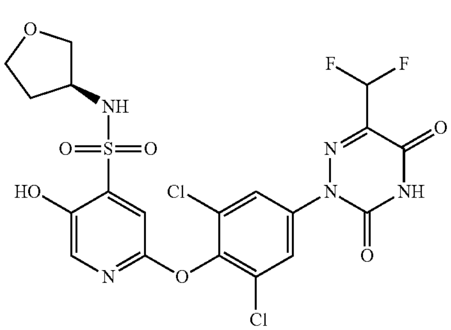 [SMILES: O=c1[nH]c(=O)n(-c2cc(Cl)c(Oc3cc(S(=O)(=O)N[C@H]4CCOC4)c(O)cn3)c(Cl)c2)nc1C(F)F] | (S)-2-(2,6-dichloro-4-(6-(difluoromethyl)-3,5-dioxo-4,5-dihydro-1,2,4-triazin-2(3H)-yl)phenoxy)-5-hydroxy-N-(tetrahydrofuran-3-yl)pyridine-4-sulfonamide , |

| Structure | Chemical Name |
|---|---|
| 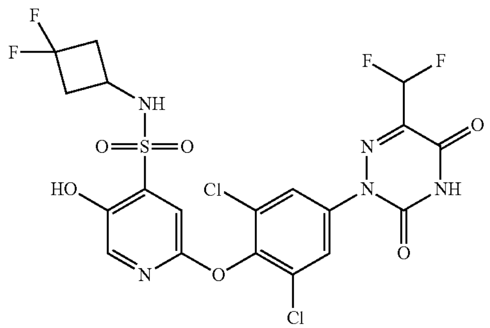 [SMILES: O=c1[nH]c(=O)n(-c2cc(Cl)c(Oc3cc(S(=O)(=O)NC4CC(F)(F)C4)c(O)cn3)c(Cl)c2)nc1C(F)F] | 2-(2,6-dichloro-4-(6-(difluoromethyl)-3,5-dioxo-4,5-dihydro-1,2,4-triazin-2(3H)-yl)phenoxy)-N-(3,3-difluorocyclobutyl)-5-hydroxypyridine-4-sulfonamide , |
| 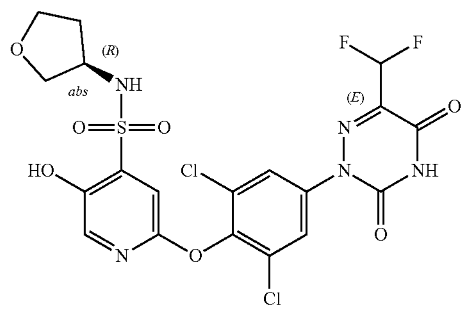 | (R)-2-(2,6-dichloro-4-(6-(difluoromethyl)-3,5-dioxo-4,5-dihydro-1,2,4-triazin-2(3H)-yl)phenoxy)-5-hydroxy-N-(tetrahydrofuran-3-yl)pyridine-4-sulfonamide , |
| 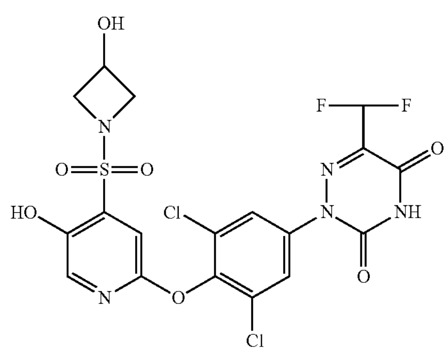 [SMILES: O=c1[nH]c(=O)n(-c2cc(Cl)c(Oc3cc(S(=O)(=O)N4CC(O)C4)c(O)cn3)c(Cl)c2)nc1C(F)F] | 2-(3,5-dichloro-4-((5-hydroxy-4-((3-hydroxyazetidin-1-yl)sulfonyl)pyridin-2-yl)oxy)phenyl)-6-(difluoromethyl)-1,2,4-triazine-3,5(2H,4H)-dione , |
| 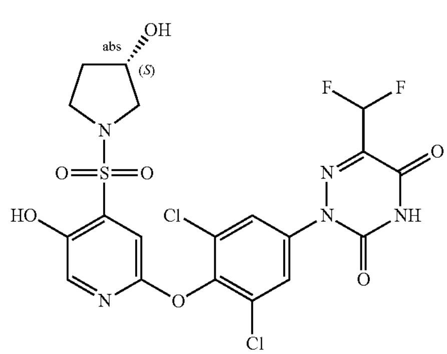 | (S)-2-(3,5-dichloro-4-((5-hydroxy-4-((3-hydroxypyrrolidin-1-yl)sulfonyl)pyridin-2-yl)oxy)phenyl)-6-(difluoromethyl)-1,2,4-triazine-3,5(2H,4H)-dione , |

| Structure | Chemical Name |
|---|---|
| | 2-(3,5-dichloro-4-((4-((3,3-difluoroazetidin-1-yl)sulfonyl)-5-hydroxypyridin-2-yl)oxy)phenyl)-6-(difluoromethyl)-1,2,4-triazine-3,5(2H,4H)-dione |
| | 2-(2,6-dichloro-4-(6-(difluoromethyl)-3,5-dioxo-4,5-dihydro-1,2,4-triazin-2(3H)-yl)phenoxy)-5-hydroxy-N-isopropylpyridine-4-sulfonamide |
| | 2-(2,6-dichloro-4-(6-(difluoromethyl)-3,5-dioxo-4,5-dihydro-1,2,4-triazin-2(3H)-yl)phenoxy)-N-(2,2-difluoroethyl)-5-hydroxypyridine-4-sulfonamide |
| | 2-(2,6-dichloro-4-(6-(difluoromethyl)-3,5-dioxo-4,5-dihydro-1,2,4-triazin-2(3H)-yl)phenoxy)-N-ethyl-5-hydroxypyridine-4-sulfonamide |
| | 2-(2,6-dichloro-4-(6-(difluoromethyl)-3,5-dioxo-4,5-dihydro-1,2,4-triazin-2(3H)-yl)phenoxy)-5-hydroxy-N,N-dimethylpyridine-4-sulfonamide |

-continued

| Structure | Chemical Name |
|---|---|
| 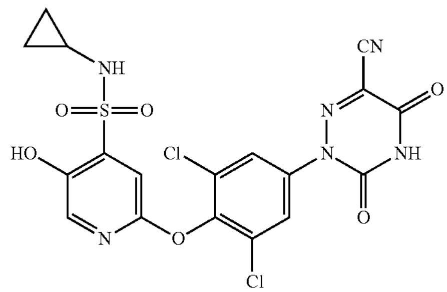 [SMILES: N#Cc1nn(-c2cc(Cl)c(Oc3cc(S(=O)(=O)NC4CC4)c(O)cn3)c(Cl)c2)c(=O)[nH]c1=O] | N-cyclopropyl-2-(2,6-dichloro-4-(6-cyano-3,5-dioxo-4,5-dihydro-1,2,4-triazin-2(3H)-yl)phenoxy)-5-hydroxypyridine-4-sulfonamide, |
| 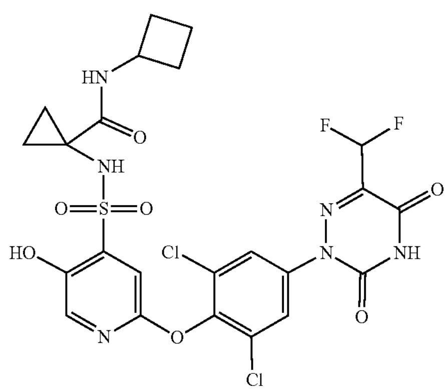 [SMILES: O=C(NC1CCC1)C1(NS(=O)(=O)c2cc(Oc3c(Cl)cc(-n4nc(C(F)F)c(=O)[nH]c4=O)cc3Cl)ncc2O)CC1] | N-cyclobutyl-1-((2-(2,6-dichloro-4-(6-(difluoromethyl)-3,5-dioxo-4,5-dihydro-1,2,4-triazin-2(3H)-yl)phenoxy)-5-hydroxypyridine)-4-sulfonamido)cyclopropane-1-carboxamide, |
| 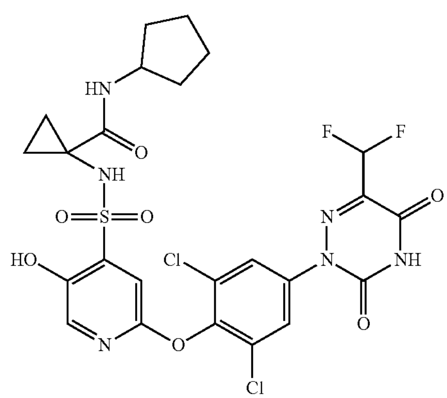 [SMILES: O=C(NC1CCCC1)C1(NS(=O)(=O)c2cc(Oc3c(Cl)cc(-n4nc(C(F)F)c(=O)[nH]c4=O)cc3Cl)ncc2O)CC1] | N-cyclopentyl-1-((2-(2,6-dichloro-4-(6-(difluoromethyl)-3,5-dioxo-4,5-dihydro-1,2,4-triazin-2(3H)-yl)phenoxy)-5-hydroxypyridine)-4-sulfonamido)cyclopropane-1-carboxamide, |
| 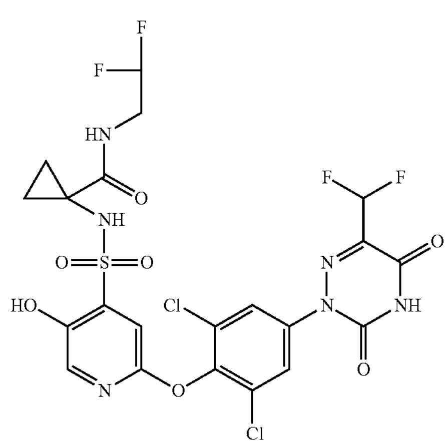 [SMILES: O=C(NCC(F)F)C1(NS(=O)(=O)c2cc(Oc3c(Cl)cc(-n4nc(C(F)F)c(=O)[nH]c4=O)cc3Cl)ncc2O)CC1] | 1-((2-(2,6-dichloro-4-(6-(difluoromethyl)-3,5-dioxo-4,5-dihydro-1,2,4-triazin-2(3H)-yl)phenoxy)-5-hydroxypyridine)-4-sulfonamido)-N-(2,2-difluoroethyl)cyclopropane-1-carboxamide, |

-continued

| Structure | Chemical Name |
|---|---|
| 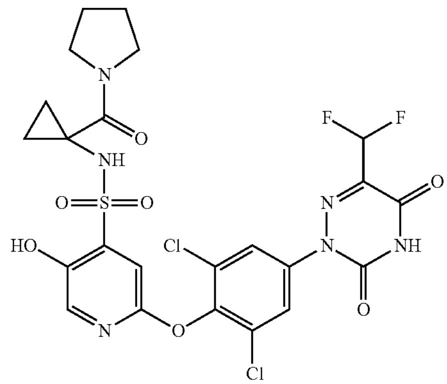 [SMILES: O=C(N1CCCC1)C1(NS(=O)(=O)c2cc(Oc3c(Cl)cc(-n4nc(C(F)F)c(=O)[nH]c4=O)cc3Cl)ncc2O)CC1] | 2-(2,6-dichloro-4-(6-(difluoromethyl)-3,5-dioxo-4,5-dihydro-1,2,4-triazin-2(3H)-yl)phenoxy)-5-hydroxy-N-(1-(pyrrolidine-1-carbonyl)cyclopropyl)pyridine-4-sulfonamide |
| 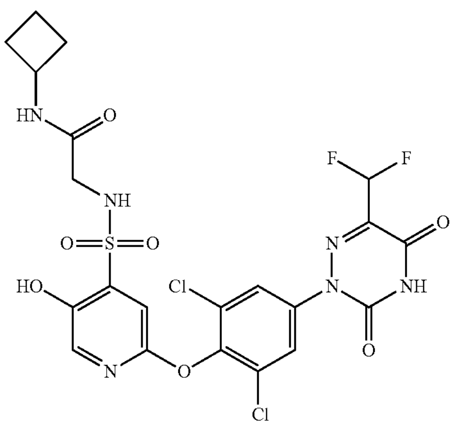 [SMILES: O=C(CNS(=O)(=O)c1cc(Oc2c(Cl)cc(-n3nc(C(F)F)c(=O)[nH]c3=O)cc2Cl)ncc1O)NC1CCC1] | N-cyclobutyl-2-((2-(2,6-dichloro-4-(6-(difluoromethyl)-3,5-dioxo-4,5-dihydro-1,2,4-triazin-2(3H)-yl)phenoxy)-5-hydroxypyridine)-4-sulfonamido)acetamide |
| 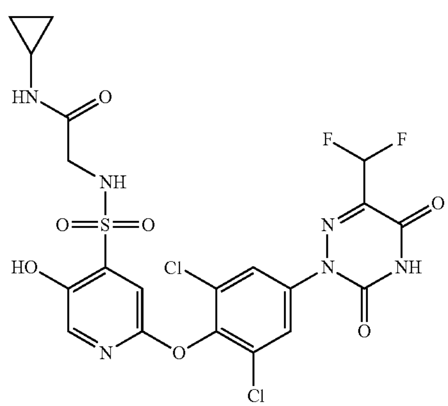 [SMILES: O=C(CNS(=O)(=O)c1cc(Oc2c(Cl)cc(-n3nc(C(F)F)c(=O)[nH]c3=O)cc2Cl)ncc1O)NC1CC1] | N-cyclopropyl-2-((2-(2,6-dichloro-4-(6-(difluoromethyl)-3,5-dioxo-4,5-dihydro-1,2,4-triazin-2(3H)-yl)phenoxy)-5-hydroxypyridine)-4-sulfonamido)acetamide |
| 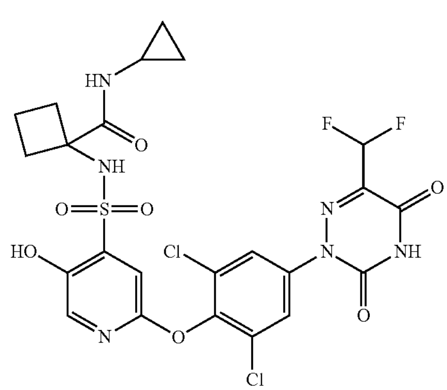 [SMILES: O=C(NC1CC1)C1(NS(=O)(=O)c2cc(Oc3c(Cl)cc(-n4nc(C(F)F)c(=O)[nH]c4=O)cc3Cl)ncc2O)CCC1] | N-cyclopropyl-1-((2-(2,6-dichloro-4-(6-(difluoromethyl)-3,5-dioxo-4,5-dihydro-1,2,4-triazin-2(3H)-yl)phenoxy)-5-hydroxypyridine)-4-sulfonamido)cyclobutane-1-carboxamide |

| Structure | Chemical Name |
|---|---|
| 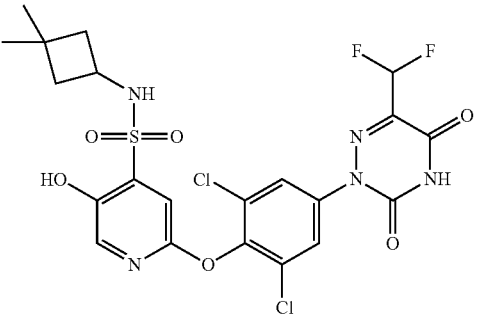 [SMILES: CC1(C)CC(NS(=O)(=O)c2cc(Oc3c(Cl)cc(-n4nc(C(F)F)c(=O)[nH]c4=O)cc3Cl)ncc2O)C1] | 2-(2,6-dichloro-4-(6-(difluoromethyl)-3,5-dioxo-4,5-dihydro-1,2,4-triazin-2(3H)-yl)phenoxy)-N-(3,3-dimethylcyclobutyl)-5-hydroxypyridine-4-sulfonamide, |
| 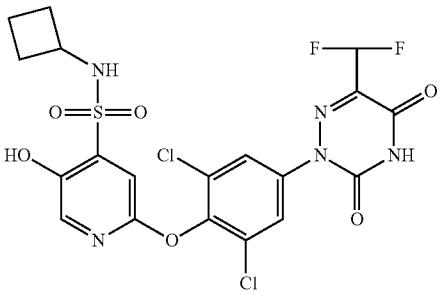 [SMILES: O=c1[nH]c(=O)n(-c2cc(Cl)c(Oc3cc(S(=O)(=O)NC4CCC4)c(O)cn3)c(Cl)c2)nc1C(F)F] | N-cyclobutyl-2-(2,6-dichloro-4-(6-(difluoromethyl)-3,5-dioxo-4,5-dihydro-1,2,4-triazin-2(3H)-yl)phenoxy)-5-hydroxypyridine-4-sulfonamide, |
| 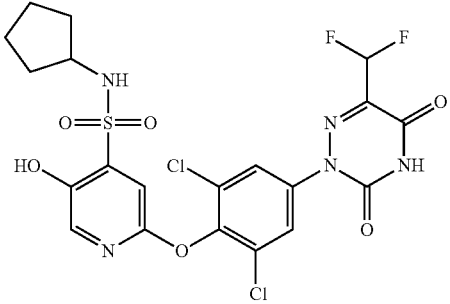 [SMILES: O=c1[nH]c(=O)n(-c2cc(Cl)c(Oc3cc(S(=O)(=O)NC4CCCC4)c(O)cn3)c(Cl)c2)nc1C(F)F] | N-cyclopentyl-2-(2,6-dichloro-4-(6-(difluoromethyl)-3,5-dioxo-4,5-dihydro-1,2,4-triazin-2(3H)-yl)phenoxy)-5-hydroxypyridine-4-sulfonamide, |
| 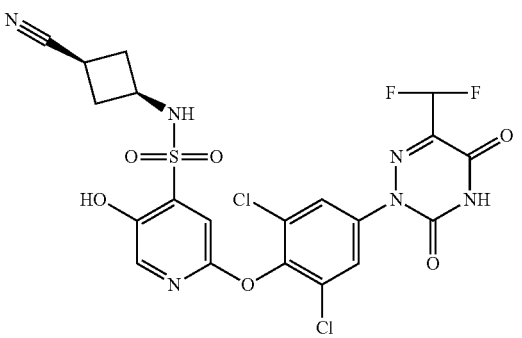 [SMILES: N#C[C@H]1C[C@@H](NS(=O)(=O)c2cc(Oc3c(Cl)cc(-n4nc(C(F)F)c(=O)[nH]c4=O)cc3Cl)ncc2O)C1] | N-((1s,3s)-3-cyanocyclobutyl)-2-(2,6-dichloro-4-(6-(difluoromethyl)-3,5-dioxo-4,5-dihydro-1,2,4-triazin-2(3H)-yl)phenoxy)-5-hydroxypyridine-4-sulfonamide, |
| 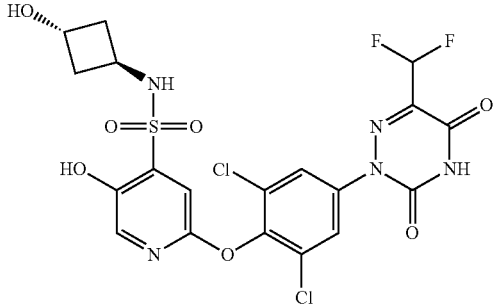 [SMILES: O=c1[nH]c(=O)n(-c2cc(Cl)c(Oc3cc(S(=O)(=O)N[C@H]4C[C@H](O)C4)c(O)cn3)c(Cl)c2)nc1C(F)F] | 2-(2,6-dichloro-4-(6-(difluoromethyl)-3,5-dioxo-4,5-dihydro-1,2,4-triazin-2(3H)-yl)phenoxy)-5-hydroxy-N-((1r,3r)-3-hydroxycyclobutyl)pyridine-4-sulfonamide, |

-continued

| Structure | Chemical Name |
|---|---|
| 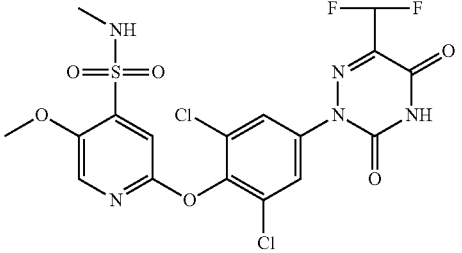 [SMILES: CNS(=O)(=O)c1cc(Oc2c(Cl)cc(-n3nc(C(F)F)c(=O)[nH]c3=O)cc2Cl)ncc1OC] | 2-(2,6-dichloro-4-(6-(difluoromethyl)-3,5-dioxo-4,5-dihydro-1,2,4-triazin-2(3H)-yl)phenoxy)-5-methoxy-N-methylpyridine-4-sulfonamide, |
| 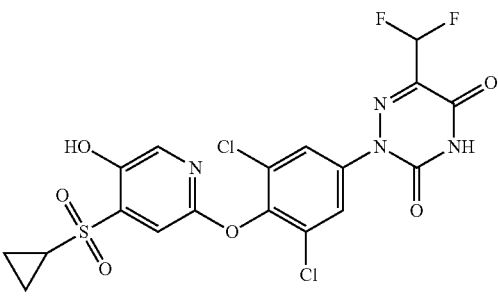 [SMILES: O=c1[nH]c(=O)n(-c2cc(Cl)c(Oc3cc(S(=O)(=O)C4CC4)c(O)cn3)c(Cl)c2)nc1C(F)F] | 2-(3,5-dichloro-4-((4-(cyclopropylsulfonyl)-5-hydroxypyridin-2-yl)oxy)phenyl)-6-(difluoromethyl)-1,2,4-triazine-3,5(2H,4H)-dione, |
| 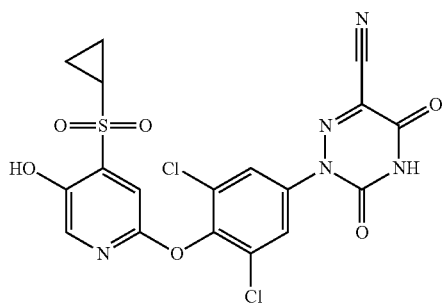 [SMILES: N#Cc1nn(-c2cc(Cl)c(Oc3cc(S(=O)(=O)C4CC4)c(O)cn3)c(Cl)c2)c(=O)[nH]c1=O] | 2-(3,5-dichloro-4-((4-(cyclopropylsulfonyl)-5-hydroxypyridin-2-yl)oxy)phenyl)-3,5-dioxo-2,3,4,5-tetrahydro-1,2,4-triazine-6-carbonitrile, |
| 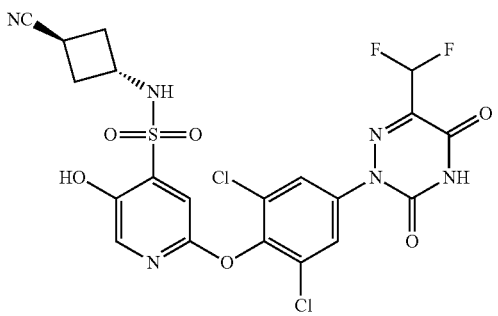 [SMILES: N#C[C@H]1C[C@H](NS(=O)(=O)c2cc(Oc3c(Cl)cc(-n4nc(C(F)F)c(=O)[nH]c4=O)cc3Cl)ncc2O)C1] | N-((1r,3r)-3-cyanocyclobutyl)-2-(2,6-dichloro-4-(6-(difluoromethyl)-3,5-dioxo-4,5-dihydro-1,2,4-triazin-2(3H)-yl)phenoxy)-5-hydroxypyridine-4-sulfonamide, |
| 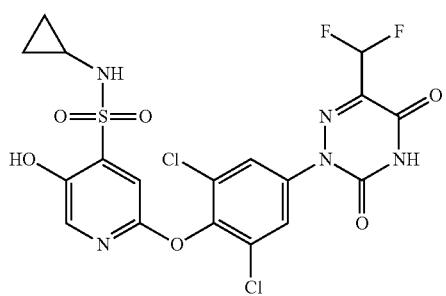 [SMILES: O=c1[nH]c(=O)n(-c2cc(Cl)c(Oc3cc(S(=O)(=O)NC4CC4)c(O)cn3)c(Cl)c2)nc1C(F)F] | N-cyclopropyl-2-(2,6-dichloro-4-(6-(difluoromethyl)-3,5-dioxo-4,5-dihydro-1,2,4-triazin-2(3H)-yl)phenoxy)-5-hydroxypyridine-4-sulfonamide, |

-continued

| Structure | Chemical Name |
|---|---|
| 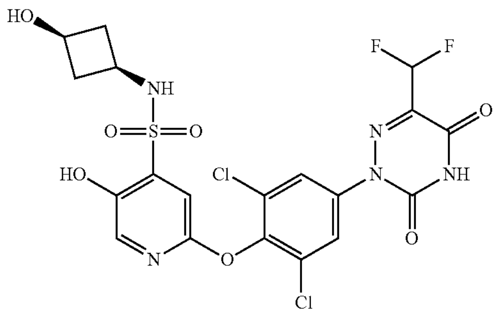 [SMILES: O=c1[nH]c(=O)n(-c2cc(Cl)c(Oc3cc(S(=O)(=O)N[C@H]4C[C@@H](O)C4)c(O)cn3)c(Cl)c2)nc1C(F)F] | 2-(2,6-dichloro-4-(6-(difluoromethyl)-3,5-dioxo-4,5-dihydro-1,2,4-triazin-2(3H)-yl)phenoxy)-5-hydroxy-N-((1s,3s)-3-hydroxycyclobutyl)pyridine-4-sulfonamide |
| 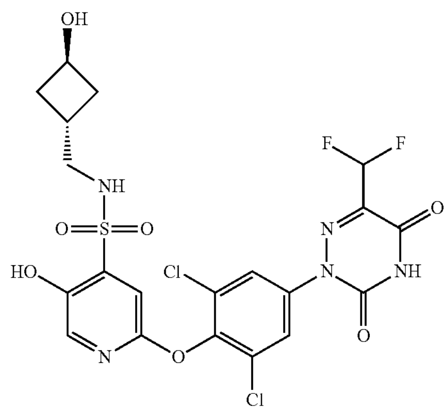 [SMILES: O=c1[nH]c(=O)n(-c2cc(Cl)c(Oc3cc(S(=O)(=O)NC[C@H]4C[C@H](O)C4)c(O)cn3)c(Cl)c2)nc1C(F)F] | 2-(2,6-dichloro-4-(6-(difluoromethyl)-3,5-dioxo-4,5-dihydro-1,2,4-triazin-2(3H)-yl)phenoxy)-5-hydroxy-N-(((1r,3r)-3-hydroxycyclobutyl)methyl)pyridine-4-sulfonamide |
| 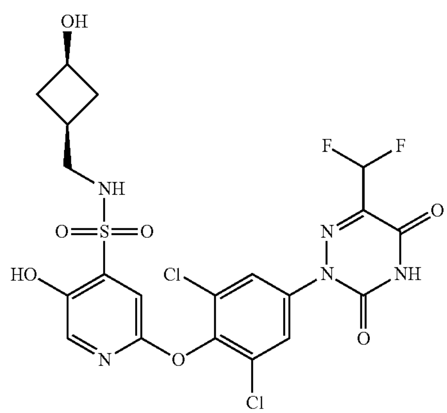 [SMILES: O=c1[nH]c(=O)n(-c2cc(Cl)c(Oc3cc(S(=O)(=O)NC[C@H]4C[C@@H](O)C4)c(O)cn3)c(Cl)c2)nc1C(F)F] | 2-(2,6-dichloro-4-(6-(difluoromethyl)-3,5-dioxo-4,5-dihydro-1,2,4-triazin-2(3H)-yl)phenoxy)-5-hydroxy-N-(((1s,3s)-3-hydroxycyclobutyl)methyl)pyridine-4-sulfonamide |
| 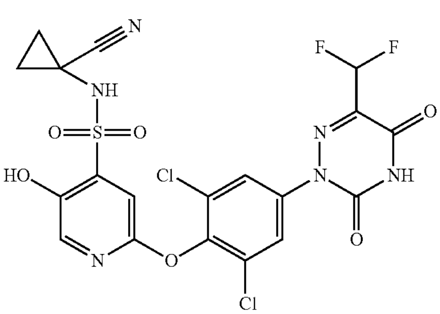 [SMILES: N#CC1(NS(=O)(=O)c2cc(Oc3c(Cl)cc(-n4nc(C(F)F)c(=O)[nH]c4=O)cc3Cl)ncc2O)CC1] | N-(1-cyanocyclopropyl)-2-(2,6-dichloro-4-(6-(difluoromethyl)-3,5-dioxo-4,5-dihydro-1,2,4-triazin-2(3H)-yl)phenoxy)-5-hydroxypyridine-4-sulfonamide |

| Structure | Chemical Name |
|---|---|
| | 2-(2,6-dichloro-4-(6-(difluoromethyl)-3,5-dioxo-4,5-dihydro-1,2,4-triazin-2(3H)-yl)phenoxy)-5-hydroxy-N-(tetrahydro-2H-pyran-4-yl)pyridine-4-sulfonamide |
| | 2-(2,6-dichloro-4-(6-(difluoromethyl)-3,5-dioxo-4,5-dihydro-1,2,4-triazin-2(3H)-yl)phenoxy)-5-hydroxy-N-(2-hydroxy-2-methylpropyl)pyridine-4-sulfonamide |
| | 2-(2,6-dichloro-4-(6-(difluoromethyl)-3,5-dioxo-4,5-dihydro-1,2,4-triazin-2(3H)-yl)phenoxy)-5-hydroxy-N-((1s,3s)-3-hydroxy-3-methylcyclobutyl)pyridine-4-sulfonamide |
| | 2-(2,6-dichloro-4-(6-(difluoromethyl)-3,5-dioxo-4,5-dihydro-1,2,4-triazin-2(3H)-yl)phenoxy)-5-hydroxy-N-((1r,3r)-3-methoxycyclobutyl)pyridine-4-sulfonamide |

| Structure | Chemical Name |
|---|---|
| 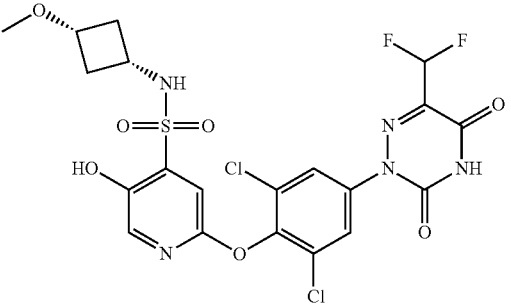 [SMILES: CO[C@H]1C[C@@H](NS(=O)(=O)c2cc(Oc3c(Cl)cc(-n4nc(C(F)F)c(=O)[nH]c4=O)cc3Cl)ncc2O)C1] | 2-(2,6-dichloro-4-(6-(difluoromethyl)-3,5-dioxo-4,5-dihydro-1,2,4-triazin-2(3H)-yl)phenoxy)-5-hydroxy-N-((1s,3s)-3-methoxycyclobutyl)pyridine-4-sulfonamide |
| 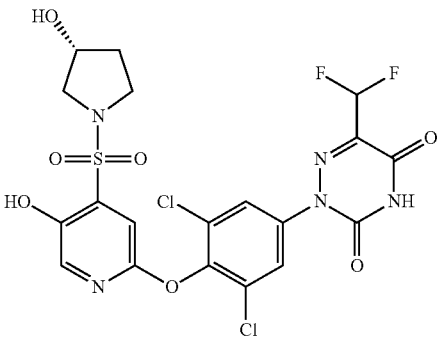 [SMILES: O=c1[nH]c(=O)n(-c2cc(Cl)c(Oc3cc(S(=O)(=O)N4CC[C@@H](O)C4)c(O)cn3)c(Cl)c2)nc1C(F)F] | (R)-2-(3,5-dichloro-4-((5-hydroxy-4-((3-hydroxypyrrolidin-1-yl)sulfonyl)pyridin-2-yl)oxy)phenyl)-6-(difluoromethyl)-1,2,4-triazine-3,5(2H,4H)-dione |
| 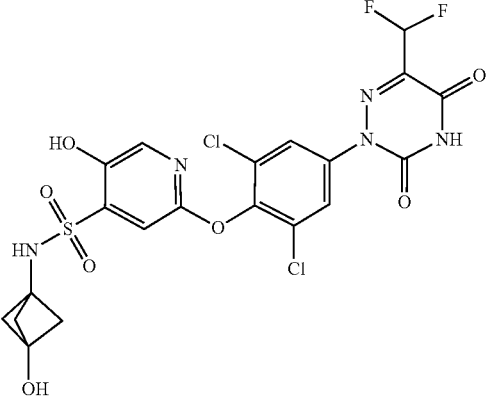 [SMILES: O=c1[nH]c(=O)n(-c2cc(Cl)c(Oc3cc(S(=O)(=O)NC45CC(O)(C4)C5)c(O)cn3)c(Cl)c2)nc1C(F)F] | 2-(2,6-dichloro-4-(6-(difluoromethyl)-3,5-dioxo-4,5-dihydro-1,2,4-triazin-2(3H)-yl)phenoxy)-5-hydroxy-N-(3-hydroxybicyclo[1.1.1]pentan-1-yl)pyridine-4-sulfonamide |
| 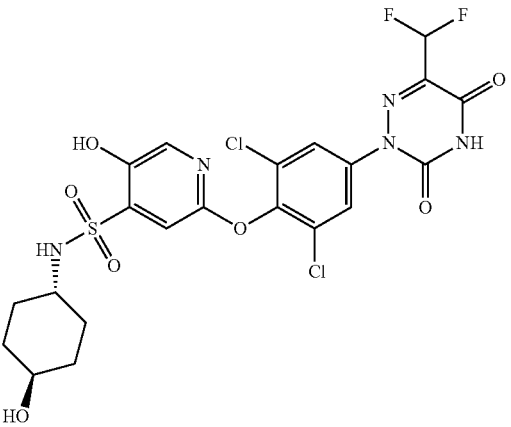 [SMILES: O=c1[nH]c(=O)n(-c2cc(Cl)c(Oc3cc(S(=O)(=O)N[C@H]4CC[C@H](O)CC4)c(O)cn3)c(Cl)c2)nc1C(F)F] | 2-(2,6-dichloro-4-(6-(difluoromethyl)-3,5-dioxo-4,5-dihydro-1,2,4-triazin-2(3H)-yl)phenoxy)-5-hydroxy-N-((1r,4r)-4-hydroxycyclohexyl)pyridine-4-sulfonamide |

| Structure | Chemical Name |
|---|---|
| 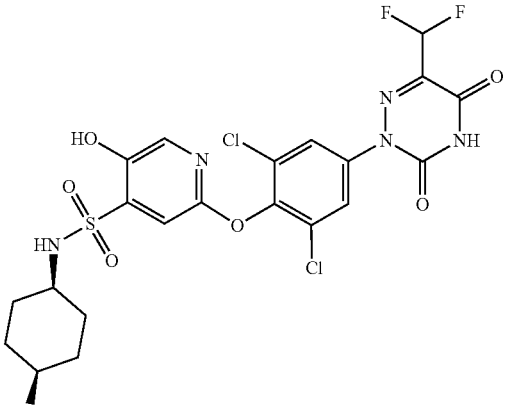 | 2-(2,6-dichloro-4-(6-(difluoromethyl)-3,5-dioxo-4,5-dihydro-1,2,4-triazin-2(3H)-yl)phenoxy)-5-hydroxy-N-((1s,4s)-4-hydroxycyclohexyl)pyridine-4-sulfonamide , |
| 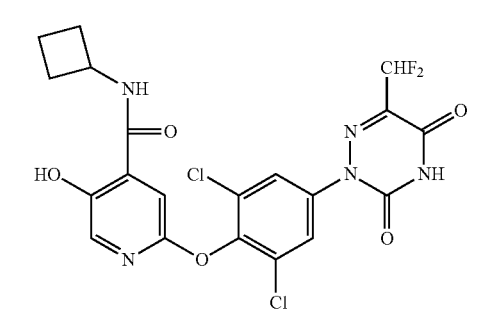 | N-cyclobutyl-2-(2,6-dichloro-4-(6-(difluoromethyl)-3,5-dioxo-4,5-dihydro-1,2,4-triazin-2(3H)-yl)phenoxy)-5-hydroxyisonicotinamide , |
| 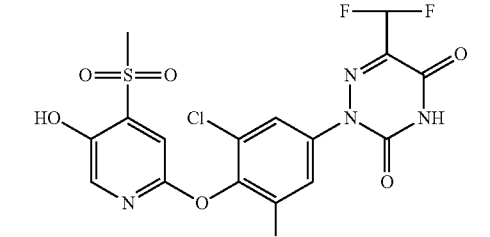 | 2-(3,5-dichloro-4-((5-hydroxy-4-(methylsulfonyl)pyridin-2-yl)oxy)phenyl)-6-(difluoromethyl)-1,2,4-triazine-3,5(2H,4H)-dione , |
| 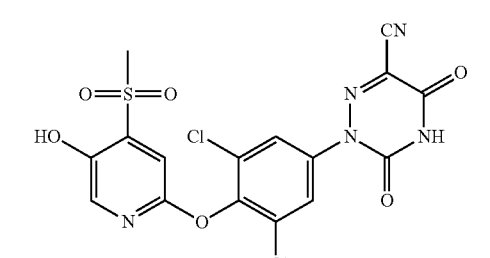 | 2-(3,5-dichloro-4-((5-hydroxy-4-(methylsulfonyl)pyridin-2-yl)oxy)phenyl)-3,5-dioxo-2,3,4,5-tetrahydro-1,2,4-triazine-6-carbonitrile , |
| 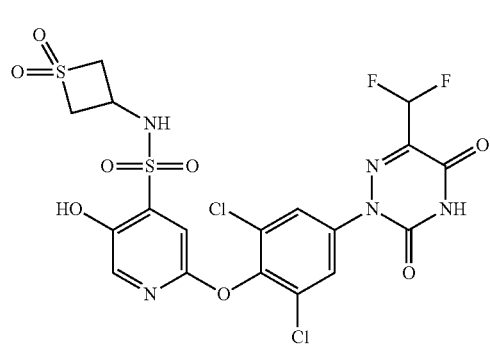 [SMILES: O=c1[nH]c(=O)n(-c2cc(Cl)c(Oc3cc(S(=O)(=O)NC4CS(=O)(=O)C4)c(O)cn3)c(Cl)c2)nc1C(F)F] | 2-(2,6-dichloro-4-(6-(difluoromethyl)-3,5-dioxo-4,5-dihydro-1,2,4-triazin-2(3H)-yl)phenoxy)-N-(1,1-dioxidothietan-3-yl)-5-hydroxypyridine-4-sulfonamide , |

| Structure | Chemical Name |
|---|---|
| 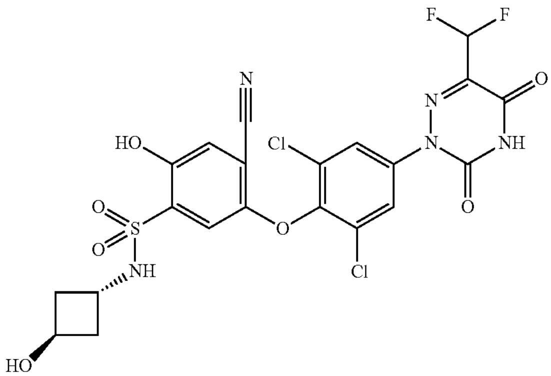 [SMILES: N#Cc1cc(O)c(S(=O)(=O)N[C@H]2C[C@H](O)C2)cc1Oc1c(Cl)cc(-n2nc(C(F)F)c(=O)[nH]c2=O)cc1Cl] | 4-cyano-5-(2,6-dichloro-4-(6-(difluoromethyl)-3,5-dioxo-4,5-dihydro-1,2,4-triazin-2(3H)-yl)phenoxy)-2-hydroxy-N-((1r,3r)-3-hydroxycyclobutyl)benzenesulfonamide, |
| 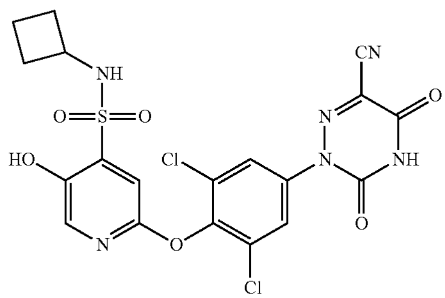 [SMILES: N#Cc1nn(-c2cc(Cl)c(Oc3cc(S(=O)(=O)NC4CCC4)c(O)cn3)c(Cl)c2)c(=O)[nH]c1=O] | N-cyclobutyl-2-(2,6-dichloro-4-(6-cyano-3,5-dioxo-4,5-dihydro-1,2,4-triazin-2(3H)-yl)phenoxy)-5-hydroxypyridine-4-sulfonamide, |
| 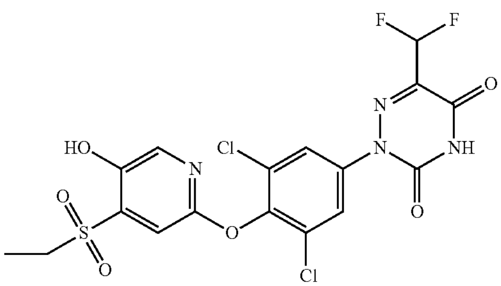 [SMILES: CCS(=O)(=O)c1cc(Oc2c(Cl)cc(-n3nc(C(F)F)c(=O)[nH]c3=O)cc2Cl)ncc1O] | 2-(3,5-dichloro-4-((4-(ethylsulfonyl)-5-hydroxypyridin-2-yl)oxy)phenyl)-6-(difluoromethyl)-1,2,4-triazine-3,5(2H,4H)-dione, |
| 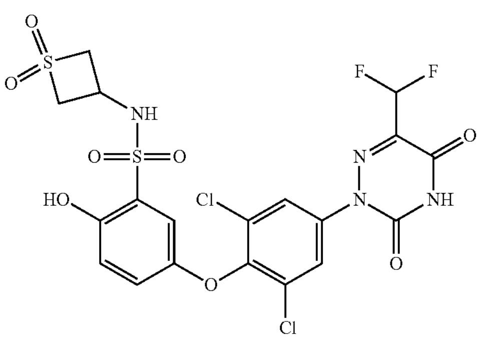 [SMILES: O=c1[nH]c(=O)n(-c2cc(Cl)c(Oc3ccc(O)c(S(=O)(=O)NC4CS(=O)(=O)C4)c3)c(Cl)c2)nc1C(F)F] | 5-(2,6-dichloro-4-(6-(difluoromethyl)-3,5-dioxo-4,5-dihydro-1,2,4-triazin-2(3H)-yl)benzyl)-N-(1,1-dioxidothietan-3-yl)-2-hydroxybenzenesulfonamide, |
| 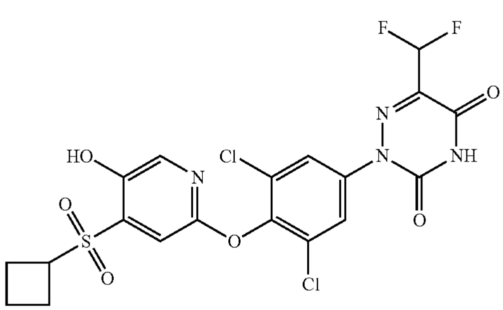 [SMILES: O=c1[nH]c(=O)n(-c2cc(Cl)c(Oc3cc(S(=O)(=O)C4CCC4)c(O)cn3)c(Cl)c2)nc1C(F)F] | 2-(3,5-dichloro-4-((4-(cyclobutylsulfonyl)-5-hydroxypyridin-2-yl)oxy)phenyl)-6-(difluoromethyl)-1,2,4-triazine-3,5(2H,4H)-dione, |

| Structure | Chemical Name |
|---|---|
| 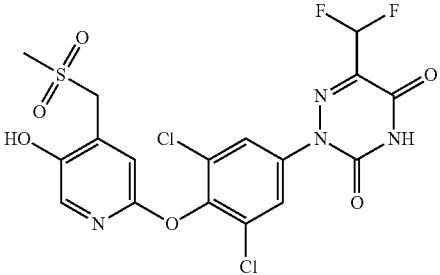 [SMILES: CS(=O)(=O)Cc1cc(Oc2c(Cl)cc(-n3nc(C(F)F)c(=O)[nH]c3=O)cc2Cl)ncc1O] | 2-(3,5-dichloro-4-((5-hydroxy-4-((methylsulfonyl)methyl)pyridin-2-yl)oxy)phenyl)-6-(difluoromethyl)-1,2,4-triazine-3,5(2H,4H)-dione , |
| 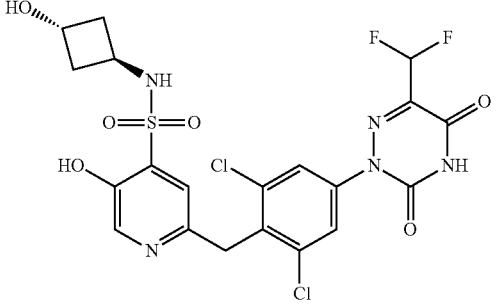 [SMILES: O=c1[nH]c(=O)n(-c2cc(Cl)c(Cc3cc(S(=O)(=O)N[C@H]4C[C@H](O)C4)c(O)cn3)c(Cl)c2)nc1C(F)F] | 2-(2,6-dichloro-4-(6-(difluoromethyl)-3,5-dioxo-4,5-dihydro-1,2,4-triazin-2(3H)-yl)benzyl)-5-hydroxy-N-((1r,3r)-3-hydroxycyclobutyl)pyridine-4-sulfonamide , |
| 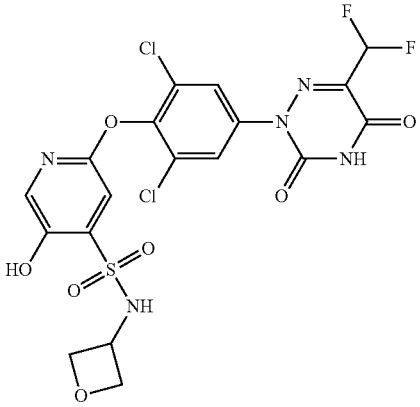 [SMILES: O=c1[nH]c(=O)n(-c2cc(Cl)c(Oc3cc(S(=O)(=O)NC4COC4)c(O)cn3)c(Cl)c2)nc1C(F)F] | 2-(2,6-dichloro-4-(6-(difluoromethyl)-3,5-dioxo-4,5-dihydro-1,2,4-triazin-2(3H)-yl)phenoxy)-5-hydroxy-N-(oxetan-3-yl)pyridine-4-sulfonamide , |
| 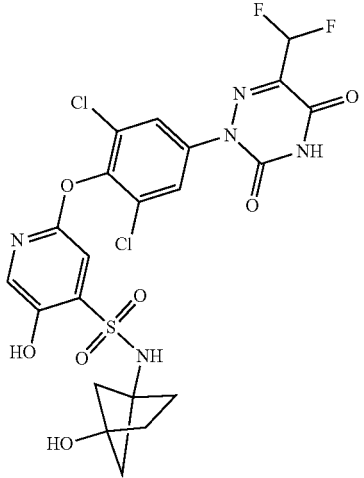 [SMILES: O=c1[nH]c(=O)n(-c2cc(Cl)c(Oc3cc(S(=O)(=O)NC45CCC(O)(C4)C5)c(O)cn3)c(Cl)c2)nc1C(F)F] | 2-(2,6-dichloro-4-(6-(difluoromethyl)-3,5-dioxo-4,5-dihydro-1,2,4-triazin-2(3H)-yl)phenoxy)-5-hydroxy-N-(4-hydroxybicyclo[2.1.1]hexan-1-yl)pyridine-4-sulfonamide , |

-continued

| Structure | Chemical Name |
|---|---|
| | 2-(2,6-dichloro-4-(6-(difluoromethyl)-3,5-dioxo-4,5-dihydro-1,2,4-triazin-2(3H)-yl)phenoxy)-5-hydroxy-N-(4-hydroxybicyclo[2.2.1]heptan-1-yl)pyridine-4-sulfonamide |
| | 2-(2,6-dichloro-4-(6-methyl-3,5-dioxo-4,5-dihydro-1,2,4-triazin-2(3H)-yl)phenoxy)-5-hydroxy-N-((1r,3r)-3-hydroxycyclobutyl)pyridine-4-sulfonamide |
| | 2-(2,6-dichloro-4-(6-methyl-3,5-dioxo-4,5-dihydro-1,2,4-triazin-2(3H)-yl)phenoxy)-5-hydroxy-N-((1s,3s)-3-hydroxycyclobutyl)pyridine-4-sulfonamide |
| | (R)-2-(2,6-dichloro-4-(6-methyl-3,5-dioxo-4,5-dihydro-1,2,4-triazin-2(3H)-yl)phenoxy)-5-hydroxy-N-(tetrahydrofuran-3-yl)pyridine-4-sulfonamide |

-continued

| Structure | Chemical Name |
|---|---|
| 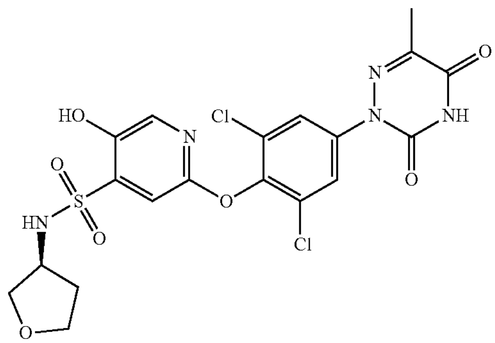 [SMILES: Cc1nn(-c2cc(Cl)c(Oc3cc(S(=O)(=O)N[C@H]4CCOC4)c(O)cn3)c(Cl)c2)c(=O)[nH]c1=O] | (S)-2-(2,6-dichloro-4-(6-methyl-3,5-dioxo-4,5-dihydro-1,2,4-triazin-2(3H)-yl)phenoxy)-5-hydroxy-N-(tetrahydrofuran-3-yl)pyridine-4-sulfonamide, |
| 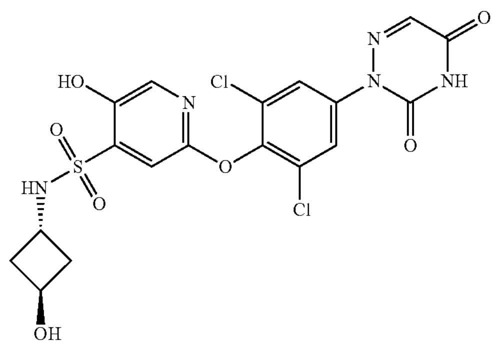 [SMILES: O=c1cnn(-c2cc(Cl)c(Oc3cc(S(=O)(=O)N[C@H]4C[C@H](O)C4)c(O)cn3)c(Cl)c2)c(=O)[nH]1] | 2-(2,6-dichloro-4-(3,5-dioxo-4,5-dihydro-1,2,4-triazin-2(3H)-yl)phenoxy)-5-hydroxy-N-((1r,3r)-3-hydroxycyclobutyl)pyridine-4-sulfonamide, |
| 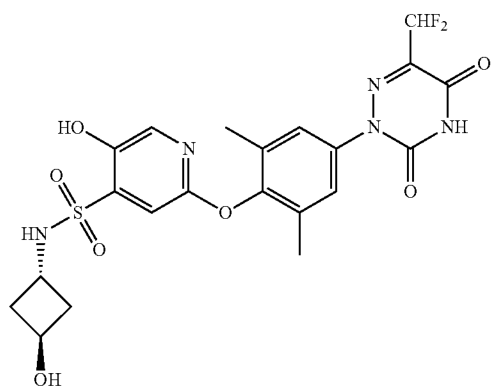 [SMILES: Cc1cc(-n2nc(C(F)F)c(=O)[nH]c2=O)cc(C)c1Oc1cc(S(=O)(=O)N[C@H]2C[C@H](O)C2)c(O)cn1] | 2-(4-(6-(difluoromethyl)-3,5-dioxo-4,5-dihydro-1,2,4-triazin-2(3H)-yl)-2,6-dimethylphenoxy)-5-hydroxy-N-((1r,3r)-3-hydroxycyclobutyl)pyridine-4-sulfonamide, |
| 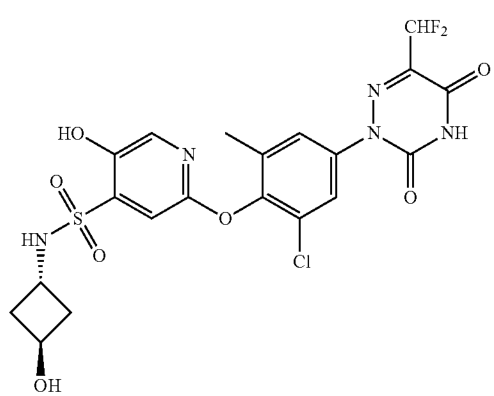 | 2-(2-chloro-4-(6-(difluoromethyl)-3,5-dioxo-4,5-dihydro-1,2,4-triazin-2(3H)-yl)-6-methylphenoxy)-5-hydroxy-N-((1r,3r)-3-hydroxycyclobutyl)pyridine-4-sulfonamide, |

-continued

| Structure | Chemical Name |
|---|---|
| | 2-[2,6-dichloro-4-[6-(difluoromethyl)-3,5-dioxo-1,2,4-triazin-2-yl]phenoxy]-5-hydroxy-N-(3-hydroxy-1-methyl-cyclobutyl)pyridine-4-sulfonamide |
| | 2-(2,6-dichloro-4-(6-(difluoromethyl)-3,5-dioxo-4,5-dihydro-1,2,4-triazin-2(3H)-yl)phenoxy)-5-hydroxy-N-(1-methylazetidin-3-yl)pyridine-4-sulfonamide |
| | 2-[2,6-dichloro-4-[6-(difluoromethyl)-3,5-dioxo-1,2,4-triazin-2-yl]phenoxy]-5-hydroxy-N-[(1R,2S)-2-hydroxycyclobutyl]pyridine-4-sulfonamide |

| Structure | Chemical Name |
|---|---|
| | 2-[2,6-dichloro-4-[6-(difluoromethyl)-3,5-dioxo-1,2,4-triazin-2-yl]phenoxy]-5-hydroxy-N-[(1R,2R)-2-hydroxycyclobutyl]pyridine-4-sulfonamide |
| | 2-(2,6-dichloro-4-(6-(difluoromethyl)-3,5-dioxo-4,5-dihydro-1,2,4-triazin-2(3H)-yl)phenoxy)-3-fluoro-5-hydroxy-N-((1r,3r)-3-hydroxycyclobutyl)pyridine-4-sulfonamide |
| | 5-(2,6-dichloro-4-(6-(difluoromethyl)-3,5-dioxo-4,5-dihydro-1,2,4-triazin-2(3H)-yl)phenoxy)-2-hydroxy-N-((1r,3r)-3-hydroxycyclobutyl-3-d)benzenesulfonamide |
| | 5-(2,6-dichloro-4-(6-(difluoromethyl)-3,5-dioxo-4,5-dihydro-1,2,4-triazin-2(3H)-yl)phenoxy)-2-hydroxy-N-((1r,3r)-3-hydroxycyclobutyl-1-d)benzenesulfonamide |

| Structure | Chemical Name |
|---|---|
| | 5-(2,6-dichloro-4-(6-(difluoromethyl)-3,5-dioxo-4,5-dihydro-1,2,4-triazin-2(3H)-yl)phenoxy-3,5-d2)-2-hydroxy-N-((1r,3r)-3-hydroxycyclobutyl)benzenesulfonamide |
| | 5-(2,6-dichloro-4-(6-(difluoromethyl-d)-3,5-dioxo-4,5-dihydro-1,2,4-triazin-2(3H)-yl)phenoxy)-2-hydroxy-N-((1r,3r)-3-hydroxycyclobutyl)benzenesulfonamide |
| | 5-(2,6-dichloro-4-(6-(difluoromethyl)-3,5-dioxo-4,5-dihydro-1,2,4-triazin-2(3H)-yl)phenoxy)-2-hydroxy-N-((1s,3s)-3-hydroxycyclobutyl-3-d)benzenesulfonamide |
| | 5-(2,6-dichloro-4-(6-(difluoromethyl)-3,5-dioxo-4,5-dihydro-1,2,4-triazin-2(3H)-yl)phenoxy)-2-hydroxy-N-((1s,3s)-3-hydroxycyclobutyl-1-d)benzenesulfonamide |
| | 5-(2,6-dichloro-4-(6-(difluoromethyl)-3,5-dioxo-4,5-dihydro-1,2,4-triazin-2(3H)-yl)phenoxy-3,5-d2)-2-hydroxy-N-((1s,3s)-3-hydroxycyclobutyl)benzenesulfonamide |

-continued

| Structure | Chemical Name |
|---|---|
| | 5-(2,6-dichloro-4-(6-(difluoromethyl-d)-3,5-dioxo-4,5-dihydro-1,2,4-triazin-2(3H)-yl)phenoxy)-2-hydroxy-N-((1s,3s)-3-hydroxycyclobutyl)benzenesulfonamide |
| | 2-(2,6-dichloro-4-(6-(difluoromethyl)-3,5-dioxo-4,5-dihydro-1,2,4-triazin-2(3H)-yl)phenoxy)-5-hydroxy-N-((1r,3r)-3-hydroxycyclobutyl-3-d)pyridine-4-sulfonamide |
| | 2-(2,6-dichloro-4-(6-(difluoromethyl)-3,5-dioxo-4,5-dihydro-1,2,4-triazin-2(3H)-yl)phenoxy)-5-hydroxy-N-((1r,3r)-3-hydroxycyclobutyl-1-d)pyridine-4-sulfonamide |
| | 2-(2,6-dichloro-4-(6-(difluoromethyl)-3,5-dioxo-4,5-dihydro-1,2,4-triazin-2(3H)-yl)phenoxy-3,5-d2)-5-hydroxy-N-((1r,3r)-3-hydroxycyclobutyl)pyridine-4-sulfonamide |
| | 2-(2,6-dichloro-4-(6-(difluoromethyl-d)-3,5-dioxo-4,5-dihydro-1,2,4-triazin-2(3H)-yl)phenoxy)-5-hydroxy-N-((1r,3r)-3-hydroxycyclobutyl)pyridine-4-sulfonamide |

| Structure | Chemical Name |
|---|---|
| 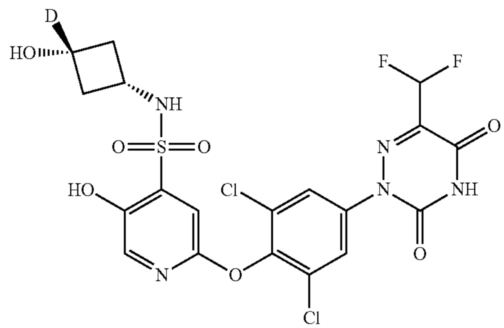 [SMILES: [2H][C@]1(O)C[C@@H](NS(=O)(=O)c2cc(Oc3c(Cl)cc(-n4nc(C(F)F)c(=O)[nH]c4=O)cc3Cl)ccc2O)C1] | 2-(2,6-dichloro-4-(6-(difluoromethyl)-3,5-dioxo-4,5-dihydro-1,2,4-triazin-2(3H)-yl)phenoxy)-5-hydroxy-N-((1s,3s)-3-hydroxycyclobutyl-3-d)pyridine-4-sulfonamide |
| 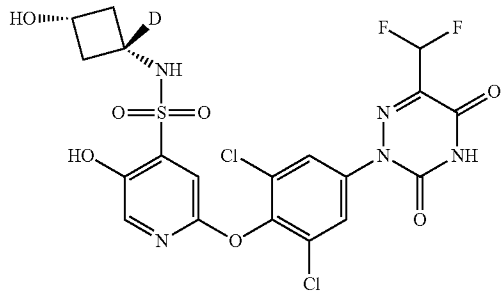 [SMILES: [2H][C@]1(NS(=O)(=O)c2cc(Oc3c(Cl)cc(-n4nc(C(F)F)c(=O)[nH]c4=O)cc3Cl)ccc2O)C[C@@H](O)C1] | 2-(2,6-dichloro-4-(6-(difluoromethyl)-3,5-dioxo-4,5-dihydro-1,2,4-triazin-2(3H)-yl)phenoxy)-5-hydroxy-N-((1s,3s)-3-hydroxycyclobutyl-1-d)pyridine-4-sulfonamide |
| 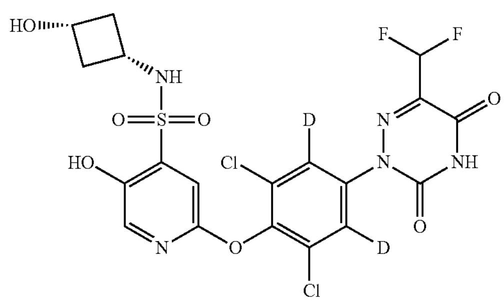 [SMILES: [2H]c1c(Cl)c(Oc2cc(S(=O)(=O)N[C@H]3C[C@@H](O)C3)c(O)cn2)c(Cl)c([2H])c1-n1nc(C(F)F)c(=O)[nH]c1=O] | 2-(2,6-dichloro-4-(6-(difluoromethyl)-3,5-dioxo-4,5-dihydro-1,2,4-triazin-2(3H)-yl)phenoxy-3,5-d2)-5-hydroxy-N-((1s,3s)-3-hydroxycyclobutyl)pyridine-4-sulfonamide |
| 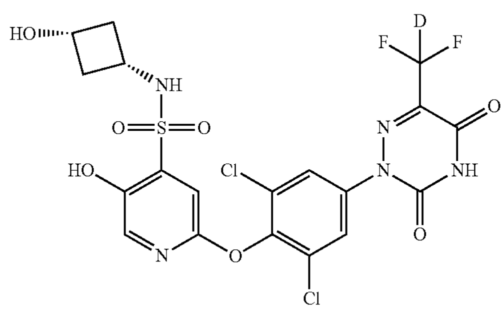 [SMILES: [2H]C(F)(F)c1nn(-c2cc(Cl)c(Oc3cc(S(=O)(=O)N[C@H]4C[C@@H](O)C4)c(O)cn3)c(Cl)c2)c(=O)[nH]c1=O] | 2-(2,6-dichloro-4-(6-(difluoromethyl-d)-3,5-dioxo-4,5-dihydro-1,2,4-triazin-2(3H)-yl)phenoxy)-5-hydroxy-N-((1s,3s)-3-hydroxycyclobutyl)pyridine-4-sulfonamide |
| 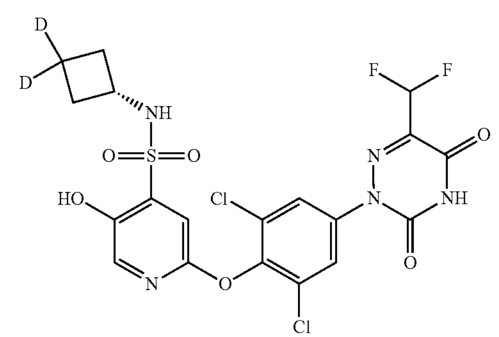 | N-(cyclobutyl-3,3-d2)-2-(2,6-dichloro-4-(6-(difluoromethyl)-3,5-dioxo-4,5-dihydro-1,2,4-triazin-2(3H)-yl)phenoxy)-5-hydroxypyridine-4-sulfonamide |

| Structure | Chemical Name |
|---|---|
| (structure) | N-cyclobutyl-2-(2,6-dichloro-4-(6-(difluoromethyl)-3,5-dioxo-4,5-dihydro-1,2,4-triazin-2(3H)-yl)phenoxy-3,5-d2)-5-hydroxypyridine-4-sulfonamide, and |
| (structure) | N-cyclobutyl-2-(2,6-dichloro-4-(6-(difluoromethyl-d)-3,5-dioxo-4,5-dihydro-1,2,4-triazin-2(3H)-yl)phenoxy)-5-hydroxypyridine-4-sulfonamide, | or a pharmaceutically acceptable salt, solvate, prodrug, stereoisomer, or tautomer thereof.

16. The compound of claim 1, wherein one or more hydrogen atoms in the compound is replaced by one or more deuterium atoms.

17. A pharmaceutical composition comprising a compound of claim 1, or a pharmaceutically acceptable salt, solvate, prodrug, stereoisomer, or tautomer thereof, and a pharmaceutically acceptable diluent, excipient or carrier.

18. A method of modulating thyroid hormone receptor, comprising administering to a subject in need thereof, a therapeutically effective amount of a compound of claim 1, or a pharmaceutically acceptable salt, solvate, prodrug, stereoisomer, or tautomer thereof.

19. A method of improving at least one symptom of a disease or disorder regulated by a thyroid hormone, comprising administering to a subject in need thereof, a therapeutically effective amount of a compound of claim 1, or a pharmaceutically acceptable salt, solvate, prodrug, stereoisomer, or tautomer thereof, wherein the disease or disorder regulated by a thyroid hormone is hyperlipidemia, nonalcoholic fatty liver disease (NAFLD), nonalcoholic steatohepatitis (NASH), liver fibrosis, hypercholesteremia, familial hypercholesterolemia (HeFH/HoFH), dyslipidemia, diabetes mellitus, atherosclerosis, coronary heart disease, or hypertriglyceridemia related pancreatitis.

20. The method of claim 19, wherein the hyperlipidemia is severe high triglyceride (SHTG), familial partial lipodystrophy (FPLD), familial chylomicronemia syndrome (FCS), xanthomas, familial dysbetalipoproteinemia/hypolipoproteinemia type III, hyperlipoproteinemia, or sitosterolemia.

21. A compound selected from the table below:

| Structure | Chemical Name |
|---|---|
| (structure) | 5-(2,6-dichloro-4-(6-(difluoromethyl)-3,5-dioxo-4,5-dihydro-1,2,4-triazin-2(3H)-yl)phenoxy)-2-hydroxy-N-((1r,3r)-3-hydroxycyclobutyl)benzenesulfonamide, |

| Structure | Chemical Name |
|---|---|
| 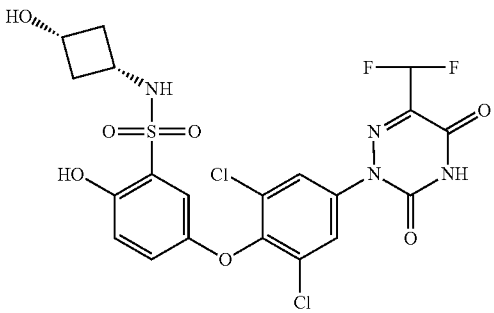 [SMILES: O=c1[nH]c(=O)n(-c2cc(Cl)c(Oc3ccc(O)c(S(=O)(=O)N[C@H]4C[C@@H](O)C4)c3)c(Cl)c2)nc1C(F)F] | 5-(2,6-dichloro-4-(6-(difluoromethyl)-3,5-dioxo-4,5-dihydro-1,2,4-triazin-2(3H)-yl)phenoxy)-2-hydroxy-N-((1s,3s)-3-hydroxycyclobutyl)benzenesulfonamide, |
| 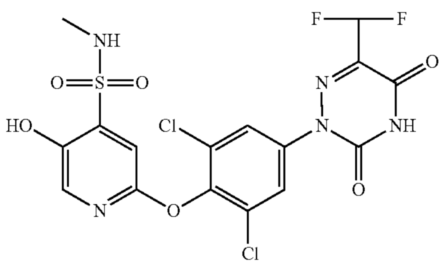 [SMILES: CNS(=O)(=O)c1cc(Oc2c(Cl)cc(-n3nc(C(F)F)c(=O)[nH]c3=O)cc2Cl)ncc1O] | 2-(2,6-dichloro-4-(6-(difluoromethyl)-3,5-dioxo-4,5-dihydro-1,2,4-triazin-2(3H)-yl)phenoxy)-5-hydroxy-N-methylpyridine-4-sulfonamide, |
| 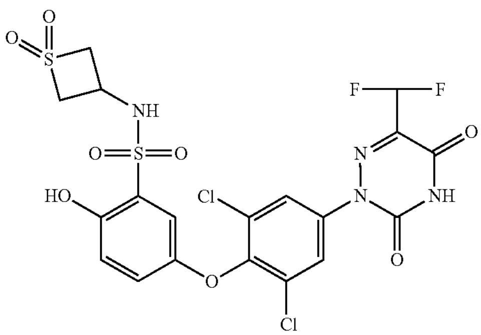 [SMILES: O=c1[nH]c(=O)n(-c2cc(Cl)c(Oc3ccc(O)c(S(=O)(=O)NC4CS(=O)(=O)C4)c3)c(Cl)c2)nc1C(F)F] | 5-(2,6-dichloro-4-(6-(difluoromethyl)-3,5-dioxo-4,5-dihydro-1,2,4-triazin-2(3H)-yl)phenoxy)-N-(1,1-dioxidothietan-3-yl)-2-hydroxybenzenesulfonamide, |
| 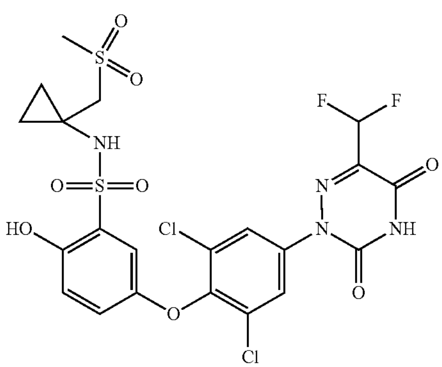 [SMILES: CS(=O)(=O)CC1(NS(=O)(=O)c2cc(Oc3c(Cl)cc(-n4nc(C(F)F)c(=O)[nH]c4=O)cc3Cl)ccc2O)CC1] | 5-(2,6-dichloro-4-(6-(difluoromethyl)-3,5-dioxo-4,5-dihydro-1,2,4-triazin-2(3H)-yl)phenoxy)-2-hydroxy-N-(1-((methylsulfonyl)methyl)cyclopropyl)benzenesulfonamide, |
| 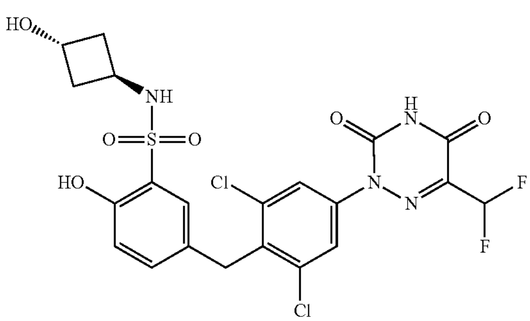 [SMILES: O=c1[nH]c(=O)n(-c2cc(Cl)c(Cc3ccc(O)c(S(=O)(=O)N[C@H]4C[C@H](O)C4)c3)c(Cl)c2)nc1C(F)F] | 5-(2,6-dichloro-4-(6-(difluoromethyl)-3,5-dioxo-4,5-dihydro-1,2,4-triazin-2(3H)-yl)benzyl)-2-hydroxy-N-((1r,3r)-3-hydroxycyclobutyl)benzenesulfonamide, |

| Structure | Chemical Name |
|---|---|
| 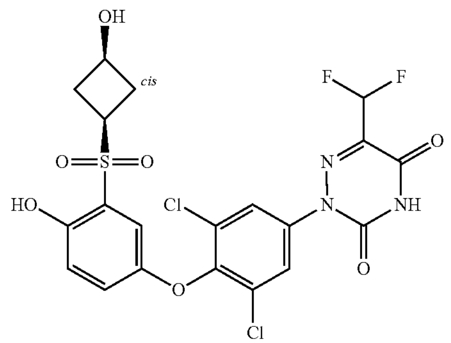 [SMILES: O=c1[nH]c(=O)n(-c2cc(Cl)c(Oc3ccc(O)c(S(=O)(=O)[C@H]4C[C@@H](O)C4)c3)c(Cl)c2)nc1C(F)F] | 2-(3,5-dichloro-4-(4-hydroxy-3-(((1s,3s)-3-hydroxycyclobutyl)sulfonyl)phenoxy)phenyl)-6-(difluoromethyl)-1,2,4-triazine-3,5(2H,4H)-dione, |
| 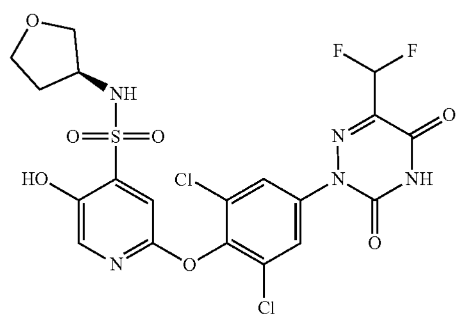 [SMILES: O=c1[nH]c(=O)n(-c2cc(Cl)c(Oc3cc(S(=O)(=O)N[C@H]4CCOC4)c(O)cn3)c(Cl)c2)nc1C(F)F] | (S)-2-(2,6-dichloro-4-(6-(difluoromethyl)-3,5-dioxo-4,5-dihydro-1,2,4-triazin-2(3H)-yl)phenoxy)-5-hydroxy-N-(tetrahydrofuran-3-yl)pyridine-4-sulfonamide, |
| 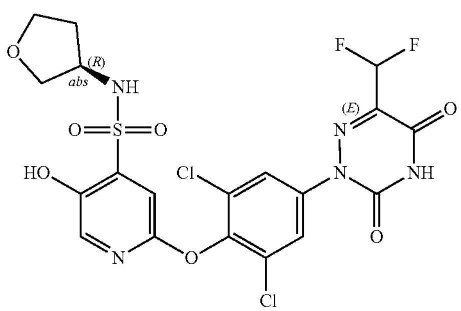 | (R)-2-(2,6-dichloro-4-(6-(difluoromethyl)-3,5-dioxo-4,5-dihydro-1,2,4-triazin-2(3H)-yl)phenoxy)-5-hydroxy-N-(tetrahydrofuran-3-yl)pyridine-4-sulfonamide, |
| 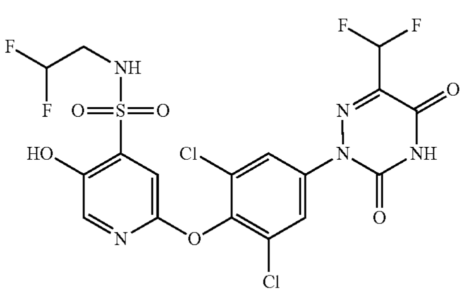 [SMILES: O=c1[nH]c(=O)n(-c2cc(Cl)c(Oc3cc(S(=O)(=O)NCC(F)F)c(O)cn3)c(Cl)c2)nc1C(F)F] | 2-(2,6-dichloro-4-(6-(difluoromethyl)-3,5-dioxo-4,5-dihydro-1,2,4-triazin-2(3H)-yl)phenoxy)-N-(2,2-difluoroethyl)-5-hydroxypyridine-4-sulfonamide, |
| 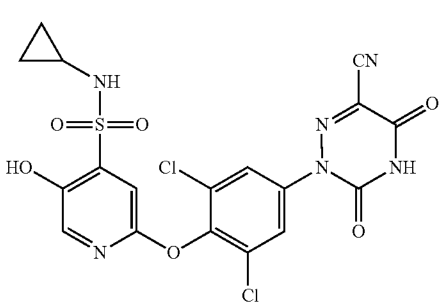 [SMILES: N#Cc1nn(-c2cc(Cl)c(Oc3cc(S(=O)(=O)NC4CC4)c(O)cn3)c(Cl)c2)c(=O)[nH]c1=O] | N-cyclopropyl-2-(2,6-dichloro-4-(6-cyano-3,5-dioxo-4,5-dihydro-1,2,4-triazin-2(3H)-yl)phenoxy)-5-hydroxypyridine-4-sulfonamide, |

| Structure | Chemical Name |
|---|---|
| 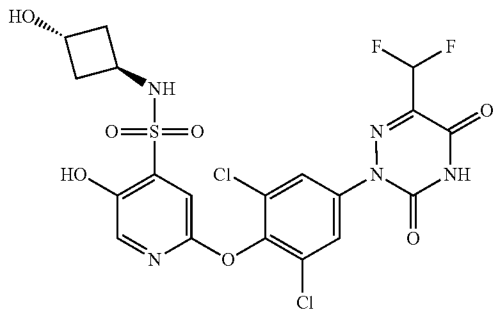 [SMILES: O=c1[nH]c(=O)n(-c2cc(Cl)c(Oc3cc(S(=O)(=O)N[C@H]4C[C@H](O)C4)c(O)cn3)c(Cl)c2)nc1C(F)F] | 2-(2,6-dichloro-4-(6-(difluoromethyl)-3,5-dioxo-4,5-dihydro-1,2,4-triazin-2(3H)-yl)phenoxy)-5-hydroxy-N-((1r,3r)-3-hydroxycyclobutyl)pyridine-4-sulfonamide, |
| 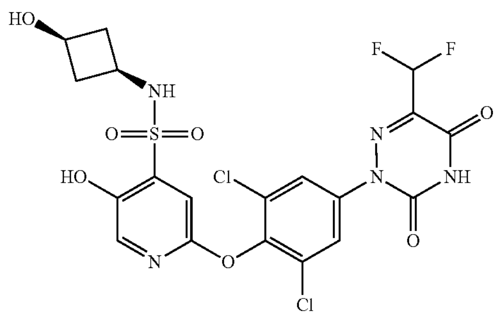 [SMILES: O=c1[nH]c(=O)n(-c2cc(Cl)c(Oc3cc(S(=O)(=O)N[C@H]4C[C@@H](O)C4)c(O)cn3)c(Cl)c2)nc1C(F)F] | 2-(2,6-dichloro-4-(6-(difluoromethyl)-3,5-dioxo-4,5-dihydro-1,2,4-triazin-2(3H)-yl)phenoxy)-5-hydroxy-N-((1s,3s)-3-hydroxycyclobutyl)pyridine-4-sulfonamide, |
| 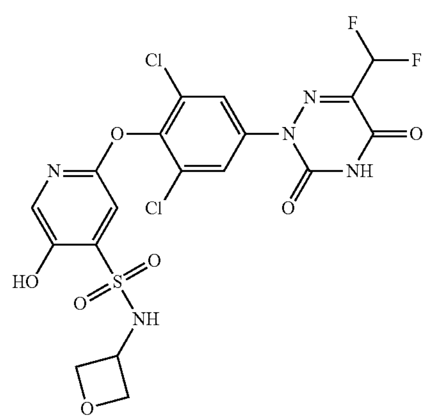 [SMILES: O=c1[nH]c(=O)n(-c2cc(Cl)c(Oc3cc(S(=O)(=O)NC4COC4)c(O)cn3)c(Cl)c2)nc1C(F)F] | 2-(2,6-dichloro-4-(6-(difluoromethyl)-3,5-dioxo-4,5-dihydro-1,2,4-triazin-2(3H)-yl)phenoxy)-5-hydroxy-N-(oxetan-3-yl)pyridine-4-sulfonamide, and |
| | 2-(2,6-dichloro-4-(6-(difluoromethyl)-3,5-dioxo-4,5-dihydro-1,2,4-triazin-2(3H)-yl)phenoxy)-5-hydroxy-N-((1r,3r)-3-hydroxycyclobutyl-3-d)pyridine-4-sulfonamide, | or a pharmaceutically acceptable salt, solvate, prodrug, stereoisomer, or tautomer thereof.

22. A pharmaceutical composition comprising a compound of claim 21, or a pharmaceutically acceptable salt, solvate, prodrug, stereoisomer, or tautomer thereof, and a pharmaceutically acceptable diluent, excipient or carrier.

23. A method of modulating thyroid hormone receptor, comprising administering to a subject in need thereof, a therapeutically effective amount of a compound of claim 21, or a pharmaceutically acceptable salt, solvate, prodrug, stereoisomer, or tautomer thereof.

24. A method of improving at least one symptom of a disease or disorder regulated by a thyroid hormone, comprising administering to a subject in need thereof, a therapeutically effective amount of a compound of claim 21, or a pharmaceutically acceptable salt, solvate, prodrug, stereoisomer, or tautomer thereof, wherein the disease or disorder regulated by a thyroid hormone is hyperlipidemia, nonalcoholic fatty liver disease (NAFLD), nonalcoholic steatohepatitis (NASH), liver fibrosis, hypercholesteremia, familial hypercholesterolemia (HeFH/HoFH), dyslipidemia, diabetes mellitus, atherosclerosis, coronary heart disease, or hypertriglyceridemia related pancreatitis.

25. The method of claim 24, wherein the hyperlipidemia is severe high triglyceride (SHTG), familial partial lipodystrophy (FPLD), familial chylomicronemia syndrome (FCS), xanthomas, familial dysbetalipoproteinemia/hypolipoproteinemia type III, hyperlipoproteinemia, or sitosterolemia.

* * * * *

UNITED STATES PATENT AND TRADEMARK OFFICE
CERTIFICATE OF CORRECTION

| | | |
|---|---|---|
| PATENT NO. | : 11,780,825 B2 | Page 1 of 1 |
| APPLICATION NO. | : 17/147538 | |
| DATED | : October 10, 2023 | |
| INVENTOR(S) | : Zhou et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 69 days.

Signed and Sealed this
Twelfth Day of November, 2024

Katherine Kelly Vidal
*Director of the United States Patent and Trademark Office*

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: synthetic construct

<400> SEQUENCE: 1
agtgccagcc tcgtctcata                                              20

<210> SEQ ID NO 2
<211> LENGTH: 20
<212> TYPE: DNA
<213> ORGANISM: Artificial Sequence
<220> FEATURE:
<223> OTHER INFORMATION: synthetic construct

<400> SEQUENCE: 2 gaagggcgtcg ttgatggcaa                                             20

<210> SEQ ID NO 3
<211> LENGTH: 20
<212> TYPE: DNA
<213> ORGANISM: Artificial Sequence
<220> FEATURE:
<223> OTHER INFORMATION: synthetic construct

<400> SEQUENCE: 3
```

```
caacctgtcc aagttccgca                                              20

<210> SEQ ID NO 4
<211> LENGTH: 23
<212> TYPE: DNA
<213> ORGANISM: Artificial Sequence
<220> FEATURE:
<223> OTHER INFORMATION: synthetic construct

<400> SEQUENCE: 4
ctcatcgtgc attttctgct tgg                                          23

<210> SEQ ID NO 5
<211> LENGTH: 21
<212> TYPE: DNA
<213> ORGANISM: Artificial Sequence
<220> FEATURE:
<223> OTHER INFORMATION: synthetic construct

<400> SEQUENCE: 5
gtggacacaa tgcagaacca g                                            21

<210> SEQ ID NO 6
<211> LENGTH: 21
<212> TYPE: DNA
<213> ORGANISM: Artificial Sequence
<220> FEATURE:
<223> OTHER INFORMATION: synthetic construct

<400> SEQUENCE: 6
acttcctcag gattgtagtt c                                            21
```